(12) United States Patent
Daanen et al.

(10) Patent No.: US 9,783,527 B2
(45) Date of Patent: Oct. 10, 2017

(54) INDAZOLE UREAS AND METHOD OF USE

(71) Applicant: AbbVie Inc., North Chicago, IL (US)

(72) Inventors: Jerome F. Daanen, Racine, WI (US);
David A. DeGoey, Salem, WI (US);
Jennifer M. Frost, Gurnee, IL (US);
John R. Koenig, Chicago, IL (US);
Steve Latshaw, Elijay, GA (US); Mark Matulenko, Libertyville, IL (US); Marc Scanio, Libertyville, IL (US); Lei Shi, Vernon Hills (CN); William H. Bunnelle, Mundelein, IL (US)

(73) Assignee: AbbVie Inc., North Chicago, IL (US)

( * ) Notice: Subject to any disclaimer, the term of this patent is extended or adjusted under 35 U.S.C. 154(b) by 0 days.

(21) Appl. No.: 14/854,433

(22) Filed: Sep. 15, 2015

(65) Prior Publication Data

US 2016/0075692 A1    Mar. 17, 2016

Related U.S. Application Data

(60) Provisional application No. 62/051,024, filed on Sep. 16, 2014.

(51) Int. Cl.
| | | |
|---|---|---|
| A61K 31/497 | (2006.01) | |
| A61K 31/4178 | (2006.01) | |
| A61K 31/4985 | (2006.01) | |
| C07D 403/04 | (2006.01) | |
| C07D 403/14 | (2006.01) | |
| C07D 487/14 | (2006.01) | |
| C07D 491/08 | (2006.01) | |
| C07D 413/14 | (2006.01) | |
| C07D 405/14 | (2006.01) | |
| C07D 417/14 | (2006.01) | |
| C07D 401/14 | (2006.01) | |

(52) U.S. Cl.
CPC ......... C07D 403/14 (2013.01); C07D 401/14 (2013.01); C07D 403/04 (2013.01); C07D 405/14 (2013.01); C07D 413/14 (2013.01); C07D 417/14 (2013.01); C07D 487/14 (2013.01); C07D 491/08 (2013.01)

(58) Field of Classification Search
CPC .............. A61K 31/497; A61K 31/4178; A61K 31/4985; C07D 403/14; C07D 403/04; C07D 487/14; C07D 491/08; C07D 413/14; C07D 405/14; C07D 417/14; C07D 401/14

See application file for complete search history.

(56) References Cited

U.S. PATENT DOCUMENTS

2005/0234095 A1* 10/2005 Xie ...................... C07D 453/02
                                                       514/305
2005/0272735 A1* 12/2005 Xie ...................... C07D 487/08
                                                       514/249

OTHER PUBLICATIONS

Harrison, Laird, New Sodium Channel Blocker Dampens Radiculopathy Pain. American Pain Society (APS) 34th Annual Scientific Meeting, May 28, 2015.*

* cited by examiner

Primary Examiner — Alexander R Pagano
Assistant Examiner — Ebenezer O Sackey
(74) Attorney, Agent, or Firm — Michael J. Ward

(57) ABSTRACT

Compounds of formula (I)

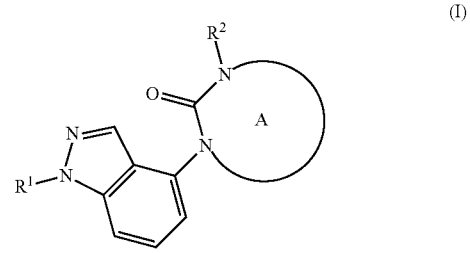

and pharmaceutically acceptable salts, esters, amides, or radiolabelled forms thereof, wherein A, $R^1$ and $R^2$ are as defined in the specification, are useful in treating conditions or disorders prevented by or ameliorated by voltage-gated sodium channels, e.g., $Na_v1.7$ and/or $Na_v1.8$. Methods for making the compounds are disclosed. Also disclosed are pharmaceutical compositions of compounds of formula (I), and methods for using such compounds and compositions.

41 Claims, No Drawings

INDAZOLE UREAS AND METHOD OF USE

BACKGROUND OF THE INVENTION

Technical Field

The invention relates to indazole ureas that are sodium channel (e.g., $Na_v1.7$ and $Na_v1.8$) blockers, useful in treating diseases and conditions mediated and modulated by the voltage-gated sodium channels. Additionally, the invention relates to compositions containing compounds of the invention and processes of their preparation.

Description of Related Technology

The voltage-gated sodium channels (VGSCs, $Na_v1.x$) contribute to the initiation and propagation of action potentials in excitable tissues such as nerve and muscle by modulating the influx of sodium ions. $Na_v1.7$, one of nine sodium channel isoforms, is preferentially expressed in the peripheral nervous system where it acts as a threshold channel for action potential firing in neurons (Cummins T R, et al. Expert Rev Neurother 2007; 7:1597-1612. Rush A M, et al. J Physiol 2007; 579:1-14.). A wealth of evidence connects abnormal activity of sodium channels in the peripheral nervous system to the pathophysiology of chronic pain (Goldin A L, et al. Neuron 2000; 28:365-368. Dib-Hajj S D, et al. Annu Rev Neurosci 2010; 33:325-347). Polymorphisms in SCN9A, the gene that encodes $Na_v1.7$, cause human pain disorders arising from either gain-of-function or loss-of-function mutations of the channel. Clinically, VGSC blockers have proven useful in the management of pain, but their utility is often limited by incomplete efficacy and poor tolerability. Local anesthetics (e.g., lidocaine), anti-arrhythmic agents (e.g., mexilitene), and anti-convulsants (e.g., lamotrigine) are all relatively weak ($IC_{50}$ values in the high micromolar range), non-selective (versus $Na_v1.x$ subtypes and other ion channels) VGSC blocking agents identified without prior knowledge of their molecular targets.

The VGSCs are integral plasma membrane proteins composed of a large (260 kDa) α-subunit and one or more smaller β-subunits (Hargus N J et al. Expert Opin Invest Drugs 2007; 16:635-646). Nine α-subunits ($Na_v1.1$-$Na_v1.9$) and four β-subunits (β1-β4) have been identified in mammals. The various VGSC subtypes exhibit diverse functional properties and distinct expression patterns, suggesting differential involvement in transmission of specific signals. $Na_v1.7$, $Na_v1.8$ and $Na_v1.9$ are expressed predominantly in the peripheral nervous system in humans and rodents (Waxman S G Brain 2010; 133:2515-2518). The biophysical characteristics of $Na_v1.7$ suggest a role in initiation of action potentials, while $Na_v1.8$ is a major contributor to the upstroke of action potentials in sensory neurons. $Na_v1.9$ produces a persistent current that is involved in setting the resting membrane potential.

The $Na_v1.7$ isoform is expressed in both small and large diameter DRG neurons, as well as in sympathetic neurons, and in peripheral axonal termini of neurons processing pain. $Na_v1.7$ is up-regulated in preclinical models of inflammatory and neuropathic pain, including diabetic neuropathy (Dib-Hajj S D, et al. Nat Rev Neurosci. 2013; 14:49-62. Hong S, et al. Journal of Biological Chemistry. 2004; 279:29341-29350. Persson A K, et al. Exp Neurol. 2011; 230:273-279.). $Na_v1.7$ has been shown to accumulate in painful neuromas, such as those in amputees with phantom limb pain, and in painful dental pulp (Beneng K, et al. BMC Neurosci. 2010; 11:71. Dib-Hajj S D, et al. Nat Rev Neurosci. 2013; 14:49-62). Rare human genetic conditions involving single-nucleotide polymorphisms in SCN9A, the gene encoding for $Na_v1.7$ highlight its importance in pain pathways. Bi-allelic gain-of-function mutations (enhancing channel activity and increasing the excitability of DRG neurons) produce severe pain syndromes with dominant genetic inheritance. Mutations that hyperpolarize activation voltage dependence (i.e., facilitate channel opening and increase the excitability of DRG neurons) result in inherited erythromelalgia (IEM), a condition characterized by excruciating burning pain, attacks of edema, increased skin temperature and flushing of the skin affecting the distal extremities. Similarly, polymorphisms that impair inactivation of the channel and enhance persistent current lead to paroxysmal extreme pain disorder (PEPD), a condition wherein episodic severe perineal, periocular and paramandibular pain is accompanied by autonomic manifestations such as skin flushing usually in the lower body (Waxman S G Nature 2011472:173-174. Dib-Hajj S D, et al. Brain 2005; 128:1847-1854.). By contrast, bi-allelic loss-of-function mutations preventing the production of functional $Na_v1.7$ channels produced channelopathy-associated congenital insensitivity to pain (CIP). CIP patients do not perceive or understand pain even when confronted with extreme pain stimuli such as bone fractures, surgery, dental extractions, burns, and childbirth.

The role of $Na_v1.7$ in pain has been confirmed in knockout studies. Global deletion of $Na_v1.7$ in knockout mice causes a disruption of normal eating behavior due to a deficit in olfaction, resulting in lethality shortly after birth (Nassar M A, et al. Proc Natl Acad Sci USA 2004; 101:12706-12711). A conditional $Na_v1.7$ knockout in $Na_v1.8$-expressing DRG neurons abrogated inflammation-induced pain and diminished responses to mechanical insult, but neuropathic pain development was not affected (Nassar M A, et al. Mol Pain 2005; 1:24-31). However, ablation of $Na_v1.7$ in both sensory and sympathetic neurons recapitulated the pain-free phenotype seen in CIP patients, abolishing inflammatory and neuropathic pain without causing any overt autonomic dysfunction (Minett M S, et al. Nat Commun 2012; 3:791). $Na_v1.7$-deficient sensory neurons also failed to release substance P in the spinal cord or to display synaptic potentiation in the dorsal horn of the spinal cord in response to electrical stimulation of the sciatic nerve (Minett M S, et al. Nat Commun 2012; 3:791).

The level of preclinical validation for the $Na_v1.8$ isoform as a target for pain is also compelling. Complementary to $Na_v1.7$ in its biophysical and functional profile, one $Na_v1.8$ isoform is expressed in nociceptive trigeminal neurons, in the vast majority of DRG neurons, and in peripheral free nerve endings (Shields S D, et al. Pain 2012; 32:10819-10832). An evaluation of $Na_v1.8$-null mice demonstrated that this channel carries the majority of current underlying the upstroke of action potential in nociceptive neurons. Knockout studies further implicate $Na_v1.8$ in visceral, cold, and inflammatory pain, but not in neuropathic pain. However, assessment of $Na_v1.8$ antisense oligonucleotides, also suggested involvement of $Na_v1.8$ in the development and maintenance of neuropathic pain, in addition to confirming the relevance of the channel in inflammatory pain (Momin A, et al. Curr Opin Neurobiol 2008; 18:383-388. Rush A M, et al. J Physiol 2007; 579:1-14. Liu M et al. Pain Med 12 Suppl 2011; 3:S93-99.). Human gain-of-function mutations in $Na_v1.8$ were recently identified in patients with SFN who were all negative for mutations in $Na_v1.7$ (Faber C G, et al. Proc Natl Acad Sci USA. 2012; 109:19444-19449).

While the literature offers preclinical validation for Na$_v$1.7 and Na$_v$1.8 as pain targets, multiple challenges confront the discovery and development of small molecule blockers. The potency needed for efficacy, the levels of selectivity versus the various isoforms required for acceptable therapeutic index, and the relevance of state- and use-dependent activity are not well understood. Although compounds and mechanisms exist that are used clinically to treat pain, there is need for new compounds that can effectively treat different types of pain. Pain of various types (e.g., inflammatory pain, post-surgical pain, osteoarthritis pain, knee pain, lower back pain, neuropathic pain) afflicts virtually all humans and animals at one time or another, and a substantial number of medical disorders and conditions produce some sort of pain as a prominent concern requiring treatment. As such, it would be particularly beneficial to identify new compounds for treating the various types of pain.

SUMMARY

The invention is directed to indazole ureas having a structure of formula (I):

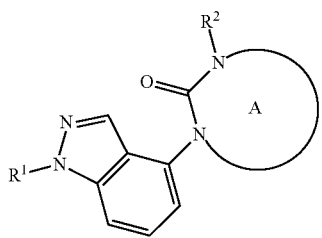

(I)

or a pharmaceutically acceptable salt or isotopically labelled form thereof, wherein:

A is selected from the group consisting of (i), (ii), (iii), and (iv), wherein the nitrogen atom on the left side of each substructure (i), (ii), (iii), or (iv) is attached to the phenyl ring of the indazole in formula (I);

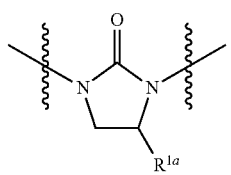
(i)

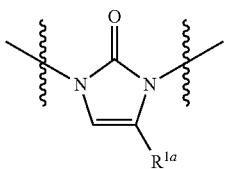
(ii)

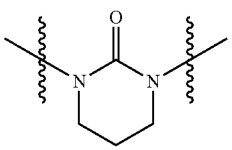
(iii)

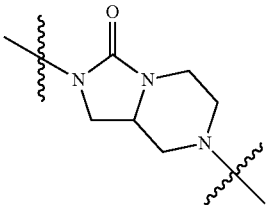
(iv)

$R^{1a}$ is hydrogen or $C_1$-$C_4$alkyl;

$R^1$ is selected from the group consisting of $C_1$-$C_8$alkyl, $C_1$-$C_8$haloalkyl, $C_3$-$C_7$cycloalkyl, phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen;

$R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$SO_2NR^{2d}R^{2e}$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OR^{2d})(R^{2d})$—$R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)R^{2c}$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2R^{2c}$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}R^{2e}$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, —$CR^{2a}$=$CHR^{2a}$—$CO_2R^{2c}$, —$CR^{2a}$=$CHR^{2a}$—$C(O)G^1$, and —$CR^{2a}$=$CHR^{2a}$—$C(O)G^3$;

$R^{2a}$ and $R^{2b}$, at each occurrence, are each independently selected from the group consisting of hydrogen, fluorine, $C_1$-$C_4$alkyl, and halo$C_1$-$C_4$alkyl;

$R^{2c}$ is selected from the group consisting of $C_2$-$C_8$alkenyl, $C_1$-$C_8$alkyl and halo$C_1$-$C_8$alkyl;

$R^{2d}$, at each occurrence, is selected from the group consisting of hydrogen, $C_1$-$C_6$alkyl and halo$C_1$-$C_6$alkyl;

$R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl;

$R^{2f}$ is selected from the group consisting of $C_1$-$C_4$alkyl, halo$C_1$-$C_4$alkyl and —$(CR^{2a}R^{2b})_m$-$G^{2a}$;

$G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo;

$G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo;

$G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen;

$G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen;

$G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, —SO$_2$(C$R^{2a}R^{2b}$)$_m$$G^{1a}$, and —(C$R^{2a}R^{2b}$)$_p$$G^{3a}$;

$G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, and —SO$_2$(C$R^{2a}R^{2b}$)$_m$$G^{1a}$;

$G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$;

m is 1, 2 or 3;

n is 1, 2 or 3; and p is 1 or 2.

Another aspect of the invention relates to pharmaceutical compositions comprising compounds of the invention. Such compositions can be administered in accordance with a method of the invention, typically as part of a therapeutic regimen for treatment or prevention of conditions and disorders related to voltage-gated sodium channel (and particularly Na$_v$1.7 and Na$_v$1.8) activity.

Yet another aspect of the invention relates to a method of selectively blocking voltage-gated sodium channels (e.g., Na$_v$1.7 and Na$_v$1.8 channels). The method is useful for treating, or preventing conditions and disorders related to blocking voltage-gated sodium channels in mammals. More particularly, the method is useful for treating or preventing conditions and disorders related to pain, neuropathy, inflammation, auto-immune disease, fibrosis, chronic kidney disease, and cancer. Accordingly, the compounds and compositions of the invention are useful as a medicament for treating or preventing voltage-gated sodium channel modulated disease.

The compounds, compositions comprising the compounds, methods for making the compounds, and methods for treating or preventing conditions and disorders by administering the compounds are further described herein.

These and other objects of the invention are described in the following paragraphs. These objects should not be deemed to narrow the scope of the invention.

DETAILED DESCRIPTION OF THE INVENTION

Compounds of formula (I) are disclosed in this invention

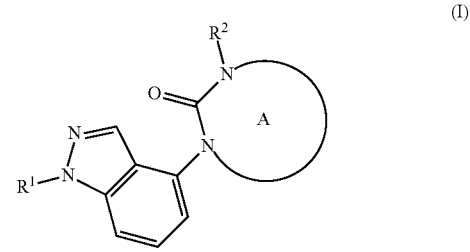

(I)

wherein $R^1$, $R^2$ and A are as defined above in the Summary. Compositions comprising such compounds and methods for treating conditions and disorders using such compounds and compositions are also disclosed.

In various embodiments, the present invention provides at least one variable that occurs more than one time in any substituent or in the compound of the invention or any other formulae herein. Definition of a variable on each occurrence is independent of its definition at another occurrence. Further, combinations of substituents are permissible only if such combinations result in stable compounds. Stable compounds are compounds which can be isolated from a reaction mixture.

Definition of Terms

Certain terms as used in the specification are intended to refer to the following definitions, as detailed below.

The term "alkenyl" as used herein, means a straight or branched hydrocarbon chain containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylene" means a divalent group derived from a straight or branched chain hydrocarbon of from 2 to 10 carbon atoms containing at least one double bond. Representative examples of alkenylene include, but are not limited to, —CH=CH, —CH=CH$_2$CH$_2$—, and —CH=C(CH$_3$)CH$_2$—.

The term "alkoxy" as used herein means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkyl" as used herein means an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl" as used herein means an alkoxy group, as defined herein, appended to the parent molecular moiety through a carbonyl group, as defined herein. Representative examples of alkoxycarbonyl include, but are not limited to, methoxycarbonyl, ethoxycarbonyl, isopropoxycarbonyl, and tert-butoxycarbonyl.

The term "alkyl" as used herein, means a straight or branched, saturated hydrocarbon chain containing from 1 to 10 carbon atoms. The term "lower alkyl" or "$C_1$-$C_6$alkyl" means a straight or branched chain hydrocarbon containing from 1 to 6 carbon atoms. The term "$C_1$-$C_3$alkyl" means a straight or branched chain hydrocarbon containing from 1 to 3 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl" as used herein means an alkyl group, as defined herein, appended to the parent molecular moiety through a carbonyl group, as defined herein. Representative examples of alkylcarbonyl include, but are not limited to, methylcarbonyl (acetyl), ethylcarbonyl, isopropylcarbonyl, n-propylcarbonyl, and the like.

The term "alkyloxime" as used herein, refers to an alkyl group, as defined herein, appended to the parent molecular moiety through an oxime group, as defined herein (i.e., =N—O-alkyl). Representative examples of alkyloxime include, but are not limited to methyloxime and ethyloxime.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkylene" denotes a divalent group derived from a straight or branched chain hydrocarbon containing from 1 to 10 carbon atoms. Representative examples of alkylene include, but are not limited to, —$CH_2$—, —$CH_2CH_2$—, —$CH_2CH_2CH_2$—, —$CH_2CH_2CH_2CH_2$—, and —$CH_2CH(CH_3)CH_2$—.

The term "alkynyl" as used herein, means a straight or branched chain hydrocarbon group containing from 2 to 10 carbon atoms and containing at least one carbon-carbon triple bond. Representative examples of alkynyl include, but are not limited to, acetylenyl, 1-propynyl, 2-propynyl, 3-butynyl, 2-pentynyl, and 1-butynyl.

The term "amino" as used herein means an —$NH_2$ group.

The term "aryl" as used herein, means phenyl or a bicyclic aryl. The bicyclic aryl is naphthyl, or a phenyl fused to a monocyclic cycloalkyl, or a phenyl fused to a monocyclic cycloalkenyl. Representative examples of the aryl groups include, but are not limited to, dihydroindenyl, indenyl, naphthyl, dihydronaphthalenyl, and tetrahydronaphthalenyl. The bicyclic aryl is attached to the parent molecular moiety through any carbon atom contained within the bicyclic ring system. The aryl groups of the present invention can be unsubstituted or substituted.

The term "benzyloxy" as used herein means —O—$CH_2$-phenyl.

The term "carbonyl" as used herein means a —C(=O)— group.

The term "cyano" as used herein, means a —CN group.

The term "cycloalkenyl" or "cycloalkene" as used herein, means a monocyclic or a bicyclic hydrocarbon ring system. The monocyclic cycloalkenyl has four-, five-, six-, seven- or eight carbon atoms and zero heteroatoms. The four-membered ring systems have one double bond, the five- or six-membered ring systems have one or two double bonds, and the seven- or eight-membered ring systems have one, two or three double bonds. Representative examples of monocyclic cycloalkenyl groups include, but are not limited to, cyclobutenyl, cyclopentenyl, cyclohexenyl, cycloheptenyl and cyclooctenyl. The bicyclic cycloalkenyl is a monocyclic cycloalkenyl fused to a monocyclic cycloalkyl group, or a monocyclic cycloalkenyl fused to a monocyclic cycloalkenyl group, or a bridged monocyclic ring system in which two non-adjacent carbon atoms of the monocyclic ring are linked by an alkylene bridge containing one, two, three, or four carbon atoms. Representative examples of the bicyclic cycloalkenyl groups include, but are not limited to, 4,5,6,7-tetrahydro-3aH-indene, octahydronaphthalenyl and 1,6-dihydro-pentalene. The monocyclic and bicyclic cycloalkenyl can be attached to the parent molecular moiety through any substitutable atom contained within the ring systems, and can be unsubstituted or substituted.

The term "cycloalkyl" or "cycloalkane" as used herein, means a monocyclic, a bicyclic, a tricyclic, or a spirocyclic cycloalkyl. The monocyclic cycloalkyl is a carbocyclic ring system containing three to eight carbon atoms, zero heteroatoms and zero double bonds. Examples of monocyclic ring systems include cyclopropyl, cyclobutyl, cyclopentyl, cyclohexyl, cycloheptyl, and cyclooctyl. The bicyclic cycloalkyl is a monocyclic cycloalkyl fused to a monocyclic cycloalkyl ring, or a bridged monocyclic ring system in which two non-adjacent carbon atoms of the monocyclic ring are linked by an alkylene bridge containing one, two, three, or four carbon atoms. Representative examples of bicyclic ring systems include, but are not limited to, bicyclo[3.1.1]heptane, bicyclo[2.2.1]heptane, bicyclo[2.2.2]octane, bicyclo[3.2.2]nonane, bicyclo[3.3.1]nonane, and bicyclo[4.2.1]nonane. Tricyclic cycloalkyls are exemplified by a bicyclic cycloalkyl fused to a monocyclic cycloalkyl, or a bicyclic cycloalkyl in which two non-adjacent carbon atoms of the ring systems are linked by an alkylene bridge of 1, 2, 3, or 4 carbon atoms. Representative examples of tricyclic-ring systems include, but are not limited to, tricyclo[3.3.1.0$^{3,7}$]nonane (octahydro-2,5-methanopentalene or noradamantane), and tricyclo[3.3.1.1$^{3,7}$]decane (adamantane). The monocyclic, bicyclic, and tricyclic cycloalkyls can be unsubstituted or substituted, and are attached to the parent molecular moiety through any substitutable atom contained within the ring system. Spirocyclic cycloalkyl is exemplified by a monocyclic or a bicyclic cycloalkyl, wherein two of the substituents on the same carbon atom of the ring, together with said carbon atom, form a 4-, 5-, or 6-membered monocyclic cycloalkyl. An example of a spirocyclic cycloalkyl is spiro[2.5]octane. The spirocyclic cycloalkyl groups of the present invention can be appended to the parent molecular moiety through any substitutable carbon atom of the groups.

The term "cycloalkylalkyl" as used herein, means a cycloalkyl group appended to the parent molecular moiety through an alkyl group, as defined herein.

The term "fluoroalkyl" as used herein, means an alkyl group, as defined herein, in which one, two, three, four, five, six, seven or eight hydrogen atoms are replaced by fluorine. Representative examples of haloalkyl include, but are not limited to, fluoromethyl, 2-fluoroethyl, 2,2-difluoroethyl, 2,2,2-trifluoroethyl, trifluoromethyl, difluoromethyl, pentafluoroethyl, 1,1,2-trifluoroisopropyl, and trifluoropropyl such as 3,3,3-trifluoropropyl.

The term "halo" or "halogen" as used herein, means Cl, Br, I, or F.

The term "haloalkoxy" means a haloalkyl group appended to the parent molecule through an oxygen atom. Representative examples of haloalkoxy include, but are not limited to, trifluoromethoxy, difluoromethoxy, and 2,2,2-trifluoroethoxy.

The term "haloalkyl" as used herein, means an alkyl group, as defined herein, in which one, two, three, four, five, six, seven or eight hydrogen atoms are replaced by halogen. Representative examples of haloalkyl include, but are not limited to, chloromethyl, 2-fluoroethyl, 2,2,2-trifluoroethyl, trifluoromethyl, difluoromethyl, pentafluoroethyl, 2-chloro-3-fluoropentyl, and trifluoropropyl such as 3,3,3-trifluoropropyl.

The term "haloalkylsulfonyl" as used herein, means a haloalkyl group, as defined herein appended to the parent molecule through a sulfonyl group, as defined herein. Representative examples of haloalkyl include, but are not limited to, trifluoromethylsulfonyl, pentafluoroethylsulfonyl, and nonafluorobutylsulfonyl.

The term "heteroaryl" as used herein, means a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl consists of a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinolinyl, thiazolo[5,4-b]pyridin-2-yl, thiazolo[5,4-d]pyrimidin-2-yl, and 5,6,7,8-tetrahydroquinolin-5-yl. The monocyclic and bicyclic heteroaryl groups of the present invention can be substituted or unsubstituted and are connected to the parent molecular moiety through any carbon atom or any nitrogen atom contained within the ring systems.

The term "heteroarylalkyl" as used herein, means a heteroaryl, as defined herein, appended to the parent molecular moiety through an alkyl group, as defined herein.

The term "heteroarylcarbonyl" means a heteroaryl group appended to the parent molecular moiety through a carbonyl group, as defined herein. Representative examples of heteroarylcarbonyl include, but are not limited to, fur-3-ylcarbonyl, 1H-imidazol-2-ylcarbonyl, 1H-imidazol-4-ylcarbonyl, pyridin-3-ylcarbonyl, 6-chloropyridin-3-ylcarbonyl, pyridin-4-ylcarbonyl, (6-(trifluoromethyl)pyridin-3-yl)carbonyl, (6-(cyano)pyridin-3-yl)carbonyl, (2-(cyano)pyridin-4-yl)carbonyl, (5-(cyano)pyridin-2-yl)carbonyl, (2-(chloro)pyridin-4-yl)carbonyl, pyrimidin-5-ylcarbonyl, pyrimidin-2-ylcarbonyl, thien-2-ylcarbonyl, and thien-3-ylcarbonyl.

The term "heterocycle" or "heterocyclic" as used herein, means a monocyclic heterocycle, a bicyclic heterocycle, a tricyclic heterocycle, or a spirocyclic heterocycle. The monocyclic heterocycle is a three-, four-, five-, six-, seven-, or eight-membered ring containing at least one heteroatom independently selected from the group consisting of O, N, and S. The three- or four-membered ring contains zero or one double bond, and one heteroatom selected from the group consisting of O, N, and S. The five-membered ring contains zero or one double bond and one, two or three heteroatoms selected from the group consisting of O, N and S. The six-membered ring contains zero, one or two double bonds and one, two, or three heteroatoms selected from the group consisting of O, N, and S. The seven- and eight-membered rings contains zero, one, two, or three double bonds and one, two, or three heteroatoms selected from the group consisting of O, N, and S. Representative examples of monocyclic heterocycles include, but are not limited to, azetidinyl, azepanyl, aziridinyl, diazepanyl, 1,3-dioxanyl, 1,3-dioxolanyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydropyridinyl, tetrahydrothienyl, thiadiazolinyl, thiadiazolidinyl, 1,2-thiazinanyl, 1,3-thiazinanyl, thiazolinyl, thiazolidinyl, thiomorpholinyl, 1,1-dioxidothiomorpholinyl (thiomorpholine sulfone), thiopyranyl, and trithianyl. The bicyclic heterocycle is a monocyclic heterocycle fused to a phenyl group, or a monocyclic heterocycle fused to a monocyclic cycloalkyl, or a monocyclic heterocycle fused to a monocyclic cycloalkenyl, or a monocyclic heterocycle fused to a monocyclic heterocycle, or a bridged monocyclic heterocycle ring system in which two non-adjacent atoms of the ring are linked by an alkylene bridge of 1, 2, 3, or 4 carbon atoms, or an alkenylene bridge of two, three, or four carbon atoms. Representative examples of bicyclic heterocycles include, but are not limited to, benzopyranyl, benzothiopyranyl, chromanyl, 2,3-dihydrobenzofuranyl, 2,3-dihydrobenzothienyl, 2,3-dihydroisoquinoline, azabicyclo[2.2.1]heptyl (including 2-azabicyclo[2.2.1]hept-2-yl), 2,3-dihydro-1H-indolyl, isoindolinyl, octahydrocyclopenta[c]pyrrolyl, octahydropyrrolopyridinyl, and tetrahydroisoquinolinyl. Tricyclic heterocycles are exemplified by a bicyclic heterocycle fused to a phenyl group, or a bicyclic heterocycle fused to a monocyclic cycloalkyl, or a bicyclic heterocycle fused to a monocyclic cycloalkenyl, or a bicyclic heterocycle fused to a monocyclic heterocycle, or a bicyclic heterocycle in which two non-adjacent atoms of the bicyclic ring are linked by an alkylene bridge of 1, 2, 3, or 4 carbon atoms, or an alkenylene bridge of two, three, or four carbon atoms. Examples of tricyclic heterocycles include, but not limited to, octahydro-2,5-epoxypentalene, hexahydro-2H-2,5-methanocyclopenta[b]furan, hexahydro-1H-1,4-methanocyclopenta[c]furan, aza-adamantane (1-azatricyclo[3.3.1.1$^{3,7}$]decane), oxa-adamantane (2-oxatricyclo[3.3.1.1$^{3,7}$]decane), and octahydro-1H-4,7-epiminoisoindole. The spirocyclic heterocycles are exemplified by a monocyclic heterocycle as defined herein wherein one carbon atom of the monocyclic heterocycle is bridged by two ends of an alkylene chain. In the spirocyclic heterocycle, one or more carbon atoms in the bridging alkylene chain may be replaced with a heteroatom. Examples of spirocyclic heterocycles include, but are not limited to, 4,7-diazaspiro[2.5]octane, 2-oxa-6-azaspiro[3.3]heptane, 2,6-diazaspiro[3.3]heptane, 2-oxa-5,8-diazaspiro[3.5]nonane, 2,7-diazaspiro[3.5]nonane, 1,4-dioxa-8-azaspiro[4.5]decane, 1,6-diazaspiro[3.3]heptane, 1-azaspiro[4.4]nonane, 7-azaspiro[3.5]nonane, 1,4-dioxa-7-azaspiro[4.4]nonane, 5,8-diazaspiro[3.5]nonane, 5,8-dioxa-2-azaspiro[3.4]octane, 2-oxa-6-azaspiro[3.4]octane, 6-oxa-1-azaspiro[3.3]heptane, 6-oxa-2-azaspiro[3.4]octane, 6-oxa-2-azaspiro[3.5]nonane, and 7-oxa-2-azaspiro[3.5]nonane. The monocyclic, bicyclic, tricyclic, and spirocyclic heterocycles are connected to the parent molecular moiety through any carbon atom or any nitrogen atom contained within the rings, and can be unsubstituted or substituted.

The term "heterocyclealkyl", as used herein, refers to refers to a heterocycle group attached to the parent molecular moiety through an alkyl group.

The term "heteroatom" as used herein, means a nitrogen, oxygen, or sulfur atom.

The term "hydroxyl" or "hydroxy" as used herein, means an —OH group.

The term "hydroxyalkyl" as used herein, means at least one hydroxy group, as defined herein, is appended to the parent molecular moiety through an alkylene group, as defined herein. Representative examples of hydroxyalkyl include, but are not limited to, hydroxymethyl, 2-hydroxyethyl, 3-hydroxypropyl, and 2-ethyl-4-hydroxyheptyl.

The term "oxime" as used herein means (=N—OH).

The term "oxo" as used herein means (=O).

The term "sulfonyl," as used herein, refers to a —S(O)$_2$— group.

In some instances, the number of carbon atoms in a hydrocarbyl substituent (e.g., alkyl, alkenyl, alkynyl, or cycloalkyl) is indicated by the prefix "$C_x$-$C_y$," wherein x is the minimum and y is the maximum number of carbon atoms in the substituent. Thus, for example, "$C_1$-$C_6$alkyl" refers to an alkyl substituent containing from 1 to 6 carbon atoms. Illustrating further, $C_3$-$C_6$cycloalkyl means a saturated hydrocarbyl ring containing from 3 to 6 carbon ring atoms.

As used herein, the term "radiolabel" refers to a compound of the invention in which at least one of the atoms is a radioactive atom or radioactive isotope, wherein the radioactive atom or isotope spontaneously emits gamma rays or energetic particles, for example alpha particles or beta particles, or positrons. Examples of such radioactive atoms include, but are not limited to, $^3$H (tritium), $^{14}$C, $^{11}$C, $^{15}$O, $^{18}$F, $^{35}$S, $^{123}$I, and $^{125}$I.

Compounds of the Invention

Compounds of the invention can have the formula (I) as described in the Summary.

Particular values of variable groups in compounds of formula (I) are as follows. Such values can be used where appropriate with any of the other values, definitions, claims or embodiments defined hereinbefore or hereinafter.

In one embodiment, A is selected from the group consisting of (i), (ii), (iii), and (iv), wherein the nitrogen atom on the left side of each substructure (i), (ii), (iii), or (iv) is attached to the phenyl ring of the indazole in formula (I);

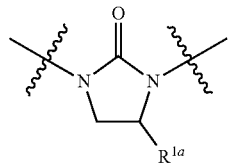

(i)

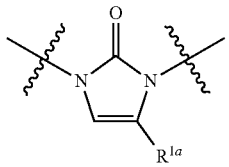

(ii)

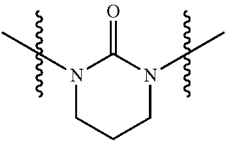

(iii)

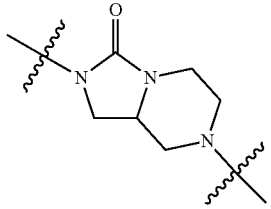

(iv)

In one embodiment, A is (i).

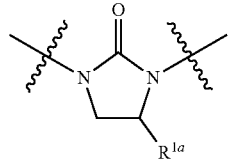

(i)

In one embodiment, A is selected from the group consisting of (i-a), (i-b), (i-c) and (i-d).

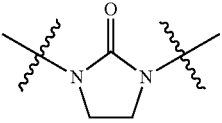

(i-a)

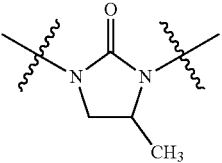

(i-b)

-continued (i-c) 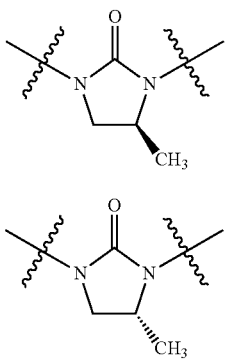

In one embodiment, A is (ii).

(ii) 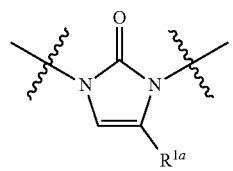

In one embodiment, A is (ii-a) or (ii-b).

(ii-a)
(ii-b) 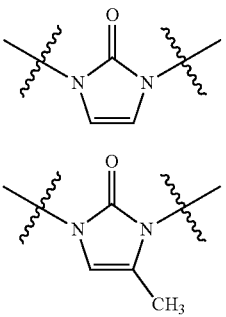

In one embodiment, A is (iii).

(iii) 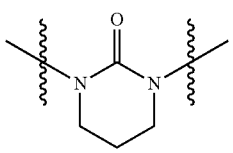

In one embodiment, A is (iv).

(iv) 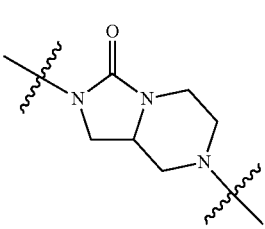

In one embodiment, $R^1$ is selected from the group consisting of $C_1$-$C_8$alkyl, $C_1$-$C_8$haloalkyl, $C_3$-$C_7$cycloalkyl, phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen.

In one embodiment, $R^1$ is selected from the group consisting of $C_1$-$C_8$alkyl, $C_1$-$C_8$haloalkyl and $C_3$-$C_7$cycloalkyl.

In one embodiment, $R^1$ is selected from the group consisting of $C_1$-$C_8$alkyl and $C_3$-$C_7$cycloalkyl.

In one embodiment, $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen.

In one embodiment, $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkyl, $C_1$-$C_4$haloalkoxy, $C_1$-$C_4$haloalkyl, and halogen.

In one embodiment, $R^1$ is phenyl, wherein the phenyl is optionally substituted with 1, 2, 3, or 4 substituents selected from the group consisting of $C_1$-$C_4$alkyl, $C_1$-$C_4$haloalkoxy, $C_1$-$C_4$haloalkyl, and halogen.

In one embodiment, $R^1$ is monocyclic heteroaryl, wherein the monocyclic heteroaryl is optionally substituted with 1, 2, 3, or 4 substituents selected from the group consisting of $C_1$-$C_4$alkyl, $C_1$-$C_4$haloalkoxy, $C_1$-$C_4$haloalkyl, and halogen.

In one embodiment, $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$SO_2NR^{2d}R^{2e}$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OR^{2d})(R^{2d})$—$R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)R^{2c}$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2R^{2c}$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}R^{2e}$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, —$CR^{2a}$=$CHR^{2a}$—$CO_2R^{2c}$, —$CR^{2a}$=$CHR^{2a}$—$C(O)G^1$, and —$CR^{2a}$=$CHR^{2a}$—$C(O)G^3$.

In one embodiment, $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$ and —CR$^{2a}$=CHR$^{2a}$—CO$_2$R$^{2c}$.

In one embodiment, R$^2$ is selected from the group consisting of hydrogen, C$_1$-C$_6$alkoxyC$_1$-C$_6$alkyl, C$_1$-C$_8$alkyl, —C(O)(CR$^{2a}$R$^{2b}$)$_m$—OR$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$ and —CR$^{2a}$=CHR$^{2a}$—CO$_2$R$^{2c}$.

In one embodiment, R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)G$^1$ and —CR$^{2a}$=CHR$^{2a}$—C(O)G$^3$.

In one embodiment, R$^2$ is selected from the group consisting of -G$^1$, -G$^3$, -G$^4$, —CO$_2$G$^1$, —C(O)G$^1$, —C(OH)(R$^{2d}$)—C(O)G$^1$, —SO$_2$G$^1$, —SO$_2$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$C(O)—(CR$^{2a}$R$^{2b}$)$_n$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^3$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)NH—(CR$^{2a}$R$^{2f}$)—C(O)NHR$^{2d}$ and —CR$^{2a}$=CHR$^{2a}$—C(O)G$^3$.

In one embodiment, R$^{2a}$ and R$^{2b}$, at each occurrence, are each independently selected from the group consisting of hydrogen, fluorine, C$_1$-C$_4$alkyl, and haloC$_1$-C$_4$alkyl.

In one embodiment, R$^{2a}$ and R$^{2b}$, at each occurrence, are each independently selected from the group consisting of hydrogen and C$_1$-C$_4$alkyl.

In one embodiment, R$^{2a}$ and R$^{2b}$, at each occurrence, are each hydrogen.

In one embodiment, R$^{2c}$ is selected from the group consisting of C$_2$-C$_8$alkenyl, C$_1$-C$_8$alkyl and haloC$_1$-C$_8$alkyl.

In one embodiment, R$^{2c}$ is C$_1$-C$_8$alkyl.

In one embodiment, R$^{2d}$, at each occurrence, is selected from the group consisting of hydrogen, C$_1$-C$_6$alkyl and haloC$_1$-C$_6$alkyl.

In one embodiment, R$^{2d}$, at each occurrence, is selected from the group consisting of hydrogen and C$_1$-C$_6$alkyl.

In one embodiment, R$^{2d}$, at each occurrence, is hydrogen.

In one embodiment, R$^{2d}$, at each occurrence, is C$_1$-C$_6$alkyl.

In one embodiment, R$^{2e}$ is selected from the group consisting of hydrogen, C$_2$-C$_8$alkenyl, C$_1$-C$_6$alkoxy, C$_1$-C$_4$alkoxyC$_1$-C$_4$alkyl, C$_1$-C$_6$alkyl, and haloC$_1$-C$_6$alkyl.

In one embodiment, R$^{2e}$ is selected from the group consisting of hydrogen, C$_2$-C$_8$alkenyl, C$_1$-C$_4$alkoxyC$_1$-C$_4$alkyl, C$_1$-C$_6$alkyl, and haloC$_1$-C$_6$alkyl.

In one embodiment, R$^{2e}$ is selected from the group consisting of hydrogen, C$_1$-C$_6$alkyl, and haloC$_1$-C$_6$alkyl.

In one embodiment, R$^{2f}$ is selected from the group consisting of C$_1$-C$_4$alkyl, haloC$_1$-C$_4$alkyl and —(CR$^{2a}$R$^{2b}$)$_m$-G$^{2a}$.

In one embodiment, R$^{2f}$ is C$_1$-C$_4$alkyl.

In one embodiment, G$^1$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo.

In one embodiment, G$^1$ is C$_3$-C$_7$cycloalkyl, wherein the C$_3$-C$_7$cycloalkyl is optionally substituted with 1 or 2 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo.

In one embodiment, G$^{1a}$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo.

In one embodiment, G$^{1a}$ is C$_3$-C$_7$cycloalkyl, wherein the C$_3$-C$_7$cycloalkyl is optionally substituted with 1 or 2, 3 substituents selected from the group consisting of halogen and hydroxy.

In one embodiment, G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen.

In one embodiment, G$^2$ is aryl, wherein the aryl is optionally substituted with 1 or 2 substituents selected from the group consisting of C$_1$-C$_4$alkoxy, C$_1$-C$_4$alkyl, 1,3-dioxole, haloC$_1$-C$_4$alkyl, and halogen.

In one embodiment, G$^2$ is phenyl, wherein the phenyl is optionally substituted with 1 or 2 substituents selected from the group consisting of C$_1$-C$_4$alkoxy, C$_1$-C$_4$alkyl, 1,3-dioxole, haloC$_1$-C$_4$alkyl, and halogen.

In one embodiment, G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen.

In one embodiment, G$^{2a}$ is aryl, wherein the aryl is optionally substituted with 1, 2 or 3 halogen.

In one embodiment, G$^{2a}$ is phenyl, wherein the phenyl is optionally substituted with 1, 2 or 3 halogen.

In one embodiment, G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$.

In one embodiment, G$^3$ is 4-8-membered-heterocycle, wherein the 4-8-membered-heterocycle is optionally substituted with 1, 2, 3 or 4 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, —SO$_2$ (CR$^{2a}$R$^{2b}$)$_m$G$^{1a}$, and —(CR$^{2a}$R$^{2b}$)$_p$G$^{3a}$.

In one embodiment, G$^{3a}$ is 4-8-membered-heterocycle, wherein the 4-8-membered-heterocycle is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$.

In one embodiment, G$^{3a}$ is 4-8-membered-heterocycle, wherein the 4-8-membered-heterocycle is optionally substituted with one G$^{2a}$.

In one embodiment, G$^{3a}$ is 4-8-membered-heterocycle, wherein the 4-8-membered-heterocycle is optionally substituted with one optionally substituted phenyl.

In one embodiment, G$^4$ is 5-10-membered heteroaryl, wherein the 5-10-membered heteroaryl is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkyl, halogen, haloC$_1$-C$_4$alkyl, G$^{1a}$, and G$^{3a}$.

In one embodiment, G$^4$ is 5-10-membered heteroaryl, wherein the 5-10-membered heteroaryl is optionally substituted with 1 or 2 substituents selected from the group consisting of C$_1$-C$_4$alkoxy, C$_1$-C$_4$alkoxyC$_1$-C$_4$alkyl, C$_1$-C$_4$alkyl, halogen, haloC$_1$-C$_4$alkyl, G$^{1a}$, and G$^{3a}$.

In one embodiment, m is 1, 2 or 3.
In one embodiment, m is 1 or 2.
In one embodiment, m is 1.
In one embodiment, m is 2.
In one embodiment, n is 1, 2 or 3.
In one embodiment, n is 1 or 2.
In one embodiment, n is 1.
In one embodiment, n is 2.
In one embodiment, p is 1 or 2.
In one embodiment, p is 1.
In one embodiment, p is 2.
In one embodiment, A is (i), wherein the nitrogen atom on the left side of (i) is attached to the phenyl ring of the indazole in formula (I);

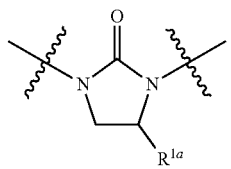

(i)

R$^{1a}$ is hydrogen or C$_1$-C$_4$alkyl; R$^1$ is selected from the group consisting of C$_1$-C$_8$alkyl, C$_1$-C$_8$haloalkyl, C$_3$-C$_7$cycloalkyl, phenyl, or monocyclic heteroaryl, wherein the phenyl and monocyclic heteroaryl are optionally substituted with 1, 2, 3, or 4 substituents selected from the group consisting of C$_1$-C$_4$alkoxy, C$_1$-C$_4$alkyl, C$_1$-C$_4$haloalkoxy, C$_1$-C$_4$haloalkyl, and halogen; R$^2$ is selected from the group consisting of hydrogen, C$_1$-C$_8$alkenyl, C$_1$-C$_6$alkoxyC$_1$-C$_6$alkyl, C$_1$-C$_8$alkyl, C$_1$-C$_8$haloalkyl, -G$^1$, -G$^2$, -G$^3$, -G$^4$, —CO$_2$R$^{2c}$, —CO$_2$G$^1$, —C(O)R$^{2c}$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(O)(CR$^{2a}$R$^{2b}$)$_m$—OR$^{2c}$, —C(OH)(R$^{2d}$)—R$^{2c}$, —C(OH)(R$^{2d}$)-G$^1$, —C(OH)(R$^{2d}$)—C(O)R$^{2c}$, —C(OH)(R$^{2d}$)—C(O)G$^1$, —C(OH)(R$^{2d}$)—(CR$^{2a}$R$^{2b}$)$_m$G$^1$, —SO$_2$R$^{2c}$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —SO$_2$NR$^{2d}$R$^{2e}$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OR$^{2d}$)(R$^{2d}$)—R$^{2e}$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)R$^{2c}$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$R$^{2c}$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$R$^{2e}$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, —CR$^{2a}$=CHR$^{2a}$—CO$_2$R$^{2c}$, —CR$^{2a}$=CHR$^{2a}$—C(O)G$^1$, and —CR$^{2a}$=CHR$^{2a}$—C(O)G$^3$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2c}$ is selected from the group consisting of C$_2$-C$_8$alkenyl, C$_1$-C$_8$alkyl and haloC$_1$-C$_8$alkyl; R$^{2d}$, at each occurrence, is selected from the group consisting of hydrogen, C$_1$-C$_6$alkyl and haloC$_1$-C$_6$alkyl; R$^{2e}$ is selected from the group consisting of hydrogen, C$_2$-C$_8$alkenyl, C$_1$-C$_6$alkoxy, C$_1$-C$_4$alkoxyC$_1$-C$_4$alkyl, C$_1$-C$_6$alkyl, and haloC$_1$-C$_6$alkyl; R$^{2f}$ is selected from the group consisting of C$_1$-C$_4$alkyl, haloC$_1$-C$_4$alkyl and —(CR$^{2a}$R$^{2b}$)$_m$-G$^{2a}$; G$^1$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^{1a}$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkyl, halogen, haloC$_1$-C$_4$alkyl, G$^{1a}$, and G$^{3a}$; m is 1, 2 or 3; n is 1, 2 or 3; and p is 1 or 2.

In one embodiment, A is (i), wherein the nitrogen atom on the left side of (i) is attached to the phenyl ring of the indazole in formula (I);

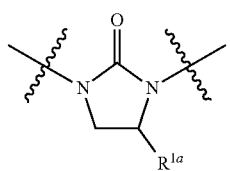

(i)

R$^{1a}$ is hydrogen or C$_1$-C$_4$alkyl; R$^1$ is selected from the group consisting of C$_1$-C$_8$alkyl and C$_3$-C$_7$cycloalkyl; R$^2$ is selected from the group consisting of hydrogen, C$_1$-C$_8$alkenyl, C$_1$-C$_6$alkoxyC$_1$-C$_6$alkyl, C$_1$-C$_8$alkyl, C$_1$-C$_8$haloalkyl, -G$^1$, -G$^2$, -G$^3$, -G$^4$, —CO$_2$R$^{2c}$, —CO$_2$G$^1$, —C(O)R$^{2c}$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(O)(CR$^{2a}$R$^{2b}$)$_m$—OR$^{2c}$, —C(OH)(R$^{2d}$)—R$^{2c}$, —C(OH)(R$^{2d}$)-G$^1$, —C(OH)(R$^{2d}$)—C(O)R$^{2c}$, —C(OH)(R$^{2d}$)—C(O)G$^1$, —C(OH)(R$^{2d}$)—(CR$^{2a}$R$^{2b}$)$_m$G$^1$, —SO$_2$R$^{2c}$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —SO$_2$NR$^{2d}$R$^{2e}$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OR$^{2d}$)(R$^{2d}$)—R$^{2e}$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)R$^{2c}$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$R$^{2c}$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$R$^{2e}$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, —CR$^{2a}$=CHR$^{2a}$—CO$_2$R$^{2c}$, —CR$^{2a}$=CHR$^{2a}$—C(O)G$^1$, and —CR$^{2a}$=CHR$^{2a}$—C(O)G$^3$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2c}$ is selected from the group consisting of C$_2$-C$_8$alkenyl, C$_1$-C$_8$alkyl and haloC$_1$-C$_8$alkyl; R$^{2d}$, at each occurrence, is selected from the group consisting of hydrogen, C$_1$-C$_6$alkyl and haloC$_1$-C$_6$alkyl; R$^{2e}$ is selected from the group consisting of hydrogen, C$_2$-C$_8$alkenyl, C$_1$-C$_6$alkoxy, C$_1$-C$_4$alkoxyC$_1$-C$_4$alkyl, C$_1$-C$_6$alkyl, and haloC$_1$-C$_6$alkyl; R$^{2f}$ is selected from the group consisting of C$_1$-C$_4$alkyl, haloC$_1$-C$_4$alkyl and —(CR$^{2a}$R$^{2b}$)$_m$-G$^{2a}$; G$^1$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^{1a}$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkyl, halogen, haloC$_1$-C$_4$alkyl, G$^{1a}$, and G$^{3a}$; m is 1, 2 or 3; n is 1, 2 or 3; and p is 1 or 2.

In one embodiment, A is (i), wherein the nitrogen atom on the left side of (i) is attached to the phenyl ring of the indazole in formula (I);

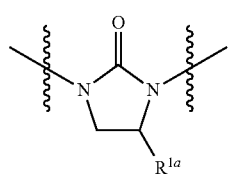

(i)

$R^{1a}$ is hydrogen or $C_1$-$C_4$alkyl; $R^1$ is selected from the group consisting of $C_1$-$C_8$alkyl and $C_3$-$C_7$cycloalkyl; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —$CO_2R^{2c}$, —$C(O)R^{2c}$, —$C(O)(CR^{2a}R^{2b})_m$—$OR^{2c}$, —$C(OH)(R^{2d})$—$R^{2c}$, —$C(OH)(R^{2d})$—$C(O)R^{2c}$, —$SO_2R^{2c}$, —$SO_2NR^{2d}R^{2e}$, —$(CR^{2a}R^{2b})_m$—$C(OR^{2d})(R^{2d})$—$R^{2e}$, —$(CR^{2a}R^{2b})_mC(O)R^{2c}$, —$(CR^{2a}R^{2b})_mCO_2R^{2c}$, —$(CR^{2a}R^{2b})_mC(O)NR^{2d}R^{2e}$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, and —$CR^{2a}$=$CHR^{2a}$—$CO_2R^{2c}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl and halo$C_1$-$C_4$alkyl; and m is 1, 2 or 3.

In one embodiment, A is (i), wherein the nitrogen atom on the left side of (i) is attached to the phenyl ring of the indazole in formula (I);

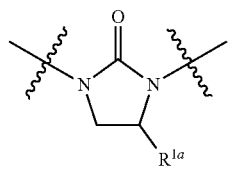

(i)

$R^{1a}$ is hydrogen or $C_1$-$C_4$alkyl; $R^1$ is selected from the group consisting of $C_1$-$C_8$alkyl and $C_3$-$C_7$cycloalkyl; $R^2$ is selected from the group consisting of -$G^1$, -$G^2$, -$G^3$, -$G^4$, —$CO_2G^1$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(OH)(R^{2d})$-$G^1$, —$C(OH)(R^{2d})$—$C(O)G^1$, —$C(OH)(R^{2d})$—$(CR^{2a}R^{2b})_mG^1$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$CR^{2a}$=$CHR^{2a}$—$C(O)G^1$, —$CR^{2a}$=$CHR^{2a}$—$C(O)G^3$ and —$(CR^{2a}R^{2b})_mC(O)NH$—$(CR^{2a}R^{2f})$—$C(O)NHR^{2d}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2d}$, at each occurrence, is selected from the group consisting of hydrogen, $C_1$-$C_6$alkyl and halo$C_1$-$C_6$alkyl; $R^{2f}$ is —$(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, —$SO_2(CR^{2a}R^{2b})_mG^{1a}$, and —$(CR^{2a}R^{2b})_pG^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, and —$SO_2(CR^{2a}R^{2b})_mG^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (i), wherein the nitrogen atom on the left side of (i) is attached to the phenyl ring of the indazole in formula (I);

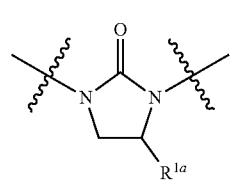

(i)

$R^{1a}$ is hydrogen or $C_1$-$C_4$alkyl; $R^1$ is selected from the group consisting of $C_1$-$C_8$alkyl and $C_3$-$C_7$cycloalkyl; $R^2$ is —$(CR^{2a}R^{2b})_mC(O)G^3$, wherein, $G^3$ is optionally substituted with 1 or 2 halogen; $R^{2a}$ and $R^{2b}$, at each occurrence, are each independently selected from the group consisting of hydrogen, fluorine, $C_1$-$C_4$alkyl, and halo$C_1$-$C_4$alkyl; $G^3$ is 4-8-membered-heterocycle, wherein the 4-8-membered-heterocycle is optionally substituted with 1 or 2 halogen; and m is 1, 2 or 3.

In one embodiment, A is (i), wherein the nitrogen atom on the left side of (i) is attached to the phenyl ring of the indazole in formula (I);

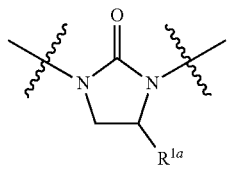

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$SO_2NR^{2d}R^{2e}$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OR^{2d})(R^{2d})$—$R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)R^{2c}$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2R^{2c}$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}R^{2e}$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, —$CR^{2a}$=$CHR^{2a}$—$CO_2R^{2c}$, —$CR^{2a}$=$CHR^{2a}$—$C(O)G^1$, and —$CR^{2a}$=$CHR^{2a}$—$C(O)G^3$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl, halo$C_1$-$C_4$alkyl and —$(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, —$SO_2(CR^{2a}R^{2b})_mG^{1a}$, and —$(CR^{2a}R^{2b})_pG^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, and —$SO_2(CR^{2a}R^{2b})_mG^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (i), wherein the nitrogen atom on the left side of (i) is attached to the phenyl ring of the indazole in formula (I);

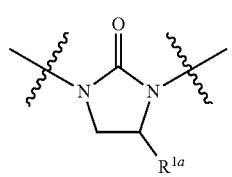

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —$CO_2R^{2c}$, —$C(O)R^{2c}$, —$C(O)(CR^{2a}R^{2b})_m$—$OR^{2c}$, —$C(OH)(R^{2d})$—$R^{2c}$, —$C(OH)(R^{2d})$—$C(O)R^{2c}$, —$SO_2R^{2c}$, —$SO_2NR^{2d}R^{2e}$, —$(CR^{2a}R^{2b})_m$—$C(OR^{2d})(R^{2d})$—$R^{2e}$, —$(CR^{2a}R^{2b})_mC(O)R^{2c}$, —$(CR^{2a}R^{2b})_mCO_2R^{2c}$, —$(CR^{2a}R^{2b})_mC(O)NR^{2d}R^{2e}$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, and —$CR^{2a}$=$CHR^{2a}$—$CO_2R^{2c}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, C₂-C₈alkenyl, C₁-C₆alkoxy, C₁-C₄alkoxyC₁-C₄alkyl, C₁-C₆alkyl, and haloC₁-C₆alkyl; R$^{2f}$ is selected from the group consisting of C₁-C₄alkyl and haloC₁-C₄alkyl; and m is 1, 2 or 3.

In one embodiment, A is (i), wherein the nitrogen atom on the left side of (i) is attached to the phenyl ring of the indazole in formula (I);

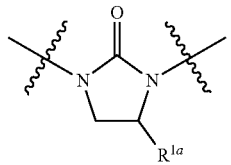

(i)

R$^{1a}$ is hydrogen or C₁-C₄alkyl; R¹ is selected from the group consisting of phenyl and monocyclic heteroaryl, wherein the phenyl and monocyclic heteroaryl are optionally substituted with 1, 2, 3, or 4 substituents selected from the group consisting of C₁-C₄alkoxy, C₁-C₄alkyl, C₁-C₄haloalkoxy, C₁-C₄haloalkyl, and halogen; R² is selected from the group consisting of hydrogen, C₁-C₆alkoxyC₁-C₆alkyl, C₁-C₈alkyl, C₁-C₈haloalkyl, and —(CR$^{2a}$R$^{2b}$)$_m$—C(OR$^{2d}$)(R$^{2d}$)—R$^{2e}$; R$^{2a}$ and R$^{2b}$, at each occurrence, are each independently selected from the group consisting of hydrogen and C₁-C₄alkyl; R$^{2d}$, at each occurrence, is selected from the group consisting of hydrogen and C₁-C₆alkyl; R$^{2e}$ is selected from the group consisting of C₂-C₈alkenyl and C₁-C₆alkyl; and m is 1.

In one embodiment, A is (i), wherein the nitrogen atom on the left side of (i) is attached to the phenyl ring of the indazole in formula (I);

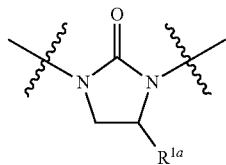

(i)

R$^{1a}$ is hydrogen or C₁-C₄alkyl; R¹ is selected from the group consisting of phenyl and monocyclic heteroaryl, wherein the phenyl and monocyclic heteroaryl are optionally substituted with 1, 2, 3, or 4 substituents selected from the group consisting of C₁-C₄alkoxy, C₁-C₄alkyl, C₁-C₄haloalkoxy, C₁-C₄haloalkyl, and halogen; R² is selected from the group consisting of —CO₂R$^{2c}$, —C(O)R$^{2c}$, —C(O)(CR$^{2a}$R$^{2b}$)$_m$—OR$^{2c}$, —SO₂R$^{2c}$, —SO₂NR$^{2d}$R$^{2e}$, —(CR$^{2a}$R$^{2b}$)$_m$C(O)R$^{2c}$, —(CR$^{2a}$R$^{2b}$)$_m$CO₂R$^{2c}$, —(CR$^{2a}$R$^{2b}$)$_m$C(O)NR$^{2d}$R$^{2e}$, —(CR$^{2a}$R$^{2b}$)$_m$SO₂NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$═CHR$^{2a}$—CO₂R$^{2c}$; R$^{2a}$ and R$^{2b}$, at each occurrence, are each independently selected from the group consisting of hydrogen and C₁-C₄alkyl; R$^{2c}$ is selected from the group consisting of C₁-C₈alkyl and haloC₁-C₈alkyl; R$^{2d}$, at each occurrence, is selected from the group consisting of hydrogen, C₁-C₆alkyl and haloC₁-C₆alkyl; R$^{2e}$ is selected from the group consisting of hydrogen, C₁-C₄alkoxyC₁-C₄alkyl, C₁-C₆alkyl, and haloC₁-C₆alkyl; R$^{2f}$ is selected from the group consisting of C₁-C₄alkyl and haloC₁-C₄alkyl; and m is 1 or 2.

In one embodiment, A is (i), wherein the nitrogen atom on the left side of (i) is attached to the phenyl ring of the indazole in formula (I);

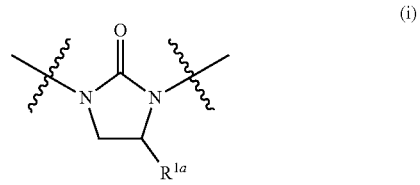

(i)

R$^{1a}$ is hydrogen or C₁-C₄alkyl; R¹ is selected from the group consisting of phenyl and monocyclic heteroaryl, wherein the phenyl and monocyclic heteroaryl are optionally substituted with 1, 2, 3, or 4 substituents selected from the group consisting of C₁-C₄alkoxy, C₁-C₄alkyl, C₁-C₄haloalkoxy, C₁-C₄haloalkyl, and halogen; R² is selected from the group consisting of -G¹, -G², -G³, -G⁴, —CO₂G¹, —C(O)G¹, —C(O)G², —C(O)G³, —C(O)G⁴, —C(O)(CR$^{2a}$R$^{2b}$)$_m$G¹, —C(O)(CR$^{2a}$R$^{2b}$)$_m$G², —C(OH)(R$^{2d}$)-G¹, —C(OH)(R$^{2d}$)—C(O)G¹, —C(OH)(R$^{2d}$)—(CR$^{2a}$R$^{2b}$)$_m$G¹, —SO₂G¹, —SO₂G², —SO₂G³, —SO₂G⁴, —SO₂—(CR$^{2a}$R$^{2b}$)$_m$G¹, —SO₂—(CR$^{2a}$R$^{2b}$)$_m$G², —SO₂—(CR$^{2a}$R$^{2b}$)$_m$G³, —SO₂—(CR$^{2a}$R$^{2b}$)$_m$G⁴, —(CR$^{2a}$R$^{2b}$)$_m$G¹, —(CR$^{2a}$R$^{2b}$)$_m$G², —(CR$^{2a}$R$^{2b}$)$_m$G³, —(CR$^{2a}$R$^{2b}$)$_m$G⁴, —(CR$^{2a}$R$^{2b}$)$_m$—C(OH)(R$^{2d}$)-G¹, —(CR$^{2a}$R$^{2b}$)$_m$—C(OH)(R$^{2d}$)-G², —(CR$^{2a}$R$^{2b}$)$_m$—C(OH)(R$^{2d}$)-G³, —(CR$^{2a}$R$^{2b}$)$_m$—C(OH)(R$^{2d}$)-G⁴, —(CR$^{2a}$R$^{2b}$)$_m$—C(OH)(R$^{2d}$)—(CR$^{2a}$R$^{2b}$)$_n$-G¹, —(CR$^{2a}$R$^{2b}$)$_m$—C(OH)(R$^{2d}$)—(CR$^{2a}$R$^{2b}$)$_n$-G², —(CR$^{2a}$R$^{2b}$)$_m$—C(OH)(R$^{2d}$)—(CR$^{2a}$R$^{2b}$)$_n$-G³, —(CR$^{2a}$R$^{2b}$)$_m$—C(OH)(R$^{2d}$)—(CR$^{2a}$R$^{2b}$)$_n$-G⁴, —(CR$^{2a}$R$^{2b}$)$_m$C(O)—(CR$^{2a}$R$^{2b}$)$_n$G¹, —(CR$^{2a}$R$^{2b}$)$_m$C(O)(CR$^{2a}$R$^{2b}$)$_n$G², —(CR$^{2a}$R$^{2b}$)$_m$C(O)(CR$^{2a}$R$^{2b}$)$_n$G³, —(CR$^{2a}$R$^{2b}$)$_m$C(O)(CR$^{2a}$R$^{2b}$)$_n$G⁴, —(CR$^{2a}$R$^{2b}$)$_m$CO₂G¹, —(CR$^{2a}$R$^{2b}$)$_m$C(O)G¹, —(CR$^{2a}$R$^{2b}$)$_m$C(O)G², —(CR$^{2a}$R$^{2b}$)$_m$C(O)G³, —(CR$^{2a}$R$^{2b}$)$_m$C(O)G⁴, —(CR$^{2a}$R$^{2b}$)$_m$C(O)NR$^{2d}$G¹, —(CR$^{2a}$R$^{2b}$)$_m$C(O)NR$^{2d}$G², —(CR$^{2a}$R$^{2b}$)$_m$C(O)NR$^{2d}$G³, —(CR$^{2a}$R$^{2b}$)$_m$C(O)NR$^{2d}$G⁴, —(CR$^{2a}$R$^{2b}$)$_m$C(O)N(R$^{2d}$)((CR$^{2a}$R$^{2b}$)$_n$G¹), —(CR$^{2a}$R$^{2b}$)$_m$C(O)N(R$^{2d}$)((CR$^{2a}$R$^{2b}$)$_n$G²), —(CR$^{2a}$R$^{2b}$)$_m$C(O)N(R$^{2d}$)((CR$^{2a}$R$^{2b}$)$_n$G³), —(CR$^{2a}$R$^{2b}$)$_m$C(O)N(R$^{2d}$)((CR$^{2a}$R$^{2b}$)$_n$G⁴), —(CR$^{2a}$R$^{2b}$)$_m$C(O)NH—(CR$^{2a}$R$^{2f}$)—C(O)NHR$^{2d}$, —CR$^{2a}$═CHR$^{2a}$—C(O)G¹, and —CR$^{2a}$═CHR$^{2a}$—C(O)G³; R$^{2a}$ and R$^{2b}$, at each occurrence, are each independently selected from the group consisting of hydrogen, fluorine, C₁-C₄alkyl, and haloC₁-C₄alkyl; R$^{2d}$, at each occurrence, is selected from the group consisting of hydrogen, C₁-C₆alkyl and haloC₁-C₆alkyl; R$^{2f}$ is —(CR$^{2a}$R$^{2b}$)$_m$-G$^{2a}$; G¹ is C₃-C₇cycloalkyl, wherein the C₃-C₇cycloalkyl is optionally substituted with 1, 2, 3 or 4 substituents selected from the group consisting of C₁-C₆alkoxy, C₁-C₄alkyl, benzyloxy, haloC₁-C₄alkyl, halogen, hydroxy, hydroxyC₁-C₄alkyl, oxime, C₁-C₆alkyloxime, and oxo; G$^{1a}$ is C₃-C₇cycloalkyl, wherein the C₃-C₇cycloalkyl is optionally substituted with 1, 2, 3 or 4 substituents selected from the group consisting of C₁-C₆alkoxy, C₁-C₄alkyl, benzyloxy, haloC₁-C₄alkyl, halogen, hydroxy, hydroxyC₁-C₄alkyl, oxime, C₁-C₆alkyloxime, and oxo; G² is aryl, wherein the aryl is optionally substituted with 1, 2, 3 or 4 substituents selected from the group consisting of C₁-C₄alkoxy, C₁-C₄alkyl, 1,3-dioxole, haloC₁-C₄alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, —SO$_2$(CR$^{2a}$R$^{2b}$)$_m$$G^{1a}$, and —(CR$^{2a}$R$^{2b}$)$_p$$G^{3a}$; $G^{3a}$ 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, and —SO$_2$(CR$^{2a}$R$^{2b}$)$_m$$G^{1a}$; m is 1, 2 or 3; n is 1, 2 or 3; and p is 1 or 2.

In one embodiment, A is (i), wherein the nitrogen atom on the left side of (i) is attached to the phenyl ring of the indazole in formula (I);

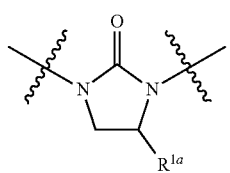

(i)

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of -$G^1$, -$G^2$, -$G^3$, -$G^4$, —(CR$^{2a}$R$^{2b}$)$_m$$G^1$, —(CR$^{2a}$R$^{2b}$)$_m$$G^2$, —(CR$^{2a}$R$^{2b}$)$_m$$G^3$, —(CR$^{2a}$R$^{2b}$)$_m$$G^4$, —(CR$^{2a}$R$^{2b}$)$_m$—C(OH)(R$^{2d}$)-$G^1$, —(CR$^{2a}$R$^{2b}$)$_m$—C(OH)(R$^{2d}$)—(CR$^{2a}$R$^{2b}$)$_n$-$G^1$, —(CR$^{2a}$R$^{2b}$)$_m$—C(OH)(R$^{2d}$)—(CR$^{2a}$R$^{2b}$)$_n$-$G^2$, —(CR$^{2a}$R$^{2b}$)$_m$—C(OH)(R$^{2d}$)—(CR$^{2a}$R$^{2b}$)$_n$-$G^3$, and —(CR$^{2a}$R$^{2b}$)$_m$—C(OH)(R$^{2d}$)—(CR$^{2a}$R$^{2b}$)$_n$-$G^4$; $R^{2a}$ and $R^{2b}$, at each occurrence, are each independently selected from the group consisting of hydrogen, $C_1$-$C_4$alkyl, and halo$C_1$-$C_4$alkyl; $R^{2d}$, at each occurrence, is selected from the group consisting of hydrogen and $C_1$-$C_6$alkyl; $R^{2f}$ is —(CR$^{2a}$R$^{2b}$)$_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, halo$C_1$-$C_4$alkyl, halogen, hydroxy, hydroxy$C_1$-$C_4$alkyl, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, —SO$_2$(CR$^{2a}$R$^{2b}$)$_m$$G^{1a}$, and —(CR$^{2a}$R$^{2b}$)$_p$$G^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, halogen, halo$C_1$-$C_4$alkyl, hydroxy, hydroxy$C_1$-$C_4$alkyl, and oxo; $G^4$ is 5-10-membered heteroaryl, wherein the 5-10-membered-heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1 or 2; n is 1; and p is 1 or 2.

In one embodiment, A is (i), wherein the nitrogen atom on the left side of (i) is attached to the phenyl ring of the indazole in formula (I);

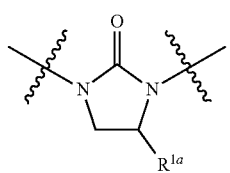

(i)

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of —CO$_2$$G^1$, —C(O)$G^1$, —C(O)$G^2$, —C(O)$G^3$, —C(O)$G^4$, —C(OH)(R$^{2d}$)—C(O)$G^1$, —SO$_2$$G^1$, —SO$_2$$G^2$, —SO$_2$$G^3$, —SO$_2$$G^4$, —(CR$^{2a}$R$^{2b}$)$_m$C(O)—(CR$^{2a}$R$^{2b}$)$_n$$G^1$, —(CR$^{2a}$R$^{2b}$)$_m$C(O)(CR$^{2a}$R$^{2b}$)$_n$$G^2$, —(CR$^{2a}$R$^{2b}$)$_m$C(O)(CR$^{2a}$R$^{2b}$)$_n$$G^3$, —(CR$^{2a}$R$^{2b}$)$_m$C(O)(CR$^{2a}$R$^{2b}$)$_n$$G^4$, —(CR$^{2a}$R$^{2b}$)$_m$C(O)$G^1$, —(CR$^{2a}$R$^{2b}$)$_m$C(O)$G^2$, —(CR$^{2a}$R$^{2b}$)$_m$C(O)$G^3$, —(CR$^{2a}$R$^{2b}$)$_m$C(O)$G^4$, —(CR$^{2a}$R$^{2b}$)$_m$C(O)NR$^{2d}$$G^1$, —(CR$^{2a}$R$^{2b}$)$_m$C(O)NR$^{2d}$$G^2$, —(CR$^{2a}$R$^{2b}$)$_m$C(O)NR$^{2d}$$G^3$, —(CR$^{2a}$R$^{2b}$)$_m$C(O)NR$^{2d}$$G^4$, —(CR$^{2a}$R$^{2b}$)$_m$C(O)N(R$^{2d}$)((CR$^{2a}$R$^{2b}$)$_n$$G^1$), —(CR$^{2a}$R$^{2b}$)$_m$C(O)N(R$^{2d}$)((CR$^{2a}$R$^{2b}$)$_n$$G^2$), —(CR$^{2a}$R$^{2b}$)$_m$C(O)N(R$^{2d}$)((CR$^{2a}$R$^{2b}$)$_n$$G^3$), —(CR$^{2a}$R$^{2b}$)$_m$C(O)N(R$^{2d}$)((CR$^{2a}$R$^{2b}$)$_n$$G^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)$G^1$, and —CR$^{2a}$=CHR$^{2a}$—C(O)$G^3$; $R^{2a}$ and $R^{2b}$, at each occurrence, are each independently selected from the group consisting of hydrogen, $C_1$-$C_4$alkyl, and halo$C_1$-$C_4$alkyl; $R^{2d}$, at each occurrence, is selected from the group consisting of hydrogen, $C_1$-$C_6$alkyl and halo$C_1$-$C_6$alkyl; $R^{2f}$ is —(CR$^{2a}$R$^{2b}$)$_m$-$G^{2a}$; $G^1$ is $C_3$-$C_7$cycloalkyl, wherein the $C_3$-$C_7$cycloalkyl is optionally substituted with 1, 2, or 3 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2 or 3 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2 or 3 substituents selected from the group consisting of $C_1$-$C_4$alkyl, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, cyano, 1,3-dioxolane, halogen, halo$C_1$-$C_4$alkyl, hydroxy, hydroxy$C_1$-$C_4$alkyl, oxo, —C(O)NHG$^{2a}$, $G^{2a}$ and —(CR$^{2a}$R$^{2b}$)$_p$G$^{3a}$; $G^{3a}$ is 4-7-membered-heterocycle, wherein the 4-7-membered-heterocycle is optionally substituted with 1, 2, 3 or 4 substituents selected from the group consisting of $C_1$-$C_6$alkyl, halogen, halo$C_1$-$C_4$alkyl, hydroxy, hydroxy$C_1$-$C_4$alkyl and oxo; $G^4$ is 5-10-membered heteroaryl, wherein the 5-10-membered-heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, and halo$C_1$-$C_4$alkyl; m is 1, 2 or 3; n is 1, 2 or 3; and p is 1.

In one embodiment, A is (ii), wherein the nitrogen atom on the left side of (ii) is attached to the phenyl ring of the indazole in formula (I);

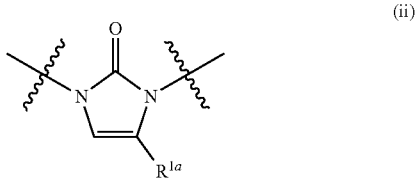

(ii)

$R^{1a}$ is hydrogen or $C_1$-$C_4$alkyl; $R^1$ is selected from the group consisting of $C_1$-$C_8$alkyl, $C_1$-$C_8$haloalkyl, $C_3$-$C_7$cycloalkyl, phenyl, or monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -G$^1$, -G$^2$, -G$^3$, -G$^4$, —CO$_2$R$^{2c}$, —CO$_2$G$^1$, —C(O)R$^{2c}$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(O)(CR$^{2a}$R$^{2b}$)$_m$—OR$^{2c}$, —C(OH)(R$^{2d}$)—R$^{2c}$, —C(OH)(R$^{2d}$)-G$^1$, —C(OH)(R$^{2d}$)—C(O)R$^{2c}$, —C(OH)(R$^{2d}$)—C(O)G$^1$, —C(OH)(R$^{2d}$)—(CR$^{2a}$R$^{2b}$)$_m$G$^1$, —SO$_2$R$^{2c}$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —SO$_2$NR$^{2d}$R$^{2e}$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OR$^{2d}$)(R$^{2d}$)—R$^{2e}$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)R$^{2c}$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$R$^{2c}$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$R$^{2e}$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, —CR$^{2a}$=CHR$^{2a}$—CO$_2$R$^{2c}$, —CR$^{2a}$=CHR$^{2a}$—C(O)G$^1$, and —CR$^{2a}$=CHR$^{2a}$—C(O)G$^3$; R$^{2a}$ and R$^{2b}$, at each occurrence, are each independently selected from the group consisting of hydrogen, fluorine, $C_1$-$C_4$alkyl, and halo$C_1$-$C_4$alkyl; R$^{2c}$ is selected from the group consisting of $C_2$-$C_8$alkenyl, $C_1$-$C_8$alkyl and halo$C_1$-$C_8$alkyl; R$^{2d}$, at each occurrence, is selected from the group consisting of hydrogen, $C_1$-$C_6$alkyl and halo$C_1$-$C_6$alkyl; R$^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; R$^{2f}$ is selected from the group consisting of $C_1$-$C_4$alkyl, halo$C_1$-$C_4$alkyl and —(CR$^{2a}$R$^{2b}$)$_m$-G$^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, G$^{1a}$, and G$^{3a}$; m is 1, 2 or 3; n is 1, 2 or 3; and p is 1 or 2.

In one embodiment, A is (ii), wherein the nitrogen atom on the left side of (ii) is attached to the phenyl ring of the indazole in formula (I);

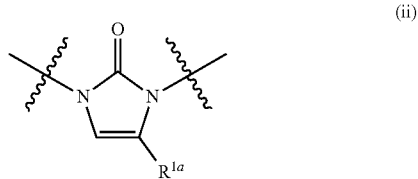

(ii)

$R^{1a}$ is hydrogen or $C_1$-$C_4$alkyl; $R^1$ is selected from the group consisting of $C_1$-$C_8$alkyl and $C_3$-$C_7$cycloalkyl; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$SO_2NR^{2d}R^{2e}$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OR^{2d})(R^{2d})$—$R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)R^{2c}$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2R^{2c}$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}R^{2e}$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, —$CR^{2a}$=$CHR^{2a}$—$CO_2R^{2c}$, —$CR^{2a}$=$CHR^{2a}$—$C(O)G^1$, and —$CR^{2a}$=$CHR^{2a}$—$C(O)G^3$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl, halo$C_1$-$C_4$alkyl and —$(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, —$SO_2(CR^{2a}R^{2b})_mG^{1a}$, and —$(CR^{2a}R^{2b})_pG^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, and —$SO_2(CR^{2a}R^{2b})_mG^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (ii), wherein the nitrogen atom on the left side of (ii) is attached to the phenyl ring of the indazole in formula (I);

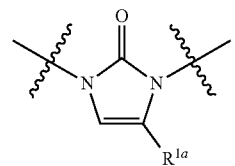

(ii)

$R^{1a}$ is hydrogen or $C_1$-$C_4$alkyl; $R^1$ is selected from the group consisting of $C_1$-$C_8$alkyl and $C_3$-$C_7$cycloalkyl; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —$CO_2R^{2c}$, —$C(O)R^{2c}$, —$C(O)(CR^{2a}R^{2b})_m$—$OR^{2c}$, —$C(OH)(R^{2d})$—$R^{2c}$, —$C(OH)(R^{2d})$—$C(O)R^{2c}$, —$SO_2R^{2c}$, —$SO_2NR^{2d}R^{2e}$, —$(CR^{2a}R^{2b})_m$—$C(OR^{2d})(R^{2d})$—$R^{2e}$, —$(CR^{2a}R^{2b})_mC(O)R^{2c}$, —$(CR^{2a}R^{2b})_mCO_2R^{2c}$, —$(CR^{2a}R^{2b})_mC(O)NR^{2d}R^{2e}$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, and —$CR^{2a}$=$CHR^{2a}$—$CO_2R^{2c}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl and halo$C_1$-$C_4$alkyl; and m is 1, 2 or 3.

In one embodiment, A is (ii), wherein the nitrogen atom on the left side of (ii) is attached to the phenyl ring of the indazole in formula (I);

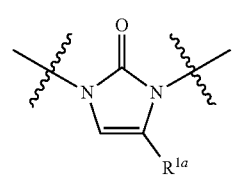

(ii)

$R^{1a}$ is hydrogen or $C_1$-$C_4$alkyl; $R^1$ is selected from the group consisting of $C_1$-$C_8$alkyl and $C_3$-$C_7$cycloalkyl; $R^2$ is selected from the group consisting of -$G^1$, -$G^2$, -$G^3$, -$G^4$, —$CO_2G^1$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(OH)(R^{2d})$-$G^1$, —$C(OH)(R^{2d})$—$C(O)G^1$, —$C(OH)(R^{2d})$—$(CR^{2a}R^{2b})_mG^1$, —$SO_2G^1$, —$SO_2G^2$, —$SO_2G^3$, —$SO_2G^4$, —$SO_2(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$CR^{2a}$=$CHR^{2a}$—$C(O)G^1$, and —$CR^{2a}$=$CHR^{2a}$—$C(O)G^3$ and —$(CR^{2a}R^{2b})_mC(O)NH$—$(CR^{2a}R^{2f})$—$C(O)NHR^{2d}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2d}$, at each occurrence, is selected from the group consisting of hydrogen, $C_1$-$C_6$alkyl and halo$C_1$-$C_6$alkyl; $R^{2f}$ is —$(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, —$SO_2(CR^{2a}R^{2b})_mG^{1a}$, and —$(CR^{2a}R^{2b})_pG^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, and —$SO_2(CR^{2a}R^{2b})_mG^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (ii), wherein the nitrogen atom on the left side of (ii) is attached to the phenyl ring of the indazole in formula (I);

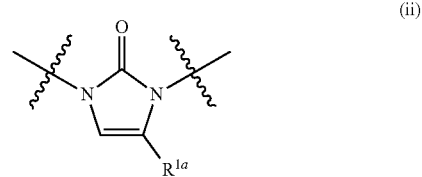

(ii)

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$SO_2NR^{2d}R^{2e}$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OR^{2d})(R^{2d})$—$R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)R^{2c}$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2R^{2c}$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}R^{2e}$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, —$CR^{2a}$=$CHR^{2a}$—$CO_2R^{2c}$, —$CR^{2a}$=$CHR^{2a}$—$C(O)G^1$, and —$CR^{2a}$=$CHR^{2a}$—$C(O)G^3$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl, halo$C_1$-$C_4$alkyl and —$(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, —SO$_2$(CR$^{2a}$R$^{2b}$)$_m$G$^{1a}$; and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, and —SO$_2$(CR$^{2a}$R$^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (ii), wherein the nitrogen atom on the left side of (ii) is attached to the phenyl ring of the indazole in formula (I);

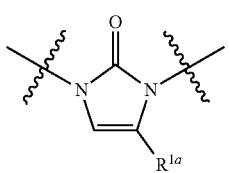

(ii)

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$; R$^{2a}$ and R$^{2b}$, at each occurrence, are each independently selected from the group consisting of hydrogen, fluorine, $C_1$-$C_4$alkyl, and halo$C_1$-$C_4$alkyl; R$^{2c}$ is selected from the group consisting of $C_2$-$C_8$alkenyl, $C_1$-$C_8$alkyl and halo$C_1$-$C_8$alkyl; R$^{2d}$, at each occurrence, is selected from the group consisting of hydrogen, $C_1$-$C_6$alkyl and halo$C_1$-$C_6$alkyl; R$^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; R$^{2f}$ is selected from the group consisting of $C_1$-$C_4$alkyl and halo$C_1$-$C_4$alkyl; and m is 1, 2 or 3.

In one embodiment, A is (ii), wherein the nitrogen atom on the left side of (ii) is attached to the phenyl ring of the indazole in formula (I);

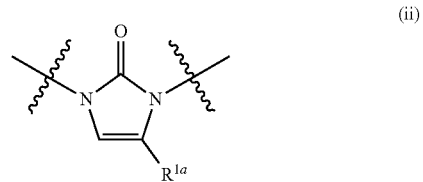

(ii)

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is —(CR$^{2a}$R$^{2b}$)$_m$C(O)NR$^{2d}$R$^{2e}$; R$^{2a}$ and R$^{2b}$, at each occurrence, are each independently selected from the group consisting of hydrogen and $C_1$-$C_4$alkyl; R$^{2d}$ and R$^{2e}$ at each occurrence, is selected from the group consisting of hydrogen and $C_1$-$C_4$alkyl; and m is 1 or 2.

In one embodiment, A is (ii), wherein the nitrogen atom on the left side of (ii) is attached to the phenyl ring of the indazole in formula (I);

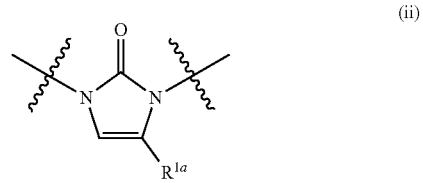

(ii)

$R^{1a}$ is hydrogen or $C_1$-$C_4$alkyl; $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR²ᵃR²ᵇ)ₘG³, —(CR²ᵃR²ᵇ)ₘG⁴, —(CR²ᵃR²ᵇ)ₘ—C(OH)(R²ᵈ)-G¹, —(CR²ᵃR²ᵇ)ₘ—C(OH)(R²ᵈ)-G², —(CR²ᵃR²ᵇ)ₘ—C(OH)(R²ᵈ)-G³, —(CR²ᵃR²ᵇ)ₘ—C(OH)(R²ᵈ)-G⁴, —(CR²ᵃR²ᵇ)ₘ—C(OH)(R²ᵈ)—(CR²ᵃR²ᵇ)ₙ-G¹, —(CR²ᵃR²ᵇ)ₘ—C(OH)(R²ᵈ)—(CR²ᵃR²ᵇ)ₙ-G², —(CR²ᵃR²ᵇ)ₘ—C(OH)(R²ᵈ)—(CR²ᵃR²ᵇ)ₙ-G³, —(CR²ᵃR²ᵇ)ₘ—C(OH)(R²ᵈ)—(CR²ᵃR²ᵇ)ₙ-G⁴, —(CR²ᵃR²ᵇ)ₘC(O)—(CR²ᵃR²ᵇ)ₙG¹, —(CR²ᵃR²ᵇ)ₘC(O)(CR²ᵃR²ᵇ)ₙG², —(CR²ᵃR²ᵇ)ₘC(O)(CR²ᵃR²ᵇ)ₙG³, —(CR²ᵃR²ᵇ)ₘC(O)(CR²ᵃR²ᵇ)ₙG⁴, —(CR²ᵃR²ᵇ)ₘCO₂G¹, —(CR²ᵃR²ᵇ)ₘC(O)G¹, —(CR²ᵃR²ᵇ)ₘC(O)G², —(CR²ᵃR²ᵇ)ₘC(O)G³, —(CR²ᵃR²ᵇ)ₘC(O)G⁴, —(CR²ᵃR²ᵇ)ₘC(O)NR²ᵈG¹, —(CR²ᵃR²ᵇ)ₘC(O)NR²ᵈG², —(CR²ᵃR²ᵇ)ₘC(O)NR²ᵈG³, —(CR²ᵃR²ᵇ)ₘC(O)NR²ᵈG⁴, —(CR²ᵃR²ᵇ)ₘC(O)N(R²ᵈ)((CR²ᵃR²ᵇ)ₙG¹), —(CR²ᵃR²ᵇ)ₘC(O)N(R²ᵈ)((CR²ᵃR²ᵇ)ₙG²), —(CR²ᵃR²ᵇ)ₘC(O)N(R²ᵈ)((CR²ᵃR²ᵇ)ₙG³), —(CR²ᵃR²ᵇ)ₘC(O)N(R²ᵈ)((CR²ᵃR²ᵇ)ₙG⁴), —CR²ᵃ=CHR²ᵃ—C(O)G¹, —CR²ᵃ=CHR²ᵃ—C(O)G³, and —(CR²ᵃR²ᵇ)ₘC(O)NH—(CR²ᵃR²ᶠ)—C(O)NHR²ᵈ; R²ᵃ and R²ᵇ, at each occurrence, are each independently selected from the group consisting of hydrogen, fluorine, $C_1$-$C_4$alkyl, and halo$C_1$-$C_4$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is —(CR²ᵃR²ᵇ)ₘ-G²ᵃ; G¹ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; G² is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; G³ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH₂, $G^{2a}$, —SO₂(CR²ᵃR²ᵇ)ₘ$G^{1a}$, and —(CR²ᵃR²ᵇ)ₚ$G^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH₂, $G^{2a}$, and —SO₂(CR²ᵃR²ᵇ)ₘ$G^{1a}$; G⁴ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (ii), wherein the nitrogen atom on the left side of (ii) is attached to the phenyl ring of the indazole in formula (I);

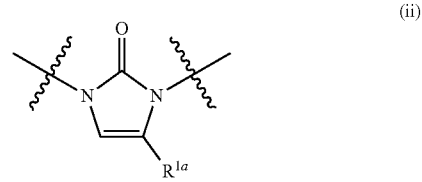

(ii)

$R^{1a}$ is hydrogen or $C_1$-$C_4$alkyl; R¹ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; R² is selected from the group consisting of —(CR²ᵃR²ᵇ)ₘC(O)G³; R²ᵃ and R²ᵇ, at each occurrence, are each independently selected from the group consisting of hydrogen and $C_1$-$C_4$alkyl; G³ is 4-8-membered-heterocycle, wherein the 4-8-membered-heterocycle is optionally substituted with 1 or 2 halogen; and m is 1 or 2.

In one embodiment, A is (iii), wherein the nitrogen atom on the left side of (iii) is attached to the phenyl ring of the indazole in formula (I);

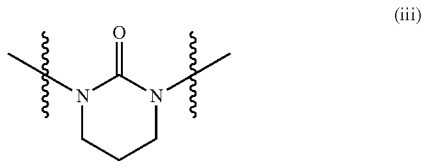 [SMILES: *N1CCCN(*)C1=O]

(iii)

R¹ is selected from the group consisting of $C_1$-$C_8$alkyl, $C_1$-$C_8$haloalkyl, $C_3$-$C_7$cycloalkyl, phenyl, or monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; R² is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -G¹, -G², -G³, -G⁴, —CO₂R²ᶜ, —CO₂G¹, —C(O)R²ᶜ, —C(O)G¹, —C(O)G², —C(O)G³, —C(O)G⁴, —C(O)(CR²ᵃR²ᵇ)ₘG¹, —C(O)(CR²ᵃR²ᵇ)ₘG², —C(O)(CR²ᵃR²ᵇ)ₘ—OR²ᶜ, —C(OH)(R²ᵈ)—R²ᶜ, —C(OH)(R²ᵈ)-G¹, —C(OH)(R²ᵈ)—C(O)R²ᶜ, —C(OH)(R²ᵈ)—C(O)G¹, —C(OH)(R²ᵈ)—(CR²ᵃR²ᵇ)ₘG¹, —SO₂R²ᶜ, —SO₂G¹, —SO₂G², —SO₂G³, —SO₂G⁴, —SO₂—(CR²ᵃR²ᵇ)ₘG¹, —SO₂—(CR²ᵃR²ᵇ)ₘG², —SO₂—(CR²ᵃR²ᵇ)ₘG³, —SO₂—(CR²ᵃR²ᵇ)ₘG⁴, —SO₂NR²ᵈR²ᵉ, —(CR²ᵃR²ᵇ)ₘG¹, —(CR²ᵃR²ᵇ)ₘG², —(CR²ᵃR²ᵇ)ₘG³, —(CR²ᵃR²ᵇ)ₘG⁴, —(CR²ᵃR²ᵇ)ₘ—C(OR²ᵈ)(R²ᵈ)—R²ᵉ, —(CR²ᵃR²ᵇ)ₘ—C(OH)(R²ᵈ)-G¹, —(CR²ᵃR²ᵇ)ₘ—C(OH)(R²ᵈ)-G², —(CR²ᵃR²ᵇ)ₘ—C(OH)(R²ᵈ)-G³, —(CR²ᵃR²ᵇ)ₘ—C(OH)(R²ᵈ)-G⁴, —(CR²ᵃR²ᵇ)ₘ—C(OH)(R²ᵈ)—(CR²ᵃR²ᵇ)ₙ-G¹, —(CR²ᵃR²ᵇ)ₘ—C(OH)(R²ᵈ)—(CR²ᵃR²ᵇ)ₙ-G², —(CR²ᵃR²ᵇ)ₘ—C(OH)(R²ᵈ)—(CR²ᵃR²ᵇ)ₙ-G³, —(CR²ᵃR²ᵇ)ₘ—C(OH)(R²ᵈ)—(CR²ᵃR²ᵇ)ₙ-G⁴, —(CR²ᵃR²ᵇ)ₘC(O)R²ᶜ, —(CR²ᵃR²ᵇ)ₘC(O)—(CR²ᵃ

$R^{2b})_nG^1$, $—(CR^{2a}R^{2b})_mC(O)(CR^{2a}R^{2b})_nG^2$, $—(CR^{2a}R^{2b})_mC(O)(CR^{2a}R^{2b})_nG^3$, $—(CR^{2a}R^{2b})_mC(O)(CR^{2a}R^{2b})_nG^4$, $—(CR^{2a}R^{2b})_mCO_2R^{2c}$, $—(CR^{2a}R^{2b})_mCO_2G^1$, $—(CR^{2a}R^{2b})_mC(O)G^1$, $—(CR^{2a}R^{2b})_mC(O)G^2$, $—(CR^{2a}R^{2b})_mC(O)G^3$, $—(CR^{2a}R^{2b})_mC(O)G^4$, $—(CR^{2a}R^{2b})_mC(O)NR^{2d}R^{2e}$, $—(CR^{2a}R^{2b})_mC(O)NR^{2d}G^1$, $—(CR^{2a}R^{2b})_mC(O)NR^{2d}G^2$, $—(CR^{2a}R^{2b})_mC(O)NR^{2d}G^3$, $—(CR^{2a}R^{2b})_mC(O)NR^{2d}G^4$, $—(CR^{2a}R^{2b})_mC(O)N(R^{2d})((CR^{2a}R^{2b})_nG^1)$, $—(CR^{2a}R^{2b})_mC(O)N(R^{2d})((CR^{2a}R^{2b})_nG^2)$, $—(CR^{2a}R^{2b})_mC(O)N(R^{2d})((CR^{2a}R^{2b})_nG^3)$, $—(CR^{2a}R^{2b})_mC(O)N(R^{2d})((CR^{2a}R^{2b})_nG^4)$, $—(CR^{2a}R^{2b})_mSO_2NR^{2d}R^{2e}$, $—(CR^{2a}R^{2b})_mC(O)NH—(CR^{2a}R^{2f})—C(O)NHR^{2d}$, $—CR^{2a}=CHR^{2a}—CO_2R^{2c}$, $—CR^{2a}=CHR^{2a}—C(O)G^1$, and $—CR^{2a}=CHR^{2a}—C(O)G^3$; $R^{2a}$ and $R^{2b}$, at each occurrence, are each independently selected from the group consisting of hydrogen, fluorine, $C_1$-$C_4$alkyl, and haloC$_1$-C$_4$alkyl; $R^{2c}$ is selected from the group consisting of $C_2$-$C_8$alkenyl, $C_1$-$C_8$alkyl and haloC$_1$-C$_8$alkyl; $R^{2d}$, at each occurrence, is selected from the group consisting of hydrogen, $C_1$-$C_6$alkyl and haloC$_1$-C$_6$alkyl; $R^{2e}$ is selected from the group consisting of hydrogen, $C_2$-$C_8$alkenyl, $C_1$-$C_6$alkoxy, $C_1$-$C_4$alkoxyC$_1$-C$_4$alkyl, $C_1$-$C_6$alkyl, and haloC$_1$-C$_6$alkyl; $R^{2f}$ is selected from the group consisting of $C_1$-$C_4$alkyl, haloC$_1$-C$_4$alkyl and $—(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, haloC$_1$-C$_4$alkyl, halogen, hydroxy, hydroxyC$_1$-C$_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, haloC$_1$-C$_4$alkyl, halogen, hydroxy, hydroxyC$_1$-C$_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, haloC$_1$-C$_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, haloC$_1$-C$_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxyC$_1$-C$_4$alkyl, $C_1$-$C_4$alkoxycarbonyl, $C_1$-$C_6$alkyl, $C_1$-$C_4$alkylcarbonyl, haloC$_1$-C$_4$alkylsulfonyl, $C_1$-$C_4$alkylsulfonyl, benzyl, cyano, 1,3-dioxolane, halogen, haloC$_1$-C$_4$alkyl, hydroxy, hydroxyC$_1$-C$_4$alkyl, oxo, $—C(O)G^{1a}$, $—C(O)NHG^{2a}$, $—C(O)C(O)NH_2$, $G^{2a}$, $—SO_2(CR^{2a}R^{2b})_m$-$G^{1a}$, and $—(CR^{2a}R^{2b})_pG^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxyC$_1$-C$_4$alkyl, $C_1$-$C_4$alkoxycarbonyl, $C_1$-$C_6$alkyl, $C_1$-$C_4$alkylcarbonyl, haloC$_1$-C$_4$alkylsulfonyl, $C_1$-$C_4$alkylsulfonyl, benzyl, cyano, 1,3-dioxolane, halogen, haloC$_1$-C$_4$alkyl, hydroxy, hydroxyC$_1$-C$_4$alkyl, oxo, $—C(O)G^{1a}$, $—C(O)NHG^{2a}$, $—C(O)C(O)NH_2$, $G^{2a}$, and $—SO_2(CR^{2a}R^{2b})_mG^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxyC$_1$-C$_4$alkyl, $C_1$-$C_4$alkyl, halogen, haloC$_1$-C$_4$alkyl, $G^{1a}$, and $G^{3a}$; m is 1, 2 or 3; n is 1, 2 or 3; and p is 1 or 2.

In one embodiment, A is (iii), wherein the nitrogen atom on the left side of (iii) is attached to the phenyl ring of the indazole in formula (I);

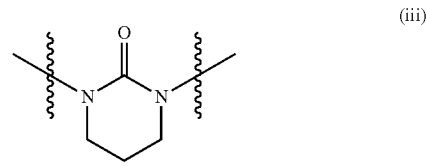 [SMILES: *N1CCCN(*)C1=O]

(iii)

$R^1$ is selected from the group consisting of $C_1$-$C_8$alkyl and $C_3$-$C_7$cycloalkyl; $R^2$ is selected from the group consisting of hydrogen, $C_1$-$C_8$alkenyl, $C_1$-$C_6$alkoxyC$_1$-C$_6$alkyl, $C_1$-$C_8$alkyl, $C_1$-$C_8$haloalkyl, -$G^1$, -$G^2$, -$G^3$, -$G^4$, $—CO_2R^{2c}$, $—CO_2G^1$, $—C(O)R^{2c}$, $—C(O)G^1$, $—C(O)G^2$, $—C(O)G^3$, $—C(O)G^4$, $—C(O)(CR^{2a}R^{2b})_mG^1$, $—C(O)(CR^{2a}R^{2b})_mG^2$, $—C(O)(CR^{2a}R^{2b})_m$—$OR^{2c}$, $—C(OH)(R^{2d})$—$R^{2c}$, $—C(OH)(R^{2d})$-$G^1$, $—C(OH)(R^{2d})$—$C(O)R^{2c}$, $—C(OH)(R^{2d})$—$C(O)G^1$, $—C(OH)(R^{2d})$—$(CR^{2a}R^{2b})_mG^1$, $—SO_2R^{2c}$, $—SO_2G^1$, $—SO_2G^2$, $—SO_2G^3$, $—SO_2G^4$, $—SO_2$—$(CR^{2a}R^{2b})_mG^1$, $—SO_2$—$(CR^{2a}R^{2b})_mG^2$, $—SO_2$—$(CR^{2a}R^{2b})_mG^3$, $—SO_2$—$(CR^{2a}R^{2b})_mG^4$, $—SO_2NR^{2d}R^{2e}$, $—(CR^{2a}R^{2b})_mG^1$, $—(CR^{2a}R^{2b})_mG^2$, $—(CR^{2a}R^{2b})_mG^3$, $—(CR^{2a}R^{2b})_mG^4$, $—(CR^{2a}R^{2b})_mC(OR^{2d})(R^{2d})$—$R^{2e}$, $—(CR^{2a}R^{2b})_m$—$C(OH)(R^{2d})$-$G^1$, $—(CR^{2a}R^{2b})_m$—$C(OH)(R^{2d})$-$G^2$, $—(CR^{2a}R^{2b})_m$—$C(OH)(R^{2d})$-$G^3$, $—(CR^{2a}R^{2b})_m$—$C(OH)(R^{2d})$-$G^4$, $—(CR^{2a}R^{2b})_m$—$C(OH)(R^{2d})$—$(CR^{2a}R^{2b})_n$-$G^1$, $—(CR^{2a}R^{2b})_m$—$C(OH)(R^{2d})$—$(CR^{2a}R^{2b})_n$-$G^2$, $—(CR^{2a}R^{2b})_m$—$C(OH)(R^{2d})$—$(CR^{2a}R^{2b})_n$-$G^3$, $—(CR^{2a}R^{2b})_m$—$C(OH)(R^{2d})$—$(CR^{2a}R^{2b})_n$-$G^4$, $—(CR^{2a}R^{2b})_mC(O)R^{2c}$, $—(CR^{2a}R^{2b})_mC(O)$—$(CR^{2a}R^{2b})_nG^1$, $—(CR^{2a}R^{2b})_mC(O)(CR^{2a}R^{2b})_nG^2$, $—(CR^{2a}R^{2b})_mC(O)(CR^{2a}R^{2b})_nG^3$, $—(CR^{2a}R^{2b})_mC(O)(CR^{2a}R^{2b})_nG^4$, $—(CR^{2a}R^{2b})_mCO_2R^{2c}$, $—(CR^{2a}R^{2b})_mCO_2G^1$, $—(CR^{2a}R^{2b})_mC(O)G^1$, $—(CR^{2a}R^{2b})_mC(O)G^2$, $—(CR^{2a}R^{2b})_mC(O)G^3$, $—(CR^{2a}R^{2b})_mC(O)G^4$, $—(CR^{2a}R^{2b})_mC(O)NR^{2d}R^{2e}$, $—(CR^{2a}R^{2b})_mC(O)NR^{2d}G^1$, $—(CR^{2a}R^{2b})_mC(O)NR^{2d}G^2$, $—(CR^{2a}R^{2b})_mC(O)NR^{2d}G^3$, $—(CR^{2a}R^{2b})_mC(O)NR^{2d}G^4$, $—(CR^{2a}R^{2b})_mC(O)N(R^{2d})((CR^{2a}R^{2b})_nG^1)$, $—(CR^{2a}R^{2b})_mC(O)N(R^{2d})((CR^{2a}R^{2b})_nG^2)$, $—(CR^{2a}R^{2b})_mC(O)N(R^{2d})((CR^{2a}R^{2b})_nG^3)$, $—(CR^{2a}R^{2b})_mC(O)N(R^{2d})((CR^{2a}R^{2b})_nG^4)$, $—(CR^{2a}R^{2b})_mSO_2NR^{2d}R^{2e}$, $—(CR^{2a}R^{2b})_mC(O)NH—(CR^{2a}R^{2f})—C(O)NHR^{2d}$, $—CR^{2a}=CHR^{2a}—CO_2R^{2c}$, $—CR^{2a}=CHR^{2a}—C(O)G^1$, and $—CR^{2a}=CHR^{2a}—C(O)G^3$; $R^{2a}$ and $R^{2b}$, at each occurrence, are each independently selected from the group consisting of hydrogen, fluorine, $C_1$-$C_4$alkyl, and haloC$_1$-C$_4$alkyl; $R^{2c}$ is selected from the group consisting of $C_2$-$C_8$alkenyl, $C_1$-$C_8$alkyl and haloC$_1$-C$_8$alkyl; $R^{2d}$, at each occurrence, is selected from the group consisting of hydrogen, $C_1$-$C_6$alkyl and haloC$_1$-C$_6$alkyl; $R^{2e}$ is selected from the group consisting of hydrogen, $C_2$-$C_8$alkenyl, $C_1$-$C_6$alkoxy, $C_1$-$C_4$alkoxyC$_1$-C$_4$alkyl, $C_6$alkyl, and haloC$_1$-C$_6$alkyl; $R^{2f}$ is selected from the group consisting of $C_1$-$C_4$alkyl, haloC$_1$-C$_4$alkyl and $—(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, haloC$_1$-C$_4$alkyl, halogen, hydroxy, hydroxyC$_1$-C$_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkyl, halogen, halo C$_1$-C$_4$alkyl, G$^{1a}$, and G$^{3a}$; m is 1, 2 or 3; n is 1, 2 or 3; and p is 1 or 2.

In one embodiment, A is (iii), wherein the nitrogen atom on the left side of (iii) is attached to the phenyl ring of the indazole in formula (I);

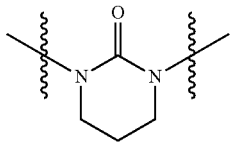

R$^1$ is selected from the group consisting of C$_1$-C$_8$alkyl and C$_3$-C$_7$cycloalkyl; R$^2$ is selected from the group consisting of hydrogen, C$_1$-C$_8$alkenyl, C$_1$-C$_6$alkoxyC$_1$-C$_6$alkyl, C$_1$-C$_8$alkyl, C$_1$-C$_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$═CHR$^{2a}$—CO$_2$R$^{2c}$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2c}$ is selected from the group consisting of C$_2$-C$_8$alkenyl, C$_1$-C$_8$alkyl and haloC$_1$-C$_8$alkyl; R$^{2d}$, at each occurrence, is selected from the group consisting of hydrogen, C$_1$-C$_6$alkyl and haloC$_1$-C$_6$alkyl; R$^{2e}$ is selected from the group consisting of hydrogen, C$_2$-C$_8$alkenyl, C$_1$-C$_6$alkoxy, C$_1$-C$_4$alkoxyC$_1$-C$_4$alkyl, C$_1$-C$_6$alkyl, and haloC$_1$-C$_6$alkyl; R$^{2f}$ is selected from the group consisting of C$_1$-C$_4$alkyl, and haloC$_1$-C$_4$alkyl; and m is 1, 2 or 3.

In one embodiment, A is (iii), wherein the nitrogen atom on the left side of (iii) is attached to the phenyl ring of the indazole in formula (I);

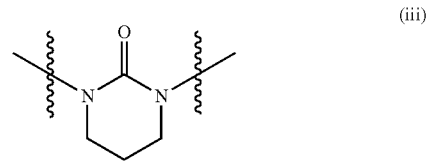 [SMILES: *N1CCCN(*)C1=O]

R$^1$ is selected from the group consisting of C$_1$-C$_8$alkyl and C$_3$-C$_7$cycloalkyl; R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —CR$^{2a}$═CHR$^{2a}$—C(O)G$^1$, —CR$^{2a}$═CHR$^{2a}$—C(O)G$^3$ and —(CR$^{2a}$R$^{2b}$)$_m$C(O)NH—(CR$^{2a}$R$^{2f}$)—C(O)NHR$^{2d}$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2d}$, at each occurrence, is selected from the group consisting of hydrogen, C$_1$-C$_6$alkyl and haloC$_1$-C$_6$alkyl; R$^{2f}$ is —(CR$^{2a}$R$^{2b}$)$_m$G$^{2a}$; G$^1$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^{1a}$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, —SO$_2$(C$R^{2a}R^{2b}$)$_m G^{1a}$, and —(C$R^{2a}R^{2b}$)$_p G^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, and —SO$_2$(C$R^{2a}R^{2b}$)$_m G^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (iii), wherein the nitrogen atom on the left side of (iii) is attached to the phenyl ring of the indazole in formula (I);

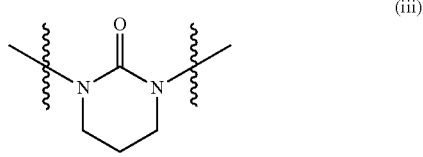

(iii)

$R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —CO$_2R^{2c}$, —CO$_2 G^1$, —C(O)$R^{2c}$, —C(O)$G^1$, —C(O)$G^2$, —C(O)$G^3$, —C(O)$G^4$, —C(O)(C$R^{2a}R^{2b}$)$_m G^1$, —C(O)(C$R^{2a}R^{2b}$)$_m G^2$, —C(O)(C$R^{2a}R^{2b}$)$_m$ O$R^{2c}$, —C(OH)($R^{2d}$)—$R^{2c}$, —C(OH)($R^{2d}$)-$G^1$, —C(OH)($R^{2d}$)—C(O)$R^{2c}$, —C(OH)($R^{2d}$)—C(O)$G^1$, —C(OH)($R^{2d}$)—(C$R^{2a}R^{2b}$)$_m G^1$, —SO$_2R^{2c}$, —SO$_2G^1$, —SO$_2G^2$, —SO$_2G^3$, —SO$_2G^4$, —SO$_2$—(C$R^{2a}R^{2b}$)$_m G^1$, —SO$_2$—(C$R^{2a}R^{2b}$)$_m G^2$, —SO$_2$—(C$R^{2a}R^{2b}$)$_m G^3$, —SO$_2$—(C$R^{2a}R^{2b}$)$_m G^4$, —SO$_2$N$R^{2d}R^{2e}$, —(C$R^{2a}R^{2b}$)$_m G^1$, —(C$R^{2a}R^{2b}$)$_m G^2$, —(C$R^{2a}R^{2b}$)$_m G^3$, —(C$R^{2a}R^{2b}$)$_m G^4$, —(C$R^{2a}R^{2b}$)$_m$—C(O$R^{2d}$)($R^{2d}$)—$R^{2e}$, —(C$R^{2a}R^{2b}$)$_m$—C(OH)($R^{2d}$)-$G^1$, —(C$R^{2a}R^{2b}$)$_m$—C(OH)($R^{2d}$)-$G^2$, —(C$R^{2a}R^{2b}$)$_m$—C(OH)($R^{2d}$)-$G^3$, —(C$R^{2a}R^{2b}$)$_m$—C(OH)($R^{2d}$)-$G^4$, —(C$R^{2a}R^{2b}$)$_m$—C(OH)($R^{2d}$)—(C$R^{2a}R^{2b}$)$_n$-$G^1$, —(C$R^{2a}R^{2b}$)$_m$—C(OH)($R^{2d}$)—(C$R^{2a}R^{2b}$)$_n$-$G^2$, —(C$R^{2a}R^{2b}$)$_m$—C(OH)($R^{2d}$)—(C$R^{2a}R^{2b}$)$_n$-$G^3$, —(C$R^{2a}R^{2b}$)$_m$—C(OH)($R^{2d}$)—(C$R^{2a}R^{2b}$)$_n$-$G^4$, —(C$R^{2a}R^{2b}$)$_m$C(O)$R^{2c}$, —(C$R^{2a}R^{2b}$)$_m$C(O)—(C$R^{2a}R^{2b}$)$_n G^1$, —(C$R^{2a}R^{2b}$)$_m$C(O)(C$R^{2a}R^{2b}$)$_n G^2$, —(C$R^{2a}R^{2b}$)$_m$C(O)(C$R^{2a}R^{2b}$)$_n G^3$, —(C$R^{2a}R^{2b}$)$_m$C(O)(C$R^{2a}R^{2b}$)$_n G^4$, —(C$R^{2a}R^{2b}$)$_m$CO$_2R^{2c}$, —(C$R^{2a}R^{2b}$)$_m$CO$_2G^1$, —(C$R^{2a}R^{2b}$)$_m$C(O)$G^1$, —(C$R^{2a}R^{2b}$)$_m$C(O)$G^2$, —(C$R^{2a}R^{2b}$)$_m$C(O)$G^3$, —(C$R^{2a}R^{2b}$)$_m$C(O)$G^4$, —(C$R^{2a}R^{2b}$)$_m$C(O)N$R^{2d}R^{2e}$, —(C$R^{2a}R^{2b}$)$_m$C(O)N$R^{2d}G^1$, —(C$R^{2a}R^{2b}$)$_m$C(O)N$R^{2d}G^2$, —(C$R^{2a}R^{2b}$)$_m$C(O)N$R^{2d}G^3$, —(C$R^{2a}R^{2b}$)$_m$C(O)N$R^{2d}G^4$, —(C$R^{2a}R^{2b}$)$_m$C(O)N($R^{2d}$)((C$R^{2a}R^{2b}$)$_n G^1$), —(C$R^{2a}R^{2b}$)$_m$C(O)N($R^{2d}$)((C$R^{2a}R^{2b}$)$_n G^2$), —(C$R^{2a}R^{2b}$)$_m$C(O)N($R^{2d}$)((C$R^{2a}R^{2b}$)$_n G^3$), —(C$R^{2a}R^{2b}$)$_m$C(O)N($R^{2d}$)((C$R^{2a}R^{2b}$)$_n G^4$), —(C$R^{2a}R^{2b}$)$_m$SO$_2$N$R^{2d}R^{2e}$, —(C$R^{2a}R^{2b}$)$_m$C(O)NH—(C$R^{2f}$)—C(O)NH$R^{2d}$, —C$R^{2a}$=CH$R^{2a}$—CO$_2R^{2c}$, —C$R^{2a}$=CH$R^{2a}$—C(O)$G^1$, and —C$R^{2a}$=CH$R^{2a}$—C(O)$G^3$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl, halo$C_1$-$C_4$alkyl and —(C$R^{2a}R^{2b}$)$_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O) $G^{1a}$, —C(O)NH$G^{2a}$, —C(O)C(O)NH$_2$, $G^{2a}$, —SO$_2$ (C$R^{2a}R^{2b}$)$_m G^{1a}$, and (C$R^{2a}R^{2b}$)$_p G^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O) $G^{1a}$, —C(O)NH$G^{2a}$, —C(O)C(O)NH$_2$, $G^{2a}$, and —SO$_2$ (C$R^{2a}R^{2b}$)$_m G^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (iii), wherein the nitrogen atom on the left side of (iii) is attached to the phenyl ring of the indazole in formula (I);

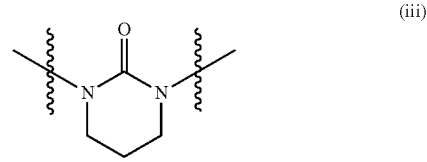 [SMILES: *N1CCCN(*)C1=O]

(iii)

$R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —$CO_2R^{2c}$, —C(O)$R^{2c}$, —C(O)($CR^{2a}R^{2b}$)$_m$—$OR^{2c}$, —C(OH)($R^{2d}$)—$R^{2c}$, —C(OH)($R^{2d}$)—C(O)$R^{2c}$, —$SO_2R^{2c}$, —$SO_2NR^{2d}R^{2e}$, —($CR^{2a}R^{2b}$)$_m$—C($OR^{2d}$)($R^{2d}$)—$R^{2e}$, —($CR^{2a}R^{2b}$)$_m$C(O)$R^{2c}$, —($CR^{2a}R^{2b}$)$_m$$CO_2R^{2c}$, —($CR^{2a}R^{2b}$)$_m$C(O)$NR^{2d}R^{2e}$, —($CR^{2a}R^{2b}$)$_m$$SO_2NR^{2d}R^{2e}$, —($CR^{2a}R^{2b}$)$_m$C(O)NH—($CR^{2a}R^{2f}$)—C(O)$NHR^{2d}$, and —$CR^{2a}$=$CHR^{2a}$—$CO_2R^{2c}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl and halo$C_1$-$C_4$alkyl; and m is 1, 2 or 3.

In one embodiment, A is (iii), wherein the nitrogen atom on the left side of (iii) is attached to the phenyl ring of the indazole in formula (I);

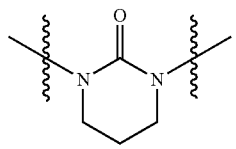
(iii)

$R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of —($CR^{2a}R^{2b}$)$_m$—C($OR^{2d}$)($R^{2d}$)—$R^{2e}$ or —($CR^{2a}R^{2b}$)$_m$C(O)$R^{2c}$; $R^{2a}$ and $R^{2b}$, at each occurrence, are each independently selected from the group consisting of hydrogen and $C_1$-$C_4$alkyl; $R^{2c}$ is selected from the group consisting of $C_1$-$C_8$alkyl and halo$C_1$-$C_8$alkyl; $R^{2d}$, at each occurrence, is selected from the group consisting of hydrogen and $C_1$-$C_6$alkyl; $R^{2e}$ is selected from the group consisting of $C_1$-$C_6$alkyl, and halo$C_1$-$C_6$alkyl; and m is 1 or 2.

In one embodiment, A is (iii), wherein the nitrogen atom on the left side of (iii) is attached to the phenyl ring of the indazole in formula (I);

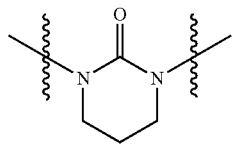
(iii)

$R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of -$G^1$, -$G^2$, -$G^3$, -$G^4$, —$CO_2G^1$, —C(O)$G^1$, —C(O)$G^2$, —C(O)$G^3$, —C(O)$G^4$, —C(O)($CR^{2a}R^{2b}$)$_m$$G^1$, —C(O)($CR^{2a}R^{2b}$)$_m$$G^2$, —C(OH)($R^{2d}$)-$G^1$, —C(OH)($R^{2d}$)—C(O)$G^1$, —C(OH)($R^{2d}$)—($CR^{2a}R^{2b}$)$_m$$G^1$, —$SO_2G^1$, —$SO_2G^2$, —$SO_2G^3$, —$SO_2G^4$, —$SO_2$—($CR^{2a}R^{2b}$)$_m$$G^1$, —$SO_2$—($CR^{2a}R^{2b}$)$_m$$G^2$, —$SO_2$—($CR^{2a}R^{2b}$)$_m$$G^3$, —$SO_2$—($CR^{2a}R^{2b}$)$_m$$G^4$, —($CR^{2a}R^{2b}$)$_m$$G^1$, —($CR^{2a}R^{2b}$)$_m$$G^2$, —($CR^{2a}R^{2b}$)$_m$$G^3$, —($CR^{2a}R^{2b}$)$_m$$G^4$, —($CR^{2a}R^{2b}$)$_m$—C(OH)($R^{2d}$)-$G^1$, —($CR^{2a}R^{2b}$)$_m$—C(OH)($R^{2d}$)-$G^2$, —($CR^{2a}R^{2b}$)$_m$—C(OH)($R^{2d}$)-$G^3$, —($CR^{2a}R^{2b}$)$_m$—C(OH)($R^{2d}$)-$G^4$, —($CR^{2a}R^{2b}$)$_m$—C(OH)($R^{2d}$)—($CR^{2a}R^{2b}$)$_n$-$G^1$, —($CR^{2a}R^{2b}$)$_m$—C(OH)($R^{2d}$)—($CR^{2a}R^{2b}$)$_n$-$G^2$, —($CR^{2a}R^{2b}$)$_m$—C(OH)($R^{2d}$)—($CR^{2a}R^{2b}$)$_n$-$G^3$, —($CR^{2a}R^{2b}$)$_m$—C(OH)($R^{2d}$)—($CR^{2a}R^{2b}$)$_n$-$G^4$, —($CR^{2a}R^{2b}$)$_m$C(O)—($CR^{2a}R^{2b}$)$_n$$G^1$, —($CR^{2a}R^{2b}$)$_m$C(O)($CR^{2a}R^{2b}$)$_n$$G^2$, —($CR^{2a}R^{2b}$)$_m$C(O)($CR^{2a}R^{2b}$)$_n$$G^3$, —($CR^{2a}R^{2b}$)$_m$C(O)($CR^{2a}R^{2b}$)$_n$$G^4$, —($CR^{2a}R^{2b}$)$_m$$CO_2G^1$, —($CR^{2a}R^{2b}$)$_m$C(O)$G^1$, —($CR^{2a}R^{2b}$)$_m$C(O)$G^2$, —($CR^{2a}R^{2b}$)$_m$C(O)$G^3$, —($CR^{2a}R^{2b}$)$_m$C(O)$G^4$, —($CR^{2a}R^{2b}$)$_m$C(O)$NR^{2d}G^1$, —($CR^{2a}R^{2b}$)$_m$C(O)$NR^{2d}G^2$, —($CR^{2a}R^{2b}$)$_m$C(O)$NR^{2d}G^3$, —($CR^{2a}R^{2b}$)$_m$C(O)$NR^{2d}G^4$, —($CR^{2a}R^{2b}$)$_m$C(O)N($R^{2d}$)(($CR^{2a}R^{2b}$)$_n$$G^1$), —($CR^{2a}R^{2b}$)$_m$C(O)N($R^{2d}$)(($CR^{2a}R^{2b}$)$_n$$G^2$), —($CR^{2a}R^{2b}$)$_m$C(O)N($R^{2d}$)(($CR^{2a}R^{2b}$)$_n$$G^3$), —($CR^{2a}R^{2b}$)$_m$C(O)N($R^{2d}$)(($CR^{2a}R^{2b}$)$_n$$G^4$), —$CR^{2a}$=$CHR^{2a}$—C(O)$G^1$, —$CR^{2a}$=$CHR^{2a}$—C(O)$G^3$ and —($CR^{2a}R^{2b}$)$_m$C(O)NH—($CR^{2a}R^{2f}$)—C(O)$NHR^{2d}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2d}$, at each occurrence, is selected from the group consisting of hydrogen, $C_1$-$C_6$alkyl and halo$C_1$-$C_6$alkyl; $R^{2f}$ is —($CR^{2a}R^{2b}$)$_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)$NHG^{2a}$, —C(O)C(O)$NH_2$, $G^{2a}$, —$SO_2$($CR^{2a}R^{2b}$)$_m$$G^{1a}$, and —($CR^{2a}R^{2b}$)$_p$$G^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, haloC₁-C₄alkyl, hydroxy, hydroxyC₁-C₄alkyl, oxo, —C(O)G$^{1a}$, —C(O)NHG$^{2a}$, —C(O)C(O)NH₂, G$^{2a}$, and —SO₂(CR$^{2a}$R$^{2b}$)$_m$G$^{1a}$; G⁴ is 5-10-membered heteroaryl, wherein the 5-10-membered heteroaryl is optionally substituted with 1, 2, 3 or 4 substituents selected from the group consisting of C₁-C₄alkoxy, C₁-C₄alkoxyC₁-C₄alkyl, C₁-C₄alkyl, halogen, haloC₁-C₄alkyl, G$^{1a}$, and G$^{3a}$; m is 1, 2 or 3; n is 1, 2 or 3; and p is 1 or 2.

In one embodiment, A is (iii), wherein the nitrogen atom on the left side of (iii) is attached to the phenyl ring of the indazole in formula (I);

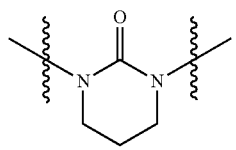

(iii)

R¹ is selected from the group consisting of phenyl and monocyclic heteroaryl, wherein the phenyl and monocyclic heteroaryl are optionally substituted with 1, 2, 3, or 4 substituents selected from the group consisting of C₁-C₄alkoxy, C₁-C₄alkyl, C₁-C₄haloalkoxy, C₁-C₄haloalkyl, and halogen; R² is selected from the group consisting of —(CR$^{2a}$R$^{2b}$)$_m$G⁴ or —(CR$^{2a}$R$^{2b}$)$_m$C(O)G³; R$^{2a}$ and R$^{2b}$, at each occurrence, are each independently selected from the group consisting of hydrogen and C₁-C₄alkyl; G³ is 4-8-membered-heterocycle, wherein the 4-8-membered-heterocycle is optionally substituted with 1 or 2 C₁-C₄alkyl or halogen; G⁴ is 5-10-membered heteroaryl, wherein the 5-10-membered heteroaryl is optionally substituted with 1, 2 or 3 substituents selected from the group consisting of C₁-C₄alkyl, halogen, and haloC₁-C₄alkyl; and m is 1 or 2.

In one embodiment, A is (iv), wherein the nitrogen atom on the left side of (iv) is attached to the phenyl ring of the indazole in formula (I);

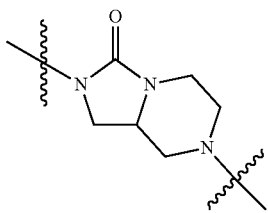

(iv)

R¹ is selected from the group consisting of C₁-C₈alkyl, C₁-C₈haloalkyl, C₃-C₇cycloalkyl, phenyl, or monocyclic heteroaryl, wherein the phenyl and monocyclic heteroaryl are optionally substituted with 1, 2, 3, or 4 substituents selected from the group consisting of C₁-C₄alkoxy, C₁-C₄alkyl, C₁-C₄haloalkoxy, C₁-C₄haloalkyl, and halogen; R² is selected from the group consisting of hydrogen, C₁-C₈alkenyl, C₁-C₆alkoxyC₁-C₆alkyl, C₁-C₈alkyl, C₁-C₈haloalkyl, -G¹, -G², -G³, -G⁴, —CO₂R$^{2c}$, —CO₂G¹, —C(O)R$^{2c}$, —C(O)G¹, —C(O)G², —C(O)G³, —C(O)G⁴, —C(O)(CR$^{2a}$R$^{2b}$)$_m$G¹, —C(O)(CR$^{2a}$R$^{2b}$)$_m$G², —C(O)(CR$^{2a}$R$^{2b}$)$_m$—OR$^{2c}$, —C(OH)(R$^{2d}$)—R$^{2c}$, —C(OH)(R$^{2d}$)-G¹, —C(OH)(R$^{2d}$)—C(O)R$^{2c}$, —C(OH)(R$^{2d}$)—C(O)G¹, —C(OH)(R$^{2d}$)—(CR$^{2a}$R$^{2b}$)$_m$G¹, —SO₂R$^{2c}$, —SO₂G¹, —SO₂G², —SO₂G³, —SO₂G⁴, —SO₂—(CR$^{2a}$R$^{2b}$)$_m$G¹, —SO₂—(CR$^{2a}$R$^{2b}$)$_m$G², —SO₂—(CR$^{2a}$R$^{2b}$)$_m$G³, —SO₂—(CR$^{2a}$R$^{2b}$)$_m$G⁴, —SO₂NR$^{2d}$R$^{2e}$, —(CR$^{2a}$R$^{2b}$)$_m$G¹, —(CR$^{2a}$R$^{2b}$)$_m$G², —(CR$^{2a}$R$^{2b}$)$_m$G³, —(CR$^{2a}$R$^{2b}$)$_m$G⁴, —(CR$^{2a}$R$^{2b}$)$_m$—C(OR$^{2d}$)(R$^{2d}$)—R$^{2e}$, —(CR$^{2a}$R$^{2b}$)$_m$—C(OH)(R$^{2d}$)-G¹, —(CR$^{2a}$R$^{2b}$)$_m$—C(OH)(R$^{2d}$)-G², —(CR$^{2a}$R$^{2b}$)$_m$—C(OH)(R$^{2d}$)-G³, —(CR$^{2a}$R$^{2b}$)$_m$—C(OH)(R$^{2d}$)-G⁴, —(CR$^{2a}$R$^{2b}$)$_m$—C(OH)(R$^{2d}$)—(CR$^{2a}$R$^{2b}$)$_n$-G¹, —(CR$^{2a}$R$^{2b}$)$_m$—C(OH)(R$^{2d}$)—(CR$^{2a}$R$^{2b}$)$_n$-G², —(CR$^{2a}$R$^{2b}$)$_m$—C(OH)(R$^{2d}$)—(CR$^{2a}$R$^{2b}$)$_n$-G³, —(CR$^{2a}$R$^{2b}$)$_m$—C(OH)(R$^{2d}$)—(CR$^{2a}$R$^{2b}$)$_n$-G⁴, —(CR$^{2a}$R$^{2b}$)$_m$C(O)R$^{2c}$, —(CR$^{2a}$R$^{2b}$)$_m$C(O)—(CR$^{2a}$R$^{2b}$)$_n$G¹, —(CR$^{2a}$R$^{2b}$)$_m$C(O)(CR$^{2a}$R$^{2b}$)$_n$G², —(CR$^{2a}$R$^{2b}$)$_m$C(O)(CR$^{2a}$R$^{2b}$)$_n$G³, —(CR$^{2a}$R$^{2b}$)$_m$C(O)(CR$^{2a}$R$^{2b}$)$_n$G⁴, —(CR$^{2a}$R$^{2b}$)$_m$CO₂R$^{2c}$, —(CR$^{2a}$R$^{2b}$)$_m$CO₂G¹, —(CR$^{2a}$R$^{2b}$)$_m$C(O)G¹, —(CR$^{2a}$R$^{2b}$)$_m$C(O)G², —(CR$^{2a}$R$^{2b}$)$_m$C(O)G³, —(CR$^{2a}$R$^{2b}$)$_m$C(O)G⁴, —(CR$^{2a}$R$^{2b}$)$_m$C(O)NR$^{2d}$R$^{2e}$, —(CR$^{2a}$R$^{2b}$)$_m$C(O)NR$^{2d}$G¹, —(CR$^{2a}$R$^{2b}$)$_m$C(O)NR$^{2d}$G², —(CR$^{2a}$R$^{2b}$)$_m$C(O)NR$^{2d}$G³, —(CR$^{2a}$R$^{2b}$)$_m$C(O)NR$^{2d}$G⁴, —(CR$^{2a}$R$^{2b}$)$_m$C(O)N(R$^{2d}$)((CR$^{2a}$R$^{2b}$)$_n$G¹), —(CR$^{2a}$R$^{2b}$)$_m$C(O)N(R$^{2d}$)((CR$^{2a}$R$^{2b}$)$_n$G²), —(CR$^{2a}$R$^{2b}$)$_m$C(O)N(R$^{2d}$)((CR$^{2a}$R$^{2b}$)$_n$G³), —(CR$^{2a}$R$^{2b}$)$_m$C(O)N(R$^{2d}$)((CR$^{2a}$R$^{2b}$)$_n$G⁴), —(CR$^{2a}$R$^{2b}$)$_m$SO₂NR$^{2d}$R$^{2e}$, —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)R$^{2c}$, —CR$^{2a}$=CHR$^{2a}$—CO₂R$^{2c}$, —CR$^{2a}$=CHR$^{2a}$—C(O)G¹, and —CR$^{2a}$=CHR$^{2a}$—C(O)G³; R$^{2a}$ and R$^{2b}$, at each occurrence, are each independently selected from the group consisting of hydrogen, fluorine, C₁-C₄alkyl, and haloC₁-C₄alkyl; R$^{2c}$ is selected from the group consisting of C₂-C₈alkenyl, C₁-C₈alkyl and haloC₁-C₈alkyl; R$^{2d}$, at each occurrence, is selected from the group consisting of hydrogen, C₁-C₆alkyl and haloC₁-C₆alkyl; R$^{2e}$ is selected from the group consisting of hydrogen, C₂-C₈alkenyl, C₁-C₆alkoxy, C₁-C₄alkoxyC₁-C₄alkyl, C₁-C₆alkyl, and haloC₁-C₆alkyl; R$^{2f}$ is selected from the group consisting of C₁-C₄alkyl, haloC₁-C₄alkyl and —(CR$^{2a}$R$^{2b}$)$_m$-G$^{2a}$; G¹ is C₃-C₇cycloalkyl, wherein the C₃-C₇cycloalkyl is optionally substituted with 1, 2, 3 or 4 substituents selected from the group consisting of C₁-C₆alkoxy, C₁-C₄alkyl, benzyloxy, haloC₁-C₄alkyl, halogen, hydroxy, hydroxyC₁-C₄alkyl, oxime, C₁-C₆alkyloxime, and oxo; G$^{1a}$ is C₃-C₇cycloalkyl, wherein the C₃-C₇cycloalkyl is optionally substituted with 1, 2, 3 or 4 substituents selected from the group consisting of C₁-C₆alkoxy, C₁-C₄alkyl, benzyloxy, haloC₁-C₄alkyl, halogen, hydroxy, hydroxyC₁-C₄alkyl, oxime, C₁-C₆alkyloxime, and oxo; G² is aryl, wherein the aryl is optionally substituted with 1, 2, 3 or 4 substituents selected from the group consisting of C₁-C₄alkoxy, C₁-C₄alkyl, 1,3-dioxole, haloC₁-C₄alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C₁-C₄alkoxy, C₁-C₄alkyl, 1,3-dioxole, haloC₁-C₄alkyl, and halogen; G³ is 4-8-membered-heterocycle, wherein the 4-8-membered-heterocycle is optionally substituted with 1, 2, 3, 4 or 5 substituents selected from the group consisting of C₁-C₆alkoxy, C₁-C₄alkoxyC₁-C₄alkyl, C₁-C₄alkoxycarbonyl, C₁-C₆alkyl, C₁-C₄alkylcarbonyl, haloC₁-C₄alkylsulfonyl, C₁-C₄alkylsulfonyl, benzyl, cyano, 1,3-dioxolane, halogen, haloC₁-C₄alkyl, hydroxy, hydroxyC₁-C₄alkyl, oxo, —C(O)G$^{1a}$, —C(O)NHG$^{2a}$, —C(O)C(O)NH₂, G$^{2a}$, —SO₂(CR$^{2a}$R$^{2b}$)$_m$G$^{1a}$, and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of C₁-C₄alkoxy, C₁-C₄alkoxyC₁-C₄alkyl, C₁-C₄alkoxycarbonyl, C₁-C₆alkyl, C₁-C₄alkylcarbonyl, haloC₁-C₄alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, and —SO$_2$(CR$^{2a}$R$^{2b}$)$_m$$G^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (iv), wherein the nitrogen atom on the left side of (iv) is attached to the phenyl ring of the indazole in formula (I);

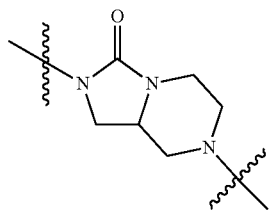

(iv)

$R^1$ is selected from the group consisting of $C_1$-$C_8$alkyl and $C_3$-$C_7$cycloalkyl; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —CO$_2$R$^{2c}$, —CO$_2$G$^1$, —C(O)R$^{2c}$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(O)(CR$^{2a}$R$^{2b}$)$_m$—OR$^{2c}$, —C(OH)(R$^{2d}$)—R$^{2c}$, —C(OH)(R$^{2d}$)-G$^1$, —C(OH)(R$^{2d}$)—C(O)R$^{2c}$, —C(OH)(R$^{2d}$)—C(O)G$^1$, —C(OH)(R$^{2d}$)—(CR$^{2a}$R$^{2b}$)$_m$G$^1$, —SO$_2$R$^{2c}$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —SO$_2$NR$^{2d}$R$^{2e}$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OR$^{2d}$)(R$^{2d}$)—R$^{2e}$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)R$^{2c}$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$R$^{2c}$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$R$^{2e}$, —(CR$^{2a}$R$^{2b}$)$_m$C(O)NR$^{2b}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, —CR$^{2a}$=CHR$^{2a}$—CO$_2$R$^{2c}$, —CR$^{2a}$=CHR$^{2a}$—C(O)G$^1$, and —CR$^{2a}$=CHR$^{2a}$—C(O)G$^3$; R$^{2a}$ and R$^{2b}$, at each occurrence, are each independently selected from the group consisting of hydrogen, fluorine, $C_1$-$C_4$alkyl, and halo$C_1$-$C_4$alkyl; R$^{2c}$ is selected from the group consisting of $C_2$-$C_8$alkenyl, $C_1$-$C_8$alkyl and halo$C_1$-$C_8$alkyl; R$^{2d}$, at each occurrence, is selected from the group consisting of hydrogen, $C_1$-$C_6$alkyl and halo$C_1$-$C_6$alkyl; R$^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_6$alkyl, and halo$C_1$-$C_6$alkyl; R$^{2f}$ is selected from the group consisting of $C_1$-$C_4$alkyl, halo$C_1$-$C_4$alkyl and —(CR$^{2a}$R$^{2b}$)$_m$-G$^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_4$alkylcarbonyl, halo$C_1$-$C_4$alkylsulfonyl, $C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, G$^{1a}$, and G$^{3a}$; m is 1, 2 or 3; n is 1, 2 or 3; and p is 1 or 2.

In one embodiment, A is (iv), wherein the nitrogen atom on the left side of (iv) is attached to the phenyl ring of the indazole in formula (I);

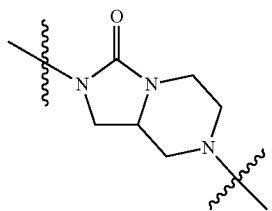

(iv)

$R^1$ is selected from the group consisting of $C_1$-$C_8$alkyl and $C_3$-$C_7$cycloalkyl; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$; R$^{2a}$ and R$^{2b}$, at each occurrence, are each independently selected from the group consisting of hydrogen, fluorine, $C_1$-$C_4$alkyl, and halo$C_1$-$C_4$alkyl; $R^{2c}$ is selected from the group consisting of $C_2$-$C_8$alkenyl, $C_1$-$C_8$alkyl and halo$C_1$-$C_8$alkyl; $R^{2d}$, at each occurrence, is selected from the group consisting of hydrogen, $C_1$-$C_6$alkyl and halo$C_1$-$C_6$alkyl; $R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl; $R^{2f}$ is selected from the group consisting of $C_1$-$C_4$alkyl and halo$C_1$-$C_4$alkyl; and m is 1, 2 or 3.

In one embodiment, A is (iv), wherein the nitrogen atom on the left side of (iv) is attached to the phenyl ring of the indazole in formula (I);

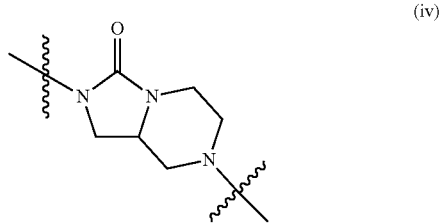 [SMILES: *N1CCN2C(=O)N(*)CC2C1]

(iv)

$R^1$ is selected from the group consisting of $C_1$-$C_8$alkyl and $C_3$-$C_7$cycloalkyl; $R^2$ is selected from the group consisting of -$G^1$, -$G^2$, -$G^3$, -$G^4$, —$CO_2G^1$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(OH)(R^{2d})$-$G^1$, —$C(OH)(R^{2d})$—$C(O)G^1$, —$C(OH)(R^{2d})$—$(CR^{2a}R^{2b})_mG^1$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$CR^{2a}$=$CHR^{2a}$—$C(O)G^1$, —$CR^{2a}$=$CHR^{2a}$—$C(O)G^3$, and —$(CR^{2a}R^{2b})_mC(O)NH$—$(CR^{2a}R^{2f})$—$C(O)NHR^{2d}$; $R^{2a}$ and $R^{2b}$, at each occurrence, are each independently selected from the group consisting of hydrogen, fluorine, $C_1$-$C_4$alkyl, and halo$C_1$-$C_4$alkyl; $R^{2d}$, at each occurrence, is selected from the group consisting of hydrogen, $C_1$-$C_6$alkyl and halo$C_1$-$C_6$alkyl; $R^{2f}$ is —$(CR^{2a}R^{2b})_m$-$G^{2a}$; $G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo; $G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen; $G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, —$SO_2(CR^{2a}R^{2b})_mG^{1a}$, and —$(CR^{2a}R^{2b})_pG^{3a}$; $G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, and —$SO_2(CR^{2a}R^{2b})_mG^{1a}$; $G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$; m is 1, 2 or 3; n is 1, 2 or 3; and p is 1 or 2.

In one embodiment, A is (iv), wherein the nitrogen atom on the left side of (iv) is attached to the phenyl ring of the indazole in formula (I);

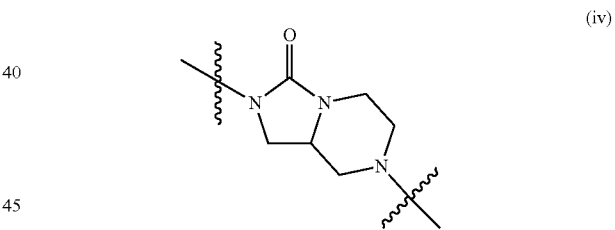

(iv)

$R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen; $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_nG^4$, —$SO_2NR^{2d}R^{2e}$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OR^{2d})(R^{2d})$—$R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}$ $R^{2b})_m$—C(OH)($R^{2d}$)-$G^4$, —(C$R^{2a}R^{2b}$)$_m$—C(OH)($R^{2d}$)—(C$R^{2a}R^{2b}$)$_n$-$G^1$, —(C$R^{2a}R^{2b}$)$_m$—C(OH)($R^{2d}$)—(C$R^{2a}R^{2b}$)$_n$-$G^2$, —(C$R^{2a}R^{2b}$)$_m$—C(OH)($R^{2d}$)—(C$R^{2a}R^{2b}$)$_n$-$G^3$, —(C$R^{2a}R^{2b}$)$_m$—C(OH)($R^{2d}$)—(C$R^{2a}R^{2b}$)$_n$-$G^4$, —(C$R^{2a}R^{2b}$)$_m$C(O)$R^{2c}$, —(C$R^{2a}R^{2b}$)$_m$C(O)—(C$R^{2a}R^{2b}$)$_n$G$^1$, —(C$R^{2a}R^{2b}$)$_m$C(O)(C$R^{2a}R^{2b}$)$_n$G$^2$, —(C$R^{2a}R^{2b}$)$_m$C(O)(C$R^{2a}R^{2b}$)$_n$G$^3$, —(C$R^{2a}R^{2b}$)$_m$C(O)(C$R^{2a}R^{2b}$)$_n$G$^4$, —(C$R^{2a}R^{2b}$)$_m$CO$_2$R$^{2c}$, —(C$R^{2a}R^{2b}$)$_m$CO$_2$G$^1$, —(C$R^{2a}R^{2b}$)$_m$C(O)G$^1$, —(C$R^{2a}R^{2b}$)$_m$C(O)G$^2$, —(C$R^{2a}R^{2b}$)$_m$C(O)G$^3$, —(C$R^{2a}R^{2b}$)$_m$C(O)G$^4$, —(C$R^{2a}R^{2b}$)$_m$C(O)NR$^{2d}$R$^{2e}$, —(C$R^{2a}R^{2b}$)$_m$C(O)NR$^{2d}$G$^1$, —(C$R^{2a}R^{2b}$)$_m$C(O)NR$^{2d}$G$^2$, —(C$R^{2a}R^{2b}$)$_m$C(O)NR$^{2d}$G$^3$, —(C$R^{2a}R^{2b}$)$_m$C(O)NR$^{2d}$G$^4$, —(C$R^{2a}R^{2b}$)$_m$C(O)N(R$^{2d}$)((C$R^{2a}R^{2b}$)$_n$G$^1$), —(C$R^{2a}R^{2b}$)$_m$C(O)N(R$^{2d}$)((C$R^{2a}R^{2b}$)$_n$G$^2$), —(C$R^{2a}R^{2b}$)$_m$C(O)N(R$^{2d}$)((C$R^{2a}R^{2b}$)$_n$G$^3$), —(C$R^{2a}R^{2b}$)$_m$C(O)N(R$^{2d}$)((C$R^{2a}R^{2b}$)$_n$G$^4$), —(C$R^{2a}R^{2b}$)$_m$SO$_2$NR$^{2d}$R$^{2e}$, —(C$R^{2a}R^{2b}$)$_m$C(O)NH—(C$R^{2a}R^{2f}$)—C(O)NHR$^{2d}$, —CR$^{2a}$=CHR$^{2a}$—CO$_2$R$^{2c}$, —CR$^{2a}$=CHR$^{2a}$—C(O)G$^1$, and —CR$^{2a}$=CHR$^{2a}$—C(O)G$^3$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2c}$ is selected from the group consisting of C$_2$-C$_8$alkenyl, C$_1$-C$_8$alkyl and haloC$_1$-C$_8$alkyl; R$^{2d}$, at each occurrence, is selected from the group consisting of hydrogen, C$_1$-C$_6$alkyl and haloC$_1$-C$_6$alkyl; R$^{2e}$ is selected from the group consisting of hydrogen, C$_2$-C$_8$alkenyl, C$_1$-C$_6$alkoxy, C$_1$-C$_4$alkoxyC$_1$-C$_4$alkyl, C$_1$-C$_6$alkyl, and haloC$_1$-C$_6$alkyl; R$^{2f}$ is selected from the group consisting of C$_1$-C$_4$alkyl, haloC$_1$-C$_4$alkyl and —(C$R^{2a}R^{2b}$)$_m$-G$^{2a}$; G$^1$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^{1a}$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, —SO$_2$(C$R^{2a}R^{2b}$)$_m$G$^{1a}$, and —(C$R^{2a}R^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, and —SO$_2$(C$R^{2a}R^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkyl, halogen, haloC$_1$-C$_4$alkyl, G$^{1a}$, and G$^{3a}$; m is 1, 2 or 3; n is 1, 2 or 3; and p is 1 or 2.

In one embodiment, A is (iv), wherein the nitrogen atom on the left side of (iv) is attached to the phenyl ring of the indazole in formula (I);

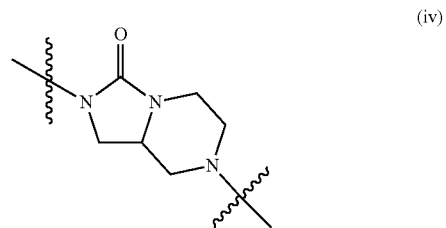 [SMILES: *N1CCN2C(=O)N(*)CC2C1]

(iv)

R$^1$ is selected from the group consisting of phenyl and monocyclic heteroaryl, wherein the phenyl and monocyclic heteroaryl are optionally substituted with 1, 2, 3, or 4 substituents selected from the group consisting of C$_1$-C$_4$alkoxy, C$_1$-C$_4$alkyl, C$_1$-C$_4$haloalkoxy, C$_1$-C$_4$haloalkyl, and halogen; R$^2$ is selected from the group consisting of hydrogen, C$_1$-C$_8$alkenyl, C$_1$-C$_6$alkoxyC$_1$-C$_6$alkyl, C$_1$-C$_8$alkyl, C$_1$-C$_8$haloalkyl, —CO$_2$R$^{2c}$, —C(O)R$^{2c}$, —C(O)(C$R^{2a}R^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(C$R^{2a}R^{2b}$)$_m$—C(OR$^{2d}$)(R$^{2d}$)—R$^{2e}$, —(C$R^{2a}R^{2b}$)$_m$C(O)R$^{2c}$, —(C$R^{2a}R^{2b}$)$_m$CO$_2$R$^{2c}$, —(C$R^{2a}R^{2b}$)$_m$C(O)NR$^{2d}$R$^{2e}$, —(C$R^{2a}R^{2b}$)$_m$SO$_2$NR$^{2d}$R$^{2e}$, —(C$R^{2a}R^{2b}$)$_m$C(O)NH—(C$R^{2a}R^{2f}$)—C(O)NHR$^{2d}$, and —CR$^{2a}$=CHR$^{2a}$—CO$_2$R$^{2c}$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2c}$ is selected from the group consisting of C$_2$-C$_8$alkenyl, C$_1$-C$_8$alkyl and haloC$_1$-C$_8$alkyl; R$^{2d}$, at each occurrence, is selected from the group consisting of hydrogen, C$_1$-C$_6$alkyl and haloC$_1$-C$_6$alkyl; R$^{2e}$ is selected from the group consisting of hydrogen, C$_2$-C$_8$alkenyl, C$_1$-C$_6$alkoxy, C$_1$-C$_4$alkoxyC$_1$-C$_4$alkyl, C$_1$-C$_6$alkyl, and haloC$_1$-C$_6$alkyl; R$^{2f}$ is selected from the group consisting of C$_1$-C$_4$alkyl and haloC$_1$-C$_4$alkyl; and m is 1, 2 or 3.

In one embodiment, A is (iv), wherein the nitrogen atom on the left side of (iv) is attached to the phenyl ring of the indazole in formula (I);

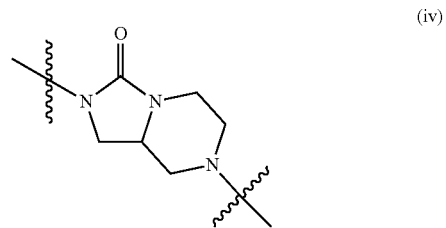 [SMILES: *N1CCN2C(=O)N(*)CC2C1]

(iv)

R$^1$ is selected from the group consisting of phenyl and monocyclic heteroaryl, wherein the phenyl and monocyclic heteroaryl are optionally substituted with 1, 2, 3, or 4 substituents selected from the group consisting of C$_1$-C$_4$alkoxy, C$_1$-C$_4$alkyl, C$_1$-C$_4$haloalkoxy, C$_1$-C$_4$haloalkyl, and halogen; R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(C$R^{2a}R^{2b}$)$_m$G$^1$, —C(O)(C$R^{2a}R^{2b}$)$_m$G$^2$, —C(OH)(R$^{2d}$)-G$^1$, —C(OH)

$(R^{2d})$—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)G$^1$, and —CR$^{2a}$=CHR$^{2a}$—C(O)G$^3$; R$^{2a}$ and R$^{2b}$, at each occurrence, are each independently selected from the group consisting of hydrogen, fluorine, C$_1$-C$_4$alkyl, and haloC$_1$-C$_4$alkyl; R$^{2d}$, at each occurrence, is selected from the group consisting of hydrogen, C$_1$-C$_6$alkyl and haloC$_1$-C$_6$alkyl; R$^{2f}$ is —(CR$^{2a}$R$^{2b}$)G$^{2a}$; G$^1$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^{1a}$ is C$_3$-C$_7$cycloalkyl, wherein the C$_3$-C$_7$cycloalkyl is optionally substituted with 1, 2, 3 or 4 substituents selected from the group consisting of C$_1$-C$_6$alkoxy, C$_1$-C$_4$alkyl, benzyloxy, haloC$_1$-C$_4$alkyl, halogen, hydroxy, hydroxyC$_1$-C$_4$alkyl, oxime, C$_1$-C$_6$alkyloxime, and oxo; G$^2$ is aryl, wherein the aryl is optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^{2a}$ is aryl or 5-6-membered heteroaryl, wherein the aryl or 5-6-membered heteroaryl are optionally substituted with 1, 2, 3 or 4 substituents selected from the group consisting of C$_1$-C$_4$alkoxy, C$_1$-C$_4$alkyl, 1,3-dioxole, haloC$_1$-C$_4$alkyl, and halogen; G$^3$ is 4-8-membered-heterocycle, wherein the 4-8-membered-heterocycle is optionally substituted with 1, 2, 3, 4 or 5 substituents selected from the group consisting of C$_1$-C$_6$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, —SO$_2$(CR$^{2a}$R$^{2b}$)$_m$G$^{1a}$, and —(CR$^{2a}$R$^{2b}$)$_p$G$^{3a}$; G$^{3a}$ is 4-8-membered-heterocycle, wherein the 4-8-membered-heterocycle is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkoxycarbonyl, C$_1$-C$_6$alkyl, C$_1$-C$_4$alkylcarbonyl, haloC$_1$-C$_4$alkylsulfonyl, C$_1$-C$_4$alkylsulfonyl, benzyl, cyano, 1,3-dioxolane, halogen, haloC$_1$-C$_4$alkyl, hydroxy, hydroxyC$_1$-C$_4$alkyl, oxo, —C(O)G$^{1a}$, —C(O)NHG$^{2a}$, —C(O)C(O)NH$_2$, G$^{2a}$, and —SO$_2$(CR$^{2a}$R$^{2b}$)$_m$G$^{1a}$; G$^4$ is 5-10-membered heteroaryl, wherein the 5-10-membered heteroaryl is optionally substituted with 1, 2, 3 or 4 substituents selected from the group consisting of C$_1$-C$_4$alkoxy, C$_1$-C$_4$alkoxyC$_1$-C$_4$alkyl, C$_1$-C$_4$alkyl, halogen, haloC$_1$-C$_4$alkyl, G$^{1a}$, and G$^{3a}$; m is 1, 2 or 3; n is 1, 2 or 3; and p is 1 or 2.

In one embodiment, A is (iv), wherein the nitrogen atom on the left side of (iv) is attached to the phenyl ring of the indazole in formula (I);

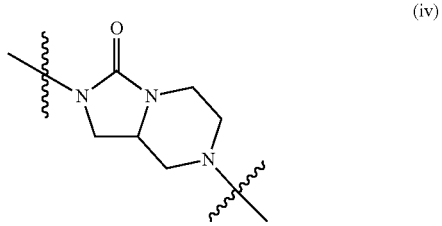 [SMILES: *N1CCN2C(=O)N(*)CC2C1]

R$^1$ is selected from the group consisting of phenyl and monocyclic heteroaryl, wherein the phenyl and monocyclic heteroaryl are optionally substituted with 1, 2, 3, or 4 substituents selected from the group consisting of C$_1$-C$_4$alkoxy, C$_1$-C$_4$alkyl, C$_1$-C$_4$haloalkoxy, C$_1$-C$_4$haloalkyl, and halogen; and R$^2$ is —CO$_2$G$^1$; G$^1$ is C$_3$-C$_7$cycloalkyl, wherein the C$_3$-C$_7$cycloalkyl is optionally substituted with 1, 2, or 3 substituents selected from the group consisting of C$_1$-C$_6$alkoxy, C$_1$-C$_4$alkyl, haloC$_1$-C$_4$alkyl, halogen, hydroxy, hydroxyC$_1$-C$_4$alkyl, and oxo.

Specific embodiments contemplated as part of the invention also include, but are not limited to, compounds of formula (I), as defined, for example:

1-[1-(2-fluorophenyl)-1H-indazol-4-yl]-3-[2-oxo-2-(pyrrolidin-1-yl)ethyl]imidazolidin-2-one;
tert-butyl 3-[1-(2-fluorophenyl)-1H-indazol-4-yl]-2-oxoimidazolidine-1-carboxylate;
2-{3-[1-(2-fluorophenyl)-1H-indazol-4-yl]-2-oxoimidazolidin-1-yl}acetamide;
isopropyl 3-[1-(2-fluorophenyl)-1H-indazol-4-yl]-2-oxoimidazolidine-1-carboxylate;
isobutyl 3-[1-(2-fluorophenyl)-1H-indazol-4-yl]-2-oxoimidazolidine-1-carboxylate;
1-[1-(2-fluorophenyl)-1H-indazol-4-yl]-3-(methylsulfonyl)imidazolidin-2-one;
1-[1-(2-fluorophenyl)-1H-indazol-4-yl]-3-{2-[(3S)-3-hydroxypyrrolidin-1-yl]-2-oxoethyl}imidazolidin-2-one;
1-[1-(2-fluorophenyl)-1H-indazol-4-yl]-3-(4-methyl-2-oxopentyl)imidazolidin-2-one;
2-{3-[1-(2-fluorophenyl)-1H-indazol-4-yl]-2-oxo-2,3-dihydro-1H-imidazol-1-yl}acetamide;
1-[1-(2-fluorophenyl)-1H-indazol-4-yl]-3-{2-[(3S)-3-fluoropyrrolidin-1-yl]-2-oxoethyl}imidazolidin-2-one;
1-[1-(2-fluorophenyl)-1H-indazol-4-yl]-3-{2-[(3S)-3-fluoropyrrolidin-1-yl]-2-oxoethyl}-1,3-dihydro-2H-imidazol-2-one;
1-[1-(2-fluorophenyl)-1H-indazol-4-yl]-3-(pyridin-2-ylmethyl)imidazolidin-2-one;
N-cyclopropyl-2-{3-[1-(2-fluorophenyl)-1H-indazol-4-yl]-2-oxoimidazolidin-1-yl}acetamide;
1-[1-(2-fluorophenyl)-1H-indazol-4-yl]-3-{[4-(trifluoromethyl)-1,3-thiazol-2-yl]methyl}imidazolidin-2-one;
1-[1-(2-fluorophenyl)-1H-indazol-4-yl]-3-{2-[(2S)-2-methylpyrrolidin-1-yl]-2-oxoethyl}imidazolidin-2-one;
1-[1-(2-fluorophenyl)-1H-indazol-4-yl]-3-{2-[(1S,4S)-2-oxa-5-azabicyclo[2.2.1]hept-5-yl]-2-oxoethyl}imidazolidin-2-one;
1-[1-(2-fluorophenyl)-1H-indazol-4-yl]-3-[2-(3-fluoropiperidin-1-yl)-2-oxoethyl]imidazolidin-2-one;

1-{2-[(2R,4S)-2-(2,5-difluorophenyl)-4-fluoropyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-(pyridin-3-yl)imidazolidin-2-one;
1-[1-(2-fluorophenyl)-1H-indazol-4-yl]-3-(pyridin-4-yl)imidazolidin-2-one;
1-{2-[(2S)-2-ethylpyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-(2-hydroxy-3,3-dimethylbutyl)imidazolidin-2-one;
1-[1-(2-fluorophenyl)-1H-indazol-4-yl]-3-{2-[(3S)-3-fluoropyrrolidin-1-yl]-2-oxoethyl}tetrahydropyrimidin-2(1H)-one;
1-[1-(2-fluorophenyl)-1H-indazol-4-yl]-3-[(4-methyl-1,3-thiazol-2-yl)methyl]imidazolidin-2-one;
1-[1-(2-fluorophenyl)-1H-indazol-4-yl]-3-{2-[(1R,4R)-2-oxa-5-azabicyclo[2.2.1]hept-5-yl]-2-oxoethyl}imidazolidin-2-one;
1-[1-(2-fluorophenyl)-1H-indazol-4-yl]-3-(1,3-oxazol-4-ylmethyl)imidazolidin-2-one;
1-[(3,5-dimethyl-1,2-oxazol-4-yl)methyl]-3-[1-(2-fluorophenyl)-1H-indazol-4-yl]imidazolidin-2-one;
1-[1-(2-fluorophenyl)-1H-indazol-4-yl]-3-(pyrimidin-2-yl)imidazolidin-2-one;
1-[1-(2-fluorophenyl)-1H-indazol-4-yl]-3-(1,3,4-oxadiazol-2-ylmethyl)imidazolidin-2-one;
1-[(5-cyclopropyl-1,3,4-thiadiazol-2-yl)methyl]-3-[1-(2-fluorophenyl)-1H-indazol-4-yl]imidazolidin-2-one;
1-[1-(2-fluorophenyl)-1H-indazol-4-yl]-3-(1,3-oxazol-2-ylmethyl)imidazolidin-2-one;
1-[1-(2-fluorophenyl)-1H-indazol-4-yl]-3-[(3R)-tetrahydrofuran-3-yl]imidazolidin-2-one;
1-[1-(2-fluorophenyl)-1H-indazol-4-yl]-3-(5-methylpyrimidin-2-yl)imidazolidin-2-one;
1-[1-(2-fluorophenyl)-1H-indazol-4-yl]-3-(1,3-thiazol-2-ylmethyl)imidazolidin-2-one;
1-[1-(2-fluorophenyl)-1H-indazol-4-yl]-3-(pyrazin-2-ylmethyl)imidazolidin-2-one;
1-[1-(2,4-difluorophenyl)-1H-indazol-4-yl]-3-(1,3-oxazol-2-ylmethyl)imidazolidin-2-one;
1-[1-(2,4-difluorophenyl)-1H-indazol-4-yl]-3-(1,3-oxazol-4-ylmethyl)imidazolidin-2-one;
(4S)-1-[1-(2-fluorophenyl)-1H-indazol-4-yl]-4-methyl-3-(1,3-oxazol-2-ylmethyl)imidazolidin-2-one;
1-[1-(2-fluorophenyl)-1H-indazol-4-yl]-3-(1,3-thiazol-4-ylmethyl)imidazolidin-2-one;
1-[1-(2-fluorophenyl)-1H-indazol-4-yl]-3-[(5-methyl-1,3,4-thiadiazol-2-yl)methyl]imidazolidin-2-one;
1-[1-(2-fluorophenyl)-1H-indazol-4-yl]-3-[(5-methyl-1,3-oxazol-2-yl)methyl]imidazolidin-2-one;
1-[1-(2-fluorophenyl)-1H-indazol-4-yl]-3-[(6-methylpyrazin-2-yl)methyl]imidazolidin-2-one;
1-[1-(2-fluorophenyl)-1H-indazol-4-yl]-3-[(3-methylpyrazin-2-yl)methyl]imidazolidin-2-one;
1-[1-(2-fluorophenyl)-1H-indazol-4-yl]-3-[(5-methyl-1,3,4-oxadiazol-2-yl)methyl]imidazolidin-2-one;
1-[(3-ethyl-1,2-oxazol-5-yl)methyl]-3-[1-(2-fluorophenyl)-1H-indazol-4-yl]imidazolidin-2-one;
1-[1-(2-fluorophenyl)-1H-indazol-4-yl]-3-[1-(3-methyl-1,2,4-oxadiazol-5-yl)ethyl]imidazolidin-2-one;
1-[(5-ethoxy-1,3,4-thiadiazol-2-yl)methyl]-3-[1-(2-fluorophenyl)-1H-indazol-4-yl]imidazolidin-2-one;
1-[(4,5-dimethyl-1,3-oxazol-2-yl)methyl]-3-[1-(2-fluorophenyl)-1H-indazol-4-yl]tetrahydropyrimidin-2(1H)-one;
1-[(5-cyclopropyl-1,3,4-oxadiazol-2-yl)methyl]-3-[1-(2-fluorophenyl)-1H-indazol-4-yl]imidazolidin-2-one;
1-[(5-cyclobutyl-1,3,4-oxadiazol-2-yl)methyl]-3-[1-(2-fluorophenyl)-1H-indazol-4-yl]imidazolidin-2-one;
1-[1-(ethylsulfonyl)azetidin-3-yl]-3-[1-(2-fluorophenyl)-1H-indazol-4-yl]imidazolidin-2-one;
1-[1-(2-fluorophenyl)-1H-indazol-4-yl]-3-{2-[(3R)-3-hydroxypiperidin-1-yl]-2-oxoethyl}imidazolidin-2-one;
1-[1-(2-fluorophenyl)-1H-indazol-4-yl]-3-{2-[(3R)-3-fluoropiperidin-1-yl]-2-oxoethyl}imidazolidin-2-one;
1-[1-(2-fluorophenyl)-1H-indazol-4-yl]-3-{2-[(3S)-3-fluoropiperidin-1-yl]-2-oxoethyl}imidazolidin-2-one;
2-{3-[1-(2-fluorophenyl)-1H-indazol-4-yl]-2-oxoimidazolidin-1-yl}-N-[(3R)-tetrahydrofuran-3-yl]acetamide;
1-{2-[(3S)-3-fluoropyrrolidin-1-yl]-2-oxoethyl}-3-[1-(3-methylphenyl)-1H-indazol-4-yl]imidazolidin-2-one;
1-[1-(2-fluorophenyl)-1H-indazol-4-yl]imidazolidin-2-one;
1-{3-[1-(2-fluorophenyl)-1H-indazol-4-yl]-2-oxoimidazolidin-1-yl}methanesulfonamide;
1-[1-(2-fluorophenyl)-1H-indazol-4-yl]-3-(2-methoxyethyl)imidazolidin-2-one;
1-(2,2-dimethylpropanoyl)-3-[1-(2-fluorophenyl)-1H-indazol-4-yl]imidazolidin-2-one;
1-[1-(2-fluorophenyl)-1H-indazol-4-yl]-3-[(3-oxocyclobutyl)carbonyl]imidazolidin-2-one;
3-[1-(2-fluorophenyl)-1H-indazol-4-yl]-N-methyl-2-oxoimidazolidine-1-sulfonamide;
1-[1-(2-fluorophenyl)-1H-indazol-4-yl]-3-[2-(2-oxoimidazolidin-1-yl)ethyl]imidazolidin-2-one;
1-[1-(2-fluorophenyl)-1H-indazol-4-yl]-3-(2-hydroxy-2-methylpropyl)imidazolidin-2-one;
1-{2-[(2R,5R)-2,5-bis(methoxymethyl)pyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-[2-(hexahydropyrrolo[1,2-c]pyrazin-2(1H)-yl)-2-oxoethyl]imidazolidin-2-one;
1-[1-(2-fluorophenyl)-1H-indazol-4-yl]-3-[2-(3-isopropoxyazetidin-1-yl)-2-oxoethyl]imidazolidin-2-one;
2-{3-[1-(2-fluorophenyl)-1H-indazol-4-yl]-2-oxoimidazolidin-1-yl}-N-methyl-N-(tetrahydro-2H-pyran-4-ylmethyl)acetamide;
1-[1-(2-fluorophenyl)-1H-indazol-4-yl]-3-[2-(4-fluoropiperidin-1-yl)-2-oxoethyl]imidazolidin-2-one;
1-[2-(2,6-dimethylmorpholin-4-yl)-2-oxoethyl]-3-[1-(2-fluorophenyl)-1H-indazol-4-yl]imidazolidin-2-one;
1-[1-(2-fluorophenyl)-1H-indazol-4-yl]-3-{2-[2-(morpholin-4-ylmethyl)pyrrolidin-1-yl]-2-oxoethyl}imidazolidin-2-one;
2-{3-[1-(2-fluorophenyl)-1H-indazol-4-yl]-2-oxoimidazolidin-1-yl}-N-methyl-N-[2-(morpholin-4-yl)ethyl]acetamide;
1-[1-(2-fluorophenyl)-1H-indazol-4-yl]-3-{2-[(3R)-3-fluoropyrrolidin-1-yl]-2-oxoethyl}imidazolidin-2-one;
N-(2-ethoxyethyl)-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-(tetrahydrofuran-3-ylmethyl)acetamide;
1-[1-(2-fluorophenyl)-1H-indazol-4-yl]-3-(4-methylpentanoyl)imidazolidin-2-one;
1-(cyclopentylsulfonyl)-3-[1-(2-fluorophenyl)-1H-indazol-4-yl]imidazolidin-2-one;
1-(cyclohexylsulfonyl)-3-[1-(2-fluorophenyl)-1H-indazol-4-yl]imidazolidin-2-one;
1-[1-(2-fluorophenyl)-1H-indazol-4-yl]-3-(2-thienylsulfonyl)imidazolidin-2-one;
1-[1-(2-fluorophenyl)-1H-indazol-4-yl]-3-(isobutylsulfonyl)imidazolidin-2-one;

1-[1-(2-fluorophenyl)-1H-indazol-4-yl]-3-(propylsulfonyl)
imidazolidin-2-one;
1-[1-(2-fluorophenyl)-1H-indazol-4-yl]-3-(isopropylsulfonyl)imidazolidin-2-one;
1-(ethylsulfonyl)-3-[1-(2-fluorophenyl)-1H-indazol-4-yl]
imidazolidin-2-one;
1-[1-(2-fluorophenyl)-1H-indazol-4-yl]-3-{2-[(3R)-3-hydroxypyrrolidin-1-yl]-2-oxoethyl}imidazolidin-2-one;
1-[1-(2-fluorophenyl)-1H-indazol-4-yl]-3-{2-[(3S)-3-(2-hydroxypropan-2-yl)pyrrolidin-1-yl]-2-oxoethyl}imidazolidin-2-one;
1-[2-(3,3-difluoropyrrolidin-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-[(3S)-tetrahydrofuran-3-yl]acetamide;
1-{2-[(3S)-3-fluoropyrrolidin-1-yl]-2-oxoethyl}-3-{1-[3-(trifluoromethoxy)phenyl]-1H-indazol-4-yl}imidazolidin-2-one;
1-[1-(2-fluorophenyl)-1H-indazol-4-yl]-3-{[5-(trifluoromethyl)pyridin-2-yl]methyl}imidazolidin-2-one;
1-[1-(2-fluorophenyl)-1H-indazol-4-yl]-3-{2-[(3S)-3-methylpyrrolidin-1-yl]-2-oxoethyl}imidazolidin-2-one;
1-[2-(3,3-difluoroazetidin-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-isobutylacetamide;
N,N-diethyl-2-{3-[1-(2-fluorophenyl)-1H-indazol-4-yl]-2-oxoimidazolidin-1-yl}acetamide;
1-[2-(azetidin-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-isopropylacetamide;
1-[1-(2-fluorophenyl)-1H-indazol-4-yl]-3-(isopropoxyacetyl)imidazolidin-2-one;
1-[1-(2-fluorophenyl)-1H-indazol-4-yl]-3-{[4-(trifluoromethyl)pyridin-2-yl]methyl}imidazolidin-2-one;
1-{2-[3-(ethoxymethyl)-3-fluoropyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-{2-[(8aS)-hexahydropyrrolo[1,2-c]pyrazin-2(1H)-yl]-2-oxoethyl}imidazolidin-2-one;
1-[1-(2-fluorophenyl)-1H-indazol-4-yl]-3-[2-(2-oxa-6-azaspiro[3.3]hept-6-yl)-2-oxoethyl]imidazolidin-2-one;
1-[2-(3,5-dimethylmorpholin-4-yl)-2-oxoethyl]-3-[1-(2-fluorophenyl)-1H-indazol-4-yl]imidazolidin-2-one;
1-[2-(1,4-dioxa-7-azaspiro[4.4]non-7-yl)-2-oxoethyl]-3-[1-(2-fluorophenyl)-1H-indazol-4-yl]imidazolidin-2-one;
4-({3-[1-(2-fluorophenyl)-1H-indazol-4-yl]-2-oxoimidazolidin-1-yl}acetyl)piperazine-2,6-dione;
1-[1-(2-fluorophenyl)-1H-indazol-4-yl]-3-[2-(5-methylhexahydropyrrolo[3,4-c]pyrrol-2(1H)-yl)-2-oxoethyl]imidazolidin-2-one;
1-[1-(2-fluorophenyl)-1H-indazol-4-yl]-3-[2-(octahydro-4H-1,4-benzoxazin-4-yl)-2-oxoethyl]imidazolidin-2-one;
1-[1-(2-fluorophenyl)-1H-indazol-4-yl]-3-[2-(hexahydrocyclopenta[c]pyrrol-2(1H)-yl)-2-oxoethyl]imidazolidin-2-one;
1-{2-[(1R,3r,6s,8S)-4-azatricyclo[4.3.1.1$^{3,8}$]undec-4-yl]-2-oxoethyl}-3-[1-(2-fluorophenyl)-1H-indazol-4-yl]imidazolidin-2-one;
(3aR,6aS)-5-({3-[1-(2-fluorophenyl)-1H-indazol-4-yl]-2-oxoimidazolidin-1-yl}acetyl)-2-methyltetrahydropyrrolo[3,4-c]pyrrole-1,3(2H,3aH)-dione;
1-[1-(2-fluorophenyl)-1H-indazol-4-yl]-3-[2-(8-methoxy-3-azabicyclo[3.2.1]oct-3-yl)-2-oxoethyl]imidazolidin-2-one;
1-[2-(1,4-dioxa-8-azaspiro[4.6]undec-8-yl)-2-oxoethyl]-3-[1-(2-fluorophenyl)-1H-indazol-4-yl]imidazolidin-2-one;
1-[1-(2-fluorophenyl)-1H-indazol-4-yl]-3-{2-[(3aR,4R,7S,7aS)-octahydro-2H-4,7-methanoisoindol-2-yl]-2-oxoethyl}imidazolidin-2-one;
1-[1-(2-fluorophenyl)-1H-indazol-4-yl]-3-[2-(1-methyloctahydro-6H-pyrrolo[3,4-b]pyridin-6-yl)-2-oxoethyl]imidazolidin-2-one;
1-[1-(2-fluorophenyl)-1H-indazol-4-yl]-3-{2-[(3R)-3-methylmorpholin-4-yl]-2-oxoethyl}imidazolidin-2-one;
1-[1-(2-fluorophenyl)-1H-indazol-4-yl]-3-{2-[(1R,6S)-9-methyl-3,9-diazabicyclo[4.2.1]non-3-yl]-2-oxoethyl}imidazolidin-2-one;
1-[2-(2-ethylpyrrolidin-1-yl)-2-oxoethyl]-3-[1-(2-fluorophenyl)-1H-indazol-4-yl]imidazolidin-2-one;
1-[1-(2-fluorophenyl)-1H-indazol-4-yl]-3-[2-(2-isopropylpyrrolidin-1-yl)-2-oxoethyl]imidazolidin-2-one;
1-[1-(2-fluorophenyl)-1H-indazol-4-yl]-3-[2-(2-isobutylpyrrolidin-1-yl)-2-oxoethyl]imidazolidin-2-one;
1-[1-(2-fluorophenyl)-1H-indazol-4-yl]-3-{2-[(2R)-2-methylpyrrolidin-1-yl]-2-oxoethyl}imidazolidin-2-one;
methyl 1-({3-[1-(2-fluorophenyl)-1H-indazol-4-yl]-2-oxoimidazolidin-1-yl}acetyl)-D-prolinate;
1-({3-[1-(2-fluorophenyl)-1H-indazol-4-yl]-2-oxoimidazolidin-1-yl}acetyl)-N-phenyl-D-prolinamide;
1-{2-[(2R,4R)-2-(2,5-difluorophenyl)-4-hydroxypyrrolidin-1-yl]-2-oxoethyl}-3-[1-(2-fluorophenyl)-1H-indazol-4-yl]imidazolidin-2-one;
1-{2-[(2R,4S)-2-(2,5-difluorophenyl)-4-hydroxypyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-(2-hydroxy-4-methylpentyl)imidazolidin-2-one;
1-[1-(2-fluorophenyl)-1H-indazol-4-yl]-3-{2-[(2R)-2-isopropylpiperidin-1-yl]-2-oxoethyl}imidazolidin-2-one;
1-[1-(2-fluorophenyl)-1H-indazol-4-yl]-3-{2-[(2S)-2-isopropylpyrrolidin-1-yl]-2-oxoethyl}imidazolidin-2-one;
1-[1-(2-fluorophenyl)-1H-indazol-4-yl]-3-{2-[(2R)-2-isopropylpyrrolidin-1-yl]-2-oxoethyl}imidazolidin-2-one;
1-{2-[(2R,4R)-2-(2,5-difluorophenyl)-4-fluoropyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-{2-oxo-2-[(2R)-2-phenylpyrrolidin-1-yl]ethyl}imidazolidin-2-one;
1-[1-(2-fluorophenyl)-1H-indazol-4-yl]-3-[2-oxo-2-(2-phenylpyrrolidin-1-yl)ethyl]imidazolidin-2-one;
1-[1-(2-fluorophenyl)-1H-indazol-4-yl]-3-(pyridin-2-yl)imidazolidin-2-one;
cyclohexyl 3-[1-(2-fluorophenyl)-1H-indazol-4-yl]-2-oxoimidazolidine-1-carboxylate;
1-[1-(2-fluorophenyl)-1H-indazol-4-yl]-3-(6-methyl-2-oxoheptyl)imidazolidin-2-one;
1-[1-(2-fluorophenyl)-1H-indazol-4-yl]-3-(2-hydroxy-6-methylheptyl)imidazolidin-2-one;
1-(3-cyclopentyl-2-oxopropyl)-3-[1-(2-fluorophenyl)-1H-indazol-4-yl]imidazolidin-2-one;
1-(3-cyclopentyl-2-hydroxypropyl)-3-[1-(2-fluorophenyl)-1H-indazol-4-yl]imidazolidin-2-one;
1-(3-cyclohexyl-2-oxopropyl)-3-[1-(2-fluorophenyl)-1H-indazol-4-yl]imidazolidin-2-one;
cyclopentyl 2-[1-(2-fluorophenyl)-1H-indazol-4-yl]-3-oxohexahydroimidazo[1,5-a]pyrazine-7(1H)-carboxylate;
1-[1-(2-fluorophenyl)-1H-indazol-4-yl]-3-(pyrimidin-5-yl)imidazolidin-2-one;
1-(3-cyclohexyl-2-hydroxypropyl)-3-[1-(2-fluorophenyl)-1H-indazol-4-yl]imidazolidin-2-one;

1-(3-cyclobutyl-2-oxopropyl)-3-[1-(2-fluorophenyl)-1H-indazol-4-yl]imidazolidin-2-one;
1-(3-cyclobutyl-2-hydroxypropyl)-3-[1-(2-fluorophenyl)-1H-indazol-4-yl]imidazolidin-2-one;
1-[3-(bicyclo[2.2.1]hept-2-yl)-2-oxopropyl]-3-[1-(2-fluorophenyl)-1H-indazol-4-yl]imidazolidin-2-one;
1-[1-(2-fluorophenyl)-1H-indazol-4-yl]-3-(2-oxo-2-phenylethyl)imidazolidin-2-one;
1-(2-cyclopentyl-2-oxoethyl)-3-[1-(2-fluorophenyl)-1H-indazol-4-yl]imidazolidin-2-one;
1-[1-(2-fluorophenyl)-1H-indazol-4-yl]-3-(2-oxopropyl)imidazolidin-2-one;
1-[1-(2-fluorophenyl)-1H-indazol-4-yl]-3-(2-hydroxy-2-methylhex-5-en-1-yl)imidazolidin-2-one;
1-[1-(2-fluorophenyl)-1H-indazol-4-yl]-3-[2-(6-fluoropyridin-3-yl)-2-oxoethyl]imidazolidin-2-one;
1-(2-ethyl-2-hydroxy-4-methylpentyl)-3-[1-(2-fluorophenyl)-1H-indazol-4-yl]imidazolidin-2-one;
1-[1-(2-fluorophenyl)-1H-indazol-4-yl]-3-[2-(3-methoxyphenyl)-2-oxoethyl]imidazolidin-2-one;
1-[1-(2-fluorophenyl)-1H-indazol-4-yl]-3-[2-(3-fluorophenyl)-2-oxoethyl]imidazolidin-2-one;
1-[1-(2-fluorophenyl)-1H-indazol-4-yl]-3-{2-oxo-2-[4-(trifluoromethyl)phenyl]ethyl}imidazolidin-2-one;
1-[1-(2-fluorophenyl)-1H-indazol-4-yl]-3-[2-oxo-2-(pyridin-3-yl)ethyl]imidazolidin-2-one;
1-[2-(1,3-benzodioxol-5-yl)-2-oxoethyl]-3-[1-(2-fluorophenyl)-1H-indazol-4-yl]imidazolidin-2-one;
1-[1-(2-fluorophenyl)-1H-indazol-4-yl]-3-(4-fluoropyridin-3-yl)imidazolidin-2-one;
1-[1-(2-fluorophenyl)-1H-indazol-4-yl]-3-[(2R)-2-hydroxy-4-methylpentyl]imidazolidin-2-one;
1-[1-(2-fluorophenyl)-1H-indazol-4-yl]-3-[(2S)-2-hydroxy-4-methylpentyl]imidazolidin-2-one;
1-[1-(2-fluorophenyl)-1H-indazol-4-yl]-3-[2-oxo-3-(tetrahydrofuran-3-yl)propyl]imidazolidin-2-one;
1-[1-(2-fluorophenyl)-1H-indazol-4-yl]-3-(1,3-thiazol-5-yl)imidazolidin-2-one;
1-[1-(2-fluorophenyl)-1H-indazol-4-yl]-3-[(2S)-1-hydroxybutan-2-yl]imidazolidin-2-one;
1-[1-(2-fluorophenyl)-1H-indazol-4-yl]-3-[(2R)-2-hydroxybutyl]imidazolidin-2-one;
1-(3,3-dimethyl-2-oxobutyl)-3-[1-(2-fluorophenyl)-1H-indazol-4-yl]imidazolidin-2-one;
1-[1-(2-fluorophenyl)-1H-indazol-4-yl]-3-(3-methyl-2-oxobutyl)imidazolidin-2-one;
1-[1-(2-fluorophenyl)-1H-indazol-4-yl]-3-(2-hydroxy-3-methylbutyl)imidazolidin-2-one;
1-(2-cyclobutyl-2-oxoethyl)-3-[1-(2-fluorophenyl)-1H-indazol-4-yl]imidazolidin-2-one;
1-(2-cyclobutyl-2-hydroxyethyl)-3-[1-(2-fluorophenyl)-1H-indazol-4-yl]imidazolidin-2-one;
1-(2-cyclobutyl-1-hydroxy-2-oxoethyl)-3-[1-(2-fluorophenyl)-1H-indazol-4-yl]imidazolidin-2-one;
1-[1-(2-fluorophenyl)-1H-indazol-4-yl]-3-[(2R)-2-hydroxy-2,4-dimethylpentyl]imidazolidin-2-one;
1-[1-(2-fluorophenyl)-1H-indazol-4-yl]-3-[(2S)-2-hydroxy-2,4-dimethylpentyl]imidazolidin-2-one;
1-[1-(2-fluorophenyl)-1H-indazol-4-yl]-3-{2-oxo-2-[(2S)-2-(trifluoromethyl)pyrrolidin-1-yl]ethyl}imidazolidin-2-one;
1-[1-(2-fluorophenyl)-1H-indazol-4-yl]-3-{2-[(2R)-2-(methoxymethyl)pyrrolidin-1-yl]-2-oxoethyl}imidazolidin-2-one;
1-[1-(2-fluorophenyl)-1H-indazol-4-yl]-3-{2-oxo-2-[(2R)-2-(trifluoromethyl)pyrrolidin-1-yl]ethyl}imidazolidin-2-one;
1-[2-(2,2-dimethylpyrrolidin-1-yl)-2-oxoethyl]-3-[1-(2-fluorophenyl)-1H-indazol-4-yl]imidazolidin-2-one;
N-(3-fluorobenzyl)-2-{3-[1-(2-fluorophenyl)-1H-indazol-4-yl]-2-oxoimidazolidin-1-yl}acetamide;
N-(2,5-difluorobenzyl)-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-(2-methylbenzyl)acetamide;
2-{3-[1-(2-fluorophenyl)-1H-indazol-4-yl]-2-oxoimidazolidin-1-yl}-N-[(1R)-1-phenylethyl]acetamide;
N-(3,5-difluorobenzyl)-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-[(1S)-1-phenylethyl]acetamide;
1-(1,3-benzothiazol-2-ylmethyl)-3-[1-(2-fluorophenyl)-1H-indazol-4-yl]imidazolidin-2-one;
1-[1-(2-fluorophenyl)-1H-indazol-4-yl]-3-(2-hydroxy-2,3-dimethylbutyl)imidazolidin-2-one;
1-(cyclopentylmethyl)-3-[1-(2-fluorophenyl)-1H-indazol-4-yl]imidazolidin-2-one;
1-[1-(2-fluorophenyl)-1H-indazol-4-yl]-3-(tetrahydrofuran-2-ylmethyl)imidazolidin-2-one;
1-(2-cyclopropyl-2-oxoethyl)-3-[1-(2-fluorophenyl)-1H-indazol-4-yl]imidazolidin-2-one;
1-cyclobutyl-3-[1-(2-fluorophenyl)-1H-indazol-4-yl]imidazolidin-2-one;
1-[1-(2-fluorophenyl)-1H-indazol-4-yl]-3-[(3R,5R)-5-(2-fluorophenyl)tetrahydrofuran-3-yl]imidazolidin-2-one;
1-[1-(2-fluorophenyl)-1H-indazol-4-yl]-3-(2-hydroxy-4-methylpentyl)tetrahydropyrimidin-2(1H)-one;
1-[1-(2-fluorophenyl)-1H-indazol-4-yl]-3-{2-[(2S)-2-methylpyrrolidin-1-yl]-2-oxoethyl}tetrahydropyrimidin-2(1H)-one;
1-[1-(2-fluorophenyl)-1H-indazol-4-yl]-3-(4-methyl-2-oxopentyl)tetrahydropyrimidin-2(1H)-one;
1-[(2,2-difluorocyclopropyl)methyl]-3-[1-(2-fluorophenyl)-1H-indazol-4-yl]imidazolidin-2-one;
1-[1-(2-fluorophenyl)-1H-indazol-4-yl]-3-(pyrazolo[1,5-a]pyrimidin-3-yl)imidazolidin-2-one;
1-[1-(2-fluorophenyl)-1H-indazol-4-yl]-3-(2-methyl-2H-indazol-5-yl)imidazolidin-2-one;
1-(5-cyclopropyl-2-furyl)-3-[1-(2-fluorophenyl)-1H-indazol-4-yl]imidazolidin-2-one;
1-[1-(2-fluorophenyl)-1H-indazol-4-yl]-3-(2-phenylethyl)imidazolidin-2-one;
1-(cyclopropylmethyl)-3-[1-(2-fluorophenyl)-1H-indazol-4-yl]imidazolidin-2-one;
2,5-anhydro-1,3,4-trideoxy-2-(3-fluorophenyl)-4-{3-[1-(2-fluorophenyl)-1H-indazol-4-yl]-2-oxoimidazolidin-1-yl}-D-erythro-pentitol;
1-[1-(2-fluorophenyl)-1H-indazol-4-yl]-3-[(3R,5S)-5-(3-fluorophenyl)tetrahydrofuran-3-yl]imidazolidin-2-one;
1-(2,5-difluorobenzyl)-3-[1-(2-fluorophenyl)-1H-indazol-4-yl]imidazolidin-2-one;
1-[1-(2-fluorophenyl)-1H-indazol-4-yl]-3-(pyridin-3-ylmethyl)imidazolidin-2-one;
1-[1-(2-fluorophenyl)-1H-indazol-4-yl]-3-[(5-methyl-1,2-oxazol-3-yl)methyl]imidazolidin-2-one;
1-[1-(2-fluorophenyl)-1H-indazol-4-yl]-3-(oxetan-3-ylmethyl)imidazolidin-2-one;
(2R)-1-({3-[1-(2-fluorophenyl)-1H-indazol-4-yl]-2-oxoimidazolidin-1-yl}acetyl)pyrrolidine-2-carbonitrile;
1-[2-(2-azabicyclo[2.2.1]hept-2-yl)-2-oxoethyl]-3-[1-(2-fluorophenyl)-1H-indazol-4-yl]imidazolidin-2-one;
2,5-anhydro-1,3,4-trideoxy-2-(3-fluorophenyl)-4-{3-[1-(2-fluorophenyl)-1H-indazol-4-yl]-2-oxoimidazolidin-1-yl}-L-threo-pentitol;

1-[1-(2-fluorophenyl)-1H-indazol-4-yl]-3-(3-hydroxycyclopentyl)imidazolidin-2-one;
1-[2-(3-ethyl-3-hydroxyazetidin-1-yl)-2-oxoethyl]-3-[1-(2-fluorophenyl)-1H-indazol-4-yl]imidazolidin-2-one;
1-[2-(3,4-difluoropyrrolidin-1-yl)-2-oxoethyl]-3-[1-(2-fluorophenyl)-1H-indazol-4-yl]imidazolidin-2-one;
1-[1-(2-fluorophenyl)-1H-indazol-4-yl]-3-[5-(morpholin-4-yl)pyridin-3-yl]imidazolidin-2-one;
1-[1-(2-fluorophenyl)-1H-indazol-4-yl]-3-(pyridazin-3-yl)imidazolidin-2-one;
N-(cyclopropylmethyl)-2-{3-[1-(2-fluorophenyl)-1H-indazol-4-yl]-2-oxoimidazolidin-1-yl}acetamide;
1-[1-(2-fluorophenyl)-1H-indazol-4-yl]-3-(pyridin-4-ylmethyl)imidazolidin-2-one;
1-[1-(2-fluorophenyl)-1H-indazol-4-yl]-3-[(2-methyl-1,3-oxazol-4-yl)methyl]imidazolidin-2-one;
1-{2-[(1s,4s)-7-azabicyclo[2.2.1]hept-7-yl]-2-oxoethyl}-3-[1-(2-fluorophenyl)-1H-indazol-4-yl]imidazolidin-2-one;
1-[1-(2-fluorophenyl)-1H-indazol-4-yl]-3-[(3-methyloxetan-3-yl)methyl]imidazolidin-2-one;
1-[1-(2-fluorophenyl)-1H-indazol-4-yl]-3-[(2R)-2-methoxy-4-methylpentyl]imidazolidin-2-one;
1-[1-(2-fluorophenyl)-1H-indazol-4-yl]-3-[(2S)-2-methoxy-4-methylpentyl]imidazolidin-2-one;
1-[(1-acetylazetidin-3-yl)methyl]-3-[1-(2-fluorophenyl)-1H-indazol-4-yl]imidazolidin-2-one;
1-[1-(2-fluorophenyl)-1H-indazol-4-yl]-3-[(2-methyl-1,3-thiazol-4-yl)methyl]imidazolidin-2-one;
1-[1-(2-fluorophenyl)-1H-indazol-4-yl]-3-(pyrimidin-2-ylmethyl)imidazolidin-2-one;
1-[1-(2-fluorophenyl)-1H-indazol-4-yl]-3-[(5-methylpyrimidin-2-yl)methyl]imidazolidin-2-one;
1-[1-(2-fluorophenyl)-1H-indazol-4-yl]-3-[2-(pyridin-3-yl)ethyl]imidazolidin-2-one;
1-[1-(2-fluorophenyl)-1H-indazol-4-yl]-3-(1,3-thiazol-2-yl)imidazolidin-2-one;
1-[1-(2-fluorophenyl)-1H-indazol-4-yl]-3-(pyrimidin-4-ylmethyl)imidazolidin-2-one;
1-[1-(2-fluorophenyl)-1H-indazol-4-yl]-3-(oxetan-2-ylmethyl)imidazolidin-2-one;
1-[1-(2-fluorophenyl)-1H-indazol-4-yl]-3-[(3S)-tetrahydrofuran-3-yl]imidazolidin-2-one;
1-[1-(2-fluorophenyl)-1H-indazol-4-yl]-3-(1,3-oxazol-4-ylmethyl)tetrahydropyrimidin-2(1H)-one;
1-[1-(2-fluorophenyl)-1H-indazol-4-yl]-3-(pyrazin-2-yl)imidazolidin-2-one;
1-[(2,5-dimethyl-1,3-oxazol-4-yl)methyl]-3-[1-(2-fluorophenyl)-1H-indazol-4-yl]imidazolidin-2-one;
1-[1-(2-fluorophenyl)-1H-indazol-4-yl]-3-[(5-methylpyridin-3-yl)methyl]imidazolidin-2-one;
1-{[1-(benzyloxy)cyclopropyl]methyl}-3-[1-(2-fluorophenyl)-1H-indazol-4-yl]imidazolidin-2-one;
1-[1-(2-fluorophenyl)-1H-indazol-4-yl]-3-(5-methoxypyridin-3-yl)imidazolidin-2-one;
1-[1-(2-fluorophenyl)-1H-indazol-4-yl]-3-(1,3-oxazol-5-ylmethyl)imidazolidin-2-one;
1-(1-benzyl-2-oxopyrrolidin-3-yl)-3-[1-(2-fluorophenyl)-1H-indazol-4-yl]imidazolidin-2-one;
1-[(5-tert-butyl-1,3-oxazol-2-yl)methyl]-3-[1-(2-fluorophenyl)-1H-indazol-4-yl]imidazolidin-2-one;
1-[1-(2,4-difluorophenyl)-1H-indazol-4-yl]-3-[(5-methyl-1,3,4-thiadiazol-2-yl)methyl]imidazolidin-2-one;
1-(1,3-oxazol-2-ylmethyl)-3-{1-[4-(trifluoromethyl)phenyl]-1H-indazol-4-yl}imidazolidin-2-one;
1-(3,5-dimethyl-1,2-oxazol-4-yl)-3-[1-(2-fluorophenyl)-1H-indazol-4-yl]imidazolidin-2-one;
1-[1-(2-fluorophenyl)-1H-indazol-4-yl]-3-[(5-isopropyl-1,3-oxazol-2-yl)methyl]imidazolidin-2-one;
1-[(4,5-dimethyl-1,3-oxazol-2-yl)methyl]-3-[1-(2-fluorophenyl)-1H-indazol-4-yl]imidazolidin-2-one;
1-[(2,5-dimethyl-1,3-thiazol-4-yl)methyl]-3-[1-(2-fluorophenyl)-1H-indazol-4-yl]imidazolidin-2-one;
1-[(5-methyl-1,3,4-thiadiazol-2-yl)methyl]-3-{1-[4-(trifluoromethyl)phenyl]-1H-indazol-4-yl}imidazolidin-2-one;
tert-butyl (5R)-3-[1-(2-fluorophenyl)-1H-indazol-4-yl]-5-methyl-2-oxoimidazolidine-1-carboxylate;
1-(1,3-oxazol-4-ylmethyl)-3-{1-[4-(trifluoromethyl)phenyl]-1H-indazol-4-yl}imidazolidin-2-one;
1-[1-(2,4-difluorophenyl)-1H-indazol-4-yl]-3-[(2-methyl-1,3-thiazol-4-yl)methyl]imidazolidin-2-one;
1-[1-(2-fluorophenyl)-1H-indazol-4-yl]-3-[(3-methyl-1,2-oxazol-5-yl)methyl]imidazolidin-2-one;
1-[1-(2-fluorophenyl)-1H-indazol-4-yl]-3-[(5-methyl-1,3-thiazol-4-yl)methyl]imidazolidin-2-one;
(4R)-1-[1-(2-fluorophenyl)-1H-indazol-4-yl]-4-methylimidazolidin-2-one;
(4R)-1-[1-(2-fluorophenyl)-1H-indazol-4-yl]-4-methyl-3-(1,3-oxazol-2-ylmethyl)imidazolidin-2-one;
1-[1-(2-fluorophenyl)-1H-indazol-4-yl]-3-[(3-methoxypyrazin-2-yl)methyl]imidazolidin-2-one;
1-[1-(2-fluorophenyl)-1H-indazol-4-yl]-3-[(3-isopropyl-1,2-oxazol-5-yl)methyl]imidazolidin-2-one;
1-[(2-ethyl-1,3-thiazol-4-yl)methyl]-3-[1-(2-fluorophenyl)-1H-indazol-4-yl]imidazolidin-2-one;
1-[1-(2-fluorophenyl)-1H-indazol-4-yl]-3-[(5-isopropyl-1,2-oxazol-3-yl)methyl]imidazolidin-2-one;
1-[(5-cyclopropyl-1,2-oxazol-3-yl)methyl]-3-[1-(2-fluorophenyl)-1H-indazol-4-yl]imidazolidin-2-one;
1-[1-(2,4-difluorophenyl)-1H-indazol-4-yl]-3-[(1R)-1-(3-methyl-1,2,4-oxadiazol-5-yl)ethyl]imidazolidin-2-one;
1-[1-(2-fluorophenyl)-1H-indazol-4-yl]-3-{[2-(methoxymethyl)-1,3-thiazol-4-yl]methyl}imidazolidin-2-one;
1-[1-(2-fluorophenyl)-1H-indazol-4-yl]-3-(1,3-oxazol-2-ylmethyl)tetrahydropyrimidin-2(1H)-one;
1-[1-(2-fluorophenyl)-1H-indazol-4-yl]-3-[(5-isopropyl-1,3,4-oxadiazol-2-yl)methyl]imidazolidin-2-one;
1-[1-(2-fluorophenyl)-1H-indazol-4-yl]-3-[(5-methylpyrazin-2-yl)methyl]imidazolidin-2-one;
1-[(3,5-dimethyl-1,2-oxazol-4-yl)methyl]-3-[1-(2-fluorophenyl)-1H-indazol-4-yl]tetrahydropyrimidin-2(1H)-one;
1-[1-(2-fluorophenyl)-1H-indazol-4-yl]-3-[(6-methylpyrazin-2-yl)methyl]tetrahydropyrimidin-2(1H)-one;
1-[1-(2-fluorophenyl)-1H-indazol-4-yl]-3-[(5-methyl-1,3,4-oxadiazol-2-yl)methyl]tetrahydropyrimidin-2(1H)-one;
1-[(5-ethyl-1,3,4-oxadiazol-2-yl)methyl]-3-[1-(2-fluorophenyl)-1H-indazol-4-yl]imidazolidin-2-one;
1-[(5-tert-butyl-1,3,4-oxadiazol-2-yl)methyl]-3-[1-(2-fluorophenyl)-1H-indazol-4-yl]imidazolidin-2-one;
1-[1-(2-fluorophenyl)-1H-indazol-4-yl]-3-[(5-methyl-1,3-thiazol-2-yl)methyl]imidazolidin-2-one;
1-[1-(2-fluorophenyl)-1H-indazol-4-yl]-3-[(3-methyl-1,2-oxazol-4-yl)methyl]imidazolidin-2-one;
1-[1-(2-fluorophenyl)-1H-indazol-4-yl]-3-(trans-4-hydroxycyclohexyl)imidazolidin-2-one;
1-[1-(2-fluorophenyl)-1H-indazol-4-yl]-3-(4-oxocyclohexyl)imidazolidin-2-one;
tert-butyl 3-{3-[1-(2-fluorophenyl)-1H-indazol-4-yl]-2-oxoimidazolidin-1-yl}azetidine-1-carboxylate;
1-(azetidin-3-yl)-3-[1-(2-fluorophenyl)-1H-indazol-4-yl]imidazolidin-2-one;
1-[1-(2-fluorophenyl)-1H-indazol-4-yl]-3-{1-[(1-hydroxycyclopropyl)carbonyl]azetidin-3-yl}imidazolidin-2-one;

2-(3-{3-[1-(2-fluorophenyl)-1H-indazol-4-yl]-2-oxoimidazolidin-1-yl}azetidin-1-yl)-2-oxoacetamide;
1-[1-(2-fluorophenyl)-1H-indazol-4-yl]-3-[1-(methylsulfonyl)azetidin-3-yl]imidazolidin-2-one;
1-[(1R,2R)-2-(benzyloxy)cyclohexyl]-3-[1-(2-fluorophenyl)-1H-indazol-4-yl]imidazolidin-2-one;
1-[1-(2-fluorophenyl)-1H-indazol-4-yl]-3-[(1R,2R)-2-hydroxycyclohexyl]imidazolidin-2-one;
1-[1-(2-fluorophenyl)-1H-indazol-4-yl]-3-[1-(propylsulfonyl)azetidin-3-yl]imidazolidin-2-one;
1-[(1S,2S)-2-(benzyloxy)cyclohexyl]-3-[1-(2-fluorophenyl)-1H-indazol-4-yl]imidazolidin-2-one;
1-[1-(2-fluorophenyl)-1H-indazol-4-yl]-3-[(1S,2S)-2-hydroxycyclohexyl]imidazolidin-2-one;
1-[2-oxo-2-(pyrrolidin-1-yl)ethyl]-3-(1-phenyl-1H-indazol-4-yl)imidazolidin-2-one;
1-[2-oxo-2-(pyrrolidin-1-yl)ethyl]-3-[1-(pyridin-2-yl)-1H-indazol-4-yl]imidazolidin-2-one;
1-[1-(2-fluorophenyl)-1H-indazol-4-yl]-3-[(1S,2S)-2-methoxycyclohexyl]imidazolidin-2-one;
1-[1-(2-fluorophenyl)-1H-indazol-4-yl]-3-[(1S,2S)-2-isobutoxycyclohexyl]imidazolidin-2-one;
1-[1-(2-fluorophenyl)-1H-indazol-4-yl]-3-[(1S)-2-oxocyclohexyl]imidazolidin-2-one;
1-(1-{[(2,2-dichlorocyclopropyl)methyl]sulfonyl}azetidin-3-yl)-3-[1-(2-fluorophenyl)-1H-indazol-4-yl]imidazolidin-2-one;
1-{1-[(cyclopropylmethyl)sulfonyl]azetidin-3-yl}-3-[1-(2-fluorophenyl)-1H-indazol-4-yl]imidazolidin-2-one;
1-[1-(2-fluorophenyl)-1H-indazol-4-yl]-3-{1-[(2,2,2-trifluoroethyl)sulfonyl]azetidin-3-yl}imidazolidin-2-one;
1-[1-(2-fluorophenyl)-1H-indazol-4-yl]-3-[1-(isobutylsulfonyl)azetidin-3-yl]imidazolidin-2-one;
tert-butyl {3-[1-(2-fluorophenyl)-1H-indazol-4-yl]-2-oxoimidazolidin-1-yl}acetate;
ethyl (2Z)-3-{3-[1-(2-fluorophenyl)-1H-indazol-4-yl]-2-oxoimidazolidin-1-yl}acrylate;
ethyl (2E)-3-{3-[1-(2-fluorophenyl)-1H-indazol-4-yl]-2-oxoimidazolidin-1-yl}acrylate;
tert-butyl 3-{3-[1-(2-fluorophenyl)-1H-indazol-4-yl]-2-oxoimidazolidin-1-yl}propanoate;
1-[1-(2-fluorophenyl)-1H-indazol-4-yl]-3-{2-[(3S)-3-hydroxypiperidin-1-yl]-2-oxoethyl}imidazolidin-2-one;
1-[1-(2-fluorophenyl)-1H-indazol-4-yl]-3-[2-(3-hydroxyazetidin-1-yl)-2-oxoethyl]imidazolidin-2-one;
1-[1-(2-fluorophenyl)-1H-indazol-4-yl]-3-{3-[(3S)-3-fluoropyrrolidin-1-yl]-3-oxopropyl}imidazolidin-2-one;
1-[1-(2-fluorophenyl)-1H-indazol-4-yl]-3-[2-(morpholin-4-yl)-2-oxoethyl]imidazolidin-2-one;
1-(1-cyclohexyl-1H-indazol-4-yl)-3-{2-[(3S)-3-fluoropyrrolidin-1-yl]-2-oxoethyl}imidazolidin-2-one;
1-[1-(2-fluorophenyl)-1H-indazol-4-yl]-3-[2-oxo-2-(piperidin-1-yl)ethyl]imidazolidin-2-one;
1-[2-(3,3-difluoropiperidin-1-yl)-2-oxoethyl]-3-[1-(2-fluorophenyl)-1H-indazol-4-yl]imidazolidin-2-one;
1-[2-(4,4-difluoropiperidin-1-yl)-2-oxoethyl]-3-[1-(2-fluorophenyl)-1H-indazol-4-yl]imidazolidin-2-one;
1-[2-(3-fluoroazetidin-1-yl)-2-oxoethyl]-3-[1-(2-fluorophenyl)-1H-indazol-4-yl]imidazolidin-2-one;
1-[1-(2-fluorophenyl)-1H-indazol-4-yl]-3-{2-oxo-2-[4-(trifluoromethyl)piperidin-1-yl]ethyl}imidazolidin-2-one;
1-[1-(2-fluorophenyl)-1H-indazol-4-yl]-3-{2-oxo-2-[3-(trifluoromethyl)piperidin-1-yl]ethyl}imidazolidin-2-one;
1-[1-(2-fluorophenyl)-1H-indazol-4-yl]-3-{2-[(1R,5S)-8-oxa-3-azabicyclo[3.2.1]oct-3-yl]-2-oxoethyl}imidazolidin-2-one;
1-[1-(2-fluorophenyl)-1H-indazol-4-yl]-3-[2-oxo-2-(3-oxopyrrolidin-1-yl)ethyl]imidazolidin-2-one;
1-[2-(azepan-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-(2,2,2-trifluoroethyl)acetamide;
1-[1-(3,3-dimethylbutyl)-1H-indazol-4-yl]-3-[2-oxo-2-(pyrrolidin-1-yl)ethyl]imidazolidin-2-one;
1-(1-tert-butyl-1H-indazol-4-yl)-3-{2-[(3S)-3-fluoropyrrolidin-1-yl]-2-oxoethyl}imidazolidin-2-one;
1-{2-[(3S)-3-fluoropyrrolidin-1-yl]-2-oxoethyl}-3-(1-phenyl-1H-indazol-4-yl)imidazolidin-2-one;
1-[1-(2-fluorophenyl)-1H-indazol-4-yl]-3-{2-oxo-2-[(3S)-3-(trifluoromethyl)pyrrolidin-1-yl]ethyl}imidazolidin-2-one;
1-[2-(3-fluoro-3-methylazetidin-1-yl)-2-oxoethyl]-3-[1-(2-fluorophenyl)-1H-indazol-4-yl]imidazolidin-2-one;
N-(3,3-difluorocyclobutyl)-2-{3-[1-(2-fluorophenyl)-1H-indazol-4-yl]-2-oxoimidazolidin-1-yl}acetamide;
(1R,5S)-8-({3-[1-(2-fluorophenyl)-1H-indazol-4-yl]-2-oxoimidazolidin-1-yl}acetyl)-8-azabicyclo[3.2.1]octan-3-one;
1-[1-(2-fluorophenyl)-1H-indazol-4-yl]-3-[2-oxo-2-(3,3,4,4-tetrafluoropyrrolidin-1-yl)ethyl]imidazolidin-2-one;
1-({3-[1-(2-fluorophenyl)-1H-indazol-4-yl]-2-oxoimidazolidin-1-yl}acetyl)azepan-4-one;
1-[1-(2-fluorophenyl)-1H-indazol-4-yl]-3-{(1Z)-3-[(3S)-3-fluoropyrrolidin-1-yl]-3-oxoprop-1-en-1-yl}imidazolidin-2-one;
N-ethyl-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-[1-(hydroxymethyl)cyclobutyl]acetamide;
1-[1-(2-fluorophenyl)-1H-indazol-4-yl]-3-{3-[(3R)-3-fluoropiperidin-1-yl]-3-oxopropyl}imidazolidin-2-one;
1-[1-(2-fluorophenyl)-1H-indazol-4-yl]-3-{3-[(3S)-3-fluoropiperidin-1-yl]-3-oxopropyl}imidazolidin-2-one;
1-[1-(2-fluorophenyl)-1H-indazol-4-yl]-3-[2-(3-methoxyazetidin-1-yl)-2-oxoethyl]imidazolidin-2-one;
2-{3-[1-(2-fluorophenyl)-1H-indazol-4-yl]-2-oxoimidazolidin-1-yl}-N-(tetrahydro-2H-pyran-4-yl)acetamide;
2-{3-[1-(2-fluorophenyl)-1H-indazol-4-yl]-2-oxoimidazolidin-1-yl}-N-(oxetan-3-yl)acetamide;
N-cyclobutyl-2-{3-[1-(2-fluorophenyl)-1H-indazol-4-yl]-2-oxoimidazolidin-1-yl}acetamide;
N-cyclopentyl-2-{3-[1-(2-fluorophenyl)-1H-indazol-4-yl]-2-oxoimidazolidin-1-yl}acetamide;
N-cyclohexyl-2-{3-[1-(2-fluorophenyl)-1H-indazol-4-yl]-2-oxoimidazolidin-1-yl}acetamide;
1-[2-(3-acetylazetidin-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-(trans-3-methoxycyclobutyl)acetamide;
1-[1-(2-fluorophenyl)-1H-indazol-4-yl]-3-{(1E)-3-[(3S)-3-fluoropyrrolidin-1-yl]-3-oxoprop-1-en-1-yl}imidazolidin-2-one;
N-(2,2-dimethylcyclopropyl)-2-{3-[1-(2-fluorophenyl)-1H-indazol-4-yl]-2-oxoimidazolidin-1-yl}acetamide;
1-[1-(2-fluorophenyl)-1H-indazol-4-yl]-3-{2-oxo-2-[3-(trifluoromethyl)azetidin-1-yl]ethyl}imidazolidin-2-one;
1-{2-[3-(difluoromethyl)pyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-[(1S,2S)-2-isopropoxycyclohexyl]imidazolidin-2-one;
2-{3-[1-(2-fluorophenyl)-1H-indazol-4-yl]-2-oxoimidazolidin-1-yl}-N-[(1R,2S)-2-hydroxycyclopentyl]acetamide;

2-{3-[1-(2-fluorophenyl)-1H-indazol-4-yl]-2-oxoimidazolidin-1-yl}-N-(1-methylcyclopropyl)acetamide;
N-[(1S,2S)-2-(benzyloxy)cyclopentyl]-2-{3-[1-(2-fluorophenyl)-1H-indazol-4-yl]-2-oxoimidazolidin-1-yl}acetamide;
N-[(1R,2R)-2-(benzyloxy)cyclopentyl]-2-{3-[1-(2-fluorophenyl)-1H-indazol-4-yl]-2-oxoimidazolidin-1-yl}acetamide;
1-[1-(2-fluorophenyl)-1H-indazol-4-yl]-3-(4-isobutoxytetrahydrofuran-3-yl)imidazolidin-2-one;
2-{3-[1-(2-fluorophenyl)-1H-indazol-4-yl]-2-oxoimidazolidin-1-yl}-N-[(1R,2S)-2-isobutoxycyclopentyl]acetamide;
1-[1-(4-chlorophenyl)-1H-indazol-4-yl]-3-{2-[(3S)-3-fluoropyrrolidin-1-yl]-2-oxoethyl}imidazolidin-2-one;
N-tert-butyl-2-{3-[1-(2-fluorophenyl)-1H-indazol-4-yl]-2-oxoimidazolidin-1-yl}acetamide;
N-(3,3-difluorocyclohexyl)-2-{3-[1-(2-fluorophenyl)-1H-indazol-4-yl]-2-oxoimidazolidin-1-yl}acetamide;
N-(3,3-difluorocyclopentyl)-2-{3-[1-(2-fluorophenyl)-1H-indazol-4-yl]-2-oxoimidazolidin-1-yl}acetamide;
1-[1-(2-fluorophenyl)-1H-indazol-4-yl]-3-{2-[(3aR,6aS)-hexahydrocyclopenta[c]pyrrol-2(1H)-yl]-2-oxoethyl}imidazolidin-2-one;
2-{3-[1-(2-fluorophenyl)-1H-indazol-4-yl]-2-oxoimidazolidin-1-yl}-N-(3,3,3-trifluoropropyl)acetamide;
1-[1-(2-fluorophenyl)-1H-indazol-4-yl]-3-methylimidazolidin-2-one;
Nα-({3-[1-(2-fluorophenyl)-1H-indazol-4-yl]-2-oxoimidazolidin-1-yl}acetyl)-D-phenylalaninamide;
N-tert-butyl-$N^2$-({3-[1-(2-fluorophenyl)-1H-indazol-4-yl]-2-oxoimidazolidin-1-yl}acetyl)-L-valinamide;
N-(2,2-difluorocyclopentyl)-2-{3-[1-(2-fluorophenyl)-1H-indazol-4-yl]-2-oxoimidazolidin-1-yl}acetamide;
1-[1-(3,5-dichlorophenyl)-1H-indazol-4-yl]-3-{2-[(3S)-3-fluoropyrrolidin-1-yl]-2-oxoethyl}imidazolidin-2-one;
2-{3-[1-(2-fluorophenyl)-1H-indazol-4-yl]-2-oxoimidazolidin-1-yl}-N-(3-oxocyclobutyl)acetamide;
2-{3-[1-(2-fluorophenyl)-1H-indazol-4-yl]-2-oxoimidazolidin-1-yl}-N-(3-hydroxycyclobutyl)acetamide;
N-cyclobutyl-2-{3-[1-(2-fluorophenyl)-1H-indazol-4-yl]-2-oxoimidazolidin-1-yl}-N-methylacetamide;
1-[1-(2-fluorophenyl)-1H-indazol-4-yl]-3-[2-(3-methylazetidin-1-yl)-2-oxoethyl]imidazolidin-2-one;
2-{3-[1-(2-fluorophenyl)-1H-indazol-4-yl]-2-oxoimidazolidin-1-yl}-N-[1-(trifluoromethyl)cyclobutyl]acetamide;
2-{3-[1-(2-fluorophenyl)-1H-indazol-4-yl]-2-oxoimidazolidin-1-yl}-N-[3-(hydroxyimino)cyclobutyl]acetamide;
2-{3-[1-(2-fluorophenyl)-1H-indazol-4-yl]-2-oxoimidazolidin-1-yl}-N-[3-(methoxyimino)cyclobutyl]acetamide;
N-(4,4-difluorocyclohexyl)-2-{3-[1-(2-fluorophenyl)-1H-indazol-4-yl]-2-oxoimidazolidin-1-yl}acetamide; and
N-(2,2-dimethylpropyl)-2-{3-[1-(2-fluorophenyl)-1H-indazol-4-yl]-2-oxoimidazolidin-1-yl}acetamide.

Compound names are assigned by using Name 2012 naming algorithm by Advanced Chemical Development or Struct=Name naming algorithm as part of CHEMDRAW® ULTRA v. 12.0.2.1076.

Compounds of the invention may exist as stereoisomers wherein asymmetric or chiral centers are present. These stereoisomers are "R" or "S" depending on the configuration of substituents around the chiral carbon atom. The terms "R" and "S" used herein are configurations as defined in IUPAC 1974 Recommendations for Section E, Fundamental Stereochemistry, in Pure Appl. Chem., 1976, 45: 13-30. The invention contemplates various stereoisomers and mixtures thereof and these are specifically included within the scope of this invention. Stereoisomers include enantiomers and diastereomers, and mixtures of enantiomers or diastereomers. Individual stereoisomers of compounds of the invention may be prepared synthetically from commercially available starting materials which contain asymmetric or chiral centers or by preparation of racemic mixtures followed by methods of resolution well-known to those of ordinary skill in the art. These methods of resolution are exemplified by (1) attachment of a mixture of enantiomers to a chiral auxiliary, separation of the resulting mixture of diastereomers by recrystallization or chromatography and optional liberation of the optically pure product from the auxiliary as described in Furniss, Hannaford, Smith, and Tatchell, "Vogel's Textbook of Practical Organic Chemistry", 5th edition (1989), Longman Scientific & Technical, Essex CM20 2JE, England, or (2) direct separation of the mixture of optical enantiomers on chiral chromatographic columns or (3) fractional recrystallization methods.

Compounds of the invention may exist as cis or trans isomers, wherein substituents on a ring may attached in such a manner that they are on the same side of the ring (cis) relative to each other, or on opposite sides of the ring relative to each other (trans). For example, cyclobutane may be present in the cis or trans configuration, and may be present as a single isomer or a mixture of the cis and trans isomers. Individual cis or trans isomers of compounds of the invention may be prepared synthetically from commercially available starting materials using selective organic transformations, or prepared in single isomeric form by purification of mixtures of the cis and trans isomers. Such methods are well-known to those of ordinary skill in the art, and may include separation of isomers by recrystallization or chromatography.

It should be understood that the compounds of the invention may possess tautomeric forms, as well as geometric isomers, and that these also constitute an aspect of the invention.

The present invention also includes isotopically-labeled compounds, which are identical to those recited in formula (I), but for the fact that one or more atoms are replaced by an atom having an atomic mass or mass number different from the atomic mass or mass number usually found in nature. Examples of isotopes suitable for inclusion in the compounds of the invention are hydrogen, carbon, nitrogen, oxygen, phosphorus, sulfur, fluorine, and chlorine, such as, but not limited to $^{2}H$, $^{3}H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. Substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Compounds incorporating positron-emitting isotopes are useful in medical imaging and positron-emitting tomography (PET) studies for determining the distribution of receptors. Suitable positron-emitting isotopes that can be incorporated in compounds of formula (I) are $^{11}C$, $^{13}N$, $^{15}O$, and $^{18}F$. Isotopically-labeled compounds of formula (I) can generally be prepared by conventional techniques known to those skilled in the art or by processes analogous to those described in the accompanying Examples using appropriate isotopically-labeled reagent in place of non-isotopically-labeled reagent.

Methods for Preparing Compounds of the Invention

The compounds of the invention can be better understood in connection with the following synthetic schemes and methods which illustrate a means by which the compounds can be prepared.

The compounds of this invention can be prepared by a variety of synthetic procedures. Representative procedures are shown in, but are not limited to, Schemes 1-12.

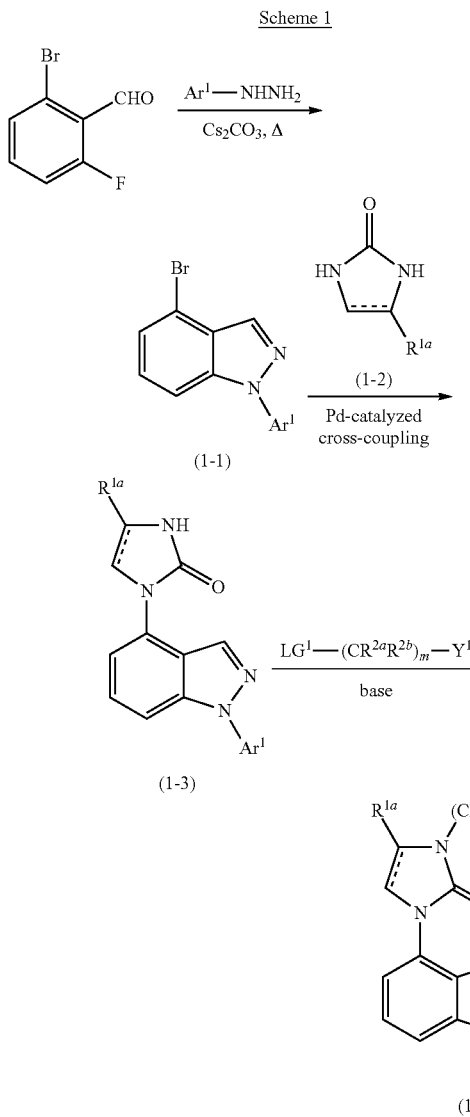

As shown in Scheme 1, compounds of formula (1-4) can be prepared in three-step process starting with 2-bromo-6-fluorobenzaldehyde. Treatment of 2-bromo-6-fluorobenzaldehyde in the presence of a hydrazine, $Ar^1$—$NHNH_2$, wherein $Ar^1$ is phenyl or monocyclic heteroaryl optionally substituted with 1, 2, 3 or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen, or the corresponding acid salt in the presence of a base, such as cesium carbonate, heated for 0.5-3 hours in a solvent, such as N-methyl-2-pyrrolidinone, delivers indazoles of formula (1-1). Indazoles of formula (1-1) can then be reacted with either an imidazolone or imidazolidinone of formula (1-2) under cross-coupling reaction conditions such as a palladium catalyst like tris(dibenzylideneacetone)dipalladium(0) ($Pd_2(dba)_3$), a phosphine ligand such as (9,9-dimethyl-9H-xanthene-4,5-diyl)bis(diphenylphosphine), and a base such as cesium carbonate heated in a solvent such as dimethoxyethane for 4-24 hours to give compounds of formula (1-3), wherein $R^{1a}$ is as defined in the Summary. Compounds of formula (1-3) can be alkylated with $LG^1$-$(CR^{2a}R^{2b})_m$—Y in the presence of a base, such as sodium hydride, in a warmed polar, aprotic solvent such as N,N-dimethylformamide over 1-12 hours to give compounds of formula (1-4). $R^{2a}$, and m are as defined in the Summary. $LG^1$ is a leaving group such as chlorine, bromine, iodine, or a sulfonate. $Y^1$ can be hydrogen, $C_1$-$C_5$alkenyl, $C_1$-$C_6$alkoxy$C_1$-$C_3$alkyl, $C_1$-$C_5$alkyl, $C_1$-$C_5$haloalkyl, $G^1$, $G^2$, $G^3$, $G^4$, $C(OR^{2d})(R^{2d})$—$R^{2e}$, $C(O)R^{2c}$, $C(O)$—$(CR^{2a}R^{2b})_nG^1$, $C(O)(CR^{2a}R^{2b})_nG^2$, $C(O)(CR^{2a}R^{2b})_nG^3$, $C(O)(CR^{2a}R^{2b})_nG^4$, $CO_2R^{2c}$, $CO_2G^1$, $C(O)G^1$, $C(O)G^2$, $C(O)G^3$, $C(O)G^4$, $C(O)NR^{2d}R^{2e}$, $C(O)NR^{2d}G^1$, $C(O)NR^{2d}G^2$, $C(O)NR^{2d}G^3$, $C(O)NR^{2d}G^4$, $C(O)N(R^{2d})((CR^{2a}R^{2b})_nG^1)$, $C(O)N(R^{2d})((CR^{2a}R^{2b})_nG^2)$, $C(O)N(R^{2d})((CR^{2a}R^{2b})_nG^3)$, $C(O)N(R^{2d})((CR^{2a}R^{2b})_nG^4)$, $SO_2NR^{2d}R^{2e}$, or $C(O)NH$—$(CR^{2a}R^{2f})$—$C(O)NHR^{2d}$, wherein $R^{2a}$, $R^{2b}$, $R^{2c}$, $R^{2d}$, $R^{2e}$, $R^{2f}$, $G^1$, $G^2$, $G^3$, $G^4$ and n are as defined in the Summary. Compounds of formula (1-4) are representative of compounds of formula (I).

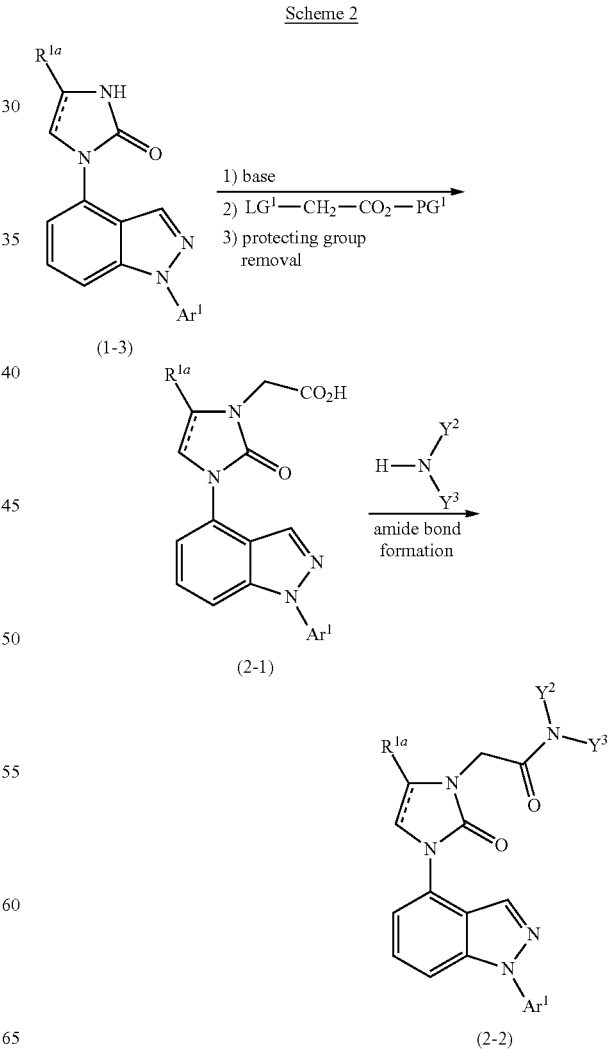

As shown in Scheme 2, compounds of formula (2-2) can be prepared from compounds of formula (1-3). Compounds of formula (1-3), wherein $R^{1a}$ is as defined in the Summary and $Ar^1$ is as defined in Scheme 1, can be deprotonated with a base such as sodium hydride in a polar, aprotic solvent such as tetrahydrofuran, dioxane, or N,N-dimethylformamide and then alkylated with $LG^1$-$CH_2$—$CO_2PG^1$ with optional warming. $LG^1$ is a leaving group such as chlorine, bromine, iodine, or a sulfonate. $PG^1$ is a carboxy protecting group such as tert-butyl. The protecting group can be removed under conditions known to one of skill in the art. When $PG^1$ is tert-butyl, treatment with trifluoroacetic acid in dichloromethane or hydrochloric acid in dioxane reveals the carboxy group and delivers compounds of formula (2-1). Compounds of formula (2-1) can be coupled with amines, H—N($Y^2$)($Y^3$), under amide bond forming conditions to give compounds of formula (2-2). Examples of conditions known to generate amides from a mixture of a carboxylic acid and an amine include but are not limited to adding a coupling reagent such as but not limited to N-(3-dimethylaminopropyl)-N'-ethylcarbodiimide or 1-(3-dimethylaminopropyl)-3-ethylcarbodiimide (EDC, EDAC or EDCI), 1,3-dicyclohexylcarbodiimide (DCC), bis(2-oxo-3-oxazolidinyl)phosphinic chloride (BOPCl), N-[(dimethylamino)-1H-1,2,3-triazolo-[4,5-b]pyridin-1-yl-methylene]-N-methylmethanaminium hexafluorophosphate N-oxide or 2-(7-azabenzotriazol-1-yl)-N,N,N',N'-tetramethyluronium hexafluorophosphate or 1-[bis(dimethylamino)methylene]-1H-1,2,3-triazolo[4,5-b]pyridinium 3-oxid hexafluorophosphate (HATU), O-(benzotriazol-1-yl)-N,N,N',N'-tetramethyluronium tetrafluoroborate (TBTU), 2-(1H-benzo[d][1,2,3]triazol-1-yl)-1,1,3,3-tetramethylisouronium hexafluorophosphate(V) (HBTU), and 2,4,6-tripropyl-1,3,5,2,4,6-trioxatriphosphinane 2,4,6-trioxide (T3P®). The coupling reagents may be added as a solid, a solution, or as the reagent bound to a solid support resin. In addition to the coupling reagents, auxiliary-coupling reagents may facilitate the coupling reaction. Auxiliary coupling reagents that are often used in the coupling reactions include but are not limited to (dimethylamino)pyridine (DMAP), 1-hydroxy-7-azabenzotriazole (HOAT) and 1-hydroxybenzotriazole (HOBT). The reaction may be carried out optionally in the presence of a base such as triethylamine or diisopropylethylamine. The coupling reaction may be carried out in solvents such as but not limited to tetrahydrofuran, N,N-dimethylformamide, N,N-dimethylacetamide, dimethyl sulfoxide, dichloromethane, and ethyl acetate. $Y^2$ and $Y^3$ are independently $R^{2d}$, $R^{2e}$, $G^1$, $G^2$, $G^3$, $G^4$, $(CR^{2a}R^{2b})_nG^1$, $(CR^{2a}R^{2b})_nG^2$, $(CR^{2a}R^{2b})_nG^3$, $(CR^{2a}R^{2b})_nG^4$ or $C(R^{2a}R^{2f})$—$C(O)NHR^{2d}$. Alternatively, $Y^2$ and $Y^3$ joined with the nitrogen atom to which they are attached form a heterocycle, $G^3$. Compounds of formula (2-2) are representative of compounds of formula (I).

Scheme 3

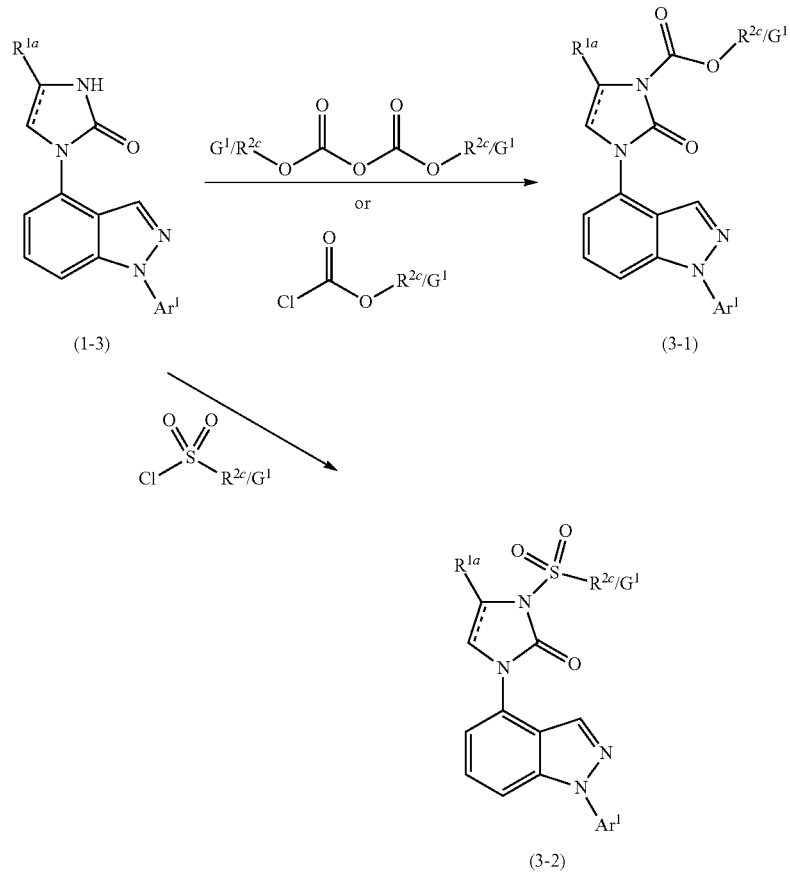

(1-3)

(3-1)

(3-2)

As shown in Scheme 3, compounds of formula (1-3) can be carboxylated or sulfonylated to give compounds of formula (3-1) or formula (3-2), respectively. Compounds of formula (1-3) can be treated with dicarbonate, $G^1OC(O)OC(O)OG^1$ or $R^{2c}OC(O)OC(O)OR^{2c}$ in the presence of 4-dimethylaminopyridine in a solvent such as acetonitrile over 4-36 hours to give compounds of formula (3-1). $R^{2c}$ and $G^1$ are as defined in the Summary. Alternatively, compounds of formula (1-3) can be reacted with chloroformates, $ClC(O)O-R^{2c}$ or $ClC(O)O-G^1$, in the presence of a tertiary amine base, such as triethylamine or diisopropylethylamine, in a solvent, such as acetonitrile, to give compounds of formula (3-1). $R^{1a}$ is as defined in the Summary, and $Ar^1$ is as defined in Scheme 1. Similarly, compounds of formula (1-3) can be reacted with sulfonyl chlorides, $R^{2c}-SO_2Cl$ or $G^1-SO_2Cl$, in the presence of a tertiary amine base, such as triethylamine or diisopropylethylamine, in a solvent, such as dichloromethane, to give compounds of formula (3-2). Compounds of formula (3-1) and formula (3-2) are representative of compounds of formula (I).

Scheme 4

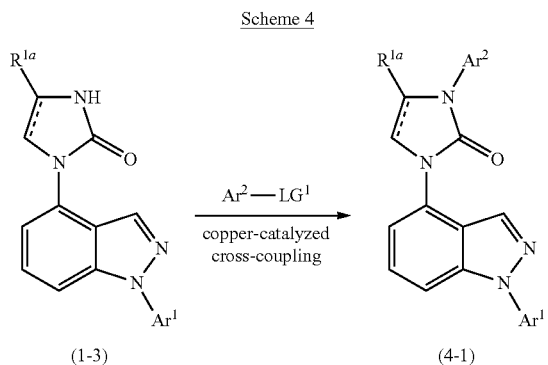

As illustrated in Scheme 4, compounds of formula (1-3) can be converted to compounds of formula (4-1). Accordingly, compounds of formula (1-3), wherein $R^{1a}$ is as defined in the Summary and $Ar^1$ is as defined in Scheme 1, can be reacted with $Ar^2$-$LG^1$ in a copper-catalyzed cross-coupling reaction to give compounds of formula (4-1). $Ar^2$ is either a phenyl or heteroaryl defined by $G^2$ or $G^4$, respectively, in the Summary. $LG^1$ is a leaving group such as chlorine, bromine, iodine, or a sulfonate. The cross-coupling reaction can be carried out in the presence of copper(I) iodide, potassium phosphate tribasic, and trans-N,N'-dimethylcyclohexane-1,2-diamine in solvent such as heated dioxane (90-120° C.) under an inert atmosphere in a sealed pressure tube over 4-36 hours. Compounds of formula (4-1) are representative of compounds of formula (I).

Scheme 5

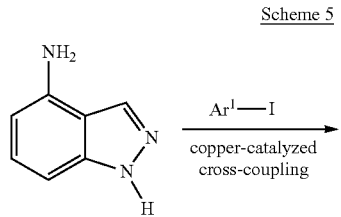

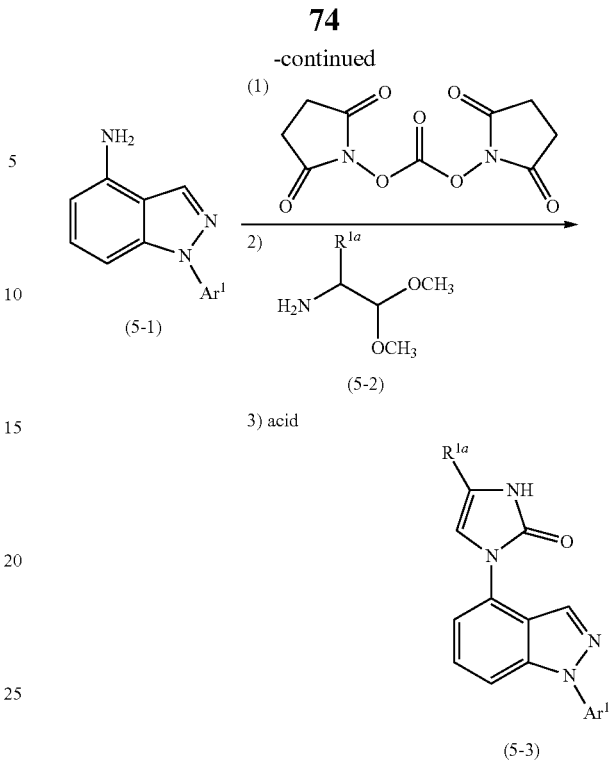

As shown in Scheme 5, 1H-indazol-4-amine can be converted to compounds of formula (5-3). 1H-Indazol-4-amine can be reacted with $Ar^1$—I in the presence of copper (I) iodide, potassium phosphate tribasic, and trans-N,N'-dimethylcyclohexane-1,2-diamine heated in a solvent such as dioxane over 8-96 hours under an inert atmosphere to give compounds of formula (5-1). $Ar^1$ is as defined in Scheme 1. Compounds of formula (5-1) can be reacted with bis(2,5-dioxopyrrolidin-1-yl) carbonate in a solvent such as acetonitrile at ambient temperature over 1-24 hours. Subsequently, a tertiary amine base such as triethylamine or diisopropylethylamine and aminoacetaldehyde dimethylacetal (5-2) can be added with continued reaction over 4-24 hours. $R^{1a}$ is as defined in the Summary. The intermediate urea acetal dissolved in a solvent such as methanol can be treated with an acid such as sulfuric acid at ambient temperature to 60° C. to give compounds of formula (5-3). Compounds of formula (5-3) can be reacted as described for compounds of formula (1-3) in Schemes 1-4 to give compounds of formula (I).

Scheme 6

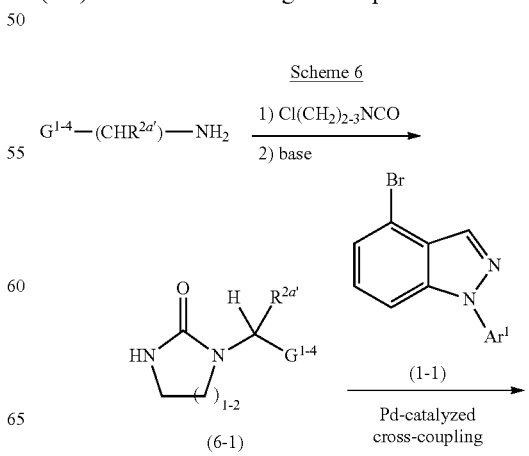

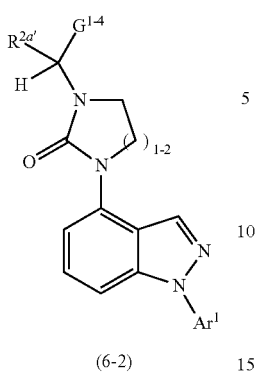

(6-2)

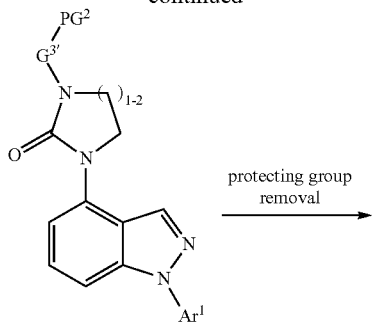

protecting group removal (7-3)

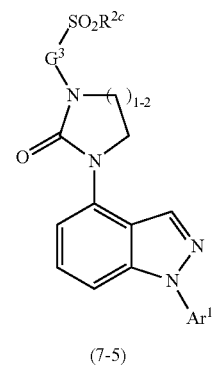

$R^{2c}SO_2Cl$ (7-4)

As shown in Scheme 6, compounds of formula (6-2) can be prepared from amines of formula $G^{1-4}$-(CHR$^{2a'}$)—NH$_2$, wherein $R^{2a'}$ is hydrogen or $C_1$-$C_4$alkyl. Accordingly, amines of formula $G^{1-4}$-(CHR$^{2a'}$)—NH$_2$ can be reacted with either 2-chloroethyl isocyanate or 3-chloropropyl isocyanate optionally in the presence of a tertiary amine such as triethylamine or diisopropylethylamine in a solvent such as dichloromethane or dioxane over 4-36 hours. The intermediate chloro-urea can then be treated with a base such as sodium hydride in a solvent such as tetrahydrofuran initially chilled to approximately 0° C. followed by warming to ambient temperature with the reaction continued for 15-24 hours to give compounds of formula (6-1). $G^{1-4}$ can be $G^1$, $G^2$, $G^3$ or $G^4$ as defined in the Summary. Compounds of formula (6-1) can reacted with compounds of formula (1-1) under palladium catalyzed cross-coupling reaction conditions to give compounds of formula (6-2). An example of the cross-coupling reaction conditions include combining compounds of formula (6-1) and formula (1-1) with a palladium catalyst such as tris(dibenzylideneacetone)dipalladium(0)-chloroform adduct, a ligand such as (9,9-dimethyl-9H-xanthene-4,5-diyl)bis(diphenylphosphine), a base such as cesium carbonate, and a solvent such as dimethoxyethane. The resultant mixture can be heated from under an inert atmosphere for 10-36 hours. Compounds of formula (6-2) are representative of compounds of formula (I).

Scheme 7

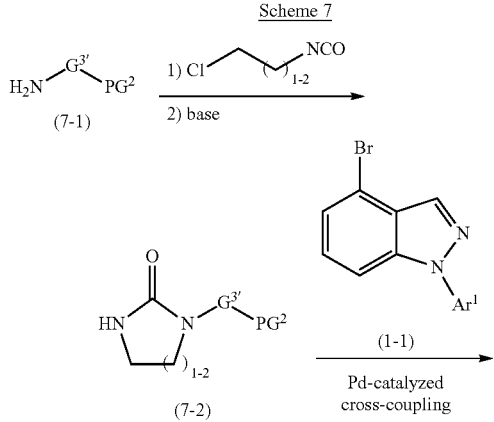

(7-5)

As illustrated in Scheme 7, compounds of formula (7-4) can be prepared from amines of formula (7-1). Amines of formula (7-1), wherein $G^{3'}$ is a heterocycle containing a ring nitrogen atom protected with an amine protecting group (PG$^2$), can be reacted with either 2-chloroethyl isocyanate or 3-chloropropyl isocyanate optionally in the presence of a tertiary amine such as triethylamine or diisopropylethylamine in a solvent such as dichloromethane or dioxane over 4-36 hours. The intermediate chloro-urea can then be treated with a base such as sodium hydride in a solvent such as tetrahydrofuran or for 24-60 hours to give compounds of formula (7-2). Compounds of formula (7-2) can be reacted with compounds of formula (1-1) under palladium-catalyzed cross-coupling reaction conditions to give compounds of formula (7-3). An example of the palladium-catalyzed cross-coupling reaction conditions are combining compounds of formula (7-2) with compounds of formula (1-1) in dioxane in the presence of a palladium catalyst such as bis(tri-tert-butylphosphine)palladium(0), an optional ligand, and a base such as cesium carbonate. The mixture is heated to 90-100° C. for 8-36 hours under an inert atmosphere. The amine protecting group (PG$^2$), can be removed from compounds of formula (7-3) to give compounds of formula (7-4) using conditions known to one of skill in the art dependent upon the particular protecting group. For example, when $PG^2$ is a tert-butoxycarbonyl group, treatment with trifluoroacetic acid in dichloromethane over 0.5 to 3 hours reveals the unprotected compound of formula (7-4). Compounds of formula (7-4) can be further modified under conditions known to one of skill in the art. For example, compounds of formula (7-4) can be alkylated or involved in formation of an amide or sulfonamide. To illustrate, compounds of formula (7-4) can be reacted with a sulfonyl chloride, $R^{2c}SO_2Cl$, in pyridine at ambient temperature optionally in the presence of a tertiary amine base such as triethylamine or diisopropylethylamine over 0.5-6 hours to give compounds of formula (7-5). Compounds of formula (7-4) and formula (7-5) are representative of compounds of formula (I).

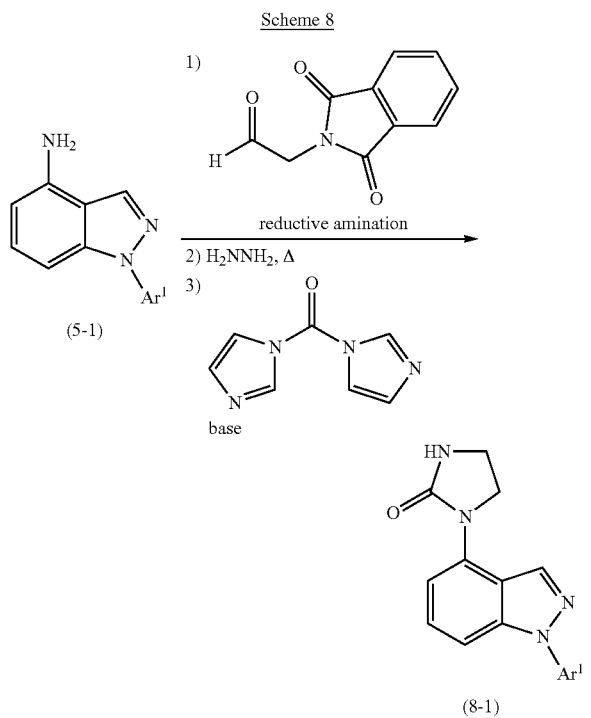

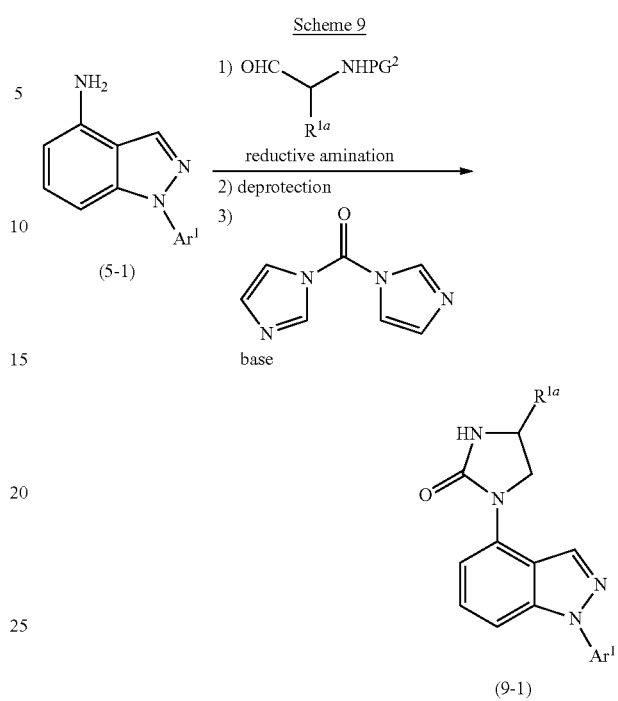

As shown in Scheme 8, compounds of formula (5-1) can be converted to compounds of formula (8-1) in a three-step process. Compounds of formula (5-1) can be reacted with N-(2-oxoethyl)phthalimide under reductive amination conditions. An example of reductive amination conditions include combining compounds of formula (5-1) with N-(2-oxoethyl)phthalimide in methanol and acetic acid followed by treatment with a reductant such as sodium cyanoborohydride, sodium borohydride, or sodium triacetoxyborohydride at ambient temperature over 2 to 24 hours. Addition of hydrazine and heating the reaction mixture close to or at the methanol boiling point removes the phthalimide revealing the primary amine. The sequence can be completed by combining the intermediate diamine in a solvent such as tetrahydrofuran with di(1H-imidazol-1-yl)methanone and a base such as 1,8-diazabicyclo[5.4.0]undec-7-ene at ambient temperature for 6 to 24 hours to give compounds of formula (8-1). Compounds of formula (8-1) can be reacted as described for compounds of formula (1-3) in Schemes 1-4 to give compounds of formula (I).

As shown in Scheme 9, compounds of formula (5-1) can be converted to compounds of formula (9-1) in a three-step process. Compounds of formula (5-1) can be reacted with a protected amino aldehyde, $PG^2(H)N$—$CH(R^{1a})$—CHO, under reductive amination conditions. $R^{1a}$ is as defined in the Summary, and $PG^2$ is an amine protecting group known to one of skill in the art. An example of reductive amination conditions include combining compounds of formula (5-1) with protected amino aldehyde, $PG^2(H)N$—$CH(R^{1a})$—CHO, in methanol and acetic acid followed by treatment with a reductant such as sodium cyanoborohydride, sodium borohydride, or sodium triacetoxyborohydride at ambient temperature over 2 to 96 hours. The amine protecting group ($PG^2$), can be removed from compounds of formula (7-3) to give compounds of formula (7-4) using conditions known to one of skill in the art dependent upon the particular protecting group. For example, when $PG^2$ is a tert-butoxycarbonyl group, treatment with trifluoroacetic acid in dichloromethane over 0.5 to 8 hours reveals an intermediate diamine. The sequence can be completed by combining the intermediate diamine in a solvent such as tetrahydrofuran with di(1H-imidazol-1-yl)methanone and a base such as 1,8-diazabicyclo[5.4.0]undec-7-ene at ambient temperature for 6 to 24 hours to give compounds of formula (9-1). Compounds of formula (9-1) can be reacted as described for compounds of formula (1-3) in Schemes 1-4 to give compounds of formula (I).

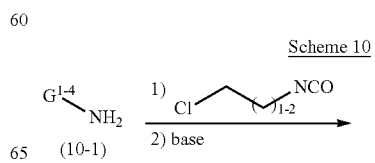

79

-continued

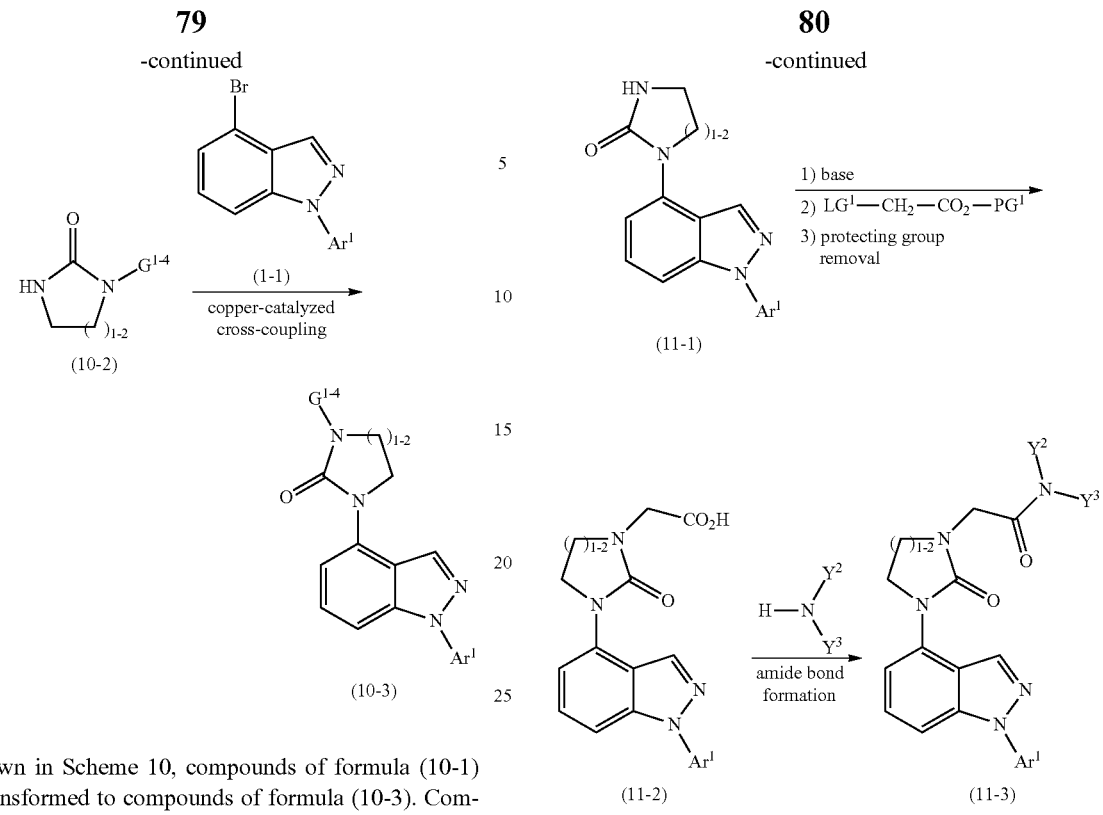

As shown in Scheme 10, compounds of formula (10-1) can be transformed to compounds of formula (10-3). Compounds of formula (10-1) can be converted to compounds of formula (10-2) in a two-step process. $G^{1-4}$ can be $G^1$, $G^2$, $G^3$ or $G^4$ as defined in the Summary. Amines of formula (10-1) can be reacted with either 2-chloroethyl isocyanate or 3-chloropropyl isocyanate optionally in the presence of a tertiary amine such as triethylamine or diisopropylethylamine in a solvent such as dichloromethane or dioxane over 4-36 hours. The intermediate chloro-urea can then be treated with a base such as sodium hydride in a solvent such as tetrahydrofuran or for 24-60 hours to give compounds of formula (10-2). Compounds of formula (10-2) can be reacted with compounds of formula (1-1) under copper-catalyzed cross-coupling reaction conditions to give compounds of formula (10-3). An example of the copper-catalyzed cross-coupling reaction conditions are combining compounds of formula (10-2) and compounds of formula (1-1) in 1,4-dioxane in the presence of copper(I) iodide, trans-N,N'-dimethylcyclohexane-1,2-diamine, and potassium phosphate tribasic in a sealed tube under an inert atmosphere heated at 100-115° C. over 10-36 hours. Compounds of formula (10-3) are representative of compounds of formula (I).

Scheme 11

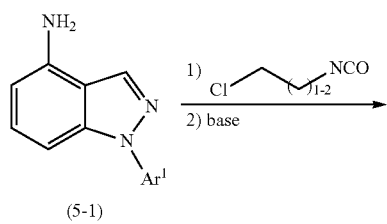

80

-continued

As illustrated in Scheme 11, compounds of formula (5-1) can be converted to compounds of formula (11-3). Compounds of formula (5-1) can be reacted with either 2-chloroethyl isocyanate or 3-chloropropyl isocyanate optionally in the presence of a tertiary amine such as triethylamine or diisopropylethylamine in a solvent such as dichloromethane or dioxane over 4-36 hours. The intermediate chloro-urea can then be treated with a base such as sodium hydride in a solvent such as tetrahydrofuran or for 2-24 hours to give compounds of formula (11-1). Compounds of formula (11-1) can be deprotonated with a base such as sodium hydride in a polar, aprotic solvent such as tetrahydrofuran, dioxane, or N,N-dimethylformamide and then alkylated with $LG^1$-$CH_2$—$CO_2PG^1$ with optional warming. $LG^1$ is a leaving group such as chlorine, bromine, iodine, or a sulfonate. $PG^1$ is a carboxy protecting group such as ethyl. The protecting group can be removed under conditions known to one of skill in the art. When $PG^1$ is ethyl, treatment with potassium hydroxide in a mixture of tetrahydrofuran and methanol reveals the carboxy group and delivers compounds of formula (11-2). Compounds of formula (11-2) can be coupled with amines, H—N($Y^2$)($Y^3$), under amide bond forming conditions to give compounds of formula (11-3). Examples of conditions known to generate amides from a mixture of a carboxylic acid and an amine are described in Scheme 2. Alternatively, $Y^2$ and $Y^3$ joined with the nitrogen atom to which they are attached form a heterocycle, $G^3$. Compounds of formula (11-3) are representative of compounds of formula (I).

Scheme 12

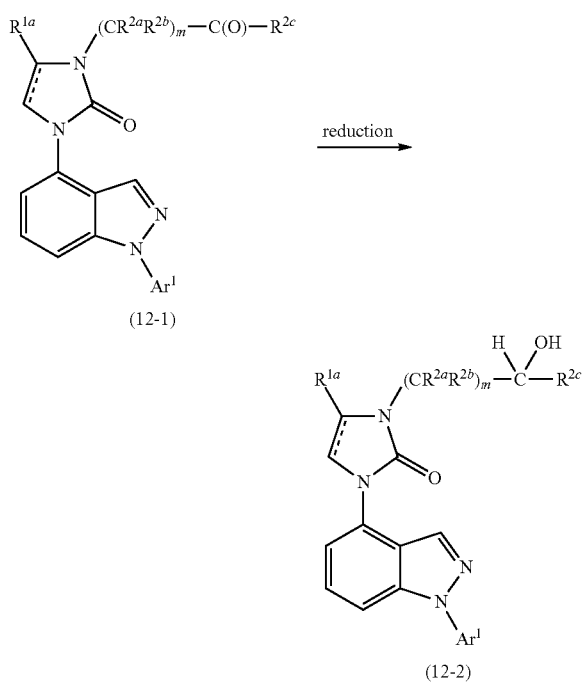

As shown in Scheme 12, compounds of formula (12-1) can be converted to compounds of formula (12-1). Compounds of formula (12-1) can be prepared as described in Scheme 1 as an example of compounds of formula (1-4). $R^{1a}$, $R^{2a}$, $R^{2b}$, $R^{2c}$ and m are as described in the Summary. $Ar^1$ is as described in Scheme 1. Compounds of formula (12-1) can be reduced with a reductant such as sodium borohydride in a solvent such as ethyl acetate over 0.5 to 4 hours. The boron complex can be hydrolyzed upon treatment with 0.2 N hydrochloric acid to give compounds of formula (12-2). Compounds of formula (12-2) are representative of compounds of formula (I).

The compounds and intermediates of the invention may be isolated and purified by methods well-known to those skilled in the art of organic synthesis. Examples of conventional methods for isolating and purifying compounds can include, but are not limited to, chromatography on solid supports such as silica gel, alumina, or silica derivatized with alkylsilane groups, by recrystallization at high or low temperature with an optional pretreatment with activated carbon, thin-layer chromatography, distillation at various pressures, sublimation under vacuum, and trituration, as described for instance in "Vogel's Textbook of Practical Organic Chemistry", 5th edition (1989), by Furniss, Hannaford, Smith, and Tatchell, pub. Longman Scientific & Technical, Essex CM20 2JE, England.

Many of the compounds of the invention have at least one basic nitrogen whereby the compound can be treated with an acid to form a desired salt. For example, a compound may be reacted with an acid at or above room temperature to provide the desired salt, which is deposited, and collected by filtration after cooling. Examples of acids suitable for the reaction include, but are not limited to tartaric acid, lactic acid, succinic acid, as well as mandelic, atrolactic, methanesulfonic, ethanesulfonic, toluenesulfonic, naphthalenesulfonic, benzenesulfonic, carbonic, fumaric, maleic, gluconic, acetic, propionic, salicylic, hydrochloric, hydrobromic, phosphoric, sulfuric, citric, hydroxybutyric, camphorsulfonic, malic, phenylacetic, aspartic, or glutamic acid, and the like.

Optimum reaction conditions and reaction times for each individual step can vary depending on the particular reactants employed and substituents present in the reactants used. Unless otherwise specified, solvents, temperatures and other reaction conditions can be readily selected by one of ordinary skill in the art. Specific procedures are provided in the Examples section. Reactions can be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or can be prepared by one skilled in the art from commercially available materials using methods described in the chemical literature.

Routine experimentations, including appropriate manipulation of the reaction conditions, reagents and sequence of the synthetic route, protection of any chemical functionality that cannot be compatible with the reaction conditions, and deprotection at a suitable point in the reaction sequence of the method are included in the scope of the invention. Suitable protecting groups and the methods for protecting and deprotecting different substituents using such suitable protecting groups are well known to those skilled in the art; examples of which can be found in P G M Wuts and T W Greene, in Greene's book titled Protective Groups in Organic Synthesis ($4^{th}$ ed.), John Wiley & Sons, NY (2006), which is incorporated herein by reference in its entirety. Synthesis of the compounds of the invention can be accomplished by methods analogous to those described in the synthetic schemes described hereinabove and in specific examples.

Starting materials, if not commercially available, can be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it can be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it can be obtained by carrying out one of the above procedures using a pure geometric isomer as a starting material, or by resolution of a mixture of the geometric isomers of the compound or intermediates using a standard procedure such as chromatographic separation.

It can be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Compositions of the Invention

The invention also provides pharmaceutical compositions comprising a therapeutically effective amount of a compound of formula (I) in combination with a pharmaceutically acceptable carrier. The compositions comprise compounds of the invention formulated together with one or more non-toxic pharmaceutically acceptable carriers. The pharmaceutical compositions can be formulated for oral administration in solid or liquid form, for parenteral injection, for topical administration, or for rectal administration.

The term "pharmaceutically acceptable carrier", as used herein, means a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; cocoa butter and suppository waxes; oils such as peanut oil, cottonseed oil, safflower oil, sesame oil, olive oil, corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of one skilled in the art of formulations.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally", as used herein, refers to modes of administration which include intravenous, intramuscular, intraperitoneal, intrasternal, subcutaneous, intraarticular injection and infusion.

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like, and suitable mixtures thereof), vegetable oils (such as olive oil) and injectable organic esters such as ethyl oleate, or suitable mixtures thereof. Suitable fluidity of the composition may be maintained, for example, by the use of a coating such as lecithin, by the maintenance of the required particle size in the case of dispersions, and by the use of surfactants.

These compositions may also contain adjuvants such as preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

In some cases, in order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Suspensions, in addition to the active compounds, may contain suspending agents, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

If desired, and for more effective distribution, the compounds of the invention can be incorporated into slow-release or targeted-delivery systems such as polymer matrices, liposomes, and microspheres. They may be sterilized, for example, by filtration through a bacteria-retaining filter or by incorporation of sterilizing agents in the form of sterile solid compositions, which may be dissolved in sterile water or some other sterile injectable medium immediately before use.

Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations also are prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Solid dosage forms for oral administration include capsules, tablets, pills, powders, and granules. In such solid dosage forms, one or more compounds of the invention is mixed with at least one inert pharmaceutically acceptable carrier such as sodium citrate or dicalcium phosphate and/or a) fillers or extenders such as starches, lactose, sucrose, glucose, mannitol, and salicylic acid; b) binders such as carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using lactose or milk sugar as well as high molecular weight polyethylene glycols.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract in a delayed manner. Examples of materials which can be useful for delaying release of the active agent can include polymeric substances and waxes.

Compositions for rectal or vaginal administration are preferably suppositories which can be prepared by mixing the compounds of this invention with suitable non-irritating carriers such as cocoa butter, polyethylene glycol or a suppository wax which are solid at ambient temperature but liquid at body temperature and therefore melt in the rectum or vaginal cavity and release the active compound.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Dosage forms for topical or transdermal administration of a compound of this invention include ointments, pastes, creams, lotions, gels, powders, solutions, sprays, inhalants or patches. A desired compound of the invention is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, lactose, talc, silicic acid, aluminum hydroxide, calcium silicates and polyamide powder, or mixtures of these substances. Sprays can additionally contain customary propellants such as chlorofluorohydrocarbons.

Compounds of the invention may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the invention, stabilizers, preservatives, and the like. The preferred lipids are the natural and synthetic phospholipids and phosphatidylcholines (lecithins) used separately or together.

Methods to form liposomes are known in the art. See, for example, Prescott, Ed., Methods in Cell Biology, Volume XIV, Academic Press, New York, N.Y., (1976), p 33 et seq.

Dosage forms for topical administration of a compound of this invention include powders, sprays, ointments and inhalants. The active compound is mixed under sterile conditions with a pharmaceutically acceptable carrier and any needed preservatives, buffers or propellants, which can be required. Ophthalmic formulations, eye ointments, powders and solutions are contemplated as being within the scope of this invention. Aqueous liquid compositions comprising compounds of the invention also are contemplated.

The compounds of the invention can be used in the form of pharmaceutically acceptable salts or esters, or amides derived from inorganic or organic acids. The term "pharmaceutically acceptable salts and esters and amides", as used herein, refer to carboxylate salts, amino acid addition salts, zwitterions, and esters and amides of compounds of formula (I) which are, within the scope of sound medical judgment, suitable for use in contact with the tissues of humans and lower animals without undue toxicity, irritation, allergic response, and the like, are commensurate with a reasonable benefit/risk ratio, and are effective for their intended use.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well-known in the art. The salts can be prepared in situ during the final isolation and purification of the compounds of the invention or separately by reacting a free base function with a suitable organic acid. An example of a suitable salt is a hydrochloride salt.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Preferred salts of the compounds of the invention are the tartrate and hydrochloride salts.

Also, the basic nitrogen-containing groups can be quaternized with such agents as lower alkyl halides such as methyl, ethyl, propyl, and butyl chlorides, bromides and iodides; dialkyl sulfates such as dimethyl, diethyl, dibutyl and diamyl sulfates; long chain halides such as decyl, lauryl, myristyl and stearyl chlorides, bromides and iodides; arylalkyl halides such as benzyl and phenethyl bromides and others. Water or oil-soluble or dispersible products are thereby obtained.

Examples of acids which can be employed to form pharmaceutically acceptable acid addition salts include such inorganic acids as hydrochloric acid, hydrobromic acid, sulfuric acid and phosphoric acid and such organic acids as oxalic acid, maleic acid, succinic acid, and citric acid.

Basic addition salts can be prepared in situ during the final isolation and purification of compounds of this invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium, and aluminum salts, and the like, and nontoxic quaternary ammonia and amine cations including ammonium, tetramethylammonium, tetraethylammonium, methylammonium, dimethylammonium, trimethylammonium, triethylammonium, diethylammonium, ethylammonium and the like. Other representative organic amines useful for the formation of base addition salts include ethylenediamine, ethanolamine, diethanolamine, piperidine, and piperazine.

The term "pharmaceutically acceptable ester", as used herein, refers to esters of compounds of the invention which hydrolyze in vivo and include those that break down readily in the human body to leave the parent compound or a salt thereof. Examples of pharmaceutically acceptable, non-toxic esters of the invention include $C_1$-to-$C_6$-alkyl esters and $C_5$-to-$C_7$-cycloalkyl esters, although $C_1$-to-$C_4$-alkyl esters are preferred. Esters of the compounds of formula (I) may be prepared according to conventional methods. For example, such esters may be appended onto hydroxy groups by reaction of the compound that contains the hydroxy group with acid and an alkylcarboxylic acid such as acetic acid, or with acid and an arylcarboxylic acid such as benzoic acid. In the case of compounds containing carboxylic acid groups, the pharmaceutically acceptable esters are prepared from compounds containing the carboxylic acid groups by reaction of the compound with base such as triethylamine and an alkyl halide, alkyl triflate, for example with methyl iodide, benzyl iodide, cyclopentyl iodide. They also may be prepared by reaction of the compound with an acid such as hydrochloric acid and an alcohol such as methanol or ethanol.

The term "pharmaceutically acceptable amide", as used herein, refers to non-toxic amides of the invention derived from ammonia, primary $C_1$-to-$C_6$-alkyl amines and secondary $C_1$-to-$C_6$-dialkyl amines. In the case of secondary amines, the amine may also be in the form of a 5- or 6-membered heterocycle containing one nitrogen atom. Amides derived from ammonia, $C_1$-to-$C_3$-alkyl primary amides and $C_1$-to-$C_2$-dialkyl secondary amides are preferred. Amides of the compounds of formula (I) may be prepared according to conventional methods. Pharmaceutically acceptable amides are prepared from compounds containing primary or secondary amine groups by reaction of the compound that contains the amino group with an alkyl anhydride, aryl anhydride, acyl halide, or aroyl halide. In the case of compounds containing carboxylic acid groups, the pharmaceutically acceptable esters are prepared from compounds containing the carboxylic acid groups by reaction of the compound with base such as triethylamine, a dehydrating agent such as dicyclohexyl carbodiimide or carbonyl diimidazole, and an alkyl amine, dialkylamine, for example with methylamine, diethylamine, piperidine. They also may be prepared by reaction of the compound with an acid such as sulfuric acid and an alkylcarboxylic acid such as acetic acid, or with acid and an arylcarboxylic acid such as benzoic acid under dehydrating conditions as with molecular sieves added. The composition can contain a compound of the invention in the form of a pharmaceutically acceptable prodrug.

The invention contemplates pharmaceutically active compounds either chemically synthesized or formed by in vivo biotransformation to compounds of formula (I).

Methods of the Invention

The compounds and compositions of the invention are useful for treating and preventing certain diseases and disorders in humans and animals. As an important consequence of the ability of the compounds of the invention to modulate the effects of voltage-gated sodium channels (e.g., $Na_v1.7$ and $Na_v1.8$) in cells, the compounds described in the invention can affect physiological processes in humans and animals. In this way, the compounds and compositions described in the invention are useful for treating and preventing diseases and disorders modulated by voltage-gated sodium channels, e.g., $Na_v1.7$ and $Na_v1.8$. Typically, treatment or prevention of such diseases and disorders can be effected by selectively modulating voltage-gated sodium channels, e.g., $Na_v1.7$ and $Na_v1.8$, in a mammal, by administering a compound or composition of the invention, either alone or in combination with another active agent as part of a therapeutic regimen.

The terms "treat," "treating," and "treatment" are readily understood by a physician of ordinary skill and, with respect to treatment of a particular condition, can include ameliorating, suppressing, eradicating, preventing, reducing the risk of, and/or delaying the onset of the disease being treated.

The term "subject" includes animals such as mammals, including primates (e.g., humans), cows, sheep, goats, horses, dogs, cats, rabbits, rats, mice and the like. The methods of treatment are particularly suitable for use with a human subject, but may be used with other animal subjects, particularly mammals.

One embodiment of the present invention provides a method of treating pain in a subject in need thereof. The method comprises administering to the subject, including a mammal, such as a human, a therapeutically effective amount of a compound of formula (I), or a pharmaceutically acceptable salt thereof. Conditions related to pain include, for example, acute pain, chronic pain, neuropathic pain, nociceptive pain, allodynia, inflammatory pain, inflammatory hyperalgesia, post herpetic neuralgia, post-operative pain, post-stroke pain, neuropathies, neuralgia, diabetic neuropathy, HIV-related neuropathy, nerve injury, rheumatoid arthritic pain, osteoarthritic pain, burns, back pain, eye pain, visceral pain, cancer pain, dental pain, headache, migraine, carpal tunnel syndrome, knee pain, fibromyalgia, neuritis, sciatica, pelvic hypersensitivity, pelvic pain, menstrual pain.

Pain generally can be classified as acute or chronic. Acute pain begins suddenly and is short-lived (usually twelve weeks or less). It is usually associated with a specific cause such as a specific injury and is often sharp and severe. It is the kind of pain that can occur after specific injuries resulting from surgery, dental work, a strain or a sprain. Acute pain does not generally result in any persistent psychological response. In contrast, chronic pain is long-term pain, typically persisting for more than three months and leading to significant psychological and emotional problems. Common examples of chronic pain include neuropathic pain (e.g., painful diabetic neuropathy, postherpetic neuralgia), carpal tunnel syndrome, back pain, headache, cancer pain, arthritic pain and chronic post-surgical pain. In one embodiment, the condition related to pain is chronic pain. In another embodiment, the condition related to pain is acute pain.

Pain also can be divided into a number of different subtypes according to differing pathophysiology, including neuropathic, nociceptive, and inflammatory pain. Some types of pain have multiple etiologies and can be classified in more than one area, e.g., back pain and cancer pain have both nociceptive and neuropathic components.

In one embodiment, the condition related to pain is selected from the group consisting of neuropathic pain, nociceptive pain, and inflammatory pain.

In another embodiment, the condition related to pain is neuropathic pain. Neuropathic pain generally is defined as pain initiated or caused by a primary lesion or dysfunction in the nervous system and can result, for example, from trauma or disease. The term neuropathic pain encompasses many conditions with diverse etiologies including peripheral neuropathy, diabetic neuropathy, post-herpetic neuralgia, trigeminal neuralgia, back pain, cancer neuropathy, HIV-neuropathy, phantom limb pain, carpal tunnel syndrome, central post-stroke pain, and pain associated with chronic alcoholism, hypothyroidism, uremia, multiple sclerosis, spinal cord injury, Parkinson's disease, epilepsy and vitamin deficiency.

In another embodiment, the condition related to pain is nociceptive pain. Nociceptive pain is induced by tissue injury or by intense stimuli with the potential to cause injury. When a substantial injury occurs to body tissue through trauma or disease, the characteristics of nociceptor activation are altered and there is sensitization in the periphery leading to a heightened sensation of pain in the subject. Moderate to severe acute nociceptive pain is a prominent feature of pain from central nervous system trauma, strains/sprains, burns, myocardial infarction and acute pancreatitis, post-operative pain (pain following any type of surgical procedure), post-traumatic pain, renal colic, cancer pain and back pain. Cancer pain can be chronic pain such as tumor related pain (e. g., bone pain, headache, facial pain or visceral pain) or pain associated with cancer therapy (e.g., post-chemotherapy syndrome, chronic postsurgical pain syndrome or post radiation syndrome). Cancer pain can also occur in response to chemotherapy, immunotherapy, hormonal therapy or radiotherapy. Back pain can be due to herniated or ruptured intervertebral discs or abnormalities of the lumber facet joints, sacroiliac joints, paraspinal muscles or the posterior longitudinal ligament.

In another embodiment, the condition related to pain is inflammatory pain. A common type of inflammatory pain is arthritic pain arising from rheumatoid disease (such as ankylosing spondylitis) or symptomatic osteoarthritis or degenerative joint disease. Another type of inflammatory pain is visceral pain. Visceral pain is pain associated with the viscera, which encompass the organs of the abdominal cavity including the sex organs, spleen and part of the digestive system. Pain associated with the viscera can be divided into digestive visceral pain and non-digestive visceral pain. Commonly encountered gastrointestinal disorders that cause pain include functional bowel disorder and inflammatory bowel disease. These gastrointestinal disorders include a wide range of disease states that are currently only moderately controlled, including, with respect to functional bowel disorder, gastro-esophageal reflux, dyspepsia, irritable bowel syndrome, and functional abdominal pain syndrome, and, in respect of inflammatory bowel disease, Crohn's disease, ileitis and ulcerative colitis, all of which regularly produce visceral pain. Other types of visceral pain include the pain associated with dysmenorrhea, cystitis and pancreatitis and pelvic pain.

In another embodiment, the condition related to pain results from a musculo-skeletal condition such as myalgia, fibromyalgia, spondylitis, sero-negative (non-rheumatoid) arthropathies, non-articular rheumatism, dystrophinopathy, glycogenolysis, polymyositis and pyomyositis; heart and vascular pain, including pain caused by angina, myocardial infarction, mitral stenosis, pericarditis, Raynaud's phenomenon, scleredoma and skeletal muscle ischemia; head pain, such as migraine (including migraine with aura and migraine without aura), cluster headache, tension-type headache mixed headache and headache associated with vascular disorders; and orofacial pain, including dental pain, otic pain, burning mouth syndrome, temporomandibular myofascial pain, and paroxysmal extreme pain disorder (PEPD); and inherited erythromelalgia (IEM).

In some embodiments, the methods comprise combination therapy, wherein the compound(s) and/or salt(s) of the invention is/are co-administered with a second (or even a third, fourth, etc.) compound, such as, for example, another therapeutic agent used to treat pain. The compound(s) and/or salt(s) of this invention can also be co-administered with therapeutic agents other than therapeutic agents used to treat pain. In these co-administration embodiments, the compound(s) and/or salt(s) of the invention and the second, etc. therapeutic agent(s) may be administered in a substantially simultaneous manner (e.g., or within about five minutes of each other), in a sequential manner, or both. It is contemplated that such combination therapies may include administering one therapeutic agent multiple times between the administrations of the other. The time period between the administration of each agent may range from a few seconds (or less) to several hours or days, and will depend on, for example, the properties of each composition and active ingredient (e.g., potency, solubility, bioavailability, half-life, and kinetic profile), as well as the condition of the patient. The compound(s) and/or salt(s) of this invention and the second, etc. therapeutic agent may also be administered in a single formulation.

In certain embodiments, the method comprises co-administering to the subject the compound(s) and/or salt(s) of the invention with one or more compounds selected from the group consisting of nonsteroidal anti-inflammatory drugs (NSAIDs), opioid analgesics, barbiturates, benzodiazapines, histamine antagonists, sedatives, skeletal muscle relaxants, transient receptor potential ion channel antagonists, α-adrenergics, tricyclic antidepressants, anticonvulsants, tachykinin antagonists, muscarinic antagonists, cyclooxygenase-2 selective inhibitors, neuroleptics, vanilloid receptor agonists, vanilloid receptor antagonists, β-adrenergics, local anesthetics, corticosteroids, 5-HT receptor agonists, 5-HT receptor antagonists, 5-HT$_{2A}$ receptor antagonists, cholinergic analgesics, α$_2$δ ligands (such as gabapentin or pregabalin), cannabinoid receptor ligands, metabotropic glutamate subtype 1 receptor antagonists, serotonin reuptake inhibitors, norepinephrine reuptake inhibitors, dual serotonin-noradrenaline reuptake inhibitors, Rho kinase inhibitors, inducible nitric oxide synthase inhibitors, acetylcholinesterase inhibitors, prostaglandin E$_2$ subtype 4 antagonists, leukotriene B4 antagonists, 5-lipoxygenase inhibitors, sodium channel blockers, 5-HT$_3$ antagonists, N-methyl-D-aspartic acid receptor antagonists, phosphodiesterase V inhibitors, voltage-gated calcium channel blockers (e.g., N-type and T-type), and KCNQ openers (e.g., KCNQ2/3 (K$_v$7.2/3)).

In one embodiment, the method comprises administering to the subject a therapeutically effective amount of a compound described herein, or a pharmaceutically acceptable salt, with or without a pharmaceutically acceptable carrier, in combination with a second therapeutic agent selected from the group consisting of acetaminophen, NSAIDs, opioid analgesics, and combinations thereof.

In one embodiment, the method comprises administering to the subject a therapeutically effective amount of a compound described herein, or a pharmaceutically acceptable salt, with or without a pharmaceutically acceptable carrier, in combination with one or more additional therapeutic agents for treating pain. In one embodiment, the additional therapeutic agent is selected from the group consisting of acetaminophen, NSAIDs (such aspirin, ibuprofen, and naproxen), and opioid analgesics. In another embodiment, the additional therapeutic agent is acetaminophen. In another embodiment, the additional therapeutic agent is an NSAID. In another embodiment, the additional therapeutic agent is an opioid analgesic.

The present invention also is directed, in part, to one or more compounds and/or salts of the invention for use in the treatment of a voltage-gated sodium channel-mediated condition, such as pain.

The present invention also is directed, in part, to one or more compounds and/or salts of the invention, and, optionally one or more additional therapeutic agents, for use as a medicament. In some embodiments, the medicament is for treating pain. In another embodiment, the medicament is for treating neuropathic pain. In another embodiment, the medicament is for treating nociceptive pain. In another embodiment, the medicament is for treating inflammatory pain.

The present invention is further directed, in part, to a use of one or more compounds and/or salts of the invention, and, optionally one or more additional therapeutic agents to prepare a medicament. In some embodiments, the medicament is for co-administration with one or more additional therapeutic agents. In some embodiments, the medicament is for treating pain. In some embodiments, the medicament is for treating neuropathic pain. In some embodiments, the medicament is for treating nociceptive pain. In some embodiments, the medicament is for treating inflammatory pain.

Compounds of the invention are particularly useful for treating and preventing a condition or disorder affecting pain.

The ability of the compounds of the invention, including, but not limited to, those specified in the examples, to treat the pain of peripheral neuropathy may be demonstrated by Faber C G, et al. Ann Neurol 2012; 72:26-39; Faber C G, et al. Proc. Natl. Acad. Sci. U.S.A. 2012; 109:19444-19449.

The ability of the compounds of the invention, including, but not limited to, those specified in the examples, to treat inflammatory and neuropathic pain may be demonstrated by McGowan E, et al. Anesth. Analg. 2009; 109:951-958.

The ability of the compounds of the invention, including, but not limited to, those specified in the examples, to treat chronic inflammatory knee pain may be demonstrated by Strickland I T, et al. European Journal of Pain 2008; 12:564-572.

The ability of the compounds of the invention, including, but not limited to, those specified in the examples, to treat osteoarthitis may be demonstrated by Schuelert N, et al. Arthritis Research & Therapy 2012; 14:R5; Malfait, A-M, et al. Nat. Rev. Rheumatol. 2013; 9:654-664; and Staunton Calif., et al. Current Pain and Headache Reports 2013; 17:378.

The ability of the compounds of the invention, including, but not limited to, those specified in the examples, to treat osteoarthitis and sciatic pain may be demonstrated by Reimann F, et al. Proceedings of the National Academy of Sciences of the United States of America 2010; 107:5148-5153.

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

When used in the above or other treatments, a therapeutically effective amount of one of the compounds of the invention can be employed in pure form or, where such forms exist, in pharmaceutically acceptable salt or ester, or amide form. Alternatively, the compound can be administered as a pharmaceutical composition containing the compound of interest in combination with one or more pharmaceutically acceptable carriers. The phrase "therapeutically effective amount" of the compound of the invention means a sufficient amount of the compound to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. For example, it is well within the skill of the art to start doses of the compound at levels lower than required to achieve the desired therapeutic effect and to gradually increase the dosage until the desired effect is achieved.

For treatment or prevention of disease, the total daily dose of the compounds of this invention administered to a human or lower animal may range from about 0.0003 to about 100 mg/kg/day. For purposes of oral administration, more preferable doses can be in the range of from about 0.0003 to about 30 mg/kg/day. If desired, the effective daily dose can be divided into multiple doses for purposes of administration; consequently, single dose compositions may contain such amounts or submultiples thereof to make up the daily dose.

The compounds and processes of the invention will be better understood by reference to the following examples, which are intended as an illustration of and not a limitation upon the scope of the invention.

EXAMPLES

Abbreviations: APCI for atmospheric pressure chemical ionization; CDI for di(1H-imidazol-1-yl)methanone or 1,1'-carbonyldiimidazole; CPME for cyclopentyl methyl ether; DBU for 1,8-diazabicyclo[5.4.0]undec-7-ene; DCI for desorption chemical ionization; DME for dimethoxyethane; DMF for N,N-dimethylformamide; DMSO for dimethyl sulfoxide; ee for enantiomeric excess; ESI for electrospray ionization; HATU for N-[(dimethylamino)-1H-1,2,3-triazolo-[4,5-b]pyridin-1-ylmethylene]-N-methylmethanaminium hexafluorophosphate N-oxide; HPLC for high performance liquid chromatography; LCMS for liquid chromatography/mass spectrometry; MTBE for methyl tert-butyl ether; NMR for nuclear magnetic resonance; and $Pd_2(dba)_3$ for tris(dibenzylideneacetone)dipalladium(0).

Example 1

1-[1-(2-fluorophenyl)-1H-indazol-4-yl]-3-[2-oxo-2-(pyrrolidin-1-yl)ethyl]imidazolidin-2-one Example 1A 4-bromo-1-(2-fluorophenyl)-1H-indazole To a mixture of 2-bromo-6-fluorobenzaldehyde (Combi-Blocks, 10 g, 49 mmol) and (2-fluorophenyl)hydrazine hydrochloride (8.01 g, 49.3 mmol) in N-methyl-2-pyrrolidinone (100 mL) at ambient temperature was added cesium carbonate (33.7 g, 103 mmol). The resulting slurry was heated to 140° C. After 1 hour, the reaction was allowed to cool to ambient temperature and water was added (300 mL). The slurry was stirred for 1 hour; then the solids were collected by filtration, washed with water and dried in a vacuum oven at 50° C. to give the titled compound (13.01 g, 44.7 mmol, 91% yield). $^1$H NMR (400 MHz, DMSO-$d_6$) δ ppm 8.41 (d, J=0.5 Hz, 1H), 7.72 (td, J=7.8, 1.6 Hz, 1H), 7.66-7.38 (m, 6H; MS (DCI) m/z 291, 293 [M+H]$^+$.

Example 1B 1-(1-(2-fluorophenyl)-1H-indazol-4-yl)imidazolidin-2-one

To a solution of the product of Example 1A (5.00 g, 17.2 mmol) and imidazolidin-2-one hydrate (16.3 g, 86.0 mmol) in dimethoxyethane (DME) (100 mL) at ambient temperature was added cesium carbonate (8.39 g, 25.8 mmol), (9,9-dimethyl-9H-xanthene-4,5-diyl)bis(diphenylphosphine) (0.80 g, 1.37 mmol) and tris(dibenzylideneacetone)dipalladium(0) ($Pd_2(dba)_3$, 0.63 g, 0.69 mmol). This mixture was heated to 80° C. and was allowed to stir for 16 hours. The mixture was allowed to cool to ambient temperature and was partitioned between water (250 mL) and ethyl acetate (200 mL). The organic phase was washed with water (200 mL) and brine (100 mL), dried over anhydrous $Na_2SO_4$, filtered and concentrated under reduced pressure. The residue was purified by column chromatography ($SiO_2$ 100% $CH_2Cl_2$ to 90% $CH_3C(O)OCH_2CH_3:CH_2Cl_2$, then 10% $CH_3OH:CH_2Cl_2$). The resulting material was dissolved in 10:1 methyl tert-butyl ether (MTBE):$CH_2Cl_2$ (5 volumes), and the resultant mixture was heated to reflux. The mixture was allowed to cool to ambient temperature with stirring. The resulting solids were isolated via filtration, washed with methyl tert-butyl ether and dried to provide the titled compound (2.58 g 8.7 mmol, 51% yield). $^1$H NMR (500 MHz, DMSO-$d_6$) δ ppm 8.43 (d, J=0.6 Hz, 1H), 7.67 (td, J=7.8, 1.5 Hz, 1H), 7.62-7.50 (m, 2H), 7.43 (ddd, J=18.7, 11.7, 4.7 Hz, 2H), 7.14 (d, J=7.4 Hz, 2H), 7.06 (dd, J=8.4, 2.9 Hz, 1H), 4.15-4.05 (m, 2H), 3.51 (t, J=7.8 Hz, 2H); MS (ESI+) m/z 297 [M+H]$^+$.

Example 1C

1-[1-(2-fluorophenyl)-1H-indazol-4-yl]-3-[2-oxo-2-(pyrrolidin-1-yl)ethyl]imidazolidin-2-one To a solution of the product of Example 1B (1.2 g, 4.05 mmol) in dimethylformamide (DMF) (20 mL) at ambient temperature was added NaH (60% dispersion in mineral oil, 0.81 g, 20.3 mmol). This mixture was stirred at ambient temperature for 30 minutes, and then 2-bromo-1-(pyrrolidin-1-yl)ethanone (ChemDiv, 2.33 g, 12.15 mmol) was added. The mixture was warmed to 45° C. and was allowed to stir for 3 hours. The mixture was quenched with saturated, aqueous $NaHCO_3$ (5 mL) and extracted with ethyl acetate (10 mL). The layers were separated and the aqueous layer was extracted with ethyl acetate (3×5 mL). The combined organic fractions were dried over anhydrous $Na_2SO_4$, filtered, and concentrated under reduced pressure. The residue was purified via column chromatography ($SiO_2$, 1% ethyl acetate/heptanes to 30% ethyl acetate/heptanes) to give the titled compound (1.25 g, 3.07 mmol, 76% yield). $^1$H NMR (400 MHz, methanol-$d_4$) δ ppm 8.43 (s, 1H), 7.62 (td, J=7.6, 1.6 Hz, 1H), 7.59-7.49 (m, 1H), 7.49-7.37 (m, 3H), 7.18-7.08 (m, 2H), 4.17 (s, 2H), 4.13 (dd, J=9.0, 7.0 Hz, 2H), 3.75 (dd, J=8.9, 6.9 Hz, 2H), 3.52 (dt, J=19.5, 6.8 Hz, 4H), 2.04 (q, J=6.8 Hz, 2H), 1.92 (q, J=6.8 Hz, 2H); MS (ESI$^+$) m/z 408 [M+H]$^+$.

Example 2 tert-butyl 3-[1-(2-fluorophenyl)-1H-indazol-4-yl]-2-oxoimidazolidine-1-carboxylate To a solution of the product of Example 1B (1.54 g, 5.20 mmol) and di-t-butyl dicarbonate (2.41 mL, 10.4 mmol) in acetonitrile (20 mL) was added 4-dimethylaminopyridine (0.063 g, 0.520 mmol). This mixture was allowed to stir at ambient temperature for 18 hours. The mixture was concentrated under reduced pressure, and the residue was purified via column chromatography ($SiO_2$, 5% ethyl acetate/heptanes to 100% ethyl acetate) to give the titled compound (1.6 g, 4.04 mmol, 78% yield). $^1$H NMR (300 MHz, methanol-$d_4$) δ ppm 8.38 (d, J=1.1 Hz, 1H), 7.62 (td, J=7.6, 1.7 Hz, 1H), 7.59-7.52 (m, 1H), 7.51-7.44 (m, 1H), 7.44-7.37 (m, 2H), 7.25-7.19 (m, 1H), 7.18 (d, J=7.5 Hz, 1H), 4.14-3.96 (m, 4H), 1.58 (s, 9H); MS (ESI$^+$) m/z 397 [M+H]$^+$.

Example 3

2-{3-[1-(2-fluorophenyl)-1H-indazol-4-yl]-2-oxoimidazolidin-1-yl}acetamide

To a solution of the product of Example 1B (0.69 g, 2.33 mmol) in N,N-dimethylformamide (10 mL) at ambient temperature was added NaH (60% dispersion in mineral oil, 0.47 g, 11.6 mmol). This mixture was stirred at ambient temperature for 30 minutes, and then 2-iodoacetamide (1.29 g, 6.99 mmol) was added. The mixture was warmed to 45° C., was allowed to stir for 3 hours, was allowed to cool to ambient temperature, and was quenched with saturated, aqueous $NaHCO_3$ (5 mL) and extracted with ethyl acetate (10 mL). The layers were separated, and the aqueous layer was extracted with ethyl acetate (3×5 mL). The combined organic fractions were dried over anhydrous $Na_2SO_4$, filtered, and concentrated under reduced pressure. The residue was purified via column chromatography ($SiO_2$, 1% ethyl acetate/heptanes to 30% ethyl acetate/heptanes) to give the title compound (0.45 g, 1.27 mmol, 55% yield). $^1$H NMR (300 MHz, methanol-$d_4$) δ ppm 8.43 (d, J=1.3 Hz, 1H), 7.62 (td, J=7.5, 1.6 Hz, 1H), 7.58-7.50 (m, 1H), 7.48-7.35 (m, 3H), 7.14 (dd, J=8.1, 3.7 Hz, 2H), 4.18-4.09 (m, 2H), 4.02 (s, 2H), 3.77-3.68 (m, 2H); MS (ESI$^+$) m/z 354 [M+H]$^+$.

Example 4 isopropyl 3-[1-(2-fluorophenyl)-1H-indazol-4-yl]-2-oxoimidazolidine-1-carboxylate To a solution of the product of Example 1B (1 g, 3.37 mmol) and triethylamine (1.88 mL, 13.5 mmol) in acetonitrile (10 mL) was added isopropyl chloroformate (1 M in toluene, 6.75 mL, 6.75 mmol). This mixture was allowed to stir at ambient temperature for 18 hours. The mixture was concentrated under reduced pressure, and the residue was purified via column chromatography ($SiO_2$, 5% ethyl acetate/heptanes to 100% ethyl acetate) to give the titled compound (0.45 g, 1.2 mmol, 35% yield). $^1$H NMR (300 MHz, methanol-$d_4$) δ ppm 8.38 (d, J=0.9 Hz, 1H), 7.62 (td, J=7.6, 1.6 Hz, 1H), 7.59-7.52 (m, 1H), 7.52-7.37 (m, 3H), 7.23 (dd, J=8.5, 2.8 Hz, 1H), 7.19 (d, J=7.5 Hz, 1H), 5.18-5.01 (m, 1H), 4.18-3.99 (m, 4H), 1.37 (d, J=6.2 Hz, 6H); MS (ESI$^+$) m/z 383 [M+H]$^+$.

Example 5 isobutyl 3-[1-(2-fluorophenyl)-1H-indazol-4-yl]-2-oxoimidazolidine-1-carboxylate To a solution of the product of Example 1B (0.12 g, 0.405 mmol) and triethylamine (0.169 mL, 1.215 mmol) in acetonitrile (3 mL) was added isobutyl chloroformate (0.079 mL, 0.607 mmol). This mixture was allowed to stir at ambient temperature for 18 hours. The mixture was concentrated under reduced pressure, and the residue was purified via column chromatography ($SiO_2$, 5% ethyl acetate/heptanes to 100% ethyl acetate) to give the titled compound (0.11 g, 0.28 mmol, 69% yield). $^1$H NMR (300 MHz, methanol-$d_4$) δ ppm 8.38 (s, 1H), 7.62 (td, J=7.6, 1.6 Hz, 1H), 7.58-7.52 (m, 1H), 7.52-7.45 (m, 1H), 7.45-7.36 (m, 2H), 7.28-7.15 (m, 2H), 4.11 (d, J=1.9 Hz, 4H), 4.06 (d, J=6.6 Hz, 2H), 2.17-1.84 (m, 1H), 1.02 (d, J=6.7 Hz, 6H); MS (ESI$^+$) m/z 397 [M+H]$^+$.

Example 6

1-[1-(2-fluorophenyl)-1H-indazol-4-yl]-3-(methylsulfonyl)imidazolidin-2-one

To a solution of the product of Example 1B (0.2 g, 0.675 mmol) and triethylamine (0.38 mL, 2.70 mmol) in $CH_2Cl_2$ (5 mL) was added methanesulfonyl chloride (0.105 mL, 1.35 mmol). This mixture was allowed to stir at ambient temperature for 18 hours and then was quenched with saturated, aqueous $NaHCO_3$ (10 mL) and extracted with ethyl acetate (10 mL). The layers were separated and the aqueous layer was extracted with ethyl acetate (3×5 mL). The combined organic layers were dried over anhydrous $Na_2SO_4$, filtered and concentrated under reduced pressure. The crude material was purified via column chromatography ($SiO_2$, 5% ethyl acetate/heptanes to 70% ethyl acetate/heptanes) to give the titled compound (0.15 g, 0.40 mmol, 59% yield). $^1$H NMR (500 MHz, CDCl$_3$) δ ppm 8.34 (d, J=1.0 Hz, 1H), 7.61 (td, J=7.9, 1.9 Hz, 1H), 7.48-7.44 (m, 1H), 7.45-7.38 (m, 1H), 7.36-7.29 (m, 2H), 7.28-7.22 (m, 1H), 7.10 (d, J=7.5 Hz, 1H), 4.20-4.08 (m, 4H), 3.42 (s, 3H); MS (ESI$^+$) m/z 375 [M+H]$^+$.

Example 7

1-[1-(2-fluorophenyl)-1H-indazol-4-yl]-3-{2-[(3S)-3-hydroxypyrrolidin-1-yl]-2-oxoethyl}imidazolidin-2-one

Example 7A tert-butyl 2-(3-(1-(2-fluorophenyl)-1H-indazol-4-yl)-2-oxoimidazolidin-1-yl)acetate To a solution of the product of Example 1B (3.0 g, 10.1 mmol) in tetrahydrofuran (20 mL) at ambient temperature was added sodium hydride (60% dispersion in mineral oil, 0.607 g, 15.2 mmol). After 5 minutes, tert-butyl 2-bromoacetate (1.9 mL, 13 mmol) was added, and the mixture was stirred for 1 hour. The mixture was quenched with water (150 mL), the layers were separated, and the aqueous layer was extracted with ethyl acetate (2×200 mL). The combined organic layers were concentrated under reduced pressure, and the residue was purified by column chromatography ($SiO_2$, 50% ethyl acetate:heptane) to provide the titled compound (3.37 g, 8.2 mmol, 81%). $^1$H NMR (400 MHz, DMSO-$d_6$) δ ppm 8.40 (s, 1H), 7.68 (td, J=7.9, 1.5 Hz, 1H), 7.63-7.50 (m, 2H), 7.48-7.38 (m, 2H), 7.18 (d, J=7.6 Hz, 1H), 7.10 (dd, J=8.4, 2.9 Hz, 1H), 4.16-4.05 (m, 2H), 3.99 (s, 2H), 3.69-3.57 (m, 2H), 1.47 (s, 9H); MS (ESI+) m/z 411 [M+H]$^+$.

Example 7B

2-(3-(1-(2-fluorophenyl)-1H-indazol-4-yl)-2-oxoimidazolidin-1-yl)acetic Acid To a solution of the product of Example 7A (19.9 g, 48.5 mmol) in $CH_2Cl_2$ (65 mL) at ambient temperature was added trifluoroacetic acid (65.0 mL) dropwise via addition funnel over 20 minutes. This mixture was allowed to stir at ambient temperature for 6 hours and then was concentrated under reduced pressure and diluted with toluene. The material was again concentrated under reduced pressure. The dilution with toluene and concentration was repeated two additional times to give the titled compound as an off-white solid (16.95 g, 47.8 mmol, 99% yield). MS (ESI$^+$) m/z 355 [M+H]$^+$.

Example 7C

1-[1-(2-fluorophenyl)-1H-indazol-4-yl]-3-{2-[(3S)-3-hydroxypyrrolidin-1-yl]-2-oxoethyl}imidazolidin-2-one To a solution of the product of Example 7B (0.2 g, 0.564 mmol), (S)-3-hydroxypyrrolindine (0.052 mL, 0.62 mmol) and N-ethyl-N-isopropylpropan-2-amine (0.81 mL, 4.66 mmol) in tetrahydrofuran (5 mL) was added N-[(dimethylamino)-1H-1,2,3-triazolo-[4,5-b]pyridin-1-ylmethylene]-N-methylmethanaminium hexafluorophosphate N-oxide (HATU, 0.24 g, 0.62 mmol). This mixture was allowed to stir at ambient temperature for 16 hours and then was quenched with $H_2O$ (5 mL) and extracted with ethyl acetate (10 mL). The layers were separated, and the aqueous layer was extracted with ethyl acetate (3×5 mL). The combined organic fractions were dried over anhydrous $Na_2SO_4$, filtered, and concentrated under reduced pressure. The residue was purified via column chromatography ($SiO_2$, 20% hexanes/ethyl acetate to 100% ethyl acetate to 9:1:0.1 ethyl acetate/methanol/triethylamine) to provide the titled compound (0.20 g, 0.47 mmol, 84% yield). $^1$H NMR (300 MHz, methanol-$d_4$) δ ppm 8.42 (d, J=0.9 Hz, 1H), 7.62 (td, J=7.6, 1.6 Hz, 1H), 7.58-7.51 (m, 1H), 7.49-7.35 (m, 3H), 7.18-7.07 (m, 2H), 4.59-4.37 (m, 1H), 4.18-4.09 (m, 4H), 3.80-3.43 (m, 6H), 2.21-1.85 (m, 2H); MS (ESI$^+$) m/z 424 [M+H]$^+$.

Example 8

1-[1-(2-fluorophenyl)-1H-indazol-4-yl]-3-(4-methyl-2-oxopentyl)imidazolidin-2-one To a solution of the product of Example 1B (2 g, 6.75 mmol) in N,N-dimethylformamide (15 mL) at ambient temperature was added NaH (60% dispersion in mineral oil, 0.810 g, 20.3 mmol). This mixture was stirred at ambient temperature for 30 minutes, and then 1-bromo-4-methylpentane-2-one (1.57 g, 8.77 mmol) was added. The mixture was allowed to stir at ambient temperature for 24 hours, and then the mixture was quenched with saturated, aqueous NaHCO$_3$ (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes to 10% methanol/ethyl acetate) to give the titled compound (0.65 g, 1.65 mmol, 24% yield). $^1$H NMR (300 MHz, methanol-$d_4$) δ ppm 8.37 (d, J=1.1 Hz, 1H), 7.66-7.58 (m, 1H), 7.58-7.50 (m, 1H), 7.50-7.36 (m, 3H), 7.19-7.09 (m, 2H), 4.21 (s, 2H), 4.17-4.07 (m, 2H), 3.73-3.62 (m, 2H), 2.41 (d, J=6.9 Hz, 2H), 2.19 (dp, J=13.5, 6.7 Hz, 1H), 0.99 (d, J=6.6 Hz, 6H); MS (ESI$^+$) m/z 395 [M+H]$^+$.

Example 9

2-{3-[1-(2-fluorophenyl)-1H-indazol-4-yl]-2-oxo-2,3-dihydro-1H-imidazol-1-yl}acetamide Example 9A 1-(2-fluorophenyl)-1H-indazol-4-amine To a round bottom flask was added 1H-indazol-4-amine (Enamine, 8.65 g, 65 mmol), CuI (Strem, 0.62 g, 3.25 mmol) and potassium phosphate tribasic (Strem, 11.30 mL, 137 mmol). This mixture was degassed three times with a nitrogen backflush each time. 1-Fluoro-2-iodobenzene (9.10 mL, 78 mmol) was added followed by trans-N,N'-dimethylcyclohexane-1,2-diamine (2.05 mL, 13.0 mmol) and dioxane (200 mL). The mixture was warmed to 110° C. and was stirred for 72 hours. The mixture was allowed to cool to ambient temperature and then was filtered through diatomaceous earth rinsing with ethyl acetate. The filtrate was concentrated under reduced pressure, and the residue was purified via column chromatography (SiO$_2$, 1% ethyl acetate/hexanes to 50% ethyl acetate/hexanes) to give the titled compound (7.53 g, 33.1 mmol, 51% yield). MS (ESI$^+$) m/z 228 [M+H]$^+$.

Example 9B 1-(1-(2-fluorophenyl)-1H-indazol-4-yl)-1H-imidazol-2(3H)-one

To a solution of the product of Example 9A (8.5 g, 37.4 mmol) in acetonitrile (100 mL) at ambient temperature was added bis(2,5-dioxopyrrolidin-1-yl) carbonate (10.54 g, 41.1 mmol). This mixture was stirred at ambient temperature for 2 hours, and then N-ethyl-N-isopropylpropan-2-amine (7.82 mL, 44.9 mmol) and aminoacetaldehyde dimethylacetal (4.45 mL, 41.1 mmol) were added. The mixture was allowed to stir for an additional 16 hours. The reaction mixture was quenched with H$_2$O (10 mL), the layers were separated and the aqueous layer was extracted with ethyl acetate (3×15 mL). The combined organic fractions were dried over anhydrous Na$_2$SO$_4$, filtered, and concentrated under reduced pressure. The intermediate urea acetal was carried on directly.

A mixture of the intermediate urea acetal was dissolved in methanol (100 mL), and sulfuric acid (1.5 M, 66.6 mL, 100 mmol) was added. This mixture was warmed to 55° C. and was stirred for 2 hours. The mixture was allowed to cool to ambient temperature and was stirred for 14 hours. The mixture was concentrated under reduced pressure, and the residue was diluted with ethyl acetate (200 mL) and quenched by the slow addition of saturated, aqueous NaHCO$_3$ (200 mL). The layers were separated, and the aqueous layer was extracted with ethyl acetate (3×10 mL). The combined organic fractions were dried over anhydrous Na$_2$SO$_4$, filtered, and concentrated under reduced pressure. The residue was purified via column chromatography (SiO$_2$, 15% ethyl acetate/heptanes to 100% ethyl acetate to 10% MeOH in ethyl acetate) to give the titled compound (3.6 g, 12.2 mmol, 33% yield). MS (ESI$^+$) m/z 295 [M+H]$^+$.

Example 9C

2-{3-[1-(2-fluorophenyl)-1H-indazol-4-yl]-2-oxo-2,3-dihydro-1H-imidazol-1-yl}acetamide To a solution of the product of Example 9B (0.65 g, 2.21 mmol) in N,N-dimethylformamide (8 mL) at 0° C. was added NaH (60% dispersion in mineral oil, 0.265 g, 6.63 mmol). This mixture was stirred at ambient temperature for 30 minutes and then 2-bromoacetamide (0.37 g, 2.65 mmol) was added. The mixture was warmed to 45° C. and was allowed to stir at ambient temperature for 3 hours. Then the mixture was allowed to cool to ambient temperature, was quenched with saturated, aqueous NaHCO$_3$ (5 mL) and was extracted with ethyl acetate (10 mL). The layers were separated and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes to 10% methanol/ethyl acetate) to give the titled compound (0.44 g, 1.25 mmol, 57% yield). $^1$H NMR (300 MHz, methanol-$d_4$) δ ppm 8.39 (d, J=1.0 Hz, 1H), 7.65 (td, J=7.6, 1.7 Hz, 1H), 7.62-7.51 (m, 2H), 7.49-7.39 (m, 2H), 7.38-7.32 (m, 2H), 6.96 (d, J=3.1 Hz, 1H), 6.77 (d, J=3.0 Hz, 1H), 4.47 (s, 2H); MS (ESI$^+$) m/z 352 [M+H]$^+$.

Example 10

1-[1-(2-fluorophenyl)-1H-indazol-4-yl]-3-{2-[(3S)-3-fluoropyrrolidin-1-yl]-2-oxoethyl}imidazolidin-2-one To a solution of the product of Example 7B (15.4 g, 32.9 mmol) and triethylamine (18 mL, 130 mmol) in tetrahydrofuran (200 mL) at ambient temperature was added (S)-(+)-3-fluoropyrrolidine hydrochloride (4.54 g, 36.2 mmol) followed by addition of 2,4,6-tripropyl-1,3,5,2,4,6-trioxatriphosphinane 2,4,6-trioxide (T$_3$P®, 50 weight % in ethyl acetate, 28.8 mL, 49.3 mmol) over 15 minutes. The reaction was complete after addition of the coupling reagent. To the reaction was added water (200 mL), and the mixture was stirred for 5 minutes. The mixture was transferred to a reparatory funnel with additional water (200 mL) and extracted with ethyl acetate (2×400 mL). The organic phases were combined and washed with 1 M NaOH (200 mL) and brine (200 mL), dried over anhydrous Na$_2$SO$_4$, filtered and concentrated under reduced pressure. The residue was dissolved in 5 volumes of CH$_2$Cl$_2$ and isopropyl alcohol (15 volumes) was added with vigorous stirring. After 15 minutes, the resulting solids were collected by filtration, washed with isopropyl alcohol and then diethyl ether, and dried under vacuum to provide the titled compound (8.2 g, 19.2 mmol, 59%). $^1$H NMR (400 MHz, DMSO-d$_6$) δ ppm 8.41 (d, J=0.8 Hz, 1H), 7.68 (td, J=7.8, 1.6 Hz, 1H), 7.63-7.49 (m, 2H), 7.49-7.34 (m, 2H), 7.18 (d, J=7.6 Hz, 1H), 7.09 (dd, J=8.4, 3.0 Hz, 1H), 5.59-5.14 (m, 1H), 4.26-3.95 (m, 4H), 3.92-3.47 (m, 6H), 2.36-1.85 (m, 2H); MS (ESI$^+$) m/z 426 [M+H]$^+$.

Example 11

1-[1-(2-fluorophenyl)-1H-indazol-4-yl]-3-{2-[(3S)-3-fluoropyrrolidin-1-yl]-2-oxoethyl}-1,3-dihydro-2H-imidazol-2-one Example 11A 2-(3-(1-(2-fluorophenyl)-1H-indazol-4-yl)-2-oxo-2,3-dihydro-1H-imidazol-1-yl)acetic Acid To a solution of the product of Example 9B (1.63 g, 5.54 mmol) in N,N-dimethylformamide (20 mL) at ambient temperature was added NaH (60% dispersion in mineral oil, 1.11 g, 27.7 mmol). This mixture was stirred at ambient temperature for 30 minutes, and then ethyl iodoacetate (1.97 mL, 16.6 mmol) was added. The mixture was warmed to 40° C. and was allowed to stir at ambient temperature for 3 hours. Then the mixture was quenched with saturated, aqueous NaHCO$_3$ (5 mL) and extracted with ethyl acetate (10 mL). The layers were separated, and the aqueous layer was further extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes) to give still impure ethyl {3-[1-(2-fluorophenyl)-1H-indazol-4-yl]-2-oxo-2,3-dihydro-1H-imidazol-1-yl}acetate. The mixture was dissolved in tetrahydrofuran (10 mL) and methanol (10 mL) and 40% aqueous KOH (10 mL) was added. The mixture was stirred for 20 hours and then was quenched with concentrated HCl (~10 mL). The mixture was concentrated under reduced pressure and washed with CH$_2$Cl$_2$ (20 mL). The layers were separated, and the aqueous layer was extracted with CH$_2$Cl$_2$ (3×7 mL). The combined organic fractions were dried over anhydrous Na$_2$SO$_4$, filtered and concentrated under reduced pressure to give the titled compound (1.9 g, 3.77 mmol, 68% yield). MS (ESI$^+$) m/z 353 [M+H]$^+$.

Example 11B

1-[1-(2-fluorophenyl)-1H-indazol-4-yl]-3-{2-[(3S)-3-fluoropyrrolidin-1-yl]-2-oxoethyl}-1,3-dihydro-2H-imidazol-2-one To a solution of the product of Example 11A (1.25 g, 3.55 mmol), (S)-3-fluoropyrrolidine hydrochloride (0.535 g, 4.26 mmol) and N-ethyl-N-isopropylpropan-2-amine (1.85 mL, 10.64 mmol) in tetrahydrofuran (15 mL) was added N-[(dimethylamino)-1H-1,2,3-triazolo-[4,5-b]pyridin-1-ylmethylene]-N-methylmethanaminium hexafluorophosphate N-oxide (HATU, 1.48 g, 3.90 mmol). This mixture was allowed to stir at ambient temperature for 16 hours and then was quenched with H$_2$O (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 20% hexanes/ethyl acetate to 100% ethyl acetate to 9:1:0.1 ethyl acetate/methanol/triethylamine) to provide the titled compound (0.6 g, 1.42 mmol, 40% yield). $^1$H NMR (300 MHz, methanol-d$_4$) δ ppm 8.38 (d, J=0.9 Hz, 1H), 7.65 (td, J=7.6, 1.7 Hz, 1H), 7.62-7.51 (m, 2H), 7.48-7.29 (m, 4H), 6.96 (d, J=3.0 Hz, 1H), 6.76 (dd, J=3.1, 1.0 Hz, 1H), 5.53-5.19 (m, 1H), 4.71-4.59 (m, 2H), 4.00-3.42 (m, 4H), 2.56-2.02 (m, 2H); MS (ESI$^+$) m/z 424 [M+H]$^+$.

Example 12

1-[1-(2-fluorophenyl)-1H-indazol-4-yl]-3-(pyridin-2-ylmethyl)imidazolidin-2-one

To a solution of the product of Example 1B (1 g, 3.37 mmol) in N,N-dimethylformamide (15 mL) at ambient temperature was added NaH (60% dispersion in mineral oil, 0.472 g, 11.8 mmol). This mixture was allowed to stir for 30 minutes, and then 2-(bromomethyl)pyridine-hydrobromide (0.871 g, 3.37 mmol) was added. The mixture was warmed to 40° C. and was allowed to stir at ambient temperature for 3 hours. The mixture was quenched with saturated, aqueous NaHCO$_3$ (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes) to provide the titled compound (0.38 g, 0.981 mmol, 29% yield). $^1$H NMR (300 MHz, methanol-d$_4$) δ ppm 8.55 (dt, J=4.9, 1.5 Hz, 1H), 8.44 (d, J=0.9 Hz, 1H), 7.88 (td, J=7.7, 1.8 Hz, 1H), 7.66-7.58 (m, 1H), 7.58-7.31 (m, 6H), 7.18-7.10 (m, 2H), 4.66 (s, 2H), 4.17-4.09 (m, 2H), 3.70-3.61 (m, 2H); MS (ESI$^+$) m/z 388 [M+H]$^+$.

Example 13

N-cyclopropyl-2-{3-[1-(2-fluorophenyl)-1H-indazol-4-yl]-2-oxoimidazolidin-1-yl}acetamide To a solution of the product of Example 7B (0.25 g, 0.706 mmol), cyclopropylamine (0.056 mL, 0.776 mmol) and N-ethyl-N-isopropylpropan-2-amine (0.493 mL, 2.82 mmol) in tetrahydrofuran (5 mL) was added N-[(dimethylamino)-1H-1,2,3-triazolo-[4,5-b]pyridin-1-ylmethylene]-N-methylmethanaminium hexafluorophosphate N-oxide (HATU, 0.295 g, 0.776 mmol). This mixture was allowed to stir at ambient temperature for 16 hours and then was quenched with H$_2$O (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 20% hexanes/ethyl acetate to 100% ethyl acetate to 9:1:0.1 ethyl acetate/methanol/triethylamine) to provide the titled compound (0.15 g, 0.381 mmol, 54% yield). $^1$H NMR (400 MHz, methanol-$d_4$) δ ppm 8.43 (d, J=0.9 Hz, 1H), 7.62 (td, J=7.7, 1.7 Hz, 1H), 7.59-7.51 (m, 1H), 7.48-7.37 (m, 3H), 7.16-7.10 (m, 2H), 4.12 (dd, J=8.9, 6.8 Hz, 2H), 3.97 (s, 2H), 3.70 (dd, J=8.9, 6.9 Hz, 2H), 2.76-2.68 (m, 1H), 0.75 (td, J=7.1, 5.1 Hz, 2H), 0.59-0.52 (m, 2H); MS (ESI$^+$) m/z 394 [M+H]$^+$.

Example 14

1-[1-(2-fluorophenyl)-1H-indazol-4-yl]-3-{[4-(trifluoromethyl)-1,3-thiazol-2-yl]methyl}imidazolidin-2-one To a solution of the product of Example 1B (0.80 g, 2.70 mmol) in N,N-dimethylformamide (6.0 mL) was added sodium hydride (60% dispersion in mineral oil, 0.162 g, 4.05 mmol), and the mixture was stirred for 20 minutes at ambient temperature. The mixture was cooled to 0° C. and 2-(bromomethyl)-4-(trifluoromethyl)-1,3-thiazole (Biogene, 1.99 g, 8.10 mmol) was added, and the mixture was stirred for 20 minutes. The reaction was quenched with saturated, aqueous NH$_4$Cl (10 mL) and was partitioned between ethyl acetate (20 mL) and 10% aqueous Na$_2$CO$_3$ (10 mL). The organic phase was washed with water (5 mL) and brine (5 mL), dried with anhydrous MgSO$_4$, filtered and concentrated under reduced pressure. The crude material was purified via column chromatography (SiO$_2$, 50% ethyl acetate in heptanes) to give the titled compound (0.70 g, 1.52 mmol, 56% yield). $^1$H NMR (400 MHz, methanol-$d_4$) δ ppm 8.41 (s, 1H), 8.19 (s, 1H), 7.62 (td, J=7.7, 1.5 Hz, 2H), 7.59-7.53 (m, 1H), 7.50-7.38 (m, 3H), 7.21-7.12 (m, 2H), 4.88 (s, 2H), 4.19-4.10 (m, 2H), 3.81-3.70 (m, 2H); MS (ESI$^+$) m/z 462 [M+H]$^+$.

Example 15

1-[1-(2-fluorophenyl)-1H-indazol-4-yl]-3-{2-[(2S)-2-methylpyrrolidin-1-yl]-2-oxoethyl}imidazolidin-2-one To a solution of the product of Example 7B (0.95 g, 2.68 mmol), (S)-2-methylpyrrolidine (0.367 mL, 3.49 mmol) and N-ethyl-N-isopropylpropan-2-amine (1.87 mL, 10.72 mmol) in tetrahydrofuran (15 mL) was added N-[(dimethylamino)-1H-1,2,3-triazolo-[4,5-b]pyridin-1-ylmethylene]-N-methylmethanaminium hexafluorophosphate N-oxide (HATU, 1.12 g, 2.95 mmol). This mixture was allowed to stir at ambient temperature for 16 hours and then was quenched with H$_2$O (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 20% hexanes/ethyl acetate to 100% ethyl acetate to 9:1:0.1 ethyl acetate/methanol/triethylamine) to give the titled compound (0.70 g, 1.661 mmol, 62% yield). $^1$H NMR (500 MHz, methanol-$d_4$) δ ppm 8.43 (s, 1H), 7.62 (td, J=7.7, 1.6 Hz, 1H), 7.58-7.52 (m, 1H), 7.48-7.36 (m, 3H), 7.14 (dd, J=8.4, 2.8 Hz, 1H), 7.11 (d, J=7.6 Hz, 1H), 4.25-4.19 (m, 1H), 4.16-4.08 (m, 4H), 3.75 (dddd, J=9.2, 7.3, 4.9, 2.6 Hz, 2H), 3.61 (ddt, J=11.1, 6.9, 3.6 Hz, 1H), 3.56-3.47 (m, 1H), 2.15-1.88 (m, 3H), 1.65 (ddd, J=11.0, 5.6, 2.7 Hz, 1H), 1.26 (dd, J=24.7, 6.4 Hz, 3H); MS (ESI$^+$) m/z 422 [M+H]$^+$.

Example 16

1-[1-(2-fluorophenyl)-1H-indazol-4-yl]-3-{2-[(1S,4S)-2-oxa-5-azabicyclo[2.2.1]hept-5-yl]-2-oxoethyl}imidazolidin-2-one To a solution of the product of Example 7B (0.75 g, 2.117 mmol), (1S,4S)-2-oxa-5-azabicyclo[2.2.1]heptane hydrochloride (Arkpharm., 0.316 g, 2.33 mmol) and N-ethyl-N-isopropylpropan-2-amine (1.48 mL, 8.47 mmol) in tetrahydrofuran (10 mL) was added N-[(dimethylamino)-1H-1,2,3-triazolo-[4,5-b]pyridin-1-ylmethylene]-N-methylmethanaminium hexafluorophosphate N-oxide (HATU, 0.885 g, 2.328 mmol). This mixture was allowed to stir at ambient temperature for 16 hours and then was quenched with H$_2$O (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 20% hexanes/ethyl acetate to 100% ethyl acetate to 9:1:0.1 ethyl acetate/methanol/triethylamine) to provide the titled compound (0.45 g, 1.03 mmol, 49% yield). $^1$H NMR (300 MHz, methanol-$d_4$) δ ppm 8.42 (t, J=1.2 Hz, 1H), 7.62 (td, J=7.6, 1.6 Hz, 1H), 7.58-7.50 (m, 1H), 7.49-7.36 (m, 3H), 7.13 (t, J=7.1 Hz, 2H), 4.78-4.65 (m, 3H), 4.17-4.07 (m, 3H), 3.88-3.71 (m, 4H), 3.66-3.51 (m, 1H), 3.44 (s, 1H), 1.99 (s, 1H), 1.92 (t, J=2.9 Hz, 1H); MS (ESI$^+$) m/z 436 [M+H]$^+$.

Example 17

1-[1-(2-fluorophenyl)-1H-indazol-4-yl]-3-[2-(3-fluoropiperidin-1-yl)-2-oxoethyl]imidazolidin-2-one The N-[(dimethylamino)-1H-1,2,3-triazolo-[4,5-b]pyridin-1-ylmethylene]-N-methylmethanaminium hexafluorophosphate N-oxide (HATU, 1.05 g, 2.77 mmol) was added to a mixture of the product of Example 7B (0.70 g, 1.98 mmol), 3-fluoropiperidine hydrochloride (0.28 g, 2.02 mmol) and triethylamine (0.83 mL, 5.93 mmol) in N,N-dimethylformamide (5.0 mL). The reaction mixture was stirred at ambient temperature for 18 hours. The mixture was concentrated in vacuo, and the residue was purified via column chromatography (SiO$_2$, 50% ethyl acetate/heptane to 100% ethyl acetate). The resulting crude material was then purified by preparative HPLC [Waters XBridge™ C18 5 μm OBD column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (0.75 g, 1.71 mmol, 86% yield). $^1$H NMR (500 MHz, DMSO-$d_6$) δ ppm 8.40 (s, 1H), 7.68 (td, J=7.8, 1.6 Hz, 1H), 7.62-7.49 (m, 2H), 7.49-7.37 (m, 2H), 7.17 (d, J=7.6 Hz, 1H), 7.08 (dd, J=8.4, 2.9 Hz, 1H), 5.02-4.57 (m, 1H), 4.25-4.04 (m, 4H), 4.04-3.77 (m, 1H), 3.64-3.56 (m, 2H), 3.56-3.32 (m, 1H), 3.31-3.24 (m, 1H), 3.11-2.96 (m, 1H), 1.94-1.81 (m, 2H), 1.80-1.42 (m, 2H); MS (ESI+) m/z 440 [M+H]$^+$.

Example 18

1-{2-[(2R,4S)-2-(2,5-difluorophenyl)-4-fluoropyrrolidin-1-yl]-2-oxoethyl}-3-[1-(2-fluorophenyl)-1H-indazol-4-yl]imidazolidin-2-one

Example 18A (S)—N—((R)-1-(2,5-difluorophenyl)but-3-en-1-yl)-2-methylpropane-2-sulfinamide To a solution of (S)-2-methylpropane-2-sulfinamide (22.5 g, 186 mmol) in tetrahydrofuran (250 mL) was added 2,5-difluorobenzaldehyde (25.2 g, 177 mmol) and tetraethoxytitanium (82 mL, 390 mmol), and the mixture was heated to 50° C. After 30 minutes, the mixture was cooled in an ice bath and was quenched with a buffered glycolic acid solution (15 weight % glycolic acid with 0.8 equivalents NaOH). The mixture was stirred vigorously for 20 minutes and then was extracted with ethyl acetate (200 mL). The layers were separated, and the aqueous layer was back extracted with ethyl acetate (2×200 mL). The organic phases were combined and washed with brine (300 mL), dried over anhydrous $Na_2SO_4$ and concentrated to give a crude oil that was used directly in the next reaction. MS ($ESI^+$) m/z 246 $[M+H]^+$.

To a slurry of the above product (44.8 g, 183 mmol) in saturated aqueous NaBr (740 mL) and indium (63 g, 550 mmol) at ambient temperature was added 3-bromoprop-1-ene (63 mL, 730 mmol) at such a rate to keep the internal temperature <25° C. The mixture was allowed to stir for 16 hours and then was slowly quenched with saturated aqueous $NaHCO_3$ (800 mL) and extracted with ethyl acetate (2×800 mL). The organic phases were combined, dried over anhydrous $Na_2SO_4$, filtered and concentrated under reduced pressure. The resulting oil was triturated with heptanes, and the resulting solids were isolated via filtration to give the titled compound (41 g, 140 mmol, 78% yield). MS ($ESI^+$) m/z 288 $[M+H]^+$.

Example 18B (3R,5R)-1-((tert-butylperoxy)thio)-5-(2,5-difluorophenyl)pyrrolidin-3-ol and (3S,5R)-1-((tert-butylperoxy)thio)-5-(2,5-difluorophenyl)pyrrolidin-3-ol To a solution of the product of Example 18A (11.1 g, 38.6 mmol) in $CH_2Cl_2$ (130 mL) at ambient temperature was added 3-chlorobenzoperoxoic acid (26.0 g, 116 mmol). The mixture was allowed to stir for 14 hours and then was quenched with saturated aqueous $Na_2S_2O_3$ (60 mL) and saturated, aqueous $NaHCO_3$ (60 mL). The layers were separated, and the aqueous layer was extracted with $CH_2Cl_2$ (2×300 mL). The combined organic fractions were dried over anhydrous $Na_2SO_4$, filtered and concentrated under reduced pressure to provide the intermediate N-((1R)-1-(2,5-difluorophenyl)-2-(oxiran-2-yl)ethyl)-2-methylpropane-2-sulfonamide which was carried on.

To a solution of the intermediate N-((1R)-1-(2,5-difluorophenyl)-2-(oxiran-2-yl)ethyl)-2-methylpropane-2-sulfonamide (13.1 g, 41.0 mmol) in N,N-dimethylformamide (140 mL) at ambient temperature was added KI (6.81 g, 41.0 mmol) and $K_2CO_3$ (17.0 g, 123 mmol). The mixture was warmed to 100° C. and was allowed to stir for 1 hour. The mixture was allowed to cool to ambient temperature and was quenched with water (400 mL). The layers were separated, and the organic layer was washed with brine (200 mL), dried over anhydrous $Na_2SO_4$, filtered and concentrated under reduced pressure. The residue was purified by column chromatography ($SiO_2$, elution with 0-100% ethyl acetate: heptanes) to provide both the (3R,5R)-isomer (first eluting isomer, 5.95 g, 18.6 mmol, 45% yield) and the (3S,5R)-isomer (second eluting isomer, 5.95 g, 18.6 mmol, 45% yield). First eluting isomer-(3R,5R) $^1$H NMR (400 MHz, $CDCl_3$) δ ppm 7.17 (ddd, J=8.9, 5.9, 3.1 Hz, 1H), 7.08-6.84 (m, 2H), 5.37 (dd, J=8.5, 6.5 Hz, 1H), 4.53 (pd, J=6.4, 4.5 Hz, 1H), 4.11 (dd, J=11.1, 6.4 Hz, 1H), 3.33 (dd, J=11.1, 6.4 Hz, 1H), 2.66 (ddd, J=13.1, 8.5, 6.5 Hz, 1H), 2.03 (dtd, J=12.9, 6.5, 1.2 Hz, 1H), 1.80 (d, J=4.8 Hz, 1H), 1.22 (s, 9H). Second eluting isomer-(3S,5R) $^1$H NMR (400 MHz, $CDCl_3$) δ ppm 7.12-6.82 (m, 3H), 5.44 (t, J=8.5 Hz, 1H), 4.50 (q, J=3.6 Hz, 1H), 3.88 (ddt, J=12.2, 2.2, 1.0 Hz, 1H), 3.56 (dd, J=12.2, 2.8 Hz, 1H), 2.49 (dddt, J=13.1, 7.9, 2.3, 1.2 Hz, 1H), 2.20-2.02 (m, 2H), 1.20 (s, 9H).

Example 18C (2R,4S)-1-((tert-butylperoxy)thio)-2-(2,5-difluorophenyl)-4-fluoropyrrolidine To a solution of the (3R,5R) isomer from Example 18B (500 mg, 2.04 mmol) in $CH_2Cl_2$ (10 mL) was added bis(2-methoxyethyl)aminosulfur trifluoride (0.40 mL, 3.1 mmol) at −75° C. The reaction mixture was allowed to warm to ambient temperature and was stirred for 1 hour. The mixture was quenched with water (30 mL). The reaction mixture was transferred to a separatory funnel and the layers were separated. The aqueous layer was extracted with ethyl acetate (10 mL), and the combined organic fractions were washed with brine (5 mL), dried over anhydrous $Na_2SO_4$, filtered and concentrated under reduced pressure. The residue was purified by column chromatography ($SiO_2$, elution with 20% ethyl acetate:hexane) to provide the titled compound (350 mg, 1.42 mmol, 69% yield). MS ($ESI^+$) m/z 339 $[M+NH_4]^+$.

Example 18D (2R,4S)-2-(2,5-difluorophenyl)-4-fluoropyrrolidine

To a solution of the product from Example 18C (860 mg, 2.68 mmol) in $CH_2Cl_2$ (30 mL) and anisole (2.9 mL, 27 mmol) at 0° C. was added trifluoromethanesulfonic acid (0.71 mL, 8.0 mmol). After stirring for 15 minutes, the mixture was diluted with $CH_2Cl_2$ (50 mL), washed with 2 N NaOH (20 mL), dried over anhydrous $Na_2SO_4$, filtered and concentrated under reduced pressure. The residue was dissolved in methyl tert-butyl ether (30 mL) and $CH_3OH/HCl$ added (HCl formed by the addition of acetyl chloride (0.48 mL, 6.8 mmol) to $CH_3OH$ (0.97 mL, 24 mmol) at 0° C.). The mixture was stirred for 5 minutes, and then the solids were collected by filtration. The solids were washed with 1:1 heptanes:diethyl ether and dried under vacuum to provide the titled compound (574 mg, 2.41 mmol, 90% yield) as a hydrochloride salt. $^1$H NMR (500 MHz, pyridine-$d_5$) δ ppm 7.98 (ddd, J=9.1, 5.8, 3.1 Hz, 1H), 7.13-6.97 (m, 2H), 5.50 (dt, J=53.6, 4.0 Hz, 1H), 5.21 (dd, J=11.3, 6.4 Hz, 1H), 3.90 (ddd, J=35.1, 13.4, 4.0 Hz, 1H), 3.72 (ddd, J=25.3, 13.4, 1.8 Hz, 1H), 2.72 (ddd, J=19.7, 14.3, 6.3 Hz, 1H), 2.32 (dddd, J=39.4, 14.9, 11.2, 4.1 Hz, 1H); MS ($ESI^+$) m/z 202 $[M+H]^+$.

Example 18E

1-{2-[(2R,4S)-2-(2,5-difluorophenyl)-4-fluoropyrrolidin-1-yl]-2-oxoethyl}-3-[1-(2-fluorophenyl)-1H-indazol-4-yl]imidazolidin-2-one N-Ethyl-N-isopropylpropan-2-amine (0.2 mL, 1.15 mmol) was added to a mixture of the product of Example 7B (0.102 g, 0.287 mmol), the product of Example 18D (0.097 g, 0.408 mmol) and N-[(dimethylamino)-1H-1,2,3-triazolo-[4,5-b]pyridin-1-ylmethylene]-N-methylmethanaminium hexafluorophosphate N-oxide (HATU, 0.1331 g, 0.350 mmol) in tetrahydrofuran (1.5 mL). The reaction was stirred at ambient temperature for 2 hours and then was extracted with ethyl acetate (10 mL) and H$_2$O (5 mL). The layers were separated, and the organic layer was washed with brine (2×5 mL), concentrated under reduced pressure and purified by column chromatography (SiO$_2$, 100% CH$_2$Cl$_2$ to 5% CH$_3$OH in CH$_2$Cl$_2$) to provide the titled compound (0.102 g, 0.19 mmol, 66% yield). $^1$H NMR (300 MHz, methanol-d$_4$) δ ppm 8.40-8.32 (m, 1H), 7.61 (td, J=7.6, 1.7 Hz, 1H), 7.57-7.50 (m, 1H), 7.46-7.35 (m, 3H), 7.29-6.92 (m, 5H), 5.54-5.21 (m, 2H), 4.37-3.81 (m, 6H), 3.80-3.55 (m, 2H), 3.04-2.68 (m, 1H), 2.45-1.93 (m, 1H); MS (ESI$^+$) m/z 538 [M+H]$^+$.

Example 19

1-[1-(2-fluorophenyl)-1H-indazol-4-yl]-3-(pyridin-3-yl)imidazolidin-2-one

To a pressure tube was added the product of Example 1B (0.28 g, 0.945 mmol) in dioxane (3 mL), CuI (Strem, 9 mg, 0.047 mmol) and potassium phosphate tribasic (Strem, 0.421 g, 1.98 mmol). This mixture was degassed three times with a nitrogen backflush each time. The 3-bromopyridine (0.120 mL, 1.228 mmol) was added followed by trans-N,N'-dimethylcyclohexane-1,2-diamine (0.030 mL, 0.189 mmol). The mixture was warmed to 110° C. and was allowed to stir for 48 hours. The mixture was cooled to ambient temperature and then was filtered through diatomaceous earth rinsing with ethyl acetate. The filtrate was concentrated under reduced pressure. The residue was purified via column chromatography (SiO$_2$, 1% ethyl acetate/hexanes to 50% ethyl acetate/hexanes) to give the titled compound (0.20 g, 0.54 mmol, 57% yield). $^1$H NMR (300 MHz, DMSO-d$_6$) δ ppm 8.92 (s, 1H), 8.46 (d, J=0.9 Hz, 1H), 8.32 (s, 1H), 8.18-8.08 (m, 1H), 7.70 (td, J=7.8, 1.6 Hz, 1H), 7.64-7.53 (m, 2H), 7.53-7.37 (m, 3H), 7.26 (d, J=7.6 Hz, 1H), 7.19 (dd, J=8.4, 3.0 Hz, 1H), 4.35-4.07 (m, 4H); MS (ESI$^+$) m/z 374 [M+H]$^+$.

Example 20

1-[1-(2-fluorophenyl)-1H-indazol-4-yl]-3-(pyridin-4-yl)imidazolidin-2-one

To a pressure tube was added the product of Example 1B (0.25 g, 0.844 mmol) in dioxane (3 mL), CuI (Strem, 8 mg, 0.042 mmol) and potassium phosphate tribasic (Strem, 0.38, 1.772 mmol). This mixture was degassed three times with a nitrogen backflush each time. 4-Iodopyridine (TCI-US, 0.114 mL, 1.097 mmol) was added followed by trans-N,N'-dimethylcyclohexane-1,2-diamine (0.027 mL, 0.169 mmol). The mixture was warmed to 110° C. and was allowed to stir for 48 hours. The material was allowed to cool to ambient temperature and then was filtered through diatomaceous earth rinsing with ethyl acetate. The filtrate was concentrated under reduced pressure. The residue was purified via column chromatography (SiO$_2$, 1% ethyl acetate/hexanes to 50% ethyl acetate/hexanes) to give the titled compound (0.26 g, 0.696 mmol, 83% yield). $^1$H NMR (300 MHz, DMSO-d$_6$) δ ppm 8.47-8.40 (m, 3H), 7.82-7.64 (m, 3H), 7.63-7.54 (m, 2H), 7.54-7.42 (m, 2H), 7.27 (d, J=7.5 Hz, 1H), 7.21 (dd, J=8.5, 3.0 Hz, 1H), 4.30-4.05 (m, 4H); MS (ESI$^+$) m/z 374 [M+H]$^+$.

Example 21

1-{2-[(2S)-2-ethylpyrrolidin-1-yl]-2-oxoethyl}-3-[1-(2-fluorophenyl)-1H-indazol-4-yl]imidazolidin-2-one N-Ethyl-N-isopropylpropan-2-amine (0.20 mL, 1.145 mmol) was added to a mixture of the product of Example 7B (0.104 g, 0.293 mmol), (S)-2-ethylpyrrolidine hydrochloride (NetChem; 0.063 g, 0.462 mmol) and N-[(dimethylamino)-1H-1,2,3-triazolo-[4,5-b]pyridin-1-ylmethylene]-N-methyl-methanaminium hexafluorophosphate N-oxide (HATU, 0.132 g, 0.346 mmol) in tetrahydrofuran (1.5 mL). The reaction was stirred at ambient temperature for 2 hours and then was partitioned between ethyl acetate (10 mL) and H$_2$O (5 mL). The layers were separated, and the organic layer was washed with brine (2×5 mL), and concentrated under reduced pressure. The residue was purified by column chromatography (SiO$_2$, 10% ethyl acetate in CH$_2$Cl$_2$ to 100% ethyl acetate) to provide the titled compound. $^1$H NMR (300 MHz, DMSO-d$_6$) δ ppm 8.43-8.37 (m, 1H), 7.68 (td, J=7.8, 1.6 Hz, 1H), 7.64-7.50 (m, 2H), 7.48-7.37 (m, 2H), 7.18 (dd, J=7.5, 3.3 Hz, 1H), 7.08 (dd, J=8.4, 3.0 Hz, 1H), 4.26-3.99 (m, 4H), 3.93-3.81 (m, 1H), 3.69-3.57 (m, 2H), 3.52-3.41 (m, 2H), 2.00-1.54 (m, 5H), 1.50-1.21 (m, 1H), 0.87 (dt, J=23.2, 7.4 Hz, 3H); MS (ESI$^+$) m/z 436 [M+H]$^+$.

Example 22

1-[1-(2-fluorophenyl)-1H-indazol-4-yl]-3-(2-hydroxy-3,3-dimethylbutyl)imidazolidin-2-one To the product of Example 161 (30 mg, 0.076 mmol; accessed using 1-bromopinacolone and the procedure described in Example 8) in ethyl acetate (1 mL) was added sodium borohydride (2.88 mg, 0.076 mmol), and the mixture was stirred for 1 hour. The reaction was quenched by slow addition of 0.2 N HCl (2 mL), and the mixture was partitioned between water (5 mL) and ethyl acetate (10 mL). The organic phase was washed with 10% aqueous NaHCO$_3$ (5 mL) and brine (5 mL), dried with anhydrous MgSO$_4$, filtered and concentrated under reduced pressure. The crude material was purified via column chromatography (SiO$_2$, 0% to 100% ethyl acetate in heptanes) to give the titled compound (28 mg, 0.071 mmol, 93% yield). $^1$H NMR (500 MHz, methanol-d$_4$) δ ppm 8.41 (d, J=0.8 Hz, 1H), 7.61 (td, J=7.7, 1.6 Hz, 1H), 7.55 (dddd, J=7.2, 6.8, 4.9, 1.7 Hz, 1H), 7.46-7.37 (m, 3H), 7.11 (dd, J=8.5, 2.9 Hz, 1H), 7.09 (d, J=7.5 Hz, 1H), 4.15-4.02 (m, 2H), 3.83 (td, J=9.0, 6.4 Hz, 1H), 3.72 (td, J=8.9, 7.2 Hz, 1H), 3.59 (dd, J=14.1, 2.2 Hz, 1H), 3.52 (dd, J=9.9, 2.2 Hz, 1H), 3.23 (dd, J=14.1, 10.0 Hz, 1H), 1.00 (s, 9H); MS (ESI$^+$) m/z 397 [M+H]$^+$.

Example 23

1-[1-(2-fluorophenyl)-1H-indazol-4-yl]-3-{2-[(3S)-3-fluoropyrrolidin-1-yl]-2-oxoethyl}tetrahydropyrimidin-2(1H)-one Example 23A 1-(3-chloropropyl)-3-(1-(2-fluorophenyl)-1H-indazol-4-yl)urea To a solution of the product of Example 9A (3.00 g, 13.2 mmol) in CH$_2$Cl$_2$ (60 mL) at ambient temperature was added 3-chloropropyl isocyanate (2.21 g, 18.5 mmol) and stirring was continued overnight. The slurry was concentrated under reduced pressure, and the residue was taken up in t-butyl methyl ether. The material was cooled to 4° C. and filtered. The collected solids were washed with additional portions of t-butyl methyl ether and dried in a vacuum oven at 45° C. to provide of the titled compound (4.34 g, 12.5 mmol, 95% yield). MS (APCI) m/z 347 [M+H]$^+$.

Example 23B 1-(1-(2-fluorophenyl)-1H-indazol-4-yl)tetrahydropyrimidin-2(1H)-one

A slurry of the product of Example 23A (4.34 g, 12.5 mmol) in tetrahydrofuran (900 mL) was warmed to 60° C. to completely dissolve the starting material, then the mixture was cooled to 0° C. To this solution was added sodium hydride (60% dispersion in mineral oil, 1.50 g, 37.5 mmol). The reaction mixture was allowed to warm to ambient temperature and was stirred for 3 hours. The mixture was cooled to 0° C., was quenched with water (200 mL) and extracted with ethyl acetate (500 mL). The organic layer was washed with water (100 mL) and brine (100 mL), dried over anhydrous MgSO$_4$, filtered, and concentrated under reduced pressure. The resulting solids were taken up in t-butyl methyl ether (1000 mL), and the resulting solids were collected via filtration. The solids were washed with additional portions of t-butyl methyl ether and dried in a vacuum oven to give of the titled compound (3.39 g, 10.9 mmol, 87% yield). $^1$H NMR (500 MHz, CDCl$_3$) δ ppm 8.20 (d, J=0.9 Hz, 1H), 7.60 (td, J=7.6, 1.7 Hz, 1H), 7.47-7.36 (m, 2H), 7.36-7.28 (m, 2H), 7.25 (dd, J=8.5, 3.5 Hz, 1H), 7.08 (d, J=7.3 Hz, 1H), 5.34 (s, 1H), 3.92-3.77 (m, 2H), 3.52 (t, J=6.0 Hz, 2H), 2.19 (p, J=5.9 Hz, 2H).

Example 23C

Ethyl 2-(3-(1-(2-fluorophenyl)-1H-indazol-4-yl)-2-oxotetrahydropyrimidin-1(2H)-yl)acetate To a solution of the product of Example 23B (2.8 g, 9.0 mmol) in N,N-dimethylformamide (45 mL) at 0° C. was added sodium hydride (60% dispersion in mineral oil, 1.80 g, 45.1 mmol). The mixture was allowed to warm to ambient temperature and was stirred for 30 minutes. To this mixture was added ethyl iodoacetate (5.33 mL, 45.1 mmol) and stirring was continued for an additional 16 hours. The mixture was quenched with saturated, aqueous NaHCO$_3$ (20 mL) and extracted with ethyl acetate (50 mL). The layers were separated, and the aqueous layer was extracted with ethyl acetate (3×20 mL). The combined organic fractions were concentrated under reduced pressure, and the residue was purified by column chromatography (SiO$_2$, eluted with 30-60% ethyl acetate/heptanes) to provide of the titled compound (2.63 g, 6.6 mmol, 73% yield). MS (APCI) m/z 397 [M+H]$^+$.

Example 23D 2-(3-(1-(2-fluorophenyl)-1H-indazol-4-yl)-2-oxotetrahydropyrimidin-1(2H)-yl)acetic Acid To a solution of the product of Example 23C (1.90 g, 4.79 mmol) in tetrahydrofuran (5 mL) and CH$_3$OH (50 mL) at ambient temperature was added 40% aqueous potassium hydroxide (3.36 g, 24.0 mmol) and stirring was continued for 20 hours. The mixture was quenched with concentrated HCl (~2.5 mL). The mixture was concentrated under reduced pressure, diluted with H$_2$O (15 mL) and the solids collected by filtration. The collected solids were washed with ether and dried under vacuum to provide of the titled compound (1.50 g, 4.1 mmol, 85% yield). MS (APCI) m/z 369 [M+H]$^+$.

Example 23E

1-[1-(2-fluorophenyl)-1H-indazol-4-yl]-3-{2-[(3S)-3-fluoropyrrolidin-1-yl]-2-oxoethyl}tetrahydropyrimidin-2(1H)-one The product of Example 23D (0.225 g, 0.611 mmol), N-ethyl-N-isopropylpropan-2-amine (0.42 mL, 2.4 mmol), (S)-3-fluoropyrrolidine hydrochloride (0.100 g, 0.794 mmol) and N-[(dimethylamino)-1H-1,2,3-triazolo-[4,5-b]pyridin-1-ylmethylene]-N-methylmethanaminium hexafluorophosphate N-oxide (HATU, 0.255 g, 0.672 mmol) in N,N-dimethylformamide (3 mL) were processed as described in Example 7C to give the titled compound (0.195 g, 0.40 mmol, 73% yield). $^1$H NMR (400 MHz, methanol-d$_4$) δ ppm 8.31 (s, 1H), 7.61 (td, J=7.6, 1.6 Hz, 1H), 7.58-7.51 (m, 1H), 7.49-7.36 (m, 3H), 7.24 (dd, J=8.5, 2.9 Hz, 1H), 7.14 (d, J=7.4 Hz, 1H), 5.31 (ddt, J=52.5, 26.7, 3.4 Hz, 1H), 4.40-4.10 (m, 2H), 3.96-3.43 (m, 8H), 2.38-2.20 (m, 4H); MS (ESI$^+$) m/z 440 [M+H]$^+$.

Example 24

1-[1-(2-fluorophenyl)-1H-indazol-4-yl]-3-[(4-methyl-1,3-thiazol-2-yl)methyl]imidazolidin-2-one To a solution of the product of Example 1B (109 mg, 0.37 mmol) in dimethylformamide (N,N-dimethylformamide) (3 mL) at 0° C. was added NaH (95 weight %, 47 mg, 1.94 mmol). The mixture was allowed to warm to ambient temperature and was stirred for 30 minutes. To the reaction mixture was added 2-(chloromethyl)-4-methylthiazole, hydrochloride (ChemBridge, 102 mg, 0.55 mmol). The mixture was stirred at ambient temperature for 18 hours and then was quenched with water (1.0 mL) and dimethyl sulfoxide (2.0 mL). The resulting solution was filtered through a glass microfiber frit and directly purified by preparative HPLC [custom packed YMC TriArt™ C18 20 µm column, 50×150 mm, flow rate 80 mL/minute, 20-100% gradient of acetonitrile in buffer (0.025 M aqueous ammonium bicarbonate, adjusted to pH 10 with ammonium hydroxide)] to give the titled compound (110 mg, 0.27 mmol, 73% yield). $^1$H NMR (500 MHz, DMSO-d$_6$) δ ppm 8.44 (d, J=1.0 Hz, 1H), 7.68 (td, J=7.8, 1.6 Hz, 1H), 7.63-7.51 (m, 2H), 7.49-7.39 (m, 2H), 7.26 (d, J=1.1 Hz, 1H), 7.20 (d, J=7.6 Hz, 1H), 7.12 (dd, J=8.4, 2.9 Hz, 1H), 4.73 (s, 2H), 4.10 (t, J=7.8 Hz, 1H), 3.62 (t, J=7.7 Hz, 2H), 2.38 (d, J=1.0 Hz, 3H); MS (ESI$^+$) m/z 408 [M+H]$^+$.

Example 25

1-[1-(2-fluorophenyl)-1H-indazol-4-yl]-3-{2-[(1R,4R)-2-oxa-5-azabicyclo[2.2.1]hept-5-yl]-2-oxoethyl}imidazolidin-2-one To a solution of the product of Example 7B (0.25 g, 0.706 mmol), (1R,4R)-2-oxa-5-azabicylco[2.2.1]heptane hydrochloric acid (0.105 g, 0.776 mmol) and N-ethyl-N-isopropylpropan-2-amine (0.493 mL, 2.82 mmol) in tetrahydrofuran (5 mL) was added N-[(dimethylamino)-1H-1,2,3-triazolo-[4,5-b]pyridin-1-ylmethylene]-N-methylmethanaminium hexafluorophosphate N-oxide (HATU, 0.295 g, 0.776 mmol). This mixture was allowed to stir at ambient temperature for 16 hours and then was quenched with $H_2O$ (5 mL) and extracted with ethyl acetate (10 mL). The layers were separated, and the aqueous layer was extracted with ethyl acetate (3×5 mL). The combined organic fractions were dried over anhydrous $Na_2SO_4$, filtered, and concentrated under reduced pressure. The residue was purified via column chromatography ($SiO_2$, 20% hexanes/ethyl acetate to 100% ethyl acetate to 9:1:0.1 ethyl acetate/methanol/triethylamine) to provide the titled compound (0.16 g, 0.367 mmol, 52% yield). $^1$H NMR (400 MHz, methanol-$d_4$) δ ppm 8.42 (dd, J=2.1, 1.0 Hz, 1H), 7.62 (td, J=7.6, 1.7 Hz, 1H), 7.59-7.51 (m, 1H), 7.48-7.37 (m, 3H), 7.17-7.08 (m, 2H), 4.78-4.65 (m, 2H), 4.20 (d, J=16.9 Hz, 1H), 4.17-4.07 (m, 2H), 3.95-3.80 (m, 2H), 3.79-3.67 (m, 3H), 3.63-3.52 (m, 1H), 3.22 (q, J=7.4 Hz, 2H), 1.97-1.86 (m, 1H); MS (ESI$^+$) m/z 436 [M+H]$^+$.

Example 26

1-[1-(2-fluorophenyl)-1H-indazol-4-yl]-3-(1,3-oxazol-4-ylmethyl)imidazolidin-2-one To a solution of the product of Example 1B (120 mg, 0.40 mmol) in tetrahydrofuran (3 mL) at 0° C. was added NaH (95 weight %, 31 mg, 1.22 mmol). The mixture was allowed to warm to ambient temperature and 4-(bromomethyl)oxazole hydrobromide (JW PharmLab, 148 mg, 0.61 mmol) was added. The resulting mixture was stirred at ambient temperature for 1 hour. The reaction mixture was quenched with water (1.0 mL) and concentrated in vacuo. The residue was dissolved in a mixture of dimethyl sulfoxide (3 mL) and water (1 mL), filtered through a glass microfiber frit and purified by preparative HPLC [Waters XBridge™ C18 5 μm column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (132 mg, 0.35 mmol, 86% yield). $^1$H NMR (400 MHz, DMSO-$d_6$) δ ppm 8.44 (d, J=0.9 Hz, 1H), 8.40 (d, J=0.9 Hz, 1H), 8.15 (d, J=1.1 Hz, 1H), 7.68 (td, J=7.9, 1.6 Hz, 1H), 7.62-7.51 (m, 2H), 7.50-7.36 (m, 2H), 7.19 (d, J=7.6 Hz, 1H), 7.09 (dd, J=8.5, 3.0 Hz, 1H), 4.40 (s, 2H), 4.06 (dd, J=8.8, 6.8 Hz, 2H), 3.61-3.49 (m, 2H); MS (ESI$^+$) m/z 378 [M+H]$^+$.

Example 27

1-[(3,5-dimethyl-1,2-oxazol-4-yl)methyl]-3-[1-(2-fluorophenyl)-1H-indazol-4-yl]imidazolidin-2-one To a solution of the product of Example 1B (120 mg, 0.40 mmol) in tetrahydrofuran (3 mL) at 0° C. was added NaH (95 weight %, 31 mg, 1.22 mmol). The mixture was allowed to warm to ambient temperature and 4-(chloromethyl)-3,5-dimethylisoxazole (88 mg, 0.61 mmol) was added. The resulting mixture was stirred at ambient temperature for 18 hours. The reaction was quenched with water (0.5 mL) and concentrated in vacuo. The residue was dissolved in a solvent mixture of dimethyl sulfoxide (3 mL), methanol (2 mL) and water (0.5 mL), filtered through a glass microfiber frit and purified by preparative HPLC [Waters XBridge™ C18 5 μm column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (155 mg, 0.38 mmol, 94% yield). $^1$H NMR (400 MHz, methanol-$d_4$) δ ppm 8.38 (s, 1H), 7.61 (td, J=7.7, 1.6 Hz, 1H), 7.58-7.51 (m, 1H), 7.49-7.34 (m, 3H), 7.13 (dd, J=8.5, 2.9 Hz, 1H), 7.10 (d, J=7.5 Hz, 1H), 4.36 (s, 2H), 4.12-3.94 (m, 2H), 3.58-3.43 (m, 2H), 2.46 (s, 3H), 2.31 (s, 3H); MS (ESI$^+$) m/z 406 [M+H]$^+$.

Example 28

1-[1-(2-fluorophenyl)-1H-indazol-4-yl]-3-(pyrimidin-2-yl)imidazolidin-2-one

A mixture of the product of Example 1B (1.62 g, 5.47 mmol), trans-N,N'-dimethylcyclohexane-1,2-diamine (0.31 g, 2.19 mmol), cuprous iodide (Strem, 104 mg, 0.55 mmol), 2-bromopyrimidine (1.74 g, 10.9 mmol) and potassium phosphate tribasic (Strem, 2.90 g, 13.7 mmol) was combined with 1,4-dioxane (15 mL). The mixture was purged with nitrogen and stirred at 110° C. for 18 hours. The reaction was cooled to ambient temperature, filtered through diatomaceous earth and rinsed with methanol (100 mL). The filtrate was concentrated in vacuo and purified by column chromatography ($SiO_2$, 50% to 100% ethyl acetate/heptane, then 0% to 10% methanol/ethyl acetate). The resulting crude material was repurified by preparative HPLC [Waters XBridge™ C18 5 μm OBD column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (1.35 g, 3.61 mmol, 66% yield). $^1$H NMR (400 MHz, DMSO-$d_6$) δ ppm 8.73 (d, J=4.8 Hz, 2H), 8.43 (d, J=0.8 Hz, 1H), 7.70 (td, J=7.8, 1.6 Hz, 1H), 7.64-7.53 (m, 2H), 7.53-7.42 (m, 2H), 7.25 (d, J=7.5 Hz, 1H), 7.23-7.15 (m, 2H), 4.28-4.04 (m, 4H); MS (ESI$^+$) m/z 375 [M+H]$^+$.

Example 29

1-[1-(2-fluorophenyl)-1H-indazol-4-yl]-3-(1,3,4-oxadiazol-2-ylmethyl)imidazolidin-2-one Example 29A 2-(3-(1-(2-fluorophenyl)-1H-indazol-4-yl)-2-oxoimidazolidin-1-yl)acetohydrazide The 2-(3H-[1,2,3]triazolo[4,5-b]pyridin-3-yl)-1,1,3,3-tetramethylisouronium hexafluorophosphate(V) (HATU, 1.27 g, 3.34 mmol) was added to a mixture of the product of Example 7B (1.15 g, 3.27 mmol) and hydrazine monohydrate (0.49 g, 9.82 mmol) in acetonitrile (40 mL). The reaction was stirred at ambient temperature for 10 minutes. The mixture was filtered through filter paper. The filtrate was concentrated in vacuo and purified by preparative HPLC [Waters XBridge™ C18 5 μm OBD column, 50×100 mm, flow rate 90 mL/minute, 30-100% gradient of methanol in buffer (0.025 M aqueous ammonium bicarbonate, adjusted to pH 10 with ammonium hydroxide)] to give the titled compound (0.65 g, 1.77 mmol, 54% yield). MS (ESI$^+$) m/z 369 [M+H]$^+$.

Example 29B

1-[1-(2-fluorophenyl)-1H-indazol-4-yl]-3-(1,3,4-oxadiazol-2-ylmethyl)imidazolidin-2-one p-Toluenesulfonic acid monohydrate (31 mg, 0.16 mmol) was added to a mixture of the product of Example 29A (348 mg, 0.95 mmol) and trimethyl orthoformate (3.0 mL, 27.4 mmol) in a sealed tube. The reaction mixture was stirred at 130° C. for 1 hour and then at 110° C. for 18 hours. The reaction mixture was cooled to ambient temperature and was then concentrated in vacuo. The resulting residue was purified by preparative HPLC [Waters XBridge™ C18 5 µm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (105 mg, 0.28 mmol, 29% yield). $^1$H NMR (400 MHz, DMSO-d$_6$) δ ppm 9.28 (s, 1H), 8.42 (s, 1H), 7.68 (td, J=7.9, 1.6 Hz, 1H), 7.63-7.51 (m, 2H), 7.48-7.40 (m, 2H), 7.21 (d, J=7.6 Hz, 1H), 7.12 (dd, J=8.4, 3.0 Hz, 1H), 4.81 (s, 2H), 4.13 (dd, J=8.8, 6.7 Hz, 2H), 3.65 (dd, J=8.8, 6.7 Hz, 2H); MS (ESI$^+$) m/z 379 [M+H]$^+$.

Example 30

1-[(5-cyclopropyl-1,3,4-thiadiazol-2-yl)methyl]-3-[1-(2-fluorophenyl)-1H-indazol-4-yl]imidazolidin-2-one To a solution of the product of Example 1B (140 mg, 0.47 mmol) in tetrahydrofuran (3 mL) at 0° C. was added NaH (95 weight %, 36 mg, 1.42 mmol). The mixture was allowed to warm up to ambient temperature and 2-chloromethyl-5-cyclopropyl-1,3,4-thiadiazole (Oakwood, 132 mg, 0.76 mmol) was added. The resulting mixture was stirred at ambient temperature for 4 hours. The reaction was quenched with CH$_3$OH (1 mL) and water (1 mL), and concentrated in vacuo. The residue was purified by preparative HPLC [custom packed YMC TriArt™ C18 20 µm column, 50×150 mm, flow rate 80 mL/minute, 20-100% gradient of acetonitrile in buffer (0.025 M aqueous ammonium bicarbonate, adjusted to pH 10 with ammonium hydroxide)] to give the titled compound (104 mg, 0.24 mmol, 54% yield). $^1$H NMR (400 MHz, methanol-d$_4$) δ ppm 8.41 (s, 1H), 7.62 (td, J=7.6, 1.6 Hz, 1H), 7.59-7.52 (m, 1H), 7.49-7.37 (m, 3H), 7.19-7.10 (m, 2H), 4.88 (s, 2H), 4.11 (dd, J=8.8, 6.8 Hz, 2H), 3.70 (dd, J=8.8, 6.8 Hz, 2H), 2.48 (tt, J=8.4, 4.9 Hz, 1H), 1.34-1.22 (m, 2H), 1.16-1.05 (m, 2H); MS (ESI$^+$) m/z 435 [M+H]$^+$.

Example 31

1-[1-(2-fluorophenyl)-1H-indazol-4-yl]-3-(1,3-oxazol-2-ylmethyl)imidazolidin-2-one To a solution of the product of Example 1B (0.26 g, 0.877 mmol) in N,N-dimethylformamide (5 mL) at 0° C. was added NaH (60% dispersion in mineral oil, 0.175 g, 4.39 mmol). This mixture was allowed to warm to ambient temperature and was stirred for 30 minutes and then 2-chloromethyloxazole (JW-Pharmlab, 0.113 g, 0.965 mmol) was added. The mixture was warmed to 40° C. and was allowed to stir for 3 hours, and then the mixture was quenched with saturated, aqueous NaHCO$_3$ (5 mL) and extracted with ethyl acetate (10 mL). The layers were separated and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes) to give the titled compound (0.18 g, 0.477 mmol, 54% yield). $^1$H NMR (300 MHz, methanol-d$_4$) δ ppm 8.41 (d, J=0.9 Hz, 1H), 7.95 (d, J=0.9 Hz, 1H), 7.62 (td, J=7.6, 1.6 Hz, 1H), 7.58-7.51 (m, 1H), 7.49-7.37 (m, 3H), 7.22-7.11 (m, 3H), 4.70 (s, 2H), 4.14 (dd, J=9.0, 6.8 Hz, 2H), 3.77-3.68 (m, 2H); MS (ESI$^+$) m/z 378 [M+H]$^+$.

Example 32

1-[1-(2-fluorophenyl)-1H-indazol-4-yl]-3-[(3R)-tetrahydrofuran-3-yl]imidazolidin-2-one Example 32A (R)-1-(tetrahydrofuran-3-yl)imidazolidin-2-one To (R)-3-aminotetrahydrofuran (Synnovator, 2.0 g, 22.96 mmol) in dichloromethane (50 mL) was added 2-chloroethyl isocyanate (2.15 mL, 25.3 mmol), and the mixture was stirred for 20 hours. The reaction was concentrated under reduced pressure to give the intermediate urea.

To this intermediate in tetrahydrofuran (100 mL) at 0° C. was added sodium hydride (60% dispersion in mineral oil, 1.40 g, 35.0 mmol). The reaction mixture was allowed to warm to ambient temperature and was stirred for 20 hours. The reaction was quenched with saturated, aqueous NaHCO$_3$ (10 mL), and the reaction mixture was concentrated under reduced pressure. The solids were triturated with ethyl acetate and filtered. The filtrate was concentrated under reduced pressure, and the resulting crude material was purified by column chromatography (SiO$_2$, 10% methanol in ethyl acetate) to afford the titled compound (2.2 g, 14.1 mmol, 60% yield). MS (ESI$^+$) m/z 157 [M+H]$^+$ Example 32B 1-[1-(2-fluorophenyl)-1H-indazol-4-yl]-3-[(3R)-tetrahydrofuran-3-yl]imidazolidin-2-one The product of Example 32A (0.805 g, 5.15 mmol), potassium phosphate tribasic (Strem, 2.3 g, 10.8 mmol), the product of Example 1A (1.5 g, 5.15 mmol), CuI (Strem, 0.049 g, 0.26 mmol) and trans-N,N'-dimethylcyclohexane-1,2-diamine (0.163 mL, 1.031 mmol) were combined in 1,4-dioxane (15 mL) under nitrogen. The tube was back-flushed with nitrogen and then sealed and heated at 110° C. for 20 hours. The reaction mixture was allowed to cool to ambient temperature, was diluted with ethyl acetate (20 mL), filtered through diatomaceous earth and the filtrate was concentrated under reduced pressure. The residue was purified by column chromatography (SiO$_2$, 75% ethyl acetate in heptanes) to give the titled compound (1.7 g, 4.64 mmol, 90% yield). $^1$H NMR (500 MHz, methanol-d$_4$) δ ppm 8.39 (d, J=0.8 Hz, 1H), 7.63-7.58 (m, 1H), 7.58-7.50 (m, 1H), 7.46-7.34 (m, 3H), 7.12 (dd, J=8.4, 2.8 Hz, 1H), 7.08 (d, J=7.5 Hz, 1H), 4.71-4.63 (m, 1H), 4.10-3.98 (m, 3H), 3.94 (dd, J=9.6, 3.4 Hz, 1H), 3.86-3.75 (m, 2H), 3.73-3.61 (m, 2H), 2.38-2.21 (m, 1H), 2.14-2.05 (m, 1H); MS (ESI$^+$) m/z 367 [M+H]$^+$.

Example 33

1-[1-(2-fluorophenyl)-1H-indazol-4-yl]-3-(5-methylpyrimidin-2-yl)imidazolidin-2-one A mixture of the product of Example 1B (140 mg, 0.47 mmol), trans-N,N'-dimethylcyclohexane-1,2-diamine (27 mg, 0.19 mmol), cuprous iodide (Strem, 9 mg, 0.05 mmol), 2-bromo-5-methylpyrimidine (ArkPharm, 123 mg, 0.71 mmol) and potassium phosphate tribasic (Strem, 251 mg, 1.18 mmol) was combined with 1,4-dioxane (2.0 mL). The reaction mixture was purged with nitrogen and stirred at 110° C. for 24 hours. The mixture was cooled to ambient temperature, filtered through diatomaceous earth and rinsed with ethyl acetate. The filtrate was concentrated in vacuo, and the residue was purified by preparative HPLC [Waters XBridge™ C18 5 μm OBD column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (110 mg, 0.28 mmol, 60% yield). $^1$H NMR (400 MHz, DMSO-$d_6$) δ ppm 8.58 (s, 2H), 8.42 (d, J=0.9 Hz, 1H), 7.70 (td, J=7.8, 1.6 Hz, 1H), 7.63-7.53 (m, 2H), 7.52-7.41 (m, 2H), 7.25 (d, J=7.5 Hz, 1H), 7.19 (dd, J=8.5, 2.9 Hz, 1H), 4.27-4.13 (m, 4H), 2.25 (s, 3H); MS (ESI$^+$) m/z 389 [M+H]$^+$.

Example 34

1-[1-(2-fluorophenyl)-1H-indazol-4-yl]-3-(1,3-thiazol-2-ylmethyl)imidazolidin-2-one To a solution of the product of Example 1B (140 mg, 0.47 mmol) in tetrahydrofuran (3 mL) at 0° C. was added NaH (60% dispersion in mineral oil, 76 mg, 1.90 mmol). The mixture was allowed to warm to ambient temperature and 2-bromomethyl-thiazole hydrobromide (JW Pharmlab, 159 mg, 0.61 mmol) was added. The resulting mixture was stirred at ambient temperature for 66 hours. The reaction was quenched with CH$_3$OH (2 mL). and the reaction mixture was concentrated in vacuo. The resulting residue was dissolved in a solvent mixture of dimethyl sulfoxide (2 mL) and N,N-dimethylformamide (2 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (142 mg, 0.36 mmol, 76% yield). $^1$H NMR (400 MHz, DMSO-$d_6$) δ ppm 8.44 (s, 1H), 7.82 (d, J=3.3 Hz, 1H), 7.74 (d, J=3.3 Hz, 1H), 7.68 (td, J=7.9, 1.6 Hz, 1H), 7.63-7.51 (m, 2H), 7.48-7.40 (m, 2H), 7.21 (d, J=7.6 Hz, 1H), 7.12 (dd, J=8.4, 2.9 Hz, 1H), 4.80 (s, 2H), 4.11 (dd, J=8.8, 6.7 Hz, 2H), 3.63 (dd, J=8.7, 6.7 Hz, 2H); MS (ESI$^+$) m/z 394 [M+H]$^+$.

Example 35

1-[1-(2-fluorophenyl)-1H-indazol-4-yl]-3-(pyrazin-2-ylmethyl)imidazolidin-2-one

To a solution of the product of Example 1B (140 mg, 0.47 mmol) in tetrahydrofuran (3 mL) at 0° C. was added NaH (60% dispersion in mineral oil, 57 mg, 1.42 mmol). The mixture was allowed to warm to ambient temperature and 2-(chloromethyl)pyrazine (Synthonix, 121 mg, 0.95 mmol) was added. The resulting mixture was stirred at ambient temperature for 18 hours. The reaction was quenched with water (0.5 mL) and concentrated in vacuo. The resulting residue was dissolved in a solvent mixture of water (0.5 mL), methanol (2 mL) and dimethyl sulfoxide (3 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (139 mg, 0.36 mmol, 76% yield). $^1$H NMR (400 MHz, DMSO-$d_6$) δ ppm 8.73 (d, J=1.5 Hz, 1H), 8.68-8.65 (m, 1H), 8.64-8.59 (m, 1H), 8.44 (s, 1H), 7.72-7.64 (m, 1H), 7.62-7.51 (m, 2H), 7.48-7.39 (m, 2H), 7.21 (d, J=7.6 Hz, 1H), 7.10 (dd, J=8.4, 3.0 Hz, 1H), 4.66 (s, 2H), 4.12 (dd, J=8.8, 6.7 Hz, 2H), 3.64 (dd, J=8.8, 6.7 Hz, 2H); MS (ESI$^+$) m/z 389 [M+H]$^+$.

Example 36

1-[1-(2,4-difluorophenyl)-1H-indazol-4-yl]-3-(1,3-oxazol-2-ylmethyl)imidazolidin-2-one Example 36A 1-(2,4-difluorophenyl)-1H-indazol-4-amine To a pressure tube was added 1H-indazol-4-amine (Enamine, 2.2 g, 16.5 mmol), CuI (Strem, 0.028 mL, 0.83 mmol) and potassium phosphate tribasic (Strem, 2.87 mL, 34.7 mmol). This mixture was degassed three times with a nitrogen backflush each time. 2,4-Difluoro-1-iodobenzene (2.339 mL, 18.17 mmol) was added followed by trans-N,N'-dimethylcyclohexane-1,2-diamine (0.521 mL, 3.30 mmol) and dioxane (25 mL). The mixture was warmed to 110° C. and was allowed to stir for 48 hours. The material was allowed to cool to ambient temperature and then was filtered through diatomaceous earth rinsing with ethyl acetate. The filtrate was concentrated under reduced pressure. The residue was purified via column chromatography (SiO$_2$, 1% ethyl acetate/hexanes to 50% ethyl acetate/hexanes) to give the titled compound (3.89 g, 15.9 mmol, 96% yield). MS (ESI$^+$) m/z 246 [M+H]$^+$.

Example 36B 1-(1-(2,4-difluorophenyl)-1H-indazol-4-yl)imidazolidin-2-one

To a mixture of the product of Example 36A (3.89 g, 15.9 mmol) and N-(2-oxoethyl)phthalimide (ArkPharm, Inc., 3.60 g, 19.0 mmol) in methanol (50 mL) and acetic acid (1 mL) was added sodium cyanoborohydride (1.83 mL, 34.9 mmol). This mixture was allowed to stir at ambient temperature for 16 hours. To this mixture was added hydrazine hydrate (3.89 mL, 79 mmol), and the mixture was warmed to 70° C. and was allowed to stir for 3 hours. A white precipitate formed, and the mixture was allowed to cool to ambient temperature and was filtered. The precipitate was washed with ethanol, and the filtrate was concentrated under reduced pressure and dissolved in CH$_2$Cl$_2$ (25 mL). This solution was washed with H$_2$O (10 mL), and the layers were separated. The aqueous layer was extracted with CH$_2$Cl$_2$ (5 mL) and the combined organic fractions were dried over anhydrous Na$_2$SO$_4$, filtered and concentrated under reduced pressure.

The intermediate diamine was dissolved in tetrahydrofuran (50 mL) and 1,8-diazabicyclo[5.4.0]undec-7-ene (DBU, 1 M in tetrahydrofuran, 1.59 mL, 1.59 mmol) was added followed by di(1H-imidazol-1-yl)methanone (CDI, 2.57 g, 15.9 mmol). This mixture was stirred at ambient temperature for 18 hours and then was quenched with H$_2$O (10 mL), diluted with ethyl acetate (15 mL) and the layers were separated. The aqueous layer was extracted with ethyl acetate (3×10 mL), and the combined organic fractions were dried over anhydrous Na$_2$SO$_4$, filtered, and concentrated under reduced pressure. The residue was purified via column chromatography (SiO$_2$, 10% ethyl acetate/heptanes to 100%

Example 36C

1-[1-(2,4-difluorophenyl)-1H-indazol-4-yl]-3-(1,3-oxazol-2-ylmethyl)imidazolidin-2-one To a solution of the product of Example 36B (0.66 g, 2.10 mmol) in tetrahydrofuran (10 mL) at 0° C. was added NaH (60% dispersion in mineral oil, 0.42 g, 10.50 mmol). This mixture was allowed to warm to ambient temperature and was stirred for 30 minutes, and then 2-chloromethyloxazole (JW Pharmlab, 0.27 g, 2.31 mmol) was added. The mixture was warmed to 40° C. and was allowed to stir for 3 hours, and then the mixture was quenched with saturated, aqueous NaHCO$_3$ (5 mL) and extracted with ethyl acetate (10 mL). The layers were separated, and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes) to give the titled compound (0.50 g, 1.27 mmol, 60% yield). $^1$H NMR (400 MHz, methanol-d$_4$) δ ppm 8.41 (s, 1H), 7.95 (s, 1H), 7.65 (td, J=8.7, 5.8 Hz, 1H), 7.45 (t, J=7.4 Hz, 1H), 7.30 (ddd, J=11.4, 8.9, 2.8 Hz, 1H), 7.25-7.17 (m, 2H), 7.13 (dd, J=8.0, 2.4 Hz, 2H), 4.69 (s, 2H), 4.12 (dd, J=8.9, 6.9 Hz, 2H), 3.72 (dd, J=8.9, 6.8 Hz, 2H); MS (ESI$^+$) m/z 396 [M+H]$^+$.

Example 37

1-[1-(2,4-difluorophenyl)-1H-indazol-4-yl]-3-(1,3-oxazol-4-ylmethyl)imidazolidin-2-one To a solution of the product of Example 36B (0.3 g, 0.955 mmol) in tetrahydrofuran (7 mL) at 0° C. was added NaH (60% dispersion in mineral oil, 0.191 g, 4.77 mmol). This mixture was allowed to warm to ambient temperature and was stirred for 30 minutes and then 4-(bromomethyl)oxazole, hydrobromic acid (JW Pharm., 0.232 g, 0.955 mmol) was added. The mixture was warmed to 40° C. and was allowed to stir for 3 hours. The mixture was quenched with saturated, aqueous NaHCO$_3$ (5 mL) and extracted with ethyl acetate (10 mL). The layers were separated and the aqueous layer was extracted with ethyl acetate (3×5 mL). The combined organic fractions were dried over anhydrous Na$_2$SO$_4$, filtered, and concentrated under reduced pressure. The residue was purified via column chromatography (SiO$_2$, 1% ethyl acetate/heptanes to 30% ethyl acetate/heptanes) to give the titled compound (0.22 g, 0.56 mmol, 58% yield). $^1$H NMR (400 MHz, methanol-d$_4$) δ ppm 8.43 (s, 1H), 8.22 (s, 1H), 7.97 (d, J=1.1 Hz, 1H), 7.65 (td, J=8.7, 5.8 Hz, 1H), 7.44 (dd, J=8.4, 7.6 Hz, 1H), 7.30 (ddd, J=10.9, 8.8, 2.8 Hz, 1H), 7.20 (dddd, J=9.2, 8.1, 2.8, 1.5 Hz, 1H), 7.15-7.07 (m, 2H), 4.49 (d, J=1.0 Hz, 2H), 4.07 (dd, J=8.9, 6.8 Hz, 2H), 3.68-3.60 (m, 2H); MS (ESI$^+$) m/z 396 [M+H]$^+$.

Example 38

(4S)-1-[1-(2-fluorophenyl)-1H-indazol-4-yl]-4-methyl-3-(1,3-oxazol-2-ylmethyl)imidazolidin-2-one

Example 38A (S)-tert-butyl (1-oxopropan-2-yl)carbamate

To a solution of oxalyl chloride (21.4 mL, 42.8 mmol) in CH$_2$Cl$_2$ (50 mL) at −78° C. was added dimethyl sulfoxide (6.07 mL, 86 mmol). This mixture was allowed to stir at −78° C. for 10 minutes. N-(tert-Butoxycarbonyl)-L-alanol (5 g, 28.5 mmol) was added, and the mixture was allowed to stir for 15 minutes. Triethylamine (15.9 mL, 114 mmol) was added, and the mixture was stirred for 15 minutes. The mixture was allowed to warm to 0° C., was stirred for 20 minutes, then was quenched with saturated, aqueous NaHCO$_3$ (15 mL), and the layers were separated. The aqueous layer was extracted with CH$_2$Cl$_2$ (3×7 mL), and the combined organic fractions were dried over anhydrous Na$_2$SO$_4$, filtered and concentrated under reduced pressure to give the titled compound (4.9 g, 28.3 mmol, 99% yield). MS (ESI$^+$) m/z 228 [M+CH$_3$OH+Na]$^+$.

Example 38B (S)-1-(1-(2-fluorophenyl)-1H-indazol-4-yl)-4-methylimidazolidin-2-one To a mixture of the product of Example 9A (6.36 g, 28.0 mmol) and the product of Example 38A (4.85 g, 28 mmol) in methanol (75 mL) and acetic acid (1.5 mL) was added sodium cyanoborohydride (3.23 mL, 61.6 mmol). This mixture was allowed to stir at ambient temperature for 72 hours and then was quenched with H$_2$O (10 mL) and extracted with CH$_2$Cl$_2$ (10 mL). The layers were separated and the aqueous layer was extracted with CH$_2$Cl$_2$ (3×7 mL). The combined organic fractions were dried over anhydrous Na$_2$SO$_4$, filtered and concentrated under reduced pressure to give a mixture of the intermediate reductive amination product and the starting aniline.

To the impure intermediate reductive amination product in CH$_2$Cl$_2$ (75 mL) was added 2,2,2-trifluoroacetic acid (43.1 mL, 560 mmol) dropwise over 30 minutes. The mixture was stirred at ambient temperature for 4 hours and then was concentrated under reduced pressure. The crude material was dissolved in CH$_2$Cl$_2$ and quenched with NaHCO$_3$. The layers were separated, and the aqueous layer was extracted with CH$_2$Cl$_2$ (3×10 mL). The combined organic fractions were dried over anhydrous Na$_2$SO$_4$, filtered and concentrated under reduced pressure to give a mixture of the intermediate diamine and the starting aniline.

To a solution of the crude diamine in tetrahydrofuran (75 mL) was added 1,8-diazabicyclo[5.4.0]undec-7-ene (DBU, 2.80 mL, 2.80 mmol) followed by di(1H-imidazol-1-yl)methanone (CDI, 4.54 g, 28.0 mmol). This mixture was stirred at ambient temperature for 18 hours and then was quenched with H$_2$O (10 mL), extracted with ethyl acetate (15 mL), and the layers were separated. The aqueous layer was extracted with ethyl acetate (3×10 mL), and the combined organic fractions were dried over anhydrous Na$_2$SO$_4$, filtered and concentrated under reduced pressure. The residue was purified via column chromatography (SiO$_2$, 10% ethyl acetate/heptanes to 100% ethyl acetate to 10% methanol in ethyl acetate) to give the titled compound (3.8 g, 12.3 mmol, 44% yield). MS (ESI$^+$) m/z 311 [M+CH$_3$OH+Na]$^+$.

Example 38C (4S)-1-[1-(2-fluorophenyl)-1H-indazol-4-yl]-4-methyl-3-(1,3-oxazol-2-ylmethyl)imidazolidin-2-one To the product of Example 38B (0.48 g, 1.547 mmol) in dimethylformamide (7.0 mL) was added sodium hydride (60% dispersion in mineral oil, 0.093 g, 2.32 mmol), and the mixture heated at 50° C. and was stirred for 20 minutes. 2-Chloromethyl-oxazole (JW-Pharmlab, 0.364 g, 3.09 mmol) was added, and the resulting mixture was stirred for 2 hours. The reaction was quenched with saturated, aqueous NH$_4$Cl (10 mL), and the mixture was pardoned between ethyl acetate (10 mL) and brine (5 mL). The layers were separated, and the organic layer was dried over anhydrous MgSO$_4$, filtered and concentrated under reduced pressure. The residue was purified via column chromatography (SiO$_2$, 50% ethyl acetate in heptanes) to give the titled compound (0.12 g, 0.307 mmol, 20% yield). $^1$H NMR (400 MHz, methanol-d$_4$) δ ppm 8.41 (d, J=0.7 Hz, 1H), 7.94 (s, 1H), 7.61 (td, J=7.7, 1.6 Hz, 1H), 7.58-7.51 (m, 1H), 7.47-7.37 (m, 3H), 7.18 (s, 1H), 7.16-7.09 (m, 2H), 4.82 (d, J=16.8 Hz, 1H), 4.59 (d, J=16.9 Hz, 1H), 4.19 (t, J=8.5 Hz, 1H), 4.06-3.94 (m, 1H), 3.73 (t, 1H), 1.39 (d, J=6.1 Hz, 3H); MS (ESI$^+$) m/z 392 [M+H]$^+$.

Example 39

1-[1-(2-fluorophenyl)-1H-indazol-4-yl]-3-(1,3-thiazol-4-ylmethyl)imidazolidin-2-one To a solution of the product of Example 1B (1.0 g, 3.37 mmol) in tetrahydrofuran (15 mL) at 0° C. was added NaH (60% dispersion in mineral oil, 0.54 g, 13.5 mmol). The mixture was allowed to warm to ambient temperature over a period of 30 minutes. 4-(Chloromethyl)thiazole hydrochloride (TCI, 0.92 g, 5.40 mmol) was added. The resulting mixture was stirred at ambient temperature for 18 hours. The reaction was quenched by the slow addition of methanol (5 mL), and the resulting mixture was partitioned between aqueous sodium carbonate (1.0 M, 200 mL) and CH$_2$Cl$_2$ (250 mL). The layers were separated, and the aqueous layer was extracted with CH$_2$Cl$_2$ (250 mL). The combined organic layers were dried over anhydrous sodium sulfate and concentrated in vacuo. The residue was purified by preparative HPLC [custom packed YMC TriArt™ C18 20 µm column, 50×150 mm, flow rate 80 mL/minute, 20-100% gradient of acetonitrile in buffer (0.025 M aqueous ammonium bicarbonate, adjusted to pH 10 with ammonium hydroxide)] to give the titled compound (0.70 g, 1.78 mmol, 53% yield). $^1$H NMR (500 MHz, DMSO-d$_6$) δ ppm 9.14 (d, J=1.9 Hz, 1H), 8.45 (d, J=1.0 Hz, 1H), 7.72-7.64 (m, 2H), 7.62-7.52 (m, 2H), 7.48-7.39 (m, 2H), 7.20 (d, J=7.7 Hz, 1H), 7.09 (dd, J=8.3, 2.9 Hz, 1H), 4.62 (s, 2H), 4.13-4.05 (m, 2H), 3.60-3.53 (m, 2H); MS (ESI$^+$) m/z 394 [M+H]$^+$.

Example 40

1-[1-(2-fluorophenyl)-1H-indazol-4-yl]-3-[(5-methyl-1,3,4-thiadiazol-2-yl)methyl]imidazolidin-2-one To a solution of the product of Example 1B (1.0 g, 3.37 mmol) in tetrahydrofuran (20 mL) at 0° C. was added NaH (60% dispersion in mineral oil, 0.68 g, 16.9 mmol). The mixture was allowed to warm to ambient temperature over a period of 30 minutes. 2-(Chloromethyl)-5-methyl-1,3,4-thiadiazole (ChemBridge, 0.90 g, 6.07 mmol) was added. The resulting mixture was stirred at ambient temperature for 18 hours. The reaction was quenched by the slow addition of methanol (5 mL), and the resulting mixture was partitioned between aqueous sodium carbonate (1.0 M, 200 mL) and CH$_2$Cl$_2$ (250 mL). The layers were separated, and the aqueous layer was extracted with CH$_2$Cl$_2$ (250 mL). The combined organic layers were dried over anhydrous sodium sulfate, concentrated in vacuo and purified by preparative HPLC [Waters XBridge™ C18 5 µm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (0.62 g, 1.51 mmol, 45% yield). $^1$H NMR (400 MHz, DMSO-d$_6$) δ ppm 8.43 (d, J=1.0 Hz, 1H), 7.68 (td, J=7.8, 1.7 Hz, 1H), 7.63-7.51 (m, 2H), 7.48-7.41 (m, 2H), 7.20 (d, J=7.6 Hz, 1H), 7.12 (dd, J=8.4, 3.0 Hz, 1H), 4.86 (s, 2H), 4.10 (dd, J=8.8, 6.6 Hz, 2H), 3.67-3.56 (m, 2H), 2.74 (s, 3H); MS (ESI$^+$) m/z 409 [M+H]$^+$.

Example 41

1-[1-(2-fluorophenyl)-1H-indazol-4-yl]-3-[(5-methyl-1,3-oxazol-2-yl)methyl]imidazolidin-2-one To a solution of the product of Example 1B (140 mg, 0.47 mmol) in tetrahydrofuran (3 mL) at 0° C. was added NaH (60% dispersion in mineral oil, 76 mg, 1.89 mmol). The mixture was allowed to warm to ambient temperature over a period of 30 minutes. 2-(Chloromethyl)-5-methyl-1,3-oxazole (Enamine, 62 mg, 0.47 mmol) was added. The resulting mixture was stirred at ambient temperature for 18 hours. The reaction was quenched by the slow addition of methanol (2 mL), and the resulting mixture was concentrated in vacuo. The residue was dissolved in a solvent mixture of N,N-dimethylformamide (2 mL) and dimethyl sulfoxide (2 mL), filtered through a glass microfiber frit, and purified by preparative HPLC [Waters XBridge™ C18 5 µm column, 30×100 mm, flow rate 35 mL/minute, 20-100% gradient of acetonitrile in buffer (0.025 M aqueous ammonium bicarbonate, adjusted to pH 10 with ammonium hydroxide)] to give the titled compound (92 mg, 0.24 mmol, 50% yield). $^1$H NMR (400 MHz, DMSO-d$_6$) δ ppm 8.42 (d, J=0.7 Hz, 1H), 7.68 (td, J=7.9, 1.6 Hz, 1H), 7.63-7.51 (m, 2H), 7.48-7.40 (m, 2H), 7.21 (d, J=7.7 Hz, 1H), 7.11 (dd, J=8.4, 3.0 Hz, 1H), 6.85-6.81 (m, 1H), 4.55 (s, 2H), 4.10 (dd, J=8.8, 6.8 Hz, 2H), 3.62 (dd, J=8.8, 6.7 Hz, 2H), 2.31 (br s, 3H); MS (ESI$^+$) m/z 392 [M+H]$^+$.

Example 42

1-[1-(2-fluorophenyl)-1H-indazol-4-yl]-3-[(6-methylpyrazin-2-yl)methyl]imidazolidin-2-one To a solution of the product of Example 1B (190 mg, 0.64 mmol) in tetrahydrofuran (4 mL) at 0° C. was added NaH (60% dispersion in mineral oil, 103 mg, 2.56 mmol). The mixture was allowed to warm to ambient temperature over a period of 30 minutes. 2-(Chloromethyl)-6-methylpyrazine (Small Molecules Inc., 155 mg, 1.09 mmol) was added. The resulting mixture was stirred at ambient temperature for 18 hours. The reaction was quenched by the slow addition of methanol (3 mL), and the resulting mixture was concentrated in vacuo. The residue was dissolved in N,N-dimethylformamide (3 mL), filtered through a glass microfiber frit and purified by preparative HPLC [custom packed YMC TriArt™ C18 20 µm column, 50×150 mm, flow rate 80 mL/minute, 20-100% gradient of acetonitrile in buffer (0.025 M aqueous ammonium bicarbonate, adjusted to pH 10 with ammonium hydroxide)] to give the titled compound (138 mg, 0.34 mmol, 54% yield). $^1$H NMR (500 MHz, DMSO-d$_6$) δ ppm 8.50 (d, J=5.1 Hz, 1H), 8.44-8.44 (m, 2H), 7.68 (td, J=7.9, 1.7 Hz, 1H), 7.62-7.51 (m, 2H), 7.48-7.39 (m, 2H), 7.20 (d, J=7.6 Hz, 1H), 7.10 (dd, J=8.3, 2.9 Hz, 1H), 4.60 (s, 2H), 4.12 (dd, J=8.8, 6.7 Hz, 2H), 3.66-3.56 (m, 2H), 2.53 (s, 3H); MS (ESI$^+$) m/z 403 [M+H]$^+$.

Example 43

1-[1-(2-fluorophenyl)-1H-indazol-4-yl]-3-[(3-methylpyrazin-2-yl)methyl]imidazolidin-2-one To a solution of the product of Example 1B (200 mg, 0.68 mmol) in tetrahydrofuran (3 mL) at 0° C. was added NaH (95 weight %, 85 mg, 3.37 mmol). The mixture was allowed to warm to ambient temperature over a period of 30 minutes. 2-(Chloromethyl)-3-methylpyrazine hydrochloride (ChemBridge, 121 mg, 0.68 mmol) was added. The resulting mixture was stirred at ambient temperature for 18 hours. The reaction was quenched by the slow addition of methanol (2 mL) and the resulting mixture was concentrated in vacuo. The residue was dissolved in N,N-dimethylformamide (3 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (176 mg, 0.44 mmol, 65% yield). $^1$H NMR (500 MHz, DMSO-$d_6$) δ ppm 8.43 (s, 2H), 8.41 (d, J=1.0 Hz, 1H), 7.64 (td, J=7.8, 1.7 Hz, 1H), 7.59-7.53 (m, 1H), 7.49 (ddd, J=10.0, 8.3, 1.4 Hz, 1H), 7.45-7.36 (m, 2H), 7.19 (d, J=7.6 Hz, 1H), 7.06 (dd, J=8.4, 2.8 Hz, 1H), 4.66 (s, 2H), 4.14-4.04 (m, 2H), 3.66-3.54 (m, 2H), 2.60 (s, 3H); MS (ESI$^+$) m/z 403 [M+H]$^+$.

Example 44

1-[1-(2-fluorophenyl)-1H-indazol-4-yl]-3-[(5-methyl-1,3,4-oxadiazol-2-yl)methyl]imidazolidin-2-one To a solution of the product of Example 1B (200 mg, 0.68 mmol) in tetrahydrofuran (3 mL) at 0° C. was added NaH (95 weight %, 85 mg, 3.37 mmol). The mixture was allowed to warm to ambient temperature over a period of 30 minutes. 2-(Bromomethyl)-5-methyl-1,3,4-oxadiazole (prepared as described in Tetrahedron 61 (2005) 9736-51, 4.1.1.5 method B; 119 mg, 0.68 mmol) was added. The resulting mixture was stirred at ambient temperature for 2 hours. The reaction was quenched by the slow addition of methanol (1 mL), and the resulting mixture was concentrated in vacuo. The residue was dissolved in N,N-dimethylformamide (3 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (115 mg, 0.29 mmol, 65% yield). $^1$H NMR (400 MHz, DMSO-$d_6$) δ ppm 8.42 (s, 1H), 7.68 (td, J=7.9, 1.6 Hz, 1H), 7.64-7.52 (m, 2H), 7.49-7.40 (m, 2H), 7.21 (d, J=7.6 Hz, 1H), 7.12 (dd, J=8.4, 2.9 Hz, 1H), 4.72 (s, 2H), 4.12 (dd, J=8.7, 6.7 Hz, 2H), 3.65 (dd, J=8.8, 6.7 Hz, 2H), 2.52 (s, 3H); MS (ESI$^+$) m/z 393 [M+H]$^+$.

Example 45

1-[(3-ethyl-1,2-oxazol-5-yl)methyl]-3-[1-(2-fluorophenyl)-1H-indazol-4-yl]imidazolidin-2-one To a solution of the product of Example 1B (200 mg, 0.68 mmol) in tetrahydrofuran (3 mL) at 0° C. was added NaH (60% dispersion in mineral oil, 108 mg, 2.70 mmol). The mixture was allowed to warm to ambient temperature over a period of 30 minutes. 5-(Chloromethyl)-3-ethylisoxazole (ChemBridge, 147 mg, 1.01 mmol) was added. The resulting mixture was stirred at ambient temperature for 18 hours. The reaction was quenched by the slow addition of methanol (2 mL), and the resulting mixture was concentrated in vacuo. The residue was dissolved in a solvent mixture of N,N-dimethylformamide (3 mL) and dimethyl sulfoxide (2 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (142 mg, 0.35 mmol, 52% yield). $^1$H NMR (400 MHz, DMSO-$d_6$) δ ppm 8.43 (d, J=0.9 Hz, 1H), 7.68 (td, J=7.8, 1.7 Hz, 1H), 7.64-7.51 (m, 2H), 7.48-7.40 (m, 2H), 7.21 (d, J=7.6 Hz, 1H), 7.11 (dd, J=8.5, 3.0 Hz, 1H), 6.46 (s, 1H), 4.60 (s, 2H), 4.19-4.04 (m, 2H), 3.64-3.53 (m, 2H), 2.64 (q, J=7.6 Hz, 2H), 1.21 (t, J=7.6 Hz, 3H); MS (ESI$^+$) m/z 406 [M+H]$^+$.

Example 46

1-[1-(2-fluorophenyl)-1H-indazol-4-yl]-3-[1-(3-methyl-1,2,4-oxadiazol-5-yl)ethyl]imidazolidin-2-one

Example 46A

(R)-tert-butyl (1-(3-methyl-1,2,4-oxadiazol-5-yl)ethyl)carbamate

A mixture of N-(tert-butoxycarbonyl)-D-alanine (13.7 g, 72.4 mmol), 1-hydroxybenzotriazole hydrate (wetted with 20 weight % water, 14.7 g, 87 mmol), and dimethyl sulfoxide (69 mL) was stirred at ambient temperature (water bath) and 1-(3-dimethylaminopropyl)-3-ethylcarbodiimide hydrochloride (16.0 g, 83 mmol) was added (exotherm from 20° C. to 25° C.). After 20 minutes (nearly homogeneous), N-hydroxyacetamidine (6.44 g, 87 mmol) (exotherm from 23° C. to 30° C.) was added followed by stirring for 5 minutes. The clear solution was then heated to 98-102° C. for 1 hour. The mixture was allowed to cool to <25° C., was partitioned between water (70 mL) and cyclopentyl methyl ether (CPME) (140 mL), and the layers were separated. The aqueous layer was extracted with CPME (70 mL+28 mL). The combined organic layers were washed with brine (28 mL), saturated aqueous NaHCO$_3$ (2×70 mL) and again with brine (28 mL). The NaHCO$_3$/brine aqueous layer was again extracted with CPME (70 mL), and the combined organic fractions were dried over anhydrous Na$_2$SO$_4$ and concentrated under reduced pressure to 35.4 g total mass (~26 mL CPME based on assumed 80% yield in line with previous experiments), giving a solution of the titled compound used without purification in the next step. Chiral HPLC (Daicel CHIRALCEL® OJ-3 column, 1% isopropyl acetate/heptanes isocratic, 1 mL/minute, detection at 210 nm) of this material showed 98% ee. MS (DCI) m/z 245 [M+NH$_4$]$^+$.

Example 46B

(R)-1-(3-methyl-1,2,4-oxadiazol-5-yl)ethanaminium chloride

A solution of the product of Example 46A (13.2 g, 57.9 mmol) in CPME (26 mL) was stirred at ambient temperature and 3 M HCl/CPME (57.9 mL, 174 mmol) was added. The mixture was heated to 40° C. After 1 hour, the mixture was heated to 50° C. and more 3 M HCl/CPME (19.3 mL) was added. After 3 hours at 50° C., the reaction was allowed to cool to ambient temperature, and the solids were collected by filtration and were washed with CPME (26 mL). The white solids was dried in a vacuum oven at 50° C., giving the titled compound (8.09 g, 49.4 mmol, 68% overall yield from N-(tert-butoxycarbonyl)-D-alanine). A 10 mg sample of this material was tert-butoxycarbonyl protected (di-tert-butyl dicarbonate, triethylamine, tetrahydrofuran) for chiral HPLC (same conditions as Example 46A) and was shown to be 96% ee. MS (DCI) m/z 145 [M+NH$_4$]$^+$.

Example 46C 1-(1-(3-methyl-1,2,4-oxadiazol-5-yl)ethyl)imidazolidin-2-one

To the product of Example 46B (1.0 g, 6.11 mmol) and N-ethyl-N-isopropylpropan-2-amine (1.601 mL, 9.17 mmol) in dichloromethane (12 mL) was added 2-chloroethylisocyanate (0.782 mL, 9.17 mmol). The mixture was stirred for 20 hours at ambient temperature and then was diluted with dichloromethane (50 mL). This solution was washed with 10% aqueous Na$_2$CO$_3$ (2×5 mL), dried over anhydrous MgSO$_4$, filtered and concentrated under reduced pressure to give the intermediate urea.

The intermediate urea in tetrahydrofuran (50 mL) was cooled to 0° C. and sodium hydride (60% dispersion in mineral oil, 0.44 g, 10.96 mmol) was added. The mixture was stirred at 0° C. for 20 minutes, then the cooling bath was removed, and the mixture was allowed to stir for 20 hours. The reaction was quenched with saturated, aqueous NH$_4$Cl (10 mL), and the mixture was concentrated under reduced pressure. The residue was concentrated from toluene until it became a white solid. The residue was triturated with dichloromethane, filtered and the filtrate was concentrated under reduced pressure. The residue from the concentrated filtrate was purified by column chromatography, (SiO$_2$, 0% to 20% methanol in ethyl acetate) to afford the titled compound (1.1 g, 5.61 mmol, 77% yield). Although not determined at this stage, it was found that the product of Example 46D was racemic, and racemization is likely to have occurred in the presence of NaH in this step. MS (ESI$^+$) m/z 197 [M+H]$^+$.

Example 46D

1-[1-(2-fluorophenyl)-1H-indazol-4-yl]-3-[1-(3-methyl-1,2,4-oxadiazol-5-yl)ethyl]imidazolidin-2-one A mixture of cesium carbonate (0.336 g, 1.031 mmol), the product of Example 46C (0.135 g, 0.687 mmol), the product of Example 1A (0.20 g, 0.687 mmol), (9,9-dimethyl-9H-xanthene-4,5-diyl)bis(diphenylphosphine) (0.032 g, 0.055 mmol) and tris(dibenzylideneacetone)dipalladium(0)-chloroform adduct (0.028 g, 0.027 mmol) in dimethoxyethane (3.0 mL) was purged with nitrogen and heated at 95° C. The mixture was stirred at 95° C. for 20 hours. The reaction mixture was allowed to cool to ambient temperature, was diluted with dichloromethane (10 mL), filtered and concentrated under reduced pressure. The crude material was purified via column chromatography (SiO$_2$, 50% ethyl acetate in heptanes) to afford the titled compound (30 mg, 0.074 mmol, 11% yield). The material was determined to be racemic (by chiral HPLC (Daicel CHIRALCEL® OJ-3 column, 1% isopropyl acetate/heptanes isocratic, 1 mL/minute, detection at 210 nm)) which likely occurred in the cyclic urea formation reaction (Example 46C). $^1$H NMR (400 MHz, methanol-d$_4$) δ ppm 8.37 (s, 1H), 7.62 (td, J=7.7, 1.4 Hz, 1H), 7.59-7.52 (m, 1H), 7.49-7.38 (m, 3H), 7.19-7.11 (m, 2H), 5.50-5.41 (m, 1H), 4.24-4.05 (m, 2H), 3.81 (td, J=8.6, 5.9 Hz, 1H), 3.70-3.59 (m, 1H), 2.40 (s, 3H), 1.75 (d, J=7.3 Hz, 3H); MS (ESI$^+$) m/z 407.1 [M+H]$^+$.

Example 47

1-[(5-ethoxy-1,3,4-thiadiazol-2-yl)methyl]-3-[1-(2-fluorophenyl)-1H-indazol-4-yl]imidazolidin-2-one To a solution of the product of Example 1B (225 mg, 0.76 mmol) in tetrahydrofuran (5 mL) at 0° C. was added NaH (60% dispersion in mineral oil, 152 mg, 3.8 mmol). The mixture was allowed to warm to ambient temperature over a period of 30 minutes. 2-(Chloromethyl)-5-ethoxy-1,3,4-thiadiazole (Enamine, 203 mg, 1.14 mmol) was added. The resulting mixture was stirred at ambient temperature for 18 hours. The reaction was quenched by the slow addition of methanol (5 mL), and the resulting mixture was concentrated in vacuo. The residue was dissolved in N,N-dimethylformamide (4 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (143 mg, 0.33 mmol, 43% yield). $^1$H NMR (400 MHz, DMSO-d$_6$) δ ppm 8.43 (d, J=0.9 Hz, 1H), 7.68 (td, J=7.9, 1.7 Hz, 1H), 7.63-7.51 (m, 2H), 7.49-7.38 (m, 2H), 7.20 (d, J=7.6 Hz, 1H), 7.12 (dd, J=8.4, 2.9 Hz, 1H), 4.73 (s, 2H), 4.52 (q, J=7.0 Hz, 2H), 4.10 (dd, J=8.7, 6.6 Hz, 2H), 3.68-3.56 (m, 2H), 1.40 (t, J=7.0 Hz, 3H); MS (ESI$^+$) m/z 439 [M+H]$^+$.

Example 48

1-[(4,5-dimethyl-1,3-oxazol-2-yl)methyl]-3-[1-(2-fluorophenyl)-1H-indazol-4-yl]tetrahydropyrimidin-2(1H)-one To the product of Example 23B (0.10 g, 0.322 mmol) in tetrahydrofuran (6 mL) was added sodium hydride (60% dispersion in mineral oil, 0.032 g, 0.81 mmol). The mixture was stirred for 15 minutes at 50° C. Tetrabutylammonium iodide (0.012 g, 0.032 mmol) was added followed by 2-(chloromethyl)-4,5-dimethyl-1,3-oxazole (Enamine, 0.094 g, 0.644 mmol), and the mixture stirred for 1 hour. The reaction was quenched with saturated, aqueous NH$_4$Cl (10 mL), and the mixture was transferred to a separatory funnel with ethyl acetate (10 mL). The layers were separated, and the organic layer was washed with brine (5 mL), dried over anhydrous MgSO$_4$, filtered and concentrated under reduced pressure. The crude material was purified via column chromatography (SiO$_2$, 0 to 100% ethyl acetate in heptane) to give the titled compound (85 mg, 0.203 mmol, 63% yield). $^1$H NMR (400 MHz, methanol-d$_4$) δ ppm 8.26 (s, 1H), 7.61 (td, J=7.7, 1.3 Hz, 1H), 7.58-7.51 (m, 1H), 7.49-7.37 (m, 3H), 7.24 (dd, J=8.5, 2.8 Hz, 1H), 7.15 (d, J=7.4 Hz, 1H), 4.67 (s, 2H), 3.97-3.84 (m, 2H), 3.62 (t, J=6.0 Hz, 2H), 2.35-2.22 (m, 2H), 2.27 (s, 3H), 2.10 (s, 3H); MS (ESI$^+$) m/z 420.1 [M+H]$^+$.

Example 49

1-[(5-cyclopropyl-1,3,4-oxadiazol-2-yl)methyl]-3-[1-(2-fluorophenyl)-1H-indazol-4-yl]imidazolidin-2-one To a solution of the product of Example 1B (240 mg, 0.76 mmol) in tetrahydrofuran (5 mL) at 0° C. was added NaH (60% dispersion in mineral oil, 162 mg, 4.05 mmol). The mixture was allowed to warm to ambient temperature over a period of 30 minutes. 2-(Chloromethyl)-5-cyclopropyl-1,3,4-oxadiazole (ChemBridge, 193 mg, 1.22 mmol) was added. The resulting mixture was stirred at ambient temperature for 18 hours. The reaction was quenched by the slow addition of methanol (5 mL), and the resulting mixture was concentrated in vacuo. The residue was dissolved in N,N-dimethylformamide (4 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (290 mg, 0.69 mmol, 86% yield). $^1$H NMR (400 MHz, DMSO-$d_6$) δ ppm 8.41 (s, 1H), 7.68 (td, J=7.8, 1.6 Hz, 1H), 7.63-7.51 (m, 2H), 7.44 (ddd, J=10.2, 5.8, 2.6 Hz, 2H), 7.20 (d, J=7.6 Hz, 1H), 7.12 (dd, J=8.3, 2.9 Hz, 1H), 4.69 (s, 2H), 4.11 (dd, J=8.8, 6.7 Hz, 2H), 3.63 (dd, J=8.7, 6.7 Hz, 2H), 2.25 (tt, J=8.4, 4.9 Hz, 1H), 1.20-1.10 (m, 2H), 1.05-0.99 (m, 2H); MS (ESI$^+$) m/z 419 [M+H]$^+$.

Example 50

1-[(5-cyclobutyl-1,3,4-oxadiazol-2-yl)methyl]-3-[1-(2-fluorophenyl)-1H-indazol-4-yl]imidazolidin-2-one To a solution of the product of Example 1B (245 mg, 0.83 mmol) in tetrahydrofuran (5 mL) at 0° C. was added NaH (60% dispersion in mineral oil, 165 mg, 4.13 mmol). The mixture was allowed to warm to ambient temperature over a period of 30 minutes. 2-(Chloromethyl)-5-cyclobutyl-1,3,4-oxadiazole (Enamine, 200 mg, 1.16 mmol) was added. The resulting mixture was stirred at ambient temperature for 18 hours. The reaction was quenched by the slow addition of methanol (5 mL), and the resulting mixture was concentrated in vacuo. The residue was dissolved in N,N-dimethylformamide (4 mL), filtered through a glass microfiber frit and purified by preparative HPLC [Waters XBridge™ C18 5 μm column, 50×100 mm, flow rate 90 mL/minute, 20-100% gradient of acetonitrile in buffer (0.025 M aqueous ammonium bicarbonate, adjusted to pH 10 with ammonium hydroxide)] to give the titled compound (270 mg, 0.62 mmol, 76% yield). $^1$H NMR (400 MHz, DMSO-$d_6$) δ ppm 8.41 (d, J=0.9 Hz, 1H), 7.68 (td, J=7.9, 1.7 Hz, 1H), 7.64-7.52 (m, 2H), 7.49-7.39 (m, 2H), 7.21 (d, J=7.6 Hz, 1H), 7.12 (dd, J=8.4, 3.0 Hz, 1H), 4.74 (s, 2H), 4.12 (dd, J=8.8, 6.7 Hz, 2H), 3.79 (pd, J=8.4, 0.9 Hz, 1H), 3.71-3.60 (m, 2H), 2.44-2.28 (m, 4H), 2.07 (dp, J=11.0, 8.7 Hz, 1H), 2.00-1.90 (m, 1H); MS (APCI) m/z 433 [M+H]$^+$.

Example 51

1-[1-(ethylsulfonyl)azetidin-3-yl]-3-[1-(2-fluorophenyl)-1H-indazol-4-yl]imidazolidin-2-one Example 51A tert-butyl 3-(2-oxoimidazolidin-1-yl)azetidine-1-carboxylate To a solution of tert-butyl 3-aminoazetidine-1-carboxylate (ArkPharm, 3.55 g, 20.6 mmol) and triethylamine (2.9 mL, 20.6 mmol) in dioxane (60 mL) in a 500 mL round bottom flask was added 2-chloroethyl isocyanate (Alfa, 1.93 mL, 22.7 mmol) portionwise over a period of 3 minutes. This mixture was allowed to stir at ambient temperature for 18 hours. Sodium hydride (60% dispersion in mineral oil, 1.24 g, 30.9 mmol) was added. The reaction mixture was stirred at ambient temperature for 48 hours and quenched by the slow addition of water (5 mL). The mixture was concentrated under reduced pressure to 30 mL, and the resulting solution was directly purified by preparative HPLC [custom packed YMC TriArt™ C18 20 μm column, 50×150 mm, flow rate 80 mL/minute, 10-100% gradient of methanol in buffer (0.025 M aqueous ammonium bicarbonate, adjusted to pH 10 with ammonium hydroxide)] to give the titled compound (3.5 g, 14.5 mmol, 70% yield). MS (ESI$^+$) m/z 300 [M+CH$_3$CN+NH$_4$]$^+$.

Example 51B tert-butyl 3-(3-(1-(2-fluorophenyl)-1H-indazol-4-yl)-2-oxoimidazolidin-1-yl)azetidine-1-carboxylate The product of Example 1A (2.90 g, 9.95 mmol), the product of Example 51A (2 g, 8.29 mmol), bis(tri-tert-butylphosphine)palladium(0) (Strem, 0.25 g, 0.50 mmol) and cesium carbonate (6.75 g, 20.72 mmol) were combined with dioxane (30 mL) under a nitrogen atmosphere and was stirred at 100° C. for 18 hours. The reaction mixture was cooled to ambient temperature, combined with silica gel (100 g) and concentrated in vacuo to provide a free-flowing powder mixture. The powder was directly applied to a chromatography column (SiO$_2$, 10% ethyl acetate/heptane to 100% ethyl acetate) to give the titled compound (2.6 g, 5.76 mmol, 70% yield). MS (APCI) m/z 452 [M+H]$^+$.

Example 51C 1-(azetidin-3-yl)-3-(1-(2-fluorophenyl)-1H-indazol-4-yl)imidazolidin-2-one The product of Example 51B (2.5 g, 5.54 mmol) was dissolved in dichloromethane (30 mL) and was cooled to 0° C. Trifluoroacetic acid (30 mL) was slowly added, and the reaction mixture was allowed to slowly warm up to ambient temperature over a period of 1 hour. The resulting solution was partitioned between aqueous sodium carbonate (1.0 M, 200 mL) and CH$_2$Cl$_2$ (200 mL). The layers were separated, and the aqueous layer was extracted with CH$_2$Cl$_2$ (200 mL). The combined organic layers were dried over anhydrous sodium sulfate to give the titled compound (1.8 g, 5.12 mmol, 93% yield). MS (APCI) m/z 352 [M+H]$^+$.

Example 51D

1-[1-(ethylsulfonyl)azetidin-3-yl]-3-[1-(2-fluorophenyl)-1H-indazol-4-yl]imidazolidin-2-one The product of Example 51C (400 mg, 1.14 mmol), ethanesulfonyl chloride (TCI, 0.15 mL, 1.59 mmol) and Hunig's base (0.60 mL, 3.42 mmol) were combined with pyridine (4 mL) and stirred at ambient temperature for 1 hour. The reaction mixture was concentrated in vacuo, and the residue was purified by preparative HPLC [Waters XBridge™ C18 5 μm column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (355 mg, 0.80 mmol, 70% yield). $^1$H NMR (500 MHz, DMSO-$d_6$) δ ppm 8.42 (d, J=1.0 Hz, 1H), 7.67 (td, J=7.8, 1.7 Hz, 1H), 7.62-7.51 (m, 2H), 7.47-7.39 (m, 2H), 7.18 (d, J=7.6

Hz, 1H), 7.10 (dd, J=8.4, 2.9 Hz, 1H), 4.81 (tt, J=8.1, 6.6 Hz, 1H), 4.21 (dd, J=8.6, 6.7 Hz, 2H), 4.15-4.00 (m, 4H), 3.78 (dd, J=8.8, 6.7 Hz, 2H), 3.21 (q, J=7.4 Hz, 2H), 1.26 (t, J=7.3 Hz, 3H); MS (ESI$^+$) m/z 444 [M+H]$^+$.

Example 52

1-[1-(2-fluorophenyl)-1H-indazol-4-yl]-3-{2-[(3R)-3-hydroxypiperidin-1-yl]-2-oxoethyl}imidazolidin-2-one The 2-(3H-[1,2,3]triazolo[4,5-b]pyridin-3-yl)-1,1,3,3-tetramethylisouronium hexafluorophosphate(V) (HATU, 349 mg, 0.92 mmol) was added to a mixture of the product of Example 7B (250 mg, 0.71 mmol) and (R)-(+)-3-hydroxypiperidine hydrochloride (146 mg, 1.06 mmol) in N,N-dimethylformamide (4 mL). The reaction was stirred at ambient temperature for 18 hours. The resulting solution was filtered through a glass microfiber frit and purified by preparative HPLC [Waters XBridge™ C18 5 μm OBD column, 50×100 mm, flow rate 90 mL/minute, 5-95% gradient of acetonitrile in buffer (0.025 M aqueous ammonium bicarbonate, adjusted to pH 10 with ammonium hydroxide)] to give the titled compound (279 mg, 0.64 mmol, 90% yield). $^1$H NMR (500 MHz, DMSO-d$_6$) δ ppm 8.40 (d, J=3.5 Hz, 1H), 7.68 (td, J=7.9, 1.6 Hz, 1H), 7.62-7.51 (m, 2H), 7.46-7.37 (m, 2H), 7.17 (d, J=7.6 Hz, 1H), 7.08 (dd, J=8.5, 2.9 Hz, 1H), 4.92 (dd, J=10.7, 4.1 Hz, 1H), 4.21-4.12 (m, 2H), 4.12-4.01 (m, 2H), 3.66-3.38 (m, 5H), 3.34-3.28 and 3.09-3.02 (two m, 1H, amide rotamers), 3.20-3.14 and 2.65-2.72 (two m, 1H, amide rotamers), 1.93-1.62 (m, 2H), 1.57-1.27 (m, 2H); MS (APCI) m/z 438 [M+H]$^+$.

Example 53

1-[1-(2-fluorophenyl)-1H-indazol-4-yl]-3-{2-[(3R)-3-fluoropiperidin-1-yl]-2-oxoethyl}imidazolidin-2-one N-[(Dimethylamino)-1H-1,2,3-triazolo-[4,5-b]pyridin-1-ylmethylene]-N-methylmethanaminium hexafluorophosphate N-oxide (HATU, 90 mg, 0.24 mmol) was added to a mixture of the product of Example 7B (60 mg, 0.17 mmol) and (R)-3-fluoropiperidine hydrochloride (Synthonix, 25 mg, 0.18 mmol) in N,N-dimethylformamide (2 mL). The reaction was stirred at ambient temperature for 1 hour. The resulting solution was filtered through a glass microfiber frit and purified by preparative HPLC [Waters XBridge™ C18 5 μm OBD column, 30×100 mm, flow rate 35 mL/minute, 5-95% gradient of acetonitrile in buffer (0.025 M aqueous ammonium bicarbonate, adjusted to pH 10 with ammonium hydroxide)] to give the titled compound (59 mg, 0.13 mmol, 79% yield). $^1$H NMR (400 MHz, DMSO-d$_6$) δ ppm 8.40 (d, J=0.9 Hz, 1H), 7.68 (td, J=7.8, 1.6 Hz, 1H), 7.62-7.51 (m, 2H), 7.48-7.36 (m, 2H), 7.17 (d, J=7.6 Hz, 1H), 7.08 (dd, J=8.4, 3.0 Hz, 1H), 4.92-4.64 (m, 1H), 4.29-3.75 (m, 6H), 3.57-3.63 (m, 2H), 3.57-3.35 (m, 1H), 3.35-3.26 and 3.08-3.00 (two m, 1H; amide rotamers), 1.95-1.41 (m, 4H); MS (ESI$^+$) m/z 440 [M+H]$^+$.

Example 54

1-[1-(2-fluorophenyl)-1H-indazol-4-yl]-3-{2-[(3S)-3-fluoropiperidin-1-yl]-2-oxoethyl}imidazolidin-2-one The N-[(dimethylamino)-1H-1,2,3-triazolo-[4,5-b]pyridin-1-ylmethylene]-N-methylmethanaminium hexafluorophosphate N-oxide (HATU, 1.42 g, 3.73 mmol) was added to a mixture of the product of Example 7B (1.10 g, 3.10 mmol) and (S)-3-fluoropiperidine hydrochloride (Synthonix, 442 mg, 3.17 mmol) in N,N-dimethylformamide (5 mL). The reaction was stirred at ambient temperature for 18 hours. The resulting solution was filtered through a glass microfiber frit and purified by preparative HPLC [custom packed YMC TriArt™ C18 20 μm column, 50×150 mm, flow rate 80 mL/minute, 10-100% gradient of acetonitrile in buffer (0.025 M aqueous ammonium bicarbonate, adjusted to pH 10 with ammonium hydroxide)] to give the titled compound (1.05 g, 2.39 mmol, 77% yield). $^1$H NMR (400 MHz, DMSO-d$_6$) δ ppm 8.40 (s, 1H), 7.68 (td, J=7.8, 1.6 Hz, 1H), 7.63-7.51 (m, 2H), 7.48-7.37 (m, 2H), 7.17 (d, J=7.6 Hz, 1H), 7.08 (dd, J=8.4, 2.9 Hz, 1H), 4.96-4.64 (m, 1H), 4.28-3.76 (m, 6H), 3.66-3.54 (m, 3H), 3.35-3.26 and 3.08-3.00 (two m, 1H; amide rotamers), 1.96-1.41 (m, 4H); MS (ESI$^+$) m/z 440 [M+H]$^+$.

Example 55

2-{3-[1-(2-fluorophenyl)-1H-indazol-4-yl]-2-oxoimidazolidin-1-yl}-N-[(3R)-tetrahydrofuran-3-yl]acetamide To the product of Example 7B (5.0 g, 14.11 mmol) in dimethylformamide (50 mL) was added (R)-3-aminotetrahydrofuran (Synnovator, 1.35 g, 15.5 mmol), N-ethyl-N-isopropylpropan-2-amine (4.93 mL, 28.2 mmol) and N-[(dimethylamino)-1H-1,2,3-triazolo-[4,5-b]pyridin-1-ylmethylene]-N-methylmethanaminium hexafluorophosphate N-oxide (HATU, 8.05 g, 21.2 mmol). The reaction mixture was stirred for 1 hour and then was partitioned between ethyl acetate (50 mL) and 10% aqueous NaHCO$_3$ (30 mL). The layers were separated and the organic layer was washed with brine (15 mL), dried over anhydrous MgSO$_4$, filtered and concentrated under reduced pressure. The crude material was purified via column chromatography (SiO$_2$, 5% methanol in ethyl acetate) to give the titled compound (4.5 g, 10.6 mmol, 75% yield). $^1$H NMR (400 MHz, methanol-d$_4$) δ ppm 8.43 (d, J=0.8 Hz, 1H), 7.61 (td, J=7.7, 1.6 Hz, 1H), 7.58-7.51 (m, 1H), 7.47-7.37 (m, 3H), 7.16-7.08 (m, 2H), 4.49-4.39 (m, 1H), 4.14-4.08 (m, 2H), 4.01 (d, J=1.4 Hz, 2H), 3.98-3.85 (m, 2H), 3.80 (td, J=8.3, 5.6 Hz, 1H), 3.73-3.63 (m, 3H), 2.34-2.16 (m, 1H), 1.96-1.83 (m, 1H); MS (ESI$^+$) m/z 424 [M+H]$^+$.

Example 56

1-{2-[(3S)-3-fluoropyrrolidin-1-yl]-2-oxoethyl}-3-[1-(3-methylphenyl)-1H-indazol-4-yl]imidazolidin-2-one

Example 56A 4-bromo-1-(m-tolyl)-1H-indazole

To a solution of 2-bromo-6-fluorobenzaldehyde (19.9 g, 98 mmol) and m-tolylhydrazine hydrochloride (15.6 g, 98 mmol) in N-methyl-2-pyrrolidinone (200 mL) at ambient temperature was added cesium carbonate (67.2 g, 206 mmol). The mixture was warmed to 70° C. and was stirred for 1 hour. Then the mixture was warmed to 120° C. and was stirred for 2 hours. The mixture was allowed to cool to 90° C. and H$_2$O (400 mL) was added. The mixture was then allowed to cool to ambient temperature and was stirred for 16 hours. The solids were collected by filtration and then dissolved in CH$_2$Cl$_2$ (500 mL). The solution was washed with 1 N HCl (100 mL) and brine (100 mL). The organic phase was treated with anhydrous MgSO$_4$ and charcoal (8 g) with stirring for 30 minutes. The mixture was filtered through diatomaceous earth, and the filtrate was concentrated under reduced pressure. The crude material was purified by column chromatography (SiO$_2$, elution with 0% to 20% tetrahydrofuran:heptane) to give the titled compound (15.5 g, 54.1 mmol, 55% yield). MS (ESI$^+$) m/z 287, 289 [M+H]$^+$.

Example 56B 1-(1-(m-tolyl)-1H-indazol-4-yl)imidazolidin-2-one

To a solution of the product of Example 56A (15.5 g, 54.0 mmol) and imidazolidin-2-one (ArkPharm, Inc., 23.2 g, 270 mmol) in dimethoxyethane (300 mL) at ambient temperature was added cesium carbonate (26.4 g, 81 mmol), (9,9-dimethyl-9H-xanthene-4,5-diyl)bis(diphenylphosphine) (2.50 g, 4.32 mmol) and tris(dibenzylideneacetone)dipalladium(0) (1.98 g, 2.16 mmol) under a nitrogen atmosphere. The mixture was heated to 80° C. and was stirred for 16 hours. The mixture was allowed to cool to ambient temperature and water (500 mL) and ethyl acetate (250 mL) were added. This mixture was stirred for 15 minutes and transferred to a separatory funnel with ethyl acetate (500 mL) and brine (500 mL), and the layers were separated. The organic layer was dried over anhydrous MgSO$_4$ with charcoal added (10 g), and the mixture was stirred for 20 minutes and then filtered through a 3-inch plug of diatomaceous earth. The filtrate was concentrated, and the residue was taken up in ether:ethyl acetate (30:1; 10 volumes; 150 mL), boiled, sonicated and stirred to pulverize. The resulting solids were collected by filtration to give the titled compound (8.9 g, 27.4 mmol, 51% yield). MS (ESI$^+$) m/z 293 [M+H]$^+$.

Example 56C tert-butyl 2-(2-oxo-3-(1-(m-tolyl)-1H-indazol-4-yl)imidazolidin-1-yl)acetate To a slurry of the product of Example 56B (8.90 g, 30.4 mmol) in tetrahydrofuran (100 mL) at ambient temperature was added sodium hydride (60% dispersion in mineral oil, 1.83 g, 45.7 mmol). After the mixture was stirred for 5 minutes, the solution was treated with tert-butyl 2-bromoacetate (5.80 mL, 39.6 mmol) followed by stirring for an additional 30 minutes. The mixture was quenched with water (300 mL) and extracted with ethyl acetate (3×200 mL). The combined organic fractions were dried over anhydrous Na$_2$SO$_4$, filtered and concentrated under reduced pressure. The crude material was purified by column chromatography (SiO$_2$, 0 to 60% ethyl acetate:heptane) to give the titled compound (10.6 g, 23.4 mmol, 77% yield). MS (ESI$^+$) m/z 407 [M+H]$^+$.

Example 56D 2-(2-oxo-3-(1-(m-tolyl)-1H-indazol-4-yl)imidazolidin-1-yl)acetic Acid To a solution of the product of Example 56C (10.6 g, 26.0 mmol) in CH$_2$Cl$_2$ (50 mL) at ambient temperature was added trifluoroacetic acid (50 mL). The mixture was allowed to stir for 1 hour and then was concentrated under reduced pressure. The residue was concentrated from toluene (2×) to give the titled compound with residual trifluoroacetic acid present (12.1 g, >26 mmol, >100% yield). MS (APCI) m/z 351 [M+H]$^+$.

Example 56E

1-{2-[(3S)-3-fluoropyrrolidin-1-yl]-2-oxoethyl}-3-[1-(3-methylphenyl)-1H-indazol-4-yl]imidazolidin-2-one To a slurry of the product of Example 56D (12.1 g, 26.0 mmol) in tetrahydrofuran (150 mL) at ambient temperature was added triethylamine (29.0 mL, 208 mmol). The starting material was not in solution so N,N-dimethylformamide (70 mL) was added. To this mixture was added 2,4,6-tripropyl-1,3,5,2,4,6-trioxatriphosphinane 2,4,6-trioxide (T$_3$P®, 50 weight % in ethyl acetate, 45.6 mL, 78 mmol) dropwise. The mixture was allowed to stir for 15 minutes, and then water (1000 mL) and ethyl acetate (1000 mL) were added. The mixture was stirred for 5 minutes and was then transferred to a separatory funnel. The layers were separated, and the organic layer was washed with water (500 mL) and brine (500 mL), dried over anhydrous Na$_2$SO$_4$, filtered and concentrated under reduced pressure. The crude material was purified by column chromatography (SiO$_2$, elution from 0% to 30% tetrahydrofuran:CH$_2$Cl$_2$) to provide the titled compound. $^1$H NMR (500 MHz, DMSO-d$_6$) δ ppm 8.36 (s, 1H), 7.59-7.51 (m, 3H), 7.45 (dt, J=17.4, 7.9 Hz, 2H), 7.23 (dd, J=7.6, 1.5 Hz, 1H), 7.17 (d, J=7.6 Hz, 1H), 5.51-5.27 (m, 1H), 4.24-4.00 (m, 4H), 3.88-3.44 (m, 6H), 2.43 (s, 3H), 2.32-2.01 (m, 2H); MS (ESI$^+$) m/z 422 [M+H]$^+$.

The compounds in the following table were prepared using the methodologies described above.

| Example | Name | NMR | MS |
| --- | --- | --- | --- |
| Example 57 | 1-[1-(2-fluorophenyl)-1H-indazol-4-yl]imidazolidin-2-one | $^1$H NMR (300 MHz, methanol-d$_4$) δ ppm 8.40 (d, J = 0.8 Hz, 1H), 7.61 (dd, J = 7.3, 1.8 Hz, 1H), 7.58-7.51 (m, 1H), 7.48-7.36 (m, 3H), 7.19-7.05 (m, 2H), 4.19-4.11 (m, 2H), 3.73-3.58 (m, 2H) | MS (DCI) m/z 297 [M + H]$^+$ |
| Example 58 | 1-{3-[1-(2-fluorophenyl)-1H-indazol-4-yl]-2-oxoimidazolidin-1-yl}methanesulfonamide | $^1$H NMR (300 MHz, methanol-d$_4$) δ ppm 8.42 (d, J = 1.1 Hz, 1H), 7.62 (td, J = 7.7, 1.7 Hz, 1H), 7.58-7.51 (m, 1H), 7.50-7.37 (m, 3H), 7.20-7.11 (m, 2H), 4.68 (s, 2H), 4.21-4.12 (m, 2H), 4.01-3.92 (m, 2H) | MS (ESI$^+$) m/z 390 [M + H]$^+$ |

-continued

| Example | Name | NMR | MS |
|---|---|---|---|
| Example 59 | 1-[1-(2-fluorophenyl)-1H-indazol-4-yl]-3-(2-methoxyethyl)imidazolidin-2-one | $^1$H NMR (300 MHz, methanol-d$_4$) δ ppm 8.39 (d, J = 1.0 Hz, 1H), 7.61 (dd, J = 7.4, 1.9 Hz, 1H), 7.57-7.51 (m, 1H), 7.47-7.37 (m, 3H), 7.15-7.07 (m, 2H), 4.12-4.02 (m, 2H), 3.77-3.68 (m, 2H), 3.67-3.58 (m, 2H), 3.58-3.50 (m, 2H), 3.41 (s, 3H) | MS (ESI$^+$) m/z 355 [M + H]$^+$ |
| Example 60 | 1-(2,2-dimethylpropanoyl)-3-[1-(2-fluorophenyl)-1H-indazol-4-yl]imidazolidin-2-one | $^1$H NMR (300 MHz, methanol-d$_4$) δ ppm 8.34 (d, J = 0.9 Hz, 1H), 7.64 (td, J = 7.6, 1.7 Hz, 1H), 7.60-7.53 (m, 1H), 7.50 (dd, J = 8.5, 7.6 Hz, 1H), 7.47-7.37 (m, 2H), 7.28-7.18 (m, 2H), 4.17-4.02 (m, 4H), 1.44 (d, J = 0.6 Hz, 9H) | MS (DCI) m/z 381 [M + H]$^+$ |
| Example 61 | 1-[1-(2-fluorophenyl)-1H-indazol-4-yl]-3-[(3-oxocyclobutyl)carbonyl]imidazolidin-2-one | $^1$H NMR (500 MHz, methanol-d$_4$) δ ppm 8.39 (d, J = 1.0 Hz, 1H), 7.63 (td, J = 7.7, 1.6 Hz, 1H), 7.60-7.54 (m, 1H), 7.53-7.47 (m, 1H), 7.46-7.38 (m, 2H), 7.26 (dd, J = 8.6, 2.8 Hz, 1H), 7.23 (d, J = 7.5 Hz, 1H), 4.46-4.38 (m, 1H), 4.20-4.08 (m, 4H), 3.51-3.42 (m, 2H), 3.38-3.32 (m, 2H) | MS (DCI) m/z 393 [M + H]$^+$ |
| Example 62 | 3-[1-(2-fluorophenyl)-1H-indazol-4-yl]-N-methyl-2-oxoimidazolidine-1-sulfonamide | $^1$H NMR (400 MHz, DMSO-d$_6$) δ ppm 8.43 (d, J = 0.9 Hz, 1H), 8.03 (q, J = 4.8 Hz, 1H), 7.75 (td, J = 7.8, 1.7 Hz, 1H), 7.70-7.59 (m, 2H), 7.58-7.47 (m, 2H), 7.32-7.26 (m, 2H), 4.21 (dd, J = 9.0, 6.4 Hz, 2H), 4.04 (dd, J = 8.9, 6.4 Hz, 2H), 2.76 (d, J = 4.8 Hz, 3H) | MS (DCI) m/z 390 [M + H]$^+$ |
| Example 63 | 1-[1-(2-fluorophenyl)-1H-indazol-4-yl]-3-[2-(2-oxoimidazolidin-1-yl)ethyl]imidazolidin-2-one | $^1$H NMR (300 MHz, methanol-d$_4$) δ ppm 8.40 (s, 1H), 7.61 (td, J = 7.6, 1.7 Hz, 1H), 7.57-7.51 (m, 1H), 7.48-7.37 (m, 3H), 7.12 (dd, J = 8.5, 2.9 Hz, 1H), 7.06 (d, J = 7.6 Hz, 1H), 4.05 (dd, J = 9.1, 6.7 Hz, 2H), 3.75 (dd, J = 9.1, 6.7 Hz, 2H), 3.68-3.60 (m, 2H), 3.55-3.50 (m, 2H), 3.49-3.38 (m, 4H) | MS (DCI) m/z 409 [M + H]$^+$ |
| Example 64 | 1-[1-(2-fluorophenyl)-1H-indazol-4-yl]-3-(2-hydroxy-2-methylpropyl)imidazolidin-2-one | $^1$H NMR (501 MHz, DMSO-d$_6$) δ ppm 8.40 (d, J = 1.0 Hz, 1H), 7.67 (td, J = 7.9, 1.7 Hz, 1H), 7.61-7.51 (m, 2H), 7.47-7.38 (m, 2H), 7.16 (dd, J = 7.7, 0.7 Hz, 1H), 7.06 (dd, J = 8.6, 2.9 Hz, 1H), 4.54 (s, 1H), 4.07-4.01 (m, 2H), 3.77-3.70 (m, 2H), 3.18 (s, 2H), 1.16 (s, 6H) | MS (DCI) m/z 369 [M + H]$^+$ |
| Example 65 | 1-{2-[(2R,5R)-2,5-bis(methoxymethyl)pyrrolidin-1-yl]-2-oxoethyl}-3-[1-(2-fluorophenyl)-1H-indazol-4-yl]imidazolidin-2-one | $^1$H NMR (500 MHz, DMSO-d$_6$) δ ppm 8.40 (d, J = 0.9 Hz, 1H), 7.67 (td, J = 7.8, 1.7 Hz, 1H), 7.63-7.51 (m, 2H), 7.49-7.43 (m, 2H), 7.16 (d, J = 7.6 Hz, 1H), 7.10 (dd, J = 8.5, 2.9 Hz, 1H), 4.27-4.12 (m, 3H), 4.11-4.03 (m, 3H), 3.62 (dd, J = 8.9, 7.1 Hz, 2H), 3.54 (dd, J = 9.2, 2.9 Hz, 1H), 3.42-3.32 (m, 2H), 3.32 (s, 3H), 3.31-3.27 (m, 1H), 3.26 (s, 3H), 2.14-1.91 (m, 2H), 1.79 (ddd, J = 11.4, 8.6, 6.0 Hz, 2H) | MS (APCI) m/z 496 [M + H]$^+$ |
| Example 66 | 1-[1-(2-fluorophenyl)-1H-indazol-4-yl]-3-[2-(hexahydropyrrolo[1,2-a]pyrazin-2(1H)-yl)-2-oxoethyl]imidazolidin-2-one | $^1$H NMR (500 MHz, DMSO-d$_6$) δ ppm 8.38 (d, J = 1.0 Hz, 1H), 7.67 (td, J = 7.8, 1.7 Hz, 1H), 7.63-7.58 (m, 1H), 7.55 (ddd, J = 10.1, 8.4, 1.5 Hz, 1H), 7.46 (td, J = 7.9, 1.5 Hz, 2H), 7.16 (d, J = 7.7 Hz, 1H), 7.11 (dd, J = 8.4, 2.9 Hz, 1H), 4.90-4.59 (m, 0H), 4.45-4.14 (m, 2H), 4.09 (t, J = 7.8 Hz, 2H), 4.09 (dd, J = 8.9, 6.9 | MS (APCI) m/z 463 [M + H]$^+$ |

-continued

| Example | Name | NMR | MS |
|---|---|---|---|
| | | Hz, 2H), 3.99-3.78 (m, 2H), 3.70-3.54 (m, 3H), 3.55-3.40 (m, 1H), 3.40-2.98 (m, 3H), 2.93-2.74 (m, 0H), 2.32-1.91 (m, 2H), 1.88-1.56 (m, 1H) | |
| Example 67 | 1-[1-(2-fluorophenyl)-1H-indazol-4-yl]-3-[2-(3-isopropoxyazetidin-1-yl)-2-oxoethyl]imidazolidin-2-one | $^1$H NMR (500 MHz, DMSO-$d_6$) δ ppm 8.39 (s, 1H), 7.67 (td, J = 7.8, 1.8 Hz, 1H), 7.63-7.51 (m, 2H), 7.49-7.41 (m, 2H), 7.20-7.06 (m, 2H), 4.49-4.37 (m, 2H), 4.22-3.97 (m, 4H), 3.94 (s, 2H), 3.72-3.69 (m, 1H), 3.67-3.56 (m, 3H), 1.11 (d, J = 6.1 Hz, 6H) | MS (APCI) m/z 452 [M + H]$^+$ |
| Example 68 | 2-{3-[1-(2-fluorophenyl)-1H-indazol-4-yl]-2-oxoimidazolidin-1-yl}-N-methyl-N-(tetrahydro-2H-pyran-4-ylmethyl)acetamide | $^1$H NMR (500 MHz, DMSO-$d_6$) δ ppm 8.43-8.35 (m, 1H), 7.67 (td, J = 7.8, 1.7 Hz, 1H), 7.63-7.51 (m, 2H), 7.51-7.40 (m, 2H), 7.21-7.12 (m, 1H), 7.10 (dd, J = 8.4, 2.9 Hz, 1H), 4.19-4.12 (m, 2H), 4.11-4.02 (m, 2H), 3.91-3.81 (m, 2H), 3.62 (dd, J = 8.8, 6.8 Hz, 2H), 3.35-3.27 (m, 2H), 3.27-3.21 (m, 2H), 3.01 (s, 2H), 2.88 (s, 1H), 1.90 (dddq, J = 22.5, 11.1, 7.4, 4.0 Hz, 1H), 1.59-1.48 (m, 2H), 1.23 (dqd, J = 45.3, 12.1, 4.4 Hz, 2H) | MS (APCI) m/z 466 [M + H]$^+$ |
| Example 69 | 1-[1-(2-fluorophenyl)-1H-indazol-4-yl]-3-[2-(4-fluoropiperidin-1-yl)-2-oxoethyl]imidazolidin-2-one | $^1$H NMR (500 MHz, DMSO-$d_6$) δ ppm 8.39 (d, J = 0.9 Hz, 1H), 7.67 (td, J = 7.8, 1.7 Hz, 1H), 7.64-7.51 (m, 2H), 7.50-7.40 (m, 2H), 7.16 (d, J = 7.6 Hz, 1H), 7.10 (dd, J = 8.4, 2.9 Hz, 1H), 5.03-4.79 (m, 1H), 4.19 (s, 2H), 4.08 (dd, J = 8.9, 6.8 Hz, 2H), 3.64-3.60 (m, 2H), 3.60-3.40 (m, 4H), 2.07-1.60 (m, 4H) | MS (APCI) m/z 440 [M + H]$^+$ |
| Example 70 | 1-[2-(2,6-dimethylmorpholin-4-yl)-2-oxoethyl]-3-[1-(2-fluorophenyl)-1H-indazol-4-yl]imidazolidin-2-one | $^1$H NMR (500 MHz, DMSO-$d_6$) δ ppm 8.40-8.36 (m, 1H), 7.67 (td, J = 7.9, 1.7 Hz, 1H), 7.64-7.50 (m, 2H), 7.50-7.42 (m, 2H), 7.19-7.13 (m, 1H), 7.10 (dd, J = 8.3, 2.9 Hz, 1H), 4.32-4.12 (m, 2H), 4.12-4.04 (m, 3H), 3.68-3.43 (m, 5H), 2.76 (dd, J = 13.2, 10.6 Hz, 1H), 2.33 (dd, J = 13.1, 10.7 Hz, 1H), 1.17-1.09 (m, 6H) | MS (APCI) m/z 452 [M + H]$^+$ |
| Example 71 | 1-[1-(2-fluorophenyl)-1H-indazol-4-yl]-3-{2-[2-(morpholin-4-ylmethyl)pyrrolidin-1-yl]-2-oxoethyl}imidazolidin-2-one | $^1$H NMR (500 MHz, DMSO-$d_6$) δ ppm 8.40 (d, J = 0.9 Hz, 1H), 7.66 (td, J = 7.8, 1.7 Hz, 1H), 7.63-7.58 (m, 1H), 7.55 (ddd, J = 10.0, 8.4, 1.5 Hz, 1H), 7.50-7.43 (m, 2H), 7.16 (d, J = 7.6 Hz, 1H), 7.12 (dd, J = 8.5, 2.9 Hz, 1H), 4.55-4.44 (m, 1H), 4.16-3.86 (m, 7H), 3.72-3.38 (m, 8H), 3.32-3.10 (m, 4H), 2.01 (ddt, J = 17.6, 6.4, 3.4 Hz, 2H), 1.79-1.70 (m, 1H) | MS (APCI) m/z 507 [M + H]$^+$ |
| Example 72 | 2-{3-[1-(2-fluorophenyl)-1H-indazol-4-yl]-2-oxoimidazolidin-1-yl}-N-methyl-N-[2-(morpholin-4-yl)ethyl]acetamide | $^1$H NMR (500 MHz, DMSO-$d_6$) δ ppm 8.40-8.35 (m, 1H), 7.66 (td, J = 7.8, 1.7 Hz, 1H), 7.64-7.52 (m, 2H), 7.46 (t, J = 8.0 Hz, 2H), 7.15 (d, J = 7.6 Hz, 1H), 7.12 (dd, J = 8.6, 2.9 Hz, 1H), 4.19 (s, 2H), 4.08 (dd, J = 8.8, 6.7 Hz, 2H), 4.05-3.98 (m, 2H), 3.76-3.72 (m, 4H), 3.70-3.56 (m, 5H), 3.34 (t, J = 6.2 Hz, 2H), 3.19-3.08 (m, 1H), 3.04 (s, 3H) | MS (APCI) m/z 481 [M + H]$^+$ |

-continued

| Example | Name | NMR | MS |
|---|---|---|---|
| Example 73 | 1-[1-(2-fluorophenyl)-1H-indazol-4-yl]-3-{2-[(3R)-3-fluoropyrrolidin-1-yl]-2-oxoethyl}imidazolidin-2-one | $^1$H NMR (500 MHz, DMSO-$d_6$) δ ppm 8.40 (d, J = 0.9 Hz, 1H), 7.67 (td, J = 7.8, 1.7 Hz, 1H), 7.63-7.51 (m, 2H), 7.50-7.42 (m, 2H), 7.16 (d, J = 7.6 Hz, 1H), 7.10 (dd, J = 8.4, 2.9 Hz, 1H), 5.51-5.27 (m, 1H), 4.22-4.01 (m, 4H), 3.70-3.61 (m, 4H), 3.60-3.45 (m, 1H), 3.36 (td, J = 11.4, 6.9 Hz, 1H), 2.35-1.95 (m, 2H) | MS (APCI) m/z 426 [M + H]$^+$ |
| Example 74 | N-(2-ethoxyethyl)-2-{3-[1-(2-fluorophenyl)-1H-indazol-4-yl]-2-oxoimidazolidin-1-yl}acetamide | $^1$H NMR (500 MHz, DMSO-$d_6$) δ ppm 8.42 (d, J = 0.9 Hz, 1H), 8.16 (t, J = 5.7 Hz, 1H), 7.67 (td, J = 7.8, 1.7 Hz, 1H), 7.63-7.51 (m, 2H), 7.51-7.41 (m, 2H), 7.18 (d, J = 7.6 Hz, 1H), 7.10 (dd, J = 8.4, 2.9 Hz, 1H), 4.08 (dd, J = 8.9, 6.7 Hz, 2H), 3.90 (s, 2H), 3.65-3.56 (m, 2H), 3.50-3.39 (m, 4H), 3.35-3.21 (m, 2H), 1.12 (t, J = 7.0 Hz, 3H) | MS (APCI) m/z 426 [M + H]$^+$ |
| Example 75 | 2-{3-[1-(2-fluorophenyl)-1H-indazol-4-yl]-2-oxoimidazolidin-1-yl}-N-(tetrahydrofuran-3-ylmethyl)acetamide | $^1$H NMR (500 MHz, DMSO-$d_6$) δ ppm 8.42 (d, J = 0.9 Hz, 1H), 7.67 (td, J = 7.9, 1.7 Hz, 1H), 7.64-7.51 (m, 2H), 7.50-7.39 (m, 2H), 7.18 (d, J = 7.6 Hz, 1H), 7.10 (dd, J = 8.4, 2.9 Hz, 1H), 4.08 (dd, J = 8.9, 6.7 Hz, 2H), 3.89 (s, 2H), 3.72-3.64 (m, 2H), 3.65-3.56 (m, 3H), 3.42 (dd, J = 8.6, 5.5 Hz, 1H), 3.19-3.05 (m, 2H), 2.45-2.33 (m, 1H), 2.00-1.88 (m, 1H), 1.62-1.52 (m, 1H) | MS (APCI) m/z 438 [M + H]$^+$ |
| Example 76 | 1-[1-(2-fluorophenyl)-1H-indazol-4-yl]-3-(4-methylpentanoyl)imidazolidin-2-one | $^1$H NMR (300 MHz, CDCl$_3$) δ ppm 8.31 (d, J = 1.0 Hz, 1H), 7.61 (td, J = 7.7, 1.9 Hz, 1H), 7.51-7.22 (m, 5H), 7.11 (d, J = 7.5 Hz, 1H), 4.09 (s, 4H), 3.10-2.98 (m, 2H), 1.71-1.57 (m, 3H), 0.94 (d, J = 6.1 Hz, 6H) | MS (DCI) m/z 395 [M + H]$^+$ |
| Example 77 | 1-(cyclopentylsulfonyl)-3-[1-(2-fluorophenyl)-1H-indazol-4-yl]imidazolidin-2-one | $^1$H NMR (400 MHz, DMSO-$d_6$) δ ppm 8.36 (d, J = 1.0 Hz, 1H), 7.68 (td, J = 7.8, 1.7 Hz, 1H), 7.65-7.44 (m, 4H), 7.26 (dd, J = 8.6, 3.1 Hz, 1H), 7.23 (d, J = 7.5 Hz, 1H), 4.24 (ddd, J = 8.8, 7.0, 1.7 Hz, 1H), 4.18 (dd, J = 9.4, 6.4 Hz, 2H), 4.10-4.02 (m, 2H), 2.15-1.95 (m, 4H), 1.81-1.60 (m, 4H) | MS (APCI) m/z 429 [M + H]$^+$ |
| Example 78 | 1-(cyclohexylsulfonyl)-3-[1-(2-fluorophenyl)-1H-indazol-4-yl]imidazolidin-2-one | $^1$H NMR (400 MHz, DMSO-$d_6$) δ ppm 8.35 (d, J = 1.0 Hz, 1H), 7.68 (td, J = 7.8, 1.7 Hz, 1H), 7.66-7.50 (m, 3H), 7.47 (td, J = 7.6, 1.5 Hz, 1H), 7.29-7.21 (m, 2H), 4.19 (dd, J = 9.2, 6.3 Hz, 2H), 4.06-3.99 (m, 2H), 3.68 (td, J = 8.7, 4.4 Hz, 1H), 2.20-2.08 (m, 2H), 1.92-1.80 (m, 2H), 1.72-1.61 (m, 1H), 1.55 (qd, J = 12.4, 3.6 Hz, 2H), 1.42-1.27 (m, 2H), 1.27-1.15 (m, 1H) | MS (APCI) m/z 443 [M + H]$^+$ |
| Example 79 | 1-[1-(2-fluorophenyl)-1H-indazol-4-yl]-3-(2-thienylsulfonyl)imidazolidin-2-one | $^1$H NMR (400 MHz, DMSO-$d_6$) δ ppm 8.16 (dd, J = 5.0, 1.4 Hz, 1H), 8.09 (d, J = 1.0 Hz, 1H), 7.97 (dd, J = 3.8, 1.4 Hz, 1H), 7.70-7.43 (m, 5H), 7.35 (dd, J = 5.0, 3.8 Hz, 1H), 7.25 (dd, J = 8.4, 2.9 Hz, 1H), 7.17 (d, J = 7.5 Hz, 1H), 4.17-4.02 (m, 4H) | MS (APCI) m/z 442 [M + H]$^+$ |
| Example 80 | 1-[1-(2-fluorophenyl)-1H-indazol-4-yl]-3-(isobutylsulfonyl)imidazolidin-2-one | $^1$H NMR (400 MHz, DMSO-$d_6$) δ ppm 8.38 (d, J = 0.9 Hz, 1H), 7.68 (td, J = 7.8, 1.7 Hz, 1H), 7.66-7.50 (m, 3H), 7.47 (td, J = 7.6, 1.6 Hz, 1H), 7.29-7.21 (m, 2H), 4.21-4.13 (m, 2H), 4.08- | MS (APCI) m/z 417 [M + H]$^+$ |

| Example | Name | NMR | MS |
|---|---|---|---|
| | | 3.99 (m, 2H), 3.52 (d, J = 6.5 Hz, 2H), 2.34-2.20 (m, 1H), 1.11 (d, J = 6.7 Hz, 6H) | |
| Example 81 | 1-[1-(2-fluorophenyl)-1H-indazol-4-yl]-3-(propylsulfonyl)imidazolidin-2-one | $^1$H NMR (400 MHz, DMSO-d$_6$) δ ppm 8.38 (d, J = 0.9 Hz, 1H), 7.68 (td, J = 7.8, 1.7 Hz, 1H), 7.65-7.57 (m, 1H), 7.57-7.50 (m, 2H), 7.47 (td, J = 7.6, 1.6 Hz, 1H), 7.29-7.20 (m, 2H), 4.18 (dd, J = 9.2, 6.2 Hz, 2H), 4.07-4.01 (m, 2H), 3.61-3.54 (m, 2H), 1.91-1.77 (m, 2H), 1.06 (t, J = 7.4 Hz, 3H) | MS (ESI$^+$) m/z 403 [M + H]$^+$ |
| Example 82 | 1-[1-(2-fluorophenyl)-1H-indazol-4-yl]-3-(isopropylsulfonyl)imidazolidin-2-one | $^1$H NMR (400 MHz, DMSO-d$_6$) δ ppm 8.36 (d, J = 1.0 Hz, 1H), 7.68 (td, J = 7.8, 1.7 Hz, 1H), 7.65-7.50 (m, 3H), 7.47 (td, J = 7.6, 1.6 Hz, 1H), 7.29-7.21 (m, 2H), 4.19 (dd, J = 9.2, 6.3 Hz, 2H), 4.08-4.02 (m, 2H), 3.98-3.87 (m, 1H), 1.40 (d, J = 6.8 Hz, 6H) | MS (ESI$^+$) m/z 403 [M + H]$^+$ |
| Example 83 | 1-(ethylsulfonyl)-3-[1-(2-fluorophenyl)-1H-indazol-4-yl]imidazolidin-2-one | $^1$H NMR (400 MHz, DMSO-d$_6$) δ ppm 8.38 (d, J = 0.9 Hz, 1H), 7.68 (td, J = 7.9, 1.8 Hz, 1H), 7.65-7.44 (m, 4H), 7.29-7.22 (m, 2H), 4.18 (dd, J = 9.1, 6.3 Hz, 2H), 4.08-4.01 (m, 2H), 3.60 (q, J = 7.4 Hz, 2H), 1.36 (t, J = 7.4 Hz, 3H) | MS (ESI$^+$) m/z 389 [M + H]$^+$ |
| Example 84 | 1-[1-(2-fluorophenyl)-1H-indazol-4-yl]-3-{2-[(3R)-3-hydroxypyrrolidin-1-yl]-2-oxoethyl}imidazolidin-2-one | $^1$H NMR (300 MHz, methanol-d$_4$) δ ppm 8.42 (d, J = 0.9 Hz, 1H), 7.62 (td, J = 7.6, 1.6 Hz, 1H), 7.58-7.50 (m, 1H), 7.49-7.36 (m, 3H), 7.18-7.06 (m, 2H), 4.54-4.39 (m, 1H), 4.17-4.09 (m, 3H), 3.75 (td, J = 7.7, 2.7 Hz, 2H), 3.71-3.43 (m, 3H), 3.35-3.32 (m, 2H), 2.23-1.85 (m, 2H) | MS (ESI$^+$) m/z 424 [M + H]$^+$ |
| Example 85 | 1-[1-(2-fluorophenyl)-1H-indazol-4-yl]-3-{2-[(3S)-3-(2-hydroxypropan-2-yl)pyrrolidin-1-yl]-2-oxoethyl}imidazolidin-2-one | $^1$H NMR (400 MHz, methanol-d$_4$) δ ppm 8.45-8.41 (m, 1H), 7.61 (td, J = 7.7, 1.6 Hz, 1H), 7.59-7.51 (m, 1H), 7.48-7.35 (m, 3H), 7.17-7.08 (m, 2H), 4.56 (s, 1H), 4.20-4.06 (m, 4H), 3.79-3.72 (m, 3H), 3.72-3.64 (m, 1H), 3.55-3.32 (m, 2H), 2.49-2.21 (m, 1H), 2.13-1.92 (m, 2H), 1.24 (d, J = 5.1 Hz, 6H) | MS (ESI$^+$) m/z 466 [M + H]$^+$ |
| Example 86 | 1-[2-(3,3-difluoropyrrolidin-1-yl)-2-oxoethyl]-3-[1-(2-fluorophenyl)-1H-indazol-4-yl]imidazolidin-2-one | $^1$H NMR (400 MHz, methanol-d$_4$) δ ppm 8.42-8.40 (m, 1H), 7.62 (td, J = 7.7, 1.7 Hz, 1H), 7.59-7.52 (m, 1H), 7.45 (dd, J = 8.5, 7.6 Hz, 2H), 7.17-7.13 (m, 1H), 7.12 (d, J = 7.6 Hz, 1H), 4.24-4.10 (m, 2H), 3.99 (t, J = 12.6 Hz, 1H), 3.88-3.79 (m, 2H), 3.78-3.71 (m, 4H), 2.62-2.35 (m, 3H) | MS (ESI$^+$) m/z 444 [M + H]$^+$ |
| Example 87 | 2-{3-[1-(2-fluorophenyl)-1H-indazol-4-yl]-2-oxoimidazolidin-1-yl}-N-[(3S)-tetrahydrofuran-3-yl]acetamide | $^1$H NMR (400 MHz, methanol-d$_4$) δ ppm 8.43 (d, J = 0.9 Hz, 1H), 7.60 (td, J = 7.7, 1.6 Hz, 1H), 7.57-7.50 (m, 1H), 7.46-7.35 (m, 3H), 7.15-7.08 (m, 2H), 4.44 (ddt, J = 7.5, 5.8, 3.7 Hz, 1H), 4.09 (dd, J = 9.0, 6.8 Hz, 2H), 4.00 (d, J = 1.4 Hz, 2H), 3.96-3.85 (m, 2H), 3.79 (td, J = 8.3, 5.6 Hz, 1H), 3.72-3.62 (m, 3H), 2.23 (dq, J = 12.9, 7.7 Hz, 1H), 1.89 (dddd, J = 13.1, 7.5, 5.5, 3.8 Hz, 1H), 1.34 (dd, J = 7.0, 2.5 Hz, 1H) | MS (ESI$^+$) m/z 424 [M + H]$^+$ |

| Example | Name | NMR | MS |
| --- | --- | --- | --- |
| Example 88 | 1-{2-[(3S)-3-fluoropyrrolidin-1-yl]-2-oxoethyl}-3-{1-[3-(trifluoromethoxy)phenyl]-1H-indazol-4-yl}imidazolidin-2-one | $^1$H NMR (500 MHz, DMSO-$d_6$) δ ppm 8.41 (s, 1H), 7.90-7.83 (m, 2H), 7.77-7.72 (m, 2H), 7.60 (d, J = 8.4 Hz, 1H), 7.50 (t, J = 8.0 Hz, 1H), 7.45-7.39 (m, 1H), 7.21 (d, J = 7.6 Hz, 1H), 5.53-5.26 (m, 1H), 4.25-3.97 (m, 4H), 3.79-3.43 (m, 5H), 2.32-2.01 (m, 2H) | MS (ESI$^+$) m/z 492 [M + H]$^+$ |
| Example 89 | 1-[1-(2-fluorophenyl)-1H-indazol-4-yl]-3-{[5-(trifluoromethyl)pyridin-2-yl]methyl}imidazolidin-2-one | $^1$H NMR (300 MHz, methanol-$d_4$) δ ppm 8.93-8.84 (m, 1H), 8.43 (d, J = 0.9 Hz, 1H), 8.16 (dd, J = 8.3, 2.4 Hz, 1H), 7.69 (d, J = 8.3 Hz, 1H), 7.62 (td, J = 7.6, 1.6 Hz, 1H), 7.55 (ddd, J = 8.7, 5.3, 1.7 Hz, 1H), 7.51-7.36 (m, 3H), 7.19-7.11 (m, 2H), 4.76 (s, 2H), 4.21-4.12 (m, 2H), 3.77-3.68 (m, 2H) | MS (ESI$^+$) m/z 456 [M + H]$^+$ |
| Example 90 | 1-[1-(2-fluorophenyl)-1H-indazol-4-yl]-3-{2-[(3S)-3-methylpyrrolidin-1-yl]-2-oxoethyl}imidazolidin-2-one | $^1$H NMR (300 MHz, methanol-$d_4$) δ ppm 8.42 (d, J = 0.9 Hz, 1H), 7.62 (td, J = 7.6, 1.6 Hz, 1H), 7.58-7.51 (m, 1H), 7.49-7.36 (m, 3H), 7.13 (t, J = 8.5 Hz, 2H), 4.18-4.10 (m, 5H), 3.75 (dd, J = 9.1, 6.8 Hz, 2H), 3.71-3.62 (m, 2H), 3.58-3.37 (m, 2H), 3.17-2.92 (m, 1H), 1.71-1.48 (m, 1H), 1.12 (t, J = 6.6 Hz, 3H) | MS (ESI$^+$) m/z 422 [M + H]$^+$ |
| Example 91 | 1-[2-(3,3-difluoroazetidin-1-yl)-2-oxoethyl]-3-[1-(2-fluorophenyl)-1H-indazol-4-yl]imidazolidin-2-one | $^1$H NMR (300 MHz, methanol-$d_4$) δ ppm 8.40 (d, J = 1.0 Hz, 1H), 7.62 (td, J = 7.6, 1.6 Hz, 1H), 7.58-7.51 (m, 1H), 7.49-7.36 (m, 2H), 7.19-7.09 (m, 2H), 4.75-4.65 (m, 2H), 4.42 (t, J = 12.2 Hz, 2H), 4.17-4.11 (m, 3H), 4.10 (s, 2H), 3.74 (dd, J = 9.0, 6.8 Hz, 2H) | MS (ESI$^+$) m/z 430 [M + H]$^+$ |
| Example 92 | 2-{3-[1-(2-fluorophenyl)-1H-indazol-4-yl]-2-oxoimidazolidin-1-yl}-N-isobutylacetamide | $^1$H NMR (300 MHz, methanol-$d_4$) δ ppm 8.43 (d, J = 1.0 Hz, 1H), 7.62 (td, J = 7.5, 1.6 Hz, 1H), 7.57-7.51 (m, 1H), 7.49-7.35 (m, 3H), 7.17-7.11 (m, 2H), 4.18-4.10 (m, 2H), 4.02 (s, 2H), 3.76-3.68 (m, 2H), 3.08 (d, J = 6.9 Hz, 2H), 1.91-1.76 (m, 1H), 0.94 (d, J = 6.7 Hz, 6H) | MS (ESI$^+$) m/z 410 [M + H]$^+$ |
| Example 93 | N,N-diethyl-2-{3-[1-(2-fluorophenyl)-1H-indazol-4-yl]-2-oxoimidazolidin-1-yl}acetamide | $^1$H NMR (400 MHz, methanol-$d_4$) δ ppm 8.43 (s, 1H), 7.62 (td, J = 7.7, 1.5 Hz, 1H), 7.58-7.51 (m, 1H), 7.48-7.37 (m, 3H), 7.17-7.07 (m, 2H), 4.24 (s, 2H), 4.16-4.09 (m, 2H), 3.78-3.70 (m, 2H), 3.44 (q, J = 7.1 Hz, 4H), 1.27 (t, J = 7.2 Hz, 3H), 1.17 (t, J = 7.1 Hz, 3H) | MS (ESI$^+$) m/z 410 [M + H]$^+$ |
| Example 94 | 1-[2-(azetidin-1-yl)-2-oxoethyl]-3-[1-(2-fluorophenyl)-1H-indazol-4-yl]imidazolidin-2-one | $^1$H NMR (400 MHz, methanol-$d_4$) δ ppm 8.41 (s, 1H), 7.61 (td, J = 7.7, 1.6 Hz, 1H), 7.58-7.52 (m, 1H), 7.49-7.37 (m, 3H), 7.17-7.08 (m, 2H), 4.33 (t, J = 7.7 Hz, 2H), 4.15-4.06 (m, 4H), 4.00 (s, 2H), 3.76-3.69 (m, 2H), 2.44-2.30 (m, 2H) | MS (ESI$^+$) m/z 394 [M + H]$^+$ |
| Example 95 | 2-{3-[1-(2-fluorophenyl)-1H-indazol-4-yl]-2-oxoimidazolidin-1-yl}-N-isopropylacetamide | $^1$H NMR (300 MHz, methanol-$d_4$) δ ppm 8.43 (d, J = 0.9 Hz, 1H), 7.62 (td, J = 7.6, 1.6 Hz, 1H), 7.58-7.51 (m, 1H), 7.45 (dd, J = 8.5, 7.4 Hz, 2H), 7.42-7.37 (m, 2H), 7.18-7.10 (m, 2H), 4.18-4.10 (m, 2H), 4.09-4.00 (m, 1H), 3.98 (s, 2H), 3.75-3.65 (m, 2H), 1.19 (d, J = 6.6 Hz, 6H) | MS (ESI$^+$) m/z 396 [M + H]$^+$ |
| Example 96 | 1-[1-(2-fluorophenyl)-1H-indazol-4-yl]-3-(isopropoxyacetyl)imidazolidin-2-one | $^1$H NMR (300 MHz, methanol-$d_4$) δ ppm 8.40 (d, J = 1.1 Hz, 1H), 7.63 (td, J = 7.6, 1.7 Hz, 1H), 7.56 (ddd, J = 8.0, 4.8, 2.7 Hz, | MS (ESI$^+$) m/z 397 [M + H]$^+$ |

-continued

| Example | Name | NMR | MS |
|---|---|---|---|
| | | 1H), 7.50 (dd, J = 8.5, 7.5 Hz, 1H), 7.47-7.38 (m, 2H), 7.28-7.19 (m, 2H), 4.26-4.02 (m, 6H), 3.84-3.71 (m, 1H), 1.23 (d, J = 6.1 Hz, 6H) | |
| Example 97 | 1-[1-(2-fluorophenyl)-1H-indazol-4-yl]-3-{[4-(trifluoromethyl)pyridin-2-yl]methyl}imidazolidin-2-one | $^1$H NMR (400 MHz, methanol-$d_4$) δ ppm 8.83 (d, J = 5.1 Hz, 1H), 8.42 (s, 1H), 7.77 (s, 1H), 7.66-7.59 (m, 2H), 7.59-7.52 (m, 1H), 7.49-7.38 (m, 3H), 7.18-7.12 (m, 2H), 4.76 (s, 2H), 4.15 (dd, J = 8.8, 7.0 Hz, 2H), 3.71 (dd, J = 8.8, 7.0 Hz, 2H) | MS (ESI$^+$) m/z 456.1 [M + H]$^+$ |
| Example 98 | 1-{2-[3-(ethoxymethyl)-3-fluoropyrrolidin-1-yl]-2-oxoethyl}-3-[1-(2-fluorophenyl)-1H-indazol-4-yl]imidazolidin-2-one | $^1$H NMR (300 MHz, methanol-$d_4$) δ ppm 8.42 (d, J = 0.9 Hz, 1H), 7.62 (td, J = 7.6, 1.6 Hz, 1H), 7.58-7.51 (m, 1H), 7.49-7.36 (m, 3H), 7.18-7.09 (m, 2H), 4.17-4.09 (m, 3H), 3.89-3.66 (m, 8H), 3.60 (qd, J = 7.1, 3.0 Hz, 3H), 2.36-1.97 (m, 2H), 1.21 (td, J = 7.0, 2.0 Hz, 3H) | MS (ESI$^+$) m/z 484 [M + H]$^+$ |
| Example 99 | 1-[1-(2-fluorophenyl)-1H-indazol-4-yl]-3-{2-[(8aS)-hexahydropyrrolo[1,2-a]pyrazin-2(1H)-yl]-2-oxoethyl}imidazolidin-2-one | $^1$H NMR (300 MHz, methanol-$d_4$) δ ppm 8.39 (s, 1H), 7.62 (td, J = 7.6, 1.6 Hz, 1H), 7.58-7.51 (m, 1H), 7.50-7.36 (m, 3H), 7.16 (dd, J = 8.5, 2.9 Hz, 1H), 7.11 (d, J = 7.5 Hz, 1H), 4.27 (dd, J = 22.7, 13.9 Hz, 2H), 4.14 (dd, J = 8.9, 7.0 Hz, 2H), 3.79-3.71 (m, 2H), 3.62-3.40 (m, 2H), 3.34-3.11 (m, 7H), 2.24 (s, 1H), 2.19-2.05 (m, 2H), 1.94-1.70 (m, 1H) | MS (ESI$^+$) m/z 463 [M + H]$^+$ |
| Example 100 | 1-[1-(2-fluorophenyl)-1H-indazol-4-yl]-3-[2-(2-oxa-6-azaspiro[3.3]hept-6-yl)-2-oxoethyl]imidazolidin-2-one | $^1$H NMR (400 MHz, DMSO-$d_6$) δ ppm 8.39 (s, 1H), 7.62 (td, J = 7.8, 1.9 Hz, 1H), 7.60-7.53 (m, 1H), 7.48 (ddd, J = 10.1, 8.6, 1.5 Hz, 1H), 7.45-7.38 (m, 2H), 7.16 (d, J = 7.6 Hz, 1H), 7.07 (dd, J = 8.4, 2.8 Hz, 1H), 4.70 (s, 4H), 4.06 (dd, J = 8.9, 6.8 Hz, 2H), 3.90 (s, 2H), 3.63 (dd, J = 8.9, 6.8 Hz, 2H), 3.26 (s, 4H) | MS (APCI) m/z 436 [M + H]$^+$ |
| Example 101 | 1-[2-(3,5-dimethylmorpholin-4-yl)-2-oxoethyl]-3-[1-(2-fluorophenyl)-1H-indazol-4-yl]imidazolidin-2-one | $^1$H NMR (400 MHz, DMSO-$d_6$) δ ppm 8.40 (d, J = 0.9 Hz, 1H), 7.62 (td, J = 7.8, 1.8 Hz, 1H), 7.60-7.53 (m, 1H), 7.52-7.37 (m, 3H), 7.17 (d, J = 7.6 Hz, 1H), 7.07 (dd, J = 8.3, 2.8 Hz, 1H), 4.08 (t, J = 7.9 Hz, 4H), 4.00-3.91 (m, 4H), 3.67 (td, J = 7.9, 4.9 Hz, 2H), 3.59-3.51 (m, 2H), 1.36 (d, J = 6.6 Hz, 6H) | MS (APCI) m/z 452 [M + H]$^+$ |
| Example 102 | 1-[2-(1,4-dioxa-7-azaspiro[4.4]non-7-yl)-2-oxoethyl]-3-[1-(2-fluorophenyl)-1H-indazol-4-yl]imidazolidin-2-one | $^1$H NMR (400 MHz, DMSO-$d_6$) δ ppm 8.40 (s, 1H), 7.62 (td, J = 7.9, 1.9 Hz, 1H), 7.55 (d, J = 6.8 Hz, 2H), 7.46-7.39 (m, 2H), 7.16 (d, J = 7.6 Hz, 1H), 7.07 (dd, J = 8.2, 2.7 Hz, 1H), 4.07 (dd, J = 9.0, 6.7 Hz, 3H), 3.95 (s, 4H), 3.66 (dd, J = 9.0, 6.8 Hz, 3H), 3.49 (d, J = 54.0 Hz, 2H), 3.24 (s, 3H), 2.02 (s, 1H) | MS (APCI) m/z 466 [M + H]$^+$ |
| Example 103 | 4-({3-[1-(2-fluorophenyl)-1H-indazol-4-yl]-2-oxoimidazolidin-1-yl}acetyl)piperazine-2,6-dione | $^1$H NMR (400 MHz, DMSO-$d_6$) δ ppm 8.39 (d, J = 1.0 Hz, 1H), 7.63 (td, J = 7.8, 1.8 Hz, 1H), 7.60-7.53 (m, 1H), 7.52-7.37 (m, 3H), 7.16 (d, J = 7.6 Hz, 1H), 7.08 (dd, J = 8.4, 2.8 Hz, 1H), 4.38 (s, 4H), 4.24 (s, 2H), 4.07 (dd, J = 8.9, 6.8 Hz, 2H), 3.63 (dd, J = 8.9, 6.8 Hz, 2H) | MS (APCI) m/z 451 [M + H]$^+$ |

| Example | Name | NMR | MS |
| --- | --- | --- | --- |
| Example 104 | 1-[1-(2-fluorophenyl)-1H-indazol-4-yl]-3-[2-(5-methylhexahydropyrrolo[3,4-c]pyrrol-2(1H)-yl)-2-oxoethyl]imidazolidin-2-one | $^1$H NMR (400 MHz, DMSO-$d_6$) δ ppm 8.40 (d, J = 1.0 Hz, 1H), 7.62 (td, J = 7.8, 1.8 Hz, 1H), 7.59-7.54 (m, 1H), 7.52-7.38 (m, 3H), 7.16 (d, J = 7.6 Hz, 1H), 7.08 (dd, J = 8.4, 2.7 Hz, 1H), 4.08 (dd, J = 8.8, 6.9 Hz, 3H), 3.67 (dd, J = 8.9, 6.7 Hz, 4H), 3.55 (d, J = 12.9 Hz, 2H), 3.25-3.09 (m, 7H), 2.88 (s, 3H) | MS (APCI) m/z 463 [M + H]$^+$ |
| Example 105 | 1-[1-(2-fluorophenyl)-1H-indazol-4-yl]-3-[2-(octahydro-4H-1,4-benzoxazin-4-yl)-2-oxoethyl]imidazolidin-2-one | $^1$H NMR (400 MHz, DMSO-$d_6$) δ ppm 8.39 (s, 1H), 7.62 (td, J = 7.8, 1.8 Hz, 1H), 7.59-7.52 (m, 1H), 7.52-7.36 (m, 4H), 7.16 (d, J = 7.6 Hz, 1H), 7.07 (dd, J = 8.3, 2.7 Hz, 1H), 4.13 (d, J = 3.7 Hz, 2H), 4.07 (dd, J = 8.8, 7.0 Hz, 2H), 3.94-3.80 (m, 2H), 3.72-3.54 (m, 5H), 3.41 (td, J = 10.6, 3.4 Hz, 1H), 2.37-2.26 (m, 1H), 1.92-1.83 (m, 1H), 1.77-1.60 (m, 2H), 1.53-1.20 (m, 3H) | MS (APCI) m/z 478 [M + H]$^+$ |
| Example 106 | 1-[1-(2-fluorophenyl)-1H-indazol-4-yl]-3-[2-(hexahydrocyclopenta[c]pyrrol-2(1H)-yl)-2-oxoethyl]imidazolidin-2-one | $^1$H NMR (400 MHz, DMSO-$d_6$) δ ppm 8.40 (d, J = 0.9 Hz, 1H), 7.62 (td, J = 7.8, 1.8 Hz, 1H), 7.60-7.52 (m, 1H), 7.52-7.37 (m, 4H), 7.16 (d, J = 7.6 Hz, 1H), 7.07 (dd, J = 8.4, 2.7 Hz, 1H), 4.12-3.99 (m, 4H), 3.66 (dd, J = 8.9, 6.8 Hz, 3H), 3.22 (s, 2H), 2.83-2.55 (m, 2H), 1.90-1.67 (m, 3H), 1.59 (dddd, J = 12.4, 7.8, 6.1, 1.5 Hz, 1H), 1.45 (s, 2H) | MS (APCI) m/z 448 [M + H]$^+$ |
| Example 107 | 1-{2-[(1R,3r,6s,8S)-4-azatricyclo[4.3.1.1$^{3,8}$]undec-4-yl]-2-oxoethyl}-3-[1-(2-fluorophenyl)-1H-indazol-4-yl]imidazolidin-2-one | $^1$H NMR (400 MHz, DMSO-$d_6$) δ ppm 8.40 (s, 1H), 7.62 (td, J = 7.8, 1.8 Hz, 1H), 7.59-7.53 (m, 1H), 7.52-7.36 (m, 3H), 7.16 (d, J = 7.6 Hz, 1H), 7.06 (dd, J = 8.4, 2.7 Hz, 1H), 4.95 (s, 1H), 4.26 (s, 0H), 4.15 (d, J = 16.0 Hz, 2H), 4.07 (dd, J = 9.0, 6.7 Hz, 2H), 3.66 (dd, J = 8.9, 6.8 Hz, 2H), 3.58 (t, J = 9.1 Hz, 2H), 2.82 (s, 1H), 2.27 (s, 1H), 1.95 (d, J = 13.7 Hz, 6H), 1.57 (t, J = 12.2 Hz, 5H) | MS (APCI) m/z 488 [M + H]$^+$ |
| Example 108 | (3aR,6aS)-5-({3-[1-(2-fluorophenyl)-1H-indazol-4-yl]-2-oxoimidazolidin-1-yl}acetyl)-2-methyltetrahydropyrrolo[3,4-c]pyrrole-1,3(2H,3aH)-dione | $^1$H NMR (400 MHz, DMSO-$d_6$) δ ppm 8.38 (d, J = 1.0 Hz, 1H), 7.62 (td, J = 7.8, 1.8 Hz, 1H), 7.59-7.53 (m, 1H), 7.53-7.38 (m, 3H), 7.15 (d, J = 7.6 Hz, 1H), 7.07 (dd, J = 8.4, 2.7 Hz, 1H), 4.07-4.01 (m, 4H), 3.89 (dd, J = 11.5, 1.9 Hz, 2H), 3.77-3.50 (m, 5H), 3.00 (d, J = 35.0 Hz, 1H), 2.87 (s, 3H) | MS (APCI) m/z 491 [M + H]$^+$ |
| Example 109 | 1-[1-(2-fluorophenyl)-1H-indazol-4-yl]-3-[2-(8-methoxy-3-azabicyclo[3.2.1]oct-3-yl)-2-oxoethyl]imidazolidin-2-one | $^1$H NMR (400 MHz, DMSO-$d_6$) δ ppm 8.39 (s, 1H), 7.62 (td, J = 7.8, 1.8 Hz, 1H), 7.59-7.53 (m, 1H), 7.52-7.38 (m, 3H), 7.16 (d, J = 7.5 Hz, 1H), 7.07 (dd, J = 8.4, 2.7 Hz, 1H), 4.23 (s, 1H), 4.12-4.02 (m, 2H), 3.90 (s, 2H), 3.65 (dd, J = 8.9, 6.8 Hz, 2H), 3.56 (t, J = 4.9 Hz, 1H), 3.45 (s, 2H), 3.37 (s, 3H), 3.12 (d, J = 58.4 Hz, 1H), 2.30-2.12 (m, 2H), 1.77-1.63 (m, 2H), 1.62-1.36 (m, 2H) | MS (APCI) m/z 478 [M + H]$^+$ |
| Example 110 | 1-[2-(1,4-dioxa-8-azaspiro[4.6]undec-8-yl)-2-oxoethyl]-3-[1-(2-fluorophenyl)-1H-indazol-4-yl]imidazolidin-2-one | $^1$H NMR (400 MHz, DMSO-$d_6$) δ ppm 8.41-8.38 (m, 1H), 7.62 (td, J = 7.8, 1.8 Hz, 1H), 7.59-7.53 (m, 1H), 7.51-7.38 (m, 3H), 7.16 (d, J = 7.6 Hz, 1H), 7.07 (dd, J = 8.3, 2.7 Hz, 1H), 4.17-4.11 (m, 2H), 4.07 (dd, J = 8.9, 6.8 Hz, 2H), 3.88 (s, 3H), 3.78-3.61 (m, 3H), 3.56-3.45 | MS (APCI) m/z 494 [M + H]$^+$ |

| Example | Name | NMR | MS |
| --- | --- | --- | --- |
| | | (m, 3H), 2.71-2.57 (m, 1H), 2.01-1.67 (m, 6H) | |
| Example 111 | 1-[1-(2-fluorophenyl)-1H-indazol-4-yl]-3-{2-[(3aR,4R,7S,7aS)-octahydro-2H-4,7-methanoisoindol-2-yl]-2-oxoethyl}imidazolidin-2-one | $^1$H NMR (400 MHz, DMSO-$d_6$) δ ppm 8.40 (d, J = 0.9 Hz, 1H), 7.62 (td, J = 7.8, 1.8 Hz, 1H), 7.59-7.52 (m, 1H), 7.52-7.37 (m, 3H), 7.16 (d, J = 7.6 Hz, 1H), 7.07 (dd, J = 8.4, 2.7 Hz, 1H), 4.20-3.94 (m, 4H), 3.66 (t, J = 7.9 Hz, 2H), 3.37-3.15 (m, 2H), 3.15-2.97 (m, 1H), 2.71-2.53 (m, 3H), 2.27-2.20 (m, 2H), 1.56-1.41 (m, 2H), 1.34 (d, J = 27.8 Hz, 4H) | MS (APCI) m/z 474 [M + H]$^+$ |
| Example 112 | 1-[1-(2-fluorophenyl)-1H-indazol-4-yl]-3-[2-(1-methyloctahydro-6H-pyrrolo[3,4-b]pyridin-6-yl)-2-oxoethyl]imidazolidin-2-one | $^1$H NMR (400 MHz, DMSO-$d_6$) δ ppm 8.40 (s, 1H), 7.62 (td, J = 7.8, 1.8 Hz, 1H), 7.59-7.53 (m, 1H), 7.52-7.38 (m, 3H), 7.16 (d, J = 7.6 Hz, 1H), 7.08 (dd, J = 8.4, 2.7 Hz, 1H), 4.30-3.30 (m, 12H), 3.14-3.01 (m, 1H), 2.91-2.80 (m, 3H), 1.80 (s, 5H) | MS (APCI) m/z All [M + H]$^+$ |
| Example 113 | 1-[1-(2-fluorophenyl)-1H-indazol-4-yl]-3-{2-[(3R)-3-methylmorpholin-4-yl]-2-oxoethyl}imidazolidin-2-one | $^1$H NMR (400 MHz, DMSO-$d_6$) δ ppm 8.39 (d, J = 1.0 Hz, 1H), 7.62 (td, J = 7.8, 1.8 Hz, 1H), 7.59-7.52 (m, 1H), 7.52-7.37 (m, 4H), 7.17 (d, J = 7.6 Hz, 1H), 7.07 (dd, J = 8.4, 2.7 Hz, 1H), 4.21 (s, 1H), 4.14 (s, 2H), 4.08 (dd, J = 8.8, 7.0 Hz, 2H), 3.89-3.82 (m, 2H), 3.65 (dd, J = 9.9, 7.4 Hz, 3H), 3.56 (dd, J = 11.6, 3.2 Hz, 1H), 3.41 (td, J = 11.7, 3.0 Hz, 1H), 1.27 (d, J = 6.8 Hz, 3H) | MS (APCI) m/z 438 [M + H]$^+$ |
| Example 114 | 1-[1-(2-fluorophenyl)-1H-indazol-4-yl]-3-{2-[(1R,6S)-9-methyl-3,9-diazabicyclo[4.2.1]non-3-yl]-2-oxoethyl}imidazolidin-2-one | $^1$H NMR (400 MHz, DMSO-$d_6$) δ ppm 8.38 (s, 1H), 7.62 (td, J = 7.7, 1.8 Hz, 1H), 7.59-7.54 (m, 1H), 7.53-7.39 (m, 3H), 7.16 (d, J = 7.6 Hz, 1H), 7.08 (dd, J = 8.4, 2.7 Hz, 1H), 4.32-4.16 (m, 2H), 4.09 (t, J = 7.9 Hz, 2H), 4.06-3.95 (m, 1H), 3.86-3.43 (m, 4H), 2.87 (s, 3H), 2.51 (p, J = 1.9 Hz, 5H), 2.27-1.85 (m, 4H) | MS (APCI) m/z All [M + H]$^+$ |
| Example 115 | 1-[2-(2-ethylpyrrolidin-1-yl)-2-oxoethyl]-3-[1-(2-fluorophenyl)-1H-indazol-4-yl]imidazolidin-2-one | $^1$H NMR (300 MHz, methanol-$d_4$) δ ppm 8.43 (d, J = 0.9 Hz, 1H), 7.62 (td, J = 7.6, 1.6 Hz, 1H), 7.58-7.50 (m, 1H), 7.49-7.36 (m, 3H), 7.17-7.08 (m, 2H), 4.55 (s, 2H), 4.17-4.12 (m, 3H), 3.80-3.72 (m, 2H), 3.59-3.53 (m, 2H), 2.13-1.70 (m, 5H), 1.52-1.32 (m, 1H), 1.04-0.88 (m, 3H) | MS (ESI$^+$) m/z 436 [M + H]$^+$ |
| Example 116 | 1-[1-(2-fluorophenyl)-1H-indazol-4-yl]-3-[2-(2-isopropylpyrrolidin-1-yl)-2-oxoethyl]imidazolidin-2-one | H NMR (300 MHz, DMSO-$d_6$) δ ppm 8.44-8.36 (m, 1H), 7.68 (td, J = 7.8, 1.6 Hz, 1H), 7.64-7.49 (m, 2H), 7.48-7.37 (m, 2H), 7.17 (dd, J = 7.3, 5.4 Hz, 1H), 7.08 (dd, J = 8.4, 3.0 Hz, 1H), 4.19-3.98 (m, 4H), 3.96-3.84 (m, 1H), 3.71-3.49 (m, 3H), 3.47-3.35 (m, 1H), 2.30-2.14 (m, 1H), 1.98-1.65 (m, 4H), 0.97-0.71 (m, 6H) | MS (ESI$^+$) m/z 450 [M + H]$^+$ |
| Example 117 | 1-[1-(2-fluorophenyl)-1H-indazol-4-yl]-3-[2-(2-isobutylpyrrolidin-1-yl)-2-oxoethyl]imidazolidin-2-one | $^1$H NMR (300 MHz, DMSO-$d_6$) δ ppm 8.41 (d, J = 0.7 Hz, 1H), 7.68 (td, J = 7.9, 1.5 Hz, 1H), 7.63-7.50 (m, 2H), 7.48-7.37 (m, 2H), 7.18 (d, J = 7.6 Hz, 1H), 7.08 (dd, J = 8.3, 3.0 Hz, 1H), 4.14-3.96 (m, 5H), 3.70-3.56 (m, 2H), 3.54-3.40 (m, 1H), 2.00-1.75 (m, 4H), 1.69-1.51 (m, 3H), 1.21-1.08 (m, 1H), 1.01-0.85 (m, 6H) | MS (ESI$^+$) m/z 464 [M + H]$^+$ |

| Example | Name | NMR | MS |
|---|---|---|---|
| Example 118 | 1-[1-(2-fluorophenyl)-1H-indazol-4-yl]-3-{2-[(2R)-2-methylpyrrolidin-1-yl]-2-oxoethyl}imidazolidin-2-one | $^1$H NMR (500 MHz, DMSO-d$_6$) δ ppm 8.20 (d, J = 4.6 Hz, 1H), 7.48 (td, J = 7.8, 1.5 Hz, 1H), 7.43-7.32 (m, 2H), 7.28-7.19 (m, 2H), 6.97 (d, J = 7.6 Hz, 1H), 6.88 (dd, J = 8.4, 2.9 Hz, 1H), 3.92-3.80 (m, 5H), 3.48-3.39 (m, 2H), 3.36-3.27 (m, 1H), 3.26-3.21 (m, 1H), 1.84-1.65 (m, 3H), 1.37-1.29 (m, 1H), 1.02-0.91 (m, 3H) | MS (ESI$^+$) m/z 422 [M + H]$^+$ |
| Example 119 | methyl 1-({3-[1-(2-fluorophenyl)-1H-indazol-4-yl]-2-oxoimidazolidin-1-yl}acetyl)-D-prolinate | $^1$H NMR (400 MHz, DMSO-d$_6$) δ ppm 8.41 (dd, J = 6.3, 0.7 Hz, 1H), 7.68 (td, J = 7.9, 1.5 Hz, 1H), 7.62-7.51 (m, 2H), 7.47-7.39 (m, 2H), 7.18 (d, J = 7.6 Hz, 1H), 7.09 (dd, J = 8.4, 2.9 Hz, 1H), 4.79 (dd, J = 8.5, 2.0 Hz, 0.2H), 4.37 (dd, J = 8.7, 4.4 Hz, 0.8H), 4.16 (s, 2H), 4.13-4.02 (m, 2H), 3.68-3.44 (m, 7H), 2.32-2.07 (m, 1H), 2.01-1.91 (m, 2H), 1.91-1.81 (m, 1H) | MS (ESI$^+$) m/z 466 [M + H]$^+$ |
| Example 120 | 1-({3-[1-(2-fluorophenyl)-1H-indazol-4-yl]-2-oxoimidazolidin-1-yl}acetyl)-N-phenyl-D-prolinamide | $^1$H NMR (300 MHz, DMSO-d$_6$) δ ppm 10.02 (s, 1H), 8.39 (d, J = 0.9 Hz, 1H), 7.68 (td, J = 7.9, 1.6 Hz, 1H), 7.63 (s, 3H), 7.50-7.37 (m, 2H), 7.30 (t, J = 7.9 Hz, 2H), 7.17 (d, J = 7.6 Hz, 1H), 7.13-6.98 (m, 2H), 4.48 (dd, J = 8.3, 3.7 Hz, 1H), 4.18 (d, J = 4.1 Hz, 1H), 4.07 (ddd, J = 15.5, 8.7, 4.8 Hz, 2H), 3.75-3.51 (m, 3H), 3.34 (s, 2H), 2.40-1.75 (m, 4H) | MS (ESI$^+$) m/z 527 [M + H]$^+$ |
| Example 121 | 1-{2-[(2R,4R)-2-(2,5-difluorophenyl)-4-hydroxypyrrolidin-1-yl]-2-oxoethyl}-3-[1-(2-fluorophenyl)-1H-indazol-4-yl]imidazolidin-2-one | $^1$H NMR (300 MHz, DMSO-d$_6$) δ ppm 8.36 (d, J = 0.8 Hz, 1H), 7.67 (td, J = 7.9, 1.5 Hz, 1H), 7.62-7.49 (m, 2H), 7.49-7.35 (m, 2H), 7.22-6.98 (m, 5H), 5.41-5.31 (m, 0.2H), 5.16 (dd, J = 9.3, 3.7 Hz, 0.8H), 5.04 (d, J = 3.2 Hz, 0.8H), 4.93 (d, J = 2.7 Hz, 0.2H), 4.49-4.32 (m, 1H), 4.22 (q, J = 17.0 Hz, 2H), 4.17-3.96 (m, 3H), 3.94-3.76 (m, 1H), 3.72-3.48 (m, 3H), 1.97-1.89 (m, 0.2H), 1.84-1.69 (m, 0.8H) | MS (ESI$^+$) m/z 536 [M + H]$^+$ |
| Example 122 | 1-{2-[(2R,4S)-2-(2,5-difluorophenyl)-4-hydroxypyrrolidin-1-yl]-2-oxoethyl}-3-[1-(2-fluorophenyl)-1H-indazol-4-yl]imidazolidin-2-one | $^1$H NMR (300 MHz, methanol-d$_4$) δ ppm 8.37 (dd, J = 6.3, 0.7 Hz, 1H), 7.61 (td, J = 7.6, 1.6 Hz, 1H), 7.57-7.50 (m, 1H), 7.47-7.35 (m, 3H), 7.26-6.90 (m, 5H), 5.43 (t, J = 7.6 Hz, 1H), 5.37 (t, J = 7.9 Hz, 1H), 4.58-4.49 (m, 1H), 4.49-4.43 (m, 1H), 4.27 (s, 1H), 4.16-3.89 (m, 4H), 3.81-3.56 (m, 3H), 2.63-2.52 (m, 1H), 2.50-2.39 (m, 1H), 2.21-2.09 (m, 1H), 2.06-1.94 (m, 1H). | MS (ESI$^+$) m/z 536 [M + H]$^+$ |
| Example 123 | 1-[1-(2-fluorophenyl)-1H-indazol-4-yl]-3-(2-hydroxy-4-methylpentyl)imidazolidin-2-one | $^1$H NMR (300 MHz, DMSO-d$_6$) δ ppm 8.42 (s, 1H), 7.67 (td, J = 7.8, 1.7 Hz, 1H), 7.63-7.49 (m, 2H), 7.47-7.35 (m, 2H), 7.16 (d, J = 7.6 Hz, 1H), 7.06 (dd, J = 8.4, 3.1 Hz, 1H), 4.71 (d, J = 5.6 Hz, 1H), 4.04 (dd, J = 9.0, 6.8 Hz, 2H), 3.85-3.71 (m, 1H), 3.67 (dd, J = 8.9, 6.7 Hz, 2H), 3.23-3.15 (m, 2H), 1.80 (dtt, J = 11.8, 8.7, 6.0 Hz, 1H), 1.40-1.16 (m, 1H), 0.90 (t, J = 6.8 Hz, 6H) | MS (ESI$^+$) m/z 397 [M + H]$^+$ |
| Example 124 | 1-[1-(2-fluorophenyl)-1H-indazol-4-yl]-3-{2-[(2R)-2-isopropylpiperidin-1-yl]-2-oxoethyl}imidazolidin-2-one | $^1$H NMR (300 MHz, DMSO-d$_6$) δ ppm 8.40 (d, J = 3.5 Hz, 1H), 7.67 (td, J = 7.8, 1.6 Hz, 1H), 7.64-7.50 (m, 2H), 7.48-7.36 (m, 2H), 7.17 (t, J = 7.5 Hz, 1H), 7.08 (dd, J = 8.4, 3.0 Hz, 1H), | MS (ESI$^+$) m/z 464 [M + H]$^+$ |

-continued

| Example | Name | NMR | MS |
|---|---|---|---|
| | | 4.40-3.99 (m, 6H), 3.73-3.43 (m, 3H), 1.83 (t, J = 13.4 Hz, 1H), 1.68-1.51 (m, 4H), 1.49-1.20 (m, 2H), 1.01-0.84 (m, 4H), 0.77 (d, J = 6.6 Hz, 2H. | |
| Example 125 | 1-[1-(2-fluorophenyl)-1H-indazol-4-yl]-3-{2-[(2S)-2-isopropylpyrrolidin-1-yl]-2-oxoethyl}imidazolidin-2-one | $^1$H NMR (300 MHz, DMSO-d$_6$) δ ppm 8.40 (t, J = 1.7 Hz, 1H), 7.68 (td, J = 7.9, 1.5 Hz, 1H), 7.64-7.50 (m, 2H), 7.48-7.37 (m, 2H), 7.22-7.14 (m, 1H), 7.08 (dd, J = 8.4, 3.0 Hz, 1H), 4.19-3.98 (m, 4H), 3.95-3.84 (m, 1H), 3.71-3.38 (m, 4H), 2.30-2.14 (m, 1H), 1.98-1.64 (m, 4H), 0.96-0.74 (m, 6H). | MS (ESI$^+$) m/z 450 [M + H]$^+$ |
| Example 126 | 1-[1-(2-fluorophenyl)-1H-indazol-4-yl]-3-{2-[(2R)-2-isopropylpyrrolidin-1-yl]-2-oxoethyl}imidazolidin-2-one | $^1$H NMR (300 MHz, DMSO-d$_6$) δ ppm 8.40 (t, J = 1.7 Hz, 1H), 7.68 (td, J = 7.9, 1.6 Hz, 1H), 7.63-7.49 (m, 2H), 7.49-7.37 (m, 2H), 7.18 (t, J = 6.4 Hz, 1H), 7.08 (dd, J = 8.4, 3.0 Hz, 1H), 4.19-3.99 (m, 4H), 3.95-3.83 (m, 1H), 3.71-3.38 (m, 4H), 2.30-2.15 (m, 1H), 1.95-1.66 (m, 4H), 0.97-0.73 (m, 6H) | MS (ESI$^+$) m/z 450 [M + H]$^+$ |
| Example 127 | 1-{2-[(2R,4R)-2-(2,5-difluorophenyl)-4-fluoropyrrolidin-1-yl]-2-oxoethyl}-3-[1-(2-fluorophenyl)-1H-indazol-4-yl]imidazolidin-2-one | $^1$H NMR (300 MHz, DMSO-d$_6$) δ ppm 8.37 (d, J = 0.9 Hz, 1H), 7.67 (td, J = 7.9, 1.5 Hz, 1H), 7.63-7.49 (m, 2H), 7.48-7.36 (m, 2H), 7.35-7.01 (m, 5H), 5.59-5.28 (m, 2H), 4.45-3.84 (m, 5H), 3.69-3.49 (m, 3H), 2.78-2.54 (m, 1H), 2.21-2.04 (m, 1H) | MS (ESI$^+$) m/z 538 [M + H]$^+$ |
| Example 128 | 1-[1-(2-fluorophenyl)-1H-indazol-4-yl]-3-{2-oxo-2-[(2R)-2-phenylpyrrolidin-1-yl]ethyl}imidazolidin-2-one | $^1$H NMR (500 MHz, DMSO-d$_6$) δ ppm 8.37 (dd, J = 6.4, 0.4 Hz, 1H), 7.67 (t, J = 7.8 Hz, 1H), 7.62-7.51 (m, 2H), 7.47-7.36 (m, 3H), 7.35-7.23 (m, 2H), 7.23-7.18 (m, 2H), 7.14 (dd, J = 13.0, 7.6 Hz, 1H), 7.09-7.02 (m, 1H), 5.22-5.07 (m, 1H), 4.21 (q, J = 17.0 Hz, 1H), 4.14-3.78 (m, 3H), 3.74-3.60 (m, 2H), 3.60-3.48 (m, 1H), 3.46-3.37 (m, 1H), 2.45-2.19 (m, 1H), 1.98-1.69 (m, 3H) | MS (ESI$^+$) m/z 484 [M + H]$^+$ |
| Example 129 | 1-[1-(2-fluorophenyl)-1H-indazol-4-yl]-3-[2-oxo-2-(2-phenylpyrrolidin-1-yl)ethyl]imidazolidin-2-one | $^1$H NMR (500 MHz, methanol-d$_4$) δ ppm 8.38 (s, 1H), 7.60 (t, J = 7.7 Hz, 1H), 7.57-7.50 (m, 1H), 7.46-7.35 (m, 4H), 7.34-7.17 (m, 4H), 7.15-6.99 (m, 2H), 5.25-5.11 (m, 1H), 4.28 (d, J = 4.0 Hz, 1H), 4.15 (d, J = 17.0 Hz, 0.5H), 4.07 (t, J = 7.9 Hz, 1H), 4.03-3.84 (m, 1.5H), 3.84-3.41 (m, 4H), 2.54-2.27 (m, 1H), 2.06-1.82 (m, 3H) | MS (ESI$^+$) m/z 484 [M + H]$^+$ |
| Example 130 | 1-[1-(2-fluorophenyl)-1H-indazol-4-yl]-3-(pyridin-2-yl)imidazolidin-2-one | $^1$H NMR (300 MHz, DMSO-d$_6$) δ ppm 8.45 (d, J = 1.0 Hz, 1H), 8.39 (ddd, J = 4.8, 2.0, 0.9 Hz, 1H), 8.27 (dd, J = 8.5, 1.0 Hz, 1H), 7.81 (ddd, J = 8.8, 7.2, 2.0 Hz, 1H), 7.70 (td, J = 7.8, 1.6 Hz, 1H), 7.65-7.54 (m, 2H), 7.54-7.41 (m, 2H), 7.26 (d, J = 7.5 Hz, 1H), 7.20 (dd, J = 8.4, 3.0 Hz, 1H), 7.09 (ddd, J = 7.3, 4.9, 1.0 Hz, 1H), 4.21 (s, 4H) | MS (ESI$^+$) m/z 374 [M + H]$^+$ |
| Example 131 | cyclohexyl 3-[1-(2-fluorophenyl)-1H-indazol-4-yl]-2-oxoimidazolidine-1-carboxylate | $^1$H NMR (300 MHz, DMSO-d$_6$) δ ppm 8.39 (d, J = 0.9 Hz, 1H), 7.69 (td, J = 7.8, 1.7 Hz, 1H), 7.64-7.52 (m, 2H), 7.52-7.40 (m, 2H), 7.22 (dd, J = 8.2, 3.0 Hz, 2H), 4.88-4.72 (m, 1H), 4.13-3.92 (m, 4H), 1.90-1.63 (m, 4H), 1.62-1.31 (m, 6H) | MS (ESI$^+$) m/z 423 [M + H]$^+$ |

-continued

| Example | Name | NMR | MS |
|---|---|---|---|
| Example 132 | 1-[1-(2-fluorophenyl)-1H-indazol-4-yl]-3-(6-methyl-2-oxoheptyl)imidazolidin-2-one | $^1$H NMR (400 MHz, methanol-$d_4$) δ ppm 8.38 (d, J = 0.6 Hz, 1H), 7.62 (td, J = 7.7, 1.5 Hz, 1H), 7.59-7.51 (m, 1H), 7.48-7.37 (m, 3H), 7.14 (dd, J = 8.5, 2.8 Hz, 1H), 7.11 (d, J = 7.5 Hz, 1H), 4.22 (s, 2H), 4.12 (dd, J = 8.8, 7.1 Hz, 2H), 3.68 (dd, J = 8.7, 7.1 Hz, 2H), 2.52 (t, J = 7.4 Hz, 2H), 1.71-1.61 (m, 2H), 1.61-1.52 (m, 1H), 1.30-1.18 (m, 2H), 0.92 (d, J = 6.6 Hz, 6H) | MS (ESI$^+$) m/z 423 [M + H]$^+$ |
| Example 133 | 1-[1-(2-fluorophenyl)-1H-indazol-4-yl]-3-(2-hydroxy-6-methylheptyl)imidazolidin-2-one | $^1$H NMR (400 MHz, methanol-$d_4$) δ ppm 8.40 (d, J = 0.4 Hz, 1H), 7.61 (td, J = 7.7, 1.5 Hz, 1H), 7.58-7.51 (m, 1H), 7.47-7.37 (m, 3H), 7.17-7.05 (m, 2H), 4.15-4.02 (m, 2H), 3.90-3.81 (m, 1H), 3.81-3.73 (m, 2H), 3.42-3.24 (m, 2H), 1.66-1.51 (m, 3H), 1.50-1.37 (m, 2H), 1.34-1.16 (m, 2H), 0.91 (d, J = 6.6 Hz, 6H) | MS (ESI$^+$) m/z 425 [M + H]$^+$ |
| Example 134 | 1-(3-cyclopentyl-2-oxopropyl)-3-[1-(2-fluorophenyl)-1H-indazol-4-yl]imidazolidin-2-one | $^1$H NMR (400 MHz, methanol-$d_4$) δ ppm 8.38 (s, 1H), 7.62 (td, J = 7.7, 1.5 Hz, 1H), 7.59-7.51 (m, 1H), 7.48-7.36 (m, 3H), 7.14 (dd, J = 8.5, 2.8 Hz, 1H), 7.11 (d, J = 7.5 Hz, 1H), 4.22 (s, 2H), 4.12 (dd, J = 8.8, 7.0 Hz, 2H), 3.74-3.63 (m, 2H), 2.56 (d, J = 7.2 Hz, 2H), 2.37-2.22 (m, 1H), 1.95-1.82 (m, 2H), 1.75-1.62 (m, 2H), 1.63-1.52 (m, 2H), 1.25-1.11 (m, 2H) | MS (ESI$^+$) m/z 421 [M + H]$^+$ |
| Example 135 | 1-(3-cyclopentyl-2-hydroxypropyl)-3-[1-(2-fluorophenyl)-1H-indazol-4-yl]imidazolidin-2-one | $^1$H NMR (400 MHz, methanol-$d_4$) δ ppm 8.39 (s, 1H), 7.61 (td, J = 7.7, 1.6 Hz, 1H), 7.59-7.51 (m, 1H), 7.47-7.37 (m, 3H), 7.15-7.07 (m, 2H), 4.14-4.03 (m, 2H), 3.93-3.86 (m, 1H), 3.83-3.72 (m, 2H), 3.39 (dd, J = 14.2, 3.7 Hz, 1H), 3.29-3.24 (m, 1H), 2.15-2.01 (m, 1H), 1.93-1.82 (m, 2H), 1.72-1.62 (m, 2H), 1.62-1.54 (m, 3H), 1.53-1.45 (m, 1H), 1.26-1.08 (m, 2H) | MS (ESI$^+$) m/z 423 [M + H]$^+$ |
| Example 136 | 1-(3-cyclohexyl-2-oxopropyl)-3-[1-(2-fluorophenyl)-1H-indazol-4-yl]imidazolidin-2-one | $^1$H NMR (400 MHz, methanol-$d_4$) δ ppm 8.37 (s, 1H), 7.62 (td, J = 7.7, 1.5 Hz, 1H), 7.58-7.51 (m, 1H), 7.48-7.37 (m, 3H), 7.14 (dd, J = 8.5, 2.8 Hz, 1H), 7.11 (d, J = 7.6 Hz, 1H), 4.20 (s, 2H), 4.15-4.09 (m, 2H), 3.72-3.62 (m, 2H), 2.40 (d, J = 6.9 Hz, 2H), 1.96-1.84 (m, 1H), 1.80-1.63 (m, 5H), 1.42-1.26 (m, 2H), 1.26-1.14 (m, 1H), 1.08-0.95 (m, 2H) | MS (ESI$^+$) m/z 435 [M + H]$^+$ |
| Example 137 | cyclopentyl 2-[1-(2-fluorophenyl)-1H-indazol-4-yl]-3-oxohexahydroimidazo[1,5-a]pyrazine-7(1H)-carboxylate | $^1$H NMR (300 MHz, DMSO-$d_6$) δ ppm 8.46 (d, J = 0.9 Hz, 1H), 7.67 (td, J = 7.8, 1.7 Hz, 1H), 7.62-7.50 (m, 2H), 7.48-7.35 (m, 2H), 7.23 (d, J = 7.6 Hz, 1H), 7.09 (dd, J = 8.3, 3.0 Hz, 1H), 5.09-4.98 (m, 1H), 4.25-4.11 (m, 2H), 4.01 (dd, J = 13.4, 6.3 Hz, 1H), 3.80 (ddd, J = 10.5, 8.6, 5.0 Hz, 3H), 3.02-2.78 (m, 3H), 1.91-1.74 (m, 2H), 1.74-1.51 (m, 6H) | MS (ESI$^+$) m/z 464 [M + H]$^+$ |

-continued

| Example | Name | NMR | MS |
|---|---|---|---|
| Example 138 | 1-[1-(2-fluorophenyl)-1H-indazol-4-yl]-3-(pyrimidin-5-yl)imidazolidin-2-one | $^1$H NMR (300 MHz, DMSO-d$_6$) δ ppm 9.15 (s, 2H), 8.92 (s, 1H), 8.47 (d, J = 0.9 Hz, 1H), 7.70 (td, J = 7.8, 1.6 Hz, 1H), 7.65-7.42 (m, 4H), 7.28 (d, J = 7.5 Hz, 1H), 7.21 (dd, J = 8.4, 3.0 Hz, 1H), 4.38-4.10 (m, 4H) | MS (ESI$^+$) m/z 375 [M + H]$^+$ |
| Example 139 | 1-(3-cyclohexyl-2-hydroxypropyl)-3-[1-(2-fluorophenyl)-1H-indazol-4-yl]imidazolidin-2-one | $^1$H NMR (400 MHz, methanol-d$_4$) δ ppm 8.39 (s, 1H), 7.61 (td, J = 7.6, 1.3 Hz, 1H), 7.58-7.51 (m, 1H), 7.42 (dt, J = 7.5, 5.6 Hz, 3H), 7.14-7.10 (m, 1H), 7.10 (d, J = 7.6 Hz, 1H), 4.14-4.03 (m, 2H), 4.03-3.92 (m, 1H), 3.85-3.71 (m, 2H), 3.36 (dd, J = 14.2, 3.8 Hz, 1H), 3.26 (dd, J = 14.2, 7.8 Hz, 1H), 1.87 (d, J = 12.4 Hz, 1H), 1.81-1.63 (m, 4H), 1.65-1.51 (m, 1H), 1.48-1.34 (m, 2H), 1.34-1.14 (m, 3H), 1.09-0.97 (m, 1H), 0.97-0.85 (m, 1H) | MS (ESI$^+$) m/z 437 [M + H]$^+$ |
| Example 140 | 1-(3-cyclobutyl-2-oxopropyl)-3-[1-(2-fluorophenyl)-1H-indazol-4-yl]imidazolidin-2-one | $^1$H NMR (400 MHz, methanol-d$_4$) δ ppm 8.43 (s, 1H), 7.62 (td, J = 7.7, 1.5 Hz, 1H), 7.58-7.51 (m, 1H), 7.48-7.37 (m, 3H), 7.17-7.07 (m, 2H), 4.24 (s, 2H), 4.16-4.09 (m, 2H), 3.78-3.70 (m, 2H), 3.44 (q, J = 7.1 Hz, 4H), 1.27 (t, J = 7.2 Hz, 3H), 1.17 (t, J = 7.1 Hz, 3H) | MS (ESI$^+$) m/z 407 [M + H]$^+$ |
| Example 141 | 1-(3-cyclobutyl-2-hydroxypropyl)-3-[1-(2-fluorophenyl)-1H-indazol-4-yl]imidazolidin-2-one | $^1$H NMR (400 MHz, methanol-d$_4$) δ ppm 8.39 (s, 1H), 7.61 (td, J = 7.7, 1.5 Hz, 1H), 7.58-7.51 (m, 1H), 7.46-7.37 (m, 3H), 7.14-7.06 (m, 2H), 4.14-4.00 (m, 2H), 3.84-3.69 (m, 3H), 3.38-3.32 (m, 1H), 3.30-3.21 (m, 2H), 2.65-2.49 (m, 1H), 2.19-2.05 (m, 2H), 1.99-1.77 (m, 2H), 1.77-1.65 (m, 2H), 1.61 (t, J = 7.0 Hz, 2H) | MS (ESI$^+$) m/z 409 [M + H]$^+$ |
| Example 142 | 1-[3-(bicyclo[2.2.1]hept-2-yl)-2-oxopropyl]-3-[1-(2-fluorophenyl)-1H-indazol-4-yl]imidazolidin-2-one | $^1$H NMR (400 MHz, methanol-d$_4$) δ ppm 8.37 (d, J = 0.8 Hz, 1H), 7.62 (td, J = 7.6, 1.5 Hz, 1H), 7.58-7.51 (m, 1H), 7.48-7.37 (m, 3H), 7.14 (dd, J = 8.5, 2.9 Hz, 1H), 7.11 (d, J = 7.4 Hz, 1H), 4.21 (d, J = 11.7 Hz, 2H), 4.14-4.07 (m, 2H), 3.72-3.62 (m, 2H), 2.57 (dd, J = 7.5, 4.5 Hz, 2H), 2.36-2.25 (m, 1H), 2.25-2.15 (m, 2H), 1.94-1.83 (m, 1H), 1.62-1.49 (m, 2H), 1.46-1.31 (m, 2H), 1.31-1.05 (m, 2H), 0.70 (ddd, J = 12.3, 5.2, 2.4 Hz, 1H) | MS (ESI$^+$) m/z 447 [M + H]$^+$ |
| Example 143 | 1-[1-(2-fluorophenyl)-1H-indazol-4-yl]-3-(2-oxo-2-phenylethyl)imidazolidin-2-one | $^1$H NMR (300 MHz, methanol-d$_4$) δ ppm 8.41 (d, J = 0.9 Hz, 1H), 8.14-8.05 (m, 2H), 7.72-7.50 (m, 5H), 7.50-7.36 (m, 3H), 7.19-7.11 (m, 2H), 4.90 (s, 2H), 4.18 (dd, J = 9.0, 6.8 Hz, 2H), 3.78 (dd, J = 9.0, 6.9 Hz, 2H) | MS (ESI$^+$) m/z 415 [M + H]$^+$ |
| Example 144 | 1-(2-cyclopentyl-2-oxoethyl)-3-[1-(2-fluorophenyl)-1H-indazol-4-yl]imidazolidin-2-one | $^1$H NMR (400 MHz, methanol-d$_4$) δ ppm 8.37 (s, 1H), 7.62 (td, J = 7.9, 1.5 Hz, 1H), 7.59-7.52 (m, 1H), 7.48-7.38 (m, 3H), 7.17-7.10 (m, 2H), 4.29 (s, 2H), 4.15-4.10 (m, 2H), 3.71-3.66 (m, 2H), 3.10-3.01 (m, 1H), 1.88-1.79 (m, 4H), 1.73-1.62 (m, 4H) | MS (ESI$^+$) m/z 407 [M + H]$^+$ |
| Example 145 | 1-[1-(2-fluorophenyl)-1H-indazol-4-yl]-3-(2-oxopropyl)imidazolidin-2-one | $^1$H NMR (400 MHz, methanol-d$_4$) δ ppm 8.37 (s, 1H), 7.61 (td, J = 7.7, 1.2 Hz, 1H), 7.59-7.51 (m, 1H), 7.48-7.37 (m, 3H), 7.14 (dd, J = 8.5, 2.7 Hz, 1H), 7.11 (d, J = 7.6 Hz, 1H), 4.24 (s, 2H), | MS (ESI$^+$) m/z 353 [M + H]$^+$ |

-continued

| Example | Name | NMR | MS |
|---|---|---|---|
| | | 4.16-4.09 (m, 2H), 3.74-3.62 (m, 2H), 2.21 (s, 3H) | |
| Example 146 | 1-[1-(2-fluorophenyl)-1H-indazol-4-yl]-3-(2-hydroxy-2-methylhex-5-en-1-yl)imidazolidin-2-one | $^1$H NMR (400 MHz, methanol-d$_4$) δ ppm 8.37 (s, 1H), 7.61 (td, J = 7.7, 1.5 Hz, 1H), 7.58-7.52 (m, 1H), 7.47-7.36 (m, 3H), 7.16-7.06 (m, 2H), 5.88 (ddt, J = 16.8, 10.2, 6.5 Hz, 1H), 5.10-5.02 (m, 1H), 4.95 (d, J = 10.2 Hz, 1H), 4.11-4.04 (m, 2H), 3.90-3.78 (m, 2H), 3.37-3.31 (m, 2H), 2.30-2.14 (m, 2H), 1.69-1.58 (m, 2H), 1.24 (s, 3H) | MS (ESI$^+$) m/z 409 [M + H]$^+$ |
| Example 147 | 1-[1-(2-fluorophenyl)-1H-indazol-4-yl]-3-[2-(6-fluoropyridin-3-yl)-2-oxoethyl]imidazolidin-2-one | $^1$H NMR (400 MHz, methanol-d$_4$) δ ppm 8.95 (d, J = 2.5 Hz, 1H), 8.58 (ddd, J = 8.7, 7.7, 2.5 Hz, 1H), 8.40 (s, 1H), 7.62 (td, J = 7.7, 1.6 Hz, 1H), 7.59-7.51 (m, 1H), 7.51-7.35 (m, 3H), 7.25 (dd, J = 8.7, 2.5 Hz, 1H), 7.20-7.12 (m, 2H), 4.89 (s, 2H), 4.18 (dd, J = 8.9, 6.8 Hz, 2H), 3.78 (dd, J = 8.9, 6.9 Hz, 2H) | MS (ESI$^+$) m/z 434 [M + H]$^+$ |
| Example 148 | 1-(2-ethyl-2-hydroxy-4-methylpentyl)-3-[1-(2-fluorophenyl)-1H-indazol-4-yl]imidazolidin-2-one | $^1$H NMR (400 MHz, methanol-d$_4$) δ ppm 8.37 (s, 1H), 7.62 (td, J = 7.7, 1.5 Hz, 1H), 7.59-7.51 (m, 1H), 7.48-7.38 (m, 3H), 7.15-7.09 (m, 2H), 4.11-4.03 (m, 2H), 3.88 (td, J = 8.9, 6.4 Hz, 1H), 3.77 (q, J = 8.6 Hz, 1H), 3.44 (d, J = 14.3 Hz, 1H), 3.23 (d, J = 14.3 Hz, 1H), 1.94-1.83 (m, 1H), 1.65 (q, J = 7.5 Hz, 2H), 1.46 (qd, J = 14.5, 5.9 Hz, 2H), 1.05-0.94 (m, 9H) | MS (ESI$^+$) m/z 425 [M + H]$^+$ |
| Example 149 | 1-[1-(2-fluorophenyl)-1H-indazol-4-yl]-3-[2-(3-methoxyphenyl)-2-oxoethyl]imidazolidin-2-one | $^1$H NMR (400 MHz, DMSO-d$_6$) δ ppm 8.40 (s, 1H), 7.71-7.42 (m, 8H), 7.29 (dd, J = 8.3, 2.5 Hz, 1H), 7.19 (d, J = 7.7 Hz, 1H), 7.12 (dd, J = 8.4, 2.9 Hz, 1H), 4.86 (s, 2H), 4.14 (dd, J = 8.8, 6.7 Hz, 2H), 3.85 (s, 3H), 3.67 (dd, J = 8.8, 6.7 Hz, 2H) | MS (ESI$^+$) m/z 445 [M + H]$^+$ |
| Example 150 | 1-[1-(2-fluorophenyl)-1H-indazol-4-yl]-3-[2-(3-fluorophenyl)-2-oxoethyl]imidazolidin-2-one | $^1$H NMR (400 MHz, DMSO-d$_6$) δ ppm 8.39 (s, 1H), 7.92 (d, J = 7.7 Hz, 1H), 7.83 (dt, J = 9.8, 2.0 Hz, 1H), 7.71-7.64 (m, 2H), 7.64-7.51 (m, 3H), 7.50-7.43 (m, 2H), 7.20 (d, J = 7.6 Hz, 1H), 7.12 (dd, J = 8.4, 2.9 Hz, 1H), 4.87 (s, 2H), 4.15 (dd, J = 8.9, 6.8 Hz, 2H), 3.67 (dd, J = 8.8, 6.8 Hz, 2H) | MS (ESI$^+$) m/z 433 [M + H]$^+$ |
| Example 151 | 1-[1-(2-fluorophenyl)-1H-indazol-4-yl]-3-{2-oxo-2-[4-(trifluoromethyl)phenyl]ethyl}imidazolidin-2-one | $^1$H NMR (400 MHz, DMSO-d$_6$) δ ppm 8.39 (s, 1H), 8.26 (d, J = 8.2 Hz, 2H), 7.97 (d, J = 8.2 Hz, 2H), 7.67 (td, J = 8.5, 1.9 Hz, 1H), 7.64-7.50 (m, 2H), 7.50-7.42 (m, 2H), 7.20 (d, J = 7.7 Hz, 1H), 7.14-7.09 (m, 1H), 4.92 (s, 2H), 4.16 (t, J = 7.8 Hz, 2H), 3.69-3.66 (m, 2H) | MS (ESI$^+$) m/z 483 [M + H]$^+$ |
| Example 152 | 1-[1-(2-fluorophenyl)-1H-indazol-4-yl]-3-[2-oxo-2-(pyridin-3-yl)ethyl]imidazolidin-2-one | $^1$H NMR (400 MHz, DMSO-d$_6$) δ ppm 9.21 (d, J = 2.1 Hz, 1H), 8.85 (dd, J = 4.9, 1.6 Hz, 1H), 8.42 (t, J = 2.0 Hz, 1H), 8.40 (s, 1H), 7.71-7.62 (m, 2H), 7.62-7.52 (m, 2H), 7.51-7.42 (m, 2H), 7.20 (d, J = 7.6 Hz, 1H), 7.12 (dd, J = 8.5, 2.9 Hz, 1H), 4.91 (s, 2H), 4.15 (dd, J = 8.9, 6.7 Hz, 2H), 3.68 (dd, J = 8.9, 6.9 Hz, 2H) | MS (ESI$^+$) m/z 416 [M + H]$^+$ |
| Example 153 | 1-[2-(1,3-benzodioxol-5-yl)-2-oxoethyl]-3-[1-(2-fluorophenyl)-1H-indazol-4-yl]imidazolidin-2-one | $^1$H NMR (400 MHz, DMSO-d$_6$) δ ppm 8.39 (s, 1H), 7.72 (dd, J = 8.3, 1.7 Hz, 1H), 7.67 (td, J = 7.7, 1.5 Hz, 1H), 7.64-7.51 (m, 3H), | MS (ESI$^+$) m/z 459 [M + H]$^+$ |

| Example | Name | NMR | MS |
|---|---|---|---|
| | | 7.50-7.43 (m, 2H), 7.19 (d, J = 7.6 Hz, 1H), 7.15-7.08 (m, 2H), 6.16 (s, 2H), 4.78 (s, 2H), 4.13 (dd, J = 8.9, 6.8 Hz, 2H), 3.65 (dd, J = 8.7, 6.9 Hz, 2H) | |
| Example 154 | 1-[1-(2-fluorophenyl)-1H-indazol-4-yl]-3-(4-fluoropyridin-3-yl)imidazolidin-2-one | $^1$H NMR (400 MHz, DMSO-d$_6$) δ ppm 8.90 (d, J = 10.3 Hz, 1H), 8.51 (dd, J = 7.4, 5.5 Hz, 1H), 8.46 (d, J = 0.9 Hz, 1H), 7.69 (td, J = 7.9, 1.6 Hz, 1H), 7.64-7.53 (m, 2H), 7.50 (dd, J = 6.6, 4.6 Hz, 1H), 7.48-7.38 (m, 2H), 7.26 (d, J = 7.5 Hz, 1H), 7.18 (dd, J = 8.4, 3.0 Hz, 1H), 4.32-4.24 (m, 2H), 4.15-4.08 (m, 2H) | MS (ESI$^+$) m/z 392 [M + H]$^+$ |
| Example 155 | 1-[1-(2-fluorophenyl)-1H-indazol-4-yl]-3-[(2R)-2-hydroxy-4-methylpentyl]imidazolidin-2-one | $^1$H NMR (500 MHz, CDCl$_3$) δ ppm 8.40 (d, J = 0.9 Hz, 1H), 7.60 (td, J = 7.8, 1.8 Hz, 1H), 7.47-7.39 (m, 1H), 7.39-7.33 (m, 1H), 7.33-7.27 (m, 2H), 7.13 (dd, J = 8.4, 3.2 Hz, 1H), 7.05 (d, J = 7.6 Hz, 1H), 4.06 (ddd, J = 8.3, 7.1, 1.5 Hz, 2H), 3.99 (ddt, J = 8.7, 7.0, 4.0 Hz, 1H), 3.79-3.65 (m, 2H), 3.43-3.30 (m, 2H), 2.40-1.80 (br s, 1H), 1.85 (dtt, J = 12.2, 8.8, 6.1 Hz, 1H), 1.50 (ddd, J = 14.3, 9.0, 5.5 Hz, 1H), 1.30 (ddd, J = 13A, 8.6, 4.3 Hz, 1H), 0.96 (dd, J = 8.8, 6.6 Hz, 6H). | MS (APCI) m/z 397 (M + H)$^+$ |
| Example 156 | 1-[1-(2-fluorophenyl)-1H-indazol-4-yl]-3-[(2S)-2-hydroxy-4-methylpentyl]imidazolidin-2-one | $^1$H NMR (300 MHz, CDCl$_3$) δ ppm 8.40 (d, J = 1.0 Hz, 1H), 7.61 (td, J = 7.7, 1.9 Hz, 1H), 7.48-7.27 (m, 4H), 7.14 (dd, J = 8.4, 3.4 Hz, 1H), 7.06 (d, J = 7.6 Hz, 1H), 4.16-3.92 (m, 3H), 3.83-3.66 (m, 2H), 3.43-3.31 (m, 2H), 1.85 (dd, J = 14.1, 7.0 Hz, 1H), 1.54-1.43 (m, 1H), 1.37-1.17 (m, 2H), 0.97 (dd, J = 6.6, 5.3 Hz, 6H). | MS (APCI) m/z 397 (M + H)$^+$ |
| Example 157 | 1-[1-(2-fluorophenyl)-1H-indazol-4-yl]-3-[2-oxo-3-(tetrahydrofuran-3-yl)propyl]imidazolidin-2-one | $^1$H NMR (400 MHz, methanol-d$_4$) δ ppm 8.37 (d, J = 0.9 Hz, 1H), 7.62 (td, J = 7.7, 1.6 Hz, 1H), 7.59-7.51 (m, 1H), 7.48-7.37 (m, 3H), 7.14 (dd, J = 8.5, 2.9 Hz, 1H), 7.11 (d, J = 7.5 Hz, 1H), 4.22 (s, 2H), 4.15-4.09 (m, 2H), 4.00-3.95 (m, 1H), 3.85 (td, J = 8.2, 5.1 Hz, 1H), 3.79-3.72 (m, 1H), 3.72-3.66 (m, 2H), 3.40-3.35 (m, 1H), 2.79-2.58 (m, 3H), 2.21-2.12 (m, 1H), 1.64-1.54 (m, 1H) | MS (ESI$^+$) m/z 423 [M + H]$^+$ |
| Example 158 | 1-[1-(2-fluorophenyl)-1H-indazol-4-yl]-3-(1,3-thiazol-5-yl)imidazolidin-2-one | $^1$H NMR (500 MHz,, DMSO-d$_6$) δ ppm 8.66 (s, 1H), 8.47 (d, J = 0.4 Hz, 1H), 7.70 (td, J = 7.8, 1.5 Hz, 1H), 7.64-7.52 (m, 3H), 7.51-7.42 (m, 2H), 7.31 (d, J = 7.5 Hz, 1H), 7.19 (dd, J = 8.4, 2.8 Hz, 1H), 4.35 (dd, J = 9.3, 6.6 Hz, 2H), 4.13 (dd, J = 9.2, 6.7 Hz, 2H) | MS (ESI$^+$) m/z 380 [M + H]$^+$ |
| Example 159 | 1-[1-(2-fluorophenyl)-1H-indazol-4-yl]-3-[(2S)-1-hydroxybutan-2-yl]imidazolidin-2-one | $^1$H NMR (400 MHz, CDCl$_3$) δ ppm 8.40 (d, J = 0.9 Hz, 1H), 7.60 (td, J = 7.7, 1.8 Hz, 1H), 7.46-7.27 (m, 4H), 7.14 (dd, J = 8.5, 3.3 Hz, 1H), 7.06 (d, J = 7.6 Hz, 1H), 4.08 (t, J = 7.8 Hz, 2H), 3.84 (s, 1H), 3.80-3.66 (m, 2H), 3.52-3.31 (m, 2H), 2.81 (s, 1H), 1.62-1.52 (m, 2H), 1.03 (t, J = 7.4 Hz, 3H). | MS (ESI$^+$) m/z 369 (M + H)$^+$ |

| Example | Name | NMR | MS |
|---|---|---|---|
| Example 160 | 1-[1-(2-fluorophenyl)-1H-indazol-4-yl]-3-[(2R)-2-hydroxybutyl]imidazolidin-2-one | $^1$H NMR (400 MHz, methanol-$d_4$) δ ppm 8.32 (d, J = 0.9 Hz, 1H), 7.63-7.46 (m, 2H), 7.44-7.32 (m, 2H), 7.29-7.19 (m, 1H), 6.56 (dd, J = 8.4, 2.7 Hz, 1H), 6.36 (d, J = 7.7 Hz, 1H), 4.45 (dtd, J = 8.5, 6.8, 5.7 Hz, 1H), 3.77 (t, J = 8.7 Hz, 1H), 3.60-3.47 (m, 5H), 1.79-1.49 (m, 3H), 0.92 (t, J = 7.4 Hz, 3H). | MS (ESI$^+$) m/z 369 (M + H)$^+$ |
| Example 161 | 1-(3,3-dimethyl-2-oxobutyl)-3-[1-(2-fluorophenyl)-1H-indazol-4-yl]imidazolidin-2-one | $^1$H NMR (400 MHz, methanol-$d_4$) δ ppm 8.38 (d, J = 0.8 Hz, 1H), 7.62 (td, J = 7.7, 1.6 Hz, 1H), 7.59-7.51 (m, 1H), 7.48-7.37 (m, 3H), 7.14 (dd, J = 8.5, 2.9 Hz, 1H), 7.10 (d, J = 7.6 Hz, 1H), 4.41 (s, 2H), 4.15-4.07 (m, 2H), 3.69-3.59 (m, 2H), 1.25 (s, 9H) | MS (ESI$^+$) m/z 395 [M + H]$^+$ |
| Example 162 | 1-[1-(2-fluorophenyl)-1H-indazol-4-yl]-3-(3-methyl-2-oxobutyl)imidazolidin-2-one | $^1$H NMR (400 MHz, methanol-$d_4$) δ ppm 8.37 (d, J = 0.9 Hz, 1H), 7.62 (td, J = 7.7, 1.6 Hz, 1H), 7.59-7.52 (m, 1H), 7.48-7.37 (m, 3H), 7.14 (dd, J = 8.5, 2.9 Hz, 1H), 7.11 (d, J = 7.4 Hz, 1H), 4.31 (s, 2H), 4.15-4.09 (m, 2H), 3.71-3.61 (m, 2H), 2.87-2.70 (m, 1H), 1.17 (dd, J = 7.0, 2.1 Hz, 6H) | MS (ESI$^+$) m/z 381 [M + H]$^+$ |
| Example 163 | 1-[1-(2-fluorophenyl)-1H-indazol-4-yl]-3-(2-hydroxy-3-methylbutyl)imidazolidin-2-one | $^1$H NMR (400 MHz, methanol-$d_4$) δ ppm 8.40 (d, J = 0.9 Hz, 1H), 7.61 (td, J = 7.7, 1.7 Hz, 1H), 7.59-7.52 (m, 1H), 7.47-7.37 (m, 3H), 7.14-7.07 (m, 2H), 4.14-3.99 (m, 2H), 3.85-3.69 (m, 2H), 3.66-3.57 (m, 1H), 3.47 (dd, J = 14.1, 3.4 Hz, 1H), 3.36-3.31 (m, 1H), 1.85-1.69 (m, 1H), 1.01 (dd, J = 6.8, 2.0 Hz, 6H) | MS (ESI$^+$) m/z 383 [M + H]$^+$ |
| Example 164 | 1-(2-cyclobutyl-2-oxoethyl)-3-[1-(2-fluorophenyl)-1H-indazol-4-yl]imidazolidin-2-one | $^1$H NMR (500 MHz, methanol-$d_4$) δ ppm 8.38 (d, J = 0.8 Hz, 1H), 7.62 (td, J = 7.7, 1.6 Hz, 1H), 7.58-7.52 (m, 1H), 7.48-7.38 (m, 3H), 7.14 (dd, J = 8.5, 2.8 Hz, 1H), 7.11 (d, J = 7.5 Hz, 1H), 4.18 (s, 2H), 4.15-4.10 (m, 2H), 3.71-3.64 (m, 2H), 3.52-3.43 (m, 1H), 2.37-2.28 (m, 2H), 2.27-2.19 (m, 2H), 2.12-2.00 (m, 1H), 1.94-1.83 (m, 1H) | MS (ESI$^+$) m/z 393 [M + H]$^+$ |
| Example 165 | 1-(2-cyclobutyl-2-hydroxyethyl)-3-[1-(2-fluorophenyl)-1H-indazol-4-yl]imidazolidin-2-one | $^1$H NMR (400 MHz, methanol-$d_4$) δ ppm 8.46-8.36 (m, 1H), 7.65-7.58 (m, 1H), 7.58-7.52 (m, 1H), 7.46-7.37 (m, 3H), 7.16-7.07 (m, 2H), 4.14-4.01 (m, 2H), 3.84-3.69 (m, 3H), 3.36-3.31 (m, 1H), 3.20 (dd, J = 14.3, 8.0 Hz, 1H), 2.52-2.38 (m, 1H), 2.13-1.78 (m, 6H) | MS (DCI) m/z 395 [M + H]$^+$ |
| Example 166 | 1-(2-cyclobutyl-1-hydroxy-2-oxoethyl)-3-[1-(2-fluorophenyl)-1H-indazol-4-yl]imidazolidin-2-one | $^1$H NMR (500 MHz, methanol-$d_4$) δ ppm 8.40 (d, J = 0.6 Hz, 1H), 7.66-7.59 (m, 1H), 7.59-7.54 (m, 1H), 7.49-7.38 (m, 3H), 7.17 (dd, J = 8.5, 2.8 Hz, 1H), 7.13 (d, J = 7.5 Hz, 1H), 5.74 (s, 1H), 4.14-4.05 (m, 2H), 3.77-3.68 (m, 2H), 3.44 (td, J = 8.9, 5.7 Hz, 1H), 2.42-2.28 (m, 2H), 2.27-2.17 (m, 2H), 2.12-2.02 (m, 1H), 1.91-1.83 (m, 1H) | MS (ESI$^+$) m/z 409 [M + H]$^+$ |
| Example 167 | 1-[1-(2-fluorophenyl)-1H-indazol-4-yl]-3-[(2R)-2-hydroxy-2,4-dimethylpentyl]imidazolidin-2-one | $^1$H NMR (400 MHz, methanol-$d_4$) δ ppm 8.37 (d, J = 0.7 Hz, 1H), 7.61 (td, J = 7.7, 1.6 Hz, 1H), 7.58-7.52 (m, 1H), 7.47-7.37 (m, 3H), 7.14-7.08 (m, 2H), 4.14-4.02 (m, 2H), 3.94-3.86 (m, 1H), 3.82-3.73 (m, 1H), | MS (ESI$^+$) m/z 411 [M + H]$^+$ |

| Example | Name | NMR | MS |
|---------|------|-----|-----|
| | | 3.40 (d, J = 14.2 Hz, 1H), 3.20 (d, J = 14.2 Hz, 1H), 1.97-1.85 (m, 1H), 1.47 (d, J = 5.8 Hz, 2H), 1.26 (s, 3H), 1.01 (dd, J = 9.1, 6.7 Hz, 6H) | |
| Example 168 | 1-[1-(2-fluorophenyl)-1H-indazol-4-yl]-3-[(2S)-2-hydroxy-2,4-dimethylpentyl]imidazolidin-2-one | $^1$H NMR (400 MHz, methanol-d$_4$) δ ppm 8.37 (d, J = 0.8 Hz, 1H), 7.61 (td, J = 7.7, 1.6 Hz, 1H), 7.58-7.52 (m, 1H), 7.47-7.37 (m, 3H), 7.16-7.07 (m, 2H), 4.15-4.03 (m, 2H), 3.90 (td, J = 8.9, 6.6 Hz, 1H), 3.81-3.73 (m, 1H), 3.40 (d, J = 14.2 Hz, 1H), 3.20 (d, J = 14.2 Hz, 1H), 1.97-1.86 (m, 1H), 1.47 (d, J = 5.8 Hz, 2H), 1.26 (s, 3H), 1.01 (dd, J = 9.0, 6.7 Hz, 6H) | MS (ESI$^+$) m/z 411 [M + H]$^+$ |
| Example 169 | 1-[1-(2-fluorophenyl)-1H-indazol-4-yl]-3-{2-oxo-2-[(2S)-2-(trifluoromethyl)pyrrolidin-1-yl]ethyl}imidazolidin-2-one | $^1$H NMR (400 MHz, DMSO-d$_6$) δ ppm 8.40 (s, 1H), 7.68 (td, J = 7.8, 1.7 Hz, 1H), 7.63-7.50 (m, 2H), 7.47-7.36 (m, 2H), 7.18 (d, J = 7.6 Hz, 1H), 7.09 (dd, J = 8.3, 3.0 Hz, 1H), 5.10-4.94 (m, 0.22H), 4.80 (p, J = 8.1 Hz, 0.82 H), 4.46-4.03 (m, 4H), 3.63 (ddd, J = 11.8, 9.7, 6.1 Hz, 4H), 2.30-1.87 (m, 4H). | MS (ESI$^+$) m/z 476 (M + H)$^+$ |
| Example 170 | 1-[1-(2-fluorophenyl)-1H-indazol-4-yl]-3-{2-[(2R)-2-(methoxymethyl)pyrrolidin-1-yl]-2-oxoethyl}imidazolidin-2-one | $^1$H NMR (400 MHz, CDCl$_3$) δ ppm 8.42 (s, 1H), 7.67-7.55 (m, 1H), 7.48-7.27 (m, 4H), 7.10 (ddd, J = 25.8, 7.8, 3.4 Hz, 2H), 4.41-4.03 (m, 5H), 3.96-3.59 (m, 3H), 3.59-3.44 (m, 3H), 3.37 (d, J = 8.9 Hz, 3H), 2.15-1.81 (m, 4H). | MS (ESI$^+$) m/z 452 (M + H)$^+$ |
| Example 171 | 1-[1-(2-fluorophenyl)-1H-indazol-4-yl]-3-{2-oxo-2-[(2R)-2-(trifluoromethyl)pyrrolidin-1-yl]ethyl}imidazolidin-2-one | $^1$H NMR (400 MHz, CDCl$_3$) δ ppm 8.43-8.35 (s, 1H), 7.60 (td, J = 7.6, 1.8 Hz, 1H), 7.47-7.27 (m, 4H), 7.14 (dd, J = 8.4, 3.3 Hz, 1H), 7.05 (d, J = 7.6 Hz, 1H), 4.86 (p, J = 7.8 Hz, 0.8H), 4.70 (m, 0.2H), 4.58 (d, J = 16.5 Hz, 0.2H), 4.37 (d, J = 16.7 Hz, 0.8H), 4.21-3.46 (m, 7H), 2.30-2.05 (m, 4H). | MS (ESI$^+$) m/z 476 (M + H)$^+$ |
| Example 172 | 1-[2-(2,2-dimethylpyrrolidin-1-yl)-2-oxoethyl]-3-[1-(2-fluorophenyl)-1H-indazol-4-yl]imidazolidin-2-one | $^1$H NMR (500 MHz, DMSO-d$_6$) δ ppm 8.41 (s, 1H), 7.68 (td, J = 7.8, 1.7 Hz, 1H), 7.63-7.50 (m, 2H), 7.48-7.36 (m, 2H), 7.18 (d, J = 7.6 Hz, 1H), 7.08 (dd, J = 8.4, 2.9 Hz, 1H), 4.08 (dd, J = 8.9, 6.7 Hz, 2H), 3.99 (s, 2H), 3.62 (dd, J = 8.8, 6.8 Hz, 2H), 3.51 (t, J = 6.7 Hz, 2H), 1.84 (p, J = 6.8 Hz, 2H), 1.74 (t, J = 6.8 Hz, 2H), 1.40 (s, 6H). | MS (APCI) m/z 436 (M + H)$^+$ |
| Example 173 | N-(3-fluorobenzyl)-2-{3-[1-(2-fluorophenyl)-1H-indazol-4-yl]-2-oxoimidazolidin-1-yl}acetamide | $^1$H NMR (500 MHz, DMSO-d$_6$) δ ppm 8.66 (t, J = 6.1 Hz, 1H), 8.42 (d, J = 1.0 Hz, 1H), 7.66 (td, J = 7.8, 1.7 Hz, 1H), 7.60-7.49 (m, 2H), 7.45-7.39 (m, 2H), 7.37 (td, J = 7.9, 6.2 Hz, 1H), 7.18 (d, J = 7.6 Hz, 1H), 7.15-7.03 (m, 4H), 4.35 (d, J = 6.0 Hz, 2H), 4.09 (dd, J = 8.9, 6.7 Hz, 2H), 3.96 (s, 2H), 3.68-3.60 (m, 2H) | MS (ESI$^+$) m/z 462 [M + H]$^+$ |
| Example 174 | N-(2,5-difluoiobenzyl)-2-{3-[1-(2-fluorophenyl)-1H-indazol-4-yl]-2-oxoimidazolidin-1-yl}acetamide | $^1$H NMR (500 MHz, DMSO-d$_6$) δ ppm 8.65 (t, J = 5.9 Hz, 1H), 8.42 (d, J = 0.9 Hz, 1H), 7.66 (td, J = 7.9, 1.7 Hz, 1H), 7.62-7.49 (m, 2H), 7.48-7.37 (m, 2H), 7.23 (td, J = 9.2, 4.5 Hz, 1H), 7.20-7.11 (m, 3H), 7.07 (dd, J = 8.4, 2.9 Hz, 1H), 4.35 (d, J = 5.8 Hz, 2H), 4.08 (dd, J = 8.9, 6.7 Hz, 2H), 3.97 (s, 2H), 3.68-3.59 (m, 2H) | MS (ESI$^+$) m/z 480 [M + H]$^+$ |

-continued

| Example | Name | NMR | MS |
|---|---|---|---|
| Example 175 | 2-{3-[1-(2-fluorophenyl)-1H-indazol-4-yl]-2-oxoimidazolidin-1-yl}-N-(2-methylbenzyl)acetamide | $^1$H NMR (500 MHz, DMSO-$d_6$) δ ppm 8.68 (t, J = 5.7 Hz, 1H), 8.63 (s, 1H), 7.87 (td, J = 7.8, 1.7 Hz, 1H), 7.82-7.72 (m, 2H), 7.67-7.59 (m, 2H), 7.48-7.42 (m, 1H), 7.40-7.34 (m, 4H), 7.28 (dd, J = 8.3, 2.9 Hz, 1H), 4.51 (d, J = 5.7 Hz, 2H), 4.29 (dd, J = 8.9, 6.7 Hz, 2H), 4.16 (s, 2H), 3.85 (dd, J = 8.9, 6.7 Hz, 2H), 2.49 (s, 3H) | MS (ESI$^+$) m/z 458 [M + H]$^+$ |
| Example 176 | 2-{3-[1-(2-fluorophenyl)-1H-indazol-4-yl]-2-oxoimidazolidin-1-yl}-N-[(1R)-1-phenylethyl]acetamide | $^1$H NMR (500 MHz, methanol-$d_4$) δ ppm 8.41 (d, J = 0.9 Hz, 1H), 7.61 (td, J = 7.7, 1.6 Hz, 1H), 7.59-7.51 (m, 1H), 7.46-7.30 (m, 8H), 7.26-7.21 (m, 1H), 7.13 (dd, J = 8.5, 2.8 Hz, 1H), 7.11 (d, J = 7.9 Hz, 1H), 5.09 (q, J = 7.0 Hz, 1H), 4.13-4.07 (m, 2H), 4.04 (d, J = 6.7 Hz, 2H), 3.69 (td, J = 7.5, 1.8 Hz, 2H), 1.49 (d, J = 7.0 Hz, 3H) | MS (ESI$^+$) m/z 458 [M + H]$^+$ |
| Example 177 | N-(3,5-difluorobenzyl)-2-{3-[1-(2-fluorophenyl)-1H-indazol-4-yl]-2-oxoimidazolidin-1-yl}acetamide | $^1$H NMR (500 MHz, DMSO-$d_6$) δ ppm 8.68 (t, J = 6.1 Hz, 1H), 8.42 (d, J = 0.9 Hz, 1H), 7.66 (td, J = 7.8, 1.7 Hz, 1H), 7.62-7.49 (m, 2H), 7.47-7.39 (m, 2H), 7.18 (d, J = 7.6 Hz, 1H), 7.13-7.04 (m, 2H), 7.04-6.96 (m, 2H), 4.36 (d, J = 5.9 Hz, 2H), 4.09 (dd, J = 8.9, 6.7 Hz, 2H), 3.97 (s, 2H), 3.72-3.60 (m, 2H) | MS (ESI$^+$) m/z 480 [M + H]$^+$ |
| Example 178 | 2-{3-[1-(2-fluorophenyl)-1H-indazol-4-yl]-2-oxoimidazolidin-1-yl}-N-[(1S)-1-phenylethyl]acetamide | $^1$H NMR (500 MHz, methanol-$d_4$) δ ppm 8.41 (s, 1H), 7.61 (td, J = 7.7, 1.5 Hz, 1H), 7.57-7.51 (m, 1H), 7.47-7.29 (m, 7H), 7.23 (td, J = 7.0, 1.5 Hz, 1H), 7.13 (dd, J = 8.6, 2.9 Hz, 1H), 7.10 (d, J = 7.6 Hz, 1H), 5.09 (q, J = 7.0 Hz, 1H), 4.14-4.07 (m, 2H), 4.04 (d, J = 6.8 Hz, 2H), 3.74-3.63 (m, 2H), 1.49 (d, J = 7.0 Hz, 3H) | MS (ESI$^+$) m/z 458 [M + H]$^+$ |
| Example 179 | 1-(1,3-benzothiazol-2-ylmethyl)-3-[1-(2-fluorophenyl)-1H-indazol-4-yl]imidazolidin-2-one | $^1$H NMR (500 MHz, DMSO-$d_6$) δ ppm 8.47 (s, 1H), 8.13 (dd, J = 7.9, 1.2 Hz, 1H), 8.07-7.99 (m, 1H), 7.69 (td, J = 7.8, 1.6 Hz, 1H), 7.63-7.52 (m, 3H), 7.50-7.41 (m, 3H), 7.23 (d, J = 7.6 Hz, 1H), 7.13 (dd, J = 8.3, 2.9 Hz, 1H), 4.93 (s, 2H), 4.15 (dd, J = 8.8, 6.7 Hz, 2H), 3.70 (dd, J = 8.7, 6.9 Hz, 2H) | MS (ESI$^+$) m/z 444 [M + H]$^+$ |
| Example 180 | 1-[1-(2-fluorophenyl)-1H-indazol-4-yl]-3-(2-hydroxy-2,3-dimethylbutyl)imidazolidin-2-one | $^1$H NMR (400 MHz, DMSO-$d_6$) δ ppm 8.40 (d, J = 0.8 Hz, 1H), 7.67 (td, J = 7.9, 1.6 Hz, 1H), 7.62-7.52 (m, 2H), 7.48-7.38 (m, 2H), 7.16 (d, J = 7.5 Hz, 1H), 7.06 (dd, J = 8.4, 3.0 Hz, 1H), 4.36 (s, 1H), 4.04 (t, J = 7.7 Hz, 2H), 3.80-3.67 (m, 2H), 3.24 (dd, J = 27.3, 14.0 Hz, 2H), 1.77-1.68 (m, 1H), 1.01 (s, 3H), 0.94-0.89 (m, 6H) | MS (ESI$^+$) m/z 397 [M + H]$^+$ |
| Example 181 | 1-(cyclopentylmethyl)-3-[1-(2-fluorophenyl)-1H-indazol-4-yl]imidazolidin-2-one | $^1$H NMR (400 MHz, methanol-$d_4$) δ ppm 8.37 (d, J = 0.9 Hz, 1H), 7.61 (td, J = 7.7, 1.6 Hz, 1H), 7.59-7.50 (m, 1H), 7.47-7.37 (m, 3H), 7.15-7.06 (m, 2H), 4.13-4.03 (m, 2H), 3.73-3.63 (m, 2H), 3.28 (d, J = 7.7 Hz, 2H), 2.36-2.24 (m, 1H), 1.88-1.78 (m, 2H), 1.78-1.67 (m, 2H), 1.67-1.56 (m, 2H), 1.43-1.22 (m, 2H) | MS (DCI) m/z 379 [M + H]$^+$ |

-continued

| Example | Name | NMR | MS |
|---|---|---|---|
| Example 182 | 1-[1-(2-fluorophenyl)-1H-indazol-4-yl]-3-(tetrahydrofuran-2-ylmethyl)imidazolidin-2-one | $^1$H NMR (500 MHz, methanol-$d_4$) δ ppm 8.39 (d, J = 0.8 Hz, 1H), 7.61 (td, J = 7.7, 1.5 Hz, 2H), 7.58-7.51 (m, 1H), 7.47-7.35 (m, 3H), 7.12 (dd, J = 8.5, 2.8 Hz, 1H), 7.09 (d, J = 7.5 Hz, 1H), 4.16 (qd, J = 7.1, 3.8 Hz, 1H), 4.11-4.02 (m, 2H), 3.96-3.90 (m, 1H), 3.82-3.70 (m, 3H), 3.46 (dd, J = 14.3, 3.8 Hz, 1H), 3.37 (dd, J = 14.3, 7.3 Hz, 1H), 2.12-2.02 (m, 1H), 2.02-1.88 (m, 2H), 1.74-1.64 (m, 1H) | MS (ESI$^+$) m/z 381 [M + H]$^+$ |
| Example 183 | 1-(2-cyclopropyl-2-oxoethyl)-3-[1-(2-fluorophenyl)-1H-indazol-4-yl]imidazolidin-2-one | $^1$H NMR (500 MHz, methanol-$d_4$) δ ppm 8.37 (d, J = 0.8 Hz, 1H), 7.61 (td, J = 7.7, 1.5 Hz, 1H), 7.58-7.52 (m, 1H), 7.48-7.37 (m, 3H), 7.14 (dd, J = 8.5, 2.8 Hz, 1H), 7.11 (d, J = 7.5 Hz, 1H), 4.40 (s, 2H), 4.14-4.09 (m, 2H), 3.71-3.65 (m, 2H), 2.20-2.08 (m, 1H), 1.10-1.05 (m, 2H), 1.05-1.00 (m, 2H) | MS (ESI$^+$) m/z 379 [M + H]$^+$ |
| Example 184 | 1-cyclobutyl-3-[1-(2-fluorophenyl)-1H-indazol-4-yl]imidazolidin-2-one | $^1$H NMR (400 MHz, methanol-$d_4$) δ ppm 8.37 (d, J = 1.3 Hz, 1H), 7.60 (td, J = 7.7, 1.6 Hz, 1H), 7.57-7.51 (m, 1H), 7.45-7.35 (m, 3H), 7.11 (dd, J = 8.4, 2.9 Hz, 1H), 7.07 (d, J = 7.6 Hz, 1H), 4.52 (tt, J = 9.6, 7.7 Hz, 1H), 4.05 (dd, J = 8.9, 6.8 Hz, 2H), 3.72 (dd, J = 8.9, 6.8 Hz, 2H), 2.35 (qdd, J = 9.7, 7.6, 2.8 Hz, 2H), 2.21-2.13 (m, 2H), 1.75 (tt, J = 10.3, 6.2 Hz, 2H) | MS (ESI$^+$) m/z 351 [M + H]$^+$ |
| Example 185 | 1-[1-(2-fluorophenyl)-1H-indazol-4-yl]-3-[(3R,5R)-5-(2-fluorophenyl)tetrahydrofuran-3-yl]imidazolidin-2-one | $^1$H NMR (400 MHz, DMSO-$d_6$) δ ppm 9.72 (s, 1H), 8.42 (d, J = 0.7 Hz, 1H), 7.73-7.50 (m, 4H), 7.50-7.32 (m, 3H), 7.32-7.11 (m, 3H), 7.08 (dd, J = 8.4, 3.0 Hz, 1H), 5.04 (dt, J = 21.4, 10.7 Hz, 1H), 4.88-4.73 (m, 1H), 4.19-3.90 (m, 1H), 3.88-3.75 (m, 1H), 3.69-3.44 (m, 2H), 2.89 (s, 1H), 2.79-2.63 (m, 1H), 2.03-1.81 (m, 1H) | MS (DCI) m/z 475 [M + H]$^+$ |
| Example 186 | 1-[1-(2-fluorophenyl)-1H-indazol-4-yl]-3-(2-hydroxy-4-methylpentyl)tetrahydropyrimidin-2(1H)-one | $^1$H NMR (500 MHz, CDCl$_3$) δ ppm 8.16 (s, 1H), 7.59 (td, J = 7.7, 1.7 Hz, 1H), 7.46-7.35 (m, 2H), 7.30 (dd, J = 8.7, 6.9 Hz, 2H), 7.24 (dd, J = 8.5, 3.3 Hz, 1H), 7.06 (d, J = 7.3 Hz, 1H), 3.99 (tdd, J = 8.6, 4.4, 2.3 Hz, 1H), 3.94-3.79 (m, 2H), 3.69-3.49 (m, 3H), 3.30 (dd, J = 14.7, 2.4 Hz, 1H), 2.62 (br s, 1H), 2.25 (p, J = 5.9 Hz, 2H), 1.85 (ddt, J = 15.1, 13.1, 6.5 Hz, 1H), 1.49 (ddd, J = 14.0, 8.8, 5.6 Hz, 1H), 1.23 (tdd, J = 13.2, 8.1, 5.1 Hz, 1H), 0.96 (t, J = 6.7 Hz, 6H). | MS (ESI$^+$) m/z 411 (M + H)$^+$ |
| Example 187 | 1-[1-(2-fluorophenyl)-1H-indazol-4-yl]-3-{2-[(2S)-2-methylpyrrolidin-1-yl]-2-oxoethyl}tetrahydropyrimidin-2(1H)-one | $^1$H NMR @ 90° C. (400 MHz, DMSO-$d_6$) δ ppm 8.21 (s, 1H), 7.62 (td, J = 7.8, 1.8 Hz, 1H), 7.58-7.34 (m, 4H), 7.15 (dd, J = 8.5, 2.9 Hz, 1H), 7.04 (d, J = 7.4 Hz, 1H), 4.09 (tq, J = 6.3, 2.8 Hz, 2H), 3.86-3.33 (m, 5H), 2.17 (p, J = 6.0 Hz, 2H), 2.06-1.71 (m, 2H), 1.27 (d, J = 6.9 Hz, 4H), 1.16 (d, J = 6.3 Hz, 3H). | MS (ESI$^+$) m/z 436 (M + H)$^+$ |
| Example 188 | 1-[1-(2-fluorophenyl)-1H-indazol-4-yl]-3-(4-methyl-2-oxopentyl)tetrahydropyrimidin-2(1H)-one | $^1$H NMR (400 MHz, CDCl$_3$) δ ppm 8.20 (d, J = 0.9 Hz, 1H), 7.59 (td, J = 7.7, 1.7 Hz, 1H), 7.45-7.34 (m, 2H), 7.34-7.27 (m, 2H), 7.24-7.19 (m, 1H), 7.09-7.01 (m, 1H), 4.20 (s, 2H), | MS (ESI$^+$) m/z 409 (M + H)$^+$ |

-continued

| Example | Name | NMR | MS |
|---|---|---|---|
| | | 3.96-3.79 (m, 2H), 3.52 (t, J = 6.0 Hz, 2H), 2.40-2.11 (m, 5H), 0.96 (d, J = 6.6 Hz, 6H). | |
| Example 189 | 1-[(2,2-difluorocyclopropyl)methyl]-3-[1-(2-fluorophenyl)-1H-indazol-4-yl]imidazolidin-2-one | $^1$H NMR (500 MHz, methanol-$d_4$) δ ppm 8.39 (d, J = 0.6 Hz, 1H), 7.61 (td, J = 7.7, 1.5 Hz, 1H), 7.58-7.52 (m, 1H), 7.47-7.38 (m, 3H), 7.16-7.08 (m, 2H), 4.15-4.05 (m, 2H), 3.81-3.73 (m, 2H), 3.66 (dd, J = 16.1, 8.3 Hz, 1H), 3.21 (dd, J = 14.7, 8.1 Hz, 1H), 2.03-1.89 (m, 1H), 1.60 (tdd, J = 12.0, 7.8, 4.5 Hz, 1H), 1.34-1.24 (m, 1H) | MS (ESI$^+$) m/z 387 [M + H]$^+$ |
| Example 190 | 1-[1-(2-fluorophenyl)-1H-indazol-4-yl]-3-(pyrazolo[1,5-a]pyrimidin-3-yl)imidazolidin-2-one | $^1$H NMR (500 MHz, methanol-$d_4$) δ ppm 8.39 (d, J = 0.6 Hz, 1H), 7.61 (td, J = 7.7, 1.5 Hz, 1H), 7.58-7.52 (m, 1H), 7.47-7.38 (m, 3H), 7.16-7.08 (m, 2H), 4.15-4.05 (m, 2H), 3.81-3.73 (m, 2H), 3.66 (dd, J = 16.1, 8.3 Hz, 1H), 3.21 (dd, J = 14.7, 8.1 Hz, 1H), 2.03-1.89 (m, 1H), 1.60 (tdd, J = 12.0, 7.8, 4.5 Hz, 1H), 1.34-1.24 (m, 1H) | MS (ESI$^+$) m/z 414 [M + H]$^+$ |
| Example 191 | 1-[1-(2-fluorophenyl)-1H-indazol-4-yl]-3-(2-methyl-2H-indazol-5-yl)imidazolidin-2-one | $^1$H NMR (400 MHz, DMSO-$d_6$) δ ppm 8.46 (d, J = 0.9 Hz, 1H), 8.30 (s, 1H), 7.83 (dd, J = 9.4, 2.1 Hz, 1H), 7.75-7.65 (m, 2H), 7.65-7.53 (m, 3H), 7.51-7.41 (m, 2H), 7.24 (d, J = 7.6 Hz, 1H), 7.15 (dd, J = 8.4, 3.0 Hz, 1H), 4.27-4.19 (m, 2H), 4.17 (s, 3H), 4.16-4.09 (m, 2H) | MS (APCI) m/z 427 [M + H]$^+$ |
| Example 192 | 1-(5-cyclopropyl-2-furyl)-3-[1-(2-fluorophenyl)-1H-indazol-4-yl]imidazolidin-2-one | $^1$H NMR (500 MHz, DMSO-$d_6$) δ ppm 8.43 (d, J = 0.9 Hz, 1H), 7.69 (td, J = 7.9, 1.7 Hz, 1H), 7.62-7.52 (m, 2H), 7.50-7.41 (m, 2H), 7.23 (d, J = 7.6 Hz, 1H), 7.16 (dd, J = 8.5, 2.9 Hz, 1H), 6.13-6.03 (m, 2H), 4.21 (dd, J = 9.1, 6.6 Hz, 2H), 4.02 (dd, J = 9.0, 6.6 Hz, 2H), 1.91 (tt, J = 8.4, 5.1 Hz, 1H), 0.89-0.84 (m, 2H), 0.71-0.66 (m, 2H) | MS (APCI) m/z 403 [M + H]$^+$ |
| Example 193 | 1-[1-(2-fluorophenyl)-1H-indazol-4-yl]-3-(2-phenylethyl)imidazolidin-2-one | $^1$H NMR (400 MHz, methanol-$d_4$) δ ppm 8.21 (d, J = 1.0 Hz, 1H), 7.60 (td, J = 7.7, 1.7 Hz, 1H), 7.57-7.51 (m, 1H), 7.44-7.37 (m, 3H), 7.34-7.30 (m, 4H), 7.27-7.20 (m, 1H), 7.12-7.08 (m, 1H), 7.05-7.01 (m, 1H), 4.02-3.95 (m, 2H), 3.65-3.55 (m, 4H), 2.95 (t, J = 7.2 Hz, 2H) | MS (ESI$^+$) m/z 401 [M + H]$^+$ |
| Example 194 | 1-(cyclopropylmethyl)-3-[1-(2-fluorophenyl)-1H-indazol-4-yl]imidazolidin-2-one | $^1$H NMR (500 MHz, methanol-$d_4$) δ ppm 8.38 (s, 1H), 7.61 (td, J = 7.7, 1.4 Hz, 1H), 7.58-7.52 (m, 1H), 7.48-7.37 (m, 3H), 7.16-7.05 (m, 2H), 4.12-4.06 (m, 2H), 3.80-3.71 (m, 2H), 3.22 (d, J = 7.1 Hz, 2H), 1.13-1.00 (m, 1H), 0.63-0.57 (m, 2H), 0.33-0.29 (m, 2H) | MS (ESI$^+$) m/z 351 |
| Example 195 | 2,5-anhydro-1,3,4-trideoxy-2-(3-fluorophenyl)-4-{3-[1-(2-fluorophenyl)-1H-indazol-4-yl]-2-oxoimidazolidin-1-yl}-D-erythro-pentitol | $^1$H NMR (400 MHz, DMSO-$d_6$) δ ppm 8.40 (d, J = 0.5 Hz, 1H), 7.66 (td, J = 7.8, 1.5 Hz, 1H), 7.60-7.51 (m, 2H), 7.47-7.38 (m, 3H), 7.32-7.23 (m, 2H), 7.16-7.00 (m, 3H), 4.89-4.72 (m, 1H), 4.16 (dd, J = 9.2, 7.2 Hz, 1H), 4.02-3.84 (m, 2H), 3.45-3.32 (m, 1H), 3.25 (p, J = 8.4 Hz, 1H), 2.60-2.45 (m, 2H), 2.23 (dd, J = 13.1, 6.8 Hz, 1H), 1.48 (s, 3H) | MS (DCI) m/z 475 [M + H]$^+$ |

-continued

| Example | Name | NMR | MS |
|---|---|---|---|
| Example 196 | 1-[1-(2-fluorophenyl)-1H-indazol-4-yl]-3-[(3R,5S)-5-(3-fluorophenyl)tetrahydrofuran-3-yl]imidazolidin-2-one | $^1$H NMR (400 MHz, DMSO-d$_6$) δ ppm 8.44 (s, 1H), 7.68 (td, J = 7.9, 1.5 Hz, 1H), 7.64-7.51 (m, 2H), 7.48-7.38 (m, 3H), 7.26-7.17 (m, 3H), 7.10 (ddd, J = 11.8, 8.8, 2.8 Hz, 2H), 5.16 (t, J = 7.6 Hz, 1H), 4.73-4.61 (m, 1H), 4.21 (dd, J = 9.3, 6.5 Hz, 1H), 4.15-4.05 (m, 2H), 3.97 (dd, J = 9.3, 4.5 Hz, 1H), 3.72 (t, J = 7.7 Hz, 2H), 2.68-2.55 (m, 1H), 2.08 (dt, J = 13.3, 8.2 Hz, 1H) | MS (DCI$^+$) m/z 461 [M + H]$^+$ |
| Example 197 | 1-(2,5-difluorobenzyl)-3-[1-(2-fluorophenyl)-1H-indazol-4-yl]imidazolidin-2-one | $^1$H NMR (500 MHz, CDCl$_3$) δ ppm 8.79-8.57 (m, 1H), 8.56-8.35 (m, 1H), 7.71-7.57 (m, 1H), 7.51-7.13 (m, 8H), 6.88-6.72 (m, 1H), 4.59-4.46 (m, 2H), 4.36-4.24 (m, 2H) | MS (ESI$^+$) m/z 414 [M + H]$^+$ |
| Example 198 | 1-[1-(2-fluorophenyl)-1H-indazol-4-yl]-3-(pyridin-3-ylmethyl)imidazolidin-2-one | $^1$H NMR (400 MHz, DMSO-d$_6$) δ ppm 8.46 (d, J = 0.9 Hz, 1H), 8.30 (s, 1H), 7.83 (dd, J = 9.4, 2.1 Hz, 1H), 7.75-7.65 (m, 2H), 7.65-7.53 (m, 3H), 7.51-7.41 (m, 2H), 7.24 (d, J = 7.6 Hz, 1H), 7.15 (dd, J = 8.4, 3.0 Hz, 1H), 4.27-4.19 (m, 2H), 4.17 (s, 3H), 4.16-4.09 (m, 2H) | MS (APCI) m/z 427 [M + H]$^+$ |
| Example 199 | 1-[1-(2-fluorophenyl)-1H-indazol-4-yl]-3-[(5-methyl-1,2-oxazol-3-yl)methyl]imidazolidin-2-one | $^1$H NMR (500 MHz, DMSO-d$_6$) δ ppm 8.43 (d, J = 0.9 Hz, 1H), 7.69 (td, J = 7.9, 1.7 Hz, 1H), 7.62-7.52 (m, 2H), 7.50-7.41 (m, 2H), 7.23 (d, J = 7.6 Hz, 1H), 7.16 (dd, J = 8.5, 2.9 Hz, 1H), 6.13-6.03 (m, 2H), 4.21 (dd, J = 9.1, 6.6 Hz, 2H), 4.02 (dd, J = 9.0, 6.6 Hz, 2H), 1.91 (tt, J = 8.4, 5.1 Hz, 1H), 0.89-0.84 (m, 2H), 0.71-0.66 (m, 2H) | MS (APCI) m/z 403 [M + H]$^+$ |
| Example 200 | 1-[1-(2-fluorophenyl)-1H-indazol-4-yl]-3-(oxetan-3-ylmethyl)imidazolidin-2-one | $^1$H NMR (400 MHz, methanol-d$_4$) δ ppm 8.21 (d, J = 1.0 Hz, 1H), 7.60 (td, J = 7.7, 1.7 Hz, 1H), 7.57-7.51 (m, 1H), 7.44-7.37 (m, 3H), 7.34-7.30 (m, 4H), 7.27-7.20 (m, 1H), 7.12-7.08 (m, 1H), 7.05-7.01 (m, 1H), 4.02-3.95 (m, 2H), 3.65-3.55 (m, 4H), 2.95 (t, J = 7.2 Hz, 2H) | MS (ESI$^+$) m/z 401 [M + H]$^+$ |
| Example 201 | (2R)-1-({3-[1-(2-fluorophenyl)-1H-indazol-4-yl]-2-oxoimidazolidin-1-yl}acetyl)pyrrolidine-2-carbonitrile | $^1$H NMR (500 MHz, DMSO-d$_6$) δ ppm 8.41 (d, J = 1.0 Hz, 1H), 7.68 (td, J = 7.9, 1.7 Hz, 1H), 7.63-7.51 (m, 2H), 7.47-7.39 (m, 2H), 7.19 (d, J = 7.6 Hz, 1H), 7.10 (dd, J = 8.5, 2.9 Hz, 1H), 4.82 (dd, J = 7.7, 3.4 Hz, 1H), 4.27-4.05 (m, 2H), 3.73-3.59 (m, 3H), 3.51 (td, J = 9.0, 6.8 Hz, 1H), 3.35-3.29 (m, 2H), 2.25-1.96 (m, 4H) | MS (ESI$^+$) m/z 433 [M + H]$^+$ |
| Example 202 | 1-[2-(2-azabicyclo[2.2.1]hept-2-yl)-2-oxoethyl]-3-[1-(2-fluorophenyl)-1H-indazol-4-yl]imidazolidin-2-one | $^1$H NMR (400 MHz, DMSO-d$_6$) δ ppm 8.40 (s, 1H), 7.68 (td, J = 7.9, 1.6 Hz, 1H), 7.63-7.51 (m, 2H), 7.48-7.38 (m, 2H), 7.17 (dd, J = 7.5, 1.6 Hz, 1H), 7.08 (dd, J = 8.4, 3.0 Hz, 1H), 4.40 (d, J = 38.9 Hz, 1H), 4.08 (ddd, J = 8.5, 6.8, 1.8 Hz, 2H), 4.05-3.97 (m, 1H), 3.97-3.86 (m, 1H), 3.67-3.56 (m, 2H), 3.46-3.20 (m, 1H), 3.20-3.00 (m, 1H), 2.58 (d, J = 29.1 Hz, 1H), 1.79-1.33 (m, 6H) | MS (ESI$^+$) m/z 434 [M + H]$^+$ |
| Example 203 | 2,5-anhydro-1,3,4-trideoxy-2-(3-fluorophenyl)-4-{3-[1-(2-fluorophenyl)-1H-indazol-4-yl]-2-oxoimidazolidin-1-yl}-L-threo-pentitol | $^1$H NMR (400 MHz, DMSO-d$_6$) δ ppm 8.40 (d, J = 0.9 Hz, 1H), 7.67 (td, J = 7.8, 1.6 Hz, 1H), 7.62-7.51 (m, 2H), 7.47-7.36 (m, 3H), 7.32-7.21 (m, 2H), 7.18-7.04 (m, 3H), 4.45-4.29 | MS (DCI) m/z 475 [M + H]+ |

-continued

| Example | Name | NMR | MS |
|---|---|---|---|
| | | (m, 1H), 4.14-4.02 (m, 2H), 4.01-3.87 (m, 2H), 3.75-3.57 (m, 2H), 2.60 (dd, J = 12.7, 7.8 Hz, 1H), 2.24 (dd, J = 12.8, 8.6 Hz, 1H), 1.56 (s, 3H) | |
| Example 204 | 1-[1-(2-fluorophenyl)-1H-indazol-4-yl]-3-(3-hydroxycyclopentyl)imidazolidin-2-one | $^1$H NMR (500 MHz, methanol-d$_4$) δ ppm 8.38 (s, 1H), 7.61 (td, J = 7.7, 1.6 Hz, 1H), 7.58-7.52 (m, 1H), 7.47-7.37 (m, 3H), 7.12 (dd, J = 8.5, 2.8 Hz, 1H), 7.09 (d, J = 7.6 Hz, 1H), 4.69-4.40 (m, 1H), 4.40-4.26 (m, 1H), 4.06 (td, J = 7.9, 4.8 Hz, 2H), 3.70 (td, J = 7.5, 1.5 Hz, 1H), 3.62 (td, J = 7.7, 2.6 Hz, 1H), 2.30-2.03 (m, 2H), 2.03-1.88 (m, 2H), 1.88-1.62 (m, 3H) | MS (ESI$^+$) m/z 381 [M + H]$^+$ |
| Example 205 | 1-[2-(3-ethyl-3-hydroxyazetidin-1-yl)-2-oxoethyl]-3-[1-(2-fluorophenyl)-1H-indazol-4-yl]imidazolidin-2-one | $^1$H NMR (400 MHz, DMSO-d$_6$) δ ppm 8.40 (d, J = 1.0 Hz, 1H), 7.68 (td, J = 7.9, 1.6 Hz, 1H), 7.63-7.50 (m, 2H), 7.49-7.36 (m, 2H), 7.17 (d, J = 7.6 Hz, 1H), 7.09 (dd, J = 8.4, 3.0 Hz, 1H), 5.61 (bs, 1H), 4.13-4.03 (m, 3H), 3.99-3.91 (m, 3H), 3.80 (d, J = 9.8 Hz, 1H), 3.69 (d, J = 9.7 Hz, 1H), 3.61 (dd, J = 9.0, 6.7 Hz, 2H), 1.66 (q, J = 7.3 Hz, 2H), 0.89 (t, J = 7.3 Hz, 3H) | MS (ESI$^+$) m/z 438 [M + H]$^+$ |
| Example 206 | 1-[2-(3,4-difluoropyrrolidin-1-yl)-2-oxoethyl]-3-[1-(2-fluorophenyl)-1H-indazol-4-yl]imidazolidin-2-one | $^1$H NMR (400 MHz, DMSO-d$_6$) δ ppm 8.40 (s, 1H), 7.68 (td, J = 7.9, 1.7 Hz, 1H), 7.63-7.51 (m, 2H), 7.43 (td, J = 8.4, 8.0, 6.3 Hz, 2H), 7.17 (d, J = 7.6 Hz, 1H), 7.09 (dd, J = 8.5, 3.0 Hz, 1H), 5.54-5.22 (m, 2H), 4.13 (s, 2H), 4.09 (t, J = 8.1 Hz, 2H), 3.99 (ddd, J = 17.8, 11.3, 5.8 Hz, 1H), 3.83-3.69 (m, 2H), 3.66-3.48 (m, 3H) | MS (ESI$^+$) m/z 444 [M + H]$^+$ |
| Example 207 | 1-[1-(2-fluorophenyl)-1H-indazol-4-yl]-3-[5-(morpholin-4-yl)pyridin-3-yl]imidazolidin-2-one | $^1$H NMR (400 MHz, DMSO-d$_6$) δ ppm 8.45 (d, J = 0.9 Hz, 1H), 8.34 (d, J = 2.1 Hz, 1H), 8.08 (d, J = 2.5 Hz, 1H), 7.73-7.66 (m, 2H), 7.64-7.52 (m, 2H), 7.51-7.42 (m, 2H), 7.26 (d, J = 7.6 Hz, 1H), 7.18 (dd, J = 8.4, 2.9 Hz, 1H), 4.29-4.20 (m, 2H), 4.18-4.05 (m, 2H), 3.82-3.73 (m, 4H), 3.24-3.16 (m, 4H) | MS (ESI$^+$) m/z 459 [M + H]$^+$ |
| Example 208 | 1-[1-(2-fluorophenyl)-1H-indazol-4-yl]-3-(pyridazin-3-yl)imidazolidin-2-one | $^1$H NMR (400 MHz, methanol-d$_4$) δ ppm 9.59 (d, J = 1.6 Hz, 1H), 8.45 (d, J = 0.9 Hz, 1H), 8.40 (dd, J = 2.7, 1.5 Hz, 1H), 8.23 (d, J = 2.7 Hz, 1H), 7.64 (td, J = 7.7, 1.6 Hz, 1H), 7.60-7.54 (m, 1H), 7.54-7.49 (m, 1H), 7.47-7.39 (m, 2H), 7.27-7.21 (m, 2H), 4.33-4.26 (m, 4H) | MS (ESI$^+$) m/z 375 [M + H]$^+$ |
| Example 209 | N-(cyclopropylmethyl)-2-{3-[1-(2-fluorophenyl)-1H-indazol-4-yl]-2-oxoimidazolidin-1-yl}acetamide | $^1$H NMR (400 MHz, DMSO-d$_6$) δ ppm 8.43 (d, J = 1.0 Hz, 1H), 8.14 (t, J = 5.8 Hz, 1H), 7.68 (td, J = 7.8, 1.6 Hz, 1H), 7.63-7.50 (m, 2H), 7.48-7.39 (m, 2H), 7.20 (d, J = 7.6 Hz, 1H), 7.08 (dd, J = 8.4, 3.0 Hz, 1H), 4.09 (dd, J = 8.9, 6.7 Hz, 2H), 3.89 (s, 2H), 3.67-3.55 (m, 2H), 3.01 (t, J = 6.2 Hz, 2H), 0.94 (dddd, J = 11.6, 8.1, 6.7, 2.6 Hz, 1H), 0.49-0.37 (m, 2H), 0.24-0.14 (m, 2H) | MS (ESI$^+$) m/z 408 [M + H]$^+$ |
| Example 210 | 1-[1-(2-fluorophenyl)-1H-indazol-4-yl]-3-(pyridin-4-ylmethyl)imidazolidin-2-one | $^1$H NMR (400 MHz, DMSO-d$_6$) δ ppm 8.62-8.56 (m, 2H), 8.46 (d, J = 0.9 Hz, 1H), 7.68 (td, J = 7.8, 1.7 Hz, 1H), 7.63-7.52 (m, 2H), 7.49-7.41 (m, 2H), 7.41-7.36 (m, 2H), 7.22 (d, J = 7.6 Hz, 1H), | MS (ESI$^+$) m/z 388 [M + H]$^+$ |

| Example | Name | NMR | MS |
| --- | --- | --- | --- |
| | | 7.11 (dd, J = 8.4, 3.0 Hz, 1H), 4.52 (s, 2H), 4.17-4.08 (m, 2H), 3.57-3.47 (m, 2H) | |
| Example 211 | 1-[1-(2-fluorophenyl)-1H-indazol-4-yl]-3-[(2-methyl-1,3-oxazol-4-yl)methyl]imidazolidin-2-one | $^1$H NMR (400 MHz, DMSO-d$_6$) δ ppm 8.44 (d, J = 1.2 Hz, 1H), 7.98-7.95 (m, 1H), 7.68 (td, J = 7.9, 1.7 Hz, 1H), 7.63-7.50 (m, 2H), 7.47-7.38 (m, 2H), 7.19 (d, J = 7.6 Hz, 1H), 7.08 (dd, J = 8.4, 3.0 Hz, 1H), 4.32 (d, J = 1.0 Hz, 2H), 4.11-3.99 (m, 2H), 3.59-3.47 (m, 2H), 2.41 (s, 3H) | MS (ESI$^+$) m/z 392 [M + H]$^+$ |
| Example 212 | 1-{2-[(1s,4s)-7-azabicyclo[2.2.1]hept-7-yl]-2-oxoethyl}-3-[1-(2-fluorophenyl)-1H-indazol-4-yl]imidazolidin-2-one | $^1$H NMR (500 MHz, DMSO-d$_6$) δ ppm 8.39 (d, J = 1.0 Hz, 1H), 7.68 (td, J = 7.9, 1.7 Hz, 1H), 7.63-7.51 (m, 2H), 7.47-7.37 (m, 2H), 7.17 (d, J = 7.6 Hz, 1H), 7.08 (dd, J = 8.4, 2.9 Hz, 1H), 4.44 (dt, J = 26.2, 4.7 Hz, 2H), 4.11-4.04 (m, 4H), 3.63-3.57 (m, 2H), 1.82-1.58 (m, 4H), 1.47 (ddt, J = 44.6, 12.6, 6.5 Hz, 4H) | MS (ESI$^+$) m/z 434 (M + H)$^+$ |
| Example 213 | 1-[1-(2-fluorophenyl)-1H-indazol-4-yl]-3-[(3-methyloxetan-3-yl)methyl]imidazolidin-2-one | $^1$H NMR (400 MHz, CDCl$_3$) δ ppm 8.39 (d, J = 1.0 Hz, 1H), 7.60 (td, J = 7.8, 1.9 Hz, 1H), 7.49-7.27 (m, 4H), 7.14 (dd, J = 8.4, 3.3 Hz, 1H), 7.04 (d, J = 7.6 Hz, 1H), 4.65 (d, J = 5.9 Hz, 2H), 4.44 (d, J = 6.0 Hz, 2H), 4.07 (dd, J = 8.6, 6.8 Hz, 2H), 3.63 (dd, J = 8.7, 6.6 Hz, 2H), 3.58 (s, 2H), 1.43 (s, 3H). | MS (ESI$^+$) m/z 381 (M + H)$^+$ |
| Example 214 | 1-[1-(2-fluorophenyl)-1H-indazol-4-yl]-3-[(2R)-2-methoxy-4-methylpentyl]imidazolidin-2-one | $^1$H NMR (400 MHz, CDCl$_3$) δ ppm 8.42 (d, J = 0.9 Hz, 1H), 7.60 (td, J = 7.7, 1.9 Hz, 1H), 7.47-7.22 (m, 4H), 7.11 (dd, J = 8.3, 3.3 Hz, 1H), 7.05 (d, J = 7.6 Hz, 1H), 4.03 (dd, J = 8.6, 7.0 Hz, 2H), 3.81-3.64 (m, 2H), 3.56-3.33 (m, 6H), 1.81 (m, 1H), 1.53 (dt, J = 13.8, 6.9 Hz, 1H), 1.33 (ddd, J = 13.5, 7.6, 5.4 Hz, 1H), 0.95 (dd, J = 6.4, 1.2 Hz, 6H). | MS (ESI$^+$) m/z 411 (M + H)$^+$ |
| Example 215 | 1-[1-(2-fluorophenyl)-1H-indazol-4-yl]-3-[(2S)-2-methoxy-4-methylpentyl]imidazolidin-2-one | $^1$H NMR (400 MHz, CDCl$_3$) δ ppm 8.42 (d, J = 1.0 Hz, 1H), 7.60 (td, J = 7.7, 1.8 Hz, 1H), 7.47-7.27 (m, 4H), 7.11 (dd, J = 8.4, 3.3 Hz, 1H), 7.05 (d, J = 7.6 Hz, 1H), 4.09-3.98 (m, 2H), 3.82-3.65 (m, 2H), 3.56-3.33 (m, 6H), 1.81 (m, 1H), 1.53 (dt, J = 13.9, 7.0 Hz, 1H), 1.33 (ddd, J = 13.4, 7.6, 5.4 Hz, 1H), 0.95 (dd, J = 6.6, 1.1 Hz, 6H). | MS (ESI$^+$) m/z 411 (M + H)$^+$ |
| Example 216 | 1-[(1-acetylazetidin-3-yl)methyl]-3-[1-(2-fluorophenyl)-1H-indazol-4-yl]imidazolidin-2-one | $^1$H NMR (400 MHz, methanol-d$_4$) δ ppm 8.39 (d, J = 0.9 Hz, 1H), 7.61 (td, J = 7.7, 1.7 Hz, 1H), 7.59-7.51 (m, 1H), 7.47-7.38 (m, 3H), 7.20-7.03 (m, 2H), 4.34 (t, J = 8.6 Hz, 1H), 4.17-4.05 (m, 3H), 4.02 (dd, J = 8.9, 5.4 Hz, 1H), 3.78 (dd, J = 10.1, 5.5 Hz, 1H), 3.69-3.63 (m, 2H), 3.63-3.51 (m, 2H), 3.07-2.92 (m, 1H), 1.87 (s, 3H) | MS (ESI$^+$) m/z 408 [M + H]$^+$ |
| Example 217 | 1-[1-(2-fluorophenyl)-1H-indazol-4-yl]-3-[(2-methyl-1,3-thiazol-4-yl)methyl]imidazolidin-2-one | $^1$H NMR (400 MHz, DMSO-d$_6$) δ ppm 8.45 (d, J = 0.7 Hz, 1H), 7.68 (td, J = 7.8, 1.6 Hz, 1H), 7.62-7.51 (m, 2H), 7.49-7.38 (m, 3H), 7.20 (d, J = 7.6 Hz, 1H), 7.09 (dd, J = 8.4, 3.0 Hz, 1H), 4.51 (s, 2H), 4.08 (dd, J = 8.8, 6.7 Hz, 2H), 3.59-3.51 (m, 2H), 2.67 (s, 3H) | MS (ESI$^+$) m/z 408 [M + H]$^+$ |

-continued

| Example | Name | NMR | MS |
|---|---|---|---|
| Example 218 | 1-[1-(2-fluorophenyl)-1H-indazol-4-yl]-3-(pyrimidin-2-ylmethyl)imidazolidin-2-one | $^1$H NMR (400 MHz, DMSO-$d_6$) δ ppm 8.84 (d, J = 4.9 Hz, 2H), 8.41 (d, J = 1.0 Hz, 1H), 7.68 (td, J = 7.8, 1.7 Hz, 1H), 7.63-7.51 (m, 2H), 7.49-7.37 (m, 3H), 7.21 (d, J = 7.6 Hz, 1H), 7.14-7.04 (m, 1H), 4.70 (s, 2H), 4.20-4.10 (m, 2H), 3.78-3.68 (m, 2H) | MS (ESI$^+$) m/z 389 [M + H]$^+$ |
| Example 219 | 1-[1-(2-fluorophenyl)-1H-indazol-4-yl]-3-[(5-methylpyrimidin-2-yl)methyl]imidazolidin-2-one | $^1$H NMR (400 MHz, DMSO-$d_6$) δ ppm 8.68 (d, J = 0.8 Hz, 2H), 8.41 (d, J = 1.1 Hz, 1H), 7.68 (td, J = 7.9, 1.7 Hz, 1H), 7.63-7.51 (m, 2H), 7.47-7.39 (m, 2H), 7.20 (d, J = 7.5 Hz, 1H), 7.13-7.04 (m, 1H), 4.65 (s, 2H), 4.18-4.08 (m, 2H), 3.75-3.66 (m, 2H), 2.29 (s, 3H) | MS (ESI$^+$) m/z 403 [M + H]$^+$ |
| Example 220 | 1-[1-(2-fluorophenyl)-1H-indazol-4-yl]-3-[2-(pyridin-3-yl)ethyl]imidazolidin-2-one | $^1$H NMR (400 MHz, DMSO-$d_6$) δ ppm 8.54 (dd, J = 2.4, 0.9 Hz, 1H), 8.44 (dd, J = 4.8, 1.7 Hz, 1H), 8.24 (d, J = 1.0 Hz, 1H), 7.76 (dt, J = 7.8, 2.0 Hz, 1H), 7.66 (td, J = 7.8, 1.7 Hz, 1H), 7.62-7.50 (m, 2H), 7.47-7.32 (m, 3H), 7.09 (d, J = 7.6 Hz, 1H), 7.05 (dd, J = 8.4, 3.1 Hz, 1H), 4.06-3.97 (m, 2H), 3.63-3.52 (m, 4H), 2.92 (t, J = 7.0 Hz, 2H) | MS (ESI$^+$) m/z 402 [M + H]$^+$ |
| Example 221 | 1-[1-(2-fluorophenyl)-1H-indazol-4-yl]-3-(1,3-thiazol-2-yl)imidazolidin-2-one | $^1$H NMR (400 MHz, DMSO-$d_6$) δ ppm 8.47 (d, J = 0.9 Hz, 1H), 7.70 (td, J = 7.8, 1.7 Hz, 1H), 7.66-7.53 (m, 2H), 7.53-7.43 (m, 3H), 7.32 (d, J = 7.6 Hz, 1H), 7.27 (d, J = 3.6 Hz, 1H), 7.22 (dd, J = 8.4, 2.9 Hz, 1H), 4.37-4.21 (m, 4H) | MS (ESI$^+$) m/z 480 [M + H]$^+$ |
| Example 222 | 1-[1-(2-fluorophenyl)-1H-indazol-4-yl]-3-(pyrimidin-4-ylmethyl)imidazolidin-2-one | $^1$H NMR (400 MHz, DMSO-$d_6$) δ ppm 9.18 (d, J = 1.4 Hz, 1H), 8.81 (d, J = 5.2 Hz, 1H), 8.44 (d, J = 1.0 Hz, 1H), 7.68 (td, J = 7.8, 1.7 Hz, 1H), 7.63-7.51 (m, 3H), 7.50-7.40 (m, 2H), 7.22 (d, J = 7.6 Hz, 1H), 7.10 (dd, J = 8.4, 3.0 Hz, 1H), 4.60 (s, 2H), 4.23-4.10 (m, 2H), 3.71-3.61 (m, 2H) | MS (ESI$^+$) m/z 489 [M + H]$^+$ |
| Example 223 | 1-[1-(2-fluorophenyl)-1H-indazol-4-yl]-3-(oxetan-2-ylmethyl)imidazolidin-2-one | $^1$H NMR (400 MHz, methanol-$d_4$) δ ppm 8.39 (d, J = 0.5 Hz, 1H), 7.61 (td, J = 7.7, 1.6 Hz, 1H), 7.58-7.51 (m, 1H), 7.48-7.36 (m, 3H), 7.16-7.07 (m, 2H), 5.10 (ddd, J = 14.0, 6.8, 3.6 Hz, 1H), 4.76-4.68 (m, 1H), 4.62 (dt, J = 9.2, 5.9 Hz, 1H), 4.16-4.03 (m, 2H), 3.84 (td, J = 8.9, 6.3 Hz, 1H), 3.77-3.65 (m, 2H), 3.49 (dd, J = 14.7, 3.6 Hz, 1H), 2.81-2.69 (m, 1H), 2.65-2.52 (m, 1H) | MS (ESI$^+$) m/z 367 [M + H]$^+$ |
| Example 224 | 1-[1-(2-fluorophenyl)-1H-indazol-4-yl]-3-[(3S)-tetrahydrofuran-3-yl]imidazolidin-2-one | $^1$H NMR (400 MHz, methanol-$d_4$) δ ppm 8.39 (d, J = 0.9 Hz, 1H), 7.61 (td, J = 7.7, 1.6 Hz, 1H), 7.58-7.50 (m, 1H), 7.45-7.36 (m, 3H), 7.12 (dd, J = 8.5, 2.9 Hz, 1H), 7.08 (d, J = 7.5 Hz, 1H), 4.74-4.63 (m, 1H), 4.11-3.98 (m, 3H), 3.94 (dd, J = 9.6, 3.5 Hz, 1H), 3.86-3.75 (m, 2H), 3.70-3.64 (m, 2H), 2.36-2.23 (m, 1H), 2.16-2.02 (m, 1H) | MS (ESI$^+$) m/z 367 [M + H]$^+$ |
| Example 225 | 1-[1-(2-fluorophenyl)-1H-indazol-4-yl]-3-(1,3-oxazol-4-ylmethyl)tetrahydropyrimidin-2(1H)-one | $^1$H NMR (400 MHz, CDCl$_3$) δ ppm 8.13 (d, J = 1.0 Hz, 1H), 7.87 (d, J = 0.9 Hz, 1H), 7.72 (t, J = 0.9 Hz, 1H), 7.59 (td, J = 7.7, 1.9 Hz, 1H), 7.47-7.34 (m, 2H), 7.34-7.27 (m, 2H), 7.22 (ddt, J = 8.5, 3.4, 0.9 Hz, 1H), 7.04 (dd, J = 7.5, 0.7 Hz, 1H), 4.56 (d, J = | MS (ESI$^+$) m/z 392 (M + H)$^+$ |

-continued

| Example | Name | NMR | MS |
|---------|------|-----|-----|
| | | 0.8 Hz, 2H), 3.92-3.78 (m, 2H), 3.68 (t, J = 6.0 Hz, 2H), 2.30-2.13 (m, 2H). | |
| Example 226 | 1-[1-(2-fluorophenyl)-1H-indazol-4-yl]-3-(pyrazin-2-yl)imidazolidin-2-one | $^1$H NMR (400 MHz, DMSO-$d_6$) δ ppm 9.54 (d, J = 1.5 Hz, 1H), 8.49 (d, J = 0.9 Hz, 1H), 8.44 (dd, J = 2.7, 1.6 Hz, 1H), 8.32 (d, J = 2.6 Hz, 1H), 7.71 (td, J = 7.9, 1.6 Hz, 1H), 7.64-7.53 (m, 2H), 7.53-7.42 (m, 2H), 7.29 (d, J = 7.6 Hz, 1H), 7.23 (dd, J = 8.4, 3.0 Hz, 1H), 4.32-4.15 (m, 4H) | MS (ESI$^+$) m/z 375 [M + H]$^+$ |
| Example 227 | 1-[(2,5-dimethyl-1,3-oxazol-4-yl)methyl]-3-[1-(2-fluorophenyl)-1H-indazol-4-yl]imidazolidin-2-one | $^1$H NMR (400 MHz, DMSO-$d_6$) δ ppm 8.43 (d, J = 1.0 Hz, 1H), 7.68 (td, J = 7.8, 1.7 Hz, 1H), 7.63-7.51 (m, 2H), 7.47-7.38 (m, 2H), 7.18 (d, J = 7.6 Hz, 1H), 7.12-7.04 (m, 1H), 4.26 (s, 2H), 4.09-3.98 (m, 2H), 3.56-3.45 (m, 2H), 2.35 (s, 3H), 2.32 (s, 3H) | MS (ESI$^+$) m/z 406 [M + H]$^+$ |
| Example 228 | 1-[1-(2-fluorophenyl)-1H-indazol-4-yl]-3-[(5-methylpyridin-3-yl)methyl]imidazolidin-2-one | $^1$H NMR (400 MHz, DMSO-$d_6$) δ ppm 8.45 (d, J = 1.0 Hz, 1H), 8.39 (dd, J = 9.6, 2.1 Hz, 2H), 7.68 (td, J = 7.8, 1.7 Hz, 1H), 7.63-7.50 (m, 3H), 7.48-7.39 (m, 2H), 7.21 (d, J = 7.6 Hz, 1H), 7.10 (dd, J = 8.5, 2.9 Hz, 1H), 4.48 (s, 2H), 4.13-4.02 (m, 2H), 3.52-3.45 (m, 2H), 2.33 (s, 3H) | MS (ESI$^+$) m/z 402 [M + H]$^+$ |
| Example 229 | 1-{[1-(benzyloxy)cyclopropyl]methyl}-3-[1-(2-fluorophenyl)-1H-indazol-4-yl]imidazolidin-2-one | $^1$H NMR (400 MHz, methanol-$d_4$) δ ppm 8.32 (d, J = 0.9 Hz, 1H), 7.60 (td, J = 7.7, 1.6 Hz, 1H), 7.58-7.51 (m, 1H), 7.46-7.37 (m, 3H), 7.36-7.22 (m, 5H), 7.11 (dd, J = 8.5, 2.9 Hz, 1H), 7.08 (d, J = 7.5 Hz, 1H), 4.67 (s, 2H), 4.07 (dd, J = 9.0, 6.8 Hz, 2H), 3.82 (dd, J = 9.2, 6.7 Hz, 2H), 3.64 (s, 2H), 1.03-0.93 (m, 2H), 0.76-0.69 (m, 2H) | MS (ESI$^+$) m/z 457 [M + H]$^+$ |
| Example 230 | 1-[1-(2-fluorophenyl)-1H-indazol-4-yl]-3-(5-methoxypyridin-3-yl)imidazolidin-2-one | $^1$H NMR (400 MHz, DMSO-$d_6$) δ ppm 8.48 (d, J = 2.1 Hz, 1H), 8.46 (s, 1H), 8.07 (d, J = 2.5 Hz, 1H), 7.80 (t, J = 2.4 Hz, 1H), 7.70 (td, J = 7.8, 1.6 Hz, 1H), 7.64-7.53 (m, 2H), 7.52-7.41 (m, 2H), 7.26 (d, J = 7.6 Hz, 1H), 7.19 (dd, J = 8.4, 2.9 Hz, 1H), 4.30-4.21 (m, 2H), 4.18-4.09 (m, 2H), 3.86 (s, 3H) | MS (ESI$^+$) m/z 404 [M + H]$^+$ |
| Example 231 | 1-[1-(2-fluorophenyl)-1H-indazol-4-yl]-3-(1,3-oxazol-5-ylmethyl)imidazolidin-2-one | $^1$H NMR (400 MHz, DMSO-$d_6$) δ ppm 8.43 (d, J = 0.8 Hz, 1H), 8.38 (s, 1H), 7.68 (td, J = 7.8, 1.7 Hz, 1H), 7.62-7.51 (m, 2H), 7.48-7.39 (m, 2H), 7.25-7.17 (m, 2H), 7.10 (dd, J = 8.4, 2.9 Hz, 1H), 4.57 (s, 2H), 4.07 (dd, J = 8.8, 6.7 Hz, 2H), 3.56-3.48 (m, 2H) | MS (ESI$^+$) m/z 378 [M + H]$^+$ |
| Example 232 | 1-(1-benzyl-2-oxopyrrolidin-3-yl)-3-[1-(2-fluorophenyl)-1H-indazol-4-yl]imidazolidin-2-one | $^1$H NMR (400 MHz, methanol-$d_4$) δ ppm 8.46 (s, 1H), 7.62 (td, J = 7.7, 1.4 Hz, 1H), 7.59-7.52 (m, 1H), 7.49-7.26 (m, 8H), 7.17-7.09 (m, 2H), 4.80 (d, J = 9.8 Hz, 1H), 4.59 (d, J = 14.8 Hz, 1H), 4.48 (d, J = 14.8 Hz, 1H), 4.21-4.05 (m, 2H), 3.81-3.70 (m, 1H), 3.64-3.54 (m, 1H), 3.37 (dd, J = 9.2, 4.5 Hz, 2H), 2.44-2.35 (m, 1H), 2.29-2.16 (m, 1H) | MS (ESI$^+$) m/z 470 [M + H]$^+$ |
| Example 233 | 1-[(5-tert-butyl-1,3-oxazol-2-yl)methyl]-3-[1-(2-fluorophenyl)-1H-indazol-4-yl]imidazolidin-2-one | $^1$H NMR (500 MHz, DMSO-$d_6$) δ ppm 8.40 (d, J = 0.9 Hz, 1H), 7.68 (td, J = 7.9, 1.7 Hz, 1H), 7.63-7.52 (m, 2H), 7.47-7.41 (m, 2H), 7.19 (d, J = 7.6 Hz, 1H), 7.11 (dd, J = 8.4, 2.9 Hz, 1H), | MS (ESI$^+$) m/z 434 [M + H]$^+$ |

| Example | Name | NMR | MS |
|---|---|---|---|
| | | 6.82 (s, 1H), 4.57 (s, 2H), 4.11 (dd, J = 8.7, 6.7 Hz, 2H), 3.69-3.57 (m, 2H), 1.27 (s, 9H) | |
| Example 234 | 1-[1-(2,4-difluorophenyl)-1H-indazol-4-yl]-3-[(5-methyl-1,3,4-thiadiazol-2-yl)methyl]imidazolidin-2-one | $^1$H NMR (500 MHz, methanol-$d_4$) δ ppm 8.41 (d, J = 1.0 Hz, 1H), 7.66 (td, J = 8.7, 5.8 Hz, 1H), 7.49-7.43 (m, 1H), 7.32 (ddd, J = 11.1, 8.7, 2.8 Hz, 1H), 7.21 (tdd, J = 9.0, 2.8, 1.4 Hz, 1H), 7.17-7.11 (m, 2H), 4.92 (s, 2H), 4.12 (dd, J = 8.8, 6.8 Hz, 2H), 3.72 (dd, J = 8.8, 6.9 Hz, 2H), 2.79 (s, 3H) | MS (ESI$^+$) m/z 427 [M + H]$^+$ |
| Example 235 | 1-(1,3-oxazol-2-ylmethyl)-3-{1-[4-(trifluoromethyl)phenyl]-1H-indazol-4-yl}imidazolidin-2-one | $^1$H NMR (500 MHz, methanol-$d_4$) δ ppm 8.42 (s, 1H), 7.99-7.86 (m, 5H), 7.68 (d, J = 8.5 Hz, 1H), 7.54-7.48 (m, 1H), 7.22-7.12 (m, 2H), 4.70 (s, 2H), 4.18-4.06 (m, 2H), 3.76-3.68 (m, 2H) | MS (ESI$^+$) m/z 428 [M + H]$^+$ |
| Example 236 | 1-(3,5-dimethyl-1,2-oxazol-4-yl)-3-[1-(2-fluorophenyl)-1H-indazol-4-yl]imidazolidin-2-one | $^1$H NMR (400 MHz, DMSO-$d_6$) δ ppm 8.41 (d, J = 0.8 Hz, 1H), 7.68 (td, J = 7.9, 1.6 Hz, 1H), 7.64-7.51 (m, 2H), 7.49-7.41 (m, 2H), 7.22 (d, J = 7.6 Hz, 1H), 7.15 (dd, J = 8.4, 2.9 Hz, 1H), 4.22 (dd, J = 9.0, 6.7 Hz, 2H), 3.94 (dd, J = 8.9, 6.7 Hz, 2H), 2.38 (s, 3H), 2.30 (s, 3H) | MS (ESI$^+$) m/z 392 [M + H]$^+$ |
| Example 237 | 1-[1-(2-fluorophenyl)-1H-indazol-4-yl]-3-[(5-isopropyl-1,3-oxazol-2-yl)methyl]imidazolidin-2-one | $^1$H NMR (500 MHz, DMSO-$d_6$) δ ppm 8.41 (d, J = 0.9 Hz, 1H), 7.68 (td, J = 7.8, 1.7 Hz, 1H), 7.62-7.52 (m, 2H), 7.47-7.41 (m, 2H), 7.20 (d, J = 7.6 Hz, 1H), 7.11 (dd, J = 8.4, 2.9 Hz, 1H), 6.84 (d, J = 1.2 Hz, 1H), 4.57 (s, 2H), 4.11 (dd, J = 8.8, 6.7 Hz, 2H), 3.67-3.59 (m, 2H), 2.99 (heptd, J = 6.8, 1.0 Hz, 1H), 1.23 (d, J = 6.9 Hz, 6H) | MS (ESI$^+$) m/z 420 [M + H]$^+$ |
| Example 238 | 1-[(4,5-dimethyl-1,3-oxazol-2-yl)methyl]-3-[1-(2-fluorophenyl)-1H-indazol-4-yl]imidazolidin-2-one | $^1$H NMR (500 MHz, DMSO-$d_6$) δ ppm 8.42 (d, J = 0.9 Hz, 1H), 7.68 (td, J = 7.8, 1.7 Hz, 1H), 7.63-7.51 (m, 2H), 7.47-7.40 (m, 2H), 7.21 (d, J = 7.6 Hz, 1H), 7.11 (dd, J = 8.4, 3.0 Hz, 1H), 4.50 (s, 2H), 4.13-4.07 (m, 2H), 3.64-3.57 (m, 2H), 2.24 (d, J = 1.1 Hz, 3H), 2.03 (d, J = 1.1 Hz, 3H) | MS (ESI$^+$) m/z 406 [M + H]$^+$ |
| Example 239 | 1-[(2,5-dimethyl-1,3-thiazol-4-yl)methyl]-3-[1-(2-fluorophenyl)-1H-indazol-4-yl]imidazolidin-2-one | $^1$H NMR (500 MHz, DMSO-$d_6$) δ ppm 8.43 (d, J = 0.9 Hz, 1H), 7.67 (td, J = 7.9, 1.7 Hz, 1H), 7.63-7.51 (m, 2H), 7.47-7.38 (m, 2H), 7.18 (d, J = 7.6 Hz, 1H), 7.08 (dd, J = 8.4, 2.9 Hz, 1H), 4.43 (s, 2H), 4.07-4.00 (m, 2H), 3.55-3.48 (m, 2H), 2.58 (s, 3H), 2.44 (s, 3H) | MS (ESI$^+$) m/z 422 [M + H]$^+$ |
| Example 240 | 1-[(5-methyl-1,3,4-thiadiazol-2-yl)methyl]-3-{1-[4-(trifluoromethyl)phenyl]-1H-indazol-4-yl}imidazolidin-2-one | $^1$H NMR (500 MHz, methanol-$d_4$) δ ppm 8.41 (s, 1H), 7.97 (d, J = 8.5 Hz, 2H), 7.88 (d, J = 8.6 Hz, 2H), 7.69 (d, J = 8.5 Hz, 1H), 7.54-7.48 (m, 1H), 7.16 (d, J = 7.6 Hz, 1H), 4.91 (s, 2H), 4.13-4.07 (m, 2H), 3.74-3.67 (m, 2H), 2.79 (s, 3H) | MS (ESI$^+$) m/z 459 [M + H]$^+$ |
| Example 241 | tert-butyl(5R)-3-[1-(2-fluorophenyl)-1H-indazol-4-yl]-5-methyl-2-oxoimidazolidine-1-carboxylate | $^1$H NMR (400 MHz, methanol-$d_4$) δ ppm 8.36 (s, 1H), 7.62 (td, J = 7.7, 1.5 Hz, 1H), 7.59-7.52 (m, 1H), 7.50-7.45 (m, 1H), 7.45-7.38 (m, 2H), 7.22 (dd, J = 8.5, 2.8 Hz, 1H), 7.16 (d, J = 7.5 Hz, 1H), 4.52-4.41 (m, 1H), 4.36 (t, J = 8.8 Hz, 1H), 3.57 (dd, J = 9.0, 2.6 Hz, 1H), 1.58 (s, 9H), 1.53 (d, J = 6.2 Hz, 3H) | MS (ESI$^+$) m/z 432 [M + Na]$^+$ |

-continued

| Example | Name | NMR | MS |
|---|---|---|---|
| Example 242 | 1-(1,3-oxazol-4-ylmethyl)-3-{1-[4-(trifluoromethyl)phenyl]-1H-indazol-4-yl}imidazolidin-2-one | $^1$H NMR (500 MHz, methanol-d$_4$) δ ppm 8.44 (d, J = 0.5 Hz, 1H), 8.22 (s, 1H), 8.00-7.95 (m, 3H), 7.88 (d, J = 8.6 Hz, 2H), 7.66 (d, J = 8.5 Hz, 1H), 7.54-7.45 (m, 1H), 7.14 (d, J = 7.6 Hz, 1H), 4.49 (s, 2H), 4.10-4.01 (m, 2H), 3.69-3.57 (m, 2H) | MS (ESI$^+$) m/z 428 [M + H]$^+$ |
| Example 243 | 1-[1-(2,4-difluorophenyl)-1H-indazol-4-yl]-3-[(2-methyl-1,3-thiazol-4-yl)methyl]imidazolidin-2-one | $^1$H NMR (400 MHz, DMSO-d$_6$) δ ppm 8.45 (s, 1H), 7.75 (td, J = 8.8, 5.9 Hz, 1H), 7.63 (ddd, J = 11.3, 9.0, 2.8 Hz, 1H), 7.46-7.38 (m, 2H), 7.38-7.30 (m, 1H), 7.20 (d, J = 7.6 Hz, 1H), 7.08 (dd, J = 8.4, 2.6 Hz, 1H), 4.50 (s, 2H), 4.07 (dd, J = 8.8, 6.7 Hz, 2H), 3.55 (dd, J = 8.8, 6.7 Hz, 2H), 2.67 (s, 3H) | MS (ESI$^+$) m/z 426 [M + H]$^+$ |
| Example 244 | 1-[1-(2-fluorophenyl)-1H-indazol-4-yl]-3-[(3-methyl-1,2-oxazol-5-yl)methyl]imidazolidin-2-one | $^1$H NMR (400 MHz, DMSO-d$_6$) δ ppm 8.43 (s, 1H), 7.68 (td, J = 7.9, 1.6 Hz, 1H), 7.63-7.50 (m, 2H), 7.48-7.39 (m, 2H), 7.21 (d, J = 7.6 Hz, 1H), 7.11 (dd, J = 8.3, 2.9 Hz, 1H), 6.40 (s, 1H), 4.60 (s, 2H), 4.10 (dd, J = 8.8, 6.7 Hz, 2H), 3.58 (dd, J = 8.7, 6.7 Hz, 2H), 2.25 (s, 3H) | MS (ESI$^+$) m/z 392 [M + H]$^+$ |
| Example 245 | 1-[1-(2-fluorophenyl)-1H-indazol-4-yl]-3-[(5-methyl-1,3-thiazol-4-yl)methyl]imidazolidin-2-one | $^1$H NMR (400 MHz, DMSO-d$_6$) δ ppm 8.90 (s, 1H), 8.42 (s, 1H), 7.67 (td, J = 7.9, 1.6 Hz, 1H), 7.62-7.52 (m, 2H), 7.47-7.39 (m, 2H), 7.18 (d, J = 7.6 Hz, 1H), 7.08 (dd, J = 8.4, 3.0 Hz, 1H), 4.54 (s, 2H), 4.04 (dd, J = 8.8, 6.8 Hz, 2H), 3.59-3.48 (m, 2H), 2.52 (s, 3H) | MS (ESI$^+$) m/z 408 [M + H]$^+$ |
| Example 246 | (4R)-1-[1-(2-fluorophenyl)-1H-indazol-4-yl]-4-methylimidazolidin-2-one | $^1$H NMR (500 MHz, methanol-d$_4$) δ ppm 1.39 (d, J = 6.2 Hz, 3H), 3.73 (dd, J = 8.8, 6.7 Hz, 1H), 4.01-4.08 (m, 1H), 4.24 (t, J = 8.5 Hz, 1H), 7.09 (d, J = 7.6 Hz, 1H), 7.12 (dd, J = 8.4, 2.9 Hz, 1H), 7.38-7.46 (m, 3H), 7.52-7.58 (m, 1H), 7.61 (td, J = 7.7, 1.6 Hz, 1H), 8.39 (d, J = 0.9 Hz, 1H) | MS (ESI$^+$) m/z 311 [M + H]$^+$ |
| Example 247 | (4R)-1-[1-(2-fluorophenyl)-1H-indazol-4-yl]-4-methyl-3-(1,3-oxazol-2-ylmethyl)imidazolidin-2-one | $^1$H NMR (400 MHz, DMSO-d$_6$) δ ppm 1.31 (d, J = 6.1 Hz, 3H), 3.72 (t, J = 8.4 Hz, 1H), 3.85-3.97 (m, 1H), 4.21 (t, J = 8.5 Hz, 1H), 4.53 (d, J = 16.6 Hz, 1H), 4.74 (d, J = 16.6 Hz, 1H), 7.10 (dd, J = 8.4, 2.9 Hz, 1H), 7.16-7.24 (m, 2H), 7.38-7.47 (m, 2H), 7.51-7.63 (m, 2H), 7.68 (td, J = 7.8, 1.3 Hz, 1H), 8.13 (s, 1H), 8.42 (s, 1H) | MS (ESI$^+$) m/z 392 [M + H]$^+$ |
| Example 248 | 1-[1-(2-fluorophenyl)-1H-indazol-4-yl]-3-[(3-methoxypyrazin-2-yl)methyl]imidazolidin-2-one | $^1$H NMR (400 MHz, DMSO-d$_6$) δ ppm 8.40 (d, J = 0.9 Hz, 1H), 8.22-8.16 (m, 2H), 7.67 (td, J = 7.9, 1.7 Hz, 1H), 7.63-7.51 (m, 2H), 7.48-7.39 (m, 2H), 7.19 (d, J = 7.6 Hz, 1H), 7.08 (dd, J = 8.4, 3.0 Hz, 1H), 4.61 (s, 2H), 4.12 (dd, J = 8.8, 6.7 Hz, 2H), 3.99 (s, 3H), 3.74-3.62 (m, 2H) | MS (ESI$^+$) m/z 419 [M + H]$^+$ |
| Example 249 | 1-[1-(2-fluorophenyl)-1H-indazol-4-yl]-3-[(3-isopropyl-1,2-oxazol-5-yl)methyl]imidazolidin-2-one | $^1$H NMR (400 MHz, DMSO-d$_6$) δ ppm 8.43 (d, J = 1.0 Hz, 1H), 7.68 (td, J = 7.8, 1.7 Hz, 1H), 7.63-7.51 (m, 2H), 7.48-7.38 (m, 2H), 7.21 (d, J = 7.6 Hz, 1H), 7.11 (dd, J = 8.4, 2.9 Hz, 1H), 6.50 (s, 1H), 4.60 (s, 2H), 4.11 (dd, J = 8.8, 6.7 Hz, 2H), 3.64-3.54 (m, 2H), 3.01 (hept, J = 6.9 Hz, 1H), 1.24 (d, J = 6.9 Hz, 6H) | MS (ESI$^+$) m/z 420 [M + H]$^+$ |

| Example | Name | NMR | MS |
|---|---|---|---|
| Example 250 | 1-[(2-ethyl-1,3-thiazol-4-yl)methyl]-3-[1-(2-fluorophenyl)-1H-indazol-4-yl]imidazolidin-2-one | $^1$H NMR (400 MHz, DMSO-$d_6$) δ ppm 8.45 (d, J = 1.2 Hz, 1H), 7.68 (td, J = 7.9, 1.7 Hz, 1H), 7.63-7.51 (m, 2H), 7.48-7.39 (m, 3H), 7.19 (d, J = 7.6 Hz, 1H), 7.09 (dd, J = 8.4, 3.0 Hz, 1H), 4.52 (s, 2H), 4.14-4.04 (m, 2H), 3.62-3.52 (m, 2H), 3.00 (q, J = 7.5 Hz, 2H), 1.31 (t, J = 7.5 Hz, 3H) | MS (ESI$^+$) m/z 422 [M + H]$^+$ |
| Example 251 | 1-[1-(2-fluorophenyl)-1H-indazol-4-yl]-3-[(5-isopropyl-1,2-oxazol-3-yl)methyl]imidazolidin-2-one | $^1$H NMR (400 MHz, DMSO-$d_6$) δ ppm 8.44 (d, J = 0.8 Hz, 1H), 7.68 (td, J = 7.8, 1.7 Hz, 1H), 7.63-7.51 (m, 2H), 7.48-7.39 (m, 2H), 7.20 (d, J = 7.6 Hz, 1H), 7.16-7.07 (m, 1H), 6.27 (d, J = 0.8 Hz, 1H), 4.50 (s, 2H), 4.17-4.01 (m, 2H), 3.62-3.53 (m, 2H), 3.10 (heptd, J = 6.9, 0.9 Hz, 1H), 1.26 (d, J = 7.0 Hz, 6H) | MS (ESI$^+$) m/z 420 [M + H]$^+$ |
| Example 252 | 1-[(5-cyclopropyl-1,2-oxazol-3-yl)methyl]-3-[1-(2-fluorophenyl)-1H-indazol-4-yl]imidazolidin-2-one | $^1$H NMR (500 MHz, DMSO-$d_6$) δ ppm 8.44 (s, 1H), 7.68 (td, J = 7.8, 1.6 Hz, 1H), 7.63-7.52 (m, 2H), 7.48-7.39 (m, 2H), 7.20 (d, J = 7.6 Hz, 1H), 7.10 (dd, J = 8.4, 2.9 Hz, 1H), 6.24 (s, 1H), 4.47 (s, 2H), 4.08 (dd, J = 8.8, 6.7 Hz, 2H), 3.61-3.49 (m, 2H), 2.15 (tt, J = 8.4, 5.0 Hz, 1H), 1.09-1.04 (m, 2H), 0.95-0.86 (m, 2H) | MS (ESI$^+$) m/z 418 [M + H]$^+$ |
| Example 253 | 1-[1-(2,4-difluorophenyl)-1H-indazol-4-yl]-3-[(1R)-1-(3-methyl-1,2,4-oxadiazol-5-yl)ethyl]imidazolidin-2-one | $^1$H NMR (400 MHz, methanol-$d_4$) δ ppm 1.74 (d, J = 7.3 Hz, 3H), 2.40 (s, 3H), 3.66 (dd, J = 16.5, 8.4 Hz, 1H), 3.80 (td, J = 8.7, 5.9 Hz, 1H), 4.03-4.24 (m, 2H), 5.46 (dd, J = 14.6, 7.3 Hz, 1H), 7.09-7.17 (m, 2H), 7.17-7.24 (m, 1H), 7.27-7.34 (m, 1H), 7.46 (t, J = 8.0 Hz, 1H), 7.65 (td, J = 8.7, 5.9 Hz, 1H), 8.37 (s, 1H) | MS (ESI$^+$) m/z 425 [M + H]$^+$ |
| Example 254 | 1-[1-(2-fluorophenyl)-1H-indazol-4-yl]-3-{[2-(methoxymethyl)-1,3-thiazol-4-yl]methyl}imidazolidin-2-one | $^1$H NMR (500 MHz, DMSO-$d_6$) δ ppm 8.45 (s, 1H), 7.68 (td, J = 7.8, 1.7 Hz, 1H), 7.63-7.53 (m, 3H), 7.47-7.39 (m, 2H), 7.20 (d, J = 7.6 Hz, 1H), 7.09 (dd, J = 8.4, 2.9 Hz, 1H), 4.71 (s, 2H), 4.55 (s, 2H), 4.08 (dd, J = 8.8, 6.7 Hz, 2H), 3.56 (dd, J = 8.7, 6.8 Hz, 2H), 3.41 (s, 3H) | MS (ESI$^+$) m/z 438 [M + H]$^+$ |
| Example 255 | 1-[1-(2-fluorophenyl)-1H-indazol-4-yl]-3-(1,3-oxazol-2-ylmethyl)tetrahydropyrimidin-2(1H)-one | $^1$H NMR (400 MHz, methanol-$d_4$) δ ppm 2.24-2.34 (m, 2H), 3.64 (t, J = 6.0 Hz, 2H), 3.87-3.93 (m, 2H), 4.77 (s, 2H), 7.14 (d, J = 7.4 Hz, 1H), 7.18 (s, 1H), 7.24 (dd, J = 8.5, 2.8 Hz, 1H), 7.42 (ddd, J = 14.9, 11.7, 6.2 Hz, 3H), 7.51-7.58 (m, 1H), 7.61 (td, J = 7.7, 1.5 Hz, 1H), 7.92 (s, 1H), 8.25 (s, 1H) | MS (ESI$^+$) m/z 392 [M + H]$^+$ |
| Example 256 | 1-[1-(2-fluorophenyl)-1H-indazol-4-yl]-3-[(5-isopropyl-1,3,4-oxadiazol-2-yl)methyl]imidazolidin-2-one | $^1$H NMR (400 MHz, DMSO-$d_6$) δ ppm 8.41 (s, 1H), 7.68 (td, J = 7.9, 1.6 Hz, 1H), 7.64-7.50 (m, 2H), 7.44 (td, J = 7.9, 2.9 Hz, 2H), 7.21 (d, J = 7.6 Hz, 1H), 7.12 (dd, J = 8.4, 2.9 Hz, 1H), 4.74 (s, 2H), 4.12 (dd, J = 8.8, 6.7 Hz, 2H), 3.65 (dd, J = 8.7, 6.7 Hz, 2H), 3.23 (hept, J = 7.0 Hz, 1H), 1.32 (d, J = 7.0 Hz, 6H) | MS (APCI) m/z 421 [M + H]$^+$ |
| Example 257 | 1-[1-(2-fluorophenyl)-1H-indazol-4-yl]-3-[(5-methylpyrazin-2-yl)methyl]imidazolidin-2-one | $^1$H NMR (500 MHz, DMSO-$d_6$) δ ppm 8.56 (dd, J = 14.1, 1.4 Hz, 2H), 8.43 (d, J = 0.9 Hz, 1H), 7.68 (td, J = 7.8, 1.7 Hz, 1H), 7.63-7.51 (m, 2H), 7.48-7.39 (m, 2H), 7.20 (d, J = 7.6 Hz, 1H), 7.09 (dd, J = 8.4, 3.0 Hz, 1H), 4.60 (s, 2H), 4.10 (dd, J = 8.8, 6.7 | MS (ESI$^+$) m/z 403 [M + H]$^+$ |

-continued

| Example | Name | NMR | MS |
|---|---|---|---|
| | | Hz, 2H), 3.63-3.56 (m, 2H), 2.51 (s, 3H) | |
| Example 258 | 1-[(3,5-dimethyl-1,2-oxazol-4-yl)methyl]-3-[1-(2-fluorophenyl)-1H-indazol-4-yl]tetrahydropyrimidin-2(1H)-one | $^1$H NMR (400 MHz, methanol-d$_4$) δ ppm 2.17-2.25 (m, 2H), 2.30 (s, 3H), 2.45 (s, 3H), 3.41 (t, J = 6.0 Hz, 2H), 3.81-3.87 (m, 2H), 4.51 (s, 2H), 7.13 (d, J = 7.4 Hz, 1H), 7.26 (dd, J = 8.5, 2.8 Hz, 1H), 7.37-7.45 (m, 2H), 7.45-7.50 (m, 1H), 7.52-7.59 (m, 1H), 7.62 (td, J = 7.7, 1.5 Hz, 1H), 8.18 (s, 1H) | MS (DCI) m/z 420 [M + H]$^+$ |
| Example 259 | 1-[1-(2-fluorophenyl)-1H-indazol-4-yl]-3-[(6-methylpyrazin-2-yl)methyl]tetrahydropyrimidin-2(1H)-one | $^1$H NMR (400 MHz, methanol-d$_4$) δ ppm 2.17-2.39 (m, 2H), 2.61 (s, 3H), 3.66 (t, J = 6.0 Hz, 2H), 3.84-3.95 (m, 2H), 4.76 (s, 2H), 7.14 (d, J = 7.4 Hz, 1H), 7.24 (dd, 1H), 7.37-7.44 (m, 2H), 7.44-7.50 (m, 1H), 7.51-7.58 (m, 1H), 7.61 (td, J = 7.7, 1.3 Hz, 1H), 8.23 (s, 1H), 8.41 (s, 1H), 8.45 (s, 1H) | MS (ESI$^+$) m/z 417 [M + H]$^+$ |
| Example 260 | 1-[1-(2-fluorophenyl)-1H-indazol-4-yl]-3-[(5-methyl-1,3,4-oxadiazol-2-yl)methyl]tetrahydropyrimidin-2(1H)-one | $^1$H NMR (400 MHz, methanol-d$_4$) δ ppm 2.24-2.36 (m, 2H), 2.55 (s, 3H), 3.69 (t, J = 6.0 Hz, 2H), 3.82-3.99 (m, 2H), 7.15 (d, J = 7.4 Hz, 1H), 7.25 (dd, J = 8.5, 2.8 Hz, 1H), 7.37-7.45 (m, 2H), 7.45-7.50 (m, 1H), 7.51-7.58 (m, 1H), 7.61 (td, J = 7.7, 1.4 Hz, 1H), 8.24 (s, 1H) | MS (DCI) m/z 407 [M + H]$^+$ |
| Example 261 | 1-[(5-ethyl-1,3,4-oxadiazol-2-yl)methyl]-3-[1-(2-fluorophenyl)-1H-indazol-4-yl]imidazolidin-2-one | $^1$H NMR (400 MHz, DMSO-d$_6$) δ ppm 8.41 (d, J = 0.9 Hz, 1H), 7.68 (td, J = 7.8, 1.6 Hz, 1H), 7.64-7.52 (m, 2H), 7.49-7.41 (m, 2H), 7.21 (d, J = 7.6 Hz, 1H), 7.12 (dd, J = 8.4, 3.0 Hz, 1H), 4.73 (s, 2H), 4.18-4.07 (m, 2H), 3.70-3.59 (m, 2H), 2.89 (q, J = 7.6 Hz, 2H), 1.28 (t, J = 7.5 Hz, 3H) | MS (ESI$^+$) m/z 407 [M + H]$^+$ |
| Example 262 | 1-[(5-tert-butyl-1,3,4-oxadiazol-2-yl)methyl]-3-[1-(2-fluorophenyl)-1H-indazol-4-yl]imidazolidin-2-one | $^1$H NMR (400 MHz, DMSO-d$_6$) δ ppm 8.41 (d, J = 1.0 Hz, 1H), 7.68 (td, J = 7.8, 1.7 Hz, 1H), 7.63-7.52 (m, 2H), 7.48-7.40 (m, 2H), 7.20 (d, J = 7.6 Hz, 1H), 7.12 (dd, J = 8.4, 3.0 Hz, 1H), 4.74 (s, 2H), 4.19-4.07 (m, 2H), 3.71-3.60 (m, 2H), 1.38 (s, 9H) | MS (APCI) m/z 435 [M + H]$^+$ |
| Example 263 | 1-[1-(2-fluorophenyl)-1H-indazol-4-yl]-3-[(5-methyl-1,3-thiazol-2-yl)methyl]imidazolidin-2-one | $^1$H NMR (400 MHz, DMSO-d$_6$) δ ppm 8.44 (d, J = 1.0 Hz, 1H), 7.68 (td, J = 7.9, 1.7 Hz, 1H), 7.63-7.51 (m, 2H), 7.49-7.40 (m, 3H), 7.20 (d, J = 7.6 Hz, 1H), 7.11 (dd, J = 8.4, 2.9 Hz, 1H), 4.70 (s, 2H), 4.09 (dd, J = 8.8, 6.7 Hz, 2H), 3.64-3.56 (m, 2H), 2.45 (d, J = 1.2 Hz, 3H) | MS (APCI) m/z 408 [M + H]$^+$ |
| Example 264 | 1-[1-(2-fluorophenyl)-1H-indazol-4-yl]-3-[(3-methyl-1,2-oxazol-4-yl)methyl]imidazolidin-2-one | $^1$H NMR (500 MHz, DMSO-d$_6$) δ ppm 8.88 (s, 1H), 8.43 (s, 1H), 7.68 (td, J = 7.8, 1.7 Hz, 1H), 7.63-7.51 (m, 2H), 7.48-7.39 (m, 2H), 7.18 (d, J = 7.6 Hz, 1H), 7.09 (dd, J = 8.4, 2.9 Hz, 1H), 4.35 (s, 2H), 4.05 (dd, J = 8.6, 6.9 Hz, 2H), 3.49-3.43 (m, 2H), 2.29 (s, 3H) | MS (ESI$^+$) m/z 392 [M + H]$^+$ |
| Example 265 | 1-[1-(2-fluorophenyl)-1H-indazol-4-yl]-3-(trans-4-hydroxycyclohexyl)imidazolidin-2-one | $^1$H NMR (400 MHz, DMSO-d$_6$) δ ppm 8.45 (d, J = 0.9 Hz, 1H), 7.67 (td, J = 7.9, 1.6 Hz, 1H), 7.63-7.51 (m, 2H), 7.48-7.41 (m, 1H), 7.38 (d, J = 8.0 Hz, 1H), 7.31 (d, J = 7.6 Hz, 1H), 7.05 (dd, J = 8.3, 3.1 Hz, 1H), 4.50-4.40 (m, 3H), 4.13 (t, J = 7.1 Hz, 2H), 3.32 (s, 2H), 1.88-1.64 (m, 4H), 1.30-1.08 (m, 4H) | MS (ESI$^+$) m/z 395 [M + H]$^+$ |

-continued

| Example | Name | NMR | MS |
|---|---|---|---|
| Example 266 | 1-[1-(2-fluorophenyl)-1H-indazol-4-yl]-3-(4-oxocyclohexyl)imidazolidin-2-one | $^1$H NMR (400 MHz, DMSO-d$_6$) δ ppm 8.48 (s, 1H), 7.67 (td, J = 7.9, 1.7 Hz, 1H), 7.62-7.51 (m, 2H), 7.49-7.36 (m, 3H), 7.12-7.03 (m, 1H), 4.52 (t, J = 7.2 Hz, 2H), 4.21 (t, J = 7.2 Hz, 2H), 3.98 (tt, J = 7.8, 3.6 Hz, 1H), 2.40-2.07 (m, 4H), 2.02-1.90 (m, 2H), 1.78-1.57 (m, 2H) | MS (ESI$^+$) m/z 393 [M + H]$^+$ |
| Example 267 | tert-butyl 3-{3-[1-(2-fluorophenyl)-1H-indazol-4-yl]-2-oxoimidazolidin-1-yl}azetidine-1-carboxylate | $^1$H NMR (500 MHz, DMSO-d$_6$) δ ppm 8.41 (s, 1H), 7.67 (td, J = 8.0, 1.7 Hz, 1H), 7.60-7.52 (m, 2H), 7.47-7.38 (m, 2H), 7.17 (d, J = 7.6 Hz, 1H), 7.09 (dd, J = 8.4, 2.9 Hz, 1H), 4.78-4.72 (m, 1H), 4.14-4.05 (m, 6H), 3.75 (dd, J = 8.7, 6.7 Hz, 2H), 1.41 (s, 9H) | MS (APCI) m/z 452 [M + H]$^+$ |
| Example 268 | 1-(azetidin-3-yl)-3-[1-(2-fluorophenyl)-1H-indazol-4-yl]imidazolidin-2-one | $^1$H NMR (400 MHz, DMSO-d$_6$) δ ppm 8.41 (s, 1H), 7.67 (td, J = 7.8, 1.7 Hz, 1H), 7.63-7.50 (m, 2H), 7.47-7.38 (m, 2H), 7.17 (d, J = 7.6 Hz, 1H), 7.08 (dd, J = 8.4, 3.0 Hz, 1H), 4.77 (p, J = 7.6 Hz, 1H), 4.09 (dd, J = 8.9, 6.6 Hz, 2H), 3.82-3.71 (m, 4H), 3.54 (t, J = 7.9 Hz, 2H) | MS (ESI$^+$) m/z 352 [M + H]$^+$ |
| Example 269 | 1-[1-(2-fluorophenyl)-1H-indazol-4-yl]-3-{1-[(1-hydroxycyclopropyl)carbonyl]azetidin-3-yl}imidazolidin-2-one | $^1$H NMR (500 MHz, methanol-d$_4$) δ ppm 8.39 (d, J = 1.0 Hz, 1H), 7.61 (td, J = 7.7, 1.6 Hz, 1H), 7.58-7.52 (m, 1H), 7.47-7.39 (m, 3H), 7.15 (dd, J = 8.5, 2.8 Hz, 1H), 7.12 (d, J = 7.6 Hz, 1H), 4.58 (s, 1H), 4.36-4.23 (m, 2H), 4.15 (t, J = 7.7 Hz, 2H), 3.91-3.79 (m, 2H), 1.30-1.16 (m, 2H), 0.99-0.88 (m, 2H) | MS (APCI) m/z 436 [M + H]$^+$ |
| Example 270 | 2-(3-{3-[1-(2-fluorophenyl)-1H-indazol-4-yl]-2-oxoimidazolidin-1-yl}azetidin-1-yl)-2-oxoacetamide | $^1$H NMR (500 MHz, DMSO-d$_6$) δ ppm 8.42 (s, 1H), 7.99 (s, 1H), 7.72-7.64 (m, 2H), 7.62-7.51 (m, 2H), 7.47-7.38 (m, 2H), 7.18 (d, J = 7.6 Hz, 1H), 7.10 (dd, J = 8.5, 2.9 Hz, 1H), 4.90-4.79 (m, 1H), 4.73-4.66 (m, 2H), 4.29-4.19 (m, 2H), 4.10 (t, J = 7.7 Hz, 2H), 3.83-3.72 (m, 2H) | MS (APCI) m/z 423 [M + H]$^+$ |
| Example 271 | 1-[1-(2-fluorophenyl)-1H-indazol-4-yl]-3-[1-(methylsulfonyl)azetidin-3-yl]imidazolidin-2-one | $^1$H NMR (500 MHz, DMSO-d$_6$) δ ppm 8.42 (d, J = 1.0 Hz, 1H), 7.68 (td, J = 7.8, 1.7 Hz, 1H), 7.62-7.52 (m, 2H), 7.47-7.40 (m, 2H), 7.18 (d, J = 7.6 Hz, 1H), 7.10 (dd, J = 8.4, 2.9 Hz, 1H), 4.82 (tt, J = 8.2, 6.6 Hz, 1H), 4.22 (dd, J = 8.8, 6.7 Hz, 2H), 4.15-4.04 (m, 4H), 3.80 (dd, J = 8.8, 6.7 Hz, 2H), 3.10 (s, 3H) | MS (ESI$^+$) m/z 430 [M + H]$^+$ |
| Example 272 | 1-[(1R,2R)-2-(benzyloxy)cyclohexyl]-3-[1-(2-fluorophenyl)-1H-indazol-4-yl]imidazolidin-2-one | 1H NMR (400 MHz, CDCl$_3$) δ ppm 1.16-1.33 (m, 1H), 1.33-1.51 (m, 2H), 1.51-1.61 (m, 1H), 1.73-1.86 (m, 2H), 1.87-1.94 (m, 1H), 2.25-2.35 (m, 1H), 3.20 (dd, J = 16.2, 8.3 Hz, 1H), 3.46 (td, J = 8.8, 5.5 Hz, 1H), 3.52 (td, J = 10.6, 4.3 Hz, 1H), 3.75-3.92 (m, 2H), 3.97 (dd, J = 16.1, 8.8 Hz, 1H), 4.45 (d, J = 12.0 Hz, 1H), 4.75 (d, J = 12.0 Hz, 1H), 7.04 (d, J = 7.6 Hz, 1H), 7.10 (dd, J = 8.4, 3.3 Hz, 1H), 7.18-7.29 (m, 4H), 7.34 (ddd, J = 16.1, 11.2, 6.5 Hz, 4H), 7.38-7.45 (m, 1H), 7.61 (td, J = 7.7, 1.7 Hz, 1H), 8.43 (d, J = 0.7 Hz, 1H) | MS (ESI$^+$) m/z 485 [M + H]$^+$ |
| Example 273 | 1-[1-(2-fluorophenyl)-1H-indazol-4-yl]-3-[(1R,2R)-2-hydroxycyclohexyl]imidazolidin-2-one | $^1$H NMR (400 MHz, CDCl$_3$) δ ppm 1.20-1.40 (m, 2H), 1.43-1.58 (m, 1H), 1.71-1.84 (m, 2H), 1.87-1.97 (m, 1H), 2.04- | MS (ESI$^+$) m/z 395 [M + H]$^+$ |

| Example | Name | NMR | MS |
|---|---|---|---|
| | | 2.23 (m, 3H), 3.52-3.68 (m, 3H), 3.70-3.84 (m, 1H), 3.95-4.10 (m, 2H), 6.94-7.03 (m, 1H), 7.11 (dd, J = 8.4, 3.3 Hz, 1H), 7.25-7.37 (m, 3H), 7.38-7.46 (m, 1H), 7.54-7.65 (m, 1H), 8.40 (d, J = 0.7 Hz, 1H) | |
| Example 274 | 1-[1-(2-fluorophenyl)-1H-indazol-4-yl]-3-[1-(propylsulfonyl)azetidin-3-yl]imidazolidin-2-one | $^1$H NMR (500 MHz, DMSO-d$_6$) δ ppm 8.42 (d, J = 1.0 Hz, 1H), 7.67 (td, J = 7.8, 1.7 Hz, 1H), 7.61-7.52 (m, 2H), 7.46-7.40 (m, 2H), 7.18 (d, J = 7.6 Hz, 1H), 7.10 (dd, J = 8.4, 2.9 Hz, 1H), 4.81 (tt, J = 8.1, 6.6 Hz, 1H), 4.20 (dd, J = 8.6, 6.6 Hz, 2H), 4.11 (dd, J = 8.8, 6.6 Hz, 2H), 4.05 (t, J = 8.4 Hz, 2H), 3.78 (dd, J = 8.8, 6.7 Hz, 2H), 3.21-3.17 (m, 2H), 1.79-1.70 (m, 2H), 1.03 (t, J = 7.4 Hz, 3H) | MS (ESI$^+$) m/z 430 [M + H]$^+$ |
| Example 275 | 1-[(1S,2S)-2-(benzyloxy)cyclohexyl]-3-[1-(2-fluorophenyl)-1H-indazol-4-yl]imidazolidin-2-one | $^1$H NMR (400 MHz, methanol-d$_4$) δ ppm 8.29 (s, 1H), 7.61 (td, J = 7.7, 1.6 Hz, 1H), 7.58-7.51 (m, 1H), 7.48-7.34 (m, 5H), 7.27-7.19 (m, 3H), 7.11 (dd, J = 8.5, 2.8 Hz, 1H), 7.03 (d, J = 7.5 Hz, 1H), 4.74 (d, J = 11.8 Hz, 1H), 4.47 (d, J = 11.8 Hz, 1H), 4.04 (q, J = 8.7 Hz, 1H), 3.88-3.76 (m, 2H), 3.61-3.50 (m, 2H), 3.31-3.24 (m, 1H), 2.46-2.33 (m, 1H), 1.95-1.76 (m, 3H), 1.72-1.56 (m, 1H), 1.50-1.26 (m, 3H) | MS (ESI$^+$) m/z 485 [M + H]$^+$ |
| Example 276 | 1-[1-(2-fluorophenyl)-1H-indazol-4-yl]-3-[(1S,2S)-2-hydroxycyclohexyl]imidazolidin-2-one | $^1$H NMR (400 MHz, methanol-d$_4$) δ ppm 8.41 (d, J = 0.9 Hz, 1H), 7.61 (td, J = 7.7, 1.6 Hz, 1H), 7.54 (dddd, J = 8.5, 6.8, 4.9, 1.8 Hz, 1H), 7.46-7.36 (m, 3H), 7.12-7.09 (m, 1H), 7.07 (d, J = 7.6 Hz, 1H), 4.13-4.01 (m, 2H), 3.72-3.58 (m, 4H), 2.10 (ddt, J = 12.7, 4.2, 2.3 Hz, 1H), 1.80 (dtdd, J = 12.9, 10.8, 5.7, 3.0 Hz, 3H), 1.70-1.55 (m, 1H), 1.48-1.28 (m, 3H) | MS (DCI) m/z 395 [M + H]$^+$ |
| Example 277 | 1-[2-oxo-2-(pyrrolidin-1-yl)ethyl]-3-(1-phenyl-1H-indazol-4-yl)imidazolidin-2-one | $^1$H NMR (400 MHz, DMSO-d$_6$) δ ppm 8.36 (s, 1H), 7.72 (dd, J = 8.2, 1.5 Hz, 2H), 7.63-7.56 (m, 2H), 7.53-7.38 (m, 3H), 7.17 (d, J = 7.4 Hz, 1H), 4.06 (q, J = 3.4, 2.8 Hz, 4H), 3.67 (dd, J = 9.0, 6.8 Hz, 2H), 3.43 (dd, J = 36.5, 7.7 Hz, 4H), 1.98-1.76 (m, 4H) | MS (APCI) m/z 390 [M + H]$^+$ |
| Example 278 | 1-[2-oxo-2-(pyrrolidin-1-yl)ethyl]-3-[1-(pyridin-2-yl)-1H-indazol-4-yl]imidazolidin-2-one | $^1$H NMR (400 MHz, DMSO-d$_6$) δ ppm 8.56 (s, 1H), 8.49 (d, J = 8.5 Hz, 1H), 8.41 (s, 1H), 7.98 (d, J = 4.3 Hz, 2H), 7.51 (t, J = 8.1 Hz, 1H), 7.31 (q, J = 4.4 Hz, 1H), 7.20 (d, J = 7.7 Hz, 1H), 4.09-4.02 (m, 4H), 3.70-3.61 (m, 2H), 3.53-3.32 (m, 4H), 2.00-1.76 (m, 4H) | MS (APCI) m/z 391 [M + H]$^+$ |
| Example 279 | 1-[1-(2-fluorophenyl)-1H-indazol-4-yl]-3-[(1S,2S)-2-methoxycyclohexyl]imidazolidin-2-one | $^1$H NMR (400 MHz, methanol-d$_4$) δ ppm 1.15-1.51 (m, 3H), 1.65 (qd, J = 12.3, 3.3 Hz, 1H), 1.74-1.93 (m, 3H), 2.15-2.37 (m, 1H), 3.34-3.41 (m, 1H), 3.42 (s, 3H), 3.52-3.79 (m, 3H), 3.95-4.18 (m, 2H), 7.07 (d, J = 7.5 Hz, 1H), 7.11 (dd, J = 8.5, 2.8 Hz, 1H), 7.37-7.46 (m, 3H), 7.51-7.58 (m, 1H), 7.61 (td, J = 7.7, 1.6 Hz, 1H), 8.38 (d, J = 0.7 Hz, 1H) | MS (ESI$^+$) m/z 409 [M + H]$^+$ |

-continued

| Example | Name | NMR | MS |
|---|---|---|---|
| Example 280 | 1-[1-(2-fluorophenyl)-1H-indazol-4-yl]-3-[(1S,2S)-2-isobutoxycyclohexyl]imidazolidin-2-one | $^1$H NMR (500 MHz, methanol-d$_4$) δ ppm 0.93 (t, J = 6.7 Hz, 6H), 1.21-1.34 (m, 2H), 1.34-1.47 (m, 1H), 1.67 (qd, J = 12.3, 3.2 Hz, 1H), 1.75-1.91 (m, 4H), 2.23-2.33 (m, 1H), 3.09 (dd, J = 8.7, 7.0 Hz, 1H), 3.39-3.45 (m, 1H), 3.53 (dd, J = 8.7, 5.8 Hz, 1H), 3.60 (q, J = 8.7 Hz, 1H), 3.68 (td, J = 8.9, 5.2 Hz, 1H), 3.76 (ddd, J = 12.6, 10.2, 4.0 Hz, 1H), 3.99 (td, J = 8.9, 5.2 Hz, 1H), 4.10 (q, J = 8.8 Hz, 1H), 7.04 (d, J = 7.3 Hz, 1H), 7.11 (dd, J = 8.5, 2.8 Hz, 1H), 7.36-7.47 (m, 3H), 7.51-7.58 (m, 1H), 7.62 (td, J = 7.7, 1.6 Hz, 1H), 8.37 (d, J = 0.8 Hz, 1H) | MS (ESI$^+$) m/z 451 [M + H]$^+$ |
| Example 281 | 1-[1-(2-fluorophenyl)-1H-indazol-4-yl]-3-[(1S)-2-oxocyclohexyl]imidazolidin-2-one | $^1$H NMR (500 MHz, methanol-d$_4$) δ ppm 1.63-1.75 (m, 1H), 1.86-1.97 (m, 1H), 1.98-2.02 (m, 1H), 2.03-2.09 (m, 1H), 2.10-2.19 (m, 1H), 2.25-2.33 (m, 1H), 2.44-2.50 (m, 1H), 2.50-2.59 (m, 1H), 3.62 (td, J = 8.5, 5.8 Hz, 1H), 3.69 (q, J = 8.4 Hz, 1H), 4.05-4.15 (m, 2H), 4.53 (dd, J = 12.7, 6.0 Hz, 1H), 7.09 (d, J = 7.5 Hz, 1H), 7.14 (dd, J = 8.5, 2.8 Hz, 1H), 7.38-7.47 (m, 3H), 7.52-7.57 (m, 1H), 7.58-7.64 (m, 1H), 8.35 (d, J = 0.8 Hz, 1H) | MS (ESI$^+$) m/z 393 [M + H]$^+$ |
| Example 282 | 1-(1-{[(2,2-dichlorocyclopropyl)methyl]sulfonyl}azetidin-3-yl)-3-[1-(2-fluorophenyl)-1H-indazol-4-yl]imidazolidin-2-one | $^1$H NMR (400 MHz, DMSO-d$_6$) δ ppm 8.42 (d, J = 0.8 Hz, 1H), 7.67 (td, J = 7.8, 1.7 Hz, 1H), 7.63-7.51 (m, 2H), 7.47-7.39 (m, 2H), 7.18 (d, J = 7.6 Hz, 1H), 7.10 (dd, J = 8.4, 3.0 Hz, 1H), 4.82 (tt, J = 8.1, 6.4 Hz, 1H), 4.28 (dd, J = 8.5, 6.4 Hz, 2H), 4.19-4.08 (m, 4H), 3.79 (dd, J = 8.9, 6.7 Hz, 2H), 3.69 (dd, J = 14.5, 6.4 Hz, 1H), 3.33 (s, 1H), 2.12-1.94 (m, 2H), 1.61 (t, J = 7.3 Hz, 1H) | MS (ESI$^+$) m/z 538 [M + H]$^+$ |
| Example 283 | 1-{1-[(cyclopropylmethyl)sulfonyl]azetidin-3-yl}-3-[1-(2-fluorophenyl)-1H-indazol-4-yl]imidazolidin-2-one | $^1$H NMR (500 MHz, DMSO-d$_6$) δ ppm 8.42 (d, J = 1.0 Hz, 1H), 7.68 (td, J = 7.8, 1.7 Hz, 1H), 7.62-7.52 (m, 2H), 7.47-7.39 (m, 2H), 7.18 (d, J = 7.6 Hz, 1H), 7.10 (dd, J = 8.4, 2.9 Hz, 1H), 4.81 (tt, J = 8.1, 6.4 Hz, 1H), 4.21 (dd, J = 8.6, 6.5 Hz, 2H), 4.14-4.05 (m, 4H), 3.78 (dd, J = 8.8, 6.7 Hz, 2H), 3.18 (d, J = 7.1 Hz, 2H), 1.11-1.02 (m, 1H), 0.66-0.60 (m, 2H), 0.43-0.38 (m, 2H) | MS (ESI$^+$) m/z 470 [M + H]$^+$ |
| Example 284 | 1-[1-(2-fluorophenyl)-1H-indazol-4-yl]-3-{1-[(2,2,2-trifluoroethyl)sulfonyl]azetidin-3-yl}imidazolidin-2-one | $^1$H NMR (400 MHz, DMSO-d$_6$) δ ppm 8.45-8.42 (m, 1H), 7.67 (td, J = 7.9, 1.7 Hz, 1H), 7.63-7.51 (m, 2H), 7.47-7.38 (m, 2H), 7.18 (d, J = 7.6 Hz, 1H), 7.11 (dd, J = 8.5, 3.0 Hz, 1H), 5.11 (s, 1H), 4.89-4.81 (m, 1H), 4.77 (q, J = 10.1 Hz, 4.44 (dd, J = 8.8, 6.4 Hz, 1H), 4.37 (dd, J = 8.8, 6.4 Hz, 1H), 4.32-4.19 (m, 2H), 4.12 (dd, J = 8.9, 6.6 Hz, 2H), 3.84-3.75 (m, 2H) | MS (ESI$^+$) m/z 498 [M + H]$^+$ |
| Example 285 | 1-[1-(2-fluorophenyl)-1H-indazol-4-yl]-3-[1-(isobutylsulfonyl)azetidin-3-yl]imidazolidin-2-one | $^1$H NMR (400 MHz, DMSO-d$_6$) δ ppm 8.42 (d, J = 1.0 Hz, 1H), 7.67 (td, J = 7.9, 1.7 Hz, 1H), 7.62-7.51 (m, 2H), 7.48-7.39 (m, 2H), 7.18 (d, J = 7.6 Hz, 1H), 7.10 (dd, J = 8.4, 2.9 Hz, 1H), 4.80 (tt, J = 8.2, 6.5 Hz, 1H), 4.19 | MS (ESI$^+$) m/z 472 [M + H]$^+$ |

-continued

| Example | Name | NMR | MS |
|---|---|---|---|
| | | (dd, J = 8.6, 6.5 Hz, 2H), 4.16-4.01 (m, 4H), 3.78 (dd, J = 8.8, 6.7 Hz, 2H), 3.11 (d, J = 6.6 Hz, 2H), 2.16 (hept, J = 6.7 Hz, 1H), 1.07 (d, J = 6.7 Hz, 6H) | |
| Example 286 | tert-butyl {3-[1-(2-fluorophenyl)-1H-indazol-4-yl]-2-oxoimidazolidin-1-yl}acetate | $^1$H NMR (500 MHz, DMSO-d$_6$) δ ppm 8.40 (d, J = 1.0 Hz, 1H), 7.68 (td, J = 7.8, 1.7 Hz, 1H), 7.62-7.52 (m, 2H), 7.47-7.40 (m, 2H), 7.18 (d, J = 7.6 Hz, 1H), 7.10 (dd, J = 8.4, 2.9 Hz, 1H), 4.10 (dd, J = 8.8, 6.7 Hz, 2H), 3.99 (s, 2H), 3.63 (dd, J = 8.7, 6.9 Hz, 2H), 1.47 (s, 9H) | MS (ESI$^+$) m/z 411 [M + H]$^+$ |
| Example 287 | ethyl (2Z)-3-{3-[1-(2-fluorophenyl)-1H-indazol-4-yl]-2-oxoimidazolidin-1-yl}acrylate | $^1$H NMR (400 MHz, DMSO-d$_6$) δ ppm 8.43 (d, J = 1.2 Hz, 1H), 7.69 (td, J = 7.9, 1.7 Hz, 1H), 7.64-7.53 (m, 2H), 7.52-7.41 (m, 2H), 7.27 (d, J = 7.5 Hz, 1H), 7.22 (dd, J = 8.4, 2.9 Hz, 1H), 7.16 (d, J = 10.3 Hz, 1H), 5.09 (d, J = 10.4 Hz, 1H), 4.19 (s, 4H), 4.10 (q, J = 7.1 Hz, 2H), 1.23 (t, J = 7.1 Hz, 3H) | MS (ESI$^+$) m/z 395 [M + H]$^+$ |
| Example 288 | ethyl (2E)-3-{3-[1-(2-fluorophenyl)-1H-indazol-4-yl]-2-oxoimidazolidin-1-yl}acrylate | $^1$H NMR (500 MHz, DMSO-d$_6$) δ ppm 8.45 (d, J = 1.0 Hz, 1H), 7.97 (d, J = 14.0 Hz, 1H), 7.70 (td, J = 7.8, 1.7 Hz, 1H), 7.64-7.53 (m, 2H), 7.51-7.42 (m, 2H), 7.29 (d, J = 7.6 Hz, 1H), 7.23 (dd, J = 8.3, 2.9 Hz, 1H), 5.27 (d, J = 14.0 Hz, 1H), 4.30-4.23 (m, 2H), 4.14 (q, J = 7.1 Hz, 2H), 3.85 (dd, J = 9.0, 6.6 Hz, 2H), 1.24 (t, J = 7.1 Hz, 3H) | MS (ESI$^+$) m/z 395 [M + H]$^+$ |
| Example 289 | tert-butyl 3-{3-[1-(2-fluorophenyl)-1H-indazol-4-yl]-2-oxoimidazolidin-1-yl}propanoate | $^1$H NMR (400 MHz, DMSO-d$_6$) δ ppm 8.43 (d, J = 0.9 Hz, 1H), 7.67 (td, J = 7.8, 1.7 Hz, 1H), 7.62-7.51 (m, 2H), 7.47-7.38 (m, 2H), 7.16 (d, J = 7.6 Hz, 1H), 7.07 (dd, J = 8.3, 3.0 Hz, 1H), 4.09-3.98 (m, 2H), 3.61-3.53 (m, 2H), 3.50 (t, J = 6.9 Hz, 2H), 2.54 (t, J = 6.9 Hz, 2H), 1.43 (s, 9H) | MS (ESI$^+$) m/z 425 [M + H]$^+$ |
| Example 290 | 1-[1-(2-fluorophenyl)-1H-indazol-4-yl]-3-{2-[(3S)-3-hydroxypiperidin-1-yl]-2-oxoethyl}imidazolidin-2-one | $^1$H NMR (400 MHz, DMSO-d$_6$) δ ppm 8.40 (d, J = 2.5 Hz, 1H), 7.68 (td, J = 7.8, 1.6 Hz, 1H), 7.63-7.50 (m, 2H), 7.47-7.38 (m, 2H), 7.17 (d, J = 7.6 Hz, 1H), 7.08 (dd, J = 8.4, 3.0 Hz, 1H), 4.92 (s, 1H), 4.19-4.13 (m, 2H), 4.12-4.01 (m, 2H), 3.67-3.39 (m, 4H), 3.23-3.01 (m, 1H), 2.97-2.59 (m, 1H), 1.92-1.62 (m, 2H), 1.56-1.27 (m, 2H) | MS (APCI) m/z 438 [M + H]$^+$ |
| Example 291 | 1-[1-(2-fluorophenyl)-1H-indazol-4-yl]-3-[2-(3-hydroxyazetidin-1-yl)-2-oxoethyl]imidazolidin-2-one | $^1$H NMR (400 MHz, DMSO-d$_6$) δ ppm 8.40 (d, J = 0.9 Hz, 1H), 7.68 (td, J = 7.9, 1.7 Hz, 1H), 7.63-7.50 (m, 2H), 7.47-7.38 (m, 2H), 7.17 (d, J = 7.6 Hz, 1H), 7.09 (dd, J = 8.4, 3.0 Hz, 1H), 5.77 (s, 1H), 4.55-4.46 (m, 1H), 4.38 (ddd, J = 8.3, 6.9, 1.3 Hz, 1H), 4.10 (ddd, J = 14.0, 9.3, 7.0 Hz, 3H), 3.97-3.90 (m, 3H), 3.66 (dd, J = 10.0, 4.4 Hz, 1H), 3.63-3.56 (m, 2H) | MS (APCI) m/z 410 [M + H]$^+$ |
| Example 292 | 1-[1-(2-fluorophenyl)-1H-indazol-4-yl]-3-{3-[(3S)-3-fluoropyrrolidin-1-yl]-3-oxopropyl}imidazolidin-2-one | $^1$H NMR (500 MHz, DMSO-d$_6$) δ ppm 8.44 (d, J = 0.9 Hz, 1H), 7.67 (td, J = 7.8, 1.7 Hz, 1H), 7.62-7.52 (m, 2H), 7.47-7.37 (m, 2H), 7.16 (d, J = 7.6 Hz, 1H), 7.07 (dd, J = 8.5, 2.9 Hz, 1H), | MS (ESI$^+$) m/z 440 [M + H]$^+$ |

-continued

| Example | Name | NMR | MS |
|---|---|---|---|
| | | 5.46-5.25 (m, 1H), 4.03 (ddd, J = 9.2, 7.1, 1.5 Hz, 2H), 3.34 (s, 8H), 2.61 (dt, J = 37.7, 7.1 Hz, 2H), 2.28-1.91 (m, 2H) | |
| Example 293 | 1-[1-(2-fluorophenyl)-1H-indazol-4-yl]-3-[2-(morpholin-4-yl)-2-oxoethyl]imidazolidin-2-one | $^1$H NMR (400 MHz, DMSO-$d_6$) δ 8.40 (d, J = 0.6 Hz, 1H), 7.68 (td, J = 7.8, 1.5 Hz, 1H), 7.52-7.62 (m, 2H), 7.40-7.46 (m, 2H), 7.17 (d, J = 7.6 Hz, 1H), 7.08 (dd, J = 8.4, 2.9 Hz, 1H), 4.18 (s, 2H), 4.07-4.11 (m, 2H), 3.59-3.63 (m, 6H), 3.47-3.49 (m, 4H). | MS (ESI$^+$) m/z 424 [M + H]$^+$ |
| Example 294 | 1-(1-cyclohexyl-1H-indazol-4-yl)-3-{2-[(3S)-3-fluoropyrrolidin-1-yl]-2-oxoethyl}imidazolidin-2-one | $^1$H NMR (400 MHz, DMSO-$d_6$) δ ppm 8.08 (s, 1H), 7.42 (d, J = 8.3 Hz, 1H), 7.31 (t, J = 7.9 Hz, 1H), 7.07 (d, J = 7.4 Hz, 1H), 5.36 (m, 1H), 4.55 (m, 1H), 4.19-3.97 (m, 5H), 3.86-3.48 (m, 5H), 2.24-2.08 (m, 2H), 2.03-1.79 (m, 8H). 1.74-1.20 (m, 2H). | MS (ESI$^+$) m/z 414 [M + H]$^+$ |
| Example 295 | 1-[1-(2-fluorophenyl)-1H-indazol-4-yl]-3-[2-oxo-2-(piperidin-1-yl)ethyl]imidazolidin-2-one | $^1$H NMR (400 MHz, DMSO-$d_6$) δ ppm 8.40 (d, J = 0.9 Hz, 1H), 7.68 (td, J = 7.8, 1.5 Hz, 1H), 7.53-7.61 (m, 2H), 7.40-7.46 (m, 2H), 7.17 (d, J = 7.3 Hz, 1H), 7.08 (dd, J = 8.4, 2.9 Hz, 1H), 4.14 (s, 2H), 4.07-4.10 (m, 2H), 3.59-3.62 (m, 2H), 3.45-3.47 (m, 2H), 3.40-3.43 (m, 2H), 1.47-1.60 (m, 6H). | MS (ESI$^+$) m/z 422 [M + H]$^+$ |
| Example 296 | 1-[2-(3,3-difluoropiperidin-1-yl)-2-oxoethyl]-3-[1-(2-fluorophenyl)-1H-indazol-4-yl]imidazolidin-2-one | $^1$H NMR (400 MHz, DMSO-$d_6$) δ ppm 3:2 rotomers 8.39 (d, J = 0.9 Hz, 1H), 7.68 (td, J = 7.8, 1.5 Hz, 1H), 7.53-7.61 (m, 2H), 7.41-7.46 (m, 2H), 7.17 (d, J = 7.6 Hz, 1H), 7.09 (dd, J = 8.4, 2.9 Hz, 1H), 4.23 (s, 1.2H), 4.17 4.23 (s, 0.8H), 4.08-4.11 (m, 2H), 3.80-3.87 (m, 2H), 3.50-3.62 (m, 4H), 2.05-2.12 (m, 2H), 1.62-1.77 (m, 2H). | MS (ESI$^+$) m/z 458 [M + H]$^+$ |
| Example 297 | 1-[2-(4,4-difluoropiperidin-1-yl)-2-oxoethyl]-3-[1-(2-fluorophenyl)-1H-indazol-4-yl]imidazolidin-2-one | $^1$H NMR (500 MHz, DMSO-$d_6$) δ 8.40 (d, J = 0.9 Hz, 1H), 7.68 (td, J = 7.8, 1.5 Hz, 1H), 7.53-7.61 (m, 2H), 7.41-7.46 (m, 2H), 7.17 (d, J = 7.6 Hz, 1H), 7.09 (dd, J = 8.4, 2.9 Hz, 1H), 4.24 (s, 2H), 4.08-4.10 (m, 2H), 3.57-3.63 (m, 6H), 2.06-2.11 (m, 2H), 1.94-2.00 (m, 2H). | MS (ESI$^+$) m/z 458 [M + H]$^+$ |
| Example 298 | 1-[2-(3-fluoroazetidin-1-yl)-2-oxoethyl]-3-[1-(2-fluorophenyl)-1H-indazol-4-yl]imidazolidin-2-one | $^1$H NMR (500 MHz, DMSO-$d_6$) δ ppm 8.40 (d, J = 0.9 Hz, 1H), 7.68 (td, J = 7.8, 1.5 Hz, 1H), 7.53-7.60 (m, 2H), 7.41-7.46 (m, 2H), 7.18 (d, J = 7.3 Hz, 1H), 7.09 (dd, J = 8.5, 3.1 Hz, 1H), 5.44 (dm, J = 57.0 Hz, 1H), 4.52-4.59 (m, 1H), 4.23-4.35 (m, 2H), 4.07-4.10 (m, 2H), 3.94-4.01 (m, 3H), 3.58-3.62 (m, 2H). | MS (ESI$^+$) m/z 412 [M + H]$^+$ |
| Example 299 | 1-[1-(2-fluorophenyl)-1H-indazol-4-yl]-3-{2-oxo-2-[4-(trifluoromethyl)piperidin-1-yl]ethyl}imidazolidin-2-one | $^1$H NMR (400 MHz, DMSO-$d_6$) δ ppm 8.40 (d, J = 0.9 Hz, 1H), 7.68 (td, J = 7.9, 1.7 Hz, 1H), 7.52-7.61 (m, 2H), 7.40-7.46 (m, 2H), 7.17 (d, J = 7.6 Hz, 1H), 7.08 (dd, J = 8.2, 3.1 Hz, 1H), 4.47-4.51 (m, 1H), 4.14-4.25 (m, 2H), 4.09 (t, J = 7.9 Hz, 2H), 3.95-3.99 (m, 1H), 3.59-3.63 (m, 2H), 3.07-3.13 (m, 1H), 2.59-2.68 (m, 2H), 1.85-1.88 (m, 2H), 1.44-1.53 (m, 1H), 1.25-1.36 (m, 1H). | MS (ESI$^+$) m/z 490 [M + H]$^+$ |

-continued

| Example | Name | NMR | MS |
|---|---|---|---|
| Example 300 | 1-[1-(2-fluorophenyl)-1H-indazol-4-yl]-3-{2-oxo-2-[3-(trifluoromethyl)piperidin-1-yl]ethyl}imidazolidin-2-one | $^1$H NMR (400 MHz, DMSO-$d_6$) δ ppm 3:2 rotomers 8.40 (d, J = 0.9 Hz, 1H), 7.68 (td, J = 7.8, 1.5 Hz, 1H), 7.53-7.60 (m, 2H), 7.41-7.46 (m, 2H), 7.17 (d, J = 7.6 Hz, 1H), 7.09 (dd, J = 8.4, 2.9 Hz, 1H), 4.44-4.46 (m, 0.67H), 4.14-4.26 (m, 2.33), 4.07-4.10 (m, 2H), 3.93-3.96 (m, 0.33H), 3.81-3.84 (m, 0.67H), 3.58-3.62 (m, 2H), 3.08-3.19 (m, 1H), 2.64-2.80 (m, 1.33H), 2.39-2.46 (m, 0.67H), 1.96-1.98 (m, 1H), 1.72-1.81 (M, 1H), 1.37-1.60 (m, 2H). | MS (ESI$^+$) m/z 490 [M + H]$^+$ |
| Example 301 | 1-[1-(2-fluorophenyl)-1H-indazol-4-yl]-3-{2-[(1R,5S)-8-oxa-3-azabicyclo[3.2.1]oct-3-yl]-2-oxoethyl}imidazolidin-2-one | $^1$H NMR (400 MHz, DMSO-$d_6$) δ ppm 8.40 (d, J = 0.9 Hz, 1H), 7.68 (td, J = 7.8, 1.7 Hz, 1H), 7.62-7.50 (m, 2H), 7.48-7.39 (m, 2H), 7.18 (d, J = 7.6 Hz, 1H), 7.08 (dd, J = 8.4, 3.0 Hz, 1H), 4.32 (dd, J = 16.6, 12.7 Hz, 3H), 4.14-4.04 (m, 2H), 4.01-3.91 (m, 2H), 3.66-3.52 (m, 3H), 3.33-3.27 (m, 1H), 2.85 (dd, J = 13.2, 2.5 Hz, 1H), 1.90-1.75 (m, 3H), 1.68-1.53 (m, 1H) | MS (ESI$^+$) m/z 450 [M + H]$^+$ |
| Example 302 | 1-[1-(2-fluorophenyl)-1H-indazol-4-yl]-3-[2-oxo-2-(3-oxopyrrolidin-1-yl)ethyl]imidazolidin-2-one | $^1$H NMR (500 MHz, DMSO-$d_6$) δ ppm 8.40 (d, J = 0.9 Hz, 1H), 7.68 (td, J = 7.8, 1.6 Hz, 1H), 7.62-7.53 (m, 2H), 7.47-7.40 (m, 2H), 7.18 (dd, J = 7.6, 1.6 Hz, 1H), 7.09 (dd, J = 8.5, 3.2 Hz, 1H), 4.31-3.85 (m, 6H), 3.84-3.38 (m, 5H), 2.72-2.55 (m, 1H) | MS (ESI$^+$) m/z 843 [2M + H]$^+$ |
| Example 303 | 1-[2-(azepan-1-yl)-2-oxoethyl]-3-[1-(2-fluorophenyl)-1H-indazol-4-yl]imidazolidin-2-one | $^1$H NMR (500 MHz, DMSO-$d_6$) δ ppm 8.40 (d, J = 1.0 Hz, 1H), 7.68 (td, J = 7.9, 1.7 Hz, 1H), 7.62-7.52 (m, 2H), 7.47-7.39 (m, 2H), 7.18 (d, J = 7.6 Hz, 1H), 7.08 (dd, J = 8.4, 2.9 Hz, 1H), 4.15 (s, 2H), 4.09 (dd, J = 8.9, 6.8 Hz, 2H), 3.69-3.59 (m, 2H), 3.51-3.42 (m, 4H), 1.72 (p, J = 5.8 Hz, 2H), 1.66-1.59 (m, 2H), 1.53 (ddp, J = 12.4, 7.8, 4.6, 3.7 Hz, 4H) | MS (ESI$^+$) m/z 436 [M + H]$^+$ |
| Example 304 | 2-{3-[1-(2-fluorophenyl)-1H-indazol-4-yl]-2-oxoimidazolidin-1-yl}-N-(2,2,2-trifluoroethyl)acetamide | $^1$H NMR (400 MHz, DMSO-$d_6$) δ ppm 8.76 (t, J = 6.4 Hz, 1H), 8.42 (d, J = 0.9 Hz, 1H), 7.68 (td, J = 7.8, 1.6 Hz, 1H), 7.63-7.51 (m, 2H), 7.48-7.39 (m, 2H), 7.20 (d, J = 7.6 Hz, 1H), 7.09 (dd, J = 8.4, 3.0 Hz, 1H), 4.14-4.06 (m, 2H), 3.99 (s, 2H), 3.99-3.91 (m, 2H), 3.66-3.59 (m, 2H) | MS (ESI$^+$) m/z 436 [M + H]$^+$ |
| Example 305 | 1-[1-(3,3-dimethylbutyl)-1H-indazol-4-yl]-3-[2-oxo-2-(pyrrolidin-1-yl)ethyl]imidazolidin-2-one | 1H NMR (500 MHz, DMSO-$d_6$) δ ppm 8.08 (s, 1H), 7.36-7.28 (m, 2H), 7.20-7.05 (m, 1H), 4.44-4.34 (m, 2H), 4.08-3.94 (m, 4H), 3.59 (dd, J = 8.6, 6.9 Hz, 2H), 3.48-3.28 (m, 4H), 2.00-1.86 (m, 2H), 1.87-1.67 (m, 4H), 0.96 (s, 9H). | MS (ESI$^+$) m/z 398 [M + H]$^+$ |
| Example 306 | 1-(1-tert-butyl-1H-indazol-4-yl)-3-{2-[(3S)-3-fluoropyrrolidin-1-yl]-2-oxoethyl}imidazolidin-2-one | 1H NMR (400 MHz, DMSO-$d_6$) δ ppm 8.01 (d, J = 0.9 Hz, 1H), 7.60 (d, J = 8.6 Hz, 1H), 7.29 (dd, J = 8.6, 7.5 Hz, 1H), 7.06 (d, J = 7.6 Hz, 1H), 5.34 (m, 1H), 4.17-3.98 (m, 4H), 3.85-3.44 (m, 6H), 2.26-2.06 (m, 2H), 1.71 (s, 9H). | MS (ESI$^+$) m/z 388 [M + H]$^+$ |

-continued

| Example | Name | NMR | MS |
|---|---|---|---|
| Example 307 | 1-{2-[(3S)-3-fluoropyrrolidin-1-yl]-2-oxoethyl}-3-(1-phenyl-1H-indazol-4-yl)imidazolidin-2-one | 1H NMR (400 MHz, DMSO-d$_6$) δ ppm 8.37 (d, J = 0.8 Hz, 1H), 7.78-7.72 (m, 2H), 7.64-7.56 (m, 2H), 7.54 (d, J = 8.3 Hz, 1H), 7.48-7.39 (m, 2H), 7.18 (d, J = 7.5 Hz, 1H), 5.36 (m, 1H), 4.23-3.95 (m, 4H), 3.82-3.48 (m, 6H), 2.31-2.03 (m, 2H). | MS (ESI$^+$) m/z 408 [M + H]$^+$ |
| Example 308 | 1-[1-(2-fluorophenyl)-1H-indazol-4-yl]-3-{2-oxo-2-[(3S)-3-(trifluoromethyl)pyrrolidin-1-yl]ethyl}imidazolidin-2-one | 1H NMR (400 MHz, DMSO-d$_6$):1:1 rotamers δ ppm 8.40-8.41 (m, 1H), 7.68 (td, J = 7.8, 1.5 Hz, 1H), 7.54-7.59 (m, 2H), 7.40-7.46 (m, 2H), 7.17 (dd, J = 7.6, 1.5 Hz, 1H), 7.09 (dd, J = 8.2, 3.1 Hz, 1H), 4.07-4.13 (m, 4H), 3.83-3.88 (m, 0.5H), 3.52-3.71 (m, 4.5H), 3.21-3.32 (m, 1H), 2.22-2.31 (m, 0.5H), 2.04-2.19 (m, 1H), 1.90-1.99 (m, 0.5H). | MS (ESI$^+$) m/z 476 [M + H]$^+$ |
| Example 309 | 1-[2-(3-fluoro-3-methylazetidin-1-yl)-2-oxoethyl]-3-[1-(2-fluorophenyl)-1H-indazol-4-yl]imidazolidin-2-one | 1H NMR (500 MHz, DMSO-d$_6$) δ ppm 8.40 (d, J = 0.6 Hz, 1H), 7.68 (td, J = 7.9, 1.5 Hz, 1H), 7.52-7.62 (m, 2H), 7.40-7.46 (m, 2H), 7.17 (d, J = 7.6 Hz, 1H), 7.09 (dd, J = 8.4, 2.9 Hz, 1H), 4.26-4.41 (m, 1H), 4.05-4.11 (m, 2H), 3.99-4.01 (m, 3H), 3.58-3.62 (m, 2H), 1.61 (d, J = 22.0 Hz, 3H). | MS (ESI$^+$) m/z 426 [M + H]$^+$ |
| Example 310 | N-(3,3-difluorocyclobutyl)-2-{3-[1-(2-fluorophenyl)-1H-indazol-4-yl]-2-oxoimidazolidin-1-yl}acetamide | 1H NMR (400 MHz, DMSO-d$_6$): δ ppm 8.52 (d, J = 6.7 Hz, 1H), 8.43 (d, J = 0.9 Hz, 1H), 7.68 (td, J = 7.9, 1.7 Hz, 1H), 7.52-7.62 (m, 2H), 7.40-7.46 (m, 2H), 7.20 (d, J = 7.6 Hz, 1H), 7.09 (dd, J = 8.4, 3.1 Hz, 1H), 4.07-4.16 (m, 3H), 3.89 (s, 2H), 3.59-3.63 (m, 2H), 2.87-2.98 (m, 2H), 2.57-2.70 (m, 2H). | MS (ESI$^+$) m/z 444 [M + H]$^+$ |
| Example 311 | (1R,5S)-8-({3-[1-(2-fluorophenyl)-1H-indazol-4-yl]-2-oxoimidazolidin-1-yl}acetyl)-8-azabicyclo[3.2.1]octan-3-one | $^1$H NMR (400 MHz, DMSO-d$_6$) δ ppm 8.41 (d, J = 0.9 Hz, 1H), 7.68 (td, J = 7.9, 1.6 Hz, 1H), 7.64-7.51 (m, 2H), 7.47-7.40 (m, 2H), 7.19 (d, J = 7.6 Hz, 1H), 7.09 (dd, J = 8.4, 3.0 Hz, 1H), 4.70 (dt, J = 42.0, 5.5 Hz, 2H), 4.35-4.16 (m, 2H), 4.11 (t, J = 8.1 Hz, 2H), 3.75-3.57 (m, 2H), 2.83 (ddd, J = 16.6, 4.9, 2.1 Hz, 1H), 2.62 (ddd, J = 16.1, 4.9, 2.0 Hz, 1H), 2.39-2.24 (m, 2H), 2.21-2.06 (m, 1H), 2.04-1.90 (m, 1H), 1.72 (ddd, J = 13.0, 9.6, 4.2 Hz, 1H), 1.67-1.54 (m, 1H) | MS (ESI$^+$) m/z 462 [M + H]$^+$ |
| Example 312 | 1-[1-(2-fluorophenyl)-1H-indazol-4-yl]-3-[2-oxo-2-(3,3,4,4-tetrafluoropyrrolidin-1-yl)ethyl]imidazolidin-2-one | $^1$H NMR (500 MHz, DMSO-d$_6$) δ ppm 8.39 (d, J = 0.9 Hz, 1H), 7.68 (td, J = 7.8, 1.5 Hz, 1H), 7.53-7.61 (m, 2H), 7.41-7.46 (m, 2H), 7.17 (d, J = 7.6 Hz, 1H), 7.10 (dd, J = 8.2, 3.1 Hz, 1H), 4.41-4.47 (m, 2H), 4.21 (s, 2H), 4.07-4.12 (m, 4H), 3.59-3.62 (m, 2H). | MS (ESI$^+$) m/z 480 [M + H]$^+$ |
| Example 313 | 1-({3-[1-(2-fluorophenyl)-1H-indazol-4-yl]-2-oxoimidazolidin-1-yl}acetyl)azepan-4-one | $^1$H NMR (500 MHz, DMSO-d$_6$) δ ppm 8.41-8.38 (m, 1H), 7.68 (td, J = 7.9, 1.7 Hz, 1H), 7.62-7.52 (m, 2H), 7.47-7.39 (m, 2H), 7.20-7.15 (m, 1H), 7.08 (dd, J = 8.4, 2.9 Hz, 1H), 4.20-4.14 (m, 2H), 4.08 (ddd, J = 8.8, 6.6, 2.6 Hz, 2H), 3.78 (t, J = 5.9 Hz, 1H), 3.71 (t, J = 5.9 Hz, 1H), 3.68-3.55 (m, 4H), 2.72-2.61 (m, 3H), 2.54 (t, J = 5.9 Hz, 1H), 1.82-1.62 (m, 2H) | MS (ESI$^+$) m/z 450 [M + H]$^+$ |

-continued

| Example | Name | NMR | MS |
|---|---|---|---|
| Example 314 | 1-[1-(2-fluorophenyl)-1H-indazol-4-yl]-3-{(1Z)-3-[(3S)-3-fluoropyrrolidin-1-yl]-3-oxoprop-1-en-1-yl}imidazolidin-2-one | $^1$H NMR (400 MHz, DMSO-d$_6$) δ ppm 8.42 (d, J = 0.9 Hz, 1H), 7.69 (td, J = 7.9, 1.7 Hz, 1H), 7.64-7.51 (m, 2H), 7.51-7.41 (m, 2H), 7.25 (d, J = 7.6 Hz, 1H), 7.19 (dd, J = 8.4, 3.0 Hz, 1H), 6.98 (dd, J = 10.3, 6.8 Hz, 1H), 5.51-5.23 (m, 2H), 4.21-4.13 (m, 2H), 4.13-4.00 (m, 1H), 3.98-3.84 (m, 1H), 3.79-3.36 (m, 5H), 2.29-2.06 (m, 1H) | MS (ESI$^+$) m/z 438 [M + H]$^+$ |
| Example 315 | N-ethyl-2-{3-[1-(2-fluorophenyl)-1H-indazol-4-yl]-2-oxoimidazolidin-1-yl}acetamide | $^1$H NMR (500 MHz, DMSO-d$_6$) δ ppm 8.43 (d, J = 1.0 Hz, 1H), 8.07 (t, J = 5.5 Hz, 1H), 7.68 (td, J = 7.8, 1.7 Hz, 1H), 7.62-7.52 (m, 2H), 7.47-7.40 (m, 2H), 7.20 (d, J = 7.6 Hz, 1H), 7.08 (dd, J = 8.3, 2.9 Hz, 1H), 4.09 (dd, J = 8.9, 6.7 Hz, 2H), 3.86 (s, 2H), 3.65-3.56 (m, 2H), 3.16-3.11 (m, 2H), 1.06 (t, J = 7.2 Hz, 3H) | MS (ESI$^+$) m/z 382 [M + H]$^+$ |
| Example 316 | 2-{3-[1-(2-fluorophenyl)-1H-indazol-4-yl]-2-oxoimidazolidin-1-yl}-N-[1-(hydroxymethyl)cyclobutyl]acetamide | $^1$H NMR (500 MHz, DMSO-d$_6$) δ ppm 8.42 (d, J = 1.0 Hz, 1H), 8.00 (s, 1H), 7.68 (td, J = 7.8, 1.7 Hz, 1H), 7.62-7.52 (m, 2H), 7.47-7.39 (m, 2H), 7.19 (d, J = 7.7 Hz, 1H), 7.08 (dd, J = 8.4, 2.9 Hz, 1H), 4.82 (t, J = 5.8 Hz, 1H), 4.08 (dd, J = 8.9, 6.7 Hz, 2H), 3.86 (s, 2H), 3.67-3.58 (m, 2H), 3.56 (d, J = 5.8 Hz, 2H), 2.17 (tdd, J = 9.9, 8.4, 2.3 Hz, 2H), 2.09-2.02 (m, 2H), 1.86-1.77 (m, 1H), 1.71 (dp, J = 11.4, 8.8 Hz, 1H) | MS (APCI) m/z 438 [M + H]$^+$ |
| Example 317 | 1-[1-(2-fluorophenyl)-1H-indazol-4-yl]-3-{3-[(3R)-3-fluoropiperidin-1-yl]-3-oxopropyl}imidazolidin-2-one | $^1$H NMR (400 MHz, DMSO-d$_6$) δ ppm 8.45-8.43 (m, 1H), 7.67 (td, J = 7.8, 1.6 Hz, 1H), 7.62-7.52 (m, 2H), 7.47-7.37 (m, 2H), 7.16 (d, J = 7.6 Hz, 1H), 7.07 (dd, J = 8.3, 3.0 Hz, 1H), 4.91-4.59 (m, 1H), 4.19-3.76 (m, 4H), 3.68-3.39 (m, 6H), 2.80-2.54 (m, 2H), 1.96-1.37 (m, 4H) | MS (ESI$^+$) m/z 454 [M + H]$^+$ |
| Example 318 | 1-[1-(2-fluorophenyl)-1H-indazol-4-yl]-3-{3-[(3S)-3-fluoropiperidin-1-yl]-3-oxopropyl}imidazolidin-2-one | $^1$H NMR (400 MHz, DMSO-d$_6$) δ ppm 8.45-8.43 (m, 1H), 7.67 (td, J = 7.8, 1.6 Hz, 1H), 7.63-7.51 (m, 2H), 7.48-7.37 (m, 2H), 7.16 (d, J = 7.6 Hz, 1H), 7.07 (dd, J = 8.4, 3.0 Hz, 1H), 4.89-4.60 (m, 1H), 4.09-3.77 (m, 4H), 3.69-3.36 (m, 6H), 2.77-2.53 (m, 2H), 1.93-1.42 (m, 4H) | MS (ESI$^+$) m/z 454 [M + H]$^+$ |
| Example 319 | 1-[1-(2-fluorophenyl)-1H-indazol-4-yl]-3-[2-(3-methoxyazetidin-1-yl)-2-oxoethyl]imidazolidin-2-one | $^1$H NMR (400 MHz, DMSO-d$_6$) δ ppm 8.40 (d, J = 0.9 Hz, 1H), 7.68 (td, J = 7.9, 1.6 Hz, 1H), 7.63-7.51 (m, 2H), 7.47-7.38 (m, 2H), 7.17 (d, J = 7.6 Hz, 1H), 7.09 (dd, J = 8.3, 2.9 Hz, 1H), 4.43-4.35 (m, 1H), 4.25 (tt, J = 6.4, 3.9 Hz, 1H), 4.14-4.01 (m, 4H), 3.95 (s, 2H), 3.73 (dd, J = 10.4, 3.9 Hz, 1H), 3.60 (dd, J = 8.9, 6.8 Hz, 2H), 3.23 (s, 3H) | MS (ESI$^+$) m/z 424 [M + H]$^+$ |
| Example 320 | 2-{3-[1-(2-fluorophenyl)-1H-indazol-4-yl]-2-oxoimidazolidin-1-yl}-N-(tetrahydro-2H-pyran-4-yl)acetamide | $^1$H NMR (400 MHz, DMSO-d$_6$) δ ppm 8.42 (d, J = 0.9 Hz, 1H), 8.04 (d, J = 7.7 Hz, 1H), 7.83-7.51 (m, 3H), 7.54-7.16 (m, 3H), 7.08 (dd, J = 8.5, 3.0 Hz, 1H), 4.24-3.99 (m, 2H), 3.89-3.79 (m, 5H), 3.72-3.45 (m, 2H), 3.39 (m, 2H), 1.72 (m, 2H), 1.63-1.30 (m, 2H). | MS (ESI$^+$) m/z 438 [M + H]$^+$ |

| Example | Name | NMR | MS |
|---|---|---|---|
| Example 321 | 2-{3-[1-(2-fluorophenyl)-1H-indazol-4-yl]-2-oxoimidazolidin-1-yl}-N-(oxetan-3-yl)acetamide | $^1$H NMR (400 MHz, DMSO-d$_6$) δ ppm 8.81 (d, J = 6.8 Hz, 1H), 8.42 (d, J = 0.9 Hz, 1H), 7.68 (td, J = 7.8, 1.6 Hz, 1H), 7.63-7.51 (m, 2H), 7.45 (d, J = 7.5 Hz, 1H), 7.41 (d, J = 8.0 Hz, 1H), 7.20 (d, J = 7.5 Hz, 1H), 7.09 (dd, J = 8.3, 3.1 Hz, 1H), 4.87 (h, J = 6.9 Hz, 1H), 4.84 (m, 1H), 4.73 (m, 2H), 4.48 (t, J = 6.3 Hz, 2H), 4.13-3.99 (m, 2H), 3.91 (s, 2H), 3.61 (t, J = 7.8 Hz, 2H). | MS (ESI$^+$) m/z 410 [M + H]$^+$ |
| Example 322 | N-cyclobutyl-2-{3-[1-(2-fluorophenyl)-1H-indazol-4-yl]-2-oxoimidazolidin-1-yl}acetamide | $^1$H NMR (400 MHz, DMSO-d$_6$) δ ppm 8.42 (d, J = 0.9 Hz, 1H), 8.28 (d, J = 7.7 Hz, 1H), 7.68 (td, J = 7.8, 1.6 Hz, 1H), 7.63-7.51 (m, 2H), 7.48-7.38 (m, 2H), 7.20 (d, J = 7.6 Hz, 1H), 7.08 (dd, J = 8.3, 3.1 Hz, 1H), 4.32-4.18 (m, 1H), 4.13-3.98 (m, 2H), 3.84 (s, 2H), 3.60 (t, J = 7.7 Hz, 2H), 2.23-2.10 (m, 2H), 2.01-1.88 (m, 2H), 1.71-1.55 (m, 2H). | MS (ESI$^+$) m/z 408 [M + H]$^+$ |
| Example 323 | N-cyclopentyl-2-{3-[1-(2-fluorophenyl)-1H-indazol-4-yl]-2-oxoimidazolidin-1-yl}acetamide | $^1$H NMR (400 MHz, DMSO-d$_6$) δ ppm 8.42 (d, J = 0.9 Hz, 1H), 8.02-7.96 (m, 1H), 7.68 (td, J = 7.8, 1.6 Hz, 1H), 7.63-7.50 (m, 2H), 7.48-7.37 (m, 2H), 7.19 (d, J = 7.6 Hz, 1H), 7.08 (dd, J = 8.3, 3.0 Hz, 1H), 4.13-3.99 (m, 3H), 3.85 (s, 2H), 3.61 (t, J = 7.7 Hz, 2H), 1.90-1.74 (m, 2H), 1.73-1.34 (m, 6H). | MS (ESI$^+$) m/z 422 [M + H]$^+$ |
| Example 324 | N-cyclohexyl-2-{3-[1-(2-fluorophenyl)-1H-indazol-4-yl]-2-oxoimidazolidin-1-yl}acetamide | $^1$H NMR (500 MHz, DMSO-d$_6$) δ ppm 8.42 (d, J = 0.9 Hz, 1H), 7.92 (d, J = 7.8 Hz, 1H), 7.68 (td, J = 7.8, 1.7 Hz, 1H), 7.62-7.51 (m, 2H), 7.48-7.39 (m, 2H), 7.19 (d, J = 7.6 Hz, 1H), 7.08 (dd, J = 8.4, 3.0 Hz, 1H), 4.12-3.99 (m, 2H), 3.86 (s, 2H), 3.65-3.54 (m, 3H), 1.81-1.57 (m, 5H), 1.32-1.17 (m, 5H). | MS (ESI$^+$) m/z 436 [M + H]$^+$ |
| Example 325 | 1-[2-(3-acetylazetidin-1-yl)-2-oxoethyl]-3-[1-(2-fluorophenyl)-1H-indazol-4-yl]imidazolidin-2-one | $^1$H NMR (400 MHz, DMSO-d$_6$) δ ppm 8.40 (d, J = 0.9 Hz, 1H), 7.68 (td, J = 7.8, 1.6 Hz, 1H), 7.63-7.51 (m, 2H), 7.48-7.38 (m, 2H), 7.17 (d, J = 7.5 Hz, 1H), 7.09 (dd, J = 8.4, 3.1 Hz, 1H), 4.37-4.25 (m, 2H), 4.12-3.88 (m, 6H), 3.71-3.55 (m, 3H), 2.16 (s, 3H). | MS (ESI$^+$) m/z 436 [M + H]$^+$ |
| Example 326 | 2-{3-[1-(2-fluorophenyl)-1H-indazol-4-yl]-2-oxoimidazolidin-1-yl}-N-(trans-3-methoxycyclobutyl)acetamide | $^1$H NMR (400 MHz, DMSO-d$_6$) δ ppm 8.42 (d, J = 0.9 Hz, 1H), 8.35 (d, J = 7.0 Hz, 1H), 7.68 (td, J = 7.8, 1.7 Hz, 1H), 7.63-7.51 (m, 2H), 7.45 (d, J = 8.3 Hz, 1H), 7.41 (d, J = 7.9 Hz, 1H), 7.20 (d, J = 7.6 Hz, 1H), 7.08 (dd, J = 8.3, 3.0 Hz, 1H), 4.33-4.20 (m, 1H), 4.16-4.04 (m, 2H), 4.06-3.92 (m, 1H), 3.86 (s, 2H), 3.64-3.57 (m, 2H), 3.14 (s, 3H), 2.27-2.07 (m, 4H). | MS (ESI$^+$) m/z 438 [M + H]$^+$ |
| Example 327 | 1-[1-(2-fluorophenyl)-1H-indazol-4-yl]-3-{(1E)-3-[(3S)-3-fluoropyrrolidin-1-yl]-3-oxoprop-1-en-1-yl}imidazolidin-2-one | $^1$H NMR (500 MHz, DMSO-d$_6$) δ ppm 2.05-2.33 (m, 2H), 3.53-3.62 (m, 1H), 3.64-3.94 (m, 5H), 4.27 (t, J = 8.1 Hz, 2H), 5.38 (dd, J = 52.9, 41.7 Hz, 1H), 5.58 (dd, J = 24.8, 13.5 Hz, 1H), 7.21 (dd, J = 8.4, 2.9 Hz, 1H), 7.30 (d, J = 7.5 Hz, 1H), 7.42-7.51 (m, 2H), 7.54-7.64 (m, 2H), 7.70 (td, J = 7.8, 1.5 Hz, 1H), 7.90 (d, J = 13.5 Hz, 1H), 8.45 (d, J = 0.8 Hz, 1H) | MS (ESI$^+$) m/z 438 [M + H]$^+$ |

-continued

| Example | Name | NMR | MS |
|---|---|---|---|
| Example 328 | N-(2,2-dimethylcyclopropyl)-2-{3-[1-(2-fluorophenyl)-1H-indazol-4-yl]-2-oxoimidazolidin-1-yl}acetamide | $^1$H NMR (500 MHz, DMSO-$d_6$) δ ppm 8.42 (d, J = 0.9 Hz, 1H), 8.02 (d, J = 3.7 Hz, 1H), 7.68 (td, J = 7.8, 1.5 Hz, 1H), 7.52-7.62 (m, 2H), 7.40-7.46 (m, 2H), 7.19 (d, J = 7.3 Hz, 1H), 7.08 (dd, J = 8.2, 3.1 Hz, 1H), 4.06-4.10 (m, 2H), 3.89 (s, 2H), 3.59-3.63 (m, 2H), 2.41-2.45 (m, 1H), 1.04 (s, 3H), 1.00 (s, 3H), 0.63 (dd, J = 7.9, 5.2 Hz, 1H), 0.39 (t, J = 4.7 Hz, 1H). | MS (ESI$^+$) m/z 422 [M + H]$^+$ |
| Example 329 | 1-[1-(2-fluorophenyl)-1H-indazol-4-yl]-3-{2-oxo-2-[3-(trifluoromethyl)azetidin-1-yl]ethyl}imidazolidin-2-one | $^1$H NMR (500 MHz, DMSO-$d_6$) δ ppm 8.39 (d, J = 0.9 Hz, 1H), 7.68 (td, J = 7.8, 1.5 Hz, 1H), 7.53-7.61 (m, 2H), 7.41-7.46 (m, 2H), 7.17 (d, J = 7.3 Hz, 1H), 7.09 (dd, J = 8.5, 3.1 Hz, 1H), 5.49 (t, J = 9.0 Hz, 1H), 4.28 (dd, J = 9.2, 5.5 Hz, 1H), 4.18 (t, J = 9.5 Hz, 1H), 4.07-4.10 (m, 2H), 3.99 (s, 2H), 3.92 (dd, J = 10.1, 5.5 Hz, 1H), 3.65-3.73 (m, 1H), 3.58-3.62 (m, 2H). | MS (ESI$^+$) m/z 462 [M + H]$^+$ |
| Example 330 | 1-{2-[3-(difluoromethyl)pyrrolidin-1-yl]-2-oxoethyl}-3-[1-(2-fluorophenyl)-1H-indazol-4-yl]imidazolidin-2-one | $^1$H NMR (500 MHz, DMSO-$d_6$) δ ppm 8.40 (s, 1H), 7.68 (td, J = 7.8, 1.7 Hz, 1H), 7.62-7.52 (m, 2H), 7.47-7.40 (m, 2H), 7.17 (dd, J = 7.6, 1.6 Hz, 1H), 7.09 (dd, J = 8.4, 2.9 Hz, 1H), 6.15 (tt, J = 56.3, 4.3 Hz, 1H), 4.16-4.03 (m, 4H), 3.62 (ddd, J = 9.8, 6.7, 2.7 Hz, 2H), 3.58-3.29 (m, 3H), 2.98-2.63 (m, 1H), 2.17-1.77 (m, 3H) | MS (ESI$^+$) m/z 458 [M + H]$^+$ |
| Example 331 | 1-[1-(2-fluorophenyl)-1H-indazol-4-yl]-3-[(1S,2S)-2-isopropoxycyclohexyl]imidazolidin-2-one | $^1$H NMR (500 MHz, methanol-$d_4$) δ ppm 8.40 (d, J = 1.0 Hz, 1H), 7.61 (td, J = 7.7, 1.6 Hz, 1H), 7.58-7.51 (m, 1H), 7.47-7.37 (m, 3H), 7.11 (dd, J = 8.6, 2.7 Hz, 1H), 7.05 (d, J = 7.6 Hz, 1H), 4.84-4.79 (m, 1H), 4.09 (td, J = 8.9, 7.3 Hz, 1H), 4.01 (td, J = 8.9, 6.3 Hz, 1H), 3.87-3.78 (m, 1H), 3.74-3.54 (m, 4H), 2.27-2.17 (m, 1H), 1.90-1.66 (m, 3H), 1.45-1.22 (m, 3H), 1.18 (t, J = 6.5 Hz, 6H) | MS (ESI$^+$) m/z 437 [M + H]$^+$ |
| Example 332 | 2-{3-[1-(2-fluorophenyl)-1H-indazol-4-yl]-2-oxoimidazolidin-1-yl}-N-[(1R,2S)-2-hydroxycyclopentyl]acetamide | $^1$H NMR (400 MHz, methanol-$d_4$) δ ppm 8.44 (s, 1H), 7.61 (td, J = 7.7, 1.6 Hz, 1H), 7.58-7.51 (m, 1H), 7.48-7.37 (m, 3H), 7.17-7.10 (m, 2H), 4.21-3.98 (m, 7H), 3.77-3.67 (m, 2H), 2.00-1.79 (m, 3H), 1.77-1.52 (m, 3H) | MS (ESI$^+$) m/z 875 [2M + H]$^+$ |
| Example 333 | 2-{3-[1-(2-fluorophenyl)-1H-indazol-4-yl]-2-oxoimidazolidin-1-yl}-N-(1-methylcyclopropyl)acetamide | $^1$H NMR (500 MHz, DMSO-$d_6$) δ ppm 8.43 (d, J = 0.6 Hz, 1H), 8.28 (s, 1H), 7.68 (td, J = 7.9, 1.5 Hz, 1H), 7.53-7.61 (m, 2H), 7.41-7.46 (m, 2H), 7.19 (d, J = 7.3 Hz, 1H), 7.08 (dd, J = 8.5, 3.1 Hz, 1H), 4.06-4.09 (m, 2H), 3.79 (s, 2H), 3.57-3.60 (m, 2H), 1.30 (s, 3H), 0.64-0.66 (m, 2H), 0.53-0.56 (m, 2H). | MS (ESI$^+$) m/z 408 [M + H]$^+$ |
| Example 334 | N-[(1S,2S)-2-(benzyloxy)cyclopentyl]-2-{3-[1-(2-fluorophenyl)-1H-indazol-4-yl]-2-oxoimidazolidin-1-yl}acetamide | $^1$H NMR (500 MHz, methanol-$d_4$) δ ppm 8.44 (d, J = 0.9 Hz, 1H), 7.61 (td, J = 7.8, 1.6 Hz, 1H), 7.55 (dddd, J = 8.1, 6.8, 4.9, 1.7 Hz, 1H), 7.48-7.37 (m, 3H), 7.37-7.28 (m, 4H), 7.27-7.21 (m, 1H), 7.16-7.06 (m, 2H), 4.59 (q, J = 11.9 Hz, 2H), 4.25 (ddd, J = 7.8, 6.3, 4.0 Hz, 1H), 4.15-4.07 (m, 2H), 3.99 (d, J = 2.1 Hz, 2H), 3.87 (dt, J = 6.4, 4.0 Hz, 1H), 3.69 (t, J = 7.9 Hz, 2H), | MS (ESI$^+$) m/z 528 [M + H]$^+$ |

-continued

| Example | Name | NMR | MS |
|---|---|---|---|
| | | 2.11 (dtd, J = 13.4, 7.7, 5.6 Hz, 1H), 1.94 (ddd, J = 12.6, 7.7, 5.9 Hz, 1H), 1.85-1.66 (m, 3H), 1.53 (dtd, J = 13.8, 7.6, 6.1 Hz, 1H) | |
| Example 335 | N-[(1R,2R)-2-(benzyloxy)cyclopentyl]-2-{3-[1-(2-fluorophenyl)-1H-indazol-4-yl]-2-oxoimidazolidin-1-yl}acetamide | $^1$H NMR (500 MHz, methanol-$d_4$) δ ppm 8.43 (s, 1H), 7.60 (td, J = 7.8, 1.6 Hz, 1H), 7.57-7.50 (m, 1H), 7.46-7.36 (m, 3H), 7.36-7.28 (m, 4H), 7.27-7.20 (m, 1H), 7.15-7.07 (m, 2H), 4.58 (q, J = 12.0 Hz, 2H), 4.25 (ddd, J = 7.7, 6.2, 4.0 Hz, 1H), 4.09 (dd, J = 9.1, 6.9 Hz, 2H), 3.99 (d, J = 2.0 Hz, 2H), 3.86 (dt, J = 6.3, 4.0 Hz, 1H), 3.67 (dd, J = 8.9, 7.0 Hz, 2H), 2.16-2.03 (m, 1H), 1.93 (ddd, J = 15.2, 7.7, 5.9 Hz, 1H), 1.81-1.64 (m, 3H), 1.52 (dq, J = 14.0, 7.4 Hz, 1H) | MS (ESI$^+$) m/z 528 [M + H]$^+$ |
| Example 336 | 1-[1-(2-fluorophenyl)-1H-indazol-4-yl]-3-(4-isobutoxytetrahydrofuran-3-yl)imidazolidin-2-one | $^1$H NMR (400 MHz, methanol-$d_4$) δ ppm 8.39 (d, J = 1.1 Hz, 1H), 7.61 (td, J = 7.7, 1.6 Hz, 1H), 7.59-7.50 (m, 1H), 7.48-7.34 (m, 3H), 7.16-7.11 (m, 1H), 7.09 (d, J = 7.5 Hz, 1H), 4.47 (ddd, J = 5.1, 3.3, 1.2 Hz, 1H), 4.20-4.13 (m, 2H), 4.11-4.03 (m, 2H), 4.03-3.95 (m, 2H), 3.78-3.67 (m, 2H), 3.61 (td, J = 8.6, 7.2 Hz, 1H), 3.48 (dd, J = 9.1, 6.7 Hz, 1H), 3.35-3.31 (m, 1H), 1.86 (dq, J = 13.3, 6.6 Hz, 1H), 0.94 (dd, J = 6.7, 3.1 Hz, 6H) | MS (ESI$^+$) m/z 439 [M + H]$^+$ |
| Example 337 | 2-{3-[1-(2-fluorophenyl)-1H-indazol-4-yl]-2-oxoimidazolidin-1-yl}-N-[(1R,2S)-2-isobutoxycyclopentyl]acetamide | $^1$H NMR (400 MHz, methanol-$d_4$) δ ppm 8.43 (d, J = 1.0 Hz, 1H), 7.61 (td, J = 7.7, 1.6 Hz, 1H), 7.55 (dddd, J = 8.4, 6.9, 4.9, 1.7 Hz, 1H), 7.48-7.36 (m, 3H), 7.16-7.08 (m, 2H), 4.19-4.08 (m, 3H), 4.08-3.97 (m, 2H), 3.81 (td, J = 4.9, 2.8 Hz, 1H), 3.71 (t, J = 7.9 Hz, 2H), 3.27-3.09 (m, 2H), 2.04-1.93 (m, 1H), 1.86-1.74 (m, 4H), 1.71-1.53 (m, 2H), 0.88 (dd, J = 6.7, 2.9 Hz, 6H) | MS (ESI$^+$) m/z 494 [M + H]$^+$ |
| Example 338 | 1-[1-(4-chlorophenyl)-1H-indazol-4-yl]-3-{2-[(3S)-3-fluoropyrrolidin-1-yl]-2-oxoethyl}imidazolidin-2-one | $^1$H NMR (500 MHz, DMSO-$d_6$) δ ppm 8.38 (d, J = 0.9 Hz, 1H), 7.82-7.77 (m, 2H), 7.68-7.62 (m, 2H), 7.55 (d, J = 8.4 Hz, 1H), 7.47 (t, J = 8.0 Hz, 1H), 7.19 (d, J = 7.5 Hz, 1H), 5.36 (m, 1H), 4.17-3.99 (m, 4H), 3.89-3.49 (m, 6H), 2.31-2.03 (m, 2H). | MS (ESI$^+$) m/z 442 [M + H]$^+$ |
| Example 339 | N-tert-butyl-2-{3-[1-(2-fluorophenyl)-1H-indazol-4-yl]-2-oxoimidazolidin-1-yl}acetamide | $^1$H NMR (500 MHz, DMSO-$d_6$) δ ppm 8.42 (d, J = 0.6 Hz, 1H), 7.68 (td, J = 7.8, 1.5 Hz, 1H), 7.63 (s, 1H), 7.52-7.60 (m, 2H), 7.40-7.46 (m, 2H), 7.19 (d, J = 7.3 Hz, 1H), 7.08 (dd, J = 8.4, 2.9 Hz, 1H), 4.05-4.09 (m, 2H), 3.82 (s, 2H), 3.59-3.63 (m, 2H), 1.30 (s, 9H). | MS (ESI$^+$) m/z 410 [M + H]$^+$ |
| Example 340 | N-(3,3-difluorocyclohexyl)-2-{3-[1-(2-fluorophenyl)-1H-indazol-4-yl]-2-oxoimidazolidin-1-yl}acetamide | $^1$H NMR (400 MHz, DMSO-$d_6$) δ ppm 8.43 (d, J = 0.9 Hz, 1H), 8.11 (d, J = 7.6 Hz, 1H), 7.68 (td, J = 7.8, 1.5 Hz, 1H), 7.52-7.62 (m, 2H), 7.40-7.46 (m, 2H), 7.20 (d, J = 7.6 Hz, 1H), 7.08 (dd, J = 8.4, 2.9 Hz, 1H), 4.07-4.11 (m, 2H), 3.88 (s, 2H), 3.60-3.86 (m, 1H), 3.59-3.63 (m, 2H), 2.19-2.27 (m, 1H), 1.95-2.02 (m, 1H), 1.65-1.83 (m, 4H), 1.25-1.48 (m, 2H). | MS (ESI$^+$) m/z 472 [M + H]$^+$ |

| Example | Name | NMR | MS |
|---|---|---|---|
| Example 341 | N-(3,3-difluorocyclopentyl)-2-{3-[1-(2-fluorophenyl)-1H-indazol-4-yl]-2-oxoimidazolidin-1-yl}acetamide | $^1$H NMR (400 MHz, DMSO-d$_6$) δ ppm 8.43 (d, J = 0.9 Hz, 1H), 8.29 (d, J = 7.3 Hz, 1H), 7.68 (td, J = 7.9, 1.7 Hz, 1H), 7.52-7.62 (m, 2H), 7.40-7.46 (m, 2H), 7.20 (d, J = 7.3 Hz, 1H), 7.08 (dd, J = 8.3, 3.1 Hz, 1H), 4.22-4.31 (m, 1H), 4.07-4.11 (m, 2H), 3.89 (s, 2H), 3.59-3.63 (m, 2H), 2.40-2.52 (m, 1H), 1.96-2.30 (m, 4H), 1.65-1.76 (m, 1H). | MS (ESI$^+$) m/z 458 [M + H]$^+$ |
| Example 342 | 1-[1-(2-fluorophenyl)-1H-indazol-4-yl]-3-{2-[(3aR,6aS)-hexahydrocyclopenta[c]pyrrol-2(1H)-yl]-2-oxoethyl}imidazolidin-2-one | $^1$H NMR (500 MHz, DMSO-d$_6$) δ ppm 8.40 (d, J = 0.9 Hz, 1H), 7.68 (td, J = 7.8, 1.5 Hz, 1H), 7.53-7.61 (m, 2H), 7.40-7.46 (m, 2H), 7.17 (d, J = 7.6 Hz, 1H), 7.08 (dd, J = 8.4, 2.9 Hz, 1H), 4.05-4.09 (m, 4H), 3.67-3.71 (m, 1H), 3.57-3.63 (m, 3H), 3.25 (dd, J = 10.7, 4.8 Hz, 1H), 3.15 (dd, J = 12.2, 4.9 Hz, 1H), 2.69-2.76 (m, 1H), 3.56-2.64 (m, 1H), 1.68-1.83 (m, 3H), 1.53-1.60 (m, 1H), 1.41-1.49 (m, 2H). | MS (ESI$^+$) m/z 448 [M + H]$^+$ |
| Example 343 | 2-{3-[1-(2-fluorophenyl)-1H-indazol-4-yl]-2-oxoimidazolidin-1-yl}-N-(3,3,3-trifluoropropyl)acetamide | $^1$H NMR (400 MHz, DMSO-d$_6$) δ ppm 8.43 (d, J = 0.9 Hz, 1H), 8.29 (t, J = 5.8 Hz, 1H), 7.68 (td, J = 7.8, 1.5 Hz, 1H), 7.52-7.62 (m, 2H), 7.41-7.46 (m, 2H), 7.20 (d, J = 7.3 Hz, 1H), 7.09 (dd, J = 8.5, 3.1 Hz, 1H), 4.07-4.11 (m, 4H), 3.89 (s, 2H), 3.58-3.62 (m, 2H), 3.35-3.39 (m, 2H), 2.41-2.50 (m, 2H). | MS (ESI$^+$) m/z 450 [M + H]$^+$ |
| Example 344 | 1-[1-(2-fluorophenyl)-1H-indazol-4-yl]-3-methylimidazolidin-2-one | $^1$H NMR (500 MHz, DMSO-d$_6$) δ ppm 8.44 (d, J = 0.9 Hz, 1H), 7.67 (td, J = 7.8, 1.7 Hz, 1H), 7.62-7.52 (m, 2H), 7.46-7.39 (m, 2H), 7.18 (d, J = 7.6 Hz, 1H), 7.07 (dd, J = 8.3, 2.9 Hz, 1H), 4.09-3.99 (m, 2H), 3.60-3.49 (m, 2H), 2.85 (s, 3H) | MS (ESI$^+$) m/z 311 [M + H]$^+$ |
| Example 345 | Nα-({3-[1-(2-fluorophenyl)-1H-indazol-4-yl]-2-oxoimidazolidin-1-yl}acetyl)-D-phenylalaninamide | $^1$H NMR (500 MHz, DMSO-d$_6$) δ ppm 8.42 (d, J = 1.0 Hz, 1H), 8.24 (d, J = 8.6 Hz, 1H), 7.68 (td, J = 7.8, 1.7 Hz, 1H), 7.62-7.49 (m, 3H), 7.48-7.39 (m, 2H), 7.32-7.25 (m, 4H), 7.23-7.16 (m, 2H), 7.14-7.10 (m, 1H), 7.08 (dd, J = 8.4, 3.0 Hz, 1H), 4.52 (ddd, J = 9.8, 8.4, 4.6 Hz, 1H), 4.09-3.96 (m, 2H), 3.86 (s, 2H), 3.41-3.34 (m, 2H), 3.08 (dd, J = 13.8, 4.6 Hz, 1H), 2.83 (dd, J = 13.7, 9.9 Hz, 1H) | MS (ESI$^+$) m/z 501 [M + H]$^+$ |
| | N-tert-butyl-N$^2$-({3-[1-(2-fluorophenyl)-1H-indazol-4-yl]-2-oxoimidazolidin-1-yl}acetyl)-L-valinamide | $^1$H NMR (500 MHz, DMSO-d$_6$) δ ppm 8.42 (d, J = 1.0 Hz, 1H), 8.24 (d, J = 8.6 Hz, 1H), 7.68 (td, J = 7.8, 1.7 Hz, 1H), 7.62-7.49 (m, 3H), 7.48-7.39 (m, 2H), 7.32-7.25 (m, 4H), 7.23-7.16 (m, 2H), 7.14-7.10 (m, 1H), 7.08 (dd, J = 8.4, 3.0 Hz, 1H), 4.52 (ddd, J = 9.8, 8.4, 4.6 Hz, 1H), 4.09-3.96 (m, 2H), 3.86 (s, 2H), 3.41-3.34 (m, 2H), 3.08 (dd, J = 13.8, 4.6 Hz, 1H), 2.83 (dd, J = 13.7, 9.9 Hz, 1H) | MS (ESI$^+$) m/z 509 [M + H]$^+$ |
| Example 347 | N-(2,2-difluorocyclopentyl)-2-{3-[1-(2-fluorophenyl)-1H-indazol-4-yl]-2-oxoimidazolidin-1-yl}acetamide | $^1$H NMR (500 MHz, DMSO-d$_6$) δ ppm 8.42 (d, J = 0.9 Hz, 1H), 8.26 (d, J = 8.9 Hz, 1H), 7.68 (td, J = 7.9, 1.5 Hz, 1H), 7.53-7.61 (m, 2H), 7.41-7.46 (m, 2H), 7.20 (d, J = 7.6 Hz, 1H), 7.08 (dd, J = 8.2, 3.1 Hz, 1H), 4.37-4.47 (m, 1H), 4.07-4.11 (m, 2H), 3.93-4.00 (m, 2H), 3.62-3.64 (m, 2H), 2.12- | MS (ESI$^+$) m/z 458 [M + H]$^+$ |

| Example | Name | NMR | MS |
|---|---|---|---|
| | | 2.23 (m, 1H), 1.99-2.09 (m, 2H), 1.59-1.81 (m, 3H). | |
| Example 348 | 1-[1-(3,5-dichlorophenyl)-1H-indazol-4-yl]-3-{2-[(3S)-3-fluoropyrrolidin-1-yl]-2-oxoethyl}imidazolidin-2-one | $^1$H NMR (500 MHz, DMSO-d$_6$) δ ppm 8.42 (d, J = 0.9 Hz, 1H), 7.86-7.82 (m, 2H), 7.66 (t, J = 1.8 Hz, 1H), 7.63 (d, J = 8.4 Hz, 1H), 7.51 (t, J = 8.0 Hz, 1H), 7.21 (d, J = 7.6 Hz, 1H), 5.37 (m, 1H), 4.22-4.01 (m, 4H), 3.86-3.46 (m, 6H), 2.29-2.06 (m, 2H). | MS (ESI$^+$) m/z 476 [M + H]$^+$ |
| Example 349 | 2-{3-[1-(2-fluorophenyl)-1H-indazol-4-yl]-2-oxoimidazolidin-1-yl}-N-(3-oxocyclobutyl)acetamide | $^1$H NMR (500 MHz, DMSO-d$_6$) δ ppm 8.59 (m, 1H), 8.43 (s, 1H), 7.68 (m, 1H), 7.62-7.51 (m, 2H), 7.44 (m, 2H), 7.21 (m, 1H), 7.08 (m, 1H), 4.40 (m, 1H), 4.10 (m, 2H), 3.91 (s, 2H), 3.63 (t, J = 7.7 Hz, 2H), 3.37 (m, 2H), 3.22-3.04 (m, 2H). | MS (ESI$^+$) m/z 422 [M + H]$^+$ |
| Example 350 | 2-{3-[1-(2-fluorophenyl)-1H-indazol-4-yl]-2-oxoimidazolidin-1-yl}-N-(3-hydroxycyclobutyl)acetamide | $^1$H NMR (500 MHz, DMSO-d$_6$) δ ppm 8.42 (d, J = 0.9 Hz, 1H), 8.32-8.20 (m, 1H), 7.68 (td, J = 7.8, 1.6 Hz, 1H), 7.62-7.51 (m, 2H), 7.48-7.39 (m, 2H), 7.19 (d, J = 7.6 Hz, 1H), 7.08 (dd, J = 8.4, 3.0 Hz, 1H), 5.09-5.00 (m, 1H), 4.27 (m, 1H), 4.13-4.04 (m, 2H), 3.88-3.68 (m, 3H), 3.64-3.56 (m, 2H), 2.19-2.07 (m, 2H), 1.83-1.73 (m, 2H). | MS (ESI$^+$) m/z 424 [M + H]$^+$ |
| Example 351 | N-cyclobutyl-2-{3-[1-(2-fluorophenyl)-1H-indazol-4-yl]-2-oxoimidazolidin-1-yl}-N-methylacetamide | $^1$H NMR (500 MHz, DMSO-d$_6$) δ ppm 8.39 (d, J = 0.9 Hz, 1H), 7.68 (td, J = 7.8, 1.6 Hz, 1H), 7.62-7.51 (m, 2H), 7.48-7.38 (m, 2H), 7.17 (d, J = 7.6 Hz, 1H), 7.08 (dd, J = 8.4, 3.0 Hz, 1H), 4.88 and 4.40 (2m, 1H), 4.16-4.05 (m, 4H), 3.63-3.55 (m, 2H), 2.95 and 2.87 (2s, 3H), 2.33-2.08 (m, 3H), 2.01 (m, 1H), 1.69-1.54 (m, 2H). | MS (ESI$^+$) m/z 422 [M + H]$^+$ |
| Example 352 | 1-[1-(2-fluorophenyl)-1H-indazol-4-yl]-3-[2-(3-methylazetidin-1-yl)-2-oxoethyl]imidazolidin-2-one | $^1$H NMR (500 MHz, DMSO-d$_6$) δ ppm 8.40 (d, J = 0.9 Hz, 1H), 7.68 (td, J = 7.8, 1.5 Hz, 1H), 7.53-7.61 (m, 2H), 7.40-7.46 (m, 2H), 7.17 (d, J = 7.3 Hz, 1H), 7.09 (dd, J = 8.2, 3.1 Hz, 1H), 4.29-4.32 (m, 1H), 4.01-4.09 (m, 4H), 3.91 (s, 2H), 3.75-3.79 (m, 1H), 3.58-3.61 (m, 2H), 3.46-3.49 (m, 1H), 2.69-2.75 (m, 1H), 1.21 (d, J = 6.7 Hz, 3H). | MS (ESI$^+$) m/z 408 [M + H]$^+$ |
| Example 353 | 2-{3-[1-(2-fluorophenyl)-1H-indazol-4-yl]-2-oxoimidazolidin-1-yl}-N-[1-(trifluoromethyl)cyclobutyl]acetamide | $^1$H NMR (500 MHz, DMSO-d$_6$) δ ppm 8.59 (s, 1H), 8.41 (d, J = 0.9 Hz, 1H), 7.68 (td, J = 7.8, 1.6 Hz, 1H), 7.63-7.51 (m, 2H), 7.48-7.39 (m, 2H), 7.19 (d, J = 7.6 Hz, 1H), 7.09 (dd, J = 8.3, 3.0 Hz, 1H), 4.09 (d, J = 15.5 Hz, 2H), 3.94 (s, 2H), 3.62 (t, J = 7.7 Hz, 2H), 2.49-2.39 (m, 4H), 2.03-1.85 (m, 2H). | MS (ESI$^+$) m/z 476 [M + H]$^+$ |
| Example 354 | 2-{3-[1-(2-fluorophenyl)-1H-indazol-4-yl]-2-oxoimidazolidin-1-yl}-N-[3-(hydroxyimino)cyclobutyl]acetamide | $^1$H NMR (400 MHz, DMSO-d$_6$) δ ppm 10.38-10.33 (m, 1H), 8.52 (d, J = 7.1 Hz, 1H), 8.43 (d, J = 0.9 Hz, 1H), 7.68 (td, J = 7.8, 1.6 Hz, 1H), 7.63-7.51 (m, 2H), 7.45 (d, J = 7.3 Hz, 1H), 7.42 (d, J = 7.9 Hz, 1H), 7.20 (d, J = 7.5 Hz, 1H), 7.09 (dd, J = 8.3, 3.0 Hz, 1H), 4.35-4.24 (m, 1H), 4.09 (dd, J = 8.9, 6.7 Hz, 2H), 3.89 (s, 2H), 3.62 (t, J = 7.7 Hz, 2H), 3.25-3.01 (m, 2H), 2.85-2.72 (m, 2H). | MS (ESI$^+$) m/z 435 [M + H]$^+$ |

| Example | Name | NMR | MS |
|---|---|---|---|
| Example 355 | 2-{3-[1-(2-fluorophenyl)-1H-indazol-4-yl]-2-oxoimidazolidin-1-yl}-N-[3-(methoxyimino)cyclobutyl]acetamide | $^1$H NMR (400 MHz, DMSO-d$_6$) δ ppm 8.53 (d, J = 7.1 Hz, 1H), 8.43 (d, J = 0.9 Hz, 1H), 7.68 (td, J = 7.8, 1.6 Hz, 1H), 7.63-7.51 (m, 2H), 7.45 (d, J = 7.5 Hz, 1H), 7.41 (d, J = 8.0 Hz, 1H), 7.20 (d, J = 7.6 Hz, 1H), 7.08 (dd, J = 8.3, 3.0 Hz, 1H), 4.38-4.25 (m, 1H), 4.15-4.03 (m, 2H), 3.88 (s, 2H), 3.72 (s, 3H), 3.61 (t, J = 7.7 Hz, 2H), 3.24-3.12 (m, 2H), 2.90-2.76 (m, 2H). | MS (ESI$^+$) m/z 449 [M + H]$^+$ |
| Example 356 | N-(4,4-difluorocyclohexyl)-2-{3-[1-(2-fluorophenyl)-1H-indazol-4-yl]-2-oxoimidazolidin-1-yl}acetamide | $^1$H NMR (400 MHz, DMSO-d$_6$) δ ppm 8.43 (d, J = 0.9 Hz, 1H), 8.04 (d, J = 7.6 Hz, 1H), 7.68 (td, J = 7.8, 1.5 Hz, 1H), 7.52-7.62 (m, 2H), 7.40-7.46 (m, 2H), 7.19 (d, J = 7.6 Hz, 1H), 7.08 (dd, J = 8.2, 3.1 Hz, 1H), 4.06-4.10 (m, 2H), 3.89 (s, 2H), 3.80-3.85 (m, 2H), 3.56-3.63 (m, 2H), 1.81-2.08 (m, 6H), 1.49-1.59 (m, 2H). | MS (ESI$^+$) m/z 472 [M + H]$^+$ |
| Example 357 | N-(2,2-dimethylpropyl)-2-{3-[1-(2-fluorophenyl)-1H-indazol-4-yl]-2-oxoimidazolidin-1-yl}acetamide | $^1$H NMR (500 MHz, DMSO-d$_6$) δ ppm 8.42 (d, J = 0.9 Hz, 1H), 7.96 (t, J = 6.1 Hz, 1H), 7.68 (td, J = 7.9, 1.7 Hz, 1H), 7.52-7.62 (m, 2H), 7.40-7.46 (m, 2H), 7.18 (d, J = 7.3 Hz, 1H), 7.08 (dd, J = 8.5, 3.1 Hz, 1H), 4.06-4.10 (m, 2H), 3.93(s, 2H), 3.60-3.64 (m, 2H), 2.95 (d, J = 6.4 Hz, 2H), 0.97 (s, 9H). | MS (ESI$^+$) m/z 424 [M + H]$^+$ |

Determination of Biological Activity

Abbreviations: CC2-DMPE for N-(6-chloro-7-hydroxycoumarin-3-carbonyl)-dimyristoylphosphatidylethanolamine; DiSBAC$_2$(3) for bis(1,3-diethylthiobarbiturate)trimethine oxonol; DMEM for Dulbecco's Modified Eagle Media; EGTA for ethylene glycol tetraacetic acid; FBS for Fetal Bovine Serum; FLIPR® for Fluorometric Imaging Plate Reader; FRET for Fluorescence Resonance Energy Transfer; HI FBS for Heat-Inactivated Fetal Bovine Serum; HBSS for Hank's Balanced Salt Solution; HEPES for N-2-Hydroxy-EthylPiperazine-N'-2-Ethane Sulfonic acid; K-aspartate for potassium aspartate; MEM for Minimal Essential Media; MgATP for magnesium adenosine triphosphate; and VABSC-1 for Voltage Assay Background Suppression Compound.

FRET-Based Membrane Potential Assays.

Recombinant, Human Sodium Channel, Na$_v$1.7.

Two days prior to the experiment, frozen HEK293 cells stably expressing recombinant human Na$_v$1.7 were quickly thawed and plated at 25,000 cells/well in growth medium [DMEM (Invitrogen #11965) with 10% HI FBS (Invitrogen #10082), 2 mM glutamine, 100 units/mL penicillin, 0.1 mg/mL streptomycin (PSG, Sigma #G1146), and 500 µg/mL Geneticin (Invitrogen #10131)] in black-walled, clear-bottom 384-well poly-D-lysine-coated assay plates (Greiner Bio-One, Frickenhausen, Germany) and incubated in a humidified 5% CO$_2$ incubator at 37° C. On the day of the assay, medium was removed by aspiration, and cells were washed with assay buffer [HBSS (Invitrogen, Carlsbad, Calif.) containing 20 mM HEPES (Invitrogen, Carlsbad, Calif.)]. After washing, 30 µL assay buffer containing the fluorescent voltage-sensor probe CC2-DMPE (Invitrogen, Carlsbad, Calif.) at 20 µM and 0.01% pluronic F-127 (Invitrogen, Carlsbad, Calif.) was added to the cells. Cells were incubated for 40 minutes at room temperature in the dark. Following the incubation, the cells were washed and 30 µL assay buffer containing 2.5 µM DiSBAC$_2$(3) substrate (Invitrogen, Carlsbad, Calif.) and 0.5 mM VABSC-1 (Invitrogen, Carlsbad, Calif.) was added to the cells. The cells were incubated for 90 minutes at room temperature in the dark. Fluorescence readings were made using a FLIPR®$^{TETRA}$ (Molecular Devices, Sunnyvale Calif.) equipped with voltage-sensor probe optics. At the start of each experiment the optimal (EC$_{80}$) concentration of depolarizing agent (veratridine) was determined by testing a dilution curve of assay buffer containing veratridine (Sigma-Aldrich, St. Louis, Mo.) and 1 mg/mL scorpion venom (SVqq, from Leiurus quinquestriatus; Sigma-Aldrich, St. Louis, Mo.). Compounds were dissolved in dimethyl sulfoxide, and 8-point, 1:3 dilution concentration-response curves were prepared in duplicate in dimethyl sulfoxide, followed by preparation of 0.8 uL/well daughter plates of the dilutions. Test compounds in the daughter plate were diluted to (~3×) solutions in assay buffer immediately before assaying. Using the FLIPR®$^{TETRA}$, 20 µL of the (3×) compound solutions were first added to the cells, then 20 µL of depolarizing solution (3×EC$_{80}$ veratridine+SVqq) were added 3 minutes later to activate the channel. Changes in fluorescence were measured at wavelengths of 440-480 nm and 565-625 nm over the course of the experimental run. Membrane depolarization was expressed as a ratio of the maximum F$_{440\text{-}480\ nm}$/F$_{565\text{-}625\ nm}$ reading above average baseline F$_{440\text{-}480\ nm}$/F$_{565\text{-}625\ nm}$ reading. IC$_{50}$ values were calculated from curve fits of the ratio data using a four-parameter logistic Hill equation (Accelrys Assay Explorer 3.3 Client, Accelrys, San Diego, Calif.) with percent inhibition plotted against compound concentration.

Data reported in Table 1.

Recombinant, Human Sodium Channel, Na$_v$1.8.

Two days prior to the experiment, frozen HEK293 cells stably expressing recombinant human Na$_v$1.8 (Essen, Ann Arbor, Mich.) were quickly thawed and plated at 22,500 cells/well in growth medium [MEM (Invitrogen #11095)

with 10% FBS (Invitrogen #10082), 1 mM sodium pyruvate (Invitrogen, #C11360), 10 units/mL penicillin/10 U/mL streptomycin/29.2 µg/mL glutamine ((PSG 1%, Invitrogen #10378), 400 µg/mL zeocin (Invitrogen #R250) in black-walled, clear-bottom 384-well poly-D-lysine-coated assay plates (Greiner Bio-One, Frickenhausen, Germany) and incubated in a humidified 5% $CO_2$ incubator at 37° C. On the day of the assay, medium was removed by aspiration, and cells were washed with assay buffer [HBSS (Invitrogen, Carlsbad, Calif.) containing 20 mM HEPES (Invitrogen, Carlsbad, Calif.)]. After washing, 30 µL assay buffer containing the fluorescent voltage-sensor probe CC2-DMPE (Invitrogen, Carlsbad, Calif.) at 20 µM and 0.01% pluronic F-127 (Invitrogen, Carlsbad, Calif.) was added to the cells. Cells were incubated for 40 minutes at room temperature in the dark. Following the incubation, the cells were washed and 30 µL assay buffer containing 2.5 µM $DiSBAC_2(3)$ substrate (Invitrogen, Carlsbad, Calif.) and 0.5 mM VABSC-1 (Invitrogen, Carlsbad, Calif.) was added to the cells. The cells were incubated for 60 minutes at room temperature in the dark. Fluorescence readings were made using a FLIPR®$^{TETRA}$ (Molecular Devices, Sunnyvale Calif.) equipped with voltage-sensor probe optics. The depolarizing agent, veratridine (Sigma-Aldrich, St. Louis, Mo.), was made up at 3× concentrations in assay buffer containing 1 mg/mL scorpion venom (SVqq, from Leiurus quinquestriatus; Sigma-Aldrich, St. Louis, Mo.). The assay agonist/opener concentration was determined each day using a 6-point veratridine concentration curve in duplicate, tested with three concentrations of tetracaine (0.1, 0.06, 0.01 µM all in 0.03% dimethyl sulfoxide) and 0.03% dimethyl sulfoxide control in assay buffer. The concentration of veratridine chosen for the assay, the "$EC_{80}$", was where the assay achieved maximum signal with the dimethyl sulfoxide control, minimal inhibition with 0.01 µM tetracaine, 50% inhibition with 0.06 µM tetracaine, and >50% inhibition with 0.1 µM tetracaine. Compounds were dissolved in dimethyl sulfoxide, and 8-point, 1:3 dilution concentration-response curves were prepared in duplicate in dimethyl sulfoxide, followed by preparation of 0.8 uL/well daughter plates of the dilutions. Test compounds in the daughter plate were diluted to (~3×) solutions in assay buffer immediately before assaying. Using the FLIPR®$^{TETRA}$, 20 µL of the (3×) compound solutions were first added to the cells, then 20 µL of depolarizing solution (3×$EC_{80}$ veratridine+SVqq) were added 3 minutes later to activate the channel. Changes in fluorescence were measured at wavelengths of 440-480 nm and 565-625 nm over the course of the experimental run. Membrane depolarization was expressed as a ratio of the maximum $F_{440-480\ nm}/F_{565-625\ nm}$ reading above average baseline $F_{440-480\ nm}/F_{565-625\ nm}$ reading. $IC_{50}$ values were calculated from curve fits of the ratio data using a four-parameter logistic Hill equation (Accelrys Assay Explorer 3.3 Client, Accelrys, San Diego, Calif.) with percent inhibition plotted against compound concentration.

Data reported in Table 1.

TABLE 1

FRET-Based membrane potential assays for human sodium channels, $Na_v1.7$ and $Na_v1.8$.

| Example | FRET-Membrane Potential Nav1.7 $IC_{50}$ (µM) | FRET-Membrane Potential Nav1.8 $IC_{50}$ (µM) |
|---|---|---|
| 1 | 0.805 | 3.38 |
| 2 | 0.733 | |
| 3 | 0.835 | 3.73 |
| 4 | 0.223 | 0.23 |
| 5 | 0.166 | 0.0572 |
| 6 | 1.3 | |
| 7 | 2.72 | |
| 8 | 0.491 | 0.666 |
| 9 | 0.959 | |
| 10 | 0.375 | 3.72 |
| 11 | 0.483 | 1.47 |
| 12 | 1.02 | 0.321 |
| 13 | 0.921 | 0.406 |
| 14 | 0.618 | |
| 15 | 0.625 | 1.81 |
| 16 | 0.738 | |
| 17 | 2.75 | 4.65 |
| 18 | 0.578 | |
| 19 | 2.92 | |
| 20 | 1.49 | |
| 21 | 0.314 | |
| 22 | 3.0 | |
| 23 | 1.47 | |
| 24 | 0.338 | |
| 25 | 0.499 | 8.51 |
| 26 | 0.382 | 0.517 |
| 27 | 0.546 | 1.04 |
| 28 | 0.457 | |
| 29 | 2.19 | |
| 30 | 1.3 | |
| 31 | 1.53 | 6.62 |
| 32 | 4.23 | 2.54 |
| 33 | 0.624 | |
| 34 | 0.42 | |
| 35 | 0.747 | |
| 36 | 0.643 | |
| 37 | 0.392 | |
| 38 | 1.39 | |
| 39 | 0.301 | |
| 40 | 3.15 | |
| 41 | 1.57 | |
| 42 | 0.265 | |
| 43 | 0.915 | |
| 44 | 2.94 | |
| 45 | 1.12 | |
| 46 | 1.87 | 8.73 |
| 47 | 1.49 | 3.98 |
| 48 | 2.01 | 1.14 |
| 49 | 2.32 | 0.538 |
| 50 | 1.53 | 3.08 |
| 51 | 3.1 | 1.14 |
| 52 | 2.49 | 10.1 |
| 53 | 2.31 | 2.7 |
| 54 | 1.08 | 2.43 |
| 55 | 2.24 | 5.28 |
| 56 | 1.83 | 4.63 |
| 57 | 9.64 | |
| 58 | 2.29 | |
| 59 | 1.89 | |
| 60 | 1.99 | |
| 61 | 2.24 | |
| 62 | 1.71 | |
| 63 | 4.12 | |
| 64 | 9.52 | |
| 65 | 0.678 | |
| 66 | 0.804 | |
| 67 | 2.43 | |
| 68 | 3.57 | |
| 69 | 2.95 | 4.8 |
| 70 | 12.2 | |
| 71 | 2.34 | |
| 72 | 1.8 | |
| 73 | 0.901 | |
| 74 | 7.54 | |
| 75 | 7.49 | 12.1 |
| 76 | 2.29 | |
| 77 | 2.79 | |
| 78 | 2.94 | |
| 79 | 2.27 | |
| 80 | 2.38 | |
| 81 | 4.08 | |

TABLE 1-continued

FRET-Based membrane potential assays for human sodium channels, Na$_v$1.7 and Na$_v$1.8.

| Example | FRET-Membrane Potential Nav1.7 IC$_{50}$ (μM) | FRET-Membrane Potential Nav1.8 IC$_{50}$ (μM) |
|---|---|---|
| 82 | 2.46 | |
| 83 | 20.0 | |
| 84 | 7.98 | |
| 85 | 12.3 | |
| 86 | 1.96 | |
| 87 | 2.46 | 5.56 |
| 88 | 0.351 | 1.37 |
| 89 | 10.6 | |
| 90 | 1.72 | |
| 91 | 1.74 | |
| 92 | 1.86 | |
| 93 | 10.7 | 5.18 |
| 94 | 11.9 | |
| 95 | 2.68 | |
| 96 | 1.64 | |
| 97 | 2.39 | |
| 98 | 1.44 | |
| 99 | 0.482 | |
| 100 | 5.01 | 20.0 |
| 101 | 3.52 | |
| 102 | 3.49 | |
| 103 | 3.62 | |
| 104 | 6.26 | |
| 105 | 1.33 | |
| 106 | 0.635 | |
| 107 | 1.28 | |
| 108 | 12.3 | |
| 109 | 1.02 | |
| 110 | 2.81 | |
| 111 | 0.835 | |
| 112 | 2.69 | |
| 113 | 2.27 | |
| 114 | 14.3 | |
| 115 | 0.887 | |
| 116 | 0.821 | |
| 117 | 1.79 | |
| 118 | 1.1 | |
| 119 | 1.76 | |
| 120 | 4.18 | |
| 121 | 2.41 | |
| 122 | 2.3 | |
| 123 | 0.346 | |
| 124 | 1.2 | |
| 125 | 1.41 | |
| 126 | 0.343 | |
| 127 | 1.56 | |
| 128 | 0.746 | |
| 129 | 0.403 | |
| 130 | 1.85 | |
| 131 | 0.286 | |
| 132 | 0.713 | |
| 133 | 0.525 | |
| 134 | 1.26 | |
| 135 | 0.904 | |
| 136 | 0.928 | |
| 137 | 2.3 | |
| 138 | 3.31 | |
| 139 | 2.41 | |
| 140 | 0.878 | |
| 141 | 1.16 | |
| 142 | 2.0 | |
| 143 | 0.874 | |
| 144 | 2.1 | |
| 145 | 6.23 | |
| 146 | 3.12 | |
| 147 | 1.05 | |
| 148 | 2.28 | |
| 149 | 2.97 | |
| 150 | 3.16 | |
| 151 | 20.0 | |
| 152 | 2.26 | |
| 153 | 1.32 | |
| 154 | 2.87 | |
| 155 | 1.88 | |
| 156 | 1.35 | |
| 157 | 3.37 | |
| 158 | 20.0 | |
| 159 | 3.59 | |
| 160 | 3.51 | |
| 161 | 1.4 | |
| 162 | 0.729 | |
| 163 | 2.16 | |
| 164 | 0.635 | |
| 165 | 0.681 | |
| 166 | 0.435 | |
| 167 | 0.893 | |
| 168 | 0.816 | |
| 169 | 1.07 | |
| 170 | 0.795 | |
| 171 | 0.285 | |
| 172 | 2.6 | |
| 173 | 0.80 | |
| 174 | 0.849 | |
| 175 | 2.65 | |
| 176 | 0.983 | |
| 177 | 0.965 | |
| 178 | 2.0 | |
| 179 | 15.4 | |
| 180 | 3.23 | |
| 181 | 6.27 | |
| 182 | 2.62 | |
| 183 | 2.93 | |
| 184 | 1.06 | |
| 185 | 0.965 | |
| 186 | 1.41 | |
| 187 | 1.91 | |
| 188 | 1.66 | |
| 189 | 1.02 | |
| 190 | 1.09 | |
| 191 | 2.95 | |
| 192 | 1.36 | |
| 193 | 0.998 | |
| 194 | 0.613 | |
| 195 | 1.39 | |
| 196 | 4.31 | |
| 197 | 2.14 | |
| 198 | 1.24 | |
| 199 | 2.97 | |
| 200 | 3.61 | |
| 201 | 0.661 | |
| 202 | 0.681 | |
| 203 | 3.67 | |
| 204 | 3.41 | |
| 205 | 0.778 | 1.5 |
| 206 | 1.06 | |
| 207 | 1.87 | |
| 208 | 3.26 | |
| 209 | 1.06 | |
| 210 | 3.33 | |
| 211 | 1.9 | |
| 212 | 1.14 | |
| 213 | 3.65 | |
| 214 | 2.02 | |
| 215 | 1.08 | |
| 216 | 20.0 | |
| 217 | 1.07 | |
| 218 | 2.76 | |
| 219 | 5.21 | |
| 220 | 1.84 | |
| 221 | 9.5 | |
| 222 | 11.2 | |
| 223 | 11.2 | |
| 224 | 3.6 | |
| 225 | 14.0 | |
| 226 | 3.37 | |
| 227 | 0.871 | |
| 228 | 1.09 | |
| 229 | 9.08 | |

TABLE 1-continued

FRET-Based membrane potential assays for human sodium channels, $Na_v1.7$ and $Na_v1.8$.

| Example | FRET-Membrane Potential Nav1.7 $IC_{50}$ (µM) | FRET-Membrane Potential Nav1.8 $IC_{50}$ (µM) |
|---|---|---|
| 230 | 3.73 | |
| 231 | 3.65 | |
| 232 | 1.15 | |
| 233 | 1.02 | |
| 234 | 2.9 | |
| 235 | 1.13 | |
| 236 | 0.924 | |
| 237 | 0.667 | |
| 238 | 0.586 | |
| 239 | 0.352 | |
| 240 | 13.4 | |
| 241 | 2.35 | |
| 242 | 3.33 | |
| 243 | 1.61 | |
| 244 | 3.08 | |
| 245 | 0.207 | |
| 246 | 2.98 | |
| 247 | 0.981 | |
| 248 | 1.04 | |
| 249 | 2.43 | |
| 250 | 1.14 | |
| 251 | 2.06 | |
| 252 | 1.76 | |
| 253 | 0.932 | |
| 254 | 0.825 | |
| 255 | 5.51 | |
| 256 | 3.12 | |
| 257 | 3.09 | |
| 258 | 11.0 | |
| 259 | 3.36 | |
| 260 | 20.0 | |
| 261 | 3.41 | |
| 262 | 2.52 | |
| 263 | 0.494 | |
| 264 | 3.35 | |
| 265 | 8.15 | |
| 266 | 3.02 | |
| 267 | 1.09 | |
| 268 | 15.0 | |
| 269 | 5.79 | |
| 270 | 5.87 | |
| 271 | 3.45 | |
| 272 | 0.338 | |
| 273 | 4.86 | |
| 274 | 2.74 | 1.4 |
| 275 | 1.41 | 3.7 |
| 276 | 15.1 | 6.44 |
| 277 | 3.06 | |
| 278 | 5.78 | |
| 279 | 1.86 | 5.64 |
| 280 | 0.518 | 10.8 |
| 281 | 11.6 | 12.4 |
| 282 | 2.49 | 1.41 |
| 283 | 2.55 | 2.21 |
| 284 | 2.43 | 1.19 |
| 285 | 2.52 | 1.47 |
| 286 | 3.17 | 3.0 |
| 287 | 5.8 | 1.67 |
| 288 | 5.3 | 4.01 |
| 289 | 2.71 | 2.05 |
| 290 | 4.15 | 13.5 |
| 291 | 5.9 | 13.1 |
| 292 | 2.96 | 4.44 |
| 293 | 3.67 | 17.6 |
| 294 | 7.17 | 18.3 |
| 295 | 2.51 | 1.79 |
| 296 | 3.18 | 1.31 |
| 297 | 3.02 | 0.881 |
| 298 | 3.37 | 1.52 |
| 299 | 0.95 | 0.398 |
| 300 | 3.11 | 1.06 |
| 301 | 3.16 | 1.56 |
| 302 | 20.0 | 7.18 |
| 303 | 2.46 | 0.93 |
| 304 | 4.79 | 1.41 |
| 305 | 3.67 | 3.33 |
| 306 | 20.0 | 20.0 |
| 307 | 0.52 | 1.42 |
| 308 | 1.02 | 0.345 |
| 309 | 0.695 | 0.725 |
| 310 | 2.81 | 0.878 |
| 311 | 5.85 | 4.35 |
| 312 | 1.71 | 1.68 |
| 313 | 2.72 | 3.25 |
| 314 | 3.25 | 0.912 |
| 315 | 2.96 | 3.56 |
| 316 | 3.11 | 1.65 |
| 317 | 2.44 | 1.28 |
| 318 | 3.14 | 3.47 |
| 319 | 3.14 | 3.02 |
| 320 | 16.8 | 10.1 |
| 321 | 5.79 | 5.67 |
| 322 | 0.973 | 1.89 |
| 323 | 1.46 | 0.695 |
| 324 | 1.41 | 0.526 |
| 325 | 3.12 | 3.86 |
| 326 | 10.5 | 5.25 |
| 327 | 2.89 | 0.678 |
| 328 | 3.02 | 2.03 |
| 329 | 2.72 | 3.13 |
| 330 | 1.15 | |
| 331 | 1.44 | 3.65 |
| 332 | 5.1 | 2.64 |
| 333 | 2.41 | 4.76 |
| 334 | 1.93 | 0.657 |
| 335 | 1.11 | 0.501 |
| 336 | 2.14 | 0.867 |
| 337 | 2.24 | 0.846 |
| 338 | 1.06 | 2.62 |
| 339 | 5.67 | 2.67 |
| 340 | 2.64 | 0.637 |
| 341 | 2.9 | 0.991 |
| 342 | 2.21 | 0.746 |
| 343 | 3.06 | 1.27 |
| 344 | 8.03 | 7.38 |
| 345 | 6.06 | 1.78 |
| 346 | 2.04 | 0.96 |
| 347 | 3.45 | 1.29 |
| 348 | 13.4 | 3.26 |
| 349 | 15.1 | 7.57 |
| 350 | 9.22 | 12.3 |
| 351 | 3.48 | 1.85 |
| 352 | 1.51 | 2.58 |
| 353 | 3.31 | 1.69 |
| 354 | 6.5 | 16.6 |
| 355 | 9.23 | 4.05 |
| 356 | 1.86 | |
| 357 | 3.06 | |

Osteoarthritic (OA) Pain Induced by Sodium Monoiodoacetate (MIA)

Pain behavior was assessed by measurement of hind limb grip force (GF) in adult osteoarthritic rats. Male Sprague Dawley rats, obtained from Charles River Laboratories, (Wilmington, Mass.), weighing 150-175 g, were injected in the unilateral knee join with a single intra-articular injection of sodium monoiodoacetate (MIA, 3 mg/rat). All rats were tested at 20 days following MIA injection. A behavioral measure of activity-induced pain was carried out. Measurements of the peak hind limb grip force were conducted by recording the maximum compressive force (CFmax), in grams of force, exerted on a hind limb strain gauge setup, in a commercially available grip force measurement system (Columbus Instruments, Columbus, Ohio).

During testing, each rat was gently restrained by grasping it around its rib cage and then allowed to grasp the wire mesh frame attached to the strain gauge. The experimenter then moved the animal in a rostral-to-caudal direction until the grip was broken. Each rat was sequentially tested twice at an approximately 2-3 minute interval to obtain a raw mean grip force (CFmax). This raw mean grip force data was in turn converted to a maximum hindlimb cumulative compressive force (CFmax), as the grams of force/kg of body weight, for each animal.

For evaluating the compound effects, the hind limb grip force was conducted 20 days following the intra-articular injection of MIA. A group of age-matched nave (not injected with MIA) animals was added as a comparator to the drug-dosed groups. The vehicle control response for each group of MIA-treated animals was defined as the 0% response (0% effect), whereas the nave control group was defined as the normal response and as 100% effect. The % effect for each dose group was expressed as % return of response to normalcy, compared to the nave group. A percent maximal possible effect (% MPE) of testing compound was calculated according to the formula: (Treatment CFmax−Vehicle CFmax)/Vehicle CFmax]×100). Higher % effect numbers indicate increased relief from the pain in the model, with 100% indicating a return to the level of response seen in normal (non-osteoarthritic) animals. All experiments evaluating drug effects in this model were conducted in a randomized blinded fashion.

The animals were housed in Association for Assessment and Accreditation of Laboratory Animal Care (AAALAC) approved facilities at AbbVie Inc. in a temperature-regulated environment under a controlled 12-hour light-dark cycle, with lights on at 6:00 a.m. Food and water were available ad libitum at all times except during testing. All testing was done following procedures outlined in protocols approved by AbbVie Inc.'s Institutional Animal Care and Use Committee.

Data reported in Table 2.

Rat Spinal Nerve Ligation (SNL) Model of Neuropathic Pain.

A model of spinal nerve ligation-induced (SNL model) neuropathic pain as originally described by Kim and Chung (Kim, S. H. and J. M. Chung, 1992, Pain 50, 355) was used to test a compound of the present application. The male Sprague Dawley rats (Charles River Laboratories, Wilmington, Mass.), weighing 150-175 g at the time of surgery, were placed under isoflurane anesthesia and a 1.5 cm incision was made dorsal to the lumbosacral plexus. The paraspinal muscles (left side) were separated from the spinous processes, the left L5 and L6 spinal nerves isolated, and tightly ligated with 5-0 silk suture distal to the dorsal root ganglion. Care was taken to avoid ligating the L4 spinal nerve. Following spinal nerve ligation, a minimum of 7 days of recovery and no more than 3 weeks was allowed prior to the behavioral testing (mechanical sensitivity). Only rats with threshold scores ≤4.5 g were considered allodynic and utilized in pharmacological experiments.

Mechanical sensitivity was measured using calibrated von Frey filaments (Stoelting, Wood Dale, Ill.). Paw withdrawal threshold (PWT) was determined by using the Dixon's up-down method (Dixon, W. J., 1980, Ann. Rev. Pharmacol. Toxicol., 20, 441). Rats were placed into inverted individual plastic containers (20×12.5×20 cm) on top of a suspended wire mesh with a 1 $cm^2$ grid to provide access to the ventral side of the hind paws, and acclimated to the test chambers for 20 minutes. The von Frey filaments were presented perpendicularly to the plantar surface of the selected hind paw, and then held in this position for approximately 8 seconds with enough force to cause a slight bend in the filament. Positive responses included an abrupt withdrawal of the hind paw from the stimulus, or flinching behavior immediately following removal of the stimulus. A 50% withdrawal threshold was determined using an up-down procedure (Dixon, 1980). A percent maximal possible effect (% MPE) of testing compound was calculated according to the formula: (Log [compound-treated threshold]−Log [vehicle-treated threshold])/(Log [maximum threshold]−Log [vehicle-treated threshold])×100%, where the maximum threshold was equal to 15 g.

The animals were housed in Association for Assessment and Accreditation of Laboratory Animal Care (AAALAC) approved facilities at AbbVie Inc. in a temperature-regulated environment under a controlled 12-hour light-dark cycle, with lights on at 6:00 a.m. Food and water were available ad libitum at all times except during testing. All testing was done following procedures outlined in protocols approved by AbbVie Inc.s' Institutional Animal Care and Use Committee.

Data reported in Table 2.

TABLE 2

In vivo data for MIA-OA and SNL pain assays.

| Example | OA Dose (mg/kg) | OA MPE (%) | SNL Dose (mg/kg) | SNL MPE (%) |
| --- | --- | --- | --- | --- |
| 1 | 30 | 55 | 100 | 52 |
| 2 | | | 100 | 38 |
| 3 | | | 100 | 30 |
| 4 | | | 100 | 68 |
| 8 | 30 | 75 | 100 | 57 |
| 10 | 30 | 91 | 100 | 0 |
| 12 | | | 100 | 25 |
| 13 | 30 | 47 | | |
| 14 | 30 | 60 | | |
| 15 | 30 | 68 | 100 | 74 |
| 16 | 30 | 67 | | |
| 17 | 30 | 91 | | |
| 18 | 10 | 65 | | |
| 19 | 10 | 67 | | |
| 20 | 10 | 91 | | |
| 21 | 10 | 21 | | |
| 22 | 30 | 38 | | |
| 23 | 30 | 45 | | |
| 24 | 10 | 62 | | |
| 25 | 10 | 24 | | |
| 26 | | | 100 | 54 |
| 27 | 10 | 57 | 100 | 63 |
| 28 | 10 | 62 | | |
| 29 | 10 | 46 | | |
| 30 | 10 | 80 | | |
| 31 | 10 | 89 | 100 | 94 |
| 32 | 30 | 65 | | |
| 33 | 10 | 17 | | |
| 34 | 10 | 43 | | |
| 35 | 10 | 19 | | |
| 36 | 10 | 27 | | |
| 37 | 10 | 35 | | |
| 38 | 10 | 33 | | |
| 39 | 10 | 38 | | |
| 40 | 10 | 41 | | |
| 41 | 10 | 47 | | |
| 42 | 10 | 35 | | |
| 43 | 30 | 71 | | |
| 44 | 30 | 71 | | |
| 45 | 10 | 43 | | |
| 46 | 30 | 69 | 100 | 59 |
| 47 | 10 | 19 | | |
| 48 | 10 | 20 | | |
| 49 | 10 | 66 | | |
| 50 | 10 | 7 | | |
| 51 | 30 | 16 | | |

TABLE 2-continued

In vivo data for MIA-OA and SNL pain assays.

| Example | OA Dose (mg/kg) | OA MPE (%) | SNL Dose (mg/kg) | SNL MPE (%) |
|---------|-----------------|------------|------------------|-------------|
| 52 | 30 | 27 | | |
| 53 | 30 | 74 | 100 | 47 |
| 54 | 30 | 57 | | |
| 55 | 30 | 66 | 100 | 91 |
| 56 | 30 | 70 | | |
| 205 | 30 | 46 | | |
| 307 | 30 | 62 | | |
| 316 | 30 | 63 | | |
| 333 | 30 | 86 | | |

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations, or methods, or any combination of such changes and modifications of use of the invention, may be made without departing from the spirit and scope thereof.

What is claimed is:

1. A compound of formula (I):

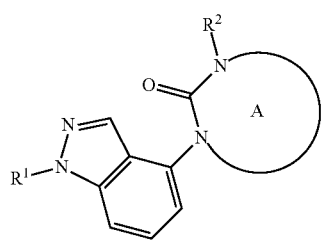

(I)

or a pharmaceutically acceptable salt or isotopically labelled form thereof, wherein:

A is selected from the group consisting of (i), (ii), (iii), and (iv), wherein the nitrogen atom on the left side of each substructure (i), (ii), (iii), or (iv) is attached to the phenyl ring of the indazole in formula (I);

(ii)

(ii)

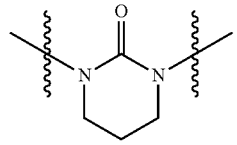

(iii)

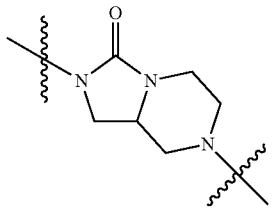

(iv)

$R^{1a}$ is hydrogen or $C_1$-$C_4$alkyl;

$R^1$ is selected from the group consisting of $C_1$-$C_8$alkyl, $C_1$-$C_8$haloalkyl, $C_3$-$C_7$cycloalkyl, phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen;

$R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, -$G^1$, -$G^2$, -$G^3$, -$G^4$, —$CO_2R^{2c}$, —$CO_2G^1$, —$C(O)R^{2c}$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(O)(CR^{2a}R^{2b})_m$—$OR^{2c}$, —$C(OH)(R^{2d})$—$R^{2c}$, —$C(OH)(R^{2d})$-$G^1$, —$C(OH)(R^{2d})$—$C(O)R^{2c}$, —$C(OH)(R^{2d})$—$C(O)G^1$, —$C(OH)(R^{2d})$—$(CR^{2a}R^{2b})_mG^1$, —$SO_2R^{2c}$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$SO_2NR^{2d}R^{2e}$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)R^{2c}$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2R^{2c}$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}R^{2e}$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, —$CR^{2a}$=$CHR^{2a}$—$CO_2R^{2c}$, —$CR^{2a}$=$CHR^{2a}$—$C(O)G^1$, and —$CR^{2a}$=$CHR^{2a}$—$C(O)G^3$;

$R^{2a}$ and $R^{2b}$, at each occurrence, are each independently selected from the group consisting of hydrogen, fluorine, $C_1$-$C_4$alkyl, and halo$C_1$-$C_4$alkyl;

$R^{2c}$ is selected from the group consisting of $C_2$-$C_8$alkenyl, $C_1$-$C_8$alkyl and halo$C_1$-$C_8$alkyl;

$R^{2d}$, at each occurrence, is selected from the group consisting of hydrogen, $C_1$-$C_6$alkyl and halo$C_1$-$C_6$alkyl;

$R^{2e}$ is selected from the group consisting of hydrogen, $C_2$-$C_8$alkenyl, $C_1$-$C_6$alkoxy, $C_1$-$C_4$alkoxy$C_1$-$C_4$alkyl, $C_1$-$C_6$alkyl, and halo$C_1$-$C_6$alkyl;

$R^{2f}$ is selected from the group consisting of $C_1$-$C_4$alkyl, halo$C_1$-$C_4$alkyl and —$(CR^{2a}R^{2b})_m$-$G^{2a}$;

$G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo;

$G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo;

$G^2$ is aryl, wherein the aryl is optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen;

$G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, 1,3-dioxole, halo$C_1$-$C_4$alkyl, and halogen;

$G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, —SO$_2$(CR$^{2a}$R$^{2b}$)$_m$$G^{1a}$, and —(CR$^{2a}$R$^{2b}$)$_p$$G^{3a}$;

$G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, 1,3-dioxolane, halogen, halo$C_1$-$C_4$alkyl, hydroxy, hydroxy$C_1$-$C_4$alkyl, oxo, —C(O)$G^{1a}$, —C(O)NH$G^{2a}$, —C(O)C(O)NH$_2$, $G^{2a}$, and —SO$_2$(CR$^{2a}$R$^{2b}$)$_m$$G^{1a}$;

$G^4$ is 5-10-membered heteroaryl, wherein the 5-10-membered heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$;

m is 1, 2 or 3;

n is 1, 2 or 3; and p is 1 or 2.

2. The compound of claim 1, wherein, A is (i)

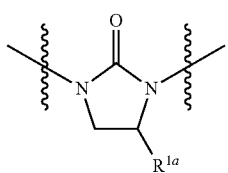

(i)

3. The compound of claim 2, wherein $R^1$ is selected from the group consisting of $C_1$-$C_8$alkyl and $C_3$-$C_7$cycloalkyl.

4. The compound of claim 3, wherein $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$.

5. The compound of claim 3, wherein $R^2$ is selected from the group consisting of -$G^1$, -$G^2$, -$G^3$, -$G^4$, —CO$_2$$G^1$, —C(O)$G^1$, —C(O)$G^2$, —C(O)$G^3$, —C(O)$G^4$, —C(O)(CR$^{2a}$R$^{2b}$)$_m$$G^1$, —C(O)(CR$^{2a}$R$^{2b}$)$_m$$G^2$, —C(OH)(R$^{2d}$)-$G^1$, —C(OH)(R$^{2d}$)—C(O)$G^1$, —C(OH)(R$^{2d}$)—(CR$^{2a}$R$^{2b}$)$_m$$G^1$, —SO$_2$$G^1$, —SO$_2$$G^2$, —SO$_2$$G^3$, —SO$_2$$G^4$, —SO$_2$—(CR$^{2a}$R$^{2b}$)$_m$$G^1$, —SO$_2$—(CR$^{2a}$R$^{2b}$)$_m$$G^2$, —SO$_2$—(CR$^{2a}$R$^{2b}$)$_m$$G^3$, —SO$_2$—(CR$^{2a}$R$^{2b}$)$_m$$G^4$, —(CR$^{2a}$R$^{2b}$)$_m$$G^1$, —(CR$^{2a}$R$^{2b}$)$_m$$G^2$, —(CR$^{2a}$R$^{2b}$)$_m$$G^3$, —(CR$^{2a}$R$^{2b}$)$_m$$G^4$, —(CR$^{2a}$R$^{2b}$)$_m$—C(OH)(R$^{2d}$)-$G^1$, —(CR$^{2a}$R$^{2b}$)$_m$—C(OH)(R$^{2d}$)-$G^2$, —(CR$^{2a}$R$^{2b}$)$_m$—C(OH)(R$^{2d}$)-$G^3$, —(CR$^{2a}$R$^{2b}$)$_m$—C(OH)(R$^{2d}$)-$G^4$, —(CR$^{2a}$R$^{2b}$)$_m$—C(OH)(R$^{2d}$)—(CR$^{2a}$R$^{2b}$)$_n$-$G^1$, —(CR$^{2a}$R$^{2b}$)$_m$—C(OH)(R$^{2d}$)—(CR$^{2a}$R$^{2b}$)$_n$-$G^2$, —(CR$^{2a}$R$^{2b}$)$_m$—C(OH)(R$^{2d}$)—(CR$^{2a}$R$^{2b}$)$_n$-$G^3$, —(CR$^{2a}$R$^{2b}$)$_m$—C(OH)(R$^{2d}$)—(CR$^{2a}$R$^{2b}$)$_n$-$G^4$, —(CR$^{2a}$R$^{2b}$)$_m$—C(O)—(CR$^{2a}$R$^{2b}$)$_n$$G^1$, —(CR$^{2a}$R$^{2b}$)$_m$C(O)(CR$^{2a}$R$^{2b}$)$_n$$G^2$, —(CR$^{2a}$R$^{2b}$)$_m$C(O)(CR$^{2a}$R$^{2b}$)$_n$$G^3$, —(CR$^{2a}$R$^{2b}$)$_m$C(O)(CR$^{2a}$R$^{2b}$)$_n$$G^4$, —(CR$^{2a}$R$^{2b}$)$_m$CO$_2$$G^1$, —(CR$^{2a}$R$^{2b}$)$_m$C(O)$G^1$, —(CR$^{2a}$R$^{2b}$)$_m$C(O)$G^2$, —(CR$^{2a}$R$^{2b}$)$_m$C(O)$G^3$, —(CR$^{2a}$R$^{2b}$)$_m$C(O)$G^4$, —(CR$^{2a}$R$^{2b}$)$_m$C(O)NR$^{2d}$$G^1$, —(CR$^{2a}$R$^{2b}$)$_m$C(O)NR$^{2d}$$G^2$, —(CR$^{2a}$R$^{2b}$)$_m$C(O)NR$^{2d}$$G^3$, —(CR$^{2a}$R$^{2b}$)$_m$C(O)NR$^{2d}$$G^4$, —(CR$^{2a}$R$^{2b}$)$_m$C(O)N(R$^{2d}$)((CR$^{2a}$R$^{2b}$)$_n$$G^1$), —(CR$^{2a}$R$^{2b}$)$_m$C(O)N(R$^{2d}$)((CR$^{2a}$R$^{2b}$)$_n$$G^2$), —(CR$^{2a}$R$^{2b}$)$_m$C(O)N(R$^{2d}$)((CR$^{2a}$R$^{2b}$)$_n$$G^3$), —(CR$^{2a}$R$^{2b}$)$_m$C(O)N(R$^{2d}$)((CR$^{2a}$R$^{2b}$)$_n$$G^4$), —(CR$^{2a}$R$^{2b}$)$_m$C(O)NH—(CR$^{2a}$R$^{2f}$)—C(O)NHR$^{2d}$, CR$^{2a}$=CHR$^{2a}$—C(O)$G^1$, and —CR$^{2a}$=CHR$^{2a}$—C(O)$G^3$.

6. The compound of claim 5, wherein $R^2$ is —(CR$^{2a}$R$^{2b}$)$_m$C(O)$G^3$, wherein, $G^3$ is optionally substituted with 1 or 2 halogen.

7. The compound of claim 2, wherein $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen.

8. The compound of claim 7, wherein $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$.

9. The compound of claim 8, wherein $R^2$ is selected from the group consisting of hydrogen, $C_1$-$C_6$alkoxy$C_1$-$C_6$alkyl, $C_1$-$C_8$alkyl, $C_1$-$C_8$haloalkyl, and —(CR$^{2a}$R$^{2b}$)$_m$—C(OR$^{2d}$)(R$^{2d}$)—R$^{2e}$;

$R^{2a}$ and $R^{2b}$, at each occurrence, are each independently selected from the group consisting of hydrogen and $C_1$-$C_4$alkyl;

$R^{2d}$, at each occurrence, is selected from the group consisting of hydrogen and $C_1$-$C_6$alkyl;

$R^{2e}$ is selected from the group consisting of $C_2$-$C_8$alkenyl and $C_1$-$C_6$alkyl; and m is 1.

10. The compound of claim 8, wherein $R^2$ is selected from the group consisting of —$CO_2R^{2c}$, —$C(O)R^{2c}$, —$C(O)(CR^{2a}R^{2b})_m$—$OR^{2c}$, —$SO_2R^{2c}$, —$SO_2NR^{2d}R^{2e}$, —$(CR^{2a}R^{2b})_mC(O)R^{2c}$, —$(CR^{2a}R^{2b})_mCO_2R^{2c}$, —$(CR^{2a}R^{2b})_mC(O)NR^{2d}R^{2e}$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, and —$CR^{2a}$=$CHR^{2a}$—$CO_2R^{2c}$;

$R^{2a}$ and $R^{2b}$, at each occurrence, are each independently selected from the group consisting of hydrogen and $C_1$-$C_4$alkyl;

$R^{2c}$ is selected from the group consisting of $C_1$-$C_8$alkyl and halo$C_1$-$C_8$alkyl;

$R^{2d}$, at each occurrence, is selected from the group consisting of hydrogen, $C_1$-$C_6$alkyl and halo$C_1$-$C_6$alkyl;

$R^{2e}$ is selected from the group consisting of hydrogen, $C_1$-$C_4$alkoxy$C_1$-$C_4$alkyl, $C_1$-$C_6$alkyl, and halo$C_1$-$C_6$alkyl;

$R^{2f}$ is selected from the group consisting of $C_1$-$C_4$alkyl and halo$C_1$-$C_4$alkyl; and m is 1 or 2.

11. The compound of claim 7, wherein $R^2$ is selected from the group consisting of -$G^1$, -$G^2$, -$G^3$, -$G^4$, —$CO_2G^1$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(OH)(R^{2d})$-$G^1$, —$C(OH)(R^{2d})$—$C(O)G^1$, —$C(OH)(R^{2d})$—$(CR^{2a}R^{2b})_mG^1$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mC(O)NH$—$(CR^{2a}R^{2f})$—$C(O)NHR^{2d}$, —$CR^{2a}$=$CHR^{2a}$—$C(O)G^1$ and —$CR^{2a}$=$CHR^{2a}$—$C(O)G^3$.

12. The compound of claim 11, wherein $R^2$ is selected from the group consisting of -$G^1$, -$G^2$, -$G^3$, -$G^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, and —$(CR^{2a}R^{2b})_m$—$C(OH)(R^{2d})$—$(CR^{2a}R^{2b})_n$-$G^4$;

$R^{2a}$ and $R^{2b}$, at each occurrence, are each independently selected from the group consisting of hydrogen, $C_1$-$C_4$alkyl, and halo$C_1$-$C_4$alkyl;

$R^{2d}$, at each occurrence, is selected from the group consisting of hydrogen and $C_1$-$C_6$alkyl;

$G^1$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, and oxo;

$G^{1a}$ is $C_3$-$C_7$cycloalkyl, wherein the $C_3$-$C_7$cycloalkyl is optionally substituted with 1, 2, 3 or 4 substituents selected from the group consisting of $C_1$-$C_6$alkoxy, $C_1$-$C_4$alkyl, halo$C_1$-$C_4$alkyl, halogen, hydroxy, hydroxy$C_1$-$C_4$alkyl, and oxo;

$G^2$ is aryl, wherein the aryl is optionally substituted with 1, 2, 3 or 4 substituents selected from the group consisting of $C_1$-$C_4$alkoxy, $C_1$-$C_4$alkyl, halo$C_1$-$C_4$alkyl, and halogen;

$G^{2a}$ is aryl or 5-6-membered heteroaryl, wherein the aryl or 5-6-membered heteroaryl are optionally substituted with 1, 2, 3 or 4 substituents selected from the group consisting of $C_1$-$C_4$alkoxy, $C_1$-$C_4$alkyl, halo$C_1$-$C_4$alkyl, and halogen;

$G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, benzyl, cyano, halogen, halo$C_1$-$C_4$alkyl, hydroxy, hydroxy$C_1$-$C_4$alkyl, oxo, —$C(O)G^{1a}$, —$C(O)NHG^{2a}$, —$C(O)C(O)NH_2$, $G^{2a}$, —$SO_2(CR^{2a}R^{2b})_mG^{1a}$, and —$(CR^{2a}R^{2b})_pG^{3a}$;

$G^{3a}$ is 4-8-membered-heterocycle, wherein the 4-8-membered-heterocycle is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, halogen, halo$C_1$-$C_4$alkyl, hydroxy, hydroxy$C_1$-$C_4$alkyl, and oxo;

$G^4$ is 5-10-membered heteroaryl, wherein the 5-10-membered-heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, halo$C_1$-$C_4$alkyl, $G^{1a}$, and $G^{3a}$;

m is 1 or 2;

n is 1; and p is 1.

13. The compound of claim 11, wherein $R^2$ is selected from the group consisting of —$CO_2G^1$, —$C(O)G^1$, —$C(O)G^2$, —$C(O)G^3$, —$C(O)G^4$, —$C(OH)(R^{2d})$—$C(O)G^1$, —$SO_2G^1$, —$SO_2G^2$, —$SO_2G^3$, —$SO_2G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mC(O)NH$—$(CR^{2a}R^{2f})$—$C(O)NHR^{2d}$, —$CR^{2a}$=$CHR^{2a}$—$C(O)G^1$, and —$CR^{2a}$=$CHR^{2a}$—$C(O)G^3$;

$R^{2a}$ and $R^{2b}$, at each occurrence, are each independently selected from the group consisting of hydrogen, $C_1$-$C_4$alkyl, and halo$C_1$-$C_4$alkyl;

$R^{2d}$, at each occurrence, is selected from the group consisting of hydrogen, $C_1$-$C_6$alkyl and halo$C_1$-$C_6$alkyl;

$R^{2f}$ is —$(CR^{2a}R^{2b})_m$-$G^{2a}$;

$G^1$ is $C_3$-$C_7$cycloalkyl, wherein the $C_3$-$C_7$cycloalkyl is optionally substituted with 1, 2, or 3 substituents selected from the group consisting of $C_1$-$C_6$alkoxy, $C_1$-$C_4$alkyl, benzyloxy, halo$C_1$-$C_4$alkyl, halogen, hydroxy, hydroxy$C_1$-$C_4$alkyl, oxime, $C_1$-$C_6$alkyloxime, and oxo;

$G^2$ is aryl, wherein the aryl is optionally substituted with 1, 2 or 3 substituents selected from the group consisting of $C_1$-$C_4$alkoxy, $C_1$-$C_4$alkyl, 1,3-dioxole, halo$C_1$-$C_4$alkyl, and halogen;

$G^{2a}$ is aryl or 5-6-membered heteroaryl, wherein the aryl or 5-6-membered heteroaryl are optionally substituted with 1, 2 or 3 substituents selected from the group consisting of $C_1$-$C_4$alkyl, halo$C_1$-$C_4$alkyl, and halogen;

$G^3$ is 4-8-membered-heterocycle, wherein the 4-8-membered-heterocycle is optionally substituted with 1, 2, 3, 4 or 5 substituents selected from the group consisting of $C_1$-$C_6$alkoxy, $C_1$-$C_4$alkoxy$C_1$-$C_4$alkyl, $C_1$-$C_4$alkoxycarbonyl, $C_1$-$C_6$alkyl, $C_1$-$C_4$alkylcarbonyl, halo$C_1$-$C_4$alkylsulfonyl, $C_1$-$C_4$alkylsulfonyl, cyano, 1,3-dioxolane, halogen, halo$C_1$-$C_4$alkyl, hydroxy, hydroxy$C_1$-$C_4$alkyl, oxo, —C(O)NHG$^{2a}$, G$^{2a}$ and —(CR$^{2a}$R$^{2b}$)$_p$G$^{3a}$;

$G^{3a}$ is 4-7-membered-heterocycle, wherein the 4-7-membered-heterocycle is optionally substituted with 1, 2, 3 or 4 substituents selected from the group consisting of $C_1$-$C_6$alkyl, halogen, halo$C_1$-$C_4$alkyl, hydroxy, hydroxy$C_1$-$C_4$alkyl and oxo;

$G^4$ is 5-10-membered heteroaryl, wherein the 5-10-membered-heteroaryl is optionally substituted with 1, 2, 3 or 4 substituents selected from the group consisting of $C_1$-$C_4$alkoxy, $C_1$-$C_4$alkoxy$C_1$-$C_4$alkyl, $C_1$-$C_4$alkyl, halogen, and halo$C_1$-$C_4$alkyl;

m is 1, 2 or 3;
n is 1, 2 or 3; and
p is 1.

14. The compound of claim 1, wherein, A is (ii)

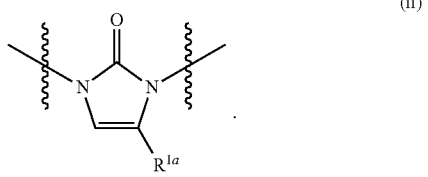

(ii)

15. The compound of claim 14, wherein R$^1$ is selected from the group consisting of $C_1$-$C_8$alkyl and $C_3$-$C_7$cycloalkyl.

16. The compound of claim 15, wherein R$^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$.

17. The compound of claim 15, wherein R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)G$^1$ and —CR$^{2a}$=CHR$^{2a}$—C(O)G$^3$.

18. The compound of claim 14, wherein R$^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen.

19. The compound of claim 18, wherein R$^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$.

20. The compound of claim 19, wherein R$^2$ is —(CR$^{2a}$R$^{2b}$)$_m$C(O)NR$^{2d}$R$^{2e}$, wherein R$^{2a}$ and R$^{2b}$, at each occurrence, are each independently selected from the group consisting of hydrogen and $C_1$-$C_4$alkyl;

R$^{2d}$ and R$^{2e}$ are each independently selected from the group consisting of hydrogen and $C_1$-$C_4$alkyl; and m is 1 or 2.

21. The compound of claim 18, wherein R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)G$^1$ and —CR$^{2a}$=CHR$^{2a}$—C(O)G$^3$.

22. The compound of claim 21, wherein R$^2$ is —(CR$^{2a}$R$^{2b}$)$_m$C(O)G$^3$, wherein,
R$^{2a}$ and R$^{2b}$, at each occurrence, are each independently selected from the group consisting of hydrogen and C$_1$-C$_4$alkyl;
G$^3$ is optionally substituted with 1 or 2 halogen; and
m is 1 or 2.

23. The compound of claim 1, wherein, A is (iii)

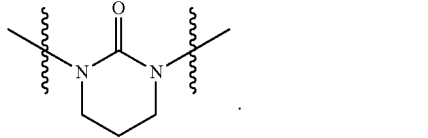

24. The compound of claim 23, wherein R$^1$ is selected from the group consisting of C$_1$-C$_8$alkyl and C$_3$-C$_7$cycloalkyl.

25. The compound of claim 24, wherein R$^2$ is selected from the group consisting of hydrogen, C$_1$-C$_8$alkenyl, C$_1$-C$_6$alkoxyC$_1$-C$_6$alkyl, C$_1$-C$_8$alkyl, C$_1$-C$_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$.

26. The compound of claim 24, wherein R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)G$^1$ and —CR$^{2a}$=CHR$^{2a}$—C(O)G$^3$.

27. The compound of claim 23, wherein R$^1$ is selected from the group consisting of phenyl and monocyclic heteroaryl, wherein the phenyl and monocyclic heteroaryl are optionally substituted with 1, 2, 3, or 4 substituents selected from the group consisting of C$_1$-C$_4$alkoxy, C$_1$-C$_4$alkyl, C$_1$-C$_4$haloalkoxy, C$_1$-C$_4$haloalkyl, and halogen.

28. The compound of claim 27, wherein R$^2$ is selected from the group consisting of hydrogen, C$_1$-C$_8$alkenyl, C$_1$-C$_6$alkoxyC$_1$-C$_6$alkyl, C$_1$-C$_8$alkyl, C$_1$-C$_8$haloalkyl, —CO$_2$R$^{2c}$, —C(O)R$^{2c}$, —C(O)(CR$^{2a}$R$^{2b}$)$_m$—OR$^{2c}$, —C(OH)(R$^{2d}$)—R$^{2c}$, —C(OH)(R$^{2d}$)—C(O)R$^{2c}$, —SO$_2$R$^{2c}$, —SO$_2$NR$^{2d}$R$^{2e}$, —(CR$^{2a}$R$^{2b}$)$_m$—C(OR$^{2d}$)(R$^{2d}$)—R$^{2e}$, —(CR$^{2a}$R$^{2b}$)$_m$C(O)R$^{2c}$, —(CR$^{2a}$R$^{2b}$)$_m$CO$_2$R$^{2c}$, —(CR$^{2a}$R$^{2b}$)$_m$C(O)NR$^{2d}$R$^{2e}$, —(CR$^{2a}$R$^{2b}$)$_m$SO$_2$NR$^{2d}$R$^{2e}$, —(CR$^{2a}$R$^{2b}$)$_m$C(O)NH—(CR$^{2a}$R$^{2f}$)—C(O)NHR$^{2d}$, and —CR$^{2a}$=CHR$^{2a}$—CO$_2$R$^{2c}$.

29. The compound of claim 28, wherein R$^2$ is —(CR$^{2a}$R$^{2b}$)$_m$—C(OR$^{2d}$)(R$^{2d}$)—R$^{2e}$ or —(CR$^{2a}$R$^{2b}$)$_m$C(O)R$^{2c}$, wherein
R$^{2a}$ and R$^{2b}$, at each occurrence, are each independently selected from the group consisting of hydrogen and C$_1$-C$_4$alkyl;
R$^{2c}$ is selected from the group consisting of C$_1$-C$_8$alkyl and haloC$_1$-C$_8$alkyl;
R$^{2d}$, at each occurrence, is selected from the group consisting of hydrogen and C$_1$-C$_6$alkyl;
R$^{2e}$ is selected from the group consisting of C$_1$-C$_6$alkyl, and haloC$_1$-C$_6$alkyl; and
m is 1 or 2.

30. The compound of claim 27, wherein R$^2$ is selected from the group consisting of -G$^1$, -G$^2$, -G$^3$, -G$^4$, —CO$_2$G$^1$, —C(O)G$^1$, —C(O)G$^2$, —C(O)G$^3$, —C(O)G$^4$, —C(O)(CR$^{2a}$R$^{2b}$)$_m$G$^1$, —C(O)(CR$^{2a}$R$^{2b}$)$_m$G$^2$, —C(OH)(R$^{2d}$)-G$^1$, —C(OH)(R$^{2d}$)—C(O)G$^1$, —C(OH)(R$^{2d}$)—(CR$^{2a}$R$^{2b}$)$_m$G$^1$, —SO$_2$G$^1$, —SO$_2$G$^2$, —SO$_2$G$^3$, —SO$_2$G$^4$, —SO$_2$—(CR$^{2a}$R$^{2b}$)$_m$G$^1$, —SO$_2$—(CR$^{2a}$R$^{2b}$)$_m$G$^2$, —SO$_2$—(CR$^{2a}$R$^{2b}$)$_m$G$^3$, —SO$_2$—(CR$^{2a}$R$^{2b}$)$_m$G$^4$, —(CR$^{2a}$R$^{2b}$)$_m$G$^1$, —(CR$^{2a}$R$^{2b}$)$_m$G$^2$, —(CR$^{2a}$R$^{2b}$)$_m$G$^3$, —(CR$^{2a}$R$^{2b}$)$_m$G$^4$, —(CR$^{2a}$R$^{2b}$)$_m$—C(OH)(R$^{2d}$)-G$^1$, —(CR$^{2a}$R$^{2b}$)$_m$—C(OH)(R$^{2d}$)-G$^2$, —(CR$^{2a}$R$^{2b}$)$_m$—C(OH)(R$^{2d}$)-G$^3$, —(CR$^{2a}$R$^{2b}$)$_m$—C(OH)(R$^{2d}$)-G$^4$, —(CR$^{2a}$R$^{2b}$)$_m$—C(OH)(R$^{2d}$)—(CR$^{2a}$R$^{2b}$)$_n$-G$^1$, —(CR$^{2a}$R$^{2b}$)$_m$—C(OH)(R$^{2d}$)—(CR$^{2a}$R$^{2b}$)$_n$-G$^2$, —(CR$^{2a}$R$^{2b}$)$_m$—C(OH)(R$^{2d}$)—(CR$^{2a}$R$^{2b}$)$_n$-G$^3$, —(CR$^{2a}$R$^{2b}$)$_m$—C(OH)(R$^{2d}$)—(CR$^{2a}$R$^{2b}$)$_n$-G$^4$, —(CR$^{2a}$R$^{2b}$)$_m$C(O)—(CR$^{2a}$R$^{2b}$)$_n$G$^1$, —(CR$^{2a}$R$^{2b}$)$_m$C(O)(CR$^{2a}$R$^{2b}$)$_n$G$^2$, —(CR$^{2a}$R$^{2b}$)$_m$C(O)(CR$^{2a}$R$^{2b}$)$_n$G$^3$, —(CR$^{2a}$R$^{2b}$)$_m$C(O)(CR$^{2a}$R$^{2b}$)$_n$G$^4$, —(CR$^{2a}$R$^{2b}$)$_m$CO$_2$G$^1$, —(CR$^{2a}$R$^{2b}$)$_m$C(O)G$^1$, —(CR$^{2a}$R$^{2b}$)$_m$C(O)G$^2$, —(CR$^{2a}$R$^{2b}$)$_m$C(O)G$^3$, —(CR$^{2a}$R$^{2b}$)$_m$C(O)G$^4$, —(CR$^{2a}$R$^{2b}$)$_m$C(O)NR$^{2d}$G$^1$, —(CR$^{2a}$R$^{2b}$)$_m$C(O)NR$^{2d}$G$^2$, —(CR$^{2a}$R$^{2b}$)$_m$C(O)NR$^{2d}$G$^3$, —(CR$^{2a}$R$^{2b}$)$_m$C(O)NR$^{2d}$G$^4$, —(CR$^{2a}$R$^{2b}$)$_m$C(O)N(R$^{2d}$)((CR$^{2a}$R$^{2b}$)$_n$G$^1$), —(CR$^{2a}$R$^{2b}$)$_m$C(O)N(R$^{2d}$)((CR$^{2a}$R$^{2b}$)$_n$G$^2$), —(CR$^{2a}$R$^{2b}$)$_m$C(O)N(R$^{2d}$)((CR$^{2a}$R$^{2b}$)$_n$G$^3$), —(CR$^{2a}$R$^{2b}$)$_m$C(O)N(R$^{2d}$)((CR$^{2a}$R$^{2b}$)$_n$G$^4$), —(CR$^{2a}$R$^{2b}$)$_m$C(O)NH—(CR$^{2a}$R$^{2f}$)—C(O)NHR$^{2d}$, —CR$^{2a}$=CHR$^{2a}$—C(O)G$^1$ and —CR$^{2a}$=CHR$^{2a}$—C(O)G$^3$.

31. The compound of claim 30, wherein R$^2$ is —(CR$^{2a}$R$^{2b}$)$_m$G$^4$ or —(CR$^{2a}$R$^{2b}$)$_m$C(O)G$^3$, wherein,
R$^{2a}$ and R$^{2b}$, at each occurrence, are each independently selected from the group consisting of hydrogen and C$_1$-C$_4$alkyl;
G$^3$ is optionally substituted with 1 or 2 C$_1$-C$_4$alkyl or halogen;
G$^4$ is optionally substituted with 1, 2 or 3 substituents selected from the group consisting of C$_1$-C$_4$alkyl, halogen, and haloC$_1$-C$_4$alkyl; and
m is 1 or 2.

32. The compound of claim 1, wherein, A is (iv)

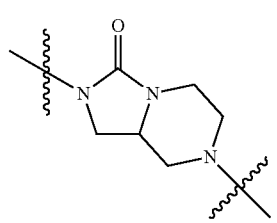

33. The compound of claim 32, wherein $R^1$ is selected from the group consisting of $C_1$-$C_8$alkyl and $C_3$-$C_7$cycloalkyl.

34. The compound of claim 33, wherein $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —$CO_2R^{2c}$, —$C(O)R^{2c}$, —$C(O)(CR^{2a}R^{2b})_m$—$OR^{2c}$, —$C(OH)(R^{2d})$—$R^{2c}$, —$C(OH)(R^{2d})$—$C(O)R^{2c}$, —$SO_2R^{2c}$, —$SO_2NR^{2d}R^{2e}$, —$(CR^{2a}R^{2b})_m$—$C(OR^{2d})(R^{2d})$—$R^{2e}$, —$(CR^{2a}R^{2b})_mC(O)R^{2c}$, —$(CR^{2a}R^{2b})_mCO_2R^{2c}$, —$(CR^{2a}R^{2b})_mC(O)NR^{2d}R^{2e}$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, and —$CR^{2a}$=$CHR^{2a}$—$CO_2R^{2c}$.

35. The compound of claim 33, wherein $R^2$ is selected from the group consisting of -$G^1$, -$G^2$, -$G^3$, -$G^4$, —$CO_2G^1$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(OH)(R^{2d})$-$G^1$, —$C(OH)(R^{2d})$—$C(O)G^1$, —$C(OH)(R^{2d})$—$(CR^{2a}R^{2b})_mG^1$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mC(O)NH$—$(CR^{2a}R^{2f})$—$C(O)NHR^{2d}$, —$CR^{2a}$=$CHR^{2a}$—$C(O)G^1$ and —$CR^{2a}$=$CHR^{2a}$—$C(O)G^3$.

36. The compound of claim 32, wherein $R^1$ is selected from the group consisting of phenyl and monocyclic heteroaryl, wherein the phenyl and monocyclic heteroaryl are optionally substituted with 1, 2, 3, or 4 substituents selected from the group consisting of $C_1$-$C_4$alkoxy, $C_1$-$C_4$alkyl, $C_1$-$C_4$haloalkoxy, $C_1$-$C_4$haloalkyl, and halogen.

37. The compound of claim 36, wherein $R^2$ is selected from the group consisting of hydrogen, $C_1$-$C_8$alkenyl, $C_1$-$C_6$alkoxy$C_1$-$C_6$alkyl, $C_1$-$C_8$alkyl, $C_1$-$C_8$haloalkyl, —$CO_2R^{2c}$, —$C(O)R^{2c}$, —$C(O)(CR^{2a}R^{2b})_m$—$OR^{2c}$, —$C(OH)(R^{2d})$—$R^{2c}$, —$C(OH)(R^{2d})$—$C(O)R^{2c}$, —$SO_2R^{2c}$, —$SO_2NR^{2d}R^{2e}$, —$(CR^{2a}R^{2b})_m$—$C(OR^{2d})(R^{2d})$—$R^{2e}$, —$(CR^{2a}R^{2b})_mC(O)R^{2c}$, —$(CR^{2a}R^{2b})_mCO_2R^{2c}$, —$(CR^{2a}R^{2b})_mC(O)NR^{2d}R^{2e}$, —$(CR^{2a}R^{2b})_mSO_2NR^{2d}R^{2e}$, —$(CR^{2a}R^{2b})_mC(O)NH$—$(CR^{2a}R^{2f})$—$C(O)NHR^{2d}$, and —$CR^{2a}$=$CHR^{2a}$—$CO_2R^{2c}$.

38. The compound of claim 36, wherein $R^2$ is selected from the group consisting of -$G^1$, -$G^2$, -$G^3$, -$G^4$, —$CO_2G^1$, —$C(O)G^1$, —$C(O)G^2$, —$C(O)G^3$, —$C(O)G^4$, —$C(O)(CR^{2a}R^{2b})_mG^1$, —$C(O)(CR^{2a}R^{2b})_mG^2$, —$C(OH)(R^{2d})$-$G^1$, —$C(OH)(R^{2d})$—$C(O)G^1$, —$C(OH)(R^{2d})$—$(CR^{2a}R^{2b})_mG^1$, —$SO_2G^1$, —$SO_2G^2$, —$SO_2G^3$, —$SO_2G^4$, —$SO_2$—$(CR^{2a}R^{2b})_mG^1$, —$SO_2$—$(CR^{2a}R^{2b})_mG^2$, —$SO_2$—$(CR^{2a}R^{2b})_mG^3$, —$SO_2$—$(CR^{2a}R^{2b})_mG^4$, —$(CR^{2a}R^{2b})_mG^1$, —$(CR^{2a}R^{2b})_mG^2$, —$(CR^{2a}R^{2b})_mG^3$, —$(CR^{2a}R^{2b})_mG^4$, —$(CR^{2a}R^{2b})_m$—$C(OH)(R^{2d})$-$G^1$, —$(CR^{2a}R^{2b})_m$—$C(OH)(R^{2d})$-$G^2$, —$(CR^{2a}R^{2b})_m$—$C(OH)(R^{2d})$-$G^3$, —$(CR^{2a}R^{2b})_m$—$C(OH)(R^{2d})$-$G^4$, —$(CR^{2a}R^{2b})_m$—$C(OH)(R^{2d})$—$(CR^{2a}R^{2b})_n$-$G^1$, —$(CR^{2a}R^{2b})_m$—$C(OH)(R^{2d})$—$(CR^{2a}R^{2b})_n$-$G^2$, —$(CR^{2a}R^{2b})_m$—$C(OH)(R^{2d})$—$(CR^{2a}R^{2b})_n$-$G^3$, —$(CR^{2a}R^{2b})_m$—$C(OH)(R^{2d})$—$(CR^{2a}R^{2b})_n$-$G^4$, —$(CR^{2a}R^{2b})_mC(O)$—$(CR^{2a}R^{2b})_nG^1$, —$(CR^{2a}R^{2b})_mC(O)(CR^{2a}R^{2b})_nG^2$, —$(CR^{2a}R^{2b})_mC(O)(CR^{2a}R^{2b})_nG^3$, —$(CR^{2a}R^{2b})_mC(O)(CR^{2a}R^{2b})_nG^4$, —$(CR^{2a}R^{2b})_mCO_2G^1$, —$(CR^{2a}R^{2b})_mC(O)G^1$, —$(CR^{2a}R^{2b})_mC(O)G^2$, —$(CR^{2a}R^{2b})_mC(O)G^3$, —$(CR^{2a}R^{2b})_mC(O)G^4$, —$(CR^{2a}R^{2b})_mC(O)NR^{2d}G^1$, —$(CR^{2a}R^{2b})_mC(O)NR^{2d}G^2$, —$(CR^{2a}R^{2b})_mC(O)NR^{2d}G^3$, —$(CR^{2a}R^{2b})_mC(O)NR^{2d}G^4$, —$(CR^{2a}R^{2b})_mC(O)N(R^{2d})((CR^{2a}R^{2b})_nG^1)$, —$(CR^{2a}R^{2b})_mC(O)N(R^{2d})((CR^{2a}R^{2b})_nG^2)$, —$(CR^{2a}R^{2b})_mC(O)N(R^{2d})((CR^{2a}R^{2b})_nG^3)$, —$(CR^{2a}R^{2b})_mC(O)N(R^{2d})((CR^{2a}R^{2b})_nG^4)$, —$(CR^{2a}R^{2b})_mC(O)NH$—$(CR^{2a}R^{2f})$—$C(O)NHR^{2d}$, —$CR^{2a}$=$CHR^{2a}$—$C(O)G^1$ and —$CR^{2a}$=$CHR^{2a}$—$C(O)G^3$.

39. The compound of claim 38, wherein $R^2$ is —$CO_2G^1$, wherein,
$G^1$ is $C_3$-$C_7$cycloalkyl, wherein the $C_3$-$C_7$cycloalkyl is optionally substituted with 1, 2, or 3 substituents selected from the group consisting of $C_1$-$C_6$alkoxy, $C_1$-$C_4$alkyl, halo$C_1$-$C_4$alkyl, halogen, hydroxy, hydroxy$C_1$-$C_4$alkyl, and oxo.

40. The compound of claim 1, selected from:
1-[1-(2-fluorophenyl)-1H-indazol-4-yl]-3-[2-oxo-2-(pyrrolidin-1-yl)ethyl]imidazolidin-2-one;
tert-butyl 3-[1-(2-fluorophenyl)-1H-indazol-4-yl]-2-oxoimidazolidine-1-carboxylate;
2-{3-[1-(2-fluorophenyl)-1H-indazol-4-yl]-2-oxoimidazolidin-1-yl}acetamide;
isopropyl 3-[1-(2-fluorophenyl)-1H-indazol-4-yl]-2-oxoimidazolidine-1-carboxylate;
isobutyl 3-[1-(2-fluorophenyl)-1H-indazol-4-yl]-2-oxoimidazolidine-1-carboxylate;
1-[1-(2-fluorophenyl)-1H-indazol-4-yl]-3-(methylsulfonyl)imidazolidin-2-one;
1-[1-(2-fluorophenyl)-1H-indazol-4-yl]-3-{2-[(3S)-3-hydroxypyrrolidin-1-yl]-2-oxoethyl}imidazolidin-2-one;
1-[1-(2-fluorophenyl)-1H-indazol-4-yl]-3-(4-methyl-2-oxopentyl)imidazolidin-2-one;
2-{3-[1-(2-fluorophenyl)-1H-indazol-4-yl]-2-oxo-2,3-dihydro-1H-imidazol-1-yl}acetamide;
1-[1-(2-fluorophenyl)-1H-indazol-4-yl]-3-{2-[(3S)-3-fluoropyrrolidin-1-yl]-2-oxoethyl}imidazolidin-2-one;
1-[1-(2-fluorophenyl)-1H-indazol-4-yl]-3-{2-[(3S)-3-fluoropyrrolidin-1-yl]-2-oxoethyl}-1,3-dihydro-2H-imidazol-2-one;
1-[1-(2-fluorophenyl)-1H-indazol-4-yl]-3-(pyridin-2-ylmethyl)imidazolidin-2-one;
N-cyclopropyl-2-{3-[1-(2-fluorophenyl)-1H-indazol-4-yl]-2-oxoimidazolidin-1-yl}acetamide;

1-[1-(2-fluorophenyl)-1H-indazol-4-yl]-3-{[4-(trifluoromethyl)-1,3-thiazol-2-yl]methyl}imidazolidin-2-one;
1-[1-(2-fluorophenyl)-1H-indazol-4-yl]-3-{2-[(2S)-2-methylpyrrolidin-1-yl]-2-oxoethyl}imidazolidin-2-one;
1-[1-(2-fluorophenyl)-1H-indazol-4-yl]-3-{2-[(1S,4S)-2-oxa-5-azabicyclo[2.2.1]hept-5-yl]-2-oxoethyl}imidazolidin-2-one;
1-[1-(2-fluorophenyl)-1H-indazol-4-yl]-3-[2-(3-fluoropiperidin-1-yl)-2-oxoethyl]imidazolidin-2-one;
1-{2-[(2R,4S)-2-(2,5-difluorophenyl)-4-fluoropyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-(pyridin-3-yl)imidazolidin-2-one;
1-[1-(2-fluorophenyl)-1H-indazol-4-yl]-3-(pyridin-4-yl)imidazolidin-2-one;
1-{2-[(2S)-2-ethylpyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-(2-hydroxy-3,3-dimethylbutyl)imidazolidin-2-one;
1-[1-(2-fluorophenyl)-1H-indazol-4-yl]-3-{2-[(3S)-3-fluoropyrrolidin-1-yl]-2-oxoethyl}tetrahydropyrimidin-2(1H)-one;
1-[1-(2-fluorophenyl)-1H-indazol-4-yl]-3-[(4-methyl-1,3-thiazol-2-yl)methyl]imidazolidin-2-one;
1-[1-(2-fluorophenyl)-1H-indazol-4-yl]-3-{2-[(1R,4R)-2-oxa-5-azabicyclo[2.2.1]hept-5-yl]-2-oxoethyl}imidazolidin-2-one;
1-[1-(2-fluorophenyl)-1H-indazol-4-yl]-3-(1,3-oxazol-4-ylmethyl)imidazolidin-2-one;
1-[(3,5-dimethyl-1,2-oxazol-4-yl)methyl]-3-[1-(2-fluorophenyl)-1H-indazol-4-yl]imidazolidin-2-one;
1-[1-(2-fluorophenyl)-1H-indazol-4-yl]-3-(pyrimidin-2-yl)imidazolidin-2-one;
1-[1-(2-fluorophenyl)-1H-indazol-4-yl]-3-(1,3,4-oxadiazol-2-ylmethyl)imidazolidin-2-one;
1-[(5-cyclopropyl-1,3,4-thiadiazol-2-yl)methyl]-3-[1-(2-fluorophenyl)-1H-indazol-4-yl]imidazolidin-2-one;
1-[1-(2-fluorophenyl)-1H-indazol-4-yl]-3-(1,3-oxazol-2-ylmethyl)imidazolidin-2-one;
1-[1-(2-fluorophenyl)-1H-indazol-4-yl]-3-[(3R)-tetrahydrofuran-3-yl]imidazolidin-2-one;
1-[1-(2-fluorophenyl)-1H-indazol-4-yl]-3-(5-methylpyrimidin-2-yl)imidazolidin-2-one;
1-[1-(2-fluorophenyl)-1H-indazol-4-yl]-3-(1,3-thiazol-2-ylmethyl)imidazolidin-2-one;
1-[1-(2-fluorophenyl)-1H-indazol-4-yl]-3-(pyrazin-2-ylmethyl)imidazolidin-2-one;
1-[1-(2,4-difluorophenyl)-1H-indazol-4-yl]-3-(1,3-oxazol-2-ylmethyl)imidazolidin-2-one;
1-[1-(2,4-difluorophenyl)-1H-indazol-4-yl]-3-(1,3-oxazol-4-ylmethyl)imidazolidin-2-one;
(4S)-1-[1-(2-fluorophenyl)-1H-indazol-4-yl]-4-methyl-3-(1,3-oxazol-2-ylmethyl)imidazolidin-2-one;
1-[1-(2-fluorophenyl)-1H-indazol-4-yl]-3-(1,3-thiazol-4-ylmethyl)imidazolidin-2-one;
1-[1-(2-fluorophenyl)-1H-indazol-4-yl]-3-[(5-methyl-1,3,4-thiadiazol-2-yl)methyl]imidazolidin-2-one;
1-[1-(2-fluorophenyl)-1H-indazol-4-yl]-3-[(5-methyl-1,3-oxazol-2-yl)methyl]imidazolidin-2-one;
1-[1-(2-fluorophenyl)-1H-indazol-4-yl]-3-[(6-methylpyrazin-2-yl)methyl]imidazolidin-2-one;
1-[1-(2-fluorophenyl)-1H-indazol-4-yl]-3-[(3-methylpyrazin-2-yl)methyl]imidazolidin-2-one;
1-[1-(2-fluorophenyl)-1H-indazol-4-yl]-3-[(5-methyl-1,3,4-oxadiazol-2-yl)methyl]imidazolidin-2-one;
1-[(3-ethyl-1,2-oxazol-5-yl)methyl]-3-[1-(2-fluorophenyl)-1H-indazol-4-yl]imidazolidin-2-one;
1-[1-(2-fluorophenyl)-1H-indazol-4-yl]-3-[1-(3-methyl-1,2,4-oxadiazol-5-yl)ethyl]imidazolidin-2-one;
1-[(5-ethoxy-1,3,4-thiadiazol-2-yl)methyl]-3-[1-(2-fluorophenyl)-1H-indazol-4-yl]imidazolidin-2-one;
1-[(4,5-dimethyl-1,3-oxazol-2-yl)methyl]-3-[1-(2-fluorophenyl)-1H-indazol-4-yl]tetrahydropyrimidin-2(1H)-one;
1-[(5-cyclopropyl-1,3,4-oxadiazol-2-yl)methyl]-3-[1-(2-fluorophenyl)-1H-indazol-4-yl]imidazolidin-2-one;
1-[(5-cyclobutyl-1,3,4-oxadiazol-2-yl)methyl]-3-[1-(2-fluorophenyl)-1H-indazol-4-yl]imidazolidin-2-one;
1-[1-(ethylsulfonyl)azetidin-3-yl]-3-[1-(2-fluorophenyl)-1H-indazol-4-yl]imidazolidin-2-one;
1-[1-(2-fluorophenyl)-1H-indazol-4-yl]-3-{2-[(3R)-3-hydroxypiperidin-1-yl]-2-oxoethyl}imidazolidin-2-one;
1-[1-(2-fluorophenyl)-1H-indazol-4-yl]-3-{2-[(3R)-3-fluoropiperidin-1-yl]-2-oxoethyl}imidazolidin-2-one;
1-[1-(2-fluorophenyl)-1H-indazol-4-yl]-3-{2-[(3S)-3-fluoropiperidin-1-yl]-2-oxoethyl}imidazolidin-2-one;
2-{3-[1-(2-fluorophenyl)-1H-indazol-4-yl]-2-oxoimidazolidin-1-yl}-N-[(3R)-tetrahydrofuran-3-yl]acetamide;
1-{2-[(3S)-3-fluoropyrrolidin-1-yl]-2-oxoethyl}-3-[1-(3-methylphenyl)-1H-indazol-4-yl]imidazolidin-2-one;
1-[1-(2-fluorophenyl)-1H-indazol-4-yl]imidazolidin-2-one;
1-{3-[1-(2-fluorophenyl)-1H-indazol-4-yl]-2-oxoimidazolidin-1-yl}methanesulfonamide;
1-[1-(2-fluorophenyl)-1H-indazol-4-yl]-3-(2-methoxyethyl)imidazolidin-2-one;
1-(2,2-dimethylpropanoyl)-3-[1-(2-fluorophenyl)-1H-indazol-4-yl]imidazolidin-2-one;
1-[1-(2-fluorophenyl)-1H-indazol-4-yl]-3-[(3-oxocyclobutyl)carbonyl]imidazolidin-2-one;
3-[1-(2-fluorophenyl)-1H-indazol-4-yl]-N-methyl-2-oxoimidazolidine-1-sulfonamide;
1-[1-(2-fluorophenyl)-1H-indazol-4-yl]-3-[2-(2-oxoimidazolidin-1-yl)ethyl]imidazolidin-2-one;
1-[1-(2-fluorophenyl)-1H-indazol-4-yl]-3-(2-hydroxy-2-methylpropyl)imidazolidin-2-one;
1-{2-[(2R,5R)-2, 5-bis(methoxymethyl)pyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-[2-(hexahydropyrrolo[1,2-a]pyrazin-2(1H)-yl)-2-oxoethyl]imidazolidin-2-one;
1-[1-(2-fluorophenyl)-1H-indazol-4-yl]-3-[2-(3-isopropoxyazetidin-1-yl)-2-oxoethyl]imidazolidin-2-one;
2-{3-[1-(2-fluorophenyl)-1H-indazol-4-yl]-2-oxoimidazolidin-1-yl}-N-methyl-N-(tetrahydro-2H-pyran-4-ylmethyl)acetamide;
1-[1-(2-fluorophenyl)-1H-indazol-4-yl]-3-[2-(4-fluoropiperidin-1-yl)-2-oxoethyl]imidazolidin-2-one;
1-[2-(2,6-dimethylmorpholin-4-yl)-2-oxoethyl]-3-[1-(2-fluorophenyl)-1H-indazol-4-yl]imidazolidin-2-one;
1-[1-(2-fluorophenyl)-1H-indazol-4-yl]-3-{2-[2-(morpholin-4-ylmethyl)pyrrolidin-1-yl]-2-oxoethyl}imidazolidin-2-one;
2-{3-[1-(2-fluorophenyl)-1H-indazol-4-yl]-2-oxoimidazolidin-1-yl}-N-methyl-N-[2-(morpholin-4-yl)ethyl]acetamide;
1-[1-(2-fluorophenyl)-1H-indazol-4-yl]-3-{2-[(3R)-3-fluoropyrrolidin-1-yl]-2-oxoethyl}imidazolidin-2-one;

N-(2-ethoxyethyl)-2-{3-[1-(2-fluorophenyl)-1H-indazol-4-yl]-2-oxoimidazolidin-1-yl}acetamide;

2-{3-[1-(2-fluorophenyl)-1H-indazol-4-yl]-2-oxoimidazolidin-1-yl}-N-(tetrahydrofuran-3-ylmethyl)acetamide;

1-[1-(2-fluorophenyl)-1H-indazol-4-yl]-3-(4-methylpentanoyl)imidazolidin-2-one;

1-(cyclopentylsulfonyl)-3-[1-(2-fluorophenyl)-1H-indazol-4-yl]imidazolidin-2-one;

1-(cyclohexylsulfonyl)-3-[1-(2-fluorophenyl)-1H-indazol-4-yl]imidazolidin-2-one;

1-[1-(2-fluorophenyl)-1H-indazol-4-yl]-3-(2-thienylsulfonyl)imidazolidin-2-one;

1-[1-(2-fluorophenyl)-1H-indazol-4-yl]-3-(isobutylsulfonyl)imidazolidin-2-one;

1-[1-(2-fluorophenyl)-1H-indazol-4-yl]-3-(propylsulfonyl)imidazolidin-2-one;

1-[1-(2-fluorophenyl)-1H-indazol-4-yl]-3-(isopropylsulfonyl)imidazolidin-2-one;

1-(ethylsulfonyl)-3-[1-(2-fluorophenyl)-1H-indazol-4-yl]imidazolidin-2-one;

1-[1-(2-fluorophenyl)-1H-indazol-4-yl]-3-{2-[(3R)-3-hydroxypyrrolidin-1-yl]-2-oxoethyl}imidazolidin-2-one;

1-[1-(2-fluorophenyl)-1H-indazol-4-yl]-3-{2-[(3S)-3-(2-hydroxypropan-2-yl)pyrrolidin-1-yl]-2-oxoethyl}imidazolidin-2-one;

1-[2-(3,3-difluoropyrrolidin-1-yl)-2-oxoethyl]-3-[1-(2-fluorophenyl)-1H-indazol-4-yl]imidazolidin-2-one;

2-{3-[1-(2-fluorophenyl)-1H-indazol-4-yl]-2-oxoimidazolidin-1-yl}-N-[(3S)-tetrahydrofuran-3-yl]acetamide;

1-{2-[(3S)-3-fluoropyrrolidin-1-yl]-2-oxoethyl}-3-{1-[3-(trifluoromethoxy)phenyl]-1H-indazol-4-yl}imidazolidin-2-one;

1-[1-(2-fluorophenyl)-1H-indazol-4-yl]-3-{[5-(trifluoromethyl)pyridin-2-yl]methyl}imidazolidin-2-one;

1-[1-(2-fluorophenyl)-1H-indazol-4-yl]-3-{2-[(3S)-3-methylpyrrolidin-1-yl]-2-oxoethyl}imidazolidin-2-one;

1-[2-(3,3-difluoroazetidin-1-yl)-2-oxoethyl]-3-[1-(2-fluorophenyl)-1H-indazol-4-yl]imidazolidin-2-one;

2-{3-[1-(2-fluorophenyl)-1H-indazol-4-yl]-2-oxoimidazolidin-1-yl}-N-isobutylacetamide;

N,N-diethyl-2-{3-[1-(2-fluorophenyl)-1H-indazol-4-yl]-2-oxoimidazolidin-1-yl}acetamide;

1-[2-(azetidin-1-yl)-2-oxoethyl]-3-[1-(2-fluorophenyl)-1H-indazol-4-yl]imidazolidin-2-one;

2-{3-[1-(2-fluorophenyl)-1H-indazol-4-yl]-2-oxoimidazolidin-1-yl}-N-isopropylacetamide;

1-[1-(2-fluorophenyl)-1H-indazol-4-yl]-3-(isopropoxyacetyl)imidazolidin-2-one;

1-[1-(2-fluorophenyl)-1H-indazol-4-yl]-3-{[4-(trifluoromethyl)pyridin-2-yl]methyl}imidazolidin-2-one;

1-{2-[3-(ethoxymethyl)-3-fluoropyrrolidin-1-yl]-2-oxoethyl}-3-[1-(2-fluorophenyl)-1H-indazol-4-yl]imidazolidin-2-one;

1-[1-(2-fluorophenyl)-1H-indazol-4-yl]-3-{2-[(8aS)-hexahydropyrrolo[1,2-c]pyrazin-2(1H)-yl]-2-oxoethyl}imidazolidin-2-one;

1-[1-(2-fluorophenyl)-1H-indazol-4-yl]-3-[2-(2-oxa-6-azaspiro[3.3]hept-6-yl)-2-oxoethyl]imidazolidin-2-one;

1-[2-(3,5-dimethylmorpholin-4-yl)-2-oxoethyl]-3-[1-(2-fluorophenyl)-1H-indazol-4-yl]imidazolidin-2-one;

1-[2-(1,4-dioxa-7-azaspiro[4.4]non-7-yl)-2-oxoethyl]-3-[1-(2-fluorophenyl)-1H-indazol-4-yl]imidazolidin-2-one;

4-({3-[1-(2-fluorophenyl)-1H-indazol-4-yl]-2-oxoimidazolidin-1-yl}acetyl)piperazine-2,6-dione;

1-[1-(2-fluorophenyl)-1H-indazol-4-yl]-3-[2-(5-methylhexahydropyrrolo[3,4-c]pyrrol-2(1H)-yl)-2-oxoethyl]imidazolidin-2-one;

1-[1-(2-fluorophenyl)-1H-indazol-4-yl]-3-[2-(octahydro-4H-1,4-benzoxazin-4-yl)-2-oxoethyl]imidazolidin-2-one;

1-[1-(2-fluorophenyl)-1H-indazol-4-yl]-3-[2-(hexahydrocyclopenta[c]pyrrol-2(1H)-yl)-2-oxoethyl]imidazolidin-2-one;

1-{2-[(1R,3r,6s,8S)-4-azatricyclo[4.3.1.1$^{3,8}$]undec-4-yl]-2-oxoethyl}-3-[1-(2-fluorophenyl)-1H-indazol-4-yl]imidazolidin-2-one;

(3aR,6aS)-5-({3-[1-(2-fluorophenyl)-1H-indazol-4-yl]-2-oxoimidazolidin-1-yl}acetyl)-2-methyltetrahydropyrrolo[3,4-c]pyrrole-1,3(2H,3aH)-dione;

1-[1-(2-fluorophenyl)-1H-indazol-4-yl]-3-[2-(8-methoxy-3-azabicyclo[3.2.1]oct-3-yl)-2-oxoethyl]imidazolidin-2-one;

1-[2-(1,4-dioxa-8-azaspiro[4.6]undec-8-yl)-2-oxoethyl]-3-[1-(2-fluorophenyl)-1H-indazol-4-yl]imidazolidin-2-one;

1-[1-(2-fluorophenyl)-1H-indazol-4-yl]-3-{2-[(3 aR,4R,7S,7aS)-octahydro-2H-4,7-methanoisoindol-2-yl]-2-oxoethyl}imidazolidin-2-one;

1-[1-(2-fluorophenyl)-1H-indazol-4-yl]-3-[2-(1-methyloctahydro-6H-pyrrolo[3,4-b]pyridin-6-yl)-2-oxoethyl]imidazolidin-2-one;

1-[1-(2-fluorophenyl)-1H-indazol-4-yl]-3-{2-[(3R)-3-methylmorpholin-4-yl]-2-oxoethyl}imidazolidin-2-one;

1-[1-(2-fluorophenyl)-1H-indazol-4-yl]-3-{2-[(1R,6S)-9-methyl-3,9-diazabicyclo[4.2.1]non-3-yl]-2-oxoethyl}imidazolidin-2-one;

1-[2-(2-ethylpyrrolidin-1-yl)-2-oxoethyl]-3-[1-(2-fluorophenyl)-1H-indazol-4-yl]imidazolidin-2-one;

1-[1-(2-fluorophenyl)-1H-indazol-4-yl]-3-[2-(2-isopropylpyrrolidin-1-yl)-2-oxoethyl]imidazolidin-2-one;

1-[1-(2-fluorophenyl)-1H-indazol-4-yl]-3-[2-(2-isobutylpyrrolidin-1-yl)-2-oxoethyl]imidazolidin-2-one;

1-[1-(2-fluorophenyl)-1H-indazol-4-yl]-3-{2-[(2R)-2-methylpyrrolidin-1-yl]-2-oxoethyl}imidazolidin-2-one;

methyl 1-({3-[1-(2-fluorophenyl)-1H-indazol-4-yl]-2-oxoimidazolidin-1-yl}acetyl)-D-prolinate;

1-({3-[1-(2-fluorophenyl)-1H-indazol-4-yl]-2-oxoimidazolidin-1-yl}acetyl)-N-phenyl-D-prolinamide;

1-{2-[(2R,4R)-2-(2,5-difluorophenyl)-4-hydroxypyrrolidin-1-yl]-2-oxoethyl}-3-[1-(2-fluorophenyl)-1H-indazol-4-yl]imidazolidin-2-one;

1-{2-[(2R,4S)-2-(2,5-difluorophenyl)-4-hydroxypyrrolidin-1-yl]-2-oxoethyl}-3-[1-(2-fluorophenyl)-1H-indazol-4-yl]imidazolidin-2-one;

1-[1-(2-fluorophenyl)-1H-indazol-4-yl]-3-(2-hydroxy-4-methylpentyl)imidazolidin-2-one;

1-[1-(2-fluorophenyl)-1H-indazol-4-yl]-3-{2-[(2R)-2-isopropylpiperidin-1-yl]-2-oxoethyl}imidazolidin-2-one;

1-[1-(2-fluorophenyl)-1H-indazol-4-yl]-3-{2-[(2S)-2-isopropylpyrrolidin-1-yl]-2-oxoethyl}imidazolidin-2-one;

1-[1-(2-fluorophenyl)-1H-indazol-4-yl]-3-{2-[(2R)-2-isopropylpyrrolidin-1-yl]-2-oxoethyl}imidazolidin-2-one;

1-{2-[(2R,4R)-2-(2,5-difluorophenyl)-4-fluoropyrrolidin-1-yl]-2-oxoethyl}-3-[1-(2-fluorophenyl)-1H-indazol-4-yl]imidazolidin-2-one;

1-[1-(2-fluorophenyl)-1H-indazol-4-yl]-3-{2-oxo-2-[(2R)-2-phenylpyrrolidin-1-yl]ethyl}imidazolidin-2-one;
1-[1-(2-fluorophenyl)-1H-indazol-4-yl]-3-[2-oxo-2-(2-phenylpyrrolidin-1-yl)ethyl]imidazolidin-2-one;
1-[1-(2-fluorophenyl)-1H-indazol-4-yl]-3-(pyridin-2-yl)imidazolidin-2-one;
cyclohexyl 3-[1-(2-fluorophenyl)-1H-indazol-4-yl]-2-oxoimidazolidine-1-carboxylate;
1-[1-(2-fluorophenyl)-1H-indazol-4-yl]-3-(6-methyl-2-oxoheptyl)imidazolidin-2-one;
1-[1-(2-fluorophenyl)-1H-indazol-4-yl]-3-(2-hydroxy-6-methylheptyl)imidazolidin-2-one;
1-(3-cyclopentyl-2-oxopropyl)-3-[1-(2-fluorophenyl)-1H-indazol-4-yl]imidazolidin-2-one;
1-(3-cyclopentyl-2-hydroxypropyl)-3-[1-(2-fluorophenyl)-1H-indazol-4-yl]imidazolidin-2-one;
1-(3-cyclohexyl-2-oxopropyl)-3-[1-(2-fluorophenyl)-1H-indazol-4-yl]imidazolidin-2-one;
cyclopentyl 2-[1-(2-fluorophenyl)-1H-indazol-4-yl]-3-oxohexahydroimidazo[1,5-a]pyrazine-7(1H)-carboxylate;
1-[1-(2-fluorophenyl)-1H-indazol-4-yl]-3-(pyrimidin-5-yl)imidazolidin-2-one;
1-(3-cyclohexyl-2-hydroxypropyl)-3-[1-(2-fluorophenyl)-1H-indazol-4-yl]imidazolidin-2-one;
1-(3-cyclobutyl-2-oxopropyl)-3-[1-(2-fluorophenyl)-1H-indazol-4-yl]imidazolidin-2-one;
1-(3-cyclobutyl-2-hydroxypropyl)-3-[1-(2-fluorophenyl)-1H-indazol-4-yl]imidazolidin-2-one;
1-[3-(bicyclo[2.2.1]hept-2-yl)-2-oxopropyl]-3-[1-(2-fluorophenyl)-1H-indazol-4-yl]imidazolidin-2-one;
1-[1-(2-fluorophenyl)-1H-indazol-4-yl]-3-(2-oxo-2-phenylethyl)imidazolidin-2-one;
1-(2-cyclopentyl-2-oxoethyl)-3-[1-(2-fluorophenyl)-1H-indazol-4-yl]imidazolidin-2-one;
1-[1-(2-fluorophenyl)-1H-indazol-4-yl]-3-(2-oxopropyl)imidazolidin-2-one;
1-[1-(2-fluorophenyl)-1H-indazol-4-yl]-3-(2-hydroxy-2-methylhex-5-en-1-yl)imidazolidin-2-one;
1-[1-(2-fluorophenyl)-1H-indazol-4-yl]-3-[2-(6-fluoropyridin-3-yl)-2-oxoethyl]imidazolidin-2-one;
1-(2-ethyl-2-hydroxy-4-methylpentyl)-3-[1-(2-fluorophenyl)-1H-indazol-4-yl]imidazolidin-2-one;
1-[1-(2-fluorophenyl)-1H-indazol-4-yl]-3-[2-(3-methoxyphenyl)-2-oxoethyl]imidazolidin-2-one;
1-[1-(2-fluorophenyl)-1H-indazol-4-yl]-3-[2-(3-fluorophenyl)-2-oxoethyl]imidazolidin-2-one;
1-[1-(2-fluorophenyl)-1H-indazol-4-yl]-3-{2-oxo-2-[4-(trifluoromethyl)phenyl]ethyl}imidazolidin-2-one;
1-[1-(2-fluorophenyl)-1H-indazol-4-yl]-3-[2-oxo-2-(pyridin-3-yl)ethyl]imidazolidin-2-one;
1-[2-(1,3-benzodioxol-5-yl)-2-oxoethyl]-3-[1-(2-fluorophenyl)-1H-indazol-4-yl]imidazolidin-2-one;
1-[1-(2-fluorophenyl)-1H-indazol-4-yl]-3-(4-fluoropyridin-3-yl)imidazolidin-2-one;
1-[1-(2-fluorophenyl)-1H-indazol-4-yl]-3-[(2R)-2-hydroxy-4-methylpentyl]imidazolidin-2-one;
1-[1-(2-fluorophenyl)-1H-indazol-4-yl]-3-[(2S)-2-hydroxy-4-methylpentyl]imidazolidin-2-one;
1-[1-(2-fluorophenyl)-1H-indazol-4-yl]-3-[2-oxo-3-(tetrahydrofuran-3-yl)propyl]imidazolidin-2-one;
1-[1-(2-fluorophenyl)-1H-indazol-4-yl]-3-(1,3-thiazol-5-yl)imidazolidin-2-one;
1-[1-(2-fluorophenyl)-1H-indazol-4-yl]-3-[(2S)-1-hydroxybutan-2-yl]imidazolidin-2-one;
1-[1-(2-fluorophenyl)-1H-indazol-4-yl]-3-[(2R)-2-hydroxybutyl]imidazolidin-2-one;
1-(3,3-dimethyl-2-oxobutyl)-3-[1-(2-fluorophenyl)-1H-indazol-4-yl]imidazolidin-2-one;
1-[1-(2-fluorophenyl)-1H-indazol-4-yl]-3-(3-methyl-2-oxobutyl)imidazolidin-2-one;
1-[1-(2-fluorophenyl)-1H-indazol-4-yl]-3-(2-hydroxy-3-methylbutyl)imidazolidin-2-one;
1-(2-cyclobutyl-2-oxoethyl)-3-[1-(2-fluorophenyl)-1H-indazol-4-yl]imidazolidin-2-one;
1-(2-cyclobutyl-2-hydroxyethyl)-3-[1-(2-fluorophenyl)-1H-indazol-4-yl]imidazolidin-2-one;
1-(2-cyclobutyl-1-hydroxy-2-oxoethyl)-3-[1-(2-fluorophenyl)-1H-indazol-4-yl]imidazolidin-2-one;
1-[1-(2-fluorophenyl)-1H-indazol-4-yl]-3-[(2R)-2-hydroxy-2,4-dimethylpentyl]imidazolidin-2-one;
1-[1-(2-fluorophenyl)-1H-indazol-4-yl]-3-[(2S)-2-hydroxy-2,4-dimethylpentyl]imidazolidin-2-one;
1-[1-(2-fluorophenyl)-1H-indazol-4-yl]-3-{2-oxo-2-[(2S)-2-(trifluoromethyl)pyrrolidin-1-yl]ethyl}imidazolidin-2-one;
1-[1-(2-fluorophenyl)-1H-indazol-4-yl]-3-{2-[(2R)-2-(methoxymethyl)pyrrolidin-1-yl]-2-oxoethyl}imidazolidin-2-one;
1-[1-(2-fluorophenyl)-1H-indazol-4-yl]-3-{2-oxo-2-[(2R)-2-(trifluoromethyl)pyrrolidin-1-yl]ethyl}imidazolidin-2-one;
1-[2-(2,2-dimethylpyrrolidin-1-yl)-2-oxoethyl]-3-[1-(2-fluorophenyl)-1H-indazol-4-yl]imidazolidin-2-one;
N-(3-fluorobenzyl)-2-{3-[1-(2-fluorophenyl)-1H-indazol-4-yl]-2-oxoimidazolidin-1-yl}acetamide;
N-(2,5-difluorobenzyl)-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-(2-methylbenzyl)acetamide;
2-{3-[1-(2-fluorophenyl)-1H-indazol-4-yl]-2-oxoimidazolidin-1-yl}-N-[(1R)-1-phenylethyl]acetamide;
N-(3,5-difluorobenzyl)-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-[(1S)-1-phenylethyl]acetamide;
1-(1,3-benzothiazol-2-ylmethyl)-3-[1-(2-fluorophenyl)-1H-indazol-4-yl]imidazolidin-2-one;
1-[1-(2-fluorophenyl)-1H-indazol-4-yl]-3-(2-hydroxy-2,3-dimethylbutyl)imidazolidin-2-one;
1-(cyclopentylmethyl)-3-[1-(2-fluorophenyl)-1H-indazol-4-yl]imidazolidin-2-one;
1-[1-(2-fluorophenyl)-1H-indazol-4-yl]-3-(tetrahydrofuran-2-ylmethyl)imidazolidin-2-one;
1-(2-cyclopropyl-2-oxoethyl)-3-[1-(2-fluorophenyl)-1H-indazol-4-yl]imidazolidin-2-one;
1-cyclobutyl-3-[1-(2-fluorophenyl)-1H-indazol-4-yl]imidazolidin-2-one;
1-[1-(2-fluorophenyl)-1H-indazol-4-yl]-3-[(3R,5R)-5-(2-fluorophenyl)tetrahydrofuran-3-yl]imidazolidin-2-one;
1-[1-(2-fluorophenyl)-1H-indazol-4-yl]-3-(2-hydroxy-4-methylpentyl)tetrahydropyrimidin-2(1H)-one;
1-[1-(2-fluorophenyl)-1H-indazol-4-yl]-3-{2-[(2S)-2-methylpyrrolidin-1-yl]-2-oxoethyl}tetrahydropyrimidin-2(1H)-one;
1-[1-(2-fluorophenyl)-1H-indazol-4-yl]-3-(4-methyl-2-oxopentyl)tetrahydropyrimidin-2(1H)-one;
1-[(2,2-difluorocyclopropyl)methyl]-3-[1-(2-fluorophenyl)-1H-indazol-4-yl]imidazolidin-2-one;
1-[1-(2-fluorophenyl)-1H-indazol-4-yl]-3-(pyrazolo[1,5-a]pyrimidin-3-yl)imidazolidin-2-one;

1-[1-(2-fluorophenyl)-1H-indazol-4-yl]-3-(2-methyl-2H-indazol-5-yl)imidazolidin-2-one;
1-(5-cyclopropyl-2-furyl)-3-[1-(2-fluorophenyl)-1H-indazol-4-yl]imidazolidin-2-one;
1-[1-(2-fluorophenyl)-1H-indazol-4-yl]-3-(2-phenylethyl)imidazolidin-2-one;
1-(cyclopropylmethyl)-3-[1-(2-fluorophenyl)-1H-indazol-4-yl]imidazolidin-2-one;
2,5-anhydro-1,3,4-trideoxy-2-(3-fluorophenyl)-4-{3-[1-(2-fluorophenyl)-1H-indazol-4-yl]-2-oxoimidazolidin-1-yl}-D-erythro-pentitol;
1-[1-(2-fluorophenyl)-1H-indazol-4-yl]-3-[(3R,5S)-5-(3-fluorophenyl)tetrahydrofuran-3-yl]imidazolidin-2-one;
1-(2,5-difluorobenzyl)-3-[1-(2-fluorophenyl)-1H-indazol-4-yl]imidazolidin-2-one;
1-[1-(2-fluorophenyl)-1H-indazol-4-yl]-3-(pyridin-3-ylmethyl)imidazolidin-2-one;
1-[1-(2-fluorophenyl)-1H-indazol-4-yl]-3-[(5-methyl-1,2-oxazol-3-yl)methyl]imidazolidin-2-one;
1-[1-(2-fluorophenyl)-1H-indazol-4-yl]-3-(oxetan-3-ylmethyl)imidazolidin-2-one;
(2R)-1-({3-[1-(2-fluorophenyl)-1H-indazol-4-yl]-2-oxoimidazolidin-1-yl}acetyl)pyrrolidine-2-carbonitrile;
1-[2-(2-azabicyclo[2.2.1]hept-2-yl)-2-oxoethyl]-3-[1-(2-fluorophenyl)-1H-indazol-4-yl]imidazolidin-2-one;
2,5-anhydro-1,3,4-trideoxy-2-(3-fluorophenyl)-4-{3-[1-(2-fluorophenyl)-1H-indazol-4-yl]-2-oxoimidazolidin-1-yl}-L-threo-pentitol;
1-[1-(2-fluorophenyl)-1H-indazol-4-yl]-3-(3-hydroxycyclopentyl)imidazolidin-2-one;
1-[2-(3-ethyl-3-hydroxyazetidin-1-yl)-2-oxoethyl]-3-[1-(2-fluorophenyl)-1H-indazol-4-yl]imidazolidin-2-one;
1-[2-(3,4-difluoropyrrolidin-1-yl)-2-oxoethyl]-3-[1-(2-fluorophenyl)-1H-indazol-4-yl]imidazolidin-2-one;
1-[1-(2-fluorophenyl)-1H-indazol-4-yl]-3-[5-(morpholin-4-yl)pyridin-3-yl]imidazolidin-2-one;
1-[1-(2-fluorophenyl)-1H-indazol-4-yl]-3-(pyridazin-3-yl)imidazolidin-2-one;
N-(cyclopropylmethyl)-2-{3-[1-(2-fluorophenyl)-1H-indazol-4-yl]-2-oxoimidazolidin-1-yl}acetamide;
1-[1-(2-fluorophenyl)-1H-indazol-4-yl]-3-(pyridin-4-ylmethyl)imidazolidin-2-one;
1-[1-(2-fluorophenyl)-1H-indazol-4-yl]-3-[(2-methyl-1,3-oxazol-4-yl)methyl]imidazolidin-2-one;
1-{2-[(1s,4s)-7-azabicyclo[2.2.1]hept-7-yl]-2-oxoethyl}-3-[1-(2-fluorophenyl)-1H-indazol-4-yl]imidazolidin-2-one;
1-[1-(2-fluorophenyl)-1H-indazol-4-yl]-3-[(3-methyloxetan-3-yl)methyl]imidazolidin-2-one;
1-[1-(2-fluorophenyl)-1H-indazol-4-yl]-3-[(2R)-2-methoxy-4-methylpentyl]imidazolidin-2-one;
1-[1-(2-fluorophenyl)-1H-indazol-4-yl]-3-[(2S)-2-methoxy-4-methylpentyl]imidazolidin-2-one;
1-[(1-acetylazetidin-3-yl)methyl]-3-[1-(2-fluorophenyl)-1H-indazol-4-yl]imidazolidin-2-one;
1-[1-(2-fluorophenyl)-1H-indazol-4-yl]-3-[(2-methyl-1,3-thiazol-4-yl)methyl]imidazolidin-2-one;
1-[1-(2-fluorophenyl)-1H-indazol-4-yl]-3-(pyrimidin-2-ylmethyl)imidazolidin-2-one;
1-[1-(2-fluorophenyl)-1H-indazol-4-yl]-3-[(5-methylpyrimidin-2-yl)methyl]imidazolidin-2-one;
1-[1-(2-fluorophenyl)-1H-indazol-4-yl]-3-[2-(pyridin-3-yl)ethyl]imidazolidin-2-one;
1-[1-(2-fluorophenyl)-1H-indazol-4-yl]-3-(1,3-thiazol-2-yl)imidazolidin-2-one;
1-[1-(2-fluorophenyl)-1H-indazol-4-yl]-3-(pyrimidin-4-ylmethyl)imidazolidin-2-one;
1-[1-(2-fluorophenyl)-1H-indazol-4-yl]-3-(oxetan-2-ylmethyl)imidazolidin-2-one;
1-[1-(2-fluorophenyl)-1H-indazol-4-yl]-3-[(3S)-tetrahydrofuran-3-yl]imidazolidin-2-one;
1-[1-(2-fluorophenyl)-1H-indazol-4-yl]-3-(1,3-oxazol-4-ylmethyl)tetrahydropyrimidin-2(1H)-one;
1-[1-(2-fluorophenyl)-1H-indazol-4-yl]-3-(pyrazin-2-yl)imidazolidin-2-one;
1-[(2,5-dimethyl-1,3-oxazol-4-yl)methyl]-3-[1-(2-fluorophenyl)-1H-indazol-4-yl]imidazolidin-2-one;
1-[1-(2-fluorophenyl)-1H-indazol-4-yl]-3-[(5-methylpyridin-3-yl)methyl]imidazolidin-2-one;
1-{[1-(benzyloxy)cyclopropyl]methyl}-3-[1-(2-fluorophenyl)-1H-indazol-4-yl]imidazolidin-2-one;
1-[1-(2-fluorophenyl)-1H-indazol-4-yl]-3-(5-methoxypyridin-3-yl)imidazolidin-2-one;
1-[1-(2-fluorophenyl)-1H-indazol-4-yl]-3-(1,3-oxazol-5-ylmethyl)imidazolidin-2-one;
1-(1-benzyl-2-oxopyrrolidin-3-yl)-3-[1-(2-fluorophenyl)-1H-indazol-4-yl]imidazolidin-2-one;
1-[(5-tert-butyl-1,3-oxazol-2-yl)methyl]-3-[1-(2-fluorophenyl)-1H-indazol-4-yl]imidazolidin-2-one;
1-[1-(2,4-difluorophenyl)-1H-indazol-4-yl]-3-[(5-methyl-1,3,4-thiadiazol-2-yl)methyl]imidazolidin-2-one;
1-(1,3-oxazol-2-ylmethyl)-3-{1-[4-(trifluoromethyl)phenyl]-1H-indazol-4-yl}imidazolidin-2-one;
1-(3,5-dimethyl-1,2-oxazol-4-yl)-3-[1-(2-fluorophenyl)-1H-indazol-4-yl]imidazolidin-2-one;
1-[1-(2-fluorophenyl)-1H-indazol-4-yl]-3-[(5-isopropyl-1,3-oxazol-2-yl)methyl]imidazolidin-2-one;
1-[(4,5-dimethyl-1,3-oxazol-2-yl)methyl]-3-[1-(2-fluorophenyl)-1H-indazol-4-yl]imidazolidin-2-one;
1-[(2,5-dimethyl-1,3-thiazol-4-yl)methyl]-3-[1-(2-fluorophenyl)-1H-indazol-4-yl]imidazolidin-2-one;
1-[(5-methyl-1,3,4-thiadiazol-2-yl)methyl]-3-{1-[4-(trifluoromethyl)phenyl]-1H-indazol-4-yl}imidazolidin-2-one;
tert-butyl (5R)-3-[1-(2-fluorophenyl)-1H-indazol-4-yl]-5-methyl-2-oxoimidazolidine-1-carboxylate;
1-(1,3-oxazol-4-ylmethyl)-3-{1-[4-(trifluoromethyl)phenyl]-1H-indazol-4-yl}imidazolidin-2-one;
1-[1-(2,4-difluorophenyl)-1H-indazol-4-yl]-3-[(2-methyl-1,3-thiazol-4-yl)methyl]imidazolidin-2-one;
1-[1-(2-fluorophenyl)-1H-indazol-4-yl]-3-[(3-methyl-1,2-oxazol-5-yl)methyl]imidazolidin-2-one;
1-[1-(2-fluorophenyl)-1H-indazol-4-yl]-3-[(5-methyl-1,3-thiazol-4-yl)methyl]imidazolidin-2-one;
(4R)-1-[1-(2-fluorophenyl)-1H-indazol-4-yl]-4-methylimidazolidin-2-one;
(4R)-1-[1-(2-fluorophenyl)-1H-indazol-4-yl]-4-methyl-3-(1,3-oxazol-2-ylmethyl)imidazolidin-2-one;
1-[1-(2-fluorophenyl)-1H-indazol-4-yl]-3-[(3-methoxypyrazin-2-yl)methyl]imidazolidin-2-one;
1-[1-(2-fluorophenyl)-1H-indazol-4-yl]-3-[(3-isopropyl-1,2-oxazol-5-yl)methyl]imidazolidin-2-one;
1-[(2-ethyl-1,3-thiazol-4-yl)methyl]-3-[1-(2-fluorophenyl)-1H-indazol-4-yl]imidazolidin-2-one;
1-[1-(2-fluorophenyl)-1H-indazol-4-yl]-3-[(5-isopropyl-1,2-oxazol-3-yl)methyl]imidazolidin-2-one;
1-[(5-cyclopropyl-1,2-oxazol-3-yl)methyl]-3-[1-(2-fluorophenyl)-1H-indazol-4-yl]imidazolidin-2-one;
1-[1-(2,4-difluorophenyl)-1H-indazol-4-yl]-3-[(1R)-1-(3-methyl-1,2,4-oxadiazol-5-yl)ethyl]imidazolidin-2-one;
1-[1-(2-fluorophenyl)-1H-indazol-4-yl]-3-{[2-(methoxymethyl)-1,3-thiazol-4-yl]methyl}imidazolidin-2-one;

1-[1-(2-fluorophenyl)-1H-indazol-4-yl]-3-(1,3-oxazol-2-ylmethyl)tetrahydropyrimidin-2(1H)-one;
1-[1-(2-fluorophenyl)-1H-indazol-4-yl]-3-[(5-isopropyl-1,3,4-oxadiazol-2-yl)methyl]imidazolidin-2-one;
1-[1-(2-fluorophenyl)-1H-indazol-4-yl]-3-[(5-methyl-pyrazin-2-yl)methyl]imidazolidin-2-one;
1-[(3,5-dimethyl-1,2-oxazol-4-yl)methyl]-3-[1-(2-fluorophenyl)-1H-indazol-4-yl]tetrahydropyrimidin-2(1H)-one;
1-[1-(2-fluorophenyl)-1H-indazol-4-yl]-3-[(6-methyl-pyrazin-2-yl)methyl]tetrahydropyrimidin-2(1H)-one;
1-[1-(2-fluorophenyl)-1H-indazol-4-yl]-3-[(5-methyl-1,3,4-oxadiazol-2-yl)methyl]tetrahydropyrimidin-2(1H)-one;
1-[(5-ethyl-1,3,4-oxadiazol-2-yl)methyl]-3-[1-(2-fluorophenyl)-1H-indazol-4-yl]imidazolidin-2-one;
1-[(5-tert-butyl-1,3,4-oxadiazol-2-yl)methyl]-3-[1-(2-fluorophenyl)-1H-indazol-4-yl]imidazolidin-2-one;
1-[1-(2-fluorophenyl)-1H-indazol-4-yl]-3-[(5-methyl-1,3-thiazol-2-yl)methyl]imidazolidin-2-one;
1-[1-(2-fluorophenyl)-1H-indazol-4-yl]-3-[(3-methyl-1,2-oxazol-4-yl)methyl]imidazolidin-2-one;
1-[1-(2-fluorophenyl)-1H-indazol-4-yl]-3-(trans-4-hydroxycyclohexyl)imidazolidin-2-one;
1-[1-(2-fluorophenyl)-1H-indazol-4-yl]-3-(4-oxocyclohexyl)imidazolidin-2-one;
tert-butyl 3-{3-[1-(2-fluorophenyl)-1H-indazol-4-yl]-2-oxoimidazolidin-1-yl}azetidine-1-carboxylate;
1-(azetidin-3-yl)-3-[1-(2-fluorophenyl)-1H-indazol-4-yl]imidazolidin-2-one;
1-[1-(2-fluorophenyl)-1H-indazol-4-yl]-3-{1-[(1-hydroxycyclopropyl)carbonyl]azetidin-3-yl}imidazolidin-2-one;
2-(3-{3-[1-(2-fluorophenyl)-1H-indazol-4-yl]-2-oxoimidazolidin-1-yl}azetidin-1-yl)-2-oxoacetamide;
1-[1-(2-fluorophenyl)-1H-indazol-4-yl]-3-[1-(methylsulfonyl)azetidin-3-yl]imidazolidin-2-one;
1-[(1R,2R)-2-(benzyloxy)cyclohexyl]-3-[1-(2-fluorophenyl)-1H-indazol-4-yl]imidazolidin-2-one;
1-[1-(2-fluorophenyl)-1H-indazol-4-yl]-3-[(1R,2R)-2-hydroxycyclohexyl]imidazolidin-2-one;
1-[1-(2-fluorophenyl)-1H-indazol-4-yl]-3-[1-(propylsulfonyl)azetidin-3-yl]imidazolidin-2-one;
1-[(1S,2S)-2-(benzyloxy)cyclohexyl]-3-[1-(2-fluorophenyl)-1H-indazol-4-yl]imidazolidin-2-one;
1-[1-(2-fluorophenyl)-1H-indazol-4-yl]-3-[(1S,2S)-2-hydroxycyclohexyl]imidazolidin-2-one;
1-[2-oxo-2-(pyrrolidin-1-yl)ethyl]-3-(1-phenyl-1H-indazol-4-yl)imidazolidin-2-one;
1-[2-oxo-2-(pyrrolidin-1-yl)ethyl]-3-[1-(pyridin-2-yl)-1H-indazol-4-yl]imidazolidin-2-one;
1-[1-(2-fluorophenyl)-1H-indazol-4-yl]-3-[(1S,2S)-2-methoxycyclohexyl]imidazolidin-2-one;
1-[1-(2-fluorophenyl)-1H-indazol-4-yl]-3-[(1S,2S)-2-isobutoxycyclohexyl]imidazolidin-2-one;
1-[1-(2-fluorophenyl)-1H-indazol-4-yl]-3-[(1S)-2-oxocyclohexyl]imidazolidin-2-one;
1-[1-{[(2,2-dichlorocyclopropyl)methyl]sulfonyl}azetidin-3-yl)-3-[1-(2-fluorophenyl)-1H-indazol-4-yl]imidazolidin-2-one;
1-{1-[(cyclopropylmethyl)sulfonyl]azetidin-3-yl}-3-[1-(2-fluorophenyl)-1H-indazol-4-yl]imidazolidin-2-one;
1-[1-(2-fluorophenyl)-1H-indazol-4-yl]-3-{1-[(2,2,2-trifluoroethyl)sulfonyl]azetidin-3-yl}imidazolidin-2-one;
1-[1-(2-fluorophenyl)-1H-indazol-4-yl]-3-(isobutylsulfonyl)azetidin-3-yl]imidazolidin-2-one;
tert-butyl {3-[1-(2-fluorophenyl)-1H-indazol-4-yl]-2-oxoimidazolidin-1-yl}acetate;
ethyl (2Z)-3-{3-[1-(2-fluorophenyl)-1H-indazol-4-yl]-2-oxoimidazolidin-1-yl}acrylate;
ethyl (2E)-3-{3-[1-(2-fluorophenyl)-1H-indazol-4-yl]-2-oxoimidazolidin-1-yl}acrylate;
tert-butyl 3-{3-[1-(2-fluorophenyl)-1H-indazol-4-yl]-2-oxoimidazolidin-1-yl}propanoate;
1-[1-(2-fluorophenyl)-1H-indazol-4-yl]-3-{2-[(3S)-3-hydroxypiperidin-1-yl]-2-oxoethyl}imidazolidin-2-one;
1-[1-(2-fluorophenyl)-1H-indazol-4-yl]-3-[2-(3-hydroxyazetidin-1-yl)-2-oxoethyl]imidazolidin-2-one;
1-[1-(2-fluorophenyl)-1H-indazol-4-yl]-3-{3-[(3S)-3-fluoropyrrolidin-1-yl]-3-oxopropyl}imidazolidin-2-one;
1-[1-(2-fluorophenyl)-1H-indazol-4-yl]-3-[2-(morpholin-4-yl)-2-oxoethyl]imidazolidin-2-one;
1-(1-cyclohexyl-1H-indazol-4-yl)-3-{2-[(3S)-3-fluoropyrrolidin-1-yl]-2-oxoethyl}imidazolidin-2-one;
1-[1-(2-fluorophenyl)-1H-indazol-4-yl]-3-[2-oxo-2-(piperidin-1-yl)ethyl]imidazolidin-2-one;
1-[2-(3,3-difluoropiperidin-1-yl)-2-oxoethyl]-3-[1-(2-fluorophenyl)-1H-indazol-4-yl]imidazolidin-2-one;
1-[2-(4,4-difluoropiperidin-1-yl)-2-oxoethyl]-3-[1-(2-fluorophenyl)-1H-indazol-4-yl]imidazolidin-2-one;
1-[2-(3-fluoroazetidin-1-yl)-2-oxoethyl]-3-[1-(2-fluorophenyl)-1H-indazol-4-yl]imidazolidin-2-one;
1-[1-(2-fluorophenyl)-1H-indazol-4-yl]-3-{2-oxo-2-[4-(trifluoromethyl)piperidin-1-yl]ethyl}imidazolidin-2-one;
1-[1-(2-fluorophenyl)-1H-indazol-4-yl]-3-{2-oxo-2-[3-(trifluoromethyl)piperidin-1-yl]ethyl}imidazolidin-2-one;
1-[1-(2-fluorophenyl)-1H-indazol-4-yl]-3-{2-[(1R,5S)-8-oxa-3-azabicyclo[3.2.1]oct-3-yl]-2-oxoethyl}imidazolidin-2-one;
1-[1-(2-fluorophenyl)-1H-indazol-4-yl]-3-[2-oxo-2-(3-oxopyrrolidin-1-yl)ethyl]imidazolidin-2-one;
1-[2-(azepan-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-(2,2,2-trifluoroethyl)acetamide;
1-[1-(3,3-dimethylbutyl)-1H-indazol-4-yl]-3-[2-oxo-2-(pyrrolidin-1-yl)ethyl]imidazolidin-2-one;
1-(1-tert-butyl-1H-indazol-4-yl)-3-{2-[(3S)-3-fluoropyrrolidin-1-yl]-2-oxoethyl}imidazolidin-2-one;
1-{2-[(3S)-3-fluoropyrrolidin-1-yl]-2-oxoethyl}-3-(1-phenyl-1H-indazol-4-yl)imidazolidin-2-one;
1-[1-(2-fluorophenyl)-1H-indazol-4-yl]-3-{2-oxo-2-[(3S)-3-(trifluoromethyl)pyrrolidin-1-yl]ethyl}imidazolidin-2-one;
1-[2-(3-fluoro-3-methylazetidin-1-yl)-2-oxoethyl]-3-[1-(2-fluorophenyl)-1H-indazol-4-yl]imidazolidin-2-one;
N-(3,3-difluorocyclobutyl)-2-{3-[1-(2-fluorophenyl)-1H-indazol-4-yl]-2-oxoimidazolidin-1-yl}acetamide;
(1R,5S)-8-({3-[1-(2-fluorophenyl)-1H-indazol-4-yl]-2-oxoimidazolidin-1-yl}acetyl)-8-azabicyclo[3.2.1]octan-3-one;
1-[1-(2-fluorophenyl)-1H-indazol-4-yl]-3-[2-oxo-2-(3,3,4,4-tetrafluoropyrrolidin-1-yl)ethyl]imidazolidin-2-one;
1-({3-[1-(2-fluorophenyl)-1H-indazol-4-yl]-2-oxoimidazolidin-1-yl}acetyl)azepan-4-one;
1-[1-(2-fluorophenyl)-1H-indazol-4-yl]-3-{(1Z)-3-[(3S)-3-fluoropyrrolidin-1-yl]-3-oxoprop-1-en-1-yl}imidazolidin-2-one;

N-ethyl-2-{3-[1-(2-fluorophenyl)-1H-indazol-4-yl]-2-oxoimidazolidin-1-yl}acetamide;
2-{3-[1-(2-fluorophenyl)-1H-indazol-4-yl]-2-oxoimidazolidin-1-yl}-N-[1-(hydroxymethyl)cyclobutyl]acetamide;
1-[1-(2-fluorophenyl)-1H-indazol-4-yl]-3-{3-[(3R)-3-fluoropiperidin-1-yl]-3-oxopropyl}imidazolidin-2-one;
1-[1-(2-fluorophenyl)-1H-indazol-4-yl]-3-{3-[(3S)-3-fluoropiperidin-1-yl]-3-oxopropyl}imidazolidin-2-one;
1-[1-(2-fluorophenyl)-1H-indazol-4-yl]-3-[2-(3-methoxyazetidin-1-yl)-2-oxoethyl]imidazolidin-2-one;
2-{3-[1-(2-fluorophenyl)-1H-indazol-4-yl]-2-oxoimidazolidin-1-yl}-N-(tetrahydro-2H-pyran-4-yl)acetamide;
2-{3-[1-(2-fluorophenyl)-1H-indazol-4-yl]-2-oxoimidazolidin-1-yl}-N-(oxetan-3-yl)acetamide;
N-cyclobutyl-2-{3-[1-(2-fluorophenyl)-1H-indazol-4-yl]-2-oxoimidazolidin-1-yl}acetamide;
N-cyclopentyl-2-{3-[1-(2-fluorophenyl)-1H-indazol-4-yl]-2-oxoimidazolidin-1-yl}acetamide;
N-cyclohexyl-2-{3-[1-(2-fluorophenyl)-1H-indazol-4-yl]-2-oxoimidazolidin-1-yl}acetamide;
1-[2-(3-acetylazetidin-1-yl)-2-oxoethyl]-3-[1-(2-fluorophenyl)-1H-indazol-4-yl]imidazolidin-2-one;
2-{3-[1-(2-fluorophenyl)-1H-indazol-4-yl]-2-oxoimidazolidin-1-yl}-N-(trans-3-methoxycyclobutyl)acetamide;
1-[1-(2-fluorophenyl)-1H-indazol-4-yl]-3-{(1E)-3-[(3S)-3-fluoropyrrolidin-1-yl]-3-oxoprop-1-en-1-yl}imidazolidin-2-one;
N-(2,2-dimethylcyclopropyl)-2-{3-[1-(2-fluorophenyl)-1H-indazol-4-yl]-2-oxoimidazolidin-1-yl}acetamide;
1-[1-(2-fluorophenyl)-1H-indazol-4-yl]-3-{2-oxo-2-[3-(trifluoromethyl)azetidin-1-yl]ethyl}imidazolidin-2-one;
1-{2-[3-(difluoromethyl)pyrrolidin-1-yl]-2-oxoethyl}-3-[1-(2-fluorophenyl)-1H-indazol-4-yl]imidazolidin-2-one;
1-[1-(2-fluorophenyl)-1H-indazol-4-yl]-3-[(1S,2S)-2-isopropoxycyclohexyl]imidazolidin-2-one;
2-{3-[1-(2-fluorophenyl)-1H-indazol-4-yl]-2-oxoimidazolidin-1-yl}-N-[(1R,2S)-2-hydroxycyclopentyl]acetamide;
2-{3-[1-(2-fluorophenyl)-1H-indazol-4-yl]-2-oxoimidazolidin-1-yl}-N-(1-methylcyclopropyl)acetamide;
N-[(1S,2S)-2-(benzyloxy)cyclopentyl]-2-{3-[1-(2-fluorophenyl)-1H-indazol-4-yl]-2-oxoimidazolidin-1-yl}acetamide;
N-[(1R,2R)-2-(benzyloxy)cyclopentyl]-2-{3-[1-(2-fluorophenyl)-1H-indazol-4-yl]-2-oxoimidazolidin-1-yl}acetamide;
1-[1-(2-fluorophenyl)-1H-indazol-4-yl]-3-(4-isobutoxytetrahydrofuran-3-yl)imidazolidin-2-one;
2-{3-[1-(2-fluorophenyl)-1H-indazol-4-yl]-2-oxoimidazolidin-1-yl}-N-[(1R,2S)-2-isobutoxycyclopentyl]acetamide;
1-[1-(4-chlorophenyl)-1H-indazol-4-yl]-3-{2-[(3S)-3-fluoropyrrolidin-1-yl]-2-oxoethyl}imidazolidin-2-one;
N-tert-butyl-2-{3-[1-(2-fluorophenyl)-1H-indazol-4-yl]-2-oxoimidazolidin-1-yl}acetamide;
N-(3,3-difluorocyclohexyl)-2-{3-[1-(2-fluorophenyl)-1H-indazol-4-yl]-2-oxoimidazolidin-1-yl}acetamide;
N-(3,3-difluorocyclopentyl)-2-{3-[1-(2-fluorophenyl)-1H-indazol-4-yl]-2-oxoimidazolidin-1-yl}acetamide;
1-[1-(2-fluorophenyl)-1H-indazol-4-yl]-3-{2-[(3 aR,6aS)-hexahydrocyclopenta[c]pyrrol-2(1H)-yl]-2-oxoethyl}imidazolidin-2-one;
2-{3-[1-(2-fluorophenyl)-1H-indazol-4-yl]-2-oxoimidazolidin-1-yl}-N-(3,3,3-trifluoropropyl)acetamide;
1-[1-(2-fluorophenyl)-1H-indazol-4-yl]-3-methylimidazolidin-2-one;
Nα-({3-[1-(2-fluorophenyl)-1H-indazol-4-yl]-2-oxoimidazolidin-1-yl}acetyl)-D-phenylalaninamide;
N-tert-butyl-N$^2$-({3-[1-(2-fluorophenyl)-1H-indazol-4-yl]-2-oxoimidazolidin-1-yl}acetyl)-L-valinamide;
N-(2,2-difluorocyclopentyl)-2-{3-[1-(2-fluorophenyl)-1H-indazol-4-yl]-2-oxoimidazolidin-1-yl}acetamide;
1-[1-(3,5-dichlorophenyl)-1H-indazol-4-yl]-3-{2-[(3S)-3-fluoropyrrolidin-1-yl]-2-oxoethyl}imidazolidin-2-one;
2-{3-[1-(2-fluorophenyl)-1H-indazol-4-yl]-2-oxoimidazolidin-1-yl}-N-(3-oxocyclobutyl)acetamide;
2-{3-[1-(2-fluorophenyl)-1H-indazol-4-yl]-2-oxoimidazolidin-1-yl}-N-(3-hydroxycyclobutyl)acetamide;
N-cyclobutyl-2-{3-[1-(2-fluorophenyl)-1H-indazol-4-yl]-2-oxoimidazolidin-1-yl}-N-methylacetamide;
1-[1-(2-fluorophenyl)-1H-indazol-4-yl]-3-[2-(3-methylazetidin-1-yl)-2-oxoethyl]imidazolidin-2-one;
2-{3-[1-(2-fluorophenyl)-1H-indazol-4-yl]-2-oxoimidazolidin-1-yl}-N-[1-(trifluoromethyl)cyclobutyl]acetamide;
2-{3-[1-(2-fluorophenyl)-1H-indazol-4-yl]-2-oxoimidazolidin-1-yl}-N-[3-(hydroxyimino)cyclobutyl]acetamide;
2-{3-[1-(2-fluorophenyl)-1H-indazol-4-yl]-2-oxoimidazolidin-1-yl}-N-[3-(methoxyimino)cyclobutyl]acetamide;
N-(4,4-difluorocyclohexyl)-2-{3-[1-(2-fluorophenyl)-1H-indazol-4-yl]-2-oxoimidazolidin-1-yl}acetamide; and
N-(2,2-dimethylpropyl)-2-{3-[1-(2-fluorophenyl)-1H-indazol-4-yl]-2-oxoimidazolidin-1-yl}acetamide.

41. A pharmaceutical composition comprising a therapeutically effective amount of a compound of claim 1 in combination with a pharmaceutically acceptable carrier.

\* \* \* \* \*